United States Patent
Zhou et al.

(10) Patent No.: US 12,042,510 B2
(45) Date of Patent: *Jul. 23, 2024

(54) MODULATORS OF IRF4 EXPRESSION

(71) Applicant: Ionis Pharmaceuticals, Inc., Carlsbad, CA (US)

(72) Inventors: Tianyuan Zhou, Shanghai (CN); Youngsoo Kim, San Diego, CA (US); Robert MacLeod, San Diego, CA (US); Huynh-Hoa Bui, San Diego, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/554,558

(22) Filed: Dec. 17, 2021

(65) Prior Publication Data

US 2022/0241320 A1 Aug. 4, 2022

Related U.S. Application Data

(63) Continuation of application No. 16/977,260, filed as application No. PCT/US2019/020201 on Mar. 1, 2019, now Pat. No. 11,241,451.

(60) Provisional application No. 62/637,981, filed on Mar. 2, 2018.

(51) Int. Cl.
*C12N 15/11* (2006.01)
*A61K 31/7125* (2006.01)

(52) U.S. Cl.
CPC ........ *A61K 31/7125* (2013.01); *C12N 15/111* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |

(Continued)

FOREIGN PATENT DOCUMENTS

| | | |
|---|---|---|
| WO | 1997045106 | 12/1997 |
| WO | WO2009078931 | 6/2009 |

(Continued)

OTHER PUBLICATIONS

Branch et al., "A good antisense molecule is hard to find," TIBS (1998) 23:45-50.

(Continued)

*Primary Examiner* — Ekaterina Poliakova-Georgantas
(74) *Attorney, Agent, or Firm* — Sheppard, Mullin, Richter & Hampton LLP

(57) ABSTRACT

The present embodiments provide methods, compounds, and compositions useful for inhibiting IRF4 expression, which may be useful for treating, preventing, or ameliorating a cancer associated with IRF4.

17 Claims, No Drawings

Specification includes a Sequence Listing.

(56) References Cited

U.S. PATENT DOCUMENTS

| | | |
|---|---|---|
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddiy et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,687,616 B1 | 3/2010 | Bentwich et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,777,022 B2 | 8/2010 | Bentwich et al. |
| 7,875,733 B2 | 1/2011 | Bhat et al. |
| 7,888,497 B2 | 2/2011 | Bentwich et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,090,542 B2 | 1/2012 | Khvorova et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,679,743 B2 | 3/2014 | Feldman et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,029,523 B2 | 5/2015 | Alexandrov et al. |
| 9,127,276 B2 | 8/2015 | Prakash et al. |
| 9,290,760 B2 | 3/2016 | Raj eev et al. |
| 11,241,451 B2 | 2/2022 | Zhou et al. |
| 2001/0053519 A1 | 12/2001 | Fodor et al. |
| 2003/0158403 A1 | 8/2003 | Manobaran et al. |
| 2003/0175906 A1 | 9/2003 | Manobaran et al. |
| 2003/0228597 A1 | 12/2003 | Cowsert et al. |
| 2004/0171570 A1 | 9/2004 | Allerson et al. |
| 2004/0241651 A1 | 12/2004 | Olek et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2008/0318210 A1 | 12/2008 | Bentwich |
| 2010/0190837 A1 | 7/2010 | Migawa et al. |
| 2010/0197762 A1 | 8/2010 | Swayze et al. |
| 2010/0260718 A1 | 10/2010 | Ren |
| 2011/0054005 A1 | 3/2011 | Naito et al. |
| 2013/0011922 A1 | 1/2013 | Quay et al. |
| 2013/0130378 A1 | 5/2013 | Manoharan et al. |
| 2014/0107330 A1 | 4/2014 | Freier et al. |
| 2014/0154783 A1 | 6/2014 | Rossomando et al. |
| 2015/0018540 A1 | 1/2015 | Prakash et al. |

(56) References Cited

U.S. PATENT DOCUMENTS

| | | |
|---|---|---|
| 2015/0099791 A1 | 4/2015 | Krieg et al. |
| 2015/0184153 A1 | 7/2015 | Freier et al. |
| 2015/0191727 A1 | 7/2015 | Migawa et al. |
| 2015/0232836 A1 | 8/2015 | Krieg et al. |
| 2015/0267195 A1 | 9/2015 | Seth et al. |
| 2015/0275212 A1 | 10/2015 | Albaek et al. |
| 2016/0369333 A1 | 12/2016 | Babiarz et al. |
| 2021/0038631 A1 | 2/2021 | Zhou et al. |

FOREIGN PATENT DOCUMENTS

| | | |
|---|---|---|
| WO | 2009132126 | 10/2009 |
| WO | WO 2011/082409 | 7/2011 |
| WO | WO 2013/159108 | 10/2013 |
| WO | 2013173637 | 11/2013 |
| WO | WO 2014/059353 A2 | 4/2014 |
| WO | WO 2016/057903 | 4/2016 |
| WO | 2016180784 | 11/2016 |
| WO | 2019169219 | 9/2019 |
| WO | WO2019200216 | 10/2019 |
| WO | WO2022226217 | 10/2022 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bc1-2/bc1-xLbispecific antisense oligonucleotide against tumors of diverse histologic origins" J. Natl. Cancer Inst. (2001) 93:463-471.

International Search Report for PCT/US19/020201 dated Jul. 19, 2019.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Morelli et al., "Selective targeting of IRF4 by synthetic microRNA-125b-5p mimics induces anti-multiple myeloma activity in vitro and in vivo" Leukemia (2015) 29: 2173-2183.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Woolf et al., "Specificity of antisense oligonucleotides in vivo" PNAS (1992) 89: 7305-7309.

Zhou et al., "Selective Downregulation of Interferon Regulatory Factor 4 by Generation 2.5 Antisense Oligonucleotides Induces Strong Apoptosis and Sensitizes Multiple Myeloma Cells to Lenalidomide or Bortezomib" Presentation at International Conference: Molecular Targets and Cancer Therapeutics—Hynes Convention Center: Boston, MA (Oct. 19-23, 2013).

Zhou et al., "Therapeutic Targeting of Interferon Regulatory Factor 4 with Next Generation Antisense Oligonucleotides Produces Robust In Vivo Antitumor Activity in Preclinical Models of Multiple Myeloma" Presentation at 59th Annual Meeting and Exposition—Georgia World Congress Center: Atlanta, GA (Dec. 9-12, 2017).

Zhou et al., "Abstract B223: Selective Downregulation of interferon regulatory factor 4 by generation 2.5 antisense oligonucleotides induces strong apoptosis and sensitizes multiple myeloma cells to lenalidomide or bortezomib" RNA and RNA Base Technologies and Therapies (2013).

Zhou et al., "Abstract: Therapeutic Targeting of Interferon Regulatory Factor 4 with Next Generation Antisense Oligonucleotides Produces Robust In Vivo Antitumor Activity in Preclinical Models of Multiple Myeloma" Myeloma: Pathology and Pre-Clinical Studies, Excluding Therapy (2017).

Cherian et al., "An activating mutation of interferon regulatory factor 4 (IRF4) in adult T-cell leukemia" J Biol Chem (2018) 293: 6844-6858.

Feldman et al., "1322: IRF4-dependent cell proliferation is a potential therapeutic target in peripheral T-cell lymphomas" Lab Invest (2010) 90: 295A.

Mondala et al., "Selective antisense oligonucleotide inhibition of human IRF4 prevents malignant myeloma regeneration via cell cycle disruption" Cell Stem Cell (2021) 28: 623-636.

Rauch et al., "Interferon regulatory factor 4 as a therapeutic target in adult T-cell leukemia lymphoma" Retrovirology (2020) 17: 1-10.

Shirasaki et al., "Mechanisms Regulating Myeloma Cell Responsiveness to Antisense Oligonucleotides Targeting IRF4" Blood (2020) 136 (Supplement 1) 32.

Zhao et al., "Inhibition of Interferon Regulatory Factor 4 Attenuates Acute Liver Allograft Rejection in Mice" Scand J Immunol (2015) 82: 262-268.

Zhou et al., "Selective Downregulation of Interferon Regulatory Factor 4 by Generation 2.5 Antisense Oligonucleotides Induces Strong Apoptosis and Sensitizes Multiple Myeloma Cells to Lenalidomide or Bortezomib" Abstract B223: (2013) Mol Cancer Ther 12(Supplement 11).

Zhou et al., "Therapeutic Targeting of Interferon Regulatory Factor 4 with Next Generation Antisense Oligonucleotides Produces Robust In Vivo Antitumor Activity in Preclinical Models of Multiple Myeloma" Presentation at 59th Annual Meeting and Exposition Generation Antisense Oligonucleotides Produces Robust In Vivo Antitumor Activity in Preclinical Models of Multiple Myeloma (2017) Blood 130(supplement 1) 295A.

MODULATORS OF IRF4 EXPRESSION

SEQUENCE LISTING

The present application is being filed along with a Sequence Listing in electronic format. The Sequence Listing is provided as a file entitled BIOL0332WOSEQ.txt created Jan. 14, 2019, which is 712 kb in size. The information in the electronic format of the sequence listing is incorporated herein by reference in its entirety.

FIELD

The present embodiments provide methods, compounds, and compositions useful for inhibiting IRF4 expression, which can be useful for treating, preventing, or ameliorating a cancer associated with IRF4.

BACKGROUND

Interferon Regulatory Factor 4 (IRF4) is a transcription factor involved in immune responses in normal B and T cells, and is strongly implicated in the development of hematological malignancies, especially multiple myeloma (MM). High IRF4 levels is associated with a poor prognosis of overall survival for MM patients. Upregulation of the cereblon/IRF4 pathway accounts for the failure of lenalidomide treatment, an IMiD approved for MM and B cell malignancies. IRF4 is a component of super enhancer in MM cells in which a positive auto-regulatory loop between the oncogene MYC and IRF4 sustains the survival of MM. IRF4 is also involved in cutaneous anaplastic large cell lymphomas DLBCL, B-cell non-Hodgkin's lymphoma, ALL, adult T cell leukemia/lymphoma (ATLL), and peripheral T cell lymphoma. Despite its role in many cancers, IRF4 is considered an undruggable target by conventional therapeutic approaches.

SUMMARY

Certain embodiments provided herein are directed to potent and tolerable compounds and compositions useful for inhibiting IRF4 expression, which can be useful for treating, preventing, ameliorating, or slowing progression of cancer associated with IRF4.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ION number indicate a combination of nucleobase sequence, chemical modification, and motif.

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O(CH$_2$)$_2$—OCH$_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of IRF4", it is implied that IRF4 levels are inhibited within a range of 60% and 80%.

"Administration" or "administering" refers to routes of introducing a compound or composition provided herein to an individual to perform its intended function. An example of a route of administration that can be used includes, but is not limited to parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Cell-targeting moiety" means a conjugate group or portion of a conjugate group that is capable of binding to a particular cell type or particular cell types.

"cEt" or "constrained ethyl" means a bicyclic furanosyl sugar moiety comprising a bridge connecting the 4'-carbon and the 2'-carbon, wherein the bridge has the formula: 4'-CH($CH_3$)—O-2'.

"cEt nucleoside" means a nucleoside comprising a cEt modified sugar moiety.

"Chemical modification" in a compound describes the substitutions or changes through chemical reaction, of any of the units in the compound relative to the original state of such unit. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Chirally enriched population" mean s a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more sterorandom chiral centers. In certain embodiments, the molecules are modified oligonucleotides. In certain embodiments, the molecules are compounds comprising modified oligonucleotides.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine ($^m$C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Conjugate group" means a group of atoms that is attached to an oligonucleotide. Conjugate groups include a conjugate moiety and a conjugate linker that attaches the conjugate moiety to the oligonucleotide.

"Conjugate linker" means a group of atoms comprising at least one bond that connects a conjugate moiety to an oligonucleotide.

"Conjugate moiety" means a group of atoms that is attached to an oligonucleotide via a conjugate linker.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g. saline solution.

"Differently modified" means chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in an individual. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded antisense compound" means an antisense compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in an individual in need of the compound. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to, the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Hybridization" means the annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g. no intervening nucleobases between the immediately adjacent nucleobases).

"Individual" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage Non-phosphate linkages are referred to herein as modified internucleoside linkages.

"Lengthened oligonucleotides" are those that have one or more additional nucleosides relative to an oligonucleotide disclosed herein, e.g. a parent oligonucleotide.

"Linked nucleosides" means adjacent nucleosides linked together by an internucleoside linkage.

"Linker-nucleoside" means a nucleoside that links an oligonucleotide to a conjugate moiety. Linker-nucleosides are located within the conjugate linker of a compound. Linker-nucleosides are not considered part of the oligonucleotide portion of a compound even if they are contiguous with the oligonucleotide.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating IRF4 RNA can mean to increase or decrease the level of IRF4 RNA and/or IRF4 protein in a cell, tissue, organ or organism. A "modulator" effects the change in the cell, tissue, organ or organism. For example, a IRF4 compound can be a modulator that decreases the amount of IRF4 RNA and/or IRF4 protein in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Pharmaceutically acceptable carrier or diluent" means any substance suitable for use in administering to an individual. For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to an individual.

"Pharmaceutical composition" means a mixture of substances suitable for administering to an individual. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to an individual, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites" are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" with reference to a target nucleic acid means to reduce or block expression of the target nucleic acid while exhibiting fewer, minimal, or no effects on non-target nucleic acids. Reduction does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary compounds or nucleic acids.

"Synergy" or "synergize" refers to an effect of a combination that is greater than additive of the effects of each component alone at the same doses.

"IRF4" means any nucleic acid or protein of IRF4. "IRF4 nucleic acid" means any nucleic acid encoding TRF4. For example, in certain embodiments, a TRF4 nucleic acid includes a DNA sequence encoding IRF4, an RNA sequence transcribed from DNA encoding IRF4 (including genomic DNA comprising introns and exons), and an mRNA sequence encoding IRF4. "IRF4 mRNA" means an mRNA encoding a IRF4 protein. The target may be referred to in either upper or lower case.

"IRF4 specific inhibitor" refers to any agent capable of specifically inhibiting IRF4 RNA and/or IRF4 protein expression or activity at the molecular level. For example, IRF4 specific inhibitors include nucleic acids (including antisense compounds), peptides, antibodies, small molecules, and other agents capable of inhibiting the expression of IRF4 RNA and/or IRF4 protein.

"Target gene" refers to a gene encoding a target.

"Targeting" means the specific hybridization of a compound to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to an individual.

"Treat" refers to administering a compound or pharmaceutical composition to an animal in order to effect an alteration or improvement of a disease, disorder, or condition in the animal.

CERTAIN EMBODIMENTS

Certain embodiments provide methods, compounds and compositions for inhibiting IRF4 expression.

Certain embodiments provide compounds targeted to a IRF4 nucleic acid. In certain embodiments, the IRF4 nucleic acid has the sequence set forth in RefSeq or GENBANK Accession No. NM_002460.3 or NT_034880.3_TRUNC_328000_354000 (incorporated by reference, disclosed herein as SEQ ID NO: 1 and SEQ ID NO: 2, respectively). In certain embodiments, the compound is an antisense compound or oligomeric compound. In certain embodiments, the compound is single-stranded. In certain embodiments, the compound is double-stranded.

Certain embodiments provide a compound comprising a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 9 to 80 linked nucleosides in length and having a nucleobase sequence comprising at least 9 contiguous nucleobases of any of the nucleobase sequences of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 10 to 80 linked nucleosides in length and having a nucleobase sequence comprising at least 10 contiguous nucleobases of any of the nucleobase sequences of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 10 to 30 linked nucleosides in length.

Certain embodiments provide a compound comprising a modified oligonucleotide 11 to 80 linked nucleosides in length and having a nucleobase sequence comprising at least 11 contiguous nucleobases of any of the nucleobase sequences of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 11 to 30 linked nucleosides in length.

Certain embodiments provide a compound comprising a modified oligonucleotide 12 to 80 linked nucleosides in length and having a nucleobase sequence comprising at least 12 contiguous nucleobases of any of the nucleobase sequences of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

Certain embodiments provide a compound comprising a modified oligonucleotide 16 to 80 linked nucleosides in length and having a nucleobase sequence comprising the nucleobase sequence of any one of SEQ ID NOs: 3-3383. In certain embodiments, the compound is an antisense compound or oligomeric compound. In certain embodiments, the compound is single-stranded. In certain embodiments, the compound is double-stranded. In certain embodiments, the modified oligonucleotide is 16 to 30 linked nucleosides in length.

Certain embodiments provide a compound comprising a modified oligonucleotide consisting of the nucleobase sequence of any one of SEQ ID NOs: 3-3383. In certain embodiments, the compound is an antisense compound or oligomeric compound. In certain embodiments, the compound is single-stranded. In certain embodiments, the compound is double-stranded.

In certain embodiments, a compound comprises a modified oligonucleotide 8 to 80 linked nucleosides in length and having at least an 8, 9, 10, 11, 12, 13, 14, 15, or 16 contiguous nucleobase portion complementary to an equal length portion within the 3'UTR of SEQ ID NO: 1. In certain embodiments, the 3'UTR corresponds to nucleotides 1483 to 5332 of SEQ ID NO: 1. In certain embodiments, a compound comprises a modified oligonucleotide 10 to 30 linked nucleosides in length having a nucleobase sequence at least 85%, at least 90%, at least 95%, or 100% complementary across its entire length to a nucleobase sequence within the 3'UTR of SEQ ID NO: 1. In certain embodiments, the 3'UTR corresponds to nucleotides 1483 to 5332 of SEQ ID NO: 1. In certain embodiments, a compound comprises a modified oligonucleotide 16 to 30 linked nucleosides in length having a nucleobase sequence at least 85%, at least 90%, at least 95%, or 100% complementary across its entire length to a nucleobase sequence within the 3'UTR of SEQ ID NO: 1. In certain embodiments, the 3'UTR corresponds to nucleotides 1483 to 5332 of SEQ ID NO: 1.

In certain embodiments, a compound comprises a modified oligonucleotide 8 to 80 linked nucleosides in length and having at least an 8, 9, 10, 11, 12, 13, 14, 15, or 16 contiguous nucleobase portion complementary to an equal length portion within nucleotides 4227-4244, 4227-4242, 4228-4243, or 4229-4244 of SEQ ID NO: 1. In certain embodiments, the modified oligonucleotide is 10 to 30 linked nucleosides in length. In certain embodiments, the modified oligonucleotide is 16 to 30 linked nucleosides in length.

In certain embodiments, a compound comprises a modified oligonucleotide 8 to 80 linked nucleosides in length and having at least an 8, 9, 10, 11, 12, 13, 14, 15, or 16 contiguous nucleobase portion complementary to an equal length portion within nucleotides 9667-9682, 11411-11426, or 18090-18105 of SEQ ID NO: 2. In certain embodiments, the modified oligonucleotide is 10 to 30 linked nucleosides in length. In certain embodiments, the modified oligonucleotide is 16 to 30 linked nucleosides in length.

In certain embodiments, a compound comprises a modified oligonucleotide 8 to 80 linked nucleosides in length and complementary within nucleotides 4227-4244, 4227-4242, 4228-4243, or 4229-4244 of SEQ ID NO: 1. In certain embodiments, the modified oligonucleotide is 10 to 30 linked nucleosides in length. In certain embodiments, the modified oligonucleotide is 16 to 30 linked nucleosides in length.

In certain embodiments, a compound comprises a modified oligonucleotide 8 to 80 linked nucleosides in length and complementary within nucleotides 9667-9682, 11411-11426, or 18090-18105 of SEQ ID NO: 2. In certain embodiments, the modified oligonucleotide is 10 to 30 linked nucleosides in length. In certain embodiments, the modified oligonucleotide is 16 to 30 linked nucleosides in length.

In certain embodiments, a compound comprises a modified oligonucleotide 8 to 80 linked nucleosides in length and having a nucleobase sequence comprising at least an 8, 9, 10, 11, 12, 13, 14, 15, or 16 contiguous nucleobase portion any one of SEQ ID NOs: 2021, 560, 559, 1330, 1540, or 3303. In certain embodiments, the modified oligonucleotide is 10 to 30 linked nucleosides in length. In certain embodiments, the modified oligonucleotide is 16 to 30 linked nucleosides in length.

In certain embodiments, a compound comprises a modified oligonucleotide 16 to 80 linked nucleosides in length and having a nucleobase sequence comprising any one of SEQ ID NOs: 2021, 560, 559, 1330, 1540, or 3303. In certain embodiments, the modified oligonucleotide is 16 to 30 linked nucleosides in length.

In certain embodiments, a compound comprises a modified oligonucleotide 16 linked nucleosides in length having a nucleobase sequence consisting of any one of SEQ ID NOs: 2021, 560, 559, 1330, 1540, or 3303.

In certain embodiments, a compound targeted to IRF4 is ION 935918. Out of over 3,000 compounds that were screened as described in the Examples section below, ION 690890, 935658, 935696, 935762, 935918, 935968, 882800, 1012795, 1014095, and 1014834 emerged as the top lead compounds. In particular, ION 935918 exhibited the best combination of properties in terms of potency and tolerability out of over 3,000 compounds.

In certain embodiments, any of the foregoing modified oligonucleotides comprises at least one modified internucleoside linkage, at least one modified sugar, and/or at least one modified nucleobase.

In certain embodiments, any of the foregoing modified oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, the modified oligonucleotide comprises at least one modified internucleoside linkage, such as a phosphorothioate internucleoside linkage.

In certain embodiments, any of the foregoing modified oligonucleotides comprises at least one modified nucleobase, such as 5-methylcytosine.

In certain embodiments, any of the foregoing modified oligonucleotides comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide is 16 to 80 linked nucleosides in length having a nucleobase sequence comprising the sequence recited in any one of SEQ ID NO: 2021, 560, 559, 1330, 1540, or 3303. In certain embodiments, the modified oligonucleotide is 16 to 30 linked nucleosides in length having a nucleobase sequence comprising the sequence recited in any one of SEQ ID NOs: 2021, 560, 559, 1330, 1540, or 3303. In certain embodiments, the modified oligonucleotide is 16 linked nucleosides in length having a nucleobase sequence consisting of the sequence recited in any one of SEQ ID NOs: 2021, 560, 559, 1330, 1540, or 3303.

In certain embodiments, a compound comprises or consists of a modified oligonucleotide 16-80 linked nucleobases in length having a nucleobase sequence comprising the sequence recited in any one of SEQ ID NOs: 3-3383, wherein the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in any one of SEQ ID NOs: 2021, 560, 559, 1330, 1540, or 3303, wherein the modified oligonucleotide comprises:
 a gap segment consisting of linked deoxynucleosides;
 a 5' wing segment consisting of linked nucleosides; and
 a 3' wing segment consisting of linked nucleosides;
 wherein the gap segment is positioned between the 5' wing segment and the 3' wing segment and wherein each nucleoside of each wing segment comprises a modified sugar. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in any one of SEQ ID NOs: 1330 or 3303, wherein the modified oligonucleotide comprises:
 a gap segment consisting of ten linked deoxynucleosides;
 a 5' wing segment consisting of three linked nucleosides; and
 a 3' wing segment consisting of three linked nucleosides;
 wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in any one of SEQ ID NOs: 559 or 560, wherein the modified oligonucleotide comprises:
 a gap segment consisting of ten linked deoxynucleosides;
 a 5' wing segment consisting of one linked nucleoside; and
 a 3' wing segment consisting of five linked nucleosides;

wherein the gap segment is positioned between the 5' wing segment and the 3' wing segment; wherein the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in any one of SEQ ID NOs: 1330 or 2021, wherein the modified oligonucleotide comprises:
a gap segment consisting of ten linked deoxynucleosides;
a 5' wing segment consisting of two linked nucleosides; and
a 3' wing segment consisting of four linked nucleosides;
wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in SEQ ID NO: 560, wherein the modified oligonucleotide comprises:
a gap segment consisting of nine linked deoxynucleosides;
a 5' wing segment consisting of two linked nucleosides; and
a 3' wing segment consisting of five linked nucleosides;
wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in SEQ ID NOs: 2021, wherein the modified oligonucleotide comprises:
a gap segment consisting of nine linked deoxynucleosides;
a 5' wing segment consisting of two linked nucleosides; and
a 3' wing segment consisting of five linked nucleosides;
wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a 2'-O-methoxyethyl nucleoside, a 2'-O-methoxyethyl nucleoside, a cEt nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in SEQ ID NOs: 1540, wherein the modified oligonucleotide comprises:
a gap segment consisting of nine linked deoxynucleosides;
a 5' wing segment consisting of two linked nucleosides; and
a 3' wing segment consisting of five linked nucleosides;
wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a 2'-O-methoxyethyl nucleoside, a 2'-O-methoxyethyl nucleoside, a cEt nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of a modified oligonucleotide 16-80 linked nucleobases in length having a nucleobase sequence comprising the sequence recited in SEQ ID NOs: 560, wherein the modified oligonucleotide comprises:
a gap segment consisting of nine linked deoxynucleosides;
a 5' wing segment consisting of two linked nucleosides; and
a 3' wing segment consisting of five linked nucleosides;
wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In certain embodiments, a compound comprises or consists of ION 935918 or salt thereof, having the following chemical structure:

17
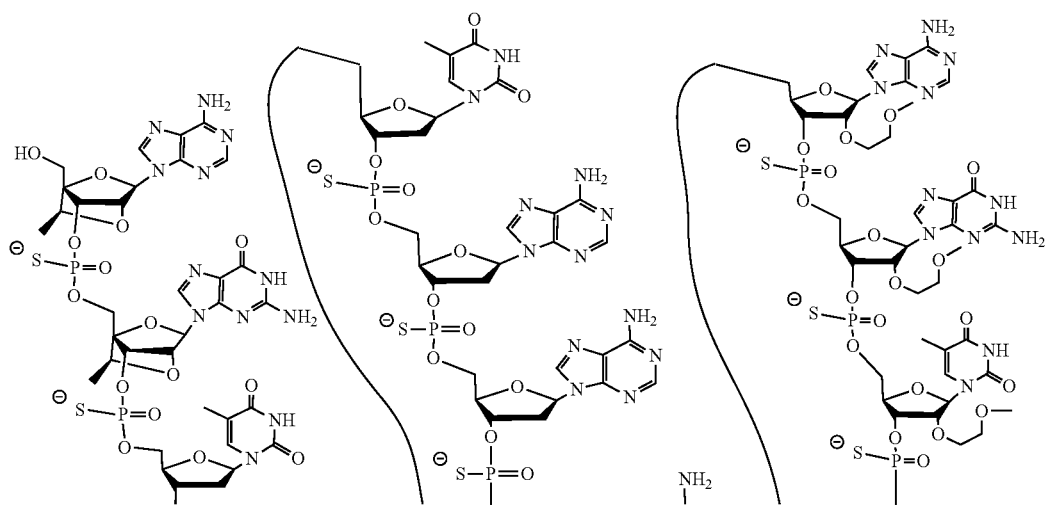
18
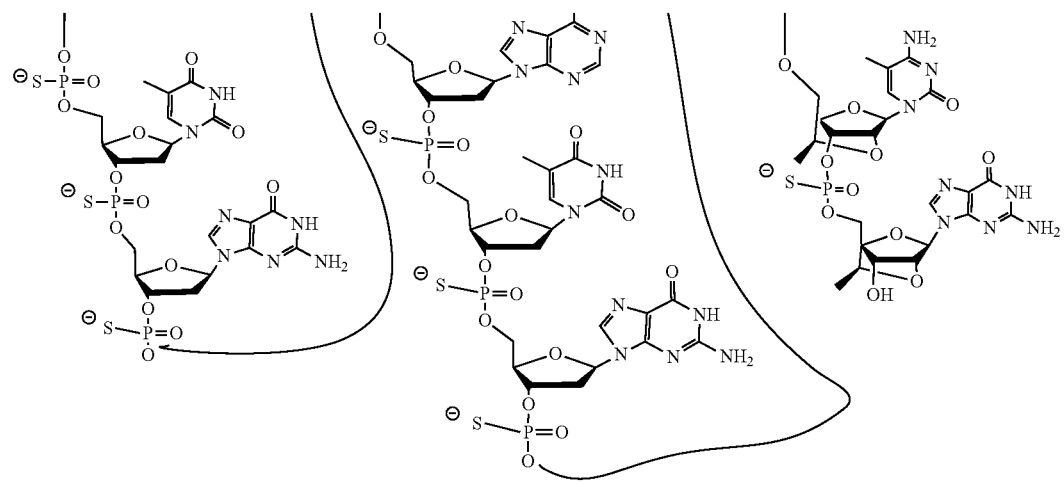
In certain embodiments, a compound comprises or consists of the sodium salt of ION 935918, having the following chemical structure:
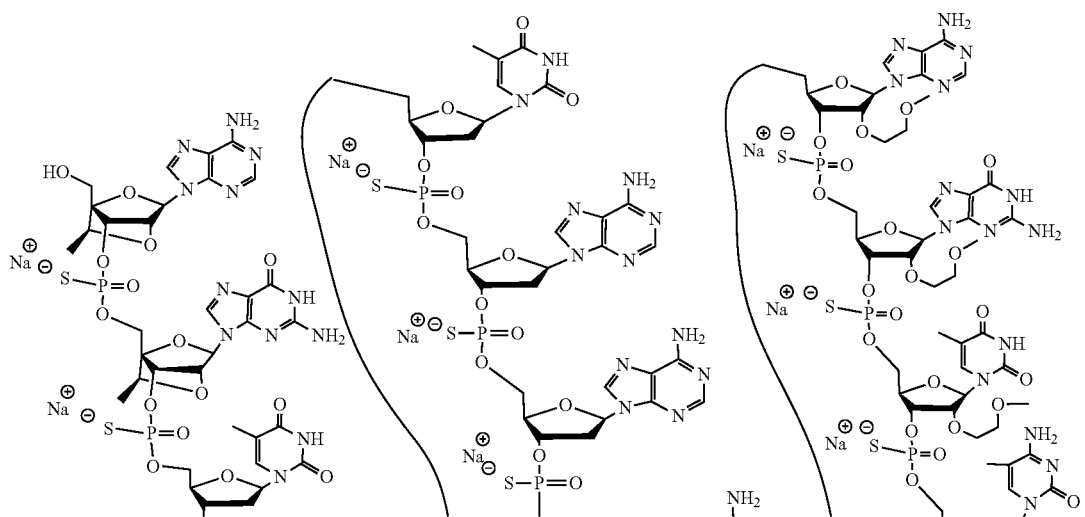

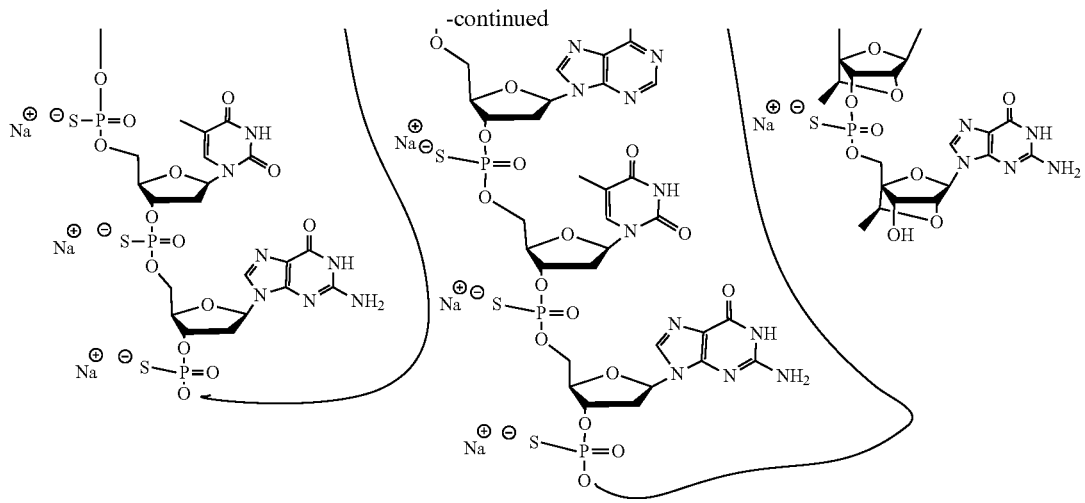
In certain embodiments, a compound comprises or consists of ION 935968 or salt thereof, having the following chemical structure:
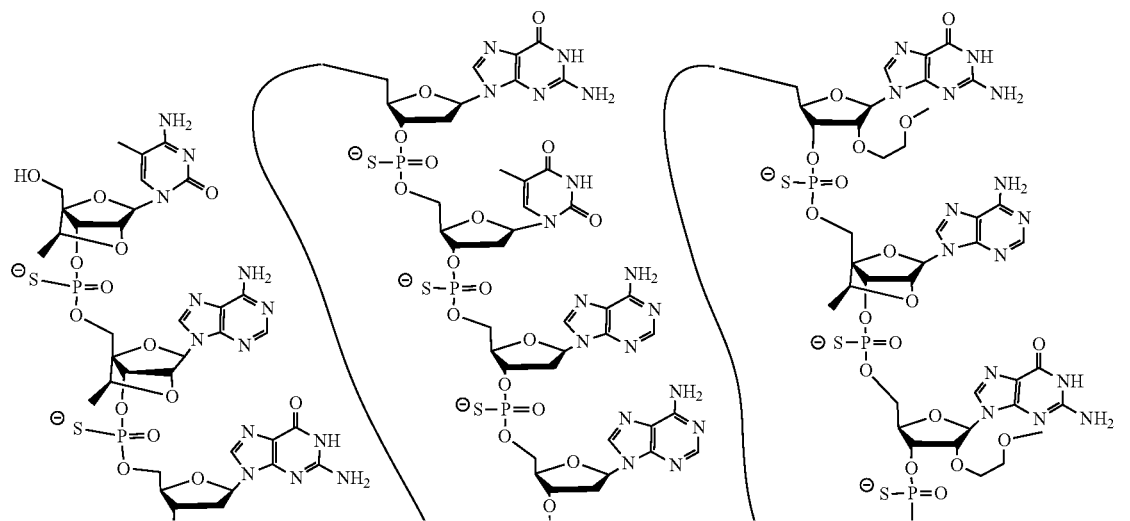
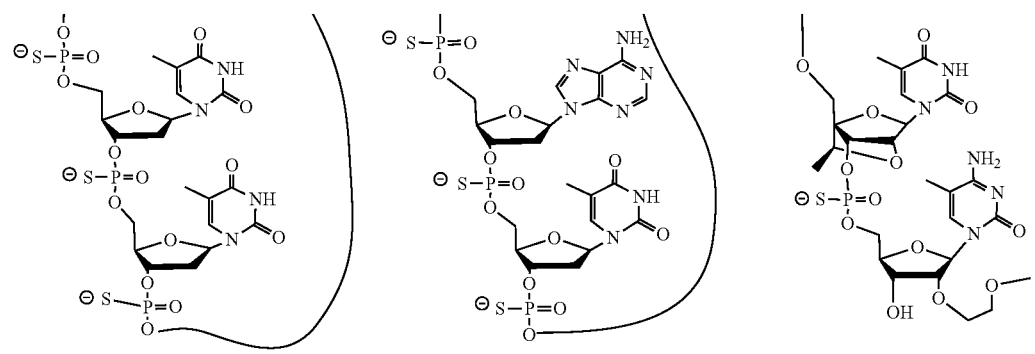

In certain embodiments, a compound comprises or consists of the sodium salt of ION 935968, having the following chemical structure:

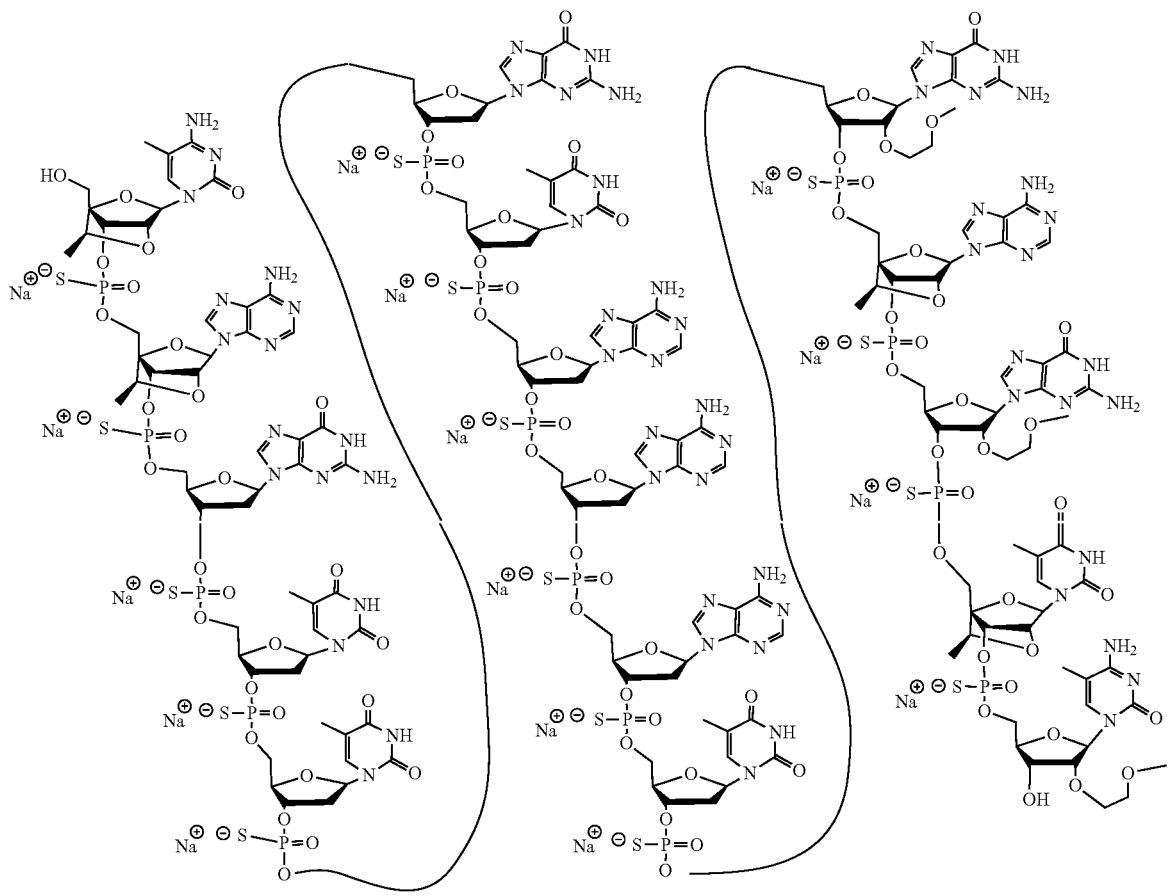

In any of the foregoing embodiments, the compound or oligonucleotide can be at least 85%, at least 90%, at least 95%, at least 98%, at least 99%, or 100% complementary to a nucleic acid encoding IRF4.

In any of the foregoing embodiments, the compound can be single-stranded. In certain embodiments, the compound comprises deoxyribonucleotides. In certain embodiments, the compound is double-stranded. In certain embodiments, the compound is double-stranded and comprises ribonucleotides. In any of the foregoing embodiments, the compound can be an antisense compound or oligomeric compound.

In any of the foregoing embodiments, the compound can be 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length. In certain embodiments, the compound comprises or consists of an oligonucleotide.

In certain embodiments, compounds or compositions provided herein comprise a salt of the modified oligonucleotide. In certain embodiments, the salt is a sodium salt. In certain embodiments, the salt is a potassium salt.

In certain embodiments, the compounds or compositions as described herein are highly tolerable as demonstrated by having at least one of an increase an alanine transaminase (ALT) or aspartate transaminase (AST) value of no more than 4 fold, 3 fold, or 2 fold over saline treated animals or an increase in liver, spleen, or kidney weight of no more than 30%, 20%, 15%, 12%, 10%, 5%, or 2% compared to control treated animals. In certain embodiments, the compounds or compositions as described herein are highly tolerable as demonstrated by having no increase of ALT or AST over control treated animals. In certain embodiments, the compounds or compositions as described herein are highly tolerable as demonstrated by having no increase in liver, spleen, or kidney weight over control animals.

Certain embodiments provide a composition comprising the compound of any of the aforementioned embodiments or salt thereof and at least one of a pharmaceutically acceptable carrier or diluent. In certain embodiments, the composition has a viscosity less than about 40 centipoise (cP), less than about 30 centipose (cP), less than about 20 centipose (cP), less than about 15 centipose (cP), or less than about 10 centipose (cP). In certain embodiments, the composition having any of the aforementioned viscosities comprises a compound provided herein at a concentration of about 100 mg/mL, about 125 mg/mL, about 150 mg/mL, about 175 mg/mL, about 200 mg/mL, about 225 mg/mL, about 250 mg/mL, about 275 mg/mL, or about 300 mg/mL. In certain embodiments, the composition having any of the aforementioned viscosities and/or compound concentrations has a temperature of room temperature or about 20° C., about 21°

C., about 22° C., about 23° C., about 24° C., about 25° C., about 26° C., about 27° C., about 28° C., about 29° C., or about 30° C.

Certain Indications

Certain embodiments provided herein relate to methods of inhibiting IRF4 expression, which can be useful for treating, preventing, or ameliorating a cancer associated with IRF4 in an individual, by administration of a compound that targets IRF4. In certain embodiments, the compound can be a IRF4 specific inhibitor. In certain embodiments, the compound can be an antisense compound, oligomeric compound, or oligonucleotide targeted to IRF4.

Examples of cancers associated with IRF4 treatable, preventable, and/or ameliorable with the methods provided herein include blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL).

In certain embodiments, a method of treating, preventing, or ameliorating a cancer associated with IRF4 in an individual comprises administering to the individual a compound comprising a IRF4 specific inhibitor, thereby treating, preventing, or ameliorating the cancer. In certain embodiments, the compound comprises an antisense compound targeted to IRF4. In certain embodiments, the compound comprises an oligonucleotide targeted to IRF4. In certain embodiments, a compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, a compound comprises a modified oligonucleotide 16 to 80 linked nucleosides in length and having a nucleobase sequence comprising the nucleobase sequence of any one of SEQ ID NOs: 3-3383. In certain embodiments, a compound comprises a modified oligonucleotide consisting of the nucleobase sequence of any one of SEQ ID NOs: 3-3383. In certain embodiments, a compound comprises a modified oligonucleotide 16 to 80 linked nucleosides in length having a nucleobase sequence comprising any one of SEQ ID NOs: 2021, 560, 559, 1330, 1540, or 3303. In certain embodiments, a compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis.

In certain embodiments, a method of treating or ameliorating caner comprises administering to the individual a compound comprising a IRF4 specific inhibitor, thereby treating or ameliorating the cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with IRF4.

In certain embodiments, a method of inhibiting expression of IRF4 in an individual having, or at risk of having, a cancer associated with IRF4 comprises administering to the individual a compound comprising a IRF4 specific inhibitor, thereby inhibiting expression of IRF4 in the individual. In certain embodiments, administering the compound inhibits expression of IRF4 in the bone marrow, lymphoid tissue, or lymph node.

In certain embodiments, the individual has, or is at risk of having blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small lymphocytic lymphoma, chronic lymphocytic leukemia, mantle cell lymphoma (MCL), Burkitt lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, administering the compound inhibits or reduces cancer cell proliferation, tumor growth, or metastasis. In certain embodiments, the individual is identified as having or at risk of having a cancer associated with IRF4.

In certain embodiments, a method of inhibiting expression of IRF4 in a cell comprises contacting the cell with a compound comprising a IRF4 specific inhibitor, thereby inhibiting expression of IRF4 in the cell. In certain embodiments, the cell is a cancer cell. In certain embodiments, the cell is a bone marrow, lymphoid tissue, or lymph node cell. In certain embodiments, the cell is in the bone marrow, lymphoid tissue, or lymph node. In certain embodiments, the cell is in the bone marrow, lymphoid tissue, or lymph node of an individual who has, or is at risk of having cancer, such as blood cancer, myeloma, multiple myeloma (MM), B cell malignancies, lymphoma, B cell lymphoma, T cell lymphoma, or leukemia. In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound.

In certain embodiments, a method of reducing or inhibiting cancer cell proliferation, tumor growth, or metastasis of an individual having, or at risk of having, a cancer associated with IRF4 comprises administering to the individual a compound comprising a IRF4 specific inhibitor, thereby reducing or inhibiting cancer cell proliferation, tumor growth, or metastasis in the individual. In certain embodiments, the individual has, or is at risk of having, blood cancer, myeloma, multiple myeloma (MM), B cell malignancies, lymphoma, B cell lymphoma, T cell lymphoma, or leukemia. Examples of cancers associated with IRF4 treatable, preventable, and/or ameliorable with the methods provided herein include blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound. In certain embodiments, the compound is administered to the individual parenterally. In certain embodiments, the individual is identified as having or at risk of having a cancer associated with IRF4.

Certain embodiments are drawn to a compound comprising a IRF4 specific inhibitor for use in treating cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenstrom macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound.

Certain embodiments are drawn to a compound comprising a IRF4 specific inhibitor for use in reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound.

Certain embodiments are drawn to use of a compound comprising a IRF4 specific inhibitor for the manufacture or preparation of a medicament for treating cancer. Certain embodiments are drawn to use of a compound comprising a IRF4 specific inhibitor for the preparation of a medicament for treating a cancer associated with IRF4. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma that can be treated with compounds provided herein include, but are not limited to, peripheral T-cell lymphoma, adult T cell leukemia/lymphoma (ATLL), and anaplastic large cell lymphoma (ALCL). In certain embodiments, the leukemia that can be treated with compounds provided herein includes, but is not limited to, acute lymphocytic leukemia (ALL). In certain embodiments, the compound comprises an antisense compound targeted to IRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303. In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound.

Certain embodiments are drawn to use of a compound comprising a IRF4 specific inhibitor for the manufacture or preparation of a medicament for reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. Certain embodiments are drawn to use of a compound comprising a TRF4 specific inhibitor for the preparation of a medicament for reducing or inhibiting cancer cell proliferation, tumor growth, or metastasis in an individual having cancer. In certain embodiments, the cancer is a blood cancer, myeloma, multiple myeloma (MM), B cell malignancy, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma includes, but is not limited to, peripheral T-cell lymphoma, adult T cell leukemia/lymphoma (ATLL), and anaplastic large cell lymphoma (ALCL). In certain embodiments, the leukemia includes, but is not limited to, acute lymphocytic leukemia (ALL). In certain embodiments, the compound comprises an antisense compound targeted to TRF4. In certain embodiments, the compound comprises an oligonucleotide targeted to IRF4. In certain embodiments, the compound comprises a modified oligonucleotide 8 to 80 linked nucleosides in length and having a nucleobase sequence comprising at least 8 contiguous nucleobases of any of the nucleobase sequences of SEQ ID NOs: 3-3383. In certain embodiments, the compound comprises a modified oligonucleotide 16 to 80 linked nucleosides in length and having a nucleobase sequence comprising the nucleobase sequence of any one of SEQ ID NOs: 3-3383. In certain embodiments, the compound comprises a modified oligonucleotide consisting of the nucleobase sequence of any one of SEQ ID NOs: 3-3383. In certain embodiments, the compound comprises a modified oligonucleotide of 16 to 80 linked nucleosides in length having a nucleobase sequence comprising any one of SEQ ID NOs: 2021, 560, 559, 1330, 1540, or 3303. In certain embodiments, the compound comprises a modified oligonucleotide having a nucleobase sequence consisting of any one of SEQ ID NOs: 2021, 560, 559, 1330, 1540, or 3303.

In any of the foregoing embodiments, the modified oligonucleotide can be 10 to 30 linked nucleosides in length. In certain embodiments, the compound is ION 690890, 935658, 935696, 935762, 935918, 935968, 882800, 1012795, 1014095, and 1014834. In any of the foregoing embodiments, the compound can be single-stranded or double-stranded. In any of the foregoing embodiments, the compound can be an antisense compound or oligomeric compound.

In any of the foregoing methods or uses, the compound can be targeted to IRF4. In certain embodiments, the compound comprises or consists of a modified oligonucleotide, for example a modified oligonucleotide 8 to 80 linked nucleosides in length, 10 to 30 linked nucleosides in length, 12 to 30 linked nucleosides in length, or 20 linked nucleosides in length. In certain embodiments, the modified oligonucleotide is at least 80%, 85%, 90%, 95% or 100% complementary to any of the nucleobase sequences recited in SEQ ID NOs: 1-2. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing embodiments, the modified oligonucleotide can be 12 to 30, 15 to 30, 15 to 25, 15 to 24, 16 to 24, 17 to 24, 18 to 24, 19 to 24, 20 to 24, 19 to 22, 20 to 22, 16 to 20, or 17 or 20 linked nucleosides in length. In certain embodiments, the modified oligonucleotide is at least 80%, 85%, 90%, 95% or 100% complementary to any of the nucleobase sequences recited in SEQ ID NOs: 1-2. In certain embodiments, the modified oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked 2'-deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar.

In any of the foregoing methods or uses, the compound can comprise or consist of a modified oligonucleotide 16 to 80 linked nucleosides in length and having a nucleobase sequence comprising any one of SEQ ID NOs: 3-3383, wherein the modified oligonucleotide comprises:
  a gap segment consisting of linked 2'-deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in any one of SEQ ID NOs: 2021, 560, 559, 1330, 1540, or 3303, wherein the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned between the 5' wing segment and the 3' wing segment and wherein each nucleoside of each wing segment comprises a modified sugar. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in any one of SEQ ID NOs: 1330 or 3303, wherein the modified oligonucleotide comprises:
  a gap segment consisting of ten linked deoxynucleosides;
  a 5' wing segment consisting of three linked nucleosides; and
  a 3' wing segment consisting of three linked nucleosides;
  wherein the gap segment is positioned between the 5' wing segment and the 3' wing segment; wherein each nucleoside of each wing segment comprises a cEt nucleoside; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in any one of SEQ ID NOs: 559 or 560, wherein the modified oligonucleotide comprises:
  a gap segment consisting of ten linked deoxynucleosides;
  a 5' wing segment consisting of one linked nucleoside; and
  a 3' wing segment consisting of five linked nucleosides;
  wherein the gap segment is positioned between the 5' wing segment and the 3' wing segment; wherein the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in any one of SEQ ID NOs: 1330 or 2021, wherein the modified oligonucleotide comprises:
   a gap segment consisting of ten linked deoxynucleosides;
   a 5' wing segment consisting of two linked nucleosides; and
   a 3' wing segment consisting of four linked nucleosides;
   wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in SEQ ID NO: 560, wherein the modified oligonucleotide comprises:
   a gap segment consisting of nine linked deoxynucleosides;
   a 5' wing segment consisting of two linked nucleosides; and
   a 3' wing segment consisting of five linked nucleosides;
   wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxyethyl nucleoside, a cEt nucleoside, a 2'-O-methoxyethyl nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in SEQ ID NOs: 2021, wherein the modified oligonucleotide comprises:
   a gap segment consisting of nine linked deoxynucleosides;
   a 5' wing segment consisting of two linked nucleosides; and
   a 3' wing segment consisting of five linked nucleosides;
   wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a 2'-O-methoxyethyl nucleoside, a 2'-O-methoxyethyl nucleoside, a cEt nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in SEQ ID NOs: 1540, wherein the modified oligonucleotide comprises:
   a gap segment consisting of nine linked deoxynucleosides;
   a 5' wing segment consisting of two linked nucleosides; and
   a 3' wing segment consisting of five linked nucleosides;
   wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a 2'-O-methoxyethyl nucleoside, a 2'-O-methoxyethyl nucleoside, a cEt nucleoside, and a cEt nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of a modified oligonucleotide 16-80 linked nucleobases in length having a nucleobase sequence comprising the sequence recited in SEQ ID NOs: 560, wherein the modified oligonucleotide comprises:
   a gap segment consisting of nine linked deoxynucleosides;
   a 5' wing segment consisting of two linked nucleosides; and
   a 3' wing segment consisting of five linked nucleosides;
   wherein the gap segment is positioned between the 5' wing segment and the 3' wing segment; wherein each nucleoside of the 5' wing segment comprises a cEt nucleoside; wherein the 3' wing segment comprises a 2'-O-methoxyethyl nucleoside, a cEt nucleoside, a 2'-O-methoxyethyl nucleoside, a cEt nucleoside, and a 2'-O-methoxyethyl nucleoside in the 5' to 3' direction; wherein each internucleoside linkage is a phosphorothioate linkage; and wherein each cytosine is a 5-methylcytosine. In certain embodiments, the modified oligonucleotide is 16-30 linked nucleosides in length. In certain embodiments, the modified oligonucleotide is 16 linked nucleosides in length.

In any of the foregoing methods or uses, the compound can comprise or consist of ION 935918 or salt thereof, having the following chemical structure:
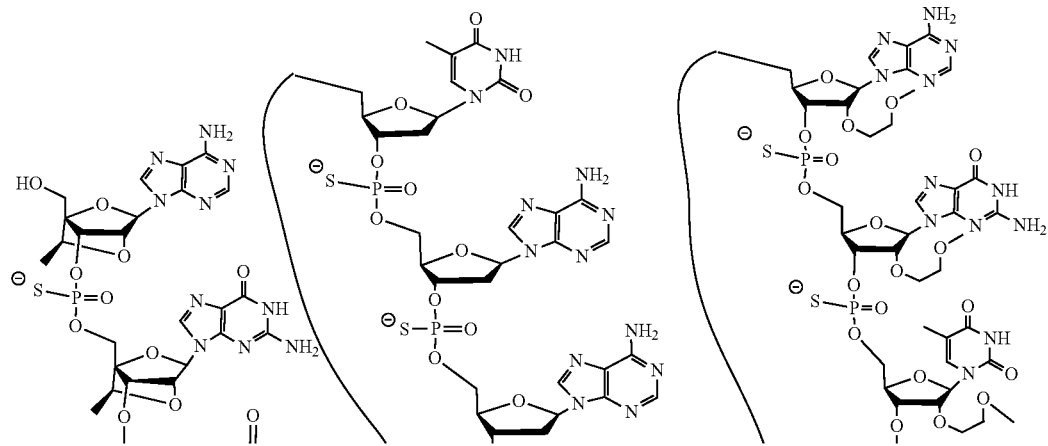
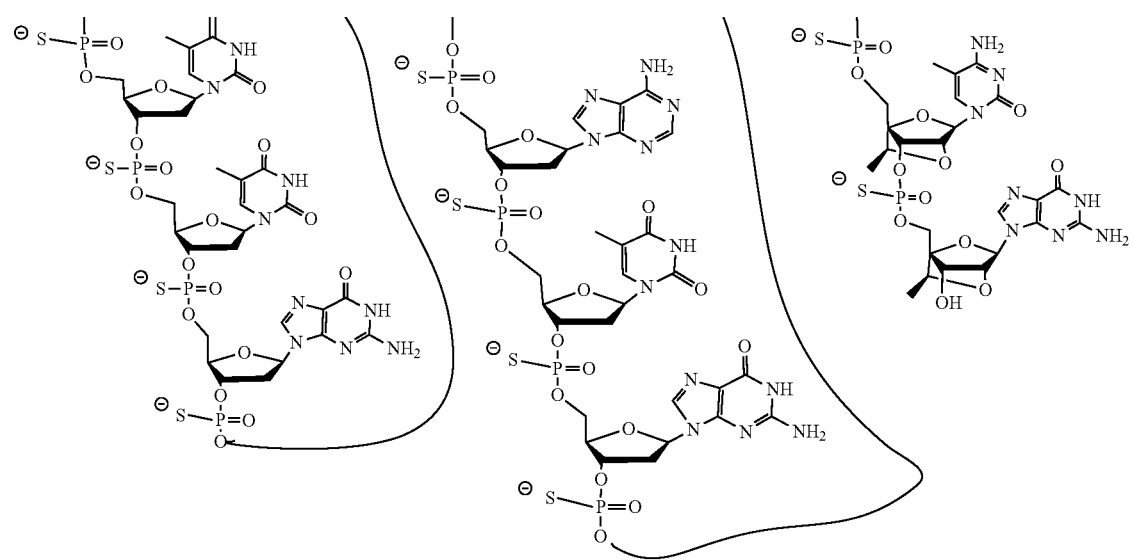

In any of the foregoing methods or uses, the compound can comprise or consist of the sodium salt of ION 935918, having the following chemical structure:
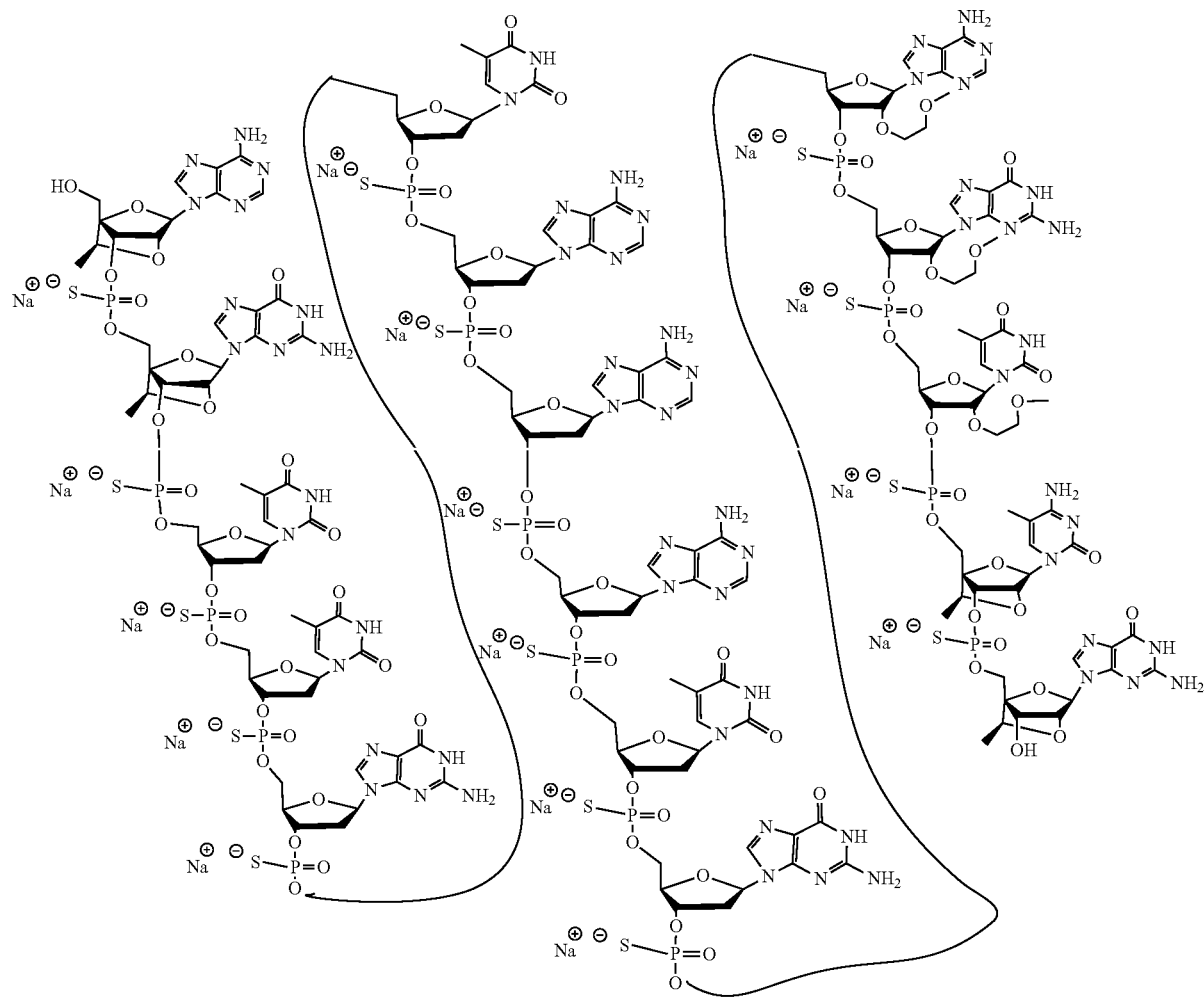
In any of the foregoing methods or uses, the compound can comprise or consist of ION 935968 or salt thereof, having the following chemical structure:
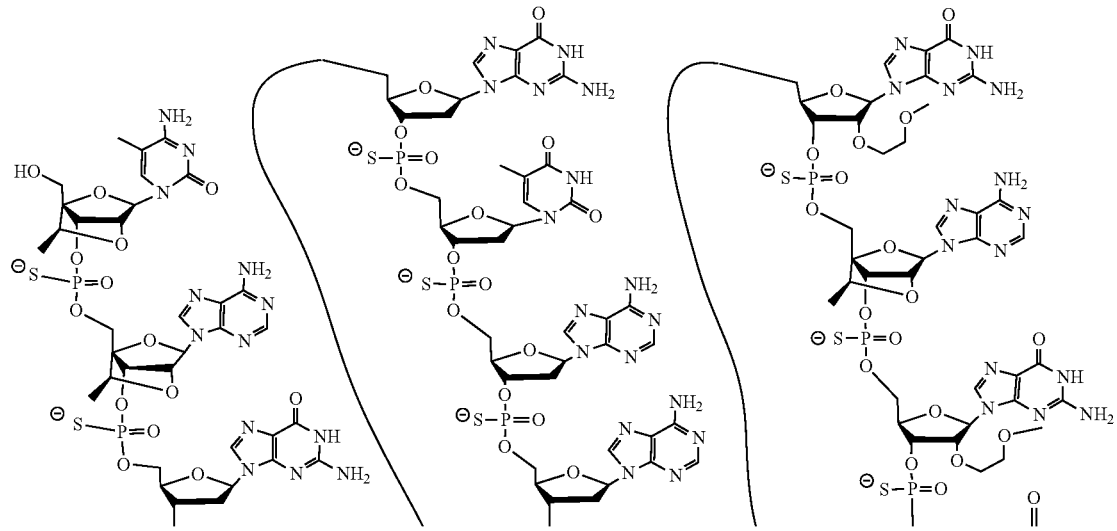

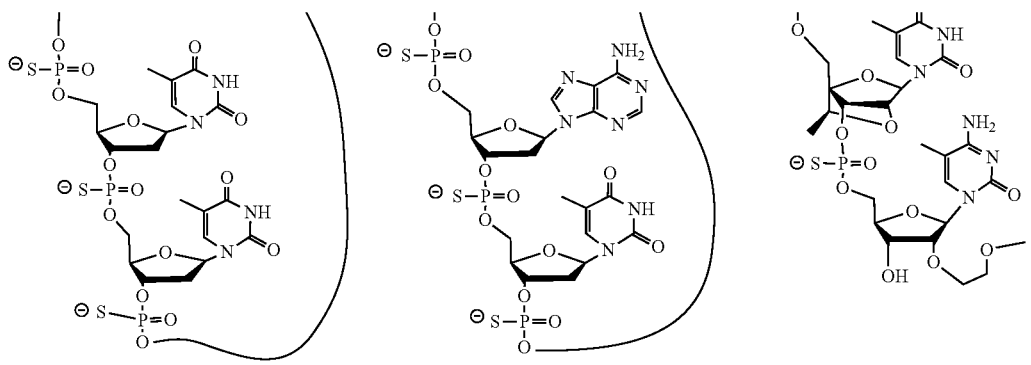

In any of the foregoing methods or uses, the compound can comprise or consist of the sodium salt of ION 935968, having the following chemical structure:

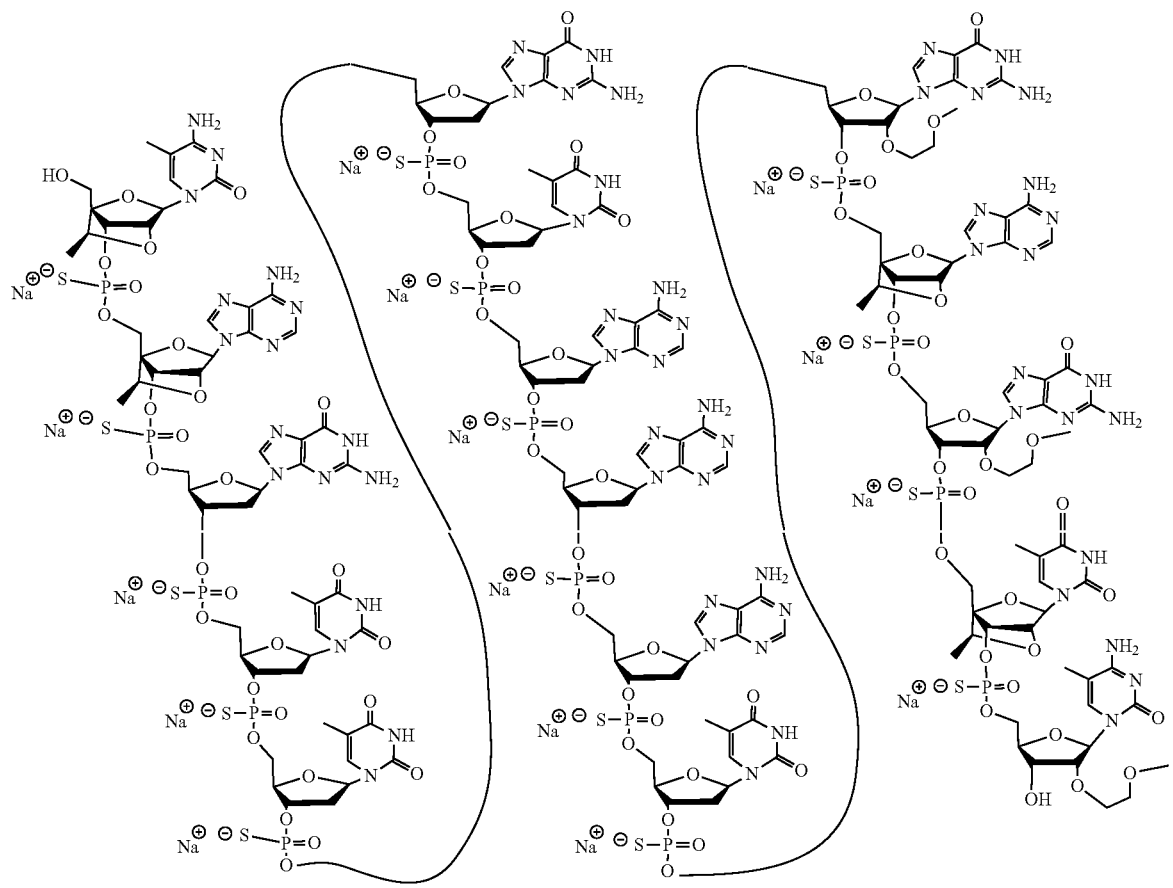

In any of the foregoing methods or uses, the compound can be administered parenterally. For example, in certain embodiments the compound can be administered through injection or infusion. Parenteral administration includes subcutaneous administration, intravenous administration, intramuscular administration, intraarterial administration, intraperitoneal administration, or intracranial administration, e.g. intrathecal or intracerebroventricular administration.

Certain Combinations and Combination Therapies

In certain embodiments, a first agent comprising a compound described herein is co-administered with one or more secondary agents. In certain embodiments, such second agents are designed to treat the same disease, disorder, or condition as the first agent described herein. In certain embodiments, such second agents are designed to treat a different disease, disorder, or condition as the first agent described herein. In certain embodiments, a first agent is designed to treat an undesired side effect of a second agent. In certain embodiments, second agents are co-administered with the first agent to treat an undesired effect of the first agent. In certain embodiments, such second agents are designed to treat an undesired side effect of one or more pharmaceutical compositions as described herein. In certain embodiments, second agents are co-administered with the first agent to produce a combinational effect. In certain embodiments, second agents are co-administered with the first agent to produce a synergistic effect. In certain embodiments, the co-administration of the first and second agents permits use of lower dosages than would be required to achieve a therapeutic or prophylactic effect if the agents were administered as independent therapy.

In certain embodiments, one or more compounds or compositions provided herein are co-administered with one or more secondary agents. In certain embodiments, one or more compounds or compositions provided herein and one or more secondary agents, are administered at different times. In certain embodiments, one or more compounds or compositions provided herein and one or more secondary agents, are prepared together in a single formulation. In certain embodiments, one or more compounds or compositions provided herein and one or more secondary agents, are prepared separately. In certain embodiments, a secondary agent is selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide.

Certain embodiments are directed to the use of a compound targeted to IRF4 as described herein in combination with a secondary agent. In particular embodiments such use is in a method of treating a patient suffering from cancer including, but not limited to, blood cancer, myeloma, multiple myeloma (MM), B cell malignancies, lymphoma, B cell lymphoma, T cell lymphoma, or leukemia. In certain embodiments, such use is in the preparation or manufacture of a medicament for treating cancer including, but not limited to, blood cancer, myeloma, multiple myeloma (MM), B cell malignancies, lymphoma, B cell lymphoma, T cell lymphoma, or leukemia. In certain embodiments, the B-cell lymphoma is a non-Hodgkin's B-cell lymphoma. Examples of non-Hodgkin's B-cell lymphoma of certain embodiments that can be treated with compounds provided herein include, but are not limited to, diffuse large B cell lymphoma (DLBCL), activated B-cell lymphoma (ABC-DLBCL), germinal center B-cell lymphoma (GCB DLBCL), follicular lymphoma, mucosa-associated lymphatic tissue lymphoma (MALT), small cell lymphocytic lymphoma, chronic lymphocytic leukemia, mantle cell lymphoma (MCL), Burkitt lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, and lymphomatoid granulomatosis. In certain embodiments, the T-cell lymphoma includes, but is not limited to, peripheral T-cell lymphoma, adult T cell leukemia/lymphoma (ATLL), and anaplastic large cell lymphoma (ALCL). In certain embodiments, the leukemia includes, but is not limited to, acute lymphocytic leukemia (ALL). In certain embodiments, a secondary agent is selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide.

Certain embodiments are drawn to a combination of a compound targeted to IRF4 as described herein and a secondary agent, such as a secondary agent selected from: proteasome inhibitors including but not limited to bortezomib, carfilzomib, and ixazomib; BTK inhibitors including but not limited to ibrutinib; IMiDs including but not limited to thalidomide, lenalidomide, and pomalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; dexamethasone, thalidomide, cisplatin, doxorubicin, cyclophosphamide, and etoposide. In certain embodiments, such a combination of a compound targeted to IRF4 as described herein and a secondary agent, such as a secondary agent selected from: proteasome inhibitors including but not limited to bortezomib, carfilzomib, and ixazomib; BTK inhibitors including but not limited to ibrutinib; IMiDs including but not limited to lenalidomide; BCL2 inhibitors including but not limited to venetoclax; HDAC inhibitors including but not limited to panobinostat; CDK inhibitors including but not limited to dinaciclib; XPO1 inhibitors including but not limited to selinexor; BET inhibitors including but not limited to CPI-0610; anti-CD38 antibodies including but not limited to daratumumab, isatuximab, and MOR202; anti-CD319 or anti-SLAMF7 antibodies including but not limited to elotuzumab; dexamethasone, cisplatin, doxorubicin, cyclophosphamide, and etoposide. Such combinations can be useful for reducing or inhibiting cancer cell proliferation, tumor growth, or metastasis and/or treating cancer including, but not limited to, blood cancer, myeloma, multiple myeloma (MM), B cell malignancies, lymphoma, B cell lymphoma, T cell lymphoma, or leukemia.

In certain embodiments the compound targeted to IRF4 as described herein and the secondary agent are used in combination treatment by administering the two agents simultaneously, separately or sequentially. In certain embodiments the two agents are formulated as a fixed dose combination product. In other embodiments the two agents are provided to the patient as separate units which can then either be taken simultaneously or serially (sequentially).

Certain Compounds

In certain embodiments, compounds described herein can be antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide and optionally a conjugate group. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, one of the modified oligonucleotides is conjugated. In certain embodiments, both the modified oligonucleotides are conjugated. In certain embodiments, the first modified oligonucleotide is conjugated. In certain embodiments, the second modified oligonucleotide is conjugated. In certain embodiments, the first modified oligonucleotide is 12-30 linked nucleosides in length and the second modified oligonucleotide is 12-30 linked nucleosides in length. In certain embodiments, one of the modified oligonucleotides has a nucleobase sequence comprising at least 8 contiguous nucleobases of any of SEQ ID NOs: 3-3383.

In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, a compound described herein comprises an oligonucleotide 12 to 30 linked subunits in length. In certain embodiments, a compound described herein comprises an oligonucleotide 12 to 22 linked subunits in length. In certain embodiments, a compound described herein comprises an oligonucleotide 14 to 30 linked subunits in length. In certain embodiments, compound described herein comprises an oligonucleotide 14 to 20 linked subunits in length. In certain embodiments, a compound described herein comprises an oligonucleotide 15 to 30 linked subunits in length. In certain embodiments, a compound described herein comprises an oligonucleotide 15 to 20 linked subunits in length. In certain embodiments, a compound described herein comprises an oligonucleotide 16 to 30 linked subunits in length. In certain embodiments, a compound described herein comprises an oligonucleotide 16 to 20 linked subunits in length. In certain embodiments, a compound described herein comprises an oligonucleotide 17 to 30 linked subunits in length. In certain embodiments, a compound described herein comprises an oligonucleotide 17 to 20 linked subunits in length. In certain embodiments, a compound described herein comprises an oligonucleotide 18 to 30 linked subunits in length. In certain embodiments, a compound described herein comprises an oligonucleotide 18 to 21 linked subunits in length. In certain embodiments, a compound described herein comprises an oligonucleotide 18 to 20 linked subunits in length. In certain embodiments, a compound described herein comprises an oligonucleotide 20 to 30 linked subunits in length. In other words, such oligonucleotides are 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits in length, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, the compound may further comprise additional features or elements, such as a conjugate group, that are attached to the oligonucleotide. In certain embodiments, such compounds are antisense compounds. In certain embodiments, such compounds are oligomeric compounds. In embodiments where a conjugate group comprises a nucleoside (i.e. a nucleoside that links the conjugate group to the oligonucleotide), the nucleoside of the conjugate group is not counted in the length of the oligonucleotide.

In certain embodiments, compounds may be shortened or truncated. For example, a single subunit may be deleted from the 5' end (5' truncation), or alternatively from the 3' end (3' truncation). A shortened or truncated compound targeted to an IRF4 nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. *Proc. Natl. Acad. Sci. USA* 1992, 89:7305-7309; Gautschi et al. *J. Natl. Cancer Inst. March* 2001, 93:463-471; Maher and Dolnick *Nuc. Acid. Res.* 1998, 16:3341-3358). However, seemingly small changes in oligonucleotide sequence, chemistry and motif can make large differences in one or more of the many properties required for clinical development (Seth et al. *J. Med. Chem.* 2009, 52, 10; Egli et al. *J. Am. Chem. Soc.* 2011, 133, 16642).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to be equivalent to other terms used to describe sequence specific RNA interference, such as post transcriptional gene silencing, translational inhibition, or epigenetics.

In certain embodiments, a compound described herein can comprise any of the oligonucleotide sequences targeted to IRF4 described herein. In certain embodiments, the compound can be double-stranded. In certain embodiments, the compound comprises a first strand comprising at least an 8, 9, 10, 11, 12, 13, 14, 15, 16, 17, 18, 19, or 20 contiguous nucleobase portion of any one of SEQ ID NOs: 3-3383 and a second strand. In certain embodiments, the compound comprises a first strand comprising the nucleobase sequence of any one of SEQ ID NOs: 3-3383 and a second strand. In certain embodiments, the compound comprises ribonucleotides in which the first strand has uracil (U) in place of thymine (T) in any one of SEQ ID NOs: 3-3383. In certain embodiments, the compound comprises (i) a first strand comprising a nucleobase sequence complementary to the site on IRF4 to which any of SEQ ID NOs: 3-3383 is targeted, and (ii) a second strand. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the compound comprises one or more linkages between adjacent nucleotides other than a naturally-occurring phosphodiester linkage Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains one or two capped strands, as disclosed, for example, by WO 00/63364, filed Apr. 19, 2000.

In certain embodiments, the first strand of the compound is an siRNA guide strand and the second strand of the compound is an siRNA passenger strand. In certain embodiments, the second strand of the compound is complementary to the first strand. In certain embodiments, each strand of the compound is 16, 17, 18, 19, 20, 21, 22, or 23 linked nucleosides in length. In certain embodiments, the first or second strand of the compound can comprise a conjugate group.

In certain embodiments, a compound described herein can comprise any of the oligonucleotide sequences targeted to IRF4 described herein. In certain embodiments, the compound is single stranded. In certain embodiments, such a compound is a single-stranded RNAi (ssRNAi) compound. In certain embodiments, the compound comprises at least an 8, 9, 10, 11, 12, 13, 14, 15, 16, 17, 18, 19, or 20 contiguous nucleobase portion of any one of SEQ ID NOs: 3-3383. In certain embodiments, the compound comprises the nucleobase sequence of any one of SEQ ID NOs: 3-3383. In certain embodiments, the compound comprises ribonucleotides in which uracil (U) is in place of thymine (T) in any one of SEQ ID NOs: 3-3383. In certain embodiments, the compound comprises a nucleobase sequence complementary to the site on IRF4 to which any of SEQ ID NOs: 3-3383 is targeted. In certain embodiments, the compound comprises one or more modified nucleotides in which the 2' position in the sugar contains a halogen (such as fluorine group; 2'-F) or contains an alkoxy group (such as a methoxy group; 2'-OMe). In certain embodiments, the compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the compound. In certain embodiments, the compound comprises one or more linkages between adjacent nucleotides other than a naturally-occurring phosphodiester linkage. Examples of such linkages include phosphoramide, phosphorothioate, and phosphorodithioate linkages. The compounds may also be chemically modified nucleic acid molecules as taught in U.S. Pat. No. 6,673,661. In other embodiments, the compound contains a capped strand, as disclosed, for example, by WO 00/63364, filed Apr. 19, 2000. In certain embodiments, the compound consists of 16, 17, 18, 19, 20, 21, 22, or 23 linked nucleosides. In certain embodiments, the compound can comprise a conjugate group.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or $^3H$ in place of $^1H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the compound that are beneficial for use as a therapeutic or research tool. In certain embodiments, radioactive isotopic substitutions may make the compound suitable for research or diagnostic purposes, such as an imaging assay.

Certain Mechanisms

In certain embodiments, compounds described herein comprise or consist of modified oligonucleotides. In certain embodiments, compounds described herein are antisense compounds. In certain embodiments, compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Nucleotide sequences that encode IRF4 include, without limitation, the following: RefSEQ No. NM_002460.3 and NT_034880.3_TRUNC_328000_354000.

Hybridization

In some embodiments, hybridization occurs between a compound disclosed herein and a IRF4 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a IRF4 nucleic acid.

Complementarily

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a IRF4 nucleic acid may be tolerated provided that the compound remains able to specifically hybridize to a target nucleic acid. Moreover, a compound may hybridize over one or more segments of a IRF4 nucleic acid such that intervening or adjacent segments are not involved in the hybridization event (e.g., a loop structure, mismatch or hairpin structure).

In certain embodiments, the compounds provided herein, or a specified portion thereof, are, are at least, or are up to 70%, 80%, 85%, 86%, 87%, 88%, 89%, 90%, 91%, 92%, 93%, 94%, 95%, 96%, 97%, 98%, 99%, or 100% complementary to a IRF4 nucleic acid, a target region, target segment, or specified portion thereof. In certain embodiments, the compounds provided herein, or a specified portion thereof, are 70% to 75%, 75% to 80%, 80% to 85%, 85% to 90%, 90% to 95%, 95% to 100%, or any number in between these ranges, complementary to a IRF4 nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid. Percent complementarity of a compound with a region of a target nucleic acid can be determined routinely using BLAST programs (basic local alignment search tools) and PowerBLAST programs known in the art (Altschul et al., *J. Mol. Biol.*, 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e. 100% complementary) to a target nucleic acid, or specified portion thereof. For example, a compound may be fully complementary to a IRF4 nucleic acid, or a target region, or a target segment or target sequence thereof. As used herein, "fully complementary" means each nucleobase of a compound is complementary to the corresponding nucleobase of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e. linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a IRF4 nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a IRF4 nucleic acid, or specified portion thereof.

In certain embodiments, compounds described herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of a compound. In certain embodiments, the— compounds, are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific ION number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific ION number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

In certain embodiments, compounds described herein comprise or consist of antisense compounds. In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein comprise or consist of oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$O N(R$_m$)(R$_n$) or OCH$_2$C(=O)—N(R$_m$)(R$_m$), where each R$_m$ and R$_n$ is, independently, H, an amino protecting group, or substituted or unsubstituted alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-

5'-methyl sugar moieties and the modified sugar moieties and modified nucleosides described in Migawa et al., US2010/190837 and Rajeev et al., US2013/0203836.

In certain embodiments, a 2'-substituted nucleoside or 2'-non-bicyclic modified nucleoside comprises a sugar moiety comprising a linear 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)-N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a linear 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)-N(H)CH_3$ ("NMA").

In certain embodiments, a 2'-substituted nucleoside or 2'-non-bicyclic modified nucleoside comprises a sugar moiety comprising a linear 2'-substituent group selected from: F, $OCH_3$, and $OCH_2CH_2OCH_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-$CH_2$-2', 4'-$(CH_2)_2$-2', 4'-$(CH_2)_3$-2', ("LNA"), 4'-$CH_2$—S-2', 4'-$(CH_2)_2$—O- 2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.*, 2009, 74, 118-134), 4'-$CH_2$—C(=$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)-O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —[C($R_a$)($R_b$)]$_n$—, —[C($R_a$)($R_b$)]$_n$—O—, —C($R_a$)=C($R_b$)—, —C($R_a$)=N—, —C(=$NR_a$)—, —C(=O)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J Am. Chem. Soc.*, 2007, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; Allerson et al., US2008/0039618; and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

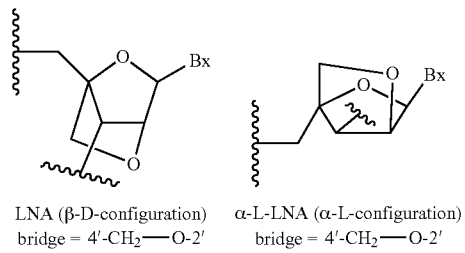

LNA (β-D-configuration)
bridge = 4'-$CH_2$—O-2'

α-L-LNA (α-L-configuration)
bridge = 4'-$CH_2$—O-2'

α-L-methyleneoxy (4'-$CH_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see e.g., Leumann, C J. *Bioorg. & Med. Chem.* 2002, 10, 841-854), fluoro HNA:

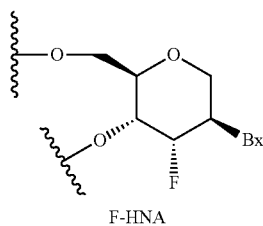

F-HNA ("F-HNA", see e.g., Swayze et al., U.S. Pat. No. 8,088,904; Swayze et al., U.S. Pat. No. 8,440,803; and Swayze et al., U.S. Pat. No. 9,005,906, F-HNA can also be referred to as a F-THP or 3'-fluoro tetrahydropyran), and nucleosides comprising additional modified THP compounds having the formula:

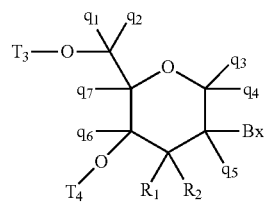

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. 5,034,506). As used here, the term "morpholino" means a sugar surrogate having the following structure:

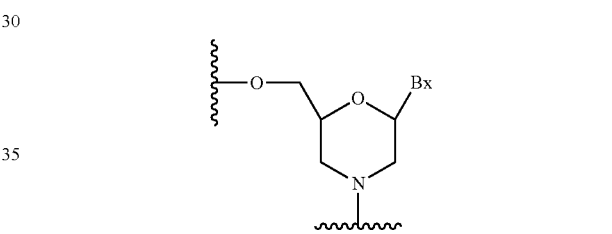

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., US2013/130378.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a IRF4 nucleic acid comprise one or more modified nucleobases. In certain embodiments, the modified nucleobase is 5-methylcytosine. In certain embodiments, each cytosine is a 5-methylcytosine.

3. Modified Internucleoside Linkages

The naturally occurring internucleoside linkage of RNA and DNA is a 3' to 5' phosphodiester linkage In certain embodiments, compounds described herein having one or more modified, i.e. non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

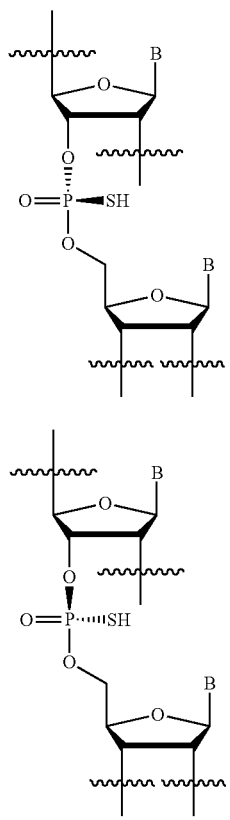

Unless otherwise indicated, chiral internucleoside linkages of modified oligonucleotides described herein can be stereorandom or in a particular stereochemical configuration.

In certain embodiments, compounds targeted to an IRF4 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS-P═S"). Representative non-phosphorus containing internucleoside linking groups include but are not limited to methylenemethylimino (—CH2-N(CH3)-O—CH2-), thiodiester, thionocarbamate (—O—C(═O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH3)-O-5'), amide-3 (3'-CH2-C(═O)—N(H)-5'), amide-4 (3'-CH2-N(H)—C(═O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

Certain Motifs

In certain embodiments, compounds described herein comprise oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

a. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

In certain embodiments, a modified oligonucleotide can comprise a sugar motif described in Swayze et al., US2010/0197762; Freier et al., US2014/0107330; Freier et al., US2015/0184153; and Seth et al., US2015/0267195, each of which is incorporated by reference in its entirety herein.

Certain embodiments provided herein are directed to modified oligomeric compounds useful for inhibiting target nucleic acid expression, which can be useful for treating, preventing, ameliorating, or slowing progression of a disease associated with such a target nucleic acid. In certain embodiments, the modified oligomeric compounds comprise antisense oligonucleotides that are gapmers having certain sugar motifs. In certain embodiments, the gapmer sugar motifs provided herein can be combined with any nucleobase sequence and any internucleoside linkage motif to form potent antisense oligonucleotides.

In certain embodiments, a method comprises contacting a cell or administering to a subject a compound comprising a modified oligonucleotide 16 linked nucleosides in length having the motif: ekk-d9-kkee, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: k-d9-kekeke, wherein represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kkk-d8-kekek, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kkk-d9-keke, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kk-d9-kdkdk, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a compound comprises a modified oligonucleotide 16 linked nucleosides in length having the motif: kk-d9-eeekk, wherein 'd' represents a 2'-deoxyribose sugar, 'k' represents a cEt nucleoside, and 'e' represents a 2'-MOE nucleoside. In certain embodiments, a method comprises contacting a cell or administering to a subject a compound comprising a modified oligonucleotide 16 linked nucleosides in length having the motif: kk-d9-eeekk, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

In certain embodiments, a method comprises contacting a cell or administering to a subject a compound comprising a modified oligonucleotide 16 linked nucleosides in length having the motif: kk-d9-kdkdk, wherein 'd' represents a 2'-deoxyribose sugar, 'k' represents a cEt nucleoside, and 'e' represents a 2'-MOE nucleoside. In certain embodiments, the cell is a cancer cell. In certain embodiments, the subject has cancer. In certain embodiments, administering the compound to the subject treats the subject's cancer.

b. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

c. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

4. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Certain Conjugated Compounds

In certain embodiments, the compounds described herein comprise or consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearanceIn certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic, a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, i, 923-937), a tocopherol group (Nishina et al., *Molecular Therapy Nucleic Acids*, 2015, 4, e220; doi:10.1038/mtna.2014.72 and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, a conjugate group is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to IRF4 nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to IRF4 nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

EXAMPLES

The Examples below describe the screening process to identify lead compounds targeted to IRF4. Out of over 3,000 oligonucleotides that were screened, ION 690890, 935658, 935696, 935762, 935918, 935968, 882800, 1012795, 1014095, and 1014834 emerged as the top lead compounds. In particular, ION 935918 exhibited the best combination of properties in terms of potency and tolerability out of over 3,000 oligonucleotides.

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^m$CGAUCG," wherein $^m$C indicates a cytosine base comprising a methyl group at the 5-position.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Effect of 5-10-5 MOE Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 60,000 cells per well were transfected using electroporation with 20,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (forward sequence AAGCCTTGGCGTTCTCAGACT, designated herein as SEQ ID NO: 3386; reverse sequence TCAGCTCCTTCACGAGGATTTC, designated herein as SEQ ID NO: 3387; probe sequence CCGGCTGCACATCTGCCTGTACTACC, designated herein as SEQ ID: 3388) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Table 1 are 5-10-5 MOE gapmers. The gapmers are 20 nucleobases in length, wherein the central gap segment comprises ten 2'-deoxynucleosides and is flanked by wing segments on both the 5' end and on the 3' end comprising five 2'-MOE nucleosides. The sugar motif for the gapmers is (from 5' to 3'): eeeeedddddddddd-deeeee; wherein 'd' represents a 2'-deoxyribose sugar and 'e' represents a 2'-MOE modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 1 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 1

Percent control of human IRF4 mRNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | IRF4 (% UTC) | SEQ ID NO |
|---|---|---|---|---|---|---|---|
| 434887 | 164 | 183 | 5191 | 5210 | GCAGCTCACCGCGCTCATGC | 57 | 3 |
| 434888 | 175 | 194 | 5202 | 5221 | TTCCCGTTGCCGCAGCTCAC | 34 | 4 |
| 434889 | 190 | 209 | 5217 | 5236 | AGCCACTGGCGGAGCTTCCC | 43 | 5 |
| 434890 | 294 | 313 | 5321 | 5340 | TGTAGTCCTGCTTGCCCGCG | 51 | 6 |
| 434891 | 304 | 323 | 5331 | 5350 | TCCTCGCGGTTGTAGTCCTG | 53 | 7 |
| 434892 | 330 | 349 | N/A | N/A | CCCAAGCCTTGAAGAGCGCG | 44 | 8 |
| 434893 | 367 | 386 | 6846 | 6865 | TTGTCGATGCCTTCTCGGAA | 47 | 9 |
| 434894 | 375 | 394 | 6854 | 6873 | GGTCCGGCTTGTCGATGCCT | 40 | 10 |
| 434895 | 430 | 449 | 6909 | 6928 | TCAAAGTCATTGCTCTTGTT | 55 | 11 |
| 434896 | 436 | 455 | 6915 | 6934 | AGTTCCTCAAAGTCATTGCT | 42 | 12 |
| 434897 | 442 | 461 | 6921 | 6940 | TCAACCAGTTCCTCAAAGTC | 75 | 13 |
| 434898 | 447 | 466 | 6926 | 6945 | TCCGCTCAACCAGTTCCTCA | 32 | 14 |
| 434899 | 474 | 493 | 6953 | 6972 | TGTACGGGTCTGAGATGTCC | 44 | 15 |
| 434900 | 532 | 551 | 7850 | 7869 | TCCAGGGTGAGCTGCTTGGC | 43 | 16 |
| 434901 | 555 | 574 | 7873 | 7892 | GGCTCATGGACATCTGCGGG | 45 | 17 |
| 434902 | 675 | 694 | 9165 | 9184 | TTTCCGGGTGTGGCTGATCC | 36 | 18 |
| 434903 | 690 | 709 | 9180 | 9199 | GACATTGGTACGGGATTTCC | 38 | 19 |
| 434904 | 732 | 751 | 9222 | 9241 | CTGGGCCTTGCCAGTGGTGG | 59 | 20 |
| 434905 | 739 | 758 | 9229 | 9248 | TCACAAGCTGGGCCTTGCCA | 30 | 21 |
| 434906 | 744 | 763 | 9234 | 9253 | CATTTTCACAAGCTGGGCCT | 37 | 22 |
| 434907 | 751 | 770 | N/A | N/A | TGGCAACCATTTTCACAAGC | 37 | 23 |
| 434908 | 758 | 777 | N/A | N/A | TGTCACCTGGCAACCATTTT | 49 | 24 |

TABLE 1-continued

Percent control of human IRF4 mRNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | IRF4 (% UTC) | SEQ ID NO |
|---|---|---|---|---|---|---|---|
| 434909 | 778 | 797 | 10843 | 10862 | GCACAAGCATAAAAGGTTCC | 26 | 25 |
| 434916 | 940 | 959 | 13493 | 13512 | TGGGAGATCCGGCAGCCCTC | 66 | 26 |
| 434917 | 1004 | 1023 | 13557 | 13576 | GCCATTGTCCTCTGGGTAGG | 38 | 27 |
| 434918 | 1042 | 1061 | 13595 | 13614 | TCCAGGTGGCTCAGCAGCTT | 25 | 28 |
| 434919 | 1063 | 1082 | 13616 | 13635 | ATCCAGAGGACCACGCCCCT | 78 | 29 |
| 434920 | 1068 | 1087 | 13621 | 13640 | GGGCCATCCAGAGGACCACG | 36 | 30 |
| 434921 | 1119 | 1138 | 13672 | 13691 | CGTCCCAGTAGATCCTGCTC | 46 | 31 |
| 434922 | 1187 | 1206 | 13740 | 13759 | GTCAAAGAGCTTGCAGGTCT | 32 | 32 |
| 434923 | 1192 | 1211 | 13745 | 13764 | TGTGTGTCAAAGAGCTTGCA | 17 | 33 |
| 434924 | 1344 | 1363 | 19461 | 19480 | GTTGTCTGGCTAGCAGAGGT | 33 | 34 |
| 434925 | 1364 | 1383 | 19481 | 19500 | TTGTTGAGCAAAATAATATA | 97 | 35 |
| 434926 | 1391 | 1410 | 19508 | 19527 | GTAGCCCCTCAGGAAATGTC | 15 | 36 |
| 434927 | 1420 | 1439 | 19537 | 19556 | TCTGGATTGCTGATGTGTTC | 46 | 37 |
| 434928 | 1430 | 1449 | 19547 | 19566 | GTGGTAATCTTCTGGATTGC | 42 | 38 |
| 434929 | 1450 | 1469 | 19567 | 19586 | GAGGAATGGCGGATAGATCT | 63 | 39 |
| 434930 | 1707 | 1726 | 19824 | 19843 | CACTAAAGTCAAATATTTAC | 88 | 40 |
| 434931 | 1712 | 1731 | 19829 | 19848 | GCTTTCACTAAAGTCAAATA | 29 | 41 |
| 434932 | 1821 | 1840 | 19938 | 19957 | CAGATGTCACTGATTTTCCA | 41 | 42 |
| 434933 | 1826 | 1845 | 19943 | 19962 | CCAATCAGATGTCACTGATT | 44 | 43 |
| 434934 | 1838 | 1857 | 19955 | 19974 | TAAGCTCATCTGCCAATCAG | 71 | 44 |
| 434935 | 2196 | 2215 | 20313 | 20332 | CCAAGGCTACAGGCACGGCT | 29 | 45 |
| 434936 | 2234 | 2253 | 20351 | 20370 | ACACCAGGAAACCGCTGGCA | 37 | 46 |
| 434937 | 2293 | 2312 | 20410 | 20429 | CTTCCAGGAAAGGCCAAGGA | 23 | 47 |
| 434938 | 2356 | 2375 | 20473 | 20492 | TGTCCCATCCAAGAGTAGCG | 30 | 48 |
| 434939 | 2662 | 2681 | 20779 | 20798 | CTTCCAGTGGTGGGTCCTGG | 53 | 49 |
| 434940 | 2705 | 2724 | 20822 | 20841 | AACAGCCCACTGAGTGTGCA | 43 | 50 |
| 434941 | 2711 | 2730 | 20828 | 20847 | AGCAGAAACAGCCCACTGAG | 58 | 51 |
| 434942 | 3435 | 3454 | 21552 | 21571 | CTGGGTACATGGCAGTGGAG | 27 | 52 |
| 434943 | 3805 | 3824 | 21922 | 21941 | GCATTTTCCAGAAAATTCAG | 33 | 53 |
| 434944 | 4477 | 4496 | 22594 | 22613 | CCCAGAGTTGTTCCACCCCT | 21 | 54 |
| 434945 | N/A | N/A | 22826 | 22845 | GCTGGCCACAGAGGACTTCG | 21 | 55 |
| 434946 | 4737 | 4756 | 22854 | 22873 | GCCTTCACGCACCATTCAGA | 52 | 56 |
| 434947 | 4812 | 4831 | 22929 | 22948 | CCACCTGCATCGAGATCAGT | 31 | 57 |
| 434948 | 4818 | 4837 | 22935 | 22954 | GGAGATCCACCTGCATCGAG | 32 | 58 |
| 434949 | 5035 | 5054 | 23152 | 23171 | GGAAGTGGACCCCATTGCCT | 17 | 59 |

TABLE 1-continued

Percent control of human IRF4 mRNA with 5-10-5 MOE gapmers with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence | IRF4 (% UTC) | SEQ ID NO |
|---|---|---|---|---|---|---|---|
| 434952 | N/A | N/A | 18834 | 18853 | ATCTAAGGCAAGCTGAATGC | 67 | 60 |
| 434953 | N/A | N/A | 18839 | 18858 | ACAGCATCTAAGGCAAGCTG | 38 | 61 |
| 434954 | N/A | N/A | 18845 | 18864 | GAATTTACAGCATCTAAGGC | 52 | 62 |
| 434955 | N/A | N/A | 18850 | 18869 | TTCCTGAATTTACAGCATCT | 21 | 63 |
| 434957 | N/A | N/A | 5359 | 5378 | GCCGGAGACCTTGAAGAGCG | 94 | 64 |
| 434958 | N/A | N/A | 7480 | 7499 | ACTGGTCAGAATCTTGAAAA | 94 | 65 |
| 434959 | N/A | N/A | 9101 | 9120 | GTTGTGAACCTGCTAAAGGA | 90 | 66 |
| 434960 | N/A | N/A | 10818 | 10837 | CCTGGCAACCTGCATTTGCA | 43 | 67 |
| 434961 | N/A | N/A | 10823 | 10842 | TGTCACCTGGCAACCTGCAT | 45 | 68 |
| 434962 | N/A | N/A | 12030 | 12049 | GGGCAGGTTTCATTTCATTT | 33 | 69 |
| 434963 | N/A | N/A | 13414 | 13433 | GCCGGCAGTCTGCAAACACA | 58 | 70 |
| 434964 | N/A | N/A | 19448 | 19467 | CAGAGGTTCTACCTTTAATA | 50 | 71 |

Example 2: Effect of 3-10-3 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 20,000 cells per well were transfected using electroporation with 4,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (described hereinabove in Example 1) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 2 and 3 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 2 and 3 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 2

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609281 | 156 | 171 | 5183 | 5198 | GCTCATGCCGAACTCT | 81 | 72 |
| 609282 | 213 | 228 | 5240 | 5255 | GCTGTCGATCTGGTCG | 91 | 73 |
| 609283 | 216 | 231 | 5243 | 5258 | GCCGCTGTCGATCTGG | 76 | 74 |
| 609284 | 219 | 234 | 5246 | 5261 | CTTGCCGCTGTCGATC | 75 | 75 |

TABLE 2-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609285 | 222 | 237 | 5249 | 5264 | GTACTTGCCGCTGTCG | 73 | 76 |
| 609286 | 238 | 253 | 5265 | 5280 | CCCACACCAGCCCGGG | 106 | 77 |
| 609287 | 241 | 256 | 5268 | 5283 | TCTCCCACACCAGCCC | 94 | 78 |
| 609288 | 244 | 259 | 5271 | 5286 | CGTTCTCCCACACCAG | 52 | 79 |
| 609289 | 294 | 309 | 5321 | 5336 | GTCCTGCTTGCCCGCG | 69 | 80 |
| 609290 | 297 | 312 | 5324 | 5339 | GTAGTCCTGCTTGCCC | 56 | 81 |
| 609291 | 334 | 349 | N/A | N/A | CCCAAGCCTTGAAGAG | 94 | 82 |
| 609292 | 431 | 446 | 6910 | 6925 | AAGTCATTGCTCTTGT | 72 | 83 |
| 609293 | 434 | 449 | 6913 | 6928 | TCAAAGTCATTGCTCT | 79 | 84 |
| 609294 | 437 | 452 | 6916 | 6931 | TCCTCAAAGTCATTGC | 68 | 85 |
| 609295 | 496 | 511 | 6975 | 6990 | GAACAATCCTGTACAC | 105 | 86 |
| 609296 | 514 | 529 | 6993 | 7008 | CTTTTTTGGCTCCCTC | 64 | 87 |
| 609297 | 517 | 532 | N/A | N/A | CTCCTTTTTTGGCTCC | 81 | 88 |
| 609298 | 610 | 625 | N/A | N/A | GAACCTGCTGGGCTGG | 64 | 89 |
| 609299 | 730 | 745 | 9220 | 9235 | CTTGCCAGTGGTGGCC | 84 | 90 |
| 609300 | 733 | 748 | 9223 | 9238 | GGCCTTGCCAGTGGTG | 112 | 91 |
| 609301 | 752 | 767 | N/A | N/A | CAACCATTTTCACAAG | 83 | 92 |
| 609302 | 755 | 770 | N/A | N/A | TGGCAACCATTTTCAC | 93 | 93 |
| 609303 | 758 | 773 | N/A | N/A | ACCTGGCAACCATTTT | 96 | 94 |
| 609304 | 761 | 776 | N/A | N/A | GTCACCTGGCAACCAT | 59 | 95 |
| 609305 | 764 | 779 | 10829 | 10844 | CCTGTCACCTGGCAAC | 59 | 96 |
| 609306 | 767 | 782 | 10832 | 10847 | GTTCCTGTCACCTGGC | 51 | 97 |
| 609307 | 770 | 785 | 10835 | 10850 | AAGGTTCCTGTCACCT | 102 | 98 |
| 609308 | 773 | 788 | 10838 | 10853 | TAAAAGGTTCCTGTCA | 94 | 99 |
| 609309 | 776 | 791 | 10841 | 10856 | GCATAAAAGGTTCCTG | 74 | 100 |
| 609310 | 780 | 795 | 10845 | 10860 | ACAAGCATAAAAGGTT | 96 | 101 |
| 609311 | 799 | 814 | 10864 | 10879 | CCTGGGACTCAGGTGG | 41 | 102 |
| 609312 | 802 | 817 | 10867 | 10882 | GAGCCTGGGACTCAGG | 51 | 103 |
| 609313 | 832 | 847 | 10897 | 10912 | ACCTTATGCTTGGCTC | 69 | 104 |
| 609314 | 835 | 850 | 10900 | 10915 | CAGACCTTATGCTTGG | 90 | 105 |
| 609317 | 943 | 958 | 13496 | 13511 | GGGAGATCCGGCAGCC | 110 | 106 |
| 609318 | 979 | 994 | 13532 | 13547 | CCTGGTCCAGGTTGCT | 74 | 107 |
| 609319 | 982 | 997 | 13535 | 13550 | GGACCTGGTCCAGGTT | 102 | 108 |
| 609320 | 985 | 1000 | 13538 | 13553 | ACAGGACCTGGTCCAG | 65 | 109 |
| 609321 | 1046 | 1061 | 13599 | 13614 | TCCAGGTGGCTCAGCA | 59 | 110 |
| 609322 | 1049 | 1064 | 13602 | 13617 | CTCTCCAGGTGGCTCA | 87 | 111 |

TABLE 2-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609323 | 1052 | 1067 | 13605 | 13620 | CCCCTCTCCAGGTGGC | 87 | 112 |
| 609324 | 1194 | 1209 | 13747 | 13762 | TGTGTCAAAGAGCTTG | 78 | 113 |
| 609325 | 1198 | 1213 | 13751 | 13766 | GCTGTGTGTCAAAGAG | 94 | 114 |
| 609326 | 1201 | 1216 | 13754 | 13769 | ACTGCTGTGTGTCAAA | 106 | 115 |
| 609327 | 1264 | 1279 | 17057 | 17072 | GAGTCACCTGGAATCT | 57 | 116 |
| 609328 | 1291 | 1306 | 17084 | 17099 | GGTCTGGAAACTCCTC | 48 | 117 |
| 609329 | 1294 | 1309 | 17087 | 17102 | GAGGGTCTGGAAACTC | 104 | 118 |
| 609330 | 1297 | 1312 | 17090 | 17105 | TCTGAGGGTCTGGAAA | 91 | 119 |
| 609331 | 1321 | 1336 | 17114 | 17129 | GAGCTGTGATGAGCTT | 90 | 120 |
| 609332 | 1342 | 1357 | 19459 | 19474 | TGGCTAGCAGAGGTTC | 44 | 121 |
| 609333 | 1345 | 1360 | 19462 | 19477 | GTCTGGCTAGCAGAGG | 34 | 122 |
| 609334 | 1348 | 1363 | 19465 | 19480 | GTTGTCTGGCTAGCAG | 41 | 123 |
| 609335 | 1389 | 1404 | 19506 | 19521 | CCTCAGGAAATGTCCA | 63 | 124 |
| 609336 | 1393 | 1408 | 19510 | 19525 | AGCCCCTCAGGAAATG | 76 | 125 |
| 609337 | 2068 | 2083 | 20185 | 20200 | CTTCCCTGAGAAATGG | 50 | 126 |
| 609338 | 2071 | 2086 | 20188 | 20203 | TTACTTCCCTGAGAAA | 80 | 127 |
| 609339 | 2719 | 2734 | 20836 | 20851 | AATAAGCAGAAACAGC | 101 | 128 |
| 609340 | 3533 | 3548 | 21650 | 21665 | ATCTATAAGATGTATA | 101 | 129 |
| 609341 | 3536 | 3551 | 21653 | 21668 | TGCATCTATAAGATGT | 68 | 130 |
| 609342 | 3803 | 3818 | 21920 | 21935 | TCCAGAAAATTCAGCT | 52 | 131 |
| 609343 | 3809 | 3824 | 21926 | 21941 | GCATTTTCCAGAAAAT | 36 | 132 |
| 609344 | N/A | N/A | 6995 | 7010 | ACCTTTTTTGGCTCCC | 79 | 133 |
| 609345 | N/A | N/A | 7740 | 7755 | ATTCTTAGAATGCATA | 62 | 134 |
| 609346 | N/A | N/A | 8504 | 8519 | CAAACTCCTCAGGGAA | 77 | 135 |
| 609347 | N/A | N/A | 9242 | 9257 | TTACCATTTTCACAAG | 92 | 136 |
| 609348 | N/A | N/A | 10796 | 10811 | AATCAGATGATGTCTA | 103 | 137 |
| 609349 | N/A | N/A | 10813 | 10828 | CTGCATTTGCAAATAA | 121 | 138 |
| 609350 | N/A | N/A | 10819 | 10834 | GGCAACCTGCATTTGC | 113 | 139 |
| 609351 | N/A | N/A | 10825 | 10840 | TCACCTGGCAACCTGC | 75 | 140 |
| 609352 | N/A | N/A | 11951 | 11966 | CACCCACACAAGTCTT | 91 | 141 |
| 609353 | N/A | N/A | 11972 | 11987 | GTTTATTTCCTACTCT | 84 | 142 |
| 609354 | N/A | N/A | 11978 | 11993 | ATAGCTGTTTATTTCC | 38 | 143 |
| 609355 | N/A | N/A | 11985 | 12000 | GATATAAATAGCTGTT | 63 | 144 |
| 609356 | N/A | N/A | 12024 | 12039 | CATTTCATTTAATGTC | 67 | 145 |
| 609357 | N/A | N/A | 12031 | 12046 | CAGGTTTCATTTCATT | 40 | 146 |
| 609358 | N/A | N/A | 13795 | 13810 | CCTCCATTCTAACAGA | 118 | 147 |

TABLE 3

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609360 | 4711 | 4726 | 22828 | 22843 | TGGCCACAGAGGACTT | 67 | 148 |
| 609361 | 1 | 16 | 3740 | 3755 | ACTGAGAGTGCGAGGT | 120 | 149 |
| 609362 | 121 | 136 | 5148 | 5163 | CCAGGTTCATGCCCCG | 46 | 150 |
| 609363 | 181 | 196 | 5208 | 5223 | GCTTCCCGTTGCCGCA | 82 | 151 |
| 609364 | 300 | 315 | 5327 | 5342 | GTTGTAGTCCTGCTTG | 78 | 152 |
| 609365 | 420 | 435 | 6899 | 6914 | CTTGTTCAAAGCGCAC | 68 | 153 |
| 609366 | 480 | 495 | 6959 | 6974 | TTTGTACGGGTCTGAG | 80 | 154 |
| 609367 | 672 | 687 | 9162 | 9177 | GTGTGGCTGATCCGGG | 73 | 155 |
| 609368 | 736 | 751 | 9226 | 9241 | CTGGGCCTTGCCAGTG | 114 | 156 |
| 609369 | 810 | 825 | 10875 | 10890 | GACTCCGGGAGCCTGG | 35 | 157 |
| 609371 | 1004 | 1019 | 13557 | 13572 | TTGTCCTCTGGGTAGG | 70 | 158 |
| 609372 | 1124 | 1139 | 13677 | 13692 | CCGTCCCAGTAGATCC | 75 | 159 |
| 609373 | 1184 | 1199 | 13737 | 13752 | AGCTTGCAGGTCTGGT | 47 | 160 |
| 609374 | 1431 | 1446 | 19548 | 19563 | GTAATCTTCTGGATTG | 71 | 161 |
| 609375 | 1527 | 1542 | 19644 | 19659 | TCCCCGTATCAAAAAA | 112 | 162 |
| 609376 | 1682 | 1697 | 19799 | 19814 | CACTTGTCTTGGGTGG | 55 | 163 |
| 609377 | 1742 | 1757 | 19859 | 19874 | AACAGTAAGAGGGCAG | 37 | 164 |
| 609378 | 1866 | 1881 | 19983 | 19998 | GCAAAGCCACCCTTCC | 40 | 165 |
| 609379 | 1986 | 2001 | 20103 | 20118 | TCTTCCAGCAAGACCT | 72 | 166 |
| 609380 | 2111 | 2126 | 20228 | 20243 | ATACATTTCTTTTACG | 78 | 167 |
| 609381 | 2171 | 2186 | 20288 | 20303 | GATTCATTTCCTTCAC | 51 | 168 |
| 609382 | 2231 | 2246 | 20348 | 20363 | GAAACCGCTGGCAGGT | 50 | 169 |
| 609383 | 2295 | 2310 | 20412 | 20427 | TCCAGGAAAGGCCAAG | 51 | 170 |
| 609384 | 2304 | 2319 | 20421 | 20436 | TAACTGGCTTCCAGGA | 70 | 171 |
| 609385 | 2365 | 2380 | 20482 | 20497 | AAAAATGTCCCATCCA | 70 | 172 |
| 609386 | 2431 | 2446 | 20548 | 20563 | GTCAAAAGATGCAGA | 50 | 173 |
| 609387 | 2494 | 2509 | 20611 | 20626 | GATTTATGTTCCTTAA | 53 | 174 |
| 609388 | 2574 | 2589 | 20691 | 20706 | AACAAACAGAGGAGCG | 84 | 175 |
| 609389 | 2634 | 2649 | 20751 | 20766 | GCCTGGGAGTCCCCGG | 82 | 176 |
| 609390 | 2694 | 2709 | 20811 | 20826 | GTGCAGTTCCGTAGTC | 79 | 177 |
| 609391 | 2754 | 2769 | 20871 | 20886 | ACTATAATTGGCACGA | 31 | 178 |
| 609392 | 2816 | 2831 | 20933 | 20948 | TCTTTGGGATTCTATA | 40 | 179 |
| 609393 | 2936 | 2951 | 21053 | 21068 | GGAGTAATAGTAAATA | 64 | 180 |
| 609394 | 3081 | 3096 | 21198 | 21213 | CTGCTCACTAAGCTTG | 27 | 181 |
| 609395 | 3147 | 3162 | 21264 | 21279 | GTATTAATATTCTGAC | 37 | 182 |
| 609396 | 3216 | 3231 | 21333 | 21348 | GGAGATCCTTTTTATT | 68 | 183 |

TABLE 3-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609397 | 3336 | 3351 | 21453 | 21468 | GACTCCATGAGGTTTT | 30 | 184 |
| 609398 | 3437 | 3452 | 21554 | 21569 | GGGTACATGGCAGTGG | 32 | 185 |
| 609399 | 3591 | 3606 | 21708 | 21723 | GCAGTTCTTAATATCA | 40 | 186 |
| 609400 | 3657 | 3672 | 21774 | 21789 | TGAAGTGCTGTGTGGG | 43 | 187 |
| 609401 | 3717 | 3732 | 21834 | 21849 | TCCGCTTGGAGAATTA | 87 | 188 |
| 609402 | 3782 | 3797 | 21899 | 21914 | GTTAAAGCAGCATAAT | 73 | 189 |
| 609403 | 3851 | 3866 | 21968 | 21983 | AGATGTAAAGATAGGA | 46 | 190 |
| 609404 | 3911 | 3926 | 22028 | 22043 | AGTTCATTCCCTAGGT | 56 | 191 |
| 609405 | 3971 | 3986 | 22088 | 22103 | GTTCCTTTTCAGAGTC | 28 | 192 |
| 609406 | 4031 | 4046 | 22148 | 22163 | AGTACAAACTAAATTC | 76 | 193 |
| 609407 | 4166 | 4181 | 22283 | 22298 | GAGGTTTTCCTAAATA | 31 | 194 |
| 609408 | 4226 | 4241 | 22343 | 22358 | TTGTAAATGAGTCGGT | 21 | 195 |
| 609409 | 4359 | 4374 | 22476 | 22491 | CTGTAGGATTTTACAT | 76 | 196 |
| 609410 | 4479 | 4494 | 22596 | 22611 | CAGAGTTGTTCCACCC | 38 | 197 |
| 609411 | 4599 | 4614 | 22716 | 22731 | AATGAACGGAAGTTTA | 67 | 198 |
| 609412 | 4665 | 4680 | 22782 | 22797 | AACCAATCCCAACACT | 88 | 199 |
| 609413 | 4727 | 4742 | 22844 | 22859 | TTCAGACAGATGCAGC | 38 | 200 |
| 609414 | 4800 | 4815 | 22917 | 22932 | CAGTCTCAAAAACGGG | 49 | 201 |
| 609415 | 4862 | 4877 | 22979 | 22994 | ACCTTTACTTCATTCC | 36 | 202 |
| 609416 | 4987 | 5002 | 23104 | 23119 | ACGGGAATTTCCATTG | 33 | 203 |
| 609417 | 5037 | 5052 | 23154 | 23169 | AAGTGGACCCCATTGC | 69 | 204 |
| 609418 | 5077 | 5092 | 23194 | 23209 | TTCAGCAGAAAGTGGG | 52 | 205 |
| 609419 | 5146 | 5161 | 23263 | 23278 | CGCAGAGCCAGTAGGG | 33 | 206 |
| 609420 | N/A | N/A | 2604 2875 | 2619 2890 | AAAAGCCCAAAATAGG | 112 | 207 |
| 609421 | N/A | N/A | 8538 8746 8850 8902 9058 | 8553 8761 8865 8917 9073 | CTGGCATTGAGACGGG | 39 | 208 |
| 609422 | N/A | N/A | 8542 8750 8854 8906 9062 | 8557 8765 8869 8921 9077 | AGCACTGGCATTGAGA | 26 | 209 |
| 609423 | N/A | N/A | 8547 8703 8807 8963 9067 | 8562 8718 8822 8978 9082 | TAAGAAGCACTGGCAT | 74 | 210 |
| 609424 | N/A | N/A | 8552 8708 8812 8968 9072 | 8567 8723 8827 8983 9087 | TGAGATAAGAAGCACT | 80 | 211 |

TABLE 3-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609425 | N/A | N/A | 8560 | 8575 | GGAGAGGCTGAGATAA | 71 | 212 |
|  |  |  | 8716 | 8731 |  |  |  |
|  |  |  | 8820 | 8835 |  |  |  |
|  |  |  | 8976 | 8991 |  |  |  |
|  |  |  | 9080 | 9095 |  |  |  |
| 609426 | N/A | N/A | 8561 | 8576 | AGGAGAGGCTGAGATA | 79 | 213 |
|  |  |  | 8613 | 8628 |  |  |  |
|  |  |  | 8665 | 8680 |  |  |  |
|  |  |  | 8717 | 8732 |  |  |  |
|  |  |  | 8769 | 8784 |  |  |  |
|  |  |  | 8821 | 8836 |  |  |  |
|  |  |  | 8873 | 8888 |  |  |  |
|  |  |  | 8925 | 8940 |  |  |  |
|  |  |  | 8977 | 8992 |  |  |  |
|  |  |  | 9029 | 9044 |  |  |  |
|  |  |  | 9081 | 9096 |  |  |  |
| 609427 | N/A | N/A | 8565 | 8580 | GTGCAGGAGAGGCTGA | 68 | 214 |
|  |  |  | 8617 | 8632 |  |  |  |
|  |  |  | 8669 | 8684 |  |  |  |
|  |  |  | 8721 | 8736 |  |  |  |
|  |  |  | 8773 | 8788 |  |  |  |
|  |  |  | 8825 | 8840 |  |  |  |
|  |  |  | 8877 | 8892 |  |  |  |
|  |  |  | 8929 | 8944 |  |  |  |
|  |  |  | 8981 | 8996 |  |  |  |
|  |  |  | 9033 | 9048 |  |  |  |
|  |  |  | 9085 | 9100 |  |  |  |
| 609428 | N/A | N/A | 8567 | 8582 | GAGTGCAGGAGAGGCT | 69 | 215 |
|  |  |  | 8619 | 8634 |  |  |  |
|  |  |  | 8671 | 8686 |  |  |  |
|  |  |  | 8723 | 8738 |  |  |  |
|  |  |  | 8775 | 8790 |  |  |  |
|  |  |  | 8827 | 8842 |  |  |  |
|  |  |  | 8879 | 8894 |  |  |  |
|  |  |  | 8931 | 8946 |  |  |  |
|  |  |  | 8983 | 8998 |  |  |  |
|  |  |  | 9035 | 9050 |  |  |  |
|  |  |  | 9087 | 9102 |  |  |  |
| 609429 | N/A | N/A | 8568 | 8583 | GGAGTGCAGGAGAGGC | 84 | 216 |
|  |  |  | 8620 | 8635 |  |  |  |
|  |  |  | 8672 | 8687 |  |  |  |
|  |  |  | 8724 | 8739 |  |  |  |
|  |  |  | 8776 | 8791 |  |  |  |
|  |  |  | 8828 | 8843 |  |  |  |
|  |  |  | 8880 | 8895 |  |  |  |
|  |  |  | 8932 | 8947 |  |  |  |
|  |  |  | 8984 | 8999 |  |  |  |
|  |  |  | 9036 | 9051 |  |  |  |
|  |  |  | 9088 | 9103 |  |  |  |
| 609430 | N/A | N/A | 8572 | 8587 | TAAAGGAGTGCAGGAG | 107 | 217 |
|  |  |  | 8624 | 8639 |  |  |  |
|  |  |  | 8676 | 8691 |  |  |  |
|  |  |  | 8728 | 8743 |  |  |  |
|  |  |  | 8780 | 8795 |  |  |  |
|  |  |  | 8832 | 8847 |  |  |  |
|  |  |  | 8884 | 8899 |  |  |  |
|  |  |  | 8936 | 8951 |  |  |  |
|  |  |  | 8988 | 9003 |  |  |  |
|  |  |  | 9040 | 9055 |  |  |  |
|  |  |  | 9092 | 9107 |  |  |  |
| 609431 | N/A | N/A | 8573 | 8588 | GTAAAGGAGTGCAGGA | 91 | 218 |
|  |  |  | 8625 | 8640 |  |  |  |
|  |  |  | 8677 | 8692 |  |  |  |
|  |  |  | 8729 | 8744 |  |  |  |
|  |  |  | 8833 | 8848 |  |  |  |

TABLE 3-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| | | | 8885 | 8900 | | | |
| | | | 8937 | 8952 | | | |
| | | | 8989 | 9004 | | | |
| | | | 9041 | 9056 | | | |
| 609432 | N/A | N/A | 8575 | 8590 | GGGTAAAGGAGTGCAG | 81 | 219 |
| | | | 8627 | 8642 | | | |
| | | | 8679 | 8694 | | | |
| | | | 8731 | 8746 | | | |
| | | | 8835 | 8850 | | | |
| | | | 8887 | 8902 | | | |
| | | | 8939 | 8954 | | | |
| | | | 8991 | 9006 | | | |
| | | | 9043 | 9058 | | | |
| 609433 | N/A | N/A | 8590 | 8605 | CTGGCATCGAGACGGG | 53 | 220 |
| | | | 8642 | 8657 | | | |
| | | | 8694 | 8709 | | | |
| | | | 8798 | 8813 | | | |
| | | | 8954 | 8969 | | | |
| | | | 9006 | 9021 | | | |
| 609434 | N/A | N/A | 8593 | 8608 | GCACTGGCATCGAGAC | 43 | 221 |
| | | | 8645 | 8660 | | | |
| | | | 8697 | 8712 | | | |
| | | | 8801 | 8816 | | | |
| | | | 8957 | 8972 | | | |
| | | | 9009 | 9024 | | | |
| 609435 | N/A | N/A | 8596 | 8611 | GAAGCACTGGCATCGA | 56 | 222 |
| | | | 8648 | 8663 | | | |
| | | | 8700 | 8715 | | | |
| | | | 8804 | 8819 | | | |
| | | | 8960 | 8975 | | | |
| | | | 9012 | 9027 | | | |
| 609436 | N/A | N/A | 18852 | 18867 | CCTGAATTTACAGCAT | 60 | 223 |

Example 3: Effect of 4-8-4 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 20,000 cells per well were transfected using electroporation with 4,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (described hereinabove in Example 1) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Table 4 are 4-8-4 cEt gapmers. The gapmers are 16 nucleobases in length, wherein the central gap segment comprises eight 2'-deoxynucleosides and is flanked by wing segments on both the 5' end and on the 3' end comprising four cEt nucleosides. The sugar motif for the gapmers is (from 5' to 3'): kkkkddddddddkkkk; wherein 'd' represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 4 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 4

Percent control of human IRF4 mRNA with 4-8-4 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609518 | 156 | 171 | 5183 | 5198 | GCTCATGCCGAACTCT | 70 | 72 |
| 609519 | 213 | 228 | 5240 | 5255 | GCTGTCGATCTGGTCG | 94 | 73 |
| 609520 | 216 | 231 | 5243 | 5258 | GCCGCTGTCGATCTGG | 85 | 74 |
| 609521 | 219 | 234 | 5246 | 5261 | CTTGCCGCTGTCGATC | 58 | 75 |
| 609522 | 222 | 237 | 5249 | 5264 | GTACTTGCCGCTGTCG | 64 | 76 |
| 609523 | 238 | 253 | 5265 | 5280 | CCCACACCAGCCCGGG | 106 | 77 |
| 609524 | 241 | 256 | 5268 | 5283 | TCTCCCACACCAGCCC | 75 | 78 |
| 609525 | 244 | 259 | 5271 | 5286 | CGTTCTCCCACACCAG | 101 | 79 |
| 609526 | 294 | 309 | 5321 | 5336 | GTCCTGCTTGCCCGCG | 86 | 80 |
| 609527 | 297 | 312 | 5324 | 5339 | GTAGTCCTGCTTGCCC | 89 | 81 |
| 609528 | 334 | 349 | N/A | N/A | CCCAAGCCTTGAAGAG | 78 | 82 |
| 609529 | 431 | 446 | 6910 | 6925 | AAGTCATTGCTCTTGT | 72 | 83 |
| 609530 | 434 | 449 | 6913 | 6928 | TCAAAGTCATTGCTCT | 43 | 84 |
| 609531 | 437 | 452 | 6916 | 6931 | TCCTCAAAGTCATTGC | 90 | 85 |
| 609532 | 496 | 511 | 6975 | 6990 | GAACAATCCTGTACAC | 100 | 86 |
| 609533 | 514 | 529 | 6993 | 7008 | CTTTTTTGGCTCCCTC | 54 | 87 |
| 609534 | 517 | 532 | N/A | N/A | CTCCTTTTTTGGCTCC | 93 | 88 |
| 609535 | 610 | 625 | N/A | N/A | GAACCTGCTGGGCTGG | 87 | 89 |
| 609536 | 730 | 745 | 9220 | 9235 | CTTGCCAGTGGTGGCC | 109 | 90 |
| 609537 | 733 | 748 | 9223 | 9238 | GGCCTTGCCAGTGGTG | 94 | 91 |
| 609538 | 752 | 767 | N/A | N/A | CAACCATTTTCACAAG | 95 | 92 |
| 609539 | 755 | 770 | N/A | N/A | TGGCAACCATTTTCAC | 93 | 93 |
| 609540 | 758 | 773 | N/A | N/A | ACCTGGCAACCATTTT | 81 | 94 |
| 609541 | 761 | 776 | N/A | N/A | GTCACCTGGCAACCAT | 59 | 95 |
| 609542 | 764 | 779 | 10829 | 10844 | CCTGTCACCTGGCAAC | 63 | 96 |
| 609543 | 767 | 782 | 10832 | 10847 | GTTCCTGTCACCTGGC | 88 | 97 |
| 609544 | 770 | 785 | 10835 | 10850 | AAGGTTCCTGTCACCT | 86 | 98 |
| 609545 | 773 | 788 | 10838 | 10853 | TAAAGGTTCCTGTCA | 57 | 99 |
| 609546 | 776 | 791 | 10841 | 10856 | GCATAAAAGGTTCCTG | 53 | 100 |
| 609547 | 780 | 795 | 10845 | 10860 | ACAAGCATAAAAGGTT | 60 | 101 |
| 609548 | 799 | 814 | 10864 | 10879 | CCTGGGACTCAGGTGG | 93 | 102 |
| 609549 | 802 | 817 | 10867 | 10882 | GAGCCTGGGACTCAGG | 81 | 103 |
| 609550 | 832 | 847 | 10897 | 10912 | ACCTTATGCTTGGCTC | 70 | 104 |
| 609551 | 835 | 850 | 10900 | 10915 | CAGACCTTATGCTTGG | 74 | 105 |
| 609554 | 943 | 958 | 13496 | 13511 | GGGAGATCCGGCAGCC | 113 | 106 |
| 609555 | 979 | 994 | 13532 | 13547 | CCTGGTCCAGGTTGCT | 66 | 107 |
| 609556 | 982 | 997 | 13535 | 13550 | GGACCTGGTCCAGGTT | 128 | 108 |

TABLE 4-continued

Percent control of human IRF4 mRNA with 4-8-4 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609557 | 985 | 1000 | 13538 | 13553 | ACAGGACCTGGTCCAG | 93 | 109 |
| 609558 | 1046 | 1061 | 13599 | 13614 | TCCAGGTGGCTCAGCA | 66 | 110 |
| 609559 | 1049 | 1064 | 13602 | 13617 | CTCTCCAGGTGGCTCA | 88 | 111 |
| 609560 | 1052 | 1067 | 13605 | 13620 | CCCCTCTCCAGGTGGC | 101 | 112 |
| 609561 | 1194 | 1209 | 13747 | 13762 | TGTGTCAAAGAGCTTG | 74 | 113 |
| 609562 | 1198 | 1213 | 13751 | 13766 | GCTGTGTGTCAAAGAG | 60 | 114 |
| 609563 | 1201 | 1216 | 13754 | 13769 | ACTGCTGTGTGTCAAA | 81 | 115 |
| 609564 | 1264 | 1279 | 17057 | 17072 | GAGTCACCTGGAATCT | 94 | 116 |
| 609565 | 1291 | 1306 | 17084 | 17099 | GGTCTGGAAACTCCTC | 69 | 117 |
| 609566 | 1294 | 1309 | 17087 | 17102 | GAGGGTCTGGAAACTC | 92 | 118 |
| 609567 | 1297 | 1312 | 17090 | 17105 | TCTGAGGGTCTGGAAA | 97 | 119 |
| 609568 | 1321 | 1336 | 17114 | 17129 | GAGCTGTGATGAGCTT | 95 | 120 |
| 609569 | 1342 | 1357 | 19459 | 19474 | TGGCTAGCAGAGGTTC | 91 | 121 |
| 609570 | 1345 | 1360 | 19462 | 19477 | GTCTGGCTAGCAGAGG | 91 | 122 |
| 609571 | 1348 | 1363 | 19465 | 19480 | GTTGTCTGGCTAGCAG | 48 | 123 |
| 609572 | 1389 | 1404 | 19506 | 19521 | CCTCAGGAAATGTCCA | 90 | 124 |
| 609574 | 2068 | 2083 | 20185 | 20200 | CTTCCCTGAGAAATGG | 64 | 126 |
| 609575 | 2071 | 2086 | 20188 | 20203 | TTACTTCCCTGAGAAA | 86 | 127 |
| 609576 | 2719 | 2734 | 20836 | 20851 | AATAAGCAGAAACAGC | 61 | 128 |
| 609577 | 3533 | 3548 | 21650 | 21665 | ATCTATAAGATGTATA | 64 | 129 |
| 609578 | 3536 | 3551 | 21653 | 21668 | TGCATCTATAAGATGT | 90 | 130 |
| 609579 | 3803 | 3818 | 21920 | 21935 | TCCAGAAAATTCAGCT | 74 | 131 |
| 609580 | 3809 | 3824 | 21926 | 21941 | GCATTTTCCAGAAAAT | 63 | 132 |
| 609581 | N/A | N/A | 6995 | 7010 | ACCTTTTTTGGCTCCC | 81 | 133 |
| 609582 | N/A | N/A | 7740 | 7755 | ATTCTTAGAATGCATA | 67 | 134 |
| 609583 | N/A | N/A | 8504 | 8519 | CAAACTCCTCAGGGAA | 83 | 135 |
| 609584 | N/A | N/A | 9242 | 9257 | TTACCATTTTCACAAG | 93 | 136 |
| 609585 | N/A | N/A | 10796 | 10811 | AATCAGATGATGTCTA | 113 | 137 |
| 609586 | N/A | N/A | 10813 | 10828 | CTGCATTTGCAAATAA | 108 | 138 |
| 609587 | N/A | N/A | 10819 | 10834 | GGCAACCTGCATTTGC | 112 | 139 |
| 609588 | N/A | N/A | 10825 | 10840 | TCACCTGGCAACCTGC | 72 | 140 |
| 609589 | N/A | N/A | 11951 | 11966 | CACCCACACAAGTCTT | 86 | 141 |
| 609590 | N/A | N/A | 11972 | 11987 | GTTTATTTCCTACTCT | 56 | 142 |
| 609591 | N/A | N/A | 11978 | 11993 | ATAGCTGTTTATTTCC | 41 | 143 |
| 609592 | N/A | N/A | 11985 | 12000 | GATATAAATAGCTGTT | 39 | 144 |
| 609593 | N/A | N/A | 12024 | 12039 | CATTTCATTTAATGTC | 56 | 145 |

TABLE 4-continued

Percent control of human IRF4 mRNA with 4-8-4 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609594 | N/A | N/A | 12031 | 12046 | CAGGTTTCATTTCATT | 46 | 146 |
| 609595 | N/A | N/A | 13795 | 13810 | CCTCCATTCTAACAGA | 122 | 147 |

Example 4: Effect of 3-10-3 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 20,000 cells per well were transfected using electroporation with 4,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (described hereinabove in Example 1) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 5 through 12 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 5 through 12 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 5

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 24 | 195 |
| 666225 | 5 | 20 | 3744 | 3759 | TGAAACTGAGAGTGCG | 81 | 224 |
| 666226 | 12 | 27 | 3751 | 3766 | CGAGCGGTGAAACTGA | 67 | 225 |
| 666227 | 19 | 34 | 3758 | 3773 | CCAAGATCGAGCGGTG | 63 | 226 |
| 666228 | 26 | 41 | 3765 | 3780 | GTGGGTCCCAAGATCG | 60 | 227 |
| 666229 | 40 | 55 | 3779 | 3794 | AGCTGAGGGCAGCGGT | 107 | 228 |
| 666230 | 47 | 62 | 3786 | 3801 | GACTCGGAGCTGAGGG | 77 | 229 |
| 666231 | 54 | 69 | 3793 | 3808 | CGCCCTGGACTCGGAG | 64 | 230 |
| 666232 | 61 | 76 | N/A | N/A | CTGCACTCGCCCTGGA | 58 | 231 |
| 666233 | 68 | 83 | N/A | N/A | CTCTGCTCTGCACTCG | 59 | 232 |
| 666234 | 75 | 90 | 5102 | 5117 | CCGCCCGCTCTGCTCT | 46 | 233 |
| 666235 | 82 | 97 | 5109 | 5124 | GGGTCCTCCGCCCGCT | 72 | 234 |
| 666236 | 101 | 116 | 5128 | 5143 | CCGTCCGCGCCCGCGC | 39 | 235 |
| 666237 | 129 | 144 | 5156 | 5171 | GCCGCCCTCCAGGTTC | 51 | 236 |
| 666238 | 136 | 151 | 5163 | 5178 | CTCGGCCGCCGCCCTC | 63 | 237 |
| 666239 | 143 | 158 | 5170 | 5185 | TCTCCGCCTCGGCCGC | 59 | 238 |

TABLE 5-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666240 | 150 | 165 | 5177 | 5192 | GCCGAACTCTCCGCCT | 49 | 239 |
| 666241 | 160 | 175 | 5187 | 5202 | CCGCGCTCATGCCGAA | 55 | 240 |
| 666242 | 167 | 182 | 5194 | 5209 | CAGCTCACCGCGCTCA | 58 | 241 |
| 666243 | 185 | 200 | 5212 | 5227 | CGGAGCTTCCCGTTGC | 65 | 242 |
| 666244 | 192 | 207 | 5219 | 5234 | CCACTGGCGGAGCTTC | 64 | 243 |
| 666245 | 304 | 319 | 5331 | 5346 | CGCGGTTGTAGTCCTG | 56 | 244 |
| 666246 | 311 | 326 | 5338 | 5353 | TCCTCCTCGCGGTTGT | 41 | 245 |
| 666247 | 327 | 342 | 5354 | 5369 | CTTGAAGAGCGCGGCG | 79 | 246 |
| 666248 | 338 | 353 | N/A | N/A | AGTGCCCAAGCCTTGA | 52 | 247 |
| 666249 | 348 | 363 | 6827 | 6842 | TCCTTTAAACAGTGCC | 50 | 248 |
| 666250 | 356 | 371 | 6835 | 6850 | CGGAACTTTCCTTTAA | 63 | 249 |
| 666251 | 363 | 378 | 6842 | 6857 | GCCTTCTCGGAACTTT | 68 | 250 |
| 666252 | 370 | 385 | 6849 | 6864 | TGTCGATGCCTTCTCG | 72 | 251 |
| 666253 | 377 | 392 | 6856 | 6871 | TCCGGCTTGTCGATGC | 59 | 252 |
| 666254 | 396 | 411 | 6875 | 6890 | CGTCTTCCAGGTGGGA | 84 | 253 |
| 666256 | 425 | 440 | 6904 | 6919 | TTGCTCTTGTTCAAAG | 71 | 254 |
| 666257 | 449 | 464 | 6928 | 6943 | CGCTCAACCAGTTCCT | 72 | 255 |
| 666258 | 456 | 471 | 6935 | 6950 | CTGGCTCCGCTCAACC | 48 | 256 |
| 666259 | 463 | 478 | 6942 | 6957 | TGTCCAGCTGGCTCCG | 61 | 257 |
| 666260 | 470 | 485 | 6949 | 6964 | TCTGAGATGTCCAGCT | 55 | 258 |
| 666261 | 484 | 499 | 6963 | 6978 | ACACTTTGTACGGGTC | 44 | 259 |
| 666262 | 507 | 522 | 6986 | 7001 | GGCTCCCTCAGGAACA | 81 | 260 |
| 666263 | 521 | 536 | N/A | N/A | TTGGCTCCTTTTTTGG | 87 | 261 |
| 666264 | 528 | 543 | 7846 | 7861 | GAGCTGCTTGGCTCCT | 81 | 262 |
| 666265 | 535 | 550 | 7853 | 7868 | CCAGGGTGAGCTGCTT | 69 | 263 |
| 666266 | 546 | 561 | 7864 | 7879 | CTGCGGGTCCTCCAGG | 80 | 264 |
| 666267 | 553 | 568 | 7871 | 7886 | TGGACATCTGCGGGTC | 56 | 265 |
| 666268 | 560 | 575 | 7878 | 7893 | TGGCTCATGGACATCT | 68 | 266 |
| 666269 | 577 | 592 | 7895 | 7910 | TTGTCATGGTGTAGGG | 59 | 267 |
| 666270 | 593 | 608 | 7911 | 7926 | AGCGAAGGGTAAGGCG | 86 | 268 |
| 666271 | 621 | 636 | 9111 | 9126 | CATGTAGTTGTGAACC | 73 | 269 |
| 666272 | 628 | 643 | 9118 | 9133 | GTGGCATCATGTAGTT | 73 | 270 |
| 666273 | 644 | 659 | 9134 | 9149 | CAGCTTCGGTCGAGGG | 42 | 271 |
| 666274 | 651 | 666 | 9141 | 9156 | GTCCCTCCAGCTTCGG | 97 | 272 |
| 666275 | 676 | 691 | 9166 | 9181 | CCGGGTGTGGCTGATC | 84 | 273 |
| 666276 | 695 | 710 | 9185 | 9200 | GGACATTGGTACGGGA | 50 | 274 |
| 666277 | 702 | 717 | 9192 | 9207 | CGTCATGGGACATTGG | 44 | 275 |

TABLE 5-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666278 | 725 | 740 | 9215 | 9230 | CAGTGGTGGCCGCGGG | 73 | 276 |
| 666279 | 740 | 755 | 9230 | 9245 | CAAGCTGGGCCTTGCC | 66 | 277 |
| 666280 | 747 | 762 | 9237 | 9252 | ATTTTCACAAGCTGGG | 61 | 278 |
| 666281 | 771 | 786 | 10836 | 10851 | AAAGGTTCCTGTCACC | 62 | 279 |
| 666282 | 775 | 790 | 10840 | 10855 | CATAAAAGGTTCCTGT | 91 | 280 |
| 666283 | 777 | 792 | 10842 | 10857 | AGCATAAAAGGTTCCT | 55 | 281 |
| 666284 | 779 | 794 | 10844 | 10859 | CAAGCATAAAAGGTTC | 71 | 282 |
| 666285 | 781 | 796 | 10846 | 10861 | CACAAGCATAAAAGGT | 74 | 283 |
| 666286 | 784 | 799 | 10849 | 10864 | GGGCACAAGCATAAAA | 80 | 284 |
| 666287 | 827 | 842 | 10892 | 10907 | ATGCTTGGCTCTGTGG | 24 | 285 |
| 666294 | 947 | 962 | 13500 | 13515 | CCATGGGAGATCCGGC | 46 | 286 |
| 666295 | 954 | 969 | 13507 | 13522 | CGTATGTCCATGGGAG | 12 | 287 |
| 666296 | 975 | 990 | 13528 | 13543 | GTCCAGGTTGCTGGCG | 47 | 288 |
| 666297 | 989 | 1004 | 13542 | 13557 | GGGAACAGGACCTGGT | 45 | 289 |
| 666298 | 1008 | 1023 | 13561 | 13576 | GCCATTGTCCTCTGGG | 75 | 290 |
| 666299 | 1015 | 1030 | 13568 | 13583 | TCCTCTGGCCATTGTC | 59 | 291 |
| 666300 | 1033 | 1048 | 13586 | 13601 | GCAGCTTCTCAATGTT | 57 | 292 |
| 666301 | 1042 | 1057 | 13595 | 13610 | GGTGGCTCAGCAGCTT | 63 | 293 |

TABLE 6

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 666302 | 1058 | 1073 | 13611 | 13626 | ACCACGCCCCTCTCCA | 91 | 294 |
| 666303 | 1065 | 1080 | 13618 | 13633 | CCAGAGGACCACGCCC | 72 | 295 |
| 666306 | 1101 | 1116 | 13654 | 13669 | GCACAGTCTTTTCGCA | 80 | 296 |
| 666307 | 1109 | 1124 | 13662 | 13677 | CTGCTCTGGCACAGTC | 17 | 297 |
| 666308 | 1116 | 1131 | 13669 | 13684 | GTAGATCCTGCTCTGG | 55 | 298 |
| 666309 | 1128 | 1143 | 13681 | 13696 | GGGCCCGTCCCAGTAG | 80 | 299 |
| 666311 | 1167 | 1182 | 13720 | 13735 | TCTCTCCAGTTTGTTG | 86 | 300 |
| 666312 | 1188 | 1203 | 13741 | 13756 | AAAGAGCTTGCAGGTC | 63 | 301 |
| 666313 | 1205 | 1220 | 13758 | 13773 | AAGAACTGCTGTGTGT | 88 | 302 |
| 666314 | 1212 | 1227 | N/A | N/A | CTCTGACAAGAACTGC | 70 | 303 |
| 666315 | 1219 | 1234 | N/A | N/A | CTTGCAGCTCTGACAA | 91 | 304 |

TABLE 6-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666317 | 1241 | 1256 | 17034 | 17049 | GAGCGGCCGTGGTGAG | 59 | 305 |
| 666318 | 1248 | 1263 | 17041 | 17056 | TGGCAGGGAGCGGCCG | 89 | 306 |
| 666319 | 1255 | 1270 | 17048 | 17063 | GGAATCTTGGCAGGGA | 52 | 307 |
| 666321 | 1275 | 1290 | 17068 | 17083 | TCCAAAGCATAGAGTC | 47 | 308 |
| 666322 | 1287 | 1302 | 17080 | 17095 | TGGAAACTCCTCTCCA | 84 | 309 |
| 666323 | 1311 | 1326 | 17104 | 17119 | GAGCTTTCTTTGCCTC | 87 | 310 |
| 666324 | 1338 | 1353 | N/A | N/A | TAGCAGAGGTTCTACG | 76 | 311 |
| 666326 | 1347 | 1362 | 19464 | 19479 | TTGTCTGGCTAGCAGA | 55 | 312 |
| 666327 | 1349 | 1364 | 19466 | 19481 | AGTTGTCTGGCTAGCA | 20 | 313 |
| 666328 | 1351 | 1366 | 19468 | 19483 | ATAGTTGTCTGGCTAG | 48 | 314 |
| 666329 | 1353 | 1368 | 19470 | 19485 | ATATAGTTGTCTGGCT | 59 | 315 |
| 666331 | 1381 | 1396 | 19498 | 19513 | AATGTCCACTGTTTTG | 53 | 316 |
| 666333 | 1417 | 1432 | 19534 | 19549 | TGCTGATGTGTTCTGG | 33 | 317 |
| 666335 | 1442 | 1457 | 19559 | 19574 | ATAGATCTGTGGTAAT | 62 | 318 |
| 666336 | 1449 | 1464 | 19566 | 19581 | ATGGCGGATAGATCTG | 43 | 319 |
| 666337 | 1456 | 1471 | 19573 | 19588 | TAGAGGAATGGCGGAT | 55 | 320 |
| 666338 | 1463 | 1478 | 19580 | 19595 | TCTTGAATAGAGGAAT | 58 | 321 |
| 666339 | 1485 | 1500 | 19602 | 19617 | CACTCATCTTGACATT | 64 | 322 |
| 666341 | 1538 | 1553 | 19655 | 19670 | AAGACCCCGTATCCCC | 58 | 323 |
| 666342 | 1686 | 1701 | 19803 | 19818 | AAATCACTTGTCTTGG | 51 | 324 |
| 666343 | 1715 | 1730 | 19832 | 19847 | CTTTCACTAAAGTCAA | 49 | 325 |
| 666344 | 1730 | 1745 | 19847 | 19862 | GCAGTCAATTGGACGC | 23 | 326 |
| 666345 | 1737 | 1752 | 19854 | 19869 | TAAGAGGGCAGTCAAT | 83 | 327 |
| 666346 | 1762 | 1777 | 19879 | 19894 | TCCACTTCTGAATTCC | 81 | 328 |
| 666347 | 1775 | 1790 | 19892 | 19907 | CTGAACTGAAATCTCC | 36 | 329 |
| 666348 | 1782 | 1797 | 19899 | 19914 | TCAACCGCTGAACTGA | 65 | 330 |
| 666349 | 1789 | 1804 | 19906 | 19921 | ATTCTCCTCAACCGCT | 65 | 331 |
| 666351 | 1803 | 1818 | 19920 | 19935 | CTTGTCTCGCCGCAAT | 35 | 332 |
| 666352 | 1810 | 1825 | 19927 | 19942 | TTCCATGCTTGTCTCG | 38 | 333 |
| 666353 | 1826 | 1841 | 19943 | 19958 | TCAGATGTCACTGATT | 65 | 334 |
| 666354 | 1840 | 1855 | 19957 | 19972 | AGCTCATCTGCCAATC | 67 | 335 |
| 666355 | 1848 | 1863 | 19965 | 19980 | TTGAAATAAGCTCATC | 67 | 336 |
| 666356 | 1885 | 1900 | 20002 | 20017 | TCTACAGAACACAAGA | 108 | 337 |
| 666357 | 1892 | 1907 | 20009 | 20024 | ATGGCAGTCTACAGAA | 102 | 338 |
| 666358 | 1899 | 1914 | 20016 | 20031 | ATCAATGATGGCAGTC | 43 | 339 |
| 666359 | 1908 | 1923 | 20025 | 20040 | ACAGTGATCATCAATG | 44 | 340 |
| 666360 | 1915 | 1930 | 20032 | 20047 | AATTTTCACAGTGATC | 66 | 341 |

TABLE 6-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666361 | 1922 | 1937 | 20039 | 20054 | CTTGGTCAATTTTCAC | 47 | 342 |
| 666362 | 1929 | 1944 | 20046 | 20061 | CACATCACTTGGTCAA | 28 | 343 |
| 666363 | 1956 | 1971 | 20073 | 20088 | TAAAGAGCGCATTTCA | 59 | 344 |
| 666364 | 1963 | 1978 | 20080 | 20095 | AACAAATTAAAGAGCG | 77 | 345 |
| 666365 | 1972 | 1987 | 20089 | 20104 | CTAATCTACAACAAAT | 77 | 346 |
| 666366 | 2000 | 2015 | 20117 | 20132 | GCAAGTTTTCTCTGTC | 44 | 347 |
| 666368 | 2023 | 2038 | 20140 | 20155 | CTAGTCAGTGTCAATA | 49 | 348 |
| 666369 | 2030 | 2045 | 20147 | 20162 | CATCACTCTAGTCAGT | 41 | 349 |
| 666370 | 2037 | 2052 | 20154 | 20169 | AAGCAGTCATCACTCT | 62 | 350 |
| 666371 | 2053 | 2068 | 20170 | 20185 | GCACAGACATACCTAC | 54 | 351 |
| 666373 | 2082 | 2097 | 20199 | 20214 | CAATTTACATCTTACT | 79 | 352 |
| 666374 | 2089 | 2104 | 20206 | 20221 | GCTTCTTCAATTTACA | 55 | 353 |
| 666375 | 2130 | 2145 | 20247 | 20262 | GCAGCTCCTACATACA | 47 | 354 |
| 666376 | 2138 | 2153 | 20255 | 20270 | CAAGAACTGCAGCTCC | 53 | 355 |
| 666377 | 2146 | 2161 | 20263 | 20278 | GTCTTCCACAAGAACT | 53 | 356 |
| 666378 | 2153 | 2168 | 20270 | 20285 | AGCAAGTGTCTTCCAC | 25 | 357 |

TABLE 7

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 666379 | 2161 | 2176 | 20278 | 20293 | CTTCACTCAGCAAGTG | 57 | 358 |
| 666380 | 2179 | 2194 | 20296 | 20311 | CAGTCAAAGATTCATT | 60 | 359 |
| 666381 | 2193 | 2208 | 20310 | 20325 | TACAGGCACGGCTTCA | 42 | 360 |
| 666382 | 2200 | 2215 | 20317 | 20332 | CCAAGGCTACAGGCAC | 37 | 361 |
| 666383 | 2207 | 2222 | 20324 | 20339 | GGCCTCCCCAAGGCTA | 82 | 362 |
| 666384 | 2235 | 2250 | 20352 | 20367 | CCAGGAAACCGCTGGC | 62 | 363 |
| 666385 | 2243 | 2258 | 20360 | 20375 | GACCCACACCAGGAAA | 98 | 364 |
| 666386 | 2250 | 2265 | 20367 | 20382 | GCAGAGGGACCCACAC | 79 | 365 |
| 666387 | 2308 | 2323 | 20425 | 20440 | TTACTAACTGGCTTCC | 51 | 366 |
| 666388 | 2315 | 2330 | 20432 | 20447 | AGGAAGTTTACTAACT | 42 | 367 |
| 666389 | 2328 | 2343 | 20445 | 20460 | GACTCAAGAAAATAGG | 36 | 368 |
| 666390 | 2335 | 2350 | 20452 | 20467 | GTTTTTTGACTCAAGA | 33 | 369 |
| 666392 | 2355 | 2370 | 20472 | 20487 | CATCCAAGAGTAGCGC | 27 | 370 |

TABLE 7-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666393 | 2376 | 2391 | 20493 | 20508 | GTAGGACAGACAAAAA | 77 | 371 |
| 666394 | 2383 | 2398 | 20500 | 20515 | CTAGATTGTAGGACAG | 52 | 372 |
| 666395 | 2390 | 2405 | 20507 | 20522 | GACATTACTAGATTGT | 30 | 373 |
| 666396 | 2397 | 2412 | 20514 | 20529 | TTACTTAGACATTACT | 52 | 374 |
| 666397 | 2404 | 2419 | 20521 | 20536 | TTAACCATTACTTAGA | 55 | 375 |
| 666398 | 2435 | 2450 | 20552 | 20567 | GAGGGTCAAAAGATG | 67 | 376 |
| 666399 | 2450 | 2465 | 20567 | 20582 | GCATCTCTAAAGAATG | 39 | 377 |
| 666400 | 2461 | 2476 | 20578 | 20593 | GAAGAATTTTAGCATC | 44 | 378 |
| 666401 | 2468 | 2483 | 20585 | 20600 | TTTATGCGAAGAATTT | 67 | 379 |
| 666402 | 2475 | 2490 | 20592 | 20607 | CTTCTTCTTTATGCGA | 34 | 380 |
| 666403 | 2498 | 2513 | 20615 | 20630 | TTAAGATTTATGTTCC | 36 | 381 |
| 666404 | 2514 | 2529 | 20631 | 20646 | GGCAACAGTTCAAGTA | 43 | 382 |
| 666405 | 2521 | 2536 | 20638 | 20653 | ACAGAAGGGCAACAGT | 57 | 383 |
| 666406 | 2528 | 2543 | 20645 | 20660 | TACTTGGACAGAAGGG | 38 | 384 |
| 666407 | 2535 | 2550 | 20652 | 20667 | AGTTAAGTACTTGGAC | 58 | 385 |
| 666408 | 2542 | 2557 | 20659 | 20674 | AACAGATAGTTAAGTA | 81 | 386 |
| 666409 | 2578 | 2593 | 20695 | 20710 | GCCAAACAAACAGAGG | 78 | 387 |
| 666410 | 2585 | 2600 | 20702 | 20717 | CTGGACAGCCAAACAA | 79 | 388 |
| 666411 | 2592 | 2607 | 20709 | 20724 | CTGATCGCTGGACAGC | 80 | 389 |
| 666412 | 2599 | 2614 | 20716 | 20731 | GCCATGGCTGATCGCT | 70 | 390 |
| 666413 | 2606 | 2621 | 20723 | 20738 | TAGTGTCGCCATGGCT | 31 | 391 |
| 666414 | 2613 | 2628 | 20730 | 20745 | CCTCCTTTAGTGTCGC | 35 | 392 |
| 666415 | 2621 | 2636 | 20738 | 20753 | CGGCTCCTCCTCCTTT | 89 | 393 |
| 666416 | 2628 | 2643 | 20745 | 20760 | GAGTCCCCGGCTCCTC | 75 | 394 |
| 666417 | 2652 | 2667 | 20769 | 20784 | TCCTGGCAGTGCTCTC | 40 | 395 |
| 666418 | 2659 | 2674 | 20776 | 20791 | TGGTGGGTCCTGGCAG | 77 | 396 |
| 666420 | 2673 | 2688 | 20790 | 20805 | CATCCTGCTTCCAGTG | 70 | 397 |
| 666421 | 2681 | 2696 | 20798 | 20813 | GTCAGCTCCATCCTGC | 48 | 398 |
| 666422 | 2688 | 2703 | 20805 | 20820 | TTCCGTAGTCAGCTCC | 32 | 399 |
| 666423 | 2698 | 2713 | 20815 | 20830 | GAGTGTGCAGTTCCGT | 33 | 400 |
| 666424 | 2705 | 2720 | 20822 | 20837 | GCCCACTGAGTGTGCA | 90 | 401 |
| 666425 | 2714 | 2729 | 20831 | 20846 | GCAGAAACAGCCCACT | 59 | 402 |
| 666426 | 2737 | 2752 | 20854 | 20869 | GAAGCATAGAACAGAT | 49 | 403 |
| 666427 | 2744 | 2759 | 20861 | 20876 | GCACGAGGAAGCATAG | 42 | 404 |
| 666428 | 2749 | 2764 | 20866 | 20881 | AATTGGCACGAGGAAG | 72 | 405 |
| 666429 | 2751 | 2766 | 20868 | 20883 | ATAATTGGCACGAGGA | 33 | 406 |
| 666430 | 2753 | 2768 | 20870 | 20885 | CTATAATTGGCACGAG | 37 | 407 |

TABLE 7-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666431 | 2755 | 2770 | 20872 | 20887 | AACTATAATTGGCACG | 27 | 408 |
| 666432 | 2757 | 2772 | 20874 | 20889 | CAAACTATAATTGGCA | 47 | 409 |
| 666433 | 2759 | 2774 | 20876 | 20891 | GTCAAACTATAATTGG | 39 | 410 |
| 666434 | 2765 | 2780 | 20882 | 20897 | GGCCCTGTCAAACTAT | 60 | 411 |
| 666435 | 2772 | 2787 | 20889 | 20904 | ATTTTAAGGCCCTGTC | 66 | 412 |
| 666436 | 2779 | 2794 | 20896 | 20911 | CCAAGTAATTTTAAGG | 66 | 413 |
| 666437 | 2793 | 2808 | 20910 | 20925 | GCATTTGGAAAAAGCC | 29 | 414 |
| 666438 | 2810 | 2825 | 20927 | 20942 | GGATTCTATAAATAGA | 75 | 415 |
| 666439 | 2820 | 2835 | 20937 | 20952 | GAGGTCTTTGGGATTC | 26 | 416 |
| 666440 | 2827 | 2842 | 20944 | 20959 | GCAAGTGGAGGTCTTT | 26 | 417 |
| 666441 | 2834 | 2849 | 20951 | 20966 | TACTTAAGCAAGTGGA | 25 | 418 |
| 666442 | 2841 | 2856 | 20958 | 20973 | ATAGGTATACTTAAGC | 20 | 419 |
| 666443 | 2848 | 2863 | 20965 | 20980 | GTAAGTGATAGGTATA | 24 | 420 |
| 666444 | 2872 | 2887 | 20989 | 21004 | GTACTTTCTCAAAACC | 30 | 421 |
| 666445 | 2879 | 2894 | 20996 | 21011 | TACTGCTGTACTTTCT | 57 | 422 |
| 666446 | 2886 | 2901 | 21003 | 21018 | CCCAGTCTACTGCTGT | 34 | 423 |
| 666447 | 2902 | 2917 | 21019 | 21034 | GGCCTGGAGGTGACGC | 59 | 424 |
| 666448 | 2909 | 2924 | 21026 | 21041 | GAGAAACGGCCTGGAG | 56 | 425 |
| 666449 | 2916 | 2931 | 21033 | 21048 | GTAGTATGAGAAACGG | 17 | 426 |
| 666450 | 2923 | 2938 | 21040 | 21055 | ATATCCTGTAGTATGA | 43 | 427 |
| 666451 | 2930 | 2945 | 21047 | 21062 | ATAGTAAATATCCTGT | 64 | 428 |
| 666452 | 2940 | 2955 | 21057 | 21072 | CCTGGGAGTAATAGTA | 47 | 429 |
| 666453 | 2947 | 2962 | 21064 | 21079 | TGCTGATCCTGGGAGT | 21 | 430 |
| 666454 | 2954 | 2969 | 21071 | 21086 | AATCTTCTGCTGATCC | 28 | 431 |
| 666455 | 2961 | 2976 | 21078 | 21093 | GCTACGCAATCTTCTG | 42 | 432 |

TABLE 8

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 20 | 195 |
| 666457 | 2975 | 2990 | 21092 | 21107 | ACACACATTTGAGAGC | 34 | 433 |
| 666458 | 2992 | 3007 | 21109 | 21124 | CCATTAGAAAAGCAGG | 20 | 434 |
| 666459 | 3021 | 3036 | 21138 | 21153 | TAGGTGCTTGTTGAAT | 50 | 435 |
| 666460 | 3031 | 3046 | 21148 | 21163 | AGGCACTTACTAGGTG | 46 | 436 |

TABLE 8-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666461 | 3039 | 3054 | 21156 | 21171 | GATACAGCAGGCACTT | 37 | 437 |
| 666462 | 3046 | 3061 | 21163 | 21178 | ATGTAGGGATACAGCA | 26 | 438 |
| 666463 | 3053 | 3068 | 21170 | 21185 | CTGTGTAATGTAGGGA | 58 | 439 |
| 666464 | 3060 | 3075 | 21177 | 21192 | GGCTGAACTGTGTAAT | 28 | 440 |
| 666465 | 3067 | 3082 | 21184 | 21199 | TGATAAAGGCTGAACT | 59 | 441 |
| 666466 | 3074 | 3089 | 21191 | 21206 | CTAAGCTTGATAAAGG | 46 | 442 |
| 666467 | 3085 | 3100 | 21202 | 21217 | CTCACTGCTCACTAAG | 36 | 443 |
| 666468 | 3092 | 3107 | 21209 | 21224 | TTCAGTGCTCACTGCT | 31 | 444 |
| 666469 | 3099 | 3114 | 21216 | 21231 | ATAATGTTTCAGTGCT | 24 | 445 |
| 666470 | 3136 | 3151 | 21253 | 21268 | CTGACTTTAATATTAG | 44 | 446 |
| 666471 | 3178 | 3193 | 21295 | 21310 | GTCTTTTCTGTAGTTA | 10 | 447 |
| 666472 | 3192 | 3207 | 21309 | 21324 | GTTCTCTACTGTTTGT | 32 | 448 |
| 666473 | 3239 | 3254 | 21356 | 21371 | GGAGAATTTGGGCTGG | 25 | 449 |
| 666474 | 3246 | 3261 | 21363 | 21378 | TTAGAGAGGAGAATTT | 65 | 450 |
| 666475 | 3253 | 3268 | 21370 | 21385 | GACACTTTTAGAGAGG | 13 | 451 |
| 666476 | 3260 | 3275 | 21377 | 21392 | TCTTGTGGACACTTTT | 35 | 452 |
| 666477 | 3267 | 3282 | 21384 | 21399 | CACCCCTTCTTGTGGA | 60 | 453 |
| 666478 | 3274 | 3289 | 21391 | 21406 | GAATAAACACCCCTTC | 56 | 454 |
| 666479 | 3288 | 3303 | 21405 | 21420 | GAAATGTGTTGGAAGA | 32 | 455 |
| 666480 | 3335 | 3350 | 21452 | 21467 | ACTCCATGAGGTTTTC | 27 | 456 |
| 666481 | 3337 | 3352 | 21454 | 21469 | TGACTCCATGAGGTTT | 35 | 457 |
| 666482 | 3339 | 3354 | 21456 | 21471 | GATGACTCCATGAGGT | 33 | 458 |
| 666483 | 3341 | 3356 | 21458 | 21473 | AAGATGACTCCATGAG | 36 | 459 |
| 666485 | 3355 | 3370 | 21472 | 21487 | ATGAAAGTGTGTGCAA | 36 | 460 |
| 666486 | 3362 | 3377 | 21479 | 21494 | GCACTGCATGAAAGTG | 60 | 461 |
| 666487 | 3371 | 3386 | 21488 | 21503 | CTACAAAGAGCACTGC | 47 | 462 |
| 666488 | 3378 | 3393 | 21495 | 21510 | CTGTTAGCTACAAAGA | 44 | 463 |
| 666489 | 3385 | 3400 | 21502 | 21517 | ATCTTCACTGTTAGCT | 26 | 464 |
| 666490 | 3392 | 3407 | 21509 | 21524 | GAGGTAAATCTTCACT | 30 | 465 |
| 666491 | 3399 | 3414 | 21516 | 21531 | GCAGAACGAGGTAAAT | 38 | 466 |
| 666492 | 3406 | 3421 | 21523 | 21538 | CCTCTGAGCAGAACGA | 24 | 467 |
| 666493 | 3413 | 3428 | 21530 | 21545 | AGCAAGGCCTCTGAGC | 45 | 468 |
| 666494 | 3420 | 3435 | 21537 | 21552 | GCTCCACAGCAAGGCC | 42 | 469 |
| 666495 | 3427 | 3442 | 21544 | 21559 | CAGTGGAGCTCCACAG | 59 | 470 |
| 666496 | 3432 | 3447 | 21549 | 21564 | CATGGCAGTGGAGCTC | 13 | 471 |
| 666497 | 3434 | 3449 | 21551 | 21566 | TACATGGCAGTGGAGC | 29 | 472 |
| 666498 | 3436 | 3451 | 21553 | 21568 | GGTACATGGCAGTGGA | 13 | 473 |

TABLE 8-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666499 | 3438 | 3453 | 21555 | 21570 | TGGGTACATGGCAGTG | 26 | 474 |
| 666500 | 3440 | 3455 | 21557 | 21572 | ACTGGGTACATGGCAG | 41 | 475 |
| 666501 | 3442 | 3457 | 21559 | 21574 | CTACTGGGTACATGGC | 16 | 476 |
| 666502 | 3448 | 3463 | 21565 | 21580 | CAAACCCTACTGGGTA | 68 | 477 |
| 666503 | 3455 | 3470 | 21572 | 21587 | GAAATGTCAAACCCTA | 29 | 478 |
| 666504 | 3462 | 3477 | 21579 | 21594 | GGCTAATGAAATGTCA | 36 | 479 |
| 666505 | 3469 | 3484 | 21586 | 21601 | GTTGCATGGCTAATGA | 39 | 480 |
| 666506 | 3476 | 3491 | 21593 | 21608 | TATCCATGTTGCATGG | 39 | 481 |
| 666507 | 3491 | 3506 | 21608 | 21623 | CTGCTGCCCAATACAT | 53 | 482 |
| 666508 | 3498 | 3513 | 21615 | 21630 | ACACAGTCTGCTGCCC | 49 | 483 |
| 666509 | 3505 | 3520 | 21622 | 21637 | TCACGAAACACAGTCT | 32 | 484 |
| 666510 | 3512 | 3527 | 21629 | 21644 | CTGCAGTTCACGAAAC | 62 | 485 |
| 666511 | 3519 | 3534 | 21636 | 21651 | TACATCACTGCAGTTC | 32 | 486 |
| 666512 | 3526 | 3541 | 21643 | 21658 | AGATGTATACATCACT | 24 | 487 |
| 666513 | 3548 | 3563 | 21665 | 21680 | CCCAAAATACTTTGCA | 36 | 488 |
| 666514 | 3558 | 3573 | 21675 | 21690 | GATAATATACCCCAAA | 67 | 489 |
| 666515 | 3565 | 3580 | 21682 | 21697 | CCCTTAGGATAATATA | 51 | 490 |
| 666516 | 3572 | 3587 | 21689 | 21704 | TTATCTTCCCTTAGGA | 72 | 491 |
| 666517 | 3599 | 3614 | 21716 | 21731 | GTGAAACAGCAGTTCT | 38 | 492 |
| 666518 | 3606 | 3621 | 21723 | 21738 | GGGCCCGTGAAACAG | 67 | 493 |
| 666519 | 3613 | 3628 | 21730 | 21745 | CAGGTAAGGGCCCCGT | 30 | 494 |
| 666520 | 3620 | 3635 | 21737 | 21752 | AGGGTCACAGGTAAGG | 32 | 495 |
| 666521 | 3627 | 3642 | 21744 | 21759 | AGCAAAGAGGGTCACA | 32 | 496 |
| 666522 | 3642 | 3657 | 21759 | 21774 | GGTTAAATATTCTTCA | 52 | 497 |
| 666523 | 3661 | 3676 | 21778 | 21793 | TCTTTGAAGTGCTGTG | 43 | 498 |
| 666524 | 3668 | 3683 | 21785 | 21800 | GACAGCTTCTTTGAAG | 64 | 499 |
| 666525 | 3675 | 3690 | 21792 | 21807 | CTTCCAAGACAGCTTC | 37 | 500 |
| 666526 | 3682 | 3697 | 21799 | 21814 | AGACAGACTTCCAAGA | 64 | 501 |
| 666527 | 3689 | 3704 | 21806 | 21821 | GCTCCTGAGACAGACT | 44 | 502 |
| 666528 | 3696 | 3711 | 21813 | 21828 | ACAGGGTGCTCCTGAG | 77 | 503 |
| 666529 | 3710 | 3725 | 21827 | 21842 | GGAGAATTAAGAAGAC | 68 | 504 |
| 666530 | 3721 | 3736 | 21838 | 21853 | AGCATCCGCTTGGAGA | 63 | 505 |
| 666531 | 3728 | 3743 | 21845 | 21860 | GAAATGGAGCATCCGC | 68 | 506 |
| 666532 | 3735 | 3750 | 21852 | 21867 | AGCAATTGAAATGGAG | 78 | 507 |

TABLE 9

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 20 | 195 |
| 666533 | 3742 | 3757 | 21859 | 21874 | GTCACAAAGCAATTGA | 33 | 508 |
| 666534 | 3786 | 3801 | 21903 | 21918 | CACTGTTAAAGCAGCA | 19 | 509 |
| 666535 | 3793 | 3808 | 21910 | 21925 | TCAGCTCCACTGTTAA | 27 | 510 |
| 666537 | 3824 | 3839 | 21941 | 21956 | GGCCCCAGCCAAGAAG | 92 | 511 |
| 666538 | 3831 | 3846 | 21948 | 21963 | AGGTAGTGGCCCCAGC | 40 | 512 |
| 666539 | 3865 | 3880 | 21982 | 21997 | GTCAACATACACATAG | 42 | 513 |
| 666540 | 3886 | 3901 | 22003 | 22018 | GATCACTCAGAATTTT | 50 | 514 |
| 666541 | 3893 | 3908 | 22010 | 22025 | TACCCTGGATCACTCA | 35 | 515 |
| 666542 | 3900 | 3915 | 22017 | 22032 | TAGGTCATACCCTGGA | 28 | 516 |
| 666543 | 3907 | 3922 | 22024 | 22039 | CATTCCCTAGGTCATA | 46 | 517 |
| 666544 | 3915 | 3930 | 22032 | 22047 | AGCTAGTTCATTCCCT | 52 | 518 |
| 666545 | 3922 | 3937 | 22039 | 22054 | ATTTCATAGCTAGTTC | 56 | 519 |
| 666546 | 3929 | 3944 | 22046 | 22061 | CCTGAGTATTTCATAG | 58 | 520 |
| 666547 | 3936 | 3951 | 22053 | 22068 | TCCTAACCCTGAGTAT | 73 | 521 |
| 666548 | 3950 | 3965 | 22067 | 22082 | ACAAGTGCTAGGATTC | 33 | 522 |
| 666549 | 3957 | 3972 | 22074 | 22089 | TCCTGAGACAAGTGCT | 45 | 523 |
| 666550 | 3964 | 3979 | 22081 | 22096 | TTCAGAGTCCTGAGAC | 54 | 524 |
| 666551 | 3968 | 3983 | 22085 | 22100 | CCTTTTCAGAGTCCTG | 42 | 525 |
| 666552 | 3972 | 3987 | 22089 | 22104 | CGTTCCTTTTCAGAGT | 70 | 526 |
| 666553 | 3974 | 3989 | 22091 | 22106 | GCCGTTCCTTTTCAGA | 38 | 527 |
| 666554 | 3976 | 3991 | 22093 | 22108 | AAGCCGTTCCTTTTCA | 71 | 528 |
| 666555 | 3982 | 3997 | 22099 | 22114 | ATGAGGAAGCCGTTCC | 42 | 529 |
| 666556 | 3996 | 4011 | 22113 | 22128 | TATCAAGACAAGGAAT | 93 | 530 |
| 666557 | 4003 | 4018 | 22120 | 22135 | TCCACTTTATCAAGAC | 35 | 531 |
| 666559 | 4017 | 4032 | 22134 | 22149 | TCTAGTTTGCCAATTC | 38 | 532 |
| 666560 | 4024 | 4039 | 22141 | 22156 | ACTAAATTCTAGTTTG | 100 | 533 |
| 666561 | 4035 | 4050 | 22152 | 22167 | ACTGAGTACAAACTAA | 68 | 534 |
| 666562 | 4042 | 4057 | 22159 | 22174 | ACTGTCCACTGAGTAC | 39 | 535 |
| 666563 | 4049 | 4064 | 22166 | 22181 | CAACAGCACTGTCCAC | 57 | 536 |
| 666564 | 4056 | 4071 | 22173 | 22188 | AAATCTTCAACAGCAC | 55 | 537 |
| 666565 | 4063 | 4078 | 22180 | 22195 | AGTCCTCAAATCTTCA | 46 | 538 |
| 666566 | 4071 | 4086 | 22188 | 22203 | CTTTAACAAGTCCTCA | 48 | 539 |
| 666567 | 4078 | 4093 | 22195 | 22210 | CAGTGCTCTTTAACAA | 63 | 540 |
| 666568 | 4085 | 4100 | 22202 | 22217 | TATGACCCAGTGCTCT | 60 | 541 |
| 666569 | 4093 | 4108 | 22210 | 22225 | TTTTTCCATATGACCC | 25 | 542 |
| 666570 | 4107 | 4122 | 22224 | 22239 | GGAGACACATACATTT | 78 | 543 |

TABLE 9-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666571 | 4117 | 4132 | 22234 | 22249 | AATGCACCTGGGAGAC | 38 | 544 |
| 666572 | 4124 | 4139 | 22241 | 22256 | ACCAAGAAATGCACCT | 43 | 545 |
| 666573 | 4134 | 4149 | 22251 | 22266 | CAAGACATAAACCAAG | 49 | 546 |
| 666574 | 4169 | 4184 | 22286 | 22301 | CTTGAGGTTTTCCTAA | 60 | 547 |
| 666575 | 4171 | 4186 | 22288 | 22303 | TGCTTGAGGTTTTCCT | 20 | 548 |
| 666576 | 4177 | 4192 | 22294 | 22309 | AATTACTGCTTGAGGT | 42 | 549 |
| 666577 | 4185 | 4200 | 22302 | 22317 | GAGATATTAATTACTG | 37 | 550 |
| 666578 | 4192 | 4207 | 22309 | 22324 | GTTCCAGGAGATATTA | 48 | 551 |
| 666579 | 4199 | 4214 | 22316 | 22331 | CTATAGTGTTCCAGGA | 34 | 552 |
| 666580 | 4206 | 4221 | 22323 | 22338 | TGGTTCTCTATAGTGT | 29 | 553 |
| 666581 | 4213 | 4228 | 22330 | 22345 | GGTCACTTGGTTCTCT | 21 | 554 |
| 666582 | 4220 | 4235 | 22337 | 22352 | ATGAGTCGGTCACTTG | 22 | 555 |
| 666583 | 4221 | 4236 | 22338 | 22353 | AATGAGTCGGTCACTT | 54 | 556 |
| 666584 | 4223 | 4238 | 22340 | 22355 | TAAATGAGTCGGTCAC | 24 | 557 |
| 666585 | 4225 | 4240 | 22342 | 22357 | TGTAAATGAGTCGGTC | 31 | 558 |
| 666586 | 4227 | 4242 | 22344 | 22359 | GTTGTAAATGAGTCGG | 13 | 559 |
| 666587 | 4229 | 4244 | 22346 | 22361 | CAGTTGTAAATGAGTC | 11 | 560 |
| 666588 | 4231 | 4246 | 22348 | 22363 | TTCAGTTGTAAATGAG | 44 | 561 |
| 666589 | 4237 | 4252 | 22354 | 22369 | CTAGGTTTCAGTTGTA | 46 | 562 |
| 666590 | 4244 | 4259 | 22361 | 22376 | GGGCTTCCTAGGTTTC | 61 | 563 |
| 666591 | 4272 | 4287 | 22389 | 22404 | AACTCTCCTGTTTTCG | 58 | 564 |
| 666592 | 4279 | 4294 | 22396 | 22411 | GGCGACTAACTCTCCT | 37 | 565 |
| 666593 | 4286 | 4301 | 22403 | 22418 | TCTGTAGGGCGACTAA | 35 | 566 |
| 666594 | 4294 | 4309 | 22411 | 22426 | CTGGGTTTTCTGTAGG | 52 | 567 |
| 666595 | 4301 | 4316 | 22418 | 22433 | AGTCTAGCTGGGTTTT | 37 | 568 |
| 666596 | 4308 | 4323 | 22425 | 22440 | ACCCAATAGTCTAGCT | 75 | 569 |
| 666598 | 4322 | 4337 | 22439 | 22454 | TCTTTTTAGTTCATAC | 74 | 570 |
| 666599 | 4330 | 4345 | 22447 | 22462 | GCACAGTCTCTTTTTA | 64 | 571 |
| 666600 | 4337 | 4352 | 22454 | 22469 | CACCATGGCACAGTCT | 21 | 572 |
| 666601 | 4344 | 4359 | 22461 | 22476 | TTTTTCTCACCATGGC | 26 | 573 |
| 666602 | 4365 | 4380 | 22482 | 22497 | ATTTCACTGTAGGATT | 62 | 574 |
| 666603 | 4372 | 4387 | 22489 | 22504 | GCTGCTCATTTCACTG | 59 | 575 |
| 666604 | 4379 | 4394 | 22496 | 22511 | TGTAAGGGCTGCTCAT | 51 | 576 |
| 666605 | 4386 | 4401 | 22503 | 22518 | ACAATACTGTAAGGGC | 25 | 577 |
| 666607 | 4407 | 4422 | 22524 | 22539 | ACCTACCTGCCCTTGG | 72 | 578 |

TABLE 9-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666608 | 4414 | 4429 | 22531 | 22546 | CACTAATACCTACCTG | 94 | 579 |
| 666609 | 4425 | 4440 | 22542 | 22557 | GCTTTTTCAAACACTA | 32 | 580 |

TABLE 10

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 25 | 195 |
| 666610 | 4434 | 4449 | 22551 | 22566 | CAAAGACCAGCTTTTT | 50 | 581 |
| 666611 | 4441 | 4456 | 22558 | 22573 | CCTCGCTCAAAGACCA | 50 | 582 |
| 666612 | 4448 | 4463 | 22565 | 22580 | TTTATGCCCTCGCTCA | 76 | 583 |
| 666613 | 4455 | 4470 | 22572 | 22587 | AGCTGTATTTATGCCC | 42 | 584 |
| 666614 | 4474 | 4489 | 22591 | 22606 | TTGTTCCACCCCTGGG | 53 | 585 |
| 666615 | 4483 | 4498 | 22600 | 22615 | CTCCCAGAGTTGTTCC | 66 | 586 |
| 666616 | 4491 | 4506 | 22608 | 22623 | ACCCAAGACTCCCAGA | 55 | 587 |
| 666617 | 4498 | 4513 | 22615 | 22630 | TGCGAGTACCCAAGAC | 41 | 588 |
| 666618 | 4505 | 4520 | 22622 | 22637 | CAAGAGGTGCGAGTAC | 78 | 589 |
| 666619 | 4520 | 4535 | 22637 | 22652 | GAGCATCAACAAAGCC | 42 | 590 |
| 666620 | 4527 | 4542 | 22644 | 22659 | CCTGGCGGAGCATCAA | 58 | 591 |
| 666621 | 4534 | 4549 | 22651 | 22666 | TGGCCTTCCTGGCGGA | 91 | 592 |
| 666622 | 4541 | 4556 | 22658 | 22673 | ACACAAGTGGCCTTCC | 69 | 593 |
| 666623 | 4575 | 4590 | 22692 | 22707 | CTGAATTGTTACTAAA | 79 | 594 |
| 666624 | 4582 | 4597 | 22699 | 22714 | ACTGGATCTGAATTGT | 43 | 595 |
| 666625 | 4589 | 4604 | 22706 | 22721 | AGTTTACACTGGATCT | 26 | 596 |
| 666626 | 4603 | 4618 | 22720 | 22735 | GAGCAATGAACGGAAG | 28 | 597 |
| 666627 | 4612 | 4627 | 22729 | 22744 | GTGACTGGAGAGCAAT | 26 | 598 |
| 666628 | 4641 | 4656 | 22758 | 22773 | AACTTTCACCTGTGGG | 50 | 599 |
| 666629 | 4669 | 4684 | 22786 | 22801 | CCTTAACCAATCCCAA | 57 | 600 |
| 666630 | 4676 | 4691 | 22793 | 22808 | ATAAAGACCTTAACCA | 73 | 601 |
| 666631 | 4686 | 4701 | 22803 | 22818 | CGTAATACAAATAAAG | 97 | 602 |
| 666632 | 4719 | 4734 | 22836 | 22851 | GATGCAGCTGGCCACA | 27 | 603 |
| 666633 | 4731 | 4746 | 22848 | 22863 | ACCATTCAGACAGATG | 70 | 604 |
| 666634 | 4738 | 4753 | 22855 | 22870 | TTCACGCACCATTCAG | 84 | 605 |
| 666635 | 4745 | 4760 | 22862 | 22877 | GAGAGCCTTCACGCAC | 77 | 606 |
| 666636 | 4752 | 4767 | 22869 | 22884 | AAGGTCTGAGAGCCTT | 83 | 607 |

TABLE 10-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666637 | 4759 | 4774 | 22876 | 22891 | GGTGTGTAAGGTCTGA | 59 | 608 |
| 666638 | 4766 | 4781 | 22883 | 22898 | ACAAAATGGTGTGTAA | 93 | 609 |
| 666639 | 4780 | 4795 | 22897 | 22912 | GTAAACATAACTTAC | 92 | 610 |
| 666640 | 4807 | 4822 | 22924 | 22939 | TCGAGATCAGTCTCAA | 18 | 611 |
| 666641 | 4814 | 4829 | 22931 | 22946 | ACCTGCATCGAGATCA | 47 | 612 |
| 666642 | 4825 | 4840 | 22942 | 22957 | CAAGGAGATCCACCTG | 121 | 613 |
| 666643 | 4836 | 4851 | 22953 | 22968 | TATCAGGATCTCAAGG | 94 | 614 |
| 666644 | 4843 | 4858 | 22960 | 22975 | AACAGGCTATCAGGAT | 83 | 615 |
| 666645 | 4850 | 4865 | 22967 | 22982 | TTCCTGTAACAGGCTA | 23 | 616 |
| 666646 | 4866 | 4881 | 22983 | 22998 | ACTGACCTTTACTTCA | 57 | 617 |
| 666647 | 4898 | 4913 | 23015 | 23030 | CCTCAAAGCTGTGAAA | 80 | 618 |
| 666648 | 4905 | 4920 | 23022 | 23037 | GCATGTTCCTCAAAGC | 24 | 619 |
| 666649 | 4912 | 4927 | 23029 | 23044 | TTCTTATGCATGTTCC | 20 | 620 |
| 666650 | 4919 | 4934 | 23036 | 23051 | GCTACATTTCTTATGC | 80 | 621 |
| 666651 | 4927 | 4942 | 23044 | 23059 | CTACTTCAGCTACATT | 53 | 622 |
| 666652 | 4934 | 4949 | 23051 | 23066 | GTCCCCTCTACTTCAG | 59 | 623 |
| 666653 | 4949 | 4964 | 23066 | 23081 | TGGCCCTTCTCTCACG | 89 | 624 |
| 666654 | 4956 | 4971 | 23073 | 23088 | GCCGGCCTGGCCCTTC | 114 | 625 |
| 666655 | 4963 | 4978 | 23080 | 23095 | TTGGCCTGCCGGCCTG | 96 | 626 |
| 666656 | 4970 | 4985 | 23087 | 23102 | AGGAGGGTTGGCCTGC | 96 | 627 |
| 666657 | 4977 | 4992 | 23094 | 23109 | CCATTGGAGGAGGGTT | 68 | 628 |
| 666658 | 4982 | 4997 | 23099 | 23114 | AATTTCCATTGGAGGA | 67 | 629 |
| 666659 | 4984 | 4999 | 23101 | 23116 | GGAATTTCCATTGGAG | 56 | 630 |
| 666660 | 4986 | 5001 | 23103 | 23118 | CGGGAATTTCCATTGG | 50 | 631 |
| 666661 | 4988 | 5003 | 23105 | 23120 | CACGGGAATTTCCATT | 29 | 632 |
| 666662 | 4990 | 5005 | 23107 | 23122 | AACACGGGAATTTCCA | 27 | 633 |
| 666663 | 4992 | 5007 | 23109 | 23124 | GCAACACGGGAATTTC | 26 | 634 |
| 666664 | 5005 | 5020 | 23122 | 23137 | GTCTCAGTTTGAAGCA | 26 | 635 |
| 666665 | 5012 | 5027 | 23129 | 23144 | CCCATCTGTCTCAGTT | 34 | 636 |
| 666666 | 5019 | 5034 | 23136 | 23151 | GTTAAGTCCCATCTGT | 60 | 637 |
| 666667 | 5026 | 5041 | 23143 | 23158 | ATTGCCTGTTAAGTCC | 27 | 638 |
| 666668 | 5086 | 5101 | 23203 | 23218 | GGCAGTTCTTTCAGCA | 63 | 639 |
| 666669 | 5093 | 5108 | 23210 | 23225 | ACCTGCTGGCAGTTCT | 39 | 640 |
| 666670 | 5100 | 5115 | 23217 | 23232 | GGGTCCTACCTGCTGG | 64 | 641 |
| 666671 | 5124 | 5139 | 23241 | 23256 | CAAGCTTTCATTTGGG | 26 | 642 |
| 666672 | 5131 | 5146 | 23248 | 23263 | GGAAATTCAAGCTTTC | 36 | 643 |
| 666673 | 5147 | 5162 | 23264 | 23279 | ACGCAGAGCCAGTAGG | 50 | 644 |

TABLE 10-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666674 | 5149 | 5164 | 23266 | 23281 | AAACGCAGAGCCAGTA | 63 | 645 |
| 666675 | 5151 | 5166 | 23268 | 23283 | CAAAACGCAGAGCCAG | 42 | 646 |
| 666676 | 5171 | 5186 | 23288 | 23303 | TCCTTTCCTACAGATC | 67 | 647 |
| 666677 | 5179 | 5194 | 23296 | 23311 | GTGAAGCATCCTTTCC | 37 | 648 |
| 666678 | 5186 | 5201 | 23303 | 23318 | TCAGTTTGTGAAGCAT | 11 | 649 |
| 666679 | 5193 | 5208 | 23310 | 23325 | ATCTACCTCAGTTTGT | 58 | 650 |
| 666680 | 5200 | 5215 | 23317 | 23332 | TAGCATTATCTACCTC | 34 | 651 |
| 666681 | 5207 | 5222 | 23324 | 23339 | GACAGCATAGCATTAT | 23 | 652 |
| 666682 | 5214 | 5229 | 23331 | 23346 | TACCAACGACAGCATA | 39 | 653 |
| 666683 | 5221 | 5236 | 23338 | 23353 | TGATGTATACCAACGA | 13 | 654 |
| 666684 | 5246 | 5261 | 23363 | 23378 | GCAGAGCAATTTACAT | 34 | 655 |
| 666685 | 5253 | 5268 | 23370 | 23385 | TTGCTTTGCAGAGCAA | 72 | 656 |

TABLE 11

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 15 | 195 |
| 666688 | N/A | N/A | 18773 | 18788 | CTTAAGCTAAACTCCT | 73 | 657 |
| 666689 | N/A | N/A | 18780 | 18795 | ATGACGACTTAAGCTA | 38 | 658 |
| 666690 | N/A | N/A | 18803 | 18818 | ATATTAGAGACTGTAT | 75 | 659 |
| 666691 | N/A | N/A | 18817 | 18832 | CTCCATCAATCATGAT | 67 | 660 |
| 666692 | N/A | N/A | 18824 | 18839 | GAATGCTCTCCATCAA | 55 | 661 |
| 666693 | N/A | N/A | 18831 | 18846 | GCAAGCTGAATGCTCT | 47 | 662 |
| 666694 | N/A | N/A | 18838 | 18853 | ATCTAAGGCAAGCTGA | 63 | 663 |
| 666695 | N/A | N/A | 18845 | 18860 | TTACAGCATCTAAGGC | 79 | 664 |
| 666696 | N/A | N/A | 18866 | 18881 | AATGTTCAGCTTTTCC | 37 | 665 |
| 666697 | N/A | N/A | 18873 | 18888 | ACGCCTTAATGTTCAG | 23 | 666 |
| 666699 | N/A | N/A | 22817 | 22832 | GACTTCGGGAGATACG | 86 | 667 |
| 666700 | N/A | N/A | 22824 | 22839 | CACAGAGGACTTCGGG | 51 | 668 |
| 666701 | N/A | N/A | 3917 | 3932 | CCCTTCCCGCTCCGAA | 84 | 669 |
| 666702 | N/A | N/A | 4018 | 4033 | AGGCTCGGGCAGAGCC | 99 | 670 |
| 666703 | N/A | N/A | 4254 | 4269 | GAGCACCGCGCCGGAG | 93 | 671 |
| 666704 | N/A | N/A | 4288 | 4303 | ATGTGGAGCTCCTCCT | 80 | 672 |
| 666705 | N/A | N/A | 4546 | 4561 | GCCCCGAATAGGACCC | 79 | 673 |

TABLE 11-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666706 | N/A | N/A | 4593 | 4608 | CCGGGTTCCTCCACCC | 91 | 674 |
| 666707 | N/A | N/A | 4653 | 4668 | CCTGGCGGCCTCCACG | 131 | 675 |
| 666709 | N/A | N/A | 4856 | 4871 | AGGCTCCTACCCGCCT | 94 | 676 |
| 666710 | N/A | N/A | 4965 | 4980 | TGCCGTGTCAGGGTCG | 89 | 677 |
| 666711 | N/A | N/A | 4993 | 5008 | GAGTCTTTGAGGCTGC | 66 | 678 |
| 666712 | N/A | N/A | 5759 | 5774 | ACAGGCGCGGACGCAC | 80 | 679 |
| 666713 | N/A | N/A | 5867 | 5882 | CGAGAAGAGAGGCTGA | 93 | 680 |
| 666714 | N/A | N/A | 6304 | 6319 | GACACATTTTCTGGGT | 36 | 681 |
| 666715 | N/A | N/A | 7071 | 7086 | GATGCTCAGAATGAAG | 57 | 682 |
| 666716 | N/A | N/A | 7190 | 7205 | CTATGCTGAACCCCAC | 99 | 683 |
| 666717 | N/A | N/A | 7197 | 7212 | AATTCTCCTATGCTGA | 87 | 684 |
| 666718 | N/A | N/A | 7380 | 7395 | AGTGATGAGATATTCC | 41 | 685 |
| 666719 | N/A | N/A | 7519 | 7534 | TCCAGATGCAGATTCC | 54 | 686 |
| 666720 | N/A | N/A | 7536 | 7551 | TCACCTGAAGGATTTG | 75 | 687 |
| 666721 | N/A | N/A | 7731 | 7746 | ATGCATAACACGGTGT | 55 | 688 |
| 666722 | N/A | N/A | 7963 | 7978 | ACACAGCCTCGCCCTC | 80 | 689 |
| 666723 | N/A | N/A | 8094 | 8109 | AGCACCGTGTGGAAAG | 43 | 690 |
| 666724 | N/A | N/A | 8126 | 8141 | ACCCTCCCCAACTTAA | 90 | 691 |
| 666725 | N/A | N/A | 8336 | 8351 | CTGGCACCAAAAGTAC | 82 | 692 |
| 666726 | N/A | N/A | 8539<br>8747<br>8851<br>8903<br>9059 | 8554<br>8762<br>8866<br>8918<br>9074 | ACTGGCATTGAGACGG | 21 | 693 |
| 666727 | N/A | N/A | 8540<br>8748<br>8852<br>8904<br>9060 | 8555<br>8763<br>8867<br>8919<br>9075 | CACTGGCATTGAGACG | 24 | 694 |
| 666728 | N/A | N/A | 8541<br>8749<br>8853<br>8905<br>9061 | 8556<br>8764<br>8868<br>8920<br>9076 | GCACTGGCATTGAGAC | 27 | 695 |
| 666729 | N/A | N/A | 8543<br>8751<br>8855<br>8907<br>9063 | 8558<br>8766<br>8870<br>8922<br>9078 | AAGCACTGGCATTGAG | 58 | 696 |
| 666730 | N/A | N/A | 8544<br>8752<br>8856<br>8908<br>9064 | 8559<br>8767<br>8871<br>8923<br>9079 | GAAGCACTGGCATTGA | 45 | 697 |
| 666731 | N/A | N/A | 8545<br>9065 | 8560<br>9080 | AGAAGCACTGGCATTG | 55 | 698 |
| 666732 | N/A | N/A | 8548<br>8704 | 8563<br>8719 | ATAAGAAGCACTGGCA | 49 | 699 |

TABLE 11-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| | | | 8808 | 8823 | | | |
| | | | 8964 | 8979 | | | |
| | | | 9068 | 9083 | | | |
| 666733 | N/A | N/A | 8549 | 8564 | GATAAGAAGCACTGGC | 37 | 700 |
| | | | 8705 | 8720 | | | |
| | | | 8809 | 8824 | | | |
| | | | 8965 | 8980 | | | |
| | | | 9069 | 9084 | | | |
| 666734 | N/A | N/A | 8551 | 8566 | GAGATAAGAAGCACTG | 56 | 701 |
| | | | 8707 | 8722 | | | |
| | | | 8811 | 8826 | | | |
| | | | 8967 | 8982 | | | |
| | | | 9071 | 9086 | | | |
| 666735 | N/A | N/A | 8553 | 8568 | CTGAGATAAGAAGCAC | 63 | 702 |
| | | | 8709 | 8724 | | | |
| | | | 8813 | 8828 | | | |
| | | | 8969 | 8984 | | | |
| | | | 9073 | 9088 | | | |
| 666737 | N/A | N/A | 8574 | 8589 | GGTAAAGGAGTGCAGG | 54 | 703 |
| | | | 8626 | 8641 | | | |
| | | | 8678 | 8693 | | | |
| | | | 8730 | 8745 | | | |
| | | | 8834 | 8849 | | | |
| | | | 8886 | 8901 | | | |
| | | | 8938 | 8953 | | | |
| | | | 8990 | 9005 | | | |
| | | | 9042 | 9057 | | | |
| 666738 | N/A | N/A | 8591 | 8606 | ACTGGCATCGAGACGG | 21 | 704 |
| | | | 8643 | 8658 | | | |
| | | | 8695 | 8710 | | | |
| | | | 8799 | 8814 | | | |
| | | | 8955 | 8970 | | | |
| | | | 9007 | 9022 | | | |
| 666739 | N/A | N/A | 8592 | 8607 | CACTGGCATCGAGACG | 39 | 705 |
| | | | 8644 | 8659 | | | |
| | | | 8696 | 8711 | | | |
| | | | 8800 | 8815 | | | |
| | | | 8956 | 8971 | | | |
| | | | 9008 | 9023 | | | |
| 666740 | N/A | N/A | 8594 | 8609 | AGCACTGGCATCGAGA | 41 | 706 |
| | | | 8646 | 8661 | | | |
| | | | 8698 | 8713 | | | |
| | | | 8802 | 8817 | | | |
| | | | 8958 | 8973 | | | |
| | | | 9010 | 9025 | | | |
| 666741 | N/A | N/A | 8595 | 8610 | AAGCACTGGCATCGAG | 73 | 707 |
| | | | 8647 | 8662 | | | |
| | | | 8699 | 8714 | | | |
| | | | 8803 | 8818 | | | |
| | | | 8959 | 8974 | | | |
| | | | 9011 | 9026 | | | |
| 666742 | N/A | N/A | 8597 | 8612 | GGAAGCACTGGCATCG | 45 | 708 |
| | | | 8649 | 8664 | | | |
| | | | 9013 | 9028 | | | |
| 666743 | N/A | N/A | 8600 | 8615 | ATAGGAAGCACTGGCA | 58 | 709 |
| | | | 8652 | 8667 | | | |
| | | | 8756 | 8771 | | | |
| | | | 8860 | 8875 | | | |
| | | | 8912 | 8927 | | | |
| | | | 9016 | 9031 | | | |
| 666744 | N/A | N/A | 8601 | 8616 | GATAGGAAGCACTGGC | 38 | 710 |
| | | | 8653 | 8668 | | | |

TABLE 11-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| | | | 8757 | 8772 | | | |
| | | | 8861 | 8876 | | | |
| | | | 8913 | 8928 | | | |
| | | | 9017 | 9032 | | | |
| 666745 | N/A | N/A | 8602 | 8617 | AGATAGGAAGCACTGG | 54 | 711 |
| | | | 8654 | 8669 | | | |
| | | | 8758 | 8773 | | | |
| | | | 8862 | 8877 | | | |
| | | | 8914 | 8929 | | | |
| | | | 9018 | 9033 | | | |
| 666746 | N/A | N/A | 8603 | 8618 | GAGATAGGAAGCACTG | 52 | 712 |
| | | | 8655 | 8670 | | | |
| | | | 8759 | 8774 | | | |
| | | | 8863 | 8878 | | | |
| | | | 8915 | 8930 | | | |
| | | | 9019 | 9034 | | | |
| 666747 | N/A | N/A | 8604 | 8619 | TGAGATAGGAAGCACT | 62 | 713 |
| | | | 8656 | 8671 | | | |
| | | | 8760 | 8775 | | | |
| | | | 8864 | 8879 | | | |
| | | | 8916 | 8931 | | | |
| | | | 9020 | 9035 | | | |
| 666748 | N/A | N/A | 8605 | 8620 | CTGAGATAGGAAGCAC | 74 | 714 |
| | | | 8657 | 8672 | | | |
| | | | 8761 | 8776 | | | |
| | | | 8865 | 8880 | | | |
| | | | 8917 | 8932 | | | |
| | | | 9021 | 9036 | | | |
| 666749 | N/A | N/A | 9410 | 9425 | GGATGCCACCATCCCA | 105 | 715 |
| 666750 | N/A | N/A | 9490 | 9505 | GGAGTGATCTCTGTGG | 32 | 716 |
| 666751 | N/A | N/A | 9708 | 9723 | GTAGGTAGGCACCTGT | 25 | 717 |
| 666752 | N/A | N/A | 9796 | 9811 | GAGGGAGCTCATTTTG | 76 | 718 |
| 666753 | N/A | N/A | 9960 | 9975 | AAAGGCCAAATTGCAA | 48 | 719 |
| 666754 | N/A | N/A | 9997 | 10012 | CTGCAGCCAAGGATAA | 52 | 720 |
| 666818 | N/A | N/A | 3925 | 3940 | GGCGCGCTCCCTTCCC | 90 | 721 |
| 666819 | N/A | N/A | 4685 | 4700 | CCCTTCCCCGCGACTC | 81 | 722 |
| 666820 | N/A | N/A | 4717 | 4732 | TTGCCTTCGCTCACTC | 78 | 723 |
| 666821 | N/A | N/A | 5757 | 5772 | AGGCGCGGACGCACGG | 69 | 724 |
| 666822 | N/A | N/A | 6997 | 7012 | CTACCTTTTTTGGCTC | 83 | 725 |
| 666823 | N/A | N/A | 7585 | 7600 | TGCCTTGTGACATAAA | 55 | 726 |
| 666824 | N/A | N/A | 8151 | 8166 | ATATTCCAACAGGCGG | 47 | 727 |
| 666825 | N/A | N/A | 8437 | 8452 | TGAACCCTTCATCAGA | 52 | 728 |
| 666826 | N/A | N/A | 9313 | 9328 | AGACCAGGATTCGCCA | 67 | 729 |

TABLE 12

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 666755 | N/A | N/A | 10003 | 10018 | CACTACCTGCAGCCAA | 69 | 730 |
| 666756 | N/A | N/A | 10020 | 10035 | AGAGTGGTACACCTCT | 78 | 731 |
| 666757 | N/A | N/A | 10256 | 10271 | GTCTCTACCTACTCCA | 59 | 732 |
| 666758 | N/A | N/A | 10308 | 10323 | AACACCTGATCTTGCT | 110 | 733 |
| 666759 | N/A | N/A | 10366 | 10381 | ACCATGTTCCTGAAGA | 56 | 734 |
| 666760 | N/A | N/A | 10660 | 10675 | CTCTTGTGAGGCAAAG | 52 | 735 |
| 666761 | N/A | N/A | 10712 | 10727 | GCGCCCAATCACCTTC | 97 | 736 |
| 666762 | N/A | N/A | 11002 | 11017 | ATCGAATCTGCCCAAA | 74 | 737 |
| 666763 | N/A | N/A | 11010 | 11025 | AAAGTCCCATCGAATC | 87 | 738 |
| 666764 | N/A | N/A | 11024 | 11039 | CAAAGCAAGTGTCTAA | 77 | 739 |
| 666765 | N/A | N/A | 11070 | 11085 | CTCACACACAGGATGT | 82 | 740 |
| 666767 | N/A | N/A | 11344 | 11359 | GAGGAGGAGGACTTAT | 49 | 741 |
| 666768 | N/A | N/A | 11408 | 11423 | TATTACTCTTAGGCAC | 56 | 742 |
| 666769 | N/A | N/A | 11545 | 11560 | GTGCCTTCTTTATAGT | 51 | 743 |
| 666770 | N/A | N/A | 11551 | 11566 | CTAGAGGTGCCTTCTT | 74 | 744 |
| 666771 | N/A | N/A | 11682 | 11697 | TGCCAGAGGGCAAGAT | 98 | 745 |
| 666772 | N/A | N/A | 11975 | 11990 | GCTGTTTATTTCCTAC | 34 | 746 |
| 666773 | N/A | N/A | 11988 | 12003 | CGAGATATAAATAGCT | 42 | 747 |
| 666774 | N/A | N/A | 11990 | 12005 | GCCGAGATATAAATAG | 60 | 748 |
| 666775 | N/A | N/A | 12032 | 12047 | GCAGGTTTCATTTCAT | 56 | 749 |
| 666776 | N/A | N/A | 12034 | 12049 | GGGCAGGTTTCATTTC | 68 | 750 |
| 666777 | N/A | N/A | 12067 | 12082 | AGAGTGGGTGTTGGCC | 75 | 751 |
| 666779 | N/A | N/A | 12274 | 12289 | ATGGAACCCCAAAATC | 76 | 752 |
| 666780 | N/A | N/A | 12292 | 12307 | GCTGCCACTGGTAACT | 74 | 753 |
| 666781 | N/A | N/A | 12374 | 12389 | TCGCCCATGAGTTGAA | 61 | 754 |
| 666782 | N/A | N/A | 12516 | 12531 | AGTTCATGTAAAGTCT | 39 | 755 |
| 666783 | N/A | N/A | 12865 | 12880 | TCGGTCCACATACCTG | 61 | 756 |
| 666784 | N/A | N/A | 13199 | 13214 | CTTGGAGAAGTCCCGT | 61 | 757 |
| 666785 | N/A | N/A | 13330 | 13345 | CCTGTGGTGGAACTCT | 73 | 758 |
| 666786 | N/A | N/A | 14020 | 14035 | AAGAGGCGACTGCTGA | 65 | 759 |
| 666787 | N/A | N/A | 14028 | 14043 | ACTGTTTTAAGAGGCG | 30 | 760 |
| 666788 | N/A | N/A | 14046 | 14061 | ATAGTGCAATGAAATG | 64 | 761 |
| 666789 | N/A | N/A | 14094 | 14109 | GGGAACCTGAAAAGAG | 79 | 762 |
| 666790 | N/A | N/A | 14338 | 14353 | GAGGTTCGCTGAATTG | 70 | 763 |
| 666791 | N/A | N/A | 14687 | 14702 | ATCGGATGAGCTTAC | 62 | 764 |
| 666792 | N/A | N/A | 14732 | 14747 | AGCTTAGTTATCTGGG | 41 | 765 |

TABLE 12-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666793 | N/A | N/A | 15213 | 15228 | GAACACCATGCCCAAC | 93 | 766 |
| 666794 | N/A | N/A | 15304 | 15319 | GAGCTCTTCCAGATCC | 95 | 767 |
| 666795 | N/A | N/A | 15596 | 15611 | TAGTCGCGCAAGTCTA | 108 | 768 |
| 666796 | N/A | N/A | 15777 | 15792 | ATCCTTAATTATGCAG | 61 | 769 |
| 666797 | N/A | N/A | 15790 | 15805 | GTGTTTGGTGGGAATC | 54 | 770 |
| 666798 | N/A | N/A | 15985 | 16000 | CTAACTTACAGGACTA | 69 | 771 |
| 666799 | N/A | N/A | 16059 | 16074 | TAGTGCTGTGCAGACC | 68 | 772 |
| 666800 | N/A | N/A | 16069 | 16084 | GGGCTGTCCCTAGTGC | 109 | 773 |
| 666801 | N/A | N/A | 16171 | 16186 | AATGTCACGCCCGCAA | 81 | 774 |
| 666802 | N/A | N/A | 16340 | 16355 | GGCCTCCCGCTTGTGG | 118 | 775 |
| 666803 | N/A | N/A | 16383 | 16398 | GAACAGTAACTTGACT | 96 | 776 |
| 666804 | N/A | N/A | 16419 | 16434 | AACTCTGAGTAGACTT | 72 | 777 |
| 666805 | N/A | N/A | 16471 | 16486 | GAGCACCAGCCATCGG | 77 | 778 |
| 666806 | N/A | N/A | 16649 | 16664 | GACCAATTTATGCCAT | 62 | 779 |
| 666807 | N/A | N/A | 16664 | 16679 | CACGCAATGGCAAAAG | 81 | 780 |
| 666808 | N/A | N/A | 16824 | 16839 | TCCTTTGGGTGCTTTC | 68 | 781 |
| 666809 | N/A | N/A | 16888 | 16903 | CTCTTACTCCGCTGAG | 105 | 782 |
| 666810 | N/A | N/A | 16953 | 16968 | ACACACCAGGTTAAAC | 88 | 783 |
| 666811 | N/A | N/A | 17135 | 17150 | AGTGTAACTGAGGACT | 107 | 784 |
| 666812 | N/A | N/A | 17740 | 17755 | TGTTACTTGCCACAGT | 61 | 785 |
| 666813 | N/A | N/A | 17916 | 17931 | ATGCAAGCCCGTTAAT | 96 | 786 |
| 666814 | N/A | N/A | 17966 | 17981 | ATGAGAACTTTGATGT | 85 | 787 |
| 666815 | N/A | N/A | 18136 | 18151 | AAGTCAATCACTGGAG | 39 | 788 |
| 666816 | N/A | N/A | 18196 | 18211 | TTAGCAATTCCTGTTG | 80 | 789 |
| 666817 | N/A | N/A | 18938 | 18953 | GCTAACTGGCCTCAAA | 91 | 790 |
| 666827 | N/A | N/A | 10288 | 10303 | CTTCATTTACTGTTAC | 69 | 791 |
| 666828 | N/A | N/A | 10484 | 10499 | CAACAGAGCTGAGAGT | 80 | 792 |
| 666829 | N/A | N/A | 11844 | 11859 | CTCACGAGCACCTCAG | 58 | 793 |
| 666830 | N/A | N/A | 13244 | 13259 | CTTGTCTCCCCCAGAG | 97 | 794 |
| 666831 | N/A | N/A | 13798 | 13813 | CCACCTCCATTCTAAC | 115 | 795 |
| 666832 | N/A | N/A | 14081 | 14096 | GAGCCGCCACATCAGC | 77 | 796 |
| 666833 | N/A | N/A | 14193 | 14208 | CCACCCTCCGTCTCAC | 67 | 797 |
| 666834 | N/A | N/A | 14242 | 14257 | TATAGCACTCTCCTAT | 98 | 798 |
| 666836 | N/A | N/A | 16203 | 16218 | CAAGACAAATCTTCTG | 87 | 799 |
| 666837 | N/A | N/A | 16641 | 16656 | TATGCCATGGACAAGT | 81 | 800 |
| 666838 | N/A | N/A | 16948 | 16963 | CCAGGTTAAACAGGAA | 94 | 801 |

TABLE 12-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 666839 | N/A | N/A | 19232 | 19247 | GACTTAATTCTGGGTT | 65 | 802 |
| 666840 | N/A | N/A | 19412 | 19427 | ACTGAGATATCCTGCA | 81 | 803 |

Example 5: Effect of 3-10-3 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 20,000 cells per well were transfected using electroporation with 4,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (described hereinabove in Example 1) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 13 through 24 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 13 through 24 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 13

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 24 | 195 |
| 881075 | 2 | 17 | 3741 | 3756 | AACTGAGAGTGCGAGG | 99 | 804 |
| 881099 | 342 | 357 | 6821 | 6836 | AAACAGTGCCCAAGCC | 75 | 805 |
| 881122 | 624 | 639 | 9114 | 9129 | CATCATGTAGTTGTGA | 59 | 806 |
| 881169 | 1192 | 1207 | 13745 | 13760 | TGTCAAAGAGCTTGCA | 89 | 807 |
| 881193 | 1416 | 1431 | 19533 | 19548 | GCTGATGTGTTCTGGT | 21 | 808 |
| 881217 | 1740 | 1755 | 19857 | 19872 | CAGTAAGAGGGCAGTC | 50 | 809 |
| 881241 | 1927 | 1942 | 20044 | 20059 | CATCACTTGGTCAATT | 71 | 810 |
| 881265 | 2042 | 2057 | 20159 | 20174 | CCTACAAGCAGTCATC | 46 | 811 |
| 881289 | 2194 | 2209 | 20311 | 20326 | CTACAGGCACGGCTTC | 48 | 812 |
| 881313 | 2385 | 2400 | 20502 | 20517 | TACTAGATTGTAGGAC | 73 | 813 |
| 881337 | 2512 | 2527 | 20629 | 20644 | CAACAGTTCAAGTATT | 65 | 814 |
| 881361 | 2665 | 2680 | 20782 | 20797 | TTCCAGTGGTGGGTCC | 71 | 815 |
| 881385 | 2826 | 2841 | 20943 | 20958 | CAAGTGGAGGTCTTTG | 33 | 816 |
| 881409 | 2911 | 2926 | 21028 | 21043 | ATGAGAAACGGCCTGG | 36 | 817 |
| 881433 | 3047 | 3062 | 21164 | 21179 | AATGTAGGGATACAGC | 38 | 818 |

TABLE 13-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881457 | 3273 | 3288 | 21390 | 21405 | AATAAACACCCCTTCT | 79 | 819 |
| 881481 | 3419 | 3434 | 21536 | 21551 | CTCCACAGCAAGGCCT | 49 | 820 |
| 881505 | 3507 | 3522 | 21624 | 21639 | GTTCACGAAACACAGT | 37 | 821 |
| 881528 | 3625 | 3640 | 21742 | 21757 | CAAAGAGGGTCACAGG | 37 | 822 |
| 881552 | 3903 | 3918 | 22020 | 22035 | CCCTAGGTCATACCCT | 43 | 823 |
| 881576 | 4052 | 4067 | 22169 | 22184 | CTTCAACAGCACTGTC | 44 | 824 |
| 881595 | 4285 | 4300 | 22402 | 22417 | CTGTAGGGCGACTAAC | 51 | 825 |
| 881619 | 4412 | 4427 | 22529 | 22544 | CTAATACCTACCTGCC | 53 | 826 |
| 881643 | 4545 | 4560 | 22662 | 22677 | GCACACACAAGTGGCC | 36 | 827 |
| 881667 | 4602 | 4617 | 22719 | 22734 | AGCAATGAACGGAAGT | 20 | 828 |
| 881691 | 4839 | 4854 | 22956 | 22971 | GGCTATCAGGATCTCA | 55 | 829 |
| 881715 | 5030 | 5045 | 23147 | 23162 | CCCCATTGCCTGTTAA | 80 | 830 |
| 881739 | 5206 | 5221 | 23323 | 23338 | ACAGCATAGCATTATC | 36 | 831 |
| 881763 | N/A | N/A | 18778 | 18793 | GACGACTTAAGCTAAA | 38 | 832 |
| 881787 | N/A | N/A | 18847 | 18862 | ATTTACAGCATCTAAG | 53 | 833 |
| 881809 | N/A | N/A | 4075 | 4090 | GCTCATCCCGTCCAGC | 85 | 834 |
| 881832 | N/A | N/A | 4402 | 4417 | GGAGAGCGGAGGCGGG | 79 | 835 |
| 881855 | N/A | N/A | 4644 | 4659 | CTCCACGCGCGGAGGA | 101 | 836 |
| 881879 | N/A | N/A | 5038 | 5053 | GGGCACCCCGCCCCGA | 99 | 837 |
| 881903 | N/A | N/A | 5660 | 5675 | GCACGGACGAACGCGC | 77 | 838 |
| 881925 | N/A | N/A | 5777 | 5792 | ACGAAAACAGCCGCCG | 86 | 839 |
| 881947 | N/A | N/A | 6136 | 6151 | GAGCAAATTGAGACCA | 45 | 840 |
| 881971 | N/A | N/A | 6415 | 6430 | GCGCATAGGTCCTTCA | 37 | 841 |
| 881993 | N/A | N/A | 7155 | 7170 | CCACATAACTCAGGCA | 30 | 842 |
| 882017 | N/A | N/A | 7376 | 7391 | ATGAGATATTCCTCTC | 68 | 843 |
| 882041 | N/A | N/A | 7696 | 7711 | CAGCAACTCCCTTGGG | 77 | 844 |
| 882065 | N/A | N/A | 8145 | 8160 | CAACAGGCGGACACGC | 58 | 845 |
| 882088 | N/A | N/A | 8385 | 8400 | ATGGAGATACTTGTAC | 38 | 846 |
| 882112 | N/A | N/A | 8554<br>8710<br>8814<br>8970<br>9074 | 8569<br>8725<br>8829<br>8985<br>9089 | GCTGAGATAAGAAGCA | 68 | 847 |
| 882135 | N/A | N/A | 9362 | 9377 | GCACACGCAGCCTCTA | 95 | 848 |
| 882158 | N/A | N/A | 9606 | 9621 | CCACTATTCGAGAGAA | 43 | 849 |
| 882182 | N/A | N/A | 9981 | 9996 | CCTGAACATGACTGGG | 62 | 850 |
| 882205 | N/A | N/A | 10162 | 10177 | GAATTTCAGGAGCTAG | 39 | 851 |
| 882229 | N/A | N/A | 10314 | 10329 | GCACAGAACACCTGAT | 44 | 852 |

TABLE 13-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882253 | N/A | N/A | 10616 | 10631 | AGCTGATGGAGAAACG | 90 | 853 |
| 882277 | N/A | N/A | 11088 | 11103 | CTAAATCACCCTGGTC | 53 | 854 |
| 882301 | N/A | N/A | 11366 | 11381 | GAACTAATGTCCCCAG | 39 | 855 |
| 882325 | N/A | N/A | 11666 | 11681 | GAGAATTCCAAACCTT | 24 | 856 |
| 882349 | N/A | N/A | 11940 | 11955 | GTCTTAGGTGTTCAAG | 44 | 857 |
| 882373 | N/A | N/A | 12157 | 12172 | CAGCAGGTTTTGAGAC | 80 | 858 |
| 882397 | N/A | N/A | 12512 | 12527 | CATGTAAAGTCTGCTG | 42 | 859 |
| 882420 | N/A | N/A | 12893 | 12908 | ATATAACGGTGTTTCA | 42 | 860 |
| 882443 | N/A | N/A | 13175 | 13190 | ACCCATTTAATCTGTC | 43 | 861 |
| 882465 | N/A | N/A | 13791 | 13806 | CATTCTAACAGATAAC | 102 | 862 |
| 882487 | N/A | N/A | 14150 | 14165 | ACACACCTGACAACCA | 64 | 863 |
| 882510 | N/A | N/A | 14374 | 14389 | GCATGACAGGGCGAGG | 57 | 864 |
| 882533 | N/A | N/A | 14708 | 14723 | TGCTTTGGGCACCAAA | 48 | 865 |
| 882557 | N/A | N/A | 15460 | 15475 | GCCCAGCAAGAGGCAC | 93 | 866 |
| 882580 | N/A | N/A | 15804 | 15819 | TAGATAACATGAGAGT | 50 | 867 |
| 882603 | N/A | N/A | 15925 | 15940 | CAAATGACTTAGTCAG | 45 | 868 |
| 882627 | N/A | N/A | 16168 | 16183 | GTCACGCCCGCAAAAG | 61 | 869 |
| 882650 | N/A | N/A | 16388 | 16403 | GGATGGAACAGTAACT | 48 | 870 |
| 882674 | N/A | N/A | 16667 | 16682 | AGTCACGCAATGGCAA | 50 | 871 |
| 882698 | N/A | N/A | 16900 | 16915 | GAGGAATGAGCACTCT | 74 | 872 |
| 882722 | N/A | N/A | 17238 | 17253 | GGTTACGCTTATTTTT | 36 | 873 |
| 882746 | N/A | N/A | 17493 | 17508 | GCTAGATAGCATTCTT | 44 | 874 |
| 882770 | N/A | N/A | 17733 | 17748 | TGCCACAGTTGAACCC | 50 | 875 |
| 882794 | N/A | N/A | 17987 | 18002 | TAGCATCAGAGCTAGA | 51 | 876 |
| 882817 | N/A | N/A | 18582 | 18597 | CTGGATTGATGTGATA | 57 | 877 |
| 882841 | N/A | N/A | 18961 | 18976 | ACTACTATTGTGGAAA | 82 | 878 |
| 882864 | N/A | N/A | 19234 | 19249 | GTGACTTAATTCTGGG | 49 | 879 |

TABLE 14

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 14 | 195 |
| 881076 | 6 | 21 | 3745 | 3760 | GTGAAACTGAGAGTGC | 120 | 880 |
| 881100 | 343 | 358 | 6822 | 6837 | TAAACAGTGCCCAAGC | 59 | 881 |
| 881123 | 682 | 697 | 9172 | 9187 | GGATTTCCGGGTGTGG | 39 | 882 |

TABLE 14-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881170 | 1206 | 1221 | 13759 | 13774 | CAAGAACTGCTGTGTG | 105 | 883 |
| 881194 | 1432 | 1447 | 19549 | 19564 | GGTAATCTTCTGGATT | 70 | 884 |
| 881218 | 1741 | 1756 | 19858 | 19873 | ACAGTAAGAGGGCAGT | 16 | 885 |
| 881242 | 1930 | 1945 | 20047 | 20062 | ACACATCACTTGGTCA | 22 | 886 |
| 881266 | 2043 | 2058 | 20160 | 20175 | ACCTACAAGCAGTCAT | 54 | 887 |
| 881290 | 2195 | 2210 | 20312 | 20327 | GCTACAGGCACGGCTT | 16 | 888 |
| 881314 | 2387 | 2402 | 20504 | 20519 | ATTACTAGATTGTAGG | 50 | 889 |
| 881338 | 2515 | 2530 | 20632 | 20647 | GGGCAACAGTTCAAGT | 64 | 890 |
| 881362 | 2686 | 2701 | 20803 | 20818 | CCGTAGTCAGCTCCAT | 27 | 891 |
| 881386 | 2828 | 2843 | 20945 | 20960 | AGCAAGTGGAGGTCTT | 37 | 892 |
| 881410 | 2912 | 2927 | 21029 | 21044 | TATGAGAAACGGCCTG | 55 | 893 |
| 881434 | 3048 | 3063 | 21165 | 21180 | TAATGTAGGGATACAG | 22 | 894 |
| 881458 | 3275 | 3290 | 21392 | 21407 | AGAATAAACACCCCTT | 26 | 895 |
| 881482 | 3429 | 3444 | 21546 | 21561 | GGCAGTGGAGCTCCAC | 27 | 896 |
| 881506 | 3510 | 3525 | 21627 | 21642 | GCAGTTCACGAAACAC | 20 | 897 |
| 881529 | 3628 | 3643 | 21745 | 21760 | CAGCAAAGAGGGTCAC | 39 | 898 |
| 881553 | 3904 | 3919 | 22021 | 22036 | TCCCTAGGTCATACCC | 42 | 899 |
| 881577 | 4058 | 4073 | 22175 | 22190 | TCAAATCTTCAACAGC | 24 | 900 |
| 881596 | 4300 | 4315 | 22417 | 22432 | GTCTAGCTGGGTTTTC | 37 | 901 |
| 881620 | 4413 | 4428 | 22530 | 22545 | ACTAATACCTACCTGC | 52 | 902 |
| 881644 | 4547 | 4562 | 22664 | 22679 | ACGCACACACAAGTGG | 41 | 903 |
| 881668 | 4608 | 4623 | 22725 | 22740 | CTGGAGAGCAATGAAC | 33 | 904 |
| 881692 | 4844 | 4859 | 22961 | 22976 | TAACAGGCTATCAGGA | 74 | 905 |
| 881716 | 5040 | 5055 | 23157 | 23172 | GGGAAGTGGACCCCAT | 91 | 906 |
| 881740 | 5208 | 5223 | 23325 | 23340 | CGACAGCATAGCATTA | 25 | 907 |
| 881764 | N/A | N/A | 18782 | 18797 | ATATGACGACTTAAGC | 62 | 908 |
| 881788 | N/A | N/A | 18849 | 18864 | GAATTTACAGCATCTA | 24 | 909 |
| 881810 | N/A | N/A | 4084 | 4099 | GTCCGGTTAGCTCATC | 55 | 910 |
| 881833 | N/A | N/A | 4403 | 4418 | GGGAGAGCGGAGGCGG | 78 | 911 |
| 881856 | N/A | N/A | 4703 | 4718 | TCCCAACCCGCTTCTC | 86 | 912 |
| 881880 | N/A | N/A | 5056 | 5071 | CACGAGGCACCGCACT | 113 | 913 |
| 881904 | N/A | N/A | 5664 | 5679 | GAACGCACGGACGAAC | 82 | 914 |
| 881926 | N/A | N/A | 5778 | 5793 | GACGAAAACAGCCGCC | 38 | 915 |
| 881948 | N/A | N/A | 6141 | 6156 | TCTGAGAGCAAATTGA | 71 | 916 |
| 881994 | N/A | N/A | 7157 | 7172 | ACCCACATAACTCAGG | 69 | 917 |
| 882018 | N/A | N/A | 7384 | 7399 | GCATAGTGATGAGATA | 41 | 918 |

TABLE 14-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882042 | N/A | N/A | 7717 | 7732 | GTTGACAAATAAGGTA | 40 | 919 |
| 882066 | N/A | N/A | 8146 | 8161 | CCAACAGGCGGACACG | 17 | 920 |
| 882089 | N/A | N/A | 8391 | 8406 | AGGACAATGGAGATAC | 28 | 921 |
| 882113 | N/A | N/A | 8566 | 8581 | AGTGCAGGAGAGGCTG | 64 | 922 |
|  |  |  | 8618 | 8633 |  |  |  |
|  |  |  | 8670 | 8685 |  |  |  |
|  |  |  | 8722 | 8737 |  |  |  |
|  |  |  | 8774 | 8789 |  |  |  |
|  |  |  | 8826 | 8841 |  |  |  |
|  |  |  | 8878 | 8893 |  |  |  |
|  |  |  | 8930 | 8945 |  |  |  |
|  |  |  | 8982 | 8997 |  |  |  |
|  |  |  | 9034 | 9049 |  |  |  |
|  |  |  | 9086 | 9101 |  |  |  |
| 882136 | N/A | N/A | 9386 | 9401 | AGAAAACCCCCCTCTC | 77 | 923 |
| 882159 | N/A | N/A | 9608 | 9623 | CACCACTATTCGAGAG | 52 | 924 |
| 882183 | N/A | N/A | 9986 | 10001 | GATAACCTGAACATGA | 83 | 925 |
| 882206 | N/A | N/A | 10172 | 10187 | ACGCAAGTCTGAATTT | 35 | 926 |
| 882230 | N/A | N/A | 10352 | 10367 | GACAATGTTGTATGAA | 28 | 927 |
| 882254 | N/A | N/A | 10634 | 10649 | GACCAACTGGAAAACC | 44 | 928 |
| 882278 | N/A | N/A | 11089 | 11104 | CCTAAATCACCCTGGT | 73 | 929 |
| 882302 | N/A | N/A | 11368 | 11383 | CAGAACTAATGTCCCC | 31 | 930 |
| 882326 | N/A | N/A | 11669 | 11684 | GATGAGAATTCCAAAC | 16 | 931 |
| 882350 | N/A | N/A | 11950 | 11965 | ACCCACACAAGTCTTA | 104 | 932 |
| 882374 | N/A | N/A | 12161 | 12176 | TCAACAGCAGGTTTTG | 59 | 933 |
| 882398 | N/A | N/A | 12515 | 12530 | GTTCATGTAAAGTCTG | 14 | 934 |
| 882421 | N/A | N/A | 12896 | 12911 | AAAATATAACGGTGTT | 69 | 935 |
| 882444 | N/A | N/A | 13196 | 13211 | GGAGAAGTCCCGTGGA | 41 | 936 |
| 882466 | N/A | N/A | 13881 | 13896 | CGCCGAAGTCAACAGG | 56 | 937 |
| 882488 | N/A | N/A | 14160 | 14175 | CATGAGGGTGACACAC | 53 | 938 |
| 882511 | N/A | N/A | 14376 | 14391 | CAGCATGACAGGGCGA | 44 | 939 |
| 882534 | N/A | N/A | 14716 | 14731 | GACATATTTGCTTTGG | 42 | 940 |
| 882558 | N/A | N/A | 15497 | 15512 | AGCTTAGTCACCACGG | 33 | 941 |
| 882581 | N/A | N/A | 15805 | 15820 | CTAGATAACATGAGAG | 47 | 942 |
| 882604 | N/A | N/A | 15926 | 15941 | CCAAATGACTTAGTCA | 49 | 943 |
| 882628 | N/A | N/A | 16177 | 16192 | CAATAAAATGTCACGC | 53 | 944 |
| 882651 | N/A | N/A | 16390 | 16405 | AGGGATGGAACAGTAA | 53 | 945 |
| 882675 | N/A | N/A | 16691 | 16706 | CGGGAGATAAAGAACA | 69 | 946 |
| 882699 | N/A | N/A | 16905 | 16920 | TGCAAGAGGAATGAGC | 16 | 947 |
| 882723 | N/A | N/A | 17239 | 17254 | GGGTTACGCTTATTTT | 35 | 948 |
| 882747 | N/A | N/A | 17508 | 17523 | AATGAAGATCCACTAG | 39 | 949 |
| 882771 | N/A | N/A | 17746 | 17761 | TTTTAGTGTTACTTGC | 68 | 950 |

TABLE 14-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882795 | N/A | N/A | 17990 | 18005 | AAATAGCATCAGAGCT | 87 | 951 |
| 882818 | N/A | N/A | 18584 | 18599 | AACTGGATTGATGTGA | 23 | 952 |
| 882842 | N/A | N/A | 18964 | 18979 | AAAACTACTATTGTGG | 86 | 953 |
| 882865 | N/A | N/A | 19240 | 19255 | GCCAAAGTGACTTAAT | 30 | 954 |
| 882898 | N/A | N/A | 6422 | 6437 | AAGAATGGCGCATAGG | 19 | 955 |

TABLE 15

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 45 | 195 |
| 881077 | 7 | 22 | 3746 | 3761 | GGTGAAACTGAGAGTG | 92 | 956 |
| 881101 | 344 | 359 | 6823 | 6838 | TTAAACAGTGCCCAAG | 79 | 957 |
| 881124 | 689 | 704 | 9179 | 9194 | TGGTACGGGATTTCCG | 63 | 958 |
| 881171 | 1207 | 1222 | 13760 | 13775 | ACAAGAACTGCTGTGT | 93 | 959 |
| 881195 | 1433 | 1448 | 19550 | 19565 | TGGTAATCTTCTGGAT | 76 | 960 |
| 881219 | 1744 | 1759 | 19861 | 19876 | AAAACAGTAAGAGGGC | 61 | 961 |
| 881243 | 1934 | 1949 | 20051 | 20066 | GTAAACACATCACTTG | 49 | 962 |
| 881267 | 2044 | 2059 | 20161 | 20176 | TACCTACAAGCAGTCA | 44 | 963 |
| 881291 | 2196 | 2211 | 20313 | 20328 | GGCTACAGGCACGGCT | 58 | 964 |
| 881315 | 2388 | 2403 | 20505 | 20520 | CATTACTAGATTGTAG | 91 | 965 |
| 881339 | 2520 | 2535 | 20637 | 20652 | CAGAAGGGCAACAGTT | 62 | 966 |
| 881363 | 2701 | 2716 | 20818 | 20833 | ACTGAGTGTGCAGTTC | 64 | 967 |
| 881387 | 2829 | 2844 | 20946 | 20961 | AAGCAAGTGGAGGTCT | 49 | 968 |
| 881411 | 2913 | 2928 | 21030 | 21045 | GTATGAGAAACGGCCT | 41 | 969 |
| 881435 | 3049 | 3064 | 21166 | 21181 | GTAATGTAGGGATACA | 52 | 970 |
| 881459 | 3277 | 3292 | 21394 | 21409 | GAAGAATAAACACCCC | 48 | 971 |
| 881483 | 3430 | 3445 | 21547 | 21562 | TGGCAGTGGAGCTCCA | 54 | 972 |
| 881507 | 3517 | 3532 | 21634 | 21649 | CATCACTGCAGTTCAC | 53 | 973 |
| 881530 | 3631 | 3646 | 21748 | 21763 | CTTCAGCAAAGAGGGT | 41 | 974 |
| 881554 | 3918 | 3933 | 22035 | 22050 | CATAGCTAGTTCATTC | 65 | 975 |
| 881578 | 4089 | 4104 | 22206 | 22221 | TCCATATGACCCAGTG | 34 | 976 |
| 881597 | 4305 | 4320 | 22422 | 22437 | CAATAGTCTAGCTGGG | 37 | 977 |
| 881621 | 4418 | 4433 | 22535 | 22550 | CAAACACTAATACCTA | 69 | 978 |
| 881645 | 4556 | 4571 | 22673 | 22688 | GTAACTGACACGCACA | 49 | 979 |

TABLE 15-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881669 | 4618 | 4633 | 22735 | 22750 | GGGCATGTGACTGGAG | 50 | 980 |
| 881693 | 4845 | 4860 | 22962 | 22977 | GTAACAGGCTATCAGG | 55 | 981 |
| 881717 | 5152 | 5167 | 23269 | 23284 | GCAAAACGCAGAGCCA | 43 | 982 |
| 881741 | 5209 | 5224 | 23326 | 23341 | ACGACAGCATAGCATT | 33 | 983 |
| 881765 | N/A | N/A | 18783 | 18798 | TATATGACGACTTAAG | 70 | 984 |
| 881789 | N/A | N/A | 18853 | 18868 | TCCTGAATTTACAGCA | 52 | 985 |
| 881834 | N/A | N/A | 4404 | 4419 | CGGGAGAGCGGAGGCG | 100 | 986 |
| 881857 | N/A | N/A | 4740 | 4755 | CCGCACTCACTCGCAG | 92 | 987 |
| 881881 | N/A | N/A | 5057 | 5072 | CCACGAGGCACCGCAC | 119 | 988 |
| 881905 | N/A | N/A | 5668 | 5683 | ACGAGAACGCACGGAC | 60 | 989 |
| 881927 | N/A | N/A | 5779 | 5794 | AGACGAAAACAGCCGC | 75 | 990 |
| 881949 | N/A | N/A | 6209 | 6224 | ACTAAGGACAGCTGTG | 85 | 991 |
| 881972 | N/A | N/A | 6424 | 6439 | GAAAGAATGGCGCATA | 51 | 992 |
| 881995 | N/A | N/A | 7168 | 7183 | TTCAACTTGTGACCCA | 51 | 993 |
| 882019 | N/A | N/A | 7385 | 7400 | TGCATAGTGATGAGAT | 63 | 994 |
| 882043 | N/A | N/A | 7726 | 7741 | TAACACGGTGTTGACA | 65 | 995 |
| 882067 | N/A | N/A | 8147 | 8162 | TCCAACAGGCGGACAC | 71 | 996 |
| 882090 | N/A | N/A | 8399 | 8414 | GATCATAAAGGACAAT | 70 | 997 |
| 882114 | N/A | N/A | 8570<br>8622<br>8674<br>8726<br>8778<br>8830<br>8882<br>8934<br>8986<br>9038<br>9090 | 8585<br>8637<br>8689<br>8741<br>8793<br>8845<br>8897<br>8949<br>9001<br>9053<br>9105 | AAGGAGTGCAGGAGAG | 87 | 998 |
| 882137 | N/A | N/A | 9387 | 9402 | GAGAAAACCCCCTCT | 83 | 999 |
| 882160 | N/A | N/A | 9611 | 9626 | ACACACCACTATTCGA | 65 | 1000 |
| 882184 | N/A | N/A | 9990 | 10005 | CAAGGATAACCTGAAC | 74 | 1001 |
| 882207 | N/A | N/A | 10179 | 10194 | GCAGTAAACGCAAGTC | 46 | 1002 |
| 882231 | N/A | N/A | 10357 | 10372 | CTGAAGACAATGTTGT | 45 | 1003 |
| 882255 | N/A | N/A | 10672 | 10687 | TAGCAGGGCACGCTCT | 69 | 1004 |
| 882279 | N/A | N/A | 11090 | 11105 | TCCTAAATCACCCTGG | 79 | 1005 |
| 882303 | N/A | N/A | 11370 | 11385 | ACCAGAACTAATGTCC | 68 | 1006 |
| 882327 | N/A | N/A | 11674 | 11689 | GGCAAGATGAGAATTC | 75 | 1007 |
| 882351 | N/A | N/A | 11987 | 12002 | GAGATATAAATAGCTG | 49 | 1008 |
| 882375 | N/A | N/A | 12175 | 12190 | AACTATCTTATTCCTC | 70 | 1009 |
| 882422 | N/A | N/A | 12897 | 12912 | AAAAATATAACGGTGT | 76 | 1010 |
| 882445 | N/A | N/A | 13203 | 13218 | AACACTTGGAGAAGTC | 57 | 1011 |

TABLE 15-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882467 | N/A | N/A | 13904 | 13919 | AGTCAAGCCCCAAGCC | 87 | 1012 |
| 882489 | N/A | N/A | 14161 | 14176 | GCATGAGGGTGACACA | 58 | 1013 |
| 882512 | N/A | N/A | 14432 | 14447 | TCCCACGCGGGAGGCT | 99 | 1014 |
| 882535 | N/A | N/A | 14717 | 14732 | GGACATATTTGCTTTG | 68 | 1015 |
| 882559 | N/A | N/A | 15501 | 15516 | TTCCAGCTTAGTCACC | 63 | 1016 |
| 882582 | N/A | N/A | 15806 | 15821 | CCTAGATAACATGAGA | 74 | 1017 |
| 882605 | N/A | N/A | 15927 | 15942 | CCCAAATGACTTAGTC | 68 | 1018 |
| 882629 | N/A | N/A | 16178 | 16193 | ACAATAAAATGTCACG | 71 | 1019 |
| 882652 | N/A | N/A | 16394 | 16409 | CTCCAGGGATGGAACA | 81 | 1020 |
| 882676 | N/A | N/A | 16705 | 16720 | GACCACAGTGAAGTCG | 86 | 1021 |
| 882700 | N/A | N/A | 16926 | 16941 | GCTTACTGTGATTCTG | 66 | 1022 |
| 882724 | N/A | N/A | 17241 | 17256 | AAGGGTTACGCTTATT | 48 | 1023 |
| 882748 | N/A | N/A | 17545 | 17560 | ATGGATAGTTTCTCAT | 75 | 1024 |
| 882772 | N/A | N/A | 17760 | 17775 | TCCTAACCCTACCCTT | 70 | 1025 |
| 882796 | N/A | N/A | 17991 | 18006 | GAAATAGCATCAGAGC | 55 | 1026 |
| 882819 | N/A | N/A | 18601 | 18616 | ATCCATGTCAACTTTA | 41 | 1027 |
| 882843 | N/A | N/A | 18965 | 18980 | CAAAACTACTATTGTG | 77 | 1028 |
| 882866 | N/A | N/A | 19241 | 19256 | AGCCAAAGTGACTTAA | 42 | 1029 |
| 882892 | N/A | N/A | 4089 | 4104 | CGACAGTCCGGTTAGC | 89 | 1030 |
| 882904 | N/A | N/A | 12597 | 12612 | TTCCACACTGGATATG | 59 | 1031 |

TABLE 16

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 39 | 195 |
| 881078 | 14 | 29 | 3753 | 3768 | ATCGAGCGGTGAAACT | 71 | 1032 |
| 881102 | 357 | 372 | 6836 | 6851 | TCGGAACTTTCCTTTA | 67 | 1033 |
| 881125 | 692 | 707 | 9182 | 9197 | CATTGGTACGGGATTT | 84 | 1034 |
| 881172 | 1208 | 1223 | 13761 | 13776 | GACAAGAACTGCTGTG | 85 | 1035 |
| 881196 | 1444 | 1459 | 19561 | 19576 | GGATAGATCTGTGGTA | 51 | 1036 |
| 881220 | 1745 | 1760 | 19862 | 19877 | CAAAACAGTAAGAGGG | 69 | 1037 |
| 881244 | 1950 | 1965 | 20067 | 20082 | GCGCATTTCAGTAAAT | 67 | 1038 |
| 881268 | 2046 | 2061 | 20163 | 20178 | CATACCTACAAGCAGT | 57 | 1039 |
| 881292 | 2199 | 2214 | 20316 | 20331 | CAAGGCTACAGGCACG | 49 | 1040 |

TABLE 16-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881316 | 2389 | 2404 | 20506 | 20521 | ACATTACTAGATTGTA | 59 | 1041 |
| 881340 | 2525 | 2540 | 20642 | 20657 | TTGGACAGAAGGGCAA | 71 | 1042 |
| 881364 | 2710 | 2725 | 20827 | 20842 | AAACAGCCCACTGAGT | 89 | 1043 |
| 881388 | 2830 | 2845 | 20947 | 20962 | TAAGCAAGTGGAGGTC | 53 | 1044 |
| 881412 | 2914 | 2929 | 21031 | 21046 | AGTATGAGAAACGGCC | 38 | 1045 |
| 881436 | 3050 | 3065 | 21167 | 21182 | TGTAATGTAGGGATAC | 47 | 1046 |
| 881460 | 3343 | 3358 | 21460 | 21475 | GCAAGATGACTCCATG | 37 | 1047 |
| 881484 | 3431 | 3446 | 21548 | 21563 | ATGGCAGTGGAGCTCC | 44 | 1048 |
| 881508 | 3520 | 3535 | 21637 | 21652 | ATACATCACTGCAGTT | 64 | 1049 |
| 881531 | 3643 | 3658 | 21760 | 21775 | GGGTTAAATATTCTTC | 48 | 1050 |
| 881555 | 3919 | 3934 | 22036 | 22051 | TCATAGCTAGTTCATT | 48 | 1051 |
| 881579 | 4125 | 4140 | 22242 | 22257 | AACCAAGAAATGCACC | 67 | 1052 |
| 881598 | 4306 | 4321 | 22423 | 22438 | CCAATAGTCTAGCTGG | 81 | 1053 |
| 881622 | 4419 | 4434 | 22536 | 22551 | TCAAACACTAATACCT | 75 | 1054 |
| 881646 | 4557 | 4572 | 22674 | 22689 | AGTAACTGACACGCAC | 49 | 1055 |
| 881670 | 4667 | 4682 | 22784 | 22799 | TTAACCAATCCCAACA | 70 | 1056 |
| 881694 | 4846 | 4861 | 22963 | 22978 | TGTAACAGGCTATCAG | 69 | 1057 |
| 881718 | 5153 | 5168 | 23270 | 23285 | AGCAAACGCAGAGCC | 39 | 1058 |
| 881742 | 5210 | 5225 | 23327 | 23342 | AACGACAGCATAGCAT | 26 | 1059 |
| 881766 | N/A | N/A | 18784 | 18799 | ATATATGACGACTTAA | 94 | 1060 |
| 881790 | N/A | N/A | 18871 | 18886 | GCCTTAATGTTCAGCT | 51 | 1061 |
| 881811 | N/A | N/A | 4126 | 4141 | GCCTTGGACGGCCCCG | 77 | 1062 |
| 881835 | N/A | N/A | 4416 | 4431 | CCGGAGCAGGCCCGGG | 113 | 1063 |
| 881858 | N/A | N/A | 4806 | 4821 | CCGACACGCGCCGCTC | 70 | 1064 |
| 881882 | N/A | N/A | 5059 | 5074 | AGCCACGAGGCACCGC | 88 | 1065 |
| 881906 | N/A | N/A | 5672 | 5687 | GGAAACGAGAACGCAC | 70 | 1066 |
| 881928 | N/A | N/A | 5783 | 5798 | TGAGAGACGAAAACAG | 109 | 1067 |
| 881950 | N/A | N/A | 6216 | 6231 | GCCTAGGACTAAGGAC | 67 | 1068 |
| 881973 | N/A | N/A | 6426 | 6441 | AAGAAAGAATGGCGCA | 37 | 1069 |
| 881996 | N/A | N/A | 7187 | 7202 | TGCTGAACCCCACAGG | 67 | 1070 |
| 882020 | N/A | N/A | 7386 | 7401 | ATGCATAGTGATGAGA | 55 | 1071 |
| 882044 | N/A | N/A | 7728 | 7743 | CATAACACGGTGTTGA | 64 | 1072 |
| 882068 | N/A | N/A | 8148 | 8163 | TTCCAACAGGCGGACA | 57 | 1073 |
| 882091 | N/A | N/A | 8406 | 8421 | CATGGAGGATCATAAA | 78 | 1074 |
| 882115 | N/A | N/A | 8598<br>8650<br>9014 | 8613<br>8665<br>9029 | AGGAAGCACTGGCATC | 43 | 1075 |

TABLE 16-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882138 | N/A | N/A | 9424 | 9439 | TAAACTTGGCTGTGGG | 73 | 1076 |
| 882161 | N/A | N/A | 9632 | 9647 | TTCCAACAATAGCAAC | 54 | 1077 |
| 882208 | N/A | N/A | 10181 | 10196 | GAGCAGTAAACGCAAG | 46 | 1078 |
| 882232 | N/A | N/A | 10367 | 10382 | AACCATGTTCCTGAAG | 59 | 1079 |
| 882256 | N/A | N/A | 10674 | 10689 | ACTAGCAGGGCACGCT | 62 | 1080 |
| 882280 | N/A | N/A | 11101 | 11116 | TCTAATGGTGCTCCTA | 49 | 1081 |
| 882304 | N/A | N/A | 11378 | 11393 | GATGAGGGACCAGAAC | 80 | 1082 |
| 882328 | N/A | N/A | 11675 | 11690 | GGGCAAGATGAGAATT | 100 | 1083 |
| 882352 | N/A | N/A | 11989 | 12004 | CCGAGATATAAATAGC | 39 | 1084 |
| 882376 | N/A | N/A | 12206 | 12221 | TATCATGCATACCAAA | 42 | 1085 |
| 882399 | N/A | N/A | 12654 | 12669 | TGGTAGAATGTGATAT | 57 | 1086 |
| 882423 | N/A | N/A | 12900 | 12915 | GCAAAAAATATAACGG | 53 | 1087 |
| 882446 | N/A | N/A | 13275 | 13290 | CGTCAAGGAGGCCTGG | 57 | 1088 |
| 882468 | N/A | N/A | 13913 | 13928 | CTCTACTGGAGTCAAG | 75 | 1089 |
| 882490 | N/A | N/A | 14162 | 14177 | TGCATGAGGGTGACAC | 55 | 1090 |
| 882513 | N/A | N/A | 14458 | 14473 | GGCGAGTGGCGGGTAG | 92 | 1091 |
| 882536 | N/A | N/A | 14736 | 14751 | CTGAAGCTTAGTTATC | 62 | 1092 |
| 882560 | N/A | N/A | 15515 | 15530 | ACTCAATGTGCACCTT | 71 | 1093 |
| 882583 | N/A | N/A | 15807 | 15822 | CCCTAGATAACATGAG | 83 | 1094 |
| 882606 | N/A | N/A | 15982 | 15997 | ACTTACAGGACTATTT | 84 | 1095 |
| 882630 | N/A | N/A | 16200 | 16215 | GACAAATCTTCTGCCT | 74 | 1096 |
| 882653 | N/A | N/A | 16422 | 16437 | TGTAACTCTGAGTAGA | 57 | 1097 |
| 882677 | N/A | N/A | 16708 | 16723 | GTAGACCACAGTGAAG | 71 | 1098 |
| 882701 | N/A | N/A | 16934 | 16949 | AAGCAAGAGCTTACTG | 86 | 1099 |
| 882725 | N/A | N/A | 17246 | 17261 | AGTTTAAGGGTTACGC | 37 | 1100 |
| 882749 | N/A | N/A | 17546 | 17561 | AATGGATAGTTTCTCA | 37 | 1101 |
| 882773 | N/A | N/A | 17771 | 17786 | TCTAACCCTAATCCTA | 95 | 1102 |
| 882797 | N/A | N/A | 18030 | 18045 | GTTCAAGATTAAACCA | 29 | 1103 |
| 882820 | N/A | N/A | 18605 | 18620 | TTGCATCCATGTCAAC | 53 | 1104 |
| 882844 | N/A | N/A | 19017 | 19032 | GTATAGTTCTCAACCA | 53 | 1105 |
| 882867 | N/A | N/A | 19266 | 19281 | TCCATAGATCAACATG | 55 | 1106 |
| 882903 | N/A | N/A | 9991 | 10006 | CCAAGGATAACCTGAA | 56 | 1107 |

TABLE 17

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 37 | 195 |
| 881079 | 15 | 30 | 3754 | 3769 | GATCGAGCGGTGAAAC | 77 | 1108 |
| 881103 | 412 | 427 | 6891 | 6906 | AAGCGCACCGCAGGCG | 96 | 1109 |
| 881126 | 694 | 709 | 9184 | 9199 | GACATTGGTACGGGAT | 64 | 1110 |
| 881173 | 1209 | 1224 | 13762 | 13777 | TGACAAGAACTGCTGT | 82 | 1111 |
| 881197 | 1446 | 1461 | 19563 | 19578 | GCGGATAGATCTGTGG | 45 | 1112 |
| 881221 | 1777 | 1792 | 19894 | 19909 | CGCTGAACTGAAATCT | 63 | 1113 |
| 881245 | 1955 | 1970 | 20072 | 20087 | AAAGAGCGCATTTCAG | 94 | 1114 |
| 881269 | 2047 | 2062 | 20164 | 20179 | ACATACCTACAAGCAG | 55 | 1115 |
| 881293 | 2202 | 2217 | 20319 | 20334 | CCCCAAGGCTACAGGC | 75 | 1116 |
| 881317 | 2391 | 2406 | 20508 | 20523 | AGACATTACTAGATTG | 34 | 1117 |
| 881341 | 2530 | 2545 | 20647 | 20662 | AGTACTTGGACAGAAG | 57 | 1118 |
| 881365 | 2740 | 2755 | 20857 | 20872 | GAGGAAGCATAGAACA | 82 | 1119 |
| 881389 | 2832 | 2847 | 20949 | 20964 | CTTAAGCAAGTGGAGG | 30 | 1120 |
| 881413 | 2915 | 2930 | 21032 | 21047 | TAGTATGAGAAACGGC | 22 | 1121 |
| 881437 | 3051 | 3066 | 21168 | 21183 | GTGTAATGTAGGGATA | 36 | 1122 |
| 881461 | 3344 | 3359 | 21461 | 21476 | TGCAAGATGACTCCAT | 43 | 1123 |
| 881485 | 3433 | 3448 | 21550 | 21565 | ACATGGCAGTGGAGCT | 36 | 1124 |
| 881509 | 3522 | 3537 | 21639 | 21654 | GTATACATCACTGCAG | 56 | 1125 |
| 881532 | 3660 | 3675 | 21777 | 21792 | CTTTGAAGTGCTGTGT | 84 | 1126 |
| 881556 | 3920 | 3935 | 22037 | 22052 | TTCATAGCTAGTTCAT | 56 | 1127 |
| 881580 | 4168 | 4183 | 22285 | 22300 | TTGAGGTTTTCCTAAA | 71 | 1128 |
| 881599 | 4307 | 4322 | 22424 | 22439 | CCCAATAGTCTAGCTG | 44 | 1129 |
| 881623 | 4430 | 4445 | 22547 | 22562 | GACCAGCTTTTTCAAA | 62 | 1130 |
| 881647 | 4558 | 4573 | 22675 | 22690 | AAGTAACTGACACGCA | 77 | 1131 |
| 881671 | 4670 | 4685 | 22787 | 22802 | ACCTTAACCAATCCCA | 29 | 1132 |
| 881695 | 4847 | 4862 | 22964 | 22979 | CTGTAACAGGCTATCA | 56 | 1133 |
| 881719 | 5154 | 5169 | 23271 | 23286 | CAGCAAAACGCAGAGC | 46 | 1134 |
| 881743 | 5212 | 5227 | 23329 | 23344 | CCAACGACAGCATAGC | 24 | 1135 |
| 881767 | N/A | N/A | 18785 | 18800 | TATATATGACGACTTA | 80 | 1136 |
| 881791 | N/A | N/A | 18872 | 18887 | CGCCTTAATGTTCAGC | 34 | 1137 |
| 881812 | N/A | N/A | 4152 | 4167 | AGGCAGTTGTGCCGTC | 162 | 1138 |
| 881836 | N/A | N/A | 4423 | 4438 | CCGGACCCCGGAGCAG | 124 | 1139 |
| 881859 | N/A | N/A | 4807 | 4822 | CCCGACACGCGCCGCT | 88 | 1140 |
| 881883 | N/A | N/A | 5062 | 5077 | TTCAGCCACGAGGCAC | 95 | 1141 |
| 881907 | N/A | N/A | 5674 | 5689 | GTGGAAACGAGAACGC | 97 | 1142 |
| 881929 | N/A | N/A | 5794 | 5809 | CAGAGACGCGGTGAGA | 161 | 1143 |

TABLE 17-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881951 | N/A | N/A | 6217 | 6232 | TGCCTAGGACTAAGGA | 74 | 1144 |
| 881974 | N/A | N/A | 6479 | 6494 | GCTAAACCCAAAATAC | 96 | 1145 |
| 881997 | N/A | N/A | 7192 | 7207 | TCCTATGCTGAACCCC | 64 | 1146 |
| 882021 | N/A | N/A | 7390 | 7405 | TACCATGCATAGTGAT | 56 | 1147 |
| 882045 | N/A | N/A | 7730 | 7745 | TGCATAACACGGTGTT | 62 | 1148 |
| 882069 | N/A | N/A | 8153 | 8168 | GCATATTCCAACAGGC | 34 | 1149 |
| 882092 | N/A | N/A | 8409 | 8424 | ACTCATGGAGGATCAT | 81 | 1150 |
| 882116 | N/A | N/A | 8599 | 8614 | TAGGAAGCACTGGCAT | 72 | 1151 |
|  |  |  | 8651 | 8666 |  |  |  |
|  |  |  | 8755 | 8770 |  |  |  |
|  |  |  | 8859 | 8874 |  |  |  |
|  |  |  | 8911 | 8926 |  |  |  |
|  |  |  | 9015 | 9030 |  |  |  |
| 882139 | N/A | N/A | 9425 | 9440 | GTAAACTTGGCTGTGG | 82 | 1152 |
| 882162 | N/A | N/A | 9669 | 9684 | TGGTATTTTTCCGTTC | 31 | 1153 |
| 882185 | N/A | N/A | 9992 | 10007 | GCCAAGGATAACCTGA | 31 | 1154 |
| 882209 | N/A | N/A | 10186 | 10201 | AGCCAGAGCAGTAAAC | 85 | 1155 |
| 882233 | N/A | N/A | 10371 | 10386 | ACTGAACCATGTTCCT | 49 | 1156 |
| 882257 | N/A | N/A | 10676 | 10691 | CAACTAGCAGGGCACG | 62 | 1157 |
| 882281 | N/A | N/A | 11102 | 11117 | TTCTAATGGTGCTCCT | 93 | 1158 |
| 882305 | N/A | N/A | 11396 | 11411 | GCACATCAATGTTTTA | 33 | 1159 |
| 882329 | N/A | N/A | 11687 | 11702 | AAAGATGCCAGAGGGC | 77 | 1160 |
| 882353 | N/A | N/A | 11991 | 12006 | TGCCGAGATATAAATA | 77 | 1161 |
| 882377 | N/A | N/A | 12207 | 12222 | GTATCATGCATACCAA | 35 | 1162 |
| 882400 | N/A | N/A | 12675 | 12690 | GCCTTAATGGTGATTT | 74 | 1163 |
| 882447 | N/A | N/A | 13289 | 13304 | ACAAAAGGTTCCCGCG | 97 | 1164 |
| 882469 | N/A | N/A | 13921 | 13936 | CAGAAGATCTCTACTG | 88 | 1165 |
| 882491 | N/A | N/A | 14163 | 14178 | CTGCATGAGGGTGACA | 81 | 1166 |
| 882514 | N/A | N/A | 14477 | 14492 | GAAGAGTTGGCGGTGG | 85 | 1167 |
| 882537 | N/A | N/A | 14737 | 14752 | CCTGAAGCTTAGTTAT | 65 | 1168 |
| 882561 | N/A | N/A | 15531 | 15546 | ACGCAGTGCACCTGTG | 107 | 1169 |
| 882584 | N/A | N/A | 15813 | 15828 | CTCCAACCCTAGATAA | 98 | 1170 |
| 882607 | N/A | N/A | 15983 | 15998 | AACTTACAGGACTATT | 87 | 1171 |
| 882631 | N/A | N/A | 16201 | 16216 | AGACAAATCTTCTGCC | 104 | 1172 |
| 882654 | N/A | N/A | 16430 | 16445 | CTGAACTGTGTAACTC | 72 | 1173 |
| 882678 | N/A | N/A | 16710 | 16725 | TAGTAGACCACAGTGA | 91 | 1174 |
| 882702 | N/A | N/A | 16950 | 16965 | CACCAGGTTAAACAGG | 108 | 1175 |
| 882726 | N/A | N/A | 17247 | 17262 | TAGTTTAAGGGTTACG | 51 | 1176 |
| 882750 | N/A | N/A | 17554 | 17569 | CTCCAGGGAATGGATA | 73 | 1177 |

TABLE 17-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882774 | N/A | N/A | 17777 | 17792 | GAAAACTCTAACCCTA | 91 | 1178 |
| 882798 | N/A | N/A | 18087 | 18102 | TTATATACTGGTTGGT | 51 | 1179 |
| 882821 | N/A | N/A | 18620 | 18635 | TTAGAGGACAGTGACT | 82 | 1180 |
| 882845 | N/A | N/A | 19018 | 19033 | TGTATAGTTCTCAACC | 57 | 1181 |
| 882868 | N/A | N/A | 19267 | 19282 | TTCCATAGATCAACAT | 56 | 1182 |
| 882905 | N/A | N/A | 12921 | 12936 | CCCTAAGTTTAATTTA | 103 | 1183 |

TABLE 18

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 38 | 195 |
| 881080 | 16 | 31 | 3755 | 3770 | AGATCGAGCGGTGAAA | 76 | 1184 |
| 881104 | 415 | 430 | 6894 | 6909 | TCAAAGCGCACCGCAG | 57 | 1185 |
| 881127 | 697 | 712 | 9187 | 9202 | TGGGACATTGGTACGG | 31 | 1186 |
| 881174 | 1210 | 1225 | 13763 | 13778 | CTGACAAGAACTGCTG | 79 | 1187 |
| 881198 | 1447 | 1462 | 19564 | 19579 | GGCGGATAGATCTGTG | 49 | 1188 |
| 881222 | 1780 | 1795 | 19897 | 19912 | AACCGCTGAACTGAAA | 87 | 1189 |
| 881246 | 1957 | 1972 | 20074 | 20089 | TTAAAGAGCGCATTTC | 59 | 1190 |
| 881270 | 2048 | 2063 | 20165 | 20180 | GACATACCTACAAGCA | 50 | 1191 |
| 881294 | 2229 | 2244 | 20346 | 20361 | AACCGCTGGCAGGTGG | 60 | 1192 |
| 881318 | 2393 | 2408 | 20510 | 20525 | TTAGACATTACTAGAT | 55 | 1193 |
| 881342 | 2531 | 2546 | 20648 | 20663 | AAGTACTTGGACAGAA | 46 | 1194 |
| 881366 | 2743 | 2758 | 20860 | 20875 | CACGAGGAAGCATAGA | 44 | 1195 |
| 881390 | 2833 | 2848 | 20950 | 20965 | ACTTAAGCAAGTGGAG | 37 | 1196 |
| 881414 | 2917 | 2932 | 21034 | 21049 | TGTAGTATGAGAAACG | 31 | 1197 |
| 881438 | 3059 | 3074 | 21176 | 21191 | GCTGAACTGTGTAATG | 42 | 1198 |
| 881462 | 3345 | 3360 | 21462 | 21477 | GTGCAAGATGACTCCA | 44 | 1199 |
| 881486 | 3435 | 3450 | 21552 | 21567 | GTACATGGCAGTGGAG | 44 | 1200 |
| 881510 | 3523 | 3538 | 21640 | 21655 | TGTATACATCACTGCA | 37 | 1201 |
| 881533 | 3665 | 3680 | 21782 | 21797 | AGCTTCTTTGAAGTGC | 38 | 1202 |
| 881557 | 3921 | 3936 | 22038 | 22053 | TTTCATAGCTAGTTCA | 44 | 1203 |
| 881581 | 4170 | 4185 | 22287 | 22302 | GCTTGAGGTTTTCCTA | 23 | 1204 |
| 881600 | 4312 | 4327 | 22429 | 22444 | TCATACCCAATAGTCT | 48 | 1205 |
| 881624 | 4438 | 4453 | 22555 | 22570 | CGCTCAAAGACCAGCT | 44 | 1206 |

TABLE 18-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881648 | 4559 | 4574 | 22676 | 22691 | AAAGTAACTGACACGC | 33 | 1207 |
| 881672 | 4671 | 4686 | 22788 | 22803 | GACCTTAACCAATCCC | 36 | 1208 |
| 881696 | 4863 | 4878 | 22980 | 22995 | GACCTTTACTTCATTC | 48 | 1209 |
| 881720 | 5157 | 5172 | 23274 | 23289 | TCTCAGCAAAACGCAG | 73 | 1210 |
| 881744 | 5213 | 5228 | 23330 | 23345 | ACCAACGACAGCATAG | 33 | 1211 |
| 881768 | N/A | N/A | 18786 | 18801 | TTATATATGACGACTT | 65 | 1212 |
| 881813 | N/A | N/A | 4156 | 4171 | TCGCAGGCAGTTGTGC | 120 | 1213 |
| 881837 | N/A | N/A | 4425 | 4440 | CGCCGGACCCCGGAGC | 91 | 1214 |
| 881860 | N/A | N/A | 4816 | 4831 | CCAAAGGCTCCCGACA | 71 | 1215 |
| 881884 | N/A | N/A | 5065 | 5080 | CCCTTCAGCCACGAGG | 92 | 1216 |
| 881908 | N/A | N/A | 5675 | 5690 | CGTGGAAACGAGAACG | 71 | 1217 |
| 881952 | N/A | N/A | 6229 | 6244 | TCTGAGTGAGCTTGCC | 51 | 1218 |
| 881975 | N/A | N/A | 6541 | 6556 | TGCATAGGCATCCTTC | 32 | 1219 |
| 881998 | N/A | N/A | 7200 | 7215 | ATTAATTCTCCTATGC | 85 | 1220 |
| 882022 | N/A | N/A | 7393 | 7408 | TATTACCATGCATAGT | 70 | 1221 |
| 882046 | N/A | N/A | 7732 | 7747 | AATGCATAACACGGTG | 51 | 1222 |
| 882070 | N/A | N/A | 8154 | 8169 | AGCATATTCCAACAGG | 31 | 1223 |
| 882093 | N/A | N/A | 8417 | 8432 | GTGAAAACACTCATGG | 40 | 1224 |
| 882117 | N/A | N/A | 8606<br>8658<br>8762<br>8866<br>8918<br>9022 | 8621<br>8673<br>8777<br>8881<br>8933<br>9037 | GCTGAGATAGGAAGCA | 81 | 1225 |
| 882140 | N/A | N/A | 9426 | 9441 | AGTAAACTTGGCTGTG | 62 | 1226 |
| 882163 | N/A | N/A | 9710 | 9725 | TGGTAGGTAGGCACCT | 65 | 1227 |
| 882186 | N/A | N/A | 10006 | 10021 | CTTCACTACCTGCAGC | 78 | 1228 |
| 882210 | N/A | N/A | 10190 | 10205 | ATAGAGCCAGAGCAGT | 34 | 1229 |
| 882234 | N/A | N/A | 10372 | 10387 | CACTGAACCATGTTCC | 39 | 1230 |
| 882258 | N/A | N/A | 10677 | 10692 | GCAACTAGCAGGGCAC | 47 | 1231 |
| 882282 | N/A | N/A | 11116 | 11131 | AGTGATGTCAGGTTTT | 28 | 1232 |
| 882306 | N/A | N/A | 11398 | 11413 | AGGCACATCAATGTTT | 49 | 1233 |
| 882330 | N/A | N/A | 11688 | 11703 | TAAAGATGCCAGAGGG | 61 | 1234 |
| 882354 | N/A | N/A | 11999 | 12014 | CACGAGGTTGCCGAGA | 36 | 1235 |
| 882378 | N/A | N/A | 12209 | 12224 | CTGTATCATGCATACC | 39 | 1236 |
| 882401 | N/A | N/A | 12682 | 12697 | CACTGAGGCCTTAATG | 66 | 1237 |
| 882424 | N/A | N/A | 12927 | 12942 | AATGAACCCTAAGTTT | 97 | 1238 |
| 882448 | N/A | N/A | 13290 | 13305 | AACAAAGGTTCCCGC | 60 | 1239 |
| 882470 | N/A | N/A | 13922 | 13937 | ACAGAAGATCTCTACT | 68 | 1240 |

TABLE 18-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882492 | N/A | N/A | 14205 | 14220 | GTACAGTCCACTCCAC | 90 | 1241 |
| 882515 | N/A | N/A | 14550 | 14565 | GGCACATGAGAAATCA | 67 | 1242 |
| 882538 | N/A | N/A | 14993 | 15008 | AACTGCAGCACCGTGG | 55 | 1243 |
| 882562 | N/A | N/A | 15533 | 15548 | TCACGCAGTGCACCTG | 54 | 1244 |
| 882585 | N/A | N/A | 15826 | 15841 | TGAGAAAGCATGGCTC | 60 | 1245 |
| 882608 | N/A | N/A | 15987 | 16002 | AGCTAACTTACAGGAC | 104 | 1246 |
| 882632 | N/A | N/A | 16208 | 16223 | GTACACAAGACAAATC | 79 | 1247 |
| 882655 | N/A | N/A | 16433 | 16448 | TGCCTGAACTGTGTAA | 65 | 1248 |
| 882679 | N/A | N/A | 16713 | 16728 | AGGTAGTAGACCACAG | 41 | 1249 |
| 882703 | N/A | N/A | 16955 | 16970 | GAACACACCAGGTTAA | 102 | 1250 |
| 882727 | N/A | N/A | 17248 | 17263 | CTAGTTTAAGGGTTAC | 73 | 1251 |
| 882751 | N/A | N/A | 17565 | 17580 | CTACAAAATGCCTCCA | 58 | 1252 |
| 882775 | N/A | N/A | 17778 | 17793 | AGAAAACTCTAACCCT | 75 | 1253 |
| 882799 | N/A | N/A | 18089 | 18104 | GATTATATACTGGTTG | 41 | 1254 |
| 882822 | N/A | N/A | 18623 | 18638 | GACTTAGAGGACAGTG | 52 | 1255 |
| 882846 | N/A | N/A | 19019 | 19034 | CTGTATAGTTCTCAAC | 48 | 1256 |
| 882869 | N/A | N/A | 19283 | 19298 | ATTTTTTGGTTAGTCC | 47 | 1257 |
| 882896 | N/A | N/A | 5796 | 5811 | AACAGAGACGCGGTGA | 90 | 1258 |

TABLE 19

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 38 | 195 |
| 881081 | 18 | 33 | 3757 | 3772 | CAAGATCGAGCGGTGA | 62 | 1259 |
| 881105 | 416 | 431 | 6895 | 6910 | TTCAAAGCGCACCGCA | 51 | 1260 |
| 881128 | 728 | 743 | 9218 | 9233 | TGCCAGTGGTGGCCGC | 70 | 1261 |
| 881175 | 1211 | 1226 | N/A | N/A | TCTGACAAGAACTGCT | 88 | 1262 |
| 881199 | 1448 | 1463 | 19565 | 19580 | TGGCGGATAGATCTGT | 66 | 1263 |
| 881223 | 1784 | 1799 | 19901 | 19916 | CCTCAACCGCTGAACT | 70 | 1264 |
| 881247 | 1958 | 1973 | 20075 | 20090 | ATTAAAGAGCGCATTT | 87 | 1265 |
| 881271 | 2049 | 2064 | 20166 | 20181 | AGACATACCTACAAGC | 50 | 1266 |
| 881295 | 2233 | 2248 | 20350 | 20365 | AGGAAACCGCTGGCAG | 44 | 1267 |
| 881319 | 2395 | 2410 | 20512 | 20527 | ACTTAGACATTACTAG | 80 | 1268 |
| 881343 | 2534 | 2549 | 20651 | 20666 | GTTAAGTACTTGGACA | 68 | 1269 |
| 881367 | 2745 | 2760 | 20862 | 20877 | GGCACGAGGAAGCATA | 38 | 1270 |

TABLE 19-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881391 | 2835 | 2850 | 20952 | 20967 | ATACTTAAGCAAGTGG | 24 | 1271 |
| 881415 | 2918 | 2933 | 21035 | 21050 | CTGTAGTATGAGAAAC | 55 | 1272 |
| 881439 | 3066 | 3081 | 21183 | 21198 | GATAAAGGCTGAACTG | 33 | 1273 |
| 881463 | 3359 | 3374 | 21476 | 21491 | CTGCATGAAAGTGTGT | 44 | 1274 |
| 881487 | 3443 | 3458 | 21560 | 21575 | CCTACTGGGTACATGG | 37 | 1275 |
| 881511 | 3524 | 3539 | 21641 | 21656 | ATGTATACATCACTGC | 33 | 1276 |
| 881534 | 3686 | 3701 | 21803 | 21818 | CCTGAGACAGACTTCC | 45 | 1277 |
| 881558 | 3924 | 3939 | 22041 | 22056 | GTATTTCATAGCTAGT | 31 | 1278 |
| 881582 | 4172 | 4187 | 22289 | 22304 | CTGCTTGAGGTTTTCC | 26 | 1279 |
| 881601 | 4314 | 4329 | 22431 | 22446 | GTTCATACCCAATAGT | 34 | 1280 |
| 881625 | 4449 | 4464 | 22566 | 22581 | ATTTATGCCCTCGCTC | 74 | 1281 |
| 881649 | 4560 | 4575 | 22677 | 22692 | AAAAGTAACTGACACG | 39 | 1282 |
| 881673 | 4675 | 4690 | 22792 | 22807 | TAAAGACCTTAACCAA | 70 | 1283 |
| 881697 | 4909 | 4924 | 23026 | 23041 | TTATGCATGTTCCTCA | 43 | 1284 |
| 881721 | 5164 | 5179 | 23281 | 23296 | CTACAGATCTCAGCAA | 82 | 1285 |
| 881745 | 5216 | 5231 | 23333 | 23348 | TATACCAACGACAGCA | 51 | 1286 |
| 881769 | N/A | N/A | 18787 | 18802 | TTTATATATGACGACT | 61 | 1287 |
| 881793 | N/A | N/A | 19455 | 19470 | TAGCAGAGGTTCTACC | 74 | 1288 |
| 881814 | N/A | N/A | 4215 | 4230 | AGGAACGAAGAGCAGG | 57 | 1289 |
| 881838 | N/A | N/A | 4447 | 4462 | GGGATTCCGCGCGCAG | 86 | 1290 |
| 881861 | N/A | N/A | 4818 | 4833 | GCCCAAAGGCTCCCGA | 89 | 1291 |
| 881885 | N/A | N/A | 5362 | 5377 | CCGGAGACCTTGAAGA | 91 | 1292 |
| 881930 | N/A | N/A | 5797 | 5812 | AAACAGAGACGCGGTG | 82 | 1293 |
| 881953 | N/A | N/A | 6241 | 6256 | ACCCACCCAGTGTCTG | 82 | 1294 |
| 881976 | N/A | N/A | 6542 | 6557 | TTGCATAGGCATCCTT | 53 | 1295 |
| 881999 | N/A | N/A | 7203 | 7218 | GTGATTAATTCTCCTA | 30 | 1296 |
| 882023 | N/A | N/A | 7414 | 7429 | CACTTTAAAAGTTGAC | 72 | 1297 |
| 882047 | N/A | N/A | 7733 | 7748 | GAATGCATAACACGGT | 39 | 1298 |
| 882071 | N/A | N/A | 8158 | 8173 | GAGAAGCATATTCCAA | 43 | 1299 |
| 882094 | N/A | N/A | 8431 | 8446 | CTTCATCAGACTAAGT | 69 | 1300 |
| 882118 | N/A | N/A | 8607<br>8659<br>8763<br>8867<br>8919<br>9023 | 8622<br>8674<br>8778<br>8882<br>8934<br>9038 | GGCTGAGATAGGAAGC | 64 | 1301 |
| 882141 | N/A | N/A | 9427 | 9442 | GAGTAAACTTGGCTGT | 62 | 1302 |
| 882164 | N/A | N/A | 9716 | 9731 | ACCCAGTGGTAGGTAG | 70 | 1303 |
| 882187 | N/A | N/A | 10014 | 10029 | GTACACCTCTTCACTA | 93 | 1304 |

TABLE 19-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882211 | N/A | N/A | 10191 | 10206 | CATAGAGCCAGAGCAG | 40 | 1305 |
| 882235 | N/A | N/A | 10448 | 10463 | GCCAAAGAGCCCAATT | 67 | 1306 |
| 882259 | N/A | N/A | 10772 | 10787 | GTCCGACGCACCGCGG | 82 | 1307 |
| 882283 | N/A | N/A | 11122 | 11137 | ACAAGCAGTGATGTCA | 27 | 1308 |
| 882307 | N/A | N/A | 11403 | 11418 | CTCTTAGGCACATCAA | 39 | 1309 |
| 882331 | N/A | N/A | 11689 | 11704 | TTAAAGATGCCAGAGG | 72 | 1310 |
| 882355 | N/A | N/A | 12000 | 12015 | TCACGAGGTTGCCGAG | 38 | 1311 |
| 882379 | N/A | N/A | 12221 | 12236 | CTGATAATTAATCTGT | 37 | 1312 |
| 882402 | N/A | N/A | 12689 | 12704 | GGGTAAGCACTGAGGC | 39 | 1313 |
| 882425 | N/A | N/A | 12990 | 13005 | TTTAAGTCATGTGTCA | 50 | 1314 |
| 882449 | N/A | N/A | 13291 | 13306 | GAACAAAGGTTCCCG | 82 | 1315 |
| 882471 | N/A | N/A | 13923 | 13938 | GACAGAAGATCTCTAC | 83 | 1316 |
| 882493 | N/A | N/A | 14210 | 14225 | AACCAGTACAGTCCAC | 65 | 1317 |
| 882516 | N/A | N/A | 14551 | 14566 | AGGCACATGAGAAATC | 77 | 1318 |
| 882539 | N/A | N/A | 15020 | 15035 | GGCAATGGAGTCTCGC | 50 | 1319 |
| 882563 | N/A | N/A | 15535 | 15550 | TCTCACGCAGTGCACC | 56 | 1320 |
| 882586 | N/A | N/A | 15837 | 15852 | GCACAATTCTCTGAGA | 66 | 1321 |
| 882609 | N/A | N/A | 16031 | 16046 | TATCAAAGATCTCCAC | 75 | 1322 |
| 882633 | N/A | N/A | 16231 | 16246 | CTTTAGCCCATGCTCC | 80 | 1323 |
| 882656 | N/A | N/A | 16438 | 16453 | CACTATGCCTGAACTG | 90 | 1324 |
| 882680 | N/A | N/A | 16718 | 16733 | TCAAAAGGTAGTAGAC | 71 | 1325 |
| 882704 | N/A | N/A | 16959 | 16974 | CACCGAACACACCAGG | 80 | 1326 |
| 882728 | N/A | N/A | 17287 | 17302 | TCAGACTGTGCTGCTC | 64 | 1327 |
| 882752 | N/A | N/A | 17566 | 17581 | CCTACAAAATGCCTCC | 53 | 1328 |
| 882776 | N/A | N/A | 17808 | 17823 | GTTATCTATGGAAACC | 58 | 1329 |
| 882800 | N/A | N/A | 18090 | 18105 | GGATTATATACTGGTT | 23 | 1330 |
| 882823 | N/A | N/A | 18682 | 18697 | ATGGACCACGCAGCCT | 61 | 1331 |
| 882847 | N/A | N/A | 19026 | 19041 | AGGTAATCTGTATAGT | 38 | 1332 |
| 882870 | N/A | N/A | 19311 | 19326 | TTCATATTTGGAGCCA | 34 | 1333 |
| 882894 | N/A | N/A | 5700 | 5715 | GCCCGGAGGAAGGGCG | 106 | 1334 |

TABLE 20

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 609408 | 4226 | 4241 | 22343 | 22358 | TTGTAAATGAGTCGGT | 26 | 195 |
| 881082 | 20 | 35 | 3759 | 3774 | CCCAAGATCGAGCGGT | 72 | 1335 |
| 881106 | 417 | 432 | 6896 | 6911 | GTTCAAAGCGCACCGC | 35 | 1336 |
| 881129 | 741 | 756 | 9231 | 9246 | ACAAGCTGGGCCTTGC | 73 | 1337 |
| 881152 | 942 | 957 | 13495 | 13510 | GGAGATCCGGCAGCCC | 77 | 1338 |
| 881176 | 1222 | 1237 | N/A | N/A | ACGCTTGCAGCTCTGA | 52 | 1339 |
| 881200 | 1452 | 1467 | 19569 | 19584 | GGAATGGCGGATAGAT | 67 | 1340 |
| 881224 | 1785 | 1800 | 19902 | 19917 | TCCTCAACCGCTGAAC | 63 | 1341 |
| 881248 | 1959 | 1974 | 20076 | 20091 | AATTAAAGAGCGCATT | 83 | 1342 |
| 881272 | 2050 | 2065 | 20167 | 20182 | CAGACATACCTACAAG | 56 | 1343 |
| 881296 | 2234 | 2249 | 20351 | 20366 | CAGGAAACCGCTGGCA | 26 | 1344 |
| 881320 | 2396 | 2411 | 20513 | 20528 | TACTTAGACATTACTA | 61 | 1345 |
| 881344 | 2536 | 2551 | 20653 | 20668 | TAGTTAAGTACTTGGA | 44 | 1346 |
| 881368 | 2746 | 2761 | 20863 | 20878 | TGGCACGAGGAAGCAT | 54 | 1347 |
| 881392 | 2836 | 2851 | 20953 | 20968 | TATACTTAAGCAAGTG | 53 | 1348 |
| 881416 | 2919 | 2934 | 21036 | 21051 | CCTGTAGTATGAGAAA | 43 | 1349 |
| 881440 | 3068 | 3083 | 21185 | 21200 | TTGATAAAGGCTGAAC | 33 | 1350 |
| 881464 | 3364 | 3379 | 21481 | 21496 | GAGCACTGCATGAAAG | 49 | 1351 |
| 881488 | 3444 | 3459 | 21561 | 21576 | CCCTACTGGGTACATG | 63 | 1352 |
| 881512 | 3525 | 3540 | 21642 | 21657 | GATGTATACATCACTG | 30 | 1353 |
| 881535 | 3722 | 3737 | 21839 | 21854 | GAGCATCCGCTTGGAG | 69 | 1354 |
| 881559 | 3926 | 3941 | 22043 | 22058 | GAGTATTTCATAGCTA | 29 | 1355 |
| 881583 | 4173 | 4188 | 22290 | 22305 | ACTGCTTGAGGTTTTC | 42 | 1356 |
| 881602 | 4319 | 4334 | 22436 | 22451 | TTTTAGTTCATACCCA | 48 | 1357 |
| 881626 | 4450 | 4465 | 22567 | 22582 | TATTTATGCCCTCGCT | 74 | 1358 |
| 881650 | 4576 | 4591 | 22693 | 22708 | TCTGAATTGTTACTAA | 65 | 1359 |
| 881674 | 4677 | 4692 | 22794 | 22809 | AATAAAGACCTTAACC | 89 | 1360 |
| 881698 | 4911 | 4926 | 23028 | 23043 | TCTTATGCATGTTCCT | 38 | 1361 |
| 881722 | 5176 | 5191 | 23293 | 23308 | AAGCATCCTTTCCTAC | 65 | 1362 |
| 881746 | 5217 | 5232 | 23334 | 23349 | GTATACCAACGACAGC | 22 | 1363 |
| 881770 | N/A | N/A | 18788 | 18803 | TTTTATATATGACGAC | 66 | 1364 |
| 881794 | N/A | N/A | 22820 | 22835 | GAGGACTTCGGGAGAT | 77 | 1365 |
| 881815 | N/A | N/A | 4217 | 4232 | TTAGGAACGAAGAGCA | 68 | 1366 |
| 881839 | N/A | N/A | 4487 | 4502 | GACAAGTGGCGCAGAC | 89 | 1367 |
| 881862 | N/A | N/A | 4853 | 4868 | CTCCTACCCGCCTGCT | 85 | 1368 |
| 881886 | N/A | N/A | 5364 | 5379 | GGCCGGAGACCTTGAA | 97 | 1369 |
| 881909 | N/A | N/A | 5712 | 5727 | CGGCAGACGGGAGCCC | 88 | 1370 |

TABLE 20-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 881931 | N/A | N/A | 5798 | 5813 | GAAACAGAGACGCGGT | 99 | 1371 |
| 881954 | N/A | N/A | 6265 | 6280 | GCGGAGGTTCCTTGAG | 56 | 1372 |
| 882000 | N/A | N/A | 7211 | 7226 | CATACAGTGTGATTAA | 47 | 1373 |
| 882024 | N/A | N/A | 7424 | 7439 | GACCATGTTACACTTT | 50 | 1374 |
| 882048 | N/A | N/A | 7736 | 7751 | TTAGAATGCATAACAC | 56 | 1375 |
| 882072 | N/A | N/A | 8159 | 8174 | TGAGAAGCATATTCCA | 28 | 1376 |
| 882095 | N/A | N/A | 8443 | 8458 | CTGGAGTGAACCCTTC | 44 | 1377 |
| 882119 | N/A | N/A | 8701 8805 8961 | 8716 8820 8976 | AGAAGCACTGGCATCG | 63 | 1378 |
| 882142 | N/A | N/A | 9430 | 9445 | TGAGAGTAAACTTGGC | 35 | 1379 |
| 882165 | N/A | N/A | 9742 | 9757 | ATCCACAATCAGCAAG | 49 | 1380 |
| 882188 | N/A | N/A | 10016 | 10031 | TGGTACACCTCTTCAC | 68 | 1381 |
| 882212 | N/A | N/A | 10192 | 10207 | CCATAGAGCCAGAGCA | 36 | 1382 |
| 882236 | N/A | N/A | 10464 | 10479 | GTCTACTTGAGTCTGT | 49 | 1383 |
| 882260 | N/A | N/A | 10780 | 10795 | GACAGAGAGTCCGACG | 101 | 1384 |
| 882284 | N/A | N/A | 11123 | 11138 | CACAAGCAGTGATGTC | 40 | 1385 |
| 882308 | N/A | N/A | 11405 | 11420 | TACTCTTAGGCACATC | 41 | 1386 |
| 882332 | N/A | N/A | 11723 | 11738 | TCAGAATTTAGTTAGT | 67 | 1387 |
| 882356 | N/A | N/A | 12001 | 12016 | ATCACGAGGTTGCCGA | 40 | 1388 |
| 882380 | N/A | N/A | 12223 | 12238 | GGCTGATAATTAATCT | 53 | 1389 |
| 882403 | N/A | N/A | 12695 | 12710 | ATTAAAGGGTAAGCAC | 68 | 1390 |
| 882426 | N/A | N/A | 13007 | 13022 | TGATAGTGGTGATGTC | 46 | 1391 |
| 882450 | N/A | N/A | 13292 | 13307 | GGAACAAAAGGTTCCC | 88 | 1392 |
| 882472 | N/A | N/A | 13956 | 13971 | TCTGATCCGGACTCTC | 59 | 1393 |
| 882494 | N/A | N/A | 14213 | 14228 | CAAAACCAGTACAGTC | 51 | 1394 |
| 882517 | N/A | N/A | 14622 | 14637 | CCAGAGCACACAGACG | 64 | 1395 |
| 882540 | N/A | N/A | 15021 | 15036 | GGGCAATGGAGTCTCG | 76 | 1396 |
| 882564 | N/A | N/A | 15538 | 15553 | GTCTCTCACGCAGTGC | 50 | 1397 |
| 882587 | N/A | N/A | 15838 | 15853 | GGCACAATTCTCTGAG | 57 | 1398 |
| 882610 | N/A | N/A | 16033 | 16048 | GATATCAAAGATCTCC | 43 | 1399 |
| 882634 | N/A | N/A | 16254 | 16269 | AAAGACAAGTGCCCAT | 76 | 1400 |
| 882657 | N/A | N/A | 16441 | 16456 | TGTCACTATGCCTGAA | 73 | 1401 |
| 882681 | N/A | N/A | 16726 | 16741 | ACGAAGATTCAAAAGG | 64 | 1402 |
| 882705 | N/A | N/A | 16962 | 16977 | CATCACCGAACACACC | 76 | 1403 |
| 882729 | N/A | N/A | 17289 | 17304 | CCTCAGACTGTGCTGC | 70 | 1404 |
| 882753 | N/A | N/A | 17567 | 17582 | ACCTACAAAATGCCTC | 58 | 1405 |

TABLE 20-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 882777 | N/A | N/A | 17826 | 17841 | GGCAAATTAATGCTTC | 24 | 1406 |
| 882801 | N/A | N/A | 18096 | 18111 | TCTATGGGATTATATA | 74 | 1407 |
| 882824 | N/A | N/A | 18684 | 18699 | TTATGGACCACGCAGC | 69 | 1408 |
| 882848 | N/A | N/A | 19030 | 19045 | TTCTAGGTAATCTGTA | 62 | 1409 |
| 882871 | N/A | N/A | 19312 | 19327 | TTTCATATTTGGAGCC | 25 | 1410 |
| 882899 | N/A | N/A | 6633 | 6648 | AGTAGCTGGGCCCTCG | 38 | 1411 |

TABLE 21

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 609408 | 4226 | 4241 | 22343 | 22358 | TTGTAAATGAGTCGGT | 31 | 195 |
| 668815 | 436 | 451 | 6915 | 6930 | CCTCAAAGTCATTGCT | 79 | 1412 |
| 881083 | 21 | 36 | 3760 | 3775 | TCCCAAGATCGAGCGG | 84 | 1413 |
| 881130 | 743 | 758 | 9233 | 9248 | TCACAAGCTGGGCCTT | 70 | 1414 |
| 881153 | 946 | 961 | 13499 | 13514 | CATGGGAGATCCGGCA | 59 | 1415 |
| 881177 | 1235 | 1250 | 17028 | 17043 | CCGTGGTGAGCAAACG | 68 | 1416 |
| 881201 | 1453 | 1468 | 19570 | 19585 | AGGAATGGCGGATAGA | 62 | 1417 |
| 881225 | 1793 | 1808 | 19910 | 19925 | CGCAATTCTCCTCAAC | 62 | 1418 |
| 881249 | 1960 | 1975 | 20077 | 20092 | AAATTAAAGAGCGCAT | 87 | 1419 |
| 881273 | 2054 | 2069 | 20171 | 20186 | GGCACAGACATACCTA | 52 | 1420 |
| 881297 | 2237 | 2252 | 20354 | 20369 | CACCAGGAAACCGCTG | 85 | 1421 |
| 881321 | 2399 | 2414 | 20516 | 20531 | CATTACTTAGACATTA | 81 | 1422 |
| 881345 | 2537 | 2552 | 20654 | 20669 | ATAGTTAAGTACTTGG | 52 | 1423 |
| 881369 | 2752 | 2767 | 20869 | 20884 | TATAATTGGCACGAGG | 59 | 1424 |
| 881393 | 2837 | 2852 | 20954 | 20969 | GTATACTTAAGCAAGT | 58 | 1425 |
| 881417 | 2921 | 2936 | 21038 | 21053 | ATCCTGTAGTATGAGA | 55 | 1426 |
| 881441 | 3069 | 3084 | 21186 | 21201 | CTTGATAAAGGCTGAA | 40 | 1427 |
| 881465 | 3372 | 3387 | 21489 | 21504 | GCTACAAAGAGCACTG | 37 | 1428 |
| 881489 | 3449 | 3464 | 21566 | 21581 | TCAAACCCTACTGGGT | 92 | 1429 |
| 881513 | 3532 | 3547 | 21649 | 21664 | TCTATAAGATGTATAC | 74 | 1430 |
| 881536 | 3726 | 3741 | 21843 | 21858 | AATGGAGCATCCGCTT | 107 | 1431 |
| 881560 | 3945 | 3960 | 22062 | 22077 | TGCTAGGATTCCTAAC | 74 | 1432 |
| 881584 | 4174 | 4189 | 22291 | 22306 | TACTGCTTGAGGTTTT | 50 | 1433 |
| 881603 | 4320 | 4335 | 22437 | 22452 | TTTTTAGTTCATACCC | 59 | 1434 |
| 881627 | 4451 | 4466 | 22568 | 22583 | GTATTTATGCCCTCGC | 47 | 1435 |

TABLE 21-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 881651 | 4577 | 4592 | 22694 | 22709 | ATCTGAATTGTTACTA | 88 | 1436 |
| 881675 | 4732 | 4747 | 22849 | 22864 | CACCATTCAGACAGAT | 167 | 1437 |
| 881699 | 4918 | 4933 | 23035 | 23050 | CTACATTTCTTATGCA | 61 | 1438 |
| 881723 | 5180 | 5195 | 23297 | 23312 | TGTGAAGCATCCTTTC | 55 | 1439 |
| 881747 | 5218 | 5233 | 23335 | 23350 | TGTATACCAACGACAG | 42 | 1440 |
| 881771 | N/A | N/A | 18804 | 18819 | GATATTAGAGACTGTA | 49 | 1441 |
| 881795 | N/A | N/A | 22823 | 22838 | ACAGAGGACTTCGGGA | 136 | 1442 |
| 881816 | N/A | N/A | 4218 | 4233 | CTTAGGAACGAAGAGC | 93 | 1443 |
| 881840 | N/A | N/A | 4491 | 4506 | AAACGACAAGTGGCGC | 79 | 1444 |
| 881863 | N/A | N/A | 4860 | 4875 | GCGAAGGCTCCTACCC | 115 | 1445 |
| 881887 | N/A | N/A | 5369 | 5384 | CCCGAGGCCGGAGACC | 94 | 1446 |
| 881910 | N/A | N/A | 5720 | 5735 | GACGGAGGCGGCAGAC | 143 | 1447 |
| 881932 | N/A | N/A | 5815 | 5830 | GAAAAGCAGCGAAAAG | 98 | 1448 |
| 881955 | N/A | N/A | 6278 | 6293 | GGTAGAGTGAGATGCG | 42 | 1449 |
| 881977 | N/A | N/A | 6663 | 6678 | GTTCTAGGGTCCTCCT | 50 | 1450 |
| 882001 | N/A | N/A | 7213 | 7228 | GGCATACAGTGTGATT | 75 | 1451 |
| 882025 | N/A | N/A | 7428 | 7443 | AGCTGACCATGTTACA | 119 | 1452 |
| 882049 | N/A | N/A | 7737 | 7752 | CTTAGAATGCATAACA | 74 | 1453 |
| 882073 | N/A | N/A | 8213 | 8228 | GGCACTACTTCCAAAA | 69 | 1454 |
| 882096 | N/A | N/A | 8452 | 8467 | CCGAAAAGACTGGAGT | 43 | 1455 |
| 882120 | N/A | N/A | 8702<br>8806<br>8962 | 8717<br>8821<br>8977 | AAGAAGCACTGGCATC | 77 | 1456 |
| 882143 | N/A | N/A | 9432 | 9447 | CCTGAGAGTAAACTTG | 82 | 1457 |
| 882166 | N/A | N/A | 9745 | 9760 | CTAATCCACAATCAGC | 55 | 1458 |
| 882189 | N/A | N/A | 10024 | 10039 | TTAAAGAGTGGTACAC | 94 | 1459 |
| 882213 | N/A | N/A | 10194 | 10209 | TTCCATAGAGCCAGAG | 63 | 1460 |
| 882237 | N/A | N/A | 10497 | 10512 | CAAAGCGGGTTCACAA | 84 | 1461 |
| 882261 | N/A | N/A | 10781 | 10796 | AGACAGAGAGTCCGAC | 93 | 1462 |
| 882285 | N/A | N/A | 11126 | 11141 | AACCACAAGCAGTGAT | 83 | 1463 |
| 882309 | N/A | N/A | 11409 | 11424 | GTATTACTCTTAGGCA | 36 | 1464 |
| 882333 | N/A | N/A | 11750 | 11765 | GCCACAACTCTCGCCT | 75 | 1465 |
| 882357 | N/A | N/A | 12004 | 12019 | GAAATCACGAGGTTGC | 38 | 1466 |
| 882381 | N/A | N/A | 12241 | 12256 | TCTAATAAATGTGCTC | 56 | 1467 |
| 882404 | N/A | N/A | 12698 | 12713 | CACATTAAAGGGTAAG | 101 | 1468 |
| 882427 | N/A | N/A | 13049 | 13064 | ACTATTAAGAACTTGC | 79 | 1469 |
| 882451 | N/A | N/A | 13293 | 13308 | GGGAACAAAAGGTTCC | 111 | 1470 |

TABLE 21-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 882473 | N/A | N/A | 13957 | 13972 | ATCTGATCCGGACTCT | 91 | 1471 |
| 882495 | N/A | N/A | 14214 | 14229 | GCAAAACCAGTACAGT | 42 | 1472 |
| 882518 | N/A | N/A | 14630 | 14645 | CAACAGTGCCAGAGCA | 89 | 1473 |
| 882541 | N/A | N/A | 15070 | 15085 | TCCTATGGTCAGCCTC | 52 | 1474 |
| 882565 | N/A | N/A | 15590 | 15605 | CGCAAGTCTACAGCCC | 41 | 1475 |
| 882588 | N/A | N/A | 15839 | 15854 | TGGCACAATTCTCTGA | 87 | 1476 |
| 882611 | N/A | N/A | 16042 | 16057 | GAATAGGAAGATATCA | 94 | 1477 |
| 882635 | N/A | N/A | 16256 | 16271 | GGAAAGACAAGTGCCC | 46 | 1478 |
| 882658 | N/A | N/A | 16447 | 16462 | TCCCACTGTCACTATG | 85 | 1479 |
| 882682 | N/A | N/A | 16727 | 16742 | CACGAAGATTCAAAAG | 90 | 1480 |
| 882706 | N/A | N/A | 16971 | 16986 | AGAAACCCTCATCACC | 105 | 1481 |
| 882730 | N/A | N/A | 17330 | 17345 | CTTTGATGAGCAGATC | 88 | 1482 |
| 882754 | N/A | N/A | 17570 | 17585 | GAGACCTACAAAATGC | 89 | 1483 |
| 882778 | N/A | N/A | 17856 | 17871 | GTCTTAAGGGTTCAAG | 51 | 1484 |
| 882802 | N/A | N/A | 18097 | 18112 | GTCTATGGGATTATAT | 79 | 1485 |
| 882825 | N/A | N/A | 18685 | 18700 | TTTATGGACCACGCAG | 62 | 1486 |
| 882849 | N/A | N/A | 19033 | 19048 | GATTTCTAGGTAATCT | 69 | 1487 |
| 882872 | N/A | N/A | 19337 | 19352 | TTACATCCTAGAACAC | 97 | 1488 |

TABLE 22

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 609408 | 4226 | 4241 | 22343 | 22358 | TTGTAAATGAGTCGGT | 35 | 195 |
| 669124 | 3537 | 3552 | 21654 | 21669 | TTGCATCTATAAGATG | 69 | 1489 |
| 881084 | 44 | 59 | 3783 | 3798 | TCGGAGCTGAGGGCAG | 82 | 1490 |
| 881107 | 448 | 463 | 6927 | 6942 | GCTCAACCAGTTCCTC | 62 | 1491 |
| 881131 | 754 | 769 | N/A | N/A | GGCAACCATTTTCACA | 117 | 1492 |
| 881154 | 949 | 964 | 13502 | 13517 | GTCCATGGGAGATCCG | 48 | 1493 |
| 881178 | 1245 | 1260 | 17038 | 17053 | CAGGGAGCGGCCGTGG | 83 | 1494 |
| 881202 | 1454 | 1469 | 19571 | 19586 | GAGGAATGGCGGATAG | 69 | 1495 |
| 881226 | 1794 | 1809 | 19911 | 19926 | CCGCAATTCTCCTCAA | 80 | 1496 |
| 881250 | 1961 | 1976 | 20078 | 20093 | CAAATTAAAGAGCGCA | 43 | 1497 |
| 881274 | 2055 | 2070 | 20172 | 20187 | TGGCACAGACATACCT | 62 | 1498 |
| 881298 | 2240 | 2255 | 20357 | 20372 | CCACACCAGGAAACCG | 86 | 1499 |
| 881322 | 2400 | 2415 | 20517 | 20532 | CCATTACTTAGACATT | 36 | 1500 |

TABLE 22-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 881346 | 2538 | 2553 | 20655 | 20670 | GATAGTTAAGTACTTG | 51 | 1501 |
| 881370 | 2756 | 2771 | 20873 | 20888 | AAACTATAATTGGCAC | 70 | 1502 |
| 881394 | 2838 | 2853 | 20955 | 20970 | GGTATACTTAAGCAAG | 32 | 1503 |
| 881418 | 2927 | 2942 | 21044 | 21059 | GTAAATATCCTGTAGT | 67 | 1504 |
| 881442 | 3070 | 3085 | 21187 | 21202 | GCTTGATAAAGGCTGA | 27 | 1505 |
| 881466 | 3373 | 3388 | 21490 | 21505 | AGCTACAAAGAGCACT | 67 | 1506 |
| 881490 | 3450 | 3465 | 21567 | 21582 | GTCAAACCCTACTGGG | 69 | 1507 |
| 881537 | 3729 | 3744 | 21846 | 21861 | TGAAATGGAGCATCCG | 91 | 1508 |
| 881561 | 3951 | 3966 | 22068 | 22083 | GACAAGTGCTAGGATT | 39 | 1509 |
| 881585 | 4176 | 4191 | 22293 | 22308 | ATTACTGCTTGAGGTT | 38 | 1510 |
| 881604 | 4321 | 4336 | 22438 | 22453 | CTTTTTAGTTCATACC | 63 | 1511 |
| 881628 | 4452 | 4467 | 22569 | 22584 | TGTATTTATGCCCTCG | 56 | 1512 |
| 881652 | 4580 | 4595 | 22697 | 22712 | TGGATCTGAATTGTTA | 45 | 1513 |
| 881676 | 4735 | 4750 | 22852 | 22867 | ACGCACCATTCAGACA | 102 | 1514 |
| 881700 | 4972 | 4987 | 23089 | 23104 | GGAGGAGGGTTGGCCT | 99 | 1515 |
| 881724 | 5181 | 5196 | 23298 | 23313 | TTGTGAAGCATCCTTT | 37 | 1516 |
| 881748 | 5219 | 5234 | 23336 | 23351 | ATGTATACCAACGACA | 37 | 1517 |
| 881772 | N/A | N/A | 18805 | 18820 | TGATATTAGAGACTGT | 40 | 1518 |
| 881796 | N/A | N/A | 22825 | 22840 | CCACAGAGGACTTCGG | 73 | 1519 |
| 881817 | N/A | N/A | 4220 | 4235 | CCCTTAGGAACGAAGA | 106 | 1520 |
| 881841 | N/A | N/A | 4494 | 4509 | TGCAAACGACAAGTGG | 79 | 1521 |
| 881864 | N/A | N/A | 4861 | 4876 | CGCGAAGGCTCCTACC | 141 | 1522 |
| 881888 | N/A | N/A | 5370 | 5385 | TCCCGAGGCCGGAGAC | 127 | 1523 |
| 881911 | N/A | N/A | 5723 | 5738 | ACGGACGGAGGCGGCA | 89 | 1524 |
| 881956 | N/A | N/A | 6279 | 6294 | CGGTAGAGTGAGATGC | 46 | 1525 |
| 881978 | N/A | N/A | 6677 | 6692 | CATCGAACTCCTGAGT | 69 | 1526 |
| 882002 | N/A | N/A | 7218 | 7233 | ATTGAGGCATACAGTG | 70 | 1527 |
| 882026 | N/A | N/A | 7437 | 7452 | AAACACCTCAGCTGAC | 84 | 1528 |
| 882050 | N/A | N/A | 7784 | 7799 | GACCTAACTAAATGTC | 118 | 1529 |
| 882074 | N/A | N/A | 8218 | 8233 | GATAAGGCACTACTTC | 53 | 1530 |
| 882097 | N/A | N/A | 8463 | 8478 | CATTTTATCATCCGAA | 45 | 1531 |
| 882121 | N/A | N/A | 8753 8857 8909 | 8768 8872 8924 | GGAAGCACTGGCATTG | 51 | 1532 |
| 882144 | N/A | N/A | 9442 | 9457 | TAGCATGGATCCTGAG | 100 | 1533 |
| 882167 | N/A | N/A | 9746 | 9761 | TCTAATCCACAATCAG | 59 | 1534 |
| 882190 | N/A | N/A | 10025 | 10040 | ATTAAAGAGTGGTACA | 107 | 1535 |

TABLE 22-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 stop Stop | Sequence | IRF4 (% UTC) | SEQ ID NO |
|---|---|---|---|---|---|---|---|
| 882214 | N/A | N/A | 10198 | 10213 | CTAATTCCATAGAGCC | 20 | 1536 |
| 882238 | N/A | N/A | 10500 | 10515 | TCACAAAGCGGGTTCA | 77 | 1537 |
| 882262 | N/A | N/A | 10785 | 10800 | GTCTAGACAGAGAGTC | 98 | 1538 |
| 882286 | N/A | N/A | 11151 | 11166 | AGCCAGTGGCTGAAAC | 79 | 1539 |
| 882310 | N/A | N/A | 11411 | 11426 | GTGTATTACTCTTAGG | 14 | 1540 |
| 882334 | N/A | N/A | 11751 | 11766 | TGCCACAACTCTCGCC | 69 | 1541 |
| 882358 | N/A | N/A | 12005 | 12020 | AGAAATCACGAGGTTG | 36 | 1542 |
| 882382 | N/A | N/A | 12260 | 12275 | TCAATGGGAATCACAG | 60 | 1543 |
| 882405 | N/A | N/A | 12699 | 12714 | ACACATTAAAGGGTAA | 89 | 1544 |
| 882428 | N/A | N/A | 13050 | 13065 | CACTATTAAGAACTTG | 67 | 1545 |
| 882452 | N/A | N/A | 13309 | 13324 | CCCACATGTCCCGTGG | 95 | 1546 |
| 882474 | N/A | N/A | 13995 | 14010 | TTGCAAGAGAACAGCC | 61 | 1547 |
| 882496 | N/A | N/A | 14215 | 14230 | TGCAAAACCAGTACAG | 72 | 1548 |
| 882519 | N/A | N/A | 14639 | 14654 | AGCACATGTCAACAGT | 69 | 1549 |
| 882542 | N/A | N/A | 15091 | 15106 | AACCAGCACAGTTCTC | 118 | 1550 |
| 882566 | N/A | N/A | 15591 | 15606 | GCGCAAGTCTACAGCC | 120 | 1551 |
| 882589 | N/A | N/A | 15854 | 15869 | ATCAGAATGGCGAGTT | 53 | 1552 |
| 882612 | N/A | N/A | 16046 | 16061 | ACCTGAATAGGAAGAT | 69 | 1553 |
| 882636 | N/A | N/A | 16258 | 16273 | TTGGAAAGACAAGTGC | 85 | 1554 |
| 882659 | N/A | N/A | 16464 | 16479 | AGCCATCGGCAGCTGA | 86 | 1555 |
| 882683 | N/A | N/A | 16733 | 16748 | TGGACCCACGAAGATT | 62 | 1556 |
| 882707 | N/A | N/A | 16972 | 16987 | CAGAAACCCTCATCAC | 96 | 1557 |
| 882731 | N/A | N/A | 17367 | 17382 | AAAGAGGCACCCTCCT | 138 | 1558 |
| 882755 | N/A | N/A | 17588 | 17603 | TGCTAGGACACAGCTG | 57 | 1559 |
| 882779 | N/A | N/A | 17862 | 17877 | TCAAAGTCTTAAGGG | 93 | 1560 |
| 882803 | N/A | N/A | 18111 | 18126 | GAGAAAACTCCTGAGT | 95 | 1561 |
| 882826 | N/A | N/A | 18686 | 18701 | TTTTATGGACCACGCA | 69 | 1562 |
| 882850 | N/A | N/A | 19079 | 19094 | CACAACTGCAGTTTGA | 86 | 1563 |
| 882873 | N/A | N/A | 19343 | 19358 | CCAAAGTTACATCCTA | 61 | 1564 |
| 882897 | N/A | N/A | 5887 | 5902 | CCGCAGAGAGCTAGCA | 106 | 1565 |

TABLE 23

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 48 | 195 |
| 881085 | 49 | 64 | 3788 | 3803 | TGGACTCGGAGCTGAG | 76 | 1566 |
| 881108 | 462 | 477 | 6941 | 6956 | GTCCAGCTGGCTCCGC | 47 | 1567 |
| 881132 | 762 | 777 | N/A | N/A | TGTCACCTGGCAACCA | 91 | 1568 |
| 881155 | 987 | 1002 | 13540 | 13555 | GAACAGGACCTGGTCC | 75 | 1569 |
| 881203 | 1455 | 1470 | 19572 | 19587 | AGAGGAATGGCGGATA | 58 | 1570 |
| 881251 | 1962 | 1977 | 20079 | 20094 | ACAAATTAAAGAGCGC | 36 | 1571 |
| 881275 | 2078 | 2093 | 20195 | 20210 | TTACATCTTACTTCCC | 58 | 1572 |
| 881299 | 2306 | 2321 | 20423 | 20438 | ACTAACTGGCTTCCAG | 69 | 1573 |
| 881323 | 2401 | 2416 | 20518 | 20533 | ACCATTACTTAGACAT | 35 | 1574 |
| 881347 | 2539 | 2554 | 20656 | 20671 | AGATAGTTAAGTACTT | 89 | 1575 |
| 881371 | 2758 | 2773 | 20875 | 20890 | TCAAACTATAATTGGC | 26 | 1576 |
| 881395 | 2839 | 2854 | 20956 | 20971 | AGGTATACTTAAGCAA | 32 | 1577 |
| 881419 | 2929 | 2944 | 21046 | 21061 | TAGTAAATATCCTGTA | 58 | 1578 |
| 881443 | 3071 | 3086 | 21188 | 21203 | AGCTTGATAAAGGCTG | 64 | 1579 |
| 881467 | 3376 | 3391 | 21493 | 21508 | GTTAGCTACAAAGAGC | 59 | 1580 |
| 881491 | 3451 | 3466 | 21568 | 21583 | TGTCAAACCCTACTGG | 77 | 1581 |
| 881514 | 3549 | 3564 | 21666 | 21681 | CCCCAAAATACTTTGC | 0 | 1582 |
| 881538 | 3730 | 3745 | 21847 | 21862 | TTGAAATGGAGCATCC | 78 | 1583 |
| 881562 | 3952 | 3967 | 22069 | 22084 | AGACAAGTGCTAGGAT | 44 | 1584 |
| 881586 | 4186 | 4201 | 22303 | 22318 | GGAGATATTAATTACT | 50 | 1585 |
| 881605 | 4369 | 4384 | 22486 | 22501 | GCTCATTTCACTGTAG | 36 | 1586 |
| 881629 | 4453 | 4468 | 22570 | 22585 | CTGTATTTATGCCCTC | 40 | 1587 |
| 881653 | 4584 | 4599 | 22701 | 22716 | ACACTGGATCTGAATT | 54 | 1588 |
| 881677 | 4742 | 4757 | 22859 | 22874 | AGCCTTCACGCACCAT | 70 | 1589 |
| 881701 | 4976 | 4991 | 23093 | 23108 | CATTGGAGGAGGGTTG | 102 | 1590 |
| 881725 | 5183 | 5198 | 23300 | 23315 | GTTTGTGAAGCATCCT | 35 | 1591 |
| 881749 | 5220 | 5235 | 23337 | 23352 | GATGTATACCAACGAC | 32 | 1592 |
| 881773 | N/A | N/A | 18806 | 18821 | ATGATATTAGAGACTG | 26 | 1593 |
| 881797 | N/A | N/A | 3804 | 3819 | AGCCCTTACCTCGCCC | 75 | 1594 |
| 881818 | N/A | N/A | 4239 | 4254 | GGCCGCCGTGAGCTTG | 97 | 1595 |
| 881865 | N/A | N/A | 4862 | 4877 | CCGCGAAGGCTCCTAC | 86 | 1596 |
| 881912 | N/A | N/A | 5724 | 5739 | CACGGACGGAGGCGGC | 82 | 1597 |
| 881933 | N/A | N/A | 5894 | 5909 | GGAGTACCCGCAGAGA | 75 | 1598 |
| 881957 | N/A | N/A | 6282 | 6297 | AACCGGTAGAGTGAGA | 94 | 1599 |
| 881979 | N/A | N/A | 6682 | 6697 | CGCAGCATCGAACTCC | 67 | 1600 |
| 882003 | N/A | N/A | 7219 | 7234 | CATTGAGGCATACAGT | 45 | 1601 |

TABLE 23-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882027 | N/A | N/A | 7439 | 7454 | ATAAACACCTCAGCTG | 79 | 1602 |
| 882051 | N/A | N/A | 7791 | 7806 | AGGAACTGACCTAACT | 69 | 1603 |
| 882075 | N/A | N/A | 8219 | 8234 | TGATAAGGCACTACTT | 65 | 1604 |
| 882098 | N/A | N/A | 8464 | 8479 | GCATTTTATCATCCGA | 37 | 1605 |
| 882122 | N/A | N/A | 8754 8858 8910 | 8769 8873 8925 | AGGAAGCACTGGCATT | 41 | 1606 |
| 882145 | N/A | N/A | 9458 | 9473 | CACGAAGGGCAGTGCC | 83 | 1607 |
| 882168 | N/A | N/A | 9747 | 9762 | ATCTAATCCACAATCA | 70 | 1608 |
| 882191 | N/A | N/A | 10026 | 10041 | CATTAAAGAGTGGTAC | 103 | 1609 |
| 882215 | N/A | N/A | 10199 | 10214 | ACTAATTCCATAGAGC | 21 | 1610 |
| 882239 | N/A | N/A | 10519 | 10534 | TGACATGCTTTGTCCT | 41 | 1611 |
| 882263 | N/A | N/A | 10795 | 10810 | ATCAGATGATGTCTAG | 103 | 1612 |
| 882287 | N/A | N/A | 11160 | 11175 | CTCCATTCAAGCCAGT | 42 | 1613 |
| 882311 | N/A | N/A | 11446 | 11461 | GCAAGCTATATTAAAG | 29 | 1614 |
| 882335 | N/A | N/A | 11757 | 11772 | CAAAAGTGCCACAACT | 90 | 1615 |
| 882359 | N/A | N/A | 12008 | 12023 | ATCAGAAATCACGAGG | 29 | 1616 |
| 882383 | N/A | N/A | 12261 | 12276 | ATCAATGGGAATCACA | 10 | 1617 |
| 882406 | N/A | N/A | 12701 | 12716 | ACACACATTAAAGGGT | 57 | 1618 |
| 882429 | N/A | N/A | 13055 | 13070 | AGCATCACTATTAAGA | 28 | 1619 |
| 882453 | N/A | N/A | 13323 | 13338 | TGGAACTCTAGTGTCC | 98 | 1620 |
| 882475 | N/A | N/A | 14002 | 14017 | ACCAGAATTGCAAGAG | 40 | 1621 |
| 882497 | N/A | N/A | 14216 | 14231 | GTGCAAAACCAGTACA | 67 | 1622 |
| 882520 | N/A | N/A | 14640 | 14655 | GAGCACATGTCAACAG | 60 | 1623 |
| 882543 | N/A | N/A | 15112 | 15127 | TCACTTGCCGCCGCCT | 51 | 1624 |
| 882567 | N/A | N/A | 15600 | 15615 | GTTCTAGTCGCGCAAG | 73 | 1625 |
| 882590 | N/A | N/A | 15855 | 15870 | AATCAGAATGGCGAGT | 61 | 1626 |
| 882613 | N/A | N/A | 16052 | 16067 | GTGCAGACCTGAATAG | 86 | 1627 |
| 882637 | N/A | N/A | 16269 | 16284 | CTGGAACATTGTTGGA | 54 | 1628 |
| 882660 | N/A | N/A | 16501 | 16516 | CAGAAAATATGTAACG | 78 | 1629 |
| 882684 | N/A | N/A | 16736 | 16751 | CATTGGACCCACGAAG | 72 | 1630 |
| 882708 | N/A | N/A | 16975 | 16990 | GTTCAGAAACCCTCAT | 87 | 1631 |
| 882732 | N/A | N/A | 17368 | 17383 | GAAAGAGGCACCCTCC | 81 | 1632 |
| 882756 | N/A | N/A | 17597 | 17612 | TAAAGAGGTGCTAGG | 73 | 1633 |
| 882780 | N/A | N/A | 17889 | 17904 | GTATGTAGCAATGTGA | 79 | 1634 |
| 882804 | N/A | N/A | 18126 | 18141 | CTGGAGAGAACTCATG | 62 | 1635 |
| 882827 | N/A | N/A | 18687 | 18702 | ATTTTATGGACCACGC | 51 | 1636 |

TABLE 23-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882851 | N/A | N/A | 19080 | 19095 | CCACAACTGCAGTTTG | 77 | 1637 |
| 882874 | N/A | N/A | 19346 | 19361 | AGCCCAAAGTTACATC | 58 | 1638 |
| 882893 | N/A | N/A | 4508 | 4523 | CACTAAGTGGGCTCTG | 59 | 1639 |

TABLE 24

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 881086 | 149 | 164 | 5176 | 5191 | CCGAACTCTCCGCCTC | 64 | 1640 |
| 881133 | 774 | 789 | 10839 | 10854 | ATAAAAGGTTCCTGTC | 16 | 1641 |
| 881180 | 1256 | 1271 | 17049 | 17064 | TGGAATCTTGGCAGGG | 60 | 1642 |
| 881204 | 1457 | 1472 | 19574 | 19589 | ATAGAGGAATGGCGGA | 35 | 1643 |
| 881228 | 1828 | 1843 | 19945 | 19960 | AATCAGATGTCACTGA | 97 | 1644 |
| 881252 | 1973 | 1988 | 20090 | 20105 | CCTAATCTACAACAAA | 85 | 1645 |
| 881276 | 2124 | 2139 | 20241 | 20256 | CCTACATACATTAATA | 107 | 1646 |
| 881300 | 2307 | 2322 | 20424 | 20439 | TACTAACTGGCTTCCA | 72 | 1647 |
| 881324 | 2402 | 2417 | 20519 | 20534 | AACCATTACTTAGACA | 55 | 1648 |
| 881348 | 2540 | 2555 | 20657 | 20672 | CAGATAGTTAAGTACT | 56 | 1649 |
| 881372 | 2760 | 2775 | 20877 | 20892 | TGTCAAACTATAATTG | 85 | 1650 |
| 881396 | 2840 | 2855 | 20957 | 20972 | TAGGTATACTTAAGCA | 21 | 1651 |
| 881420 | 2933 | 2948 | 21050 | 21065 | GTAATAGTAAATATCC | 39 | 1652 |
| 881444 | 3076 | 3091 | 21193 | 21208 | CACTAAGCTTGATAAA | 111 | 1653 |
| 881468 | 3377 | 3392 | 21494 | 21509 | TGTTAGCTACAAAGAG | 53 | 1654 |
| 881492 | 3456 | 3471 | 21573 | 21588 | TGAAATGTCAAACCCT | 46 | 1655 |
| 881515 | 3559 | 3574 | 21676 | 21691 | GGATAATATACCCCAA | 36 | 1656 |
| 881539 | 3731 | 3746 | 21848 | 21863 | ATTGAAATGGAGCATC | 101 | 1657 |
| 881587 | 4187 | 4202 | 22304 | 22319 | AGGAGATATTAATTAC | 43 | 1658 |
| 881606 | 4378 | 4393 | 22495 | 22510 | GTAAGGGCTGCTCATT | 48 | 1659 |
| 881630 | 4459 | 4474 | 22576 | 22591 | GGCTAGCTGTATTTAT | 63 | 1660 |
| 881654 | 4586 | 4601 | 22703 | 22718 | TTACACTGGATCTGAA | 62 | 1661 |
| 881678 | 4755 | 4770 | 22872 | 22887 | TGTAAGGTCTGAGAGC | 75 | 1662 |
| 881702 | 4978 | 4993 | 23095 | 23110 | TCCATTGGAGGAGGGT | 67 | 1663 |
| 881726 | 5184 | 5199 | 23301 | 23316 | AGTTTGTGAAGCATCC | 31 | 1664 |
| 881750 | 5222 | 5237 | 23339 | 23354 | ATGATGTATACCAACG | 14 | 1665 |
| 881774 | N/A | N/A | 18807 | 18822 | CATGATATTAGAGACT | 44 | 1666 |

TABLE 24-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881798 | N/A | N/A | 3865 | 3880 | CTGGTTCGCGCTCCGG | 93 | 1667 |
| 881819 | N/A | N/A | 4244 | 4259 | CCGGAGGCCGCCGTGA | 87 | 1668 |
| 881842 | N/A | N/A | 4510 | 4525 | CGCACTAAGTGGGCTC | 86 | 1669 |
| 881866 | N/A | N/A | 4892 | 4907 | GCACAGCCGTCCGCCT | 84 | 1670 |
| 881890 | N/A | N/A | 5492 | 5507 | CGCCACCTGATGCCTC | 70 | 1671 |
| 881913 | N/A | N/A | 5726 | 5741 | CCCACGGACGGAGGCG | 109 | 1672 |
| 881934 | N/A | N/A | 5896 | 5911 | TGGGAGTACCCGCAGA | 74 | 1673 |
| 881958 | N/A | N/A | 6284 | 6299 | ATAACCGGTAGAGTGA | 50 | 1674 |
| 881980 | N/A | N/A | 6683 | 6698 | CCGCAGCATCGAACTC | 58 | 1675 |
| 882028 | N/A | N/A | 7481 | 7496 | GGTCAGAATCTTGAAA | 91 | 1676 |
| 882052 | N/A | N/A | 7795 | 7810 | AAACAGGAACTGACCT | 80 | 1677 |
| 882076 | N/A | N/A | 8220 | 8235 | ATGATAAGGCACTACT | 87 | 1678 |
| 882099 | N/A | N/A | 8465 | 8480 | AGCATTTTATCATCCG | 19 | 1679 |
| 882123 | N/A | N/A | 8781 | 8796 | TTAAAGGAGTGCAGGA | 84 | 1680 |
| 882146 | N/A | N/A | 9460 | 9475 | CCCACGAAGGGCAGTG | 65 | 1681 |
| 882169 | N/A | N/A | 9751 | 9766 | CCACATCTAATCCACA | 33 | 1682 |
| 882192 | N/A | N/A | 10049 | 10064 | GTGAACATGCCACTCA | 38 | 1683 |
| 882216 | N/A | N/A | 10200 | 10215 | TACTAATTCCATAGAG | 74 | 1684 |
| 882240 | N/A | N/A | 10520 | 10535 | ATGACATGCTTTGTCC | 54 | 1685 |
| 882264 | N/A | N/A | 10939 | 10954 | AGCAAACCCTGCACTC | 92 | 1686 |
| 882288 | N/A | N/A | 11215 | 11230 | GGTAAAGGCACATTCC | 53 | 1687 |
| 882312 | N/A | N/A | 11448 | 11463 | TTGCAAGCTATATTAA | 66 | 1688 |
| 882336 | N/A | N/A | 11790 | 11805 | TGGTAGGTCAAACTCC | 113 | 1689 |
| 882360 | N/A | N/A | 12009 | 12024 | CATCAGAAATCACGAG | 45 | 1690 |
| 882384 | N/A | N/A | 12283 | 12298 | GGTAACTGTATGGAAC | 24 | 1691 |
| 882407 | N/A | N/A | 12757 | 12772 | GAATTAGGTGCTTAAT | 41 | 1692 |
| 882430 | N/A | N/A | 13060 | 13075 | TATAGAGCATCACTAT | 59 | 1693 |
| 882454 | N/A | N/A | 13324 | 13339 | GTGGAACTCTAGTGTC | 88 | 1694 |
| 882476 | N/A | N/A | 14021 | 14036 | TAAGAGGCGACTGCTG | 145 | 1695 |
| 882498 | N/A | N/A | 14233 | 14248 | CTCCTATAACTTCTCC | 67 | 1696 |
| 882521 | N/A | N/A | 14643 | 14658 | TACGAGCACATGTCAA | 64 | 1697 |
| 882544 | N/A | N/A | 15146 | 15161 | TAGAATGAGAGGTGTC | 71 | 1698 |
| 882568 | N/A | N/A | 15609 | 15624 | TAATAGTAAGTTCTAG | 100 | 1699 |
| 882591 | N/A | N/A | 15860 | 15875 | AGGCTAATCAGAATGG | 58 | 1700 |
| 882614 | N/A | N/A | 16099 | 16114 | TCAGATACACACCCTC | 63 | 1701 |
| 882638 | N/A | N/A | 16276 | 16291 | AAACGGACTGGAACAT | 93 | 1702 |

TABLE 24-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882661 | N/A | N/A | 16516 | 16531 | GTAACTCAGGCACCAC | 53 | 1703 |
| 882685 | N/A | N/A | 16758 | 16773 | GCTAAAGAACACTGCT | 97 | 1704 |
| 882709 | N/A | N/A | 16981 | 16996 | GACCATGTTCAGAAAC | 4 | 1705 |
| 882733 | N/A | N/A | 17369 | 17384 | GGAAAGAGGCACCCTC | 72 | 1706 |
| 882757 | N/A | N/A | 17640 | 17655 | TATCATATGCCCAATA | 68 | 1707 |
| 882781 | N/A | N/A | 17894 | 17909 | TGCAAGTATGTAGCAA | 97 | 1708 |
| 882805 | N/A | N/A | 18131 | 18146 | AATCACTGGAGAGAAC | 71 | 1709 |
| 882828 | N/A | N/A | 18688 | 18703 | CATTTTATGGACCACG | 38 | 1710 |
| 882852 | N/A | N/A | 19099 | 19114 | GGCCAATGATTTTGTT | 94 | 1711 |
| 882875 | N/A | N/A | 19350 | 19365 | GTAAAGCCCAAAGTTA | 73 | 1712 |

Example 6: Effect of 3-10-3 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured SK-MEL-28 cells at a density of 20,000 cells per well were transfected using electroporation with 4,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS3114 (described hereinabove in Example 1) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 25 through 36 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein 'd' represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 25 through 36 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 25

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 44 | 195 |
| 881087 | 151 | 166 | 5178 | 5193 | TGCCGAACTCTCCGCC | 57 | 1713 |
| 881110 | 482 | 497 | 6961 | 6976 | ACTTTGTACGGGTCTG | 61 | 1714 |
| 881134 | 778 | 793 | 10843 | 10858 | AAGCATAAAAGGTTCC | 72 | 1715 |
| 881157 | 1059 | 1074 | 13612 | 13627 | GACCACGCCCCTCTCC | 45 | 1716 |
| 881181 | 1263 | 1278 | 17056 | 17071 | AGTCACCTGGAATCTT | 53 | 1717 |
| 881205 | 1458 | 1473 | 19575 | 19590 | AATAGAGGAATGGCGG | 47 | 1718 |
| 881229 | 1831 | 1846 | 19948 | 19963 | GCCAATCAGATGTCAC | 54 | 1719 |

TABLE 25-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881253 | 1974 | 1989 | 20091 | 20106 | ACCTAATCTACAACAA | 83 | 1720 |
| 881277 | 2128 | 2143 | 20245 | 20260 | AGCTCCTACATACATT | 56 | 1721 |
| 881301 | 2309 | 2324 | 20426 | 20441 | TTTACTAACTGGCTTC | 55 | 1722 |
| 881325 | 2432 | 2447 | 20549 | 20564 | GGTCAAAAAGATGCAG | 49 | 1723 |
| 881349 | 2541 | 2556 | 20658 | 20673 | ACAGATAGTTAAGTAC | 65 | 1724 |
| 881373 | 2770 | 2785 | 20887 | 20902 | TTTAAGGCCCTGTCAA | 117 | 1725 |
| 881397 | 2842 | 2857 | 20959 | 20974 | GATAGGTATACTTAAG | 49 | 1726 |
| 881421 | 2938 | 2953 | 21055 | 21070 | TGGGAGTAATAGTAAA | 84 | 1727 |
| 881445 | 3077 | 3092 | 21194 | 21209 | TCACTAAGCTTGATAA | 63 | 1728 |
| 881469 | 3383 | 3398 | 21500 | 21515 | CTTCACTGTTAGCTAC | 49 | 1729 |
| 881493 | 3468 | 3483 | 21585 | 21600 | TTGCATGGCTAATGAA | 58 | 1730 |
| 881516 | 3560 | 3575 | 21677 | 21692 | AGGATAATATACCCCA | 26 | 1731 |
| 881540 | 3733 | 3748 | 21850 | 21865 | CAATTGAAATGGAGCA | 74 | 1732 |
| 881564 | 3956 | 3971 | 22073 | 22088 | CCTGAGACAAGTGCTA | 57 | 1733 |
| 881588 | 4200 | 4215 | 22317 | 22332 | TCTATAGTGTTCCAGG | 20 | 1734 |
| 881607 | 4380 | 4395 | 22497 | 22512 | CTGTAAGGGCTGCTCA | 44 | 1735 |
| 881631 | 4482 | 4497 | 22599 | 22614 | TCCCAGAGTTGTTCCA | 74 | 1736 |
| 881655 | 4587 | 4602 | 22704 | 22719 | TTTACACTGGATCTGA | 75 | 1737 |
| 881679 | 4756 | 4771 | 22873 | 22888 | GTGTAAGGTCTGAGAG | 84 | 1738 |
| 881703 | 4979 | 4994 | 23096 | 23111 | TTCCATTGGAGGAGGG | 72 | 1739 |
| 881727 | 5185 | 5200 | 23302 | 23317 | CAGTTTGTGAAGCATC | 22 | 1740 |
| 881751 | 5223 | 5238 | 23340 | 23355 | CATGATGTATACCAAC | 49 | 1741 |
| 881775 | N/A | N/A | 18808 | 18823 | TCATGATATTAGAGAC | 65 | 1742 |
| 881799 | N/A | N/A | 3874 | 3889 | GTCGAACCTCTGGTTC | 110 | 1743 |
| 881820 | N/A | N/A | 4246 | 4261 | CGCCGGAGGCCGCCGT | 97 | 1744 |
| 881843 | N/A | N/A | 4511 | 4526 | GCGCACTAAGTGGGCT | 110 | 1745 |
| 881867 | N/A | N/A | 4893 | 4908 | GGCACAGCCGTCCGCC | 89 | 1746 |
| 881891 | N/A | N/A | 5535 | 5550 | CTGAGAGCCGAGGCCT | 117 | 1747 |
| 881914 | N/A | N/A | 5727 | 5742 | ACCCACGGACGGAGGC | 109 | 1748 |
| 881935 | N/A | N/A | 5903 | 5918 | ACAGAGGTGGGAGTAC | 174 | 1749 |
| 881959 | N/A | N/A | 6285 | 6300 | TATAACCGGTAGAGTG | 79 | 1750 |
| 881981 | N/A | N/A | 6697 | 6712 | ACGATGATAGCTCACC | 92 | 1751 |
| 882005 | N/A | N/A | 7221 | 7236 | TACATTGAGGCATACA | 59 | 1752 |
| 882029 | N/A | N/A | 7547 | 7562 | CCCAAGTGAGGTCACC | 80 | 1753 |
| 882053 | N/A | N/A | 7837 | 7852 | GGCTCCTACATGTTTG | 146 | 1754 |
| 882077 | N/A | N/A | 8222 | 8237 | ACATGATAAGGCACTA | 39 | 1755 |

TABLE 25-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882100 | N/A | N/A | 8470 | 8485 | GCCGAAGCATTTTATC | 71 | 1756 |
| 882124 | N/A | N/A | 8782 | 8797 | GTTAAAGGAGTGCAGG | 114 | 1757 |
| 882147 | N/A | N/A | 9461 | 9476 | TCCCACGAAGGGCAGT | 94 | 1758 |
| 882170 | N/A | N/A | 9788 | 9803 | TCATTTTGATGTCTGG | 37 | 1759 |
| 882193 | N/A | N/A | 10078 | 10093 | GCCAATGCAACTGAAT | 64 | 1760 |
| 882217 | N/A | N/A | 10202 | 10217 | GTTACTAATTCCATAG | 51 | 1761 |
| 882241 | N/A | N/A | 10525 | 10540 | GACAGATGACATGCTT | 91 | 1762 |
| 882265 | N/A | N/A | 10940 | 10955 | GAGCAAACCCTGCACT | 116 | 1763 |
| 882289 | N/A | N/A | 11216 | 11231 | AGGTAAAGGCACATTC | 81 | 1764 |
| 882313 | N/A | N/A | 11469 | 11484 | TCAGATTGAATCCATA | 36 | 1765 |
| 882337 | N/A | N/A | 11793 | 11808 | AGCTGGTAGGTCAAAC | 105 | 1766 |
| 882361 | N/A | N/A | 12050 | 12065 | TTCGAGGTGATTCTCG | 95 | 1767 |
| 882385 | N/A | N/A | 12284 | 12299 | TGGTAACTGTATGGAA | 52 | 1768 |
| 882408 | N/A | N/A | 12758 | 12773 | AGAATTAGGTGCTTAA | 39 | 1769 |
| 882431 | N/A | N/A | 13064 | 13079 | CTATTATAGAGCATCA | 45 | 1770 |
| 882455 | N/A | N/A | 13356 | 13371 | GGCCAACGACTCCACA | 77 | 1771 |
| 882477 | N/A | N/A | 14022 | 14037 | TTAAGAGGCGACTGCT | 88 | 1772 |
| 882499 | N/A | N/A | 14244 | 14259 | CTTATAGCACTCTCCT | 67 | 1773 |
| 882522 | N/A | N/A | 14645 | 14660 | AGTACGAGCACATGTC | 66 | 1774 |
| 882545 | N/A | N/A | 15191 | 15206 | AAGGATGGGACCGCCC | 61 | 1775 |
| 882569 | N/A | N/A | 15613 | 15628 | AGATTAATAGTAAGTT | 96 | 1776 |
| 882592 | N/A | N/A | 15864 | 15879 | ACACAGGCTAATCAGA | 93 | 1777 |
| 882615 | N/A | N/A | 16100 | 16115 | ATCAGATACACACCCT | 108 | 1778 |
| 882639 | N/A | N/A | 16278 | 16293 | CAAAACGGACTGGAAC | 84 | 1779 |
| 882662 | N/A | N/A | 16517 | 16532 | CGTAACTCAGGCACCA | 70 | 1780 |
| 882686 | N/A | N/A | 16762 | 16777 | GACAGCTAAAGAACAC | 81 | 1781 |
| 882710 | N/A | N/A | 16993 | 17008 | CCACAAGAAAGAGACC | 109 | 1782 |
| 882734 | N/A | N/A | 17400 | 17415 | CGACAACTTTCCTGAA | 79 | 1783 |
| 882758 | N/A | N/A | 17644 | 17659 | CAAATATCATATGCCC | 31 | 1784 |
| 882782 | N/A | N/A | 17904 | 17919 | TAATAATGCTTGCAAG | 88 | 1785 |
| 882806 | N/A | N/A | 18135 | 18150 | AGTCAATCACTGGAGA | 40 | 1786 |
| 882829 | N/A | N/A | 18691 | 18706 | ATTCATTTTATGGACC | 58 | 1787 |
| 882853 | N/A | N/A | 19108 | 19123 | GGTAATTTAGGCCAAT | 65 | 1788 |
| 882876 | N/A | N/A | 19366 | 19381 | CTAAGGAGACAGTAAC | 71 | 1789 |

TABLE 26

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 42 | 195 |
| 881088 | 157 | 172 | 5184 | 5199 | CGCTCATGCCGAACTC | 89 | 1790 |
| 881111 | 485 | 500 | 6964 | 6979 | TACACTTTGTACGGGT | 72 | 1791 |
| 881135 | 782 | 797 | 10847 | 10862 | GCACAAGCATAAAAGG | 84 | 1792 |
| 881158 | 1062 | 1077 | 13615 | 13630 | GAGGACCACGCCCCTC | 103 | 1793 |
| 881182 | 1269 | 1284 | 17062 | 17077 | GCATAGAGTCACCTGG | 61 | 1794 |
| 881206 | 1459 | 1474 | 19576 | 19591 | GAATAGAGGAATGGCG | 61 | 1795 |
| 881230 | 1832 | 1847 | 19949 | 19964 | TGCCAATCAGATGTCA | 78 | 1796 |
| 881254 | 1975 | 1990 | 20092 | 20107 | GACCTAATCTACAACA | 67 | 1797 |
| 881278 | 2150 | 2165 | 20267 | 20282 | AAGTGTCTTCCACAAG | 46 | 1798 |
| 881302 | 2310 | 2325 | 20427 | 20442 | GTTTACTAACTGGCTT | 73 | 1799 |
| 881326 | 2443 | 2458 | 20560 | 20575 | TAAAGAATGAGGGTCA | 55 | 1800 |
| 881350 | 2543 | 2558 | 20660 | 20675 | GAACAGATAGTTAAGT | 83 | 1801 |
| 881374 | 2771 | 2786 | 20888 | 20903 | TTTTAAGGCCCTGTCA | 82 | 1802 |
| 881398 | 2843 | 2858 | 20960 | 20975 | TGATAGGTATACTTAA | 72 | 1803 |
| 881422 | 2957 | 2972 | 21074 | 21089 | CGCAATCTTCTGCTGA | 36 | 1804 |
| 881446 | 3079 | 3094 | 21196 | 21211 | GCTCACTAAGCTTGAT | 44 | 1805 |
| 881470 | 3390 | 3405 | 21507 | 21522 | GGTAAATCTTCACTGT | 35 | 1806 |
| 881494 | 3475 | 3490 | 21592 | 21607 | ATCCATGTTGCATGGC | 39 | 1807 |
| 881517 | 3561 | 3576 | 21678 | 21693 | TAGGATAATATACCCC | 26 | 1808 |
| 881541 | 3734 | 3749 | 21851 | 21866 | GCAATTGAAATGGAGC | 76 | 1809 |
| 881565 | 3979 | 3994 | 22096 | 22111 | AGGAAGCCGTTCCTTT | 58 | 1810 |
| 881589 | 4201 | 4216 | 22318 | 22333 | CTCTATAGTGTTCCAG | 34 | 1811 |
| 881608 | 4381 | 4396 | 22498 | 22513 | ACTGTAAGGGCTGCTC | 31 | 1812 |
| 881632 | 4495 | 4510 | 22612 | 22627 | GAGTACCCAAGACTCC | 75 | 1813 |
| 881656 | 4588 | 4603 | 22705 | 22720 | GTTTACACTGGATCTG | 39 | 1814 |
| 881680 | 4765 | 4780 | 22882 | 22897 | CAAAATGGTGTGTAAG | 75 | 1815 |
| 881704 | 4983 | 4998 | 23100 | 23115 | GAATTTCCATTGGAGG | 57 | 1816 |
| 881728 | 5187 | 5202 | 23304 | 23319 | CTCAGTTTGTGAAGCA | 15 | 1817 |
| 881752 | 5224 | 5239 | 23341 | 23356 | TCATGATGTATACCAA | 35 | 1818 |
| 881776 | N/A | N/A | 18810 | 18825 | AATCATGATATTAGAG | 69 | 1819 |
| 881800 | N/A | N/A | 3880 | 3895 | CTGGAGGTCGAACCTC | 98 | 1820 |
| 881821 | N/A | N/A | 4257 | 4272 | GGTGAGCACCGCGCCG | 108 | 1821 |
| 881844 | N/A | N/A | 4522 | 4537 | GCCCAGCTAGCGCGCA | 71 | 1822 |
| 881868 | N/A | N/A | 4909 | 4924 | GCGCATCCCCTGGGCG | 104 | 1823 |
| 881892 | N/A | N/A | 5538 | 5553 | CCGCTGAGAGCCGAGG | 104 | 1824 |
| 881915 | N/A | N/A | 5730 | 5745 | GGGACCCACGGACGGA | 91 | 1825 |

TABLE 26-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881936 | N/A | N/A | 5972 | 5987 | CTCTAGACAGAGGCCC | 80 | 1826 |
| 881960 | N/A | N/A | 6286 | 6301 | TTATAACCGGTAGAGT | 62 | 1827 |
| 881982 | N/A | N/A | 6761 | 6776 | GGTTTATTAGCTTTCT | 101 | 1828 |
| 882006 | N/A | N/A | 7226 | 7241 | CCATATACATTGAGGC | 56 | 1829 |
| 882030 | N/A | N/A | 7574 | 7589 | ATAAAGGACCCCGCCA | 82 | 1830 |
| 882054 | N/A | N/A | 8019 | 8034 | GGCAAGTTCTGCTGTC | 42 | 1831 |
| 882078 | N/A | N/A | 8226 | 8241 | TTTCACATGATAAGGC | 57 | 1832 |
| 882101 | N/A | N/A | 8471 | 8486 | AGCCGAAGCATTTTAT | 56 | 1833 |
| 882125 | N/A | N/A | 9093 | 9108 | CTAAAGGAGTGCAGGA | 94 | 1834 |
| 882148 | N/A | N/A | 9467 | 9482 | ATAAGATCCCACGAAG | 142 | 1835 |
| 882171 | N/A | N/A | 9816 | 9831 | AGCTAATGAGAGCTTC | 83 | 1836 |
| 882194 | N/A | N/A | 10086 | 10101 | CTTGAAAAGCCAATGC | 42 | 1837 |
| 882218 | N/A | N/A | 10203 | 10218 | GGTTACTAATTCCATA | 44 | 1838 |
| 882242 | N/A | N/A | 10526 | 10541 | AGACAGATGACATGCT | 50 | 1839 |
| 882266 | N/A | N/A | 11013 | 11028 | TCTAAAGTCCCATCGA | 69 | 1840 |
| 882290 | N/A | N/A | 11220 | 11235 | GTAAAGGTAAAGGCAC | 58 | 1841 |
| 882314 | N/A | N/A | 11528 | 11543 | GGTAAGATCTCCATGG | 55 | 1842 |
| 882338 | N/A | N/A | 11798 | 11813 | GAAAGAGCTGGTAGGT | 100 | 1843 |
| 882362 | N/A | N/A | 12054 | 12069 | GCCATTCGAGGTGATT | 44 | 1844 |
| 882386 | N/A | N/A | 12355 | 12370 | ACCAAGCTGGGTTTGC | 47 | 1845 |
| 882409 | N/A | N/A | 12760 | 12775 | ATAGAATTAGGTGCTT | 36 | 1846 |
| 882432 | N/A | N/A | 13065 | 13080 | CCTATTATAGAGCATC | 32 | 1847 |
| 882456 | N/A | N/A | 13361 | 13376 | CTCGAGGCCAACGACT | 99 | 1848 |
| 882478 | N/A | N/A | 14025 | 14040 | GTTTTAAGAGGCGACT | 67 | 1849 |
| 882500 | N/A | N/A | 14246 | 14261 | AACTTATAGCACTCTC | 72 | 1850 |
| 882523 | N/A | N/A | 14648 | 14663 | AGAAGTACGAGCACAT | 56 | 1851 |
| 882546 | N/A | N/A | 15192 | 15207 | GAAGGATGGGACCGCC | 59 | 1852 |
| 882570 | N/A | N/A | 15617 | 15632 | TCACAGATTAATAGTA | 77 | 1853 |
| 882593 | N/A | N/A | 15867 | 15882 | CCTACACAGGCTAATC | 87 | 1854 |
| 882616 | N/A | N/A | 16101 | 16116 | TATCAGATACACACCC | 81 | 1855 |
| 882640 | N/A | N/A | 16279 | 16294 | ACAAAACGGACTGGAA | 86 | 1856 |
| 882663 | N/A | N/A | 16535 | 16550 | TGCTACTGCGGACATC | 57 | 1857 |
| 882687 | N/A | N/A | 16763 | 16778 | CGACAGCTAAAGAACA | 63 | 1858 |
| 882711 | N/A | N/A | 17000 | 17015 | TAGAAGCCCACAAGAA | 99 | 1859 |
| 882735 | N/A | N/A | 17402 | 17417 | TACGACAACTTTCCTG | 59 | 1860 |
| 882759 | N/A | N/A | 17662 | 17677 | GAAAGATTCAGCCTCT | 55 | 1861 |

TABLE 26-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882783 | N/A | N/A | 17906 | 17921 | GTTAATAATGCTTGCA | 98 | 1862 |
| 882807 | N/A | N/A | 18141 | 18156 | TTATTAAGTCAATCAC | 101 | 1863 |
| 882830 | N/A | N/A | 18714 | 18729 | CTCATAGGTGTACACG | 41 | 1864 |
| 882854 | N/A | N/A | 19114 | 19129 | CTGCAGGGTAATTTAG | 66 | 1865 |
| 882877 | N/A | N/A | 19379 | 19394 | CAGCACTCAGATTCTA | 88 | 1866 |

TABLE 27

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 41 | 195 |
| 668855 | 783 | 798 | 10848 | 10863 | GGCACAAGCATAAAAG | 99 | 1867 |
| 690520 | 4222 | 4237 | 22339 | 22354 | AAATGAGTCGGTCACT | 45 | 1868 |
| 881089 | 165 | 180 | 5192 | 5207 | GCTCACCGCGCTCATG | 52 | 1869 |
| 881112 | 486 | 501 | 6965 | 6980 | GTACACTTTGTACGGG | 36 | 1870 |
| 881159 | 1067 | 1082 | 13620 | 13635 | ATCCAGAGGACCACGC | 81 | 1871 |
| 881183 | 1270 | 1285 | 17063 | 17078 | AGCATAGAGTCACCTG | 37 | 1872 |
| 881207 | 1460 | 1475 | 19577 | 19592 | TGAATAGAGGAATGGC | 79 | 1873 |
| 881231 | 1844 | 1859 | 19961 | 19976 | AATAAGCTCATCTGCC | 64 | 1874 |
| 881255 | 1978 | 1993 | 20095 | 20110 | CAAGACCTAATCTACA | 88 | 1875 |
| 881279 | 2151 | 2166 | 20268 | 20283 | CAAGTGTCTTCCACAA | 35 | 1876 |
| 881303 | 2311 | 2326 | 20428 | 20443 | AGTTTACTAACTGGCT | 37 | 1877 |
| 881327 | 2444 | 2459 | 20561 | 20576 | CTAAAGAATGAGGGTC | 38 | 1878 |
| 881351 | 2545 | 2560 | 20662 | 20677 | GGGAACAGATAGTTAA | 74 | 1879 |
| 881375 | 2773 | 2788 | 20890 | 20905 | AATTTTAAGGCCCTGT | 76 | 1880 |
| 881399 | 2844 | 2859 | 20961 | 20976 | GTGATAGGTATACTTA | 35 | 1881 |
| 881423 | 2958 | 2973 | 21075 | 21090 | ACGCAATCTTCTGCTG | 48 | 1882 |
| 881447 | 3086 | 3101 | 21203 | 21218 | GCTCACTGCTCACTAA | 67 | 1883 |
| 881471 | 3391 | 3406 | 21508 | 21523 | AGGTAAATCTTCACTG | 46 | 1884 |
| 881495 | 3479 | 3494 | 21596 | 21611 | ACATATCCATGTTGCA | 21 | 1885 |
| 881518 | 3562 | 3577 | 21679 | 21694 | TTAGGATAATATACCC | 48 | 1886 |
| 881542 | 3785 | 3800 | 21902 | 21917 | ACTGTTAAAGCAGCAT | 29 | 1887 |
| 881566 | 3980 | 3995 | 22097 | 22112 | GAGGAAGCCGTTCCTT | 49 | 1888 |
| 881609 | 4383 | 4398 | 22500 | 22515 | ATACTGTAAGGGCTGC | 46 | 1889 |
| 881633 | 4504 | 4519 | 22621 | 22636 | AAGAGGTGCGAGTACC | 66 | 1890 |
| 881657 | 4590 | 4605 | 22707 | 22722 | AAGTTTACACTGGATC | 42 | 1891 |

TABLE 27-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881681 | 4786 | 4801 | 22903 | 22918 | GGGCATGTAAAACATA | 77 | 1892 |
| 881705 | 4985 | 5000 | 23102 | 23117 | GGGAATTTCCATTGGA | 56 | 1893 |
| 881729 | 5188 | 5203 | 23305 | 23320 | CCTCAGTTTGTGAAGC | 31 | 1894 |
| 881753 | 5226 | 5241 | 23343 | 23358 | ATTCATGATGTATACC | 38 | 1895 |
| 881777 | N/A | N/A | 18811 | 18826 | CAATCATGATATTAGA | 62 | 1896 |
| 881801 | N/A | N/A | 3897 | 3912 | GGGTACCCTGCGCTGC | 56 | 1897 |
| 881822 | N/A | N/A | 4292 | 4307 | CCAAATGTGGAGCTCC | 77 | 1898 |
| 881845 | N/A | N/A | 4542 | 4557 | CGAATAGGACCCCTAT | 91 | 1899 |
| 881869 | N/A | N/A | 4916 | 4931 | GGCCCGGGCGCATCCC | 95 | 1900 |
| 881893 | N/A | N/A | 5548 | 5563 | CCCCGCGGTCCCGCTG | 59 | 1901 |
| 881916 | N/A | N/A | 5749 | 5764 | ACGCACGGAGAGGGCG | 99 | 1902 |
| 881937 | N/A | N/A | 5974 | 5989 | AGCTCTAGACAGAGGC | 65 | 1903 |
| 881961 | N/A | N/A | 6287 | 6302 | TTTATAACCGGTAGAG | 46 | 1904 |
| 881983 | N/A | N/A | 6783 | 6798 | CGAAAAGTCAAAATAC | 100 | 1905 |
| 882007 | N/A | N/A | 7228 | 7243 | CCCCATATACATTGAG | 63 | 1906 |
| 882031 | N/A | N/A | 7576 | 7591 | ACATAAAGGACCCCGC | 72 | 1907 |
| 882055 | N/A | N/A | 8027 | 8042 | TAGCAAATGGCAAGTT | 83 | 1908 |
| 882079 | N/A | N/A | 8248 | 8263 | GAAGAGATCAGCTGCC | 58 | 1909 |
| 882102 | N/A | N/A | 8475 | 8490 | TGACAGCCGAAGCATT | 62 | 1910 |
| 882126 | N/A | N/A | 9094 | 9109 | GCTAAAGGAGTGCAGG | 93 | 1911 |
| 882149 | N/A | N/A | 9468 | 9483 | AATAAGATCCCACGAA | 85 | 1912 |
| 882172 | N/A | N/A | 9820 | 9835 | ACCCAGCTAATGAGAG | 65 | 1913 |
| 882195 | N/A | N/A | 10098 | 10113 | CTGCAAATCCCTCTTG | 133 | 1914 |
| 882219 | N/A | N/A | 10230 | 10245 | CAGTTCTAAGCATTGC | 67 | 1915 |
| 882243 | N/A | N/A | 10551 | 10566 | GACTAACAGGGAGACT | 109 | 1916 |
| 882267 | N/A | N/A | 11014 | 11029 | GTCTAAAGTCCCATCG | 60 | 1917 |
| 882291 | N/A | N/A | 11251 | 11266 | CGTGAGAATGTTGGCT | 51 | 1918 |
| 882315 | N/A | N/A | 11533 | 11548 | TAGTAGGTAAGATCTC | 77 | 1919 |
| 882339 | N/A | N/A | 11799 | 11814 | AGAAAGAGCTGGTAGG | 64 | 1920 |
| 882363 | N/A | N/A | 12074 | 12089 | CCCAAAGAGAGTGGGT | 100 | 1921 |
| 882387 | N/A | N/A | 12364 | 12379 | GTTGAAAGAACCAAGC | 89 | 1922 |
| 882410 | N/A | N/A | 12761 | 12776 | TATAGAATTAGGTGCT | 60 | 1923 |
| 882433 | N/A | N/A | 13112 | 13127 | GGAACAAGTGTATCTT | 24 | 1924 |
| 882457 | N/A | N/A | 13367 | 13382 | CACCACCTCGAGGCCA | 76 | 1925 |
| 882479 | N/A | N/A | 14027 | 14042 | CTGTTTTAAGAGGCGA | 42 | 1926 |
| 882501 | N/A | N/A | 14250 | 14265 | AGCCAACTTATAGCAC | 46 | 1927 |

TABLE 27-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882524 | N/A | N/A | 14649 | 14664 | CAGAAGTACGAGCACA | 53 | 1928 |
| 882547 | N/A | N/A | 15195 | 15210 | CAAGAAGGATGGGACC | 75 | 1929 |
| 882571 | N/A | N/A | 15619 | 15634 | GCTCACAGATTAATAG | 84 | 1930 |
| 882594 | N/A | N/A | 15871 | 15886 | TACACCTACACAGGCT | 81 | 1931 |
| 882617 | N/A | N/A | 16121 | 16136 | CTGCAGAACAGACGCG | 89 | 1932 |
| 882641 | N/A | N/A | 16280 | 16295 | TACAAAACGGACTGGA | 62 | 1933 |
| 882664 | N/A | N/A | 16551 | 16566 | CATAATCCAGTATCTG | 82 | 1934 |
| 882688 | N/A | N/A | 16767 | 16782 | TAGTCGACAGCTAAAG | 54 | 1935 |
| 882712 | N/A | N/A | 17001 | 17016 | GTAGAAGCCCACAAGA | 104 | 1936 |
| 882736 | N/A | N/A | 17404 | 17419 | AATACGACAACTTTCC | 50 | 1937 |
| 882760 | N/A | N/A | 17664 | 17679 | TTGAAAGATTCAGCCT | 97 | 1938 |
| 882784 | N/A | N/A | 17918 | 17933 | GCATGCAAGCCCGTTA | 101 | 1939 |
| 882808 | N/A | N/A | 18183 | 18198 | TTGTTAACAATGTATC | 53 | 1940 |
| 882831 | N/A | N/A | 18715 | 18730 | ACTCATAGGTGTACAC | 55 | 1941 |
| 882855 | N/A | N/A | 19126 | 19141 | GTCTGAGGGAATCTGC | 51 | 1942 |
| 882878 | N/A | N/A | 19384 | 19399 | TTAAACAGCACTCAGA | 67 | 1943 |

TABLE 28

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 20 | 195 |
| 690521 | 4224 | 4239 | 22341 | 22356 | GTAAATGAGTCGGTCA | 21 | 1944 |
| 881090 | 170 | 185 | 5197 | 5212 | CCGCAGCTCACCGCGC | 64 | 1945 |
| 881113 | 488 | 503 | 6967 | 6982 | CTGTACACTTTGTACG | 66 | 1946 |
| 881136 | 837 | 852 | 10902 | 10917 | GGCAGACCTTATGCTT | 79 | 1947 |
| 881160 | 1071 | 1086 | 13624 | 13639 | GGCCATCCAGAGGACC | 75 | 1948 |
| 881184 | 1271 | 1286 | 17064 | 17079 | AAGCATAGAGTCACCT | 64 | 1949 |
| 881208 | 1461 | 1476 | 19578 | 19593 | TTGAATAGAGGAATGG | 58 | 1950 |
| 881232 | 1886 | 1901 | 20003 | 20018 | GTCTACAGAACACAAG | 76 | 1951 |
| 881256 | 1984 | 1999 | 20101 | 20116 | TTCCAGCAAGACCTAA | 73 | 1952 |
| 881280 | 2152 | 2167 | 20269 | 20284 | GCAAGTGTCTTCCACA | 23 | 1953 |
| 881304 | 2312 | 2327 | 20429 | 20444 | AAGTTTACTAACTGGC | 37 | 1954 |
| 881328 | 2462 | 2477 | 20579 | 20594 | CGAAGAATTTTAGCAT | 42 | 1955 |
| 881352 | 2546 | 2561 | 20663 | 20678 | AGGGAACAGATAGTTA | 66 | 1956 |
| 881376 | 2774 | 2789 | 20891 | 20906 | TAATTTTAAGGCCCTG | 61 | 1957 |

TABLE 28-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881400 | 2845 | 2860 | 20962 | 20977 | AGTGATAGGTATACTT | 61 | 1958 |
| 881424 | 2962 | 2977 | 21079 | 21094 | AGCTACGCAATCTTCT | 53 | 1959 |
| 881448 | 3250 | 3265 | 21367 | 21382 | ACTTTTAGAGAGGAGA | 36 | 1960 |
| 881472 | 3394 | 3409 | 21511 | 21526 | ACGAGGTAAATCTTCA | 39 | 1961 |
| 881496 | 3480 | 3495 | 21597 | 21612 | TACATATCCATGTTGC | 26 | 1962 |
| 881519 | 3564 | 3579 | 21681 | 21696 | CCTTAGGATAATATAC | 77 | 1963 |
| 881543 | 3787 | 3802 | 21904 | 21919 | CCACTGTTAAAGCAGC | 34 | 1964 |
| 881567 | 3983 | 3998 | 22100 | 22115 | AATGAGGAAGCCGTTC | 53 | 1965 |
| 881610 | 4384 | 4399 | 22501 | 22516 | AATACTGTAAGGGCTG | 36 | 1966 |
| 881634 | 4506 | 4521 | 22623 | 22638 | CCAAGAGGTGCGAGTA | 67 | 1967 |
| 881658 | 4591 | 4606 | 22708 | 22723 | GAAGTTTACACTGGAT | 35 | 1968 |
| 881682 | 4802 | 4817 | 22919 | 22934 | ATCAGTCTCAAAAACG | 59 | 1969 |
| 881706 | 4989 | 5004 | 23106 | 23121 | ACACGGGAATTTCCAT | 44 | 1970 |
| 881730 | 5189 | 5204 | 23306 | 23321 | ACCTCAGTTTGTGAAG | 61 | 1971 |
| 881754 | 5248 | 5263 | 23365 | 23380 | TTGCAGAGCAATTTAC | 50 | 1972 |
| 881778 | N/A | N/A | 18814 | 18829 | CATCAATCATGATATT | 75 | 1973 |
| 881823 | N/A | N/A | 4304 | 4319 | GCTCGGAGCGACCCAA | 92 | 1974 |
| 881846 | N/A | N/A | 4543 | 4558 | CCGAATAGGACCCCTA | 68 | 1975 |
| 881870 | N/A | N/A | 4920 | 4935 | GGCCGGCCCGGGCGCA | 99 | 1976 |
| 881894 | N/A | N/A | 5566 | 5581 | CAGGACCCGGCTCCCG | 86 | 1977 |
| 881917 | N/A | N/A | 5752 | 5767 | CGGACGCACGGAGAGG | 72 | 1978 |
| 881938 | N/A | N/A | 5982 | 5997 | AGGGAGACAGCTCTAG | 75 | 1979 |
| 881962 | N/A | N/A | 6290 | 6305 | GTATTTATAACCGGTA | 33 | 1980 |
| 881984 | N/A | N/A | 7014 | 7029 | CAAATTCAGGAGAGCC | 81 | 1981 |
| 882008 | N/A | N/A | 7247 | 7262 | ACATATTCAATGCACC | 53 | 1982 |
| 882032 | N/A | N/A | 7578 | 7593 | TGACATAAAGGACCCC | 52 | 1983 |
| 882056 | N/A | N/A | 8032 | 8047 | AGCCATAGCAAATGGC | 95 | 1984 |
| 882080 | N/A | N/A | 8302 | 8317 | CTTTTACCCACCAAAG | 82 | 1985 |
| 882103 | N/A | N/A | 8481 | 8496 | TTAGACTGACAGCCGA | 47 | 1986 |
| 882127 | N/A | N/A | 9278 | 9293 | CAATTAGCTCTTCTAT | 86 | 1987 |
| 882150 | N/A | N/A | 9471 | 9486 | TTAAATAAGATCCCAC | 77 | 1988 |
| 882173 | N/A | N/A | 9835 | 9850 | CTAGATTCTCCCTGCA | 66 | 1989 |
| 882196 | N/A | N/A | 10110 | 10125 | AACCAGCCCTTGCTGC | 79 | 1990 |
| 882220 | N/A | N/A | 10237 | 10252 | CTTTACACAGTTCTAA | 113 | 1991 |
| 882244 | N/A | N/A | 10554 | 10569 | ACTGACTAACAGGGAG | 51 | 1992 |
| 882268 | N/A | N/A | 11021 | 11036 | AGCAAGTGTCTAAAGT | 38 | 1993 |

TABLE 28-continued

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882292 | N/A | N/A | 11271 | 11286 | TCCAAGCAATTATTCC | 88 | 1994 |
| 882316 | N/A | N/A | 11534 | 11549 | ATAGTAGGTAAGATCT | 113 | 1995 |
| 882340 | N/A | N/A | 11800 | 11815 | TAGAAAGAGCTGGTAG | 91 | 1996 |
| 882364 | N/A | N/A | 12075 | 12090 | CCCCAAGAGAGTGGG | 111 | 1997 |
| 882388 | N/A | N/A | 12372 | 12387 | GCCCATGAGTTGAAAG | 68 | 1998 |
| 882411 | N/A | N/A | 12762 | 12777 | ATATAGAATTAGGTGC | 84 | 1999 |
| 882434 | N/A | N/A | 13113 | 13128 | AGGAACAAGTGTATCT | 54 | 2000 |
| 882502 | N/A | N/A | 14254 | 14269 | ACAGAGCCAACTTATA | 94 | 2001 |
| 882525 | N/A | N/A | 14652 | 14667 | ACCCAGAAGTACGAGC | 79 | 2002 |
| 882548 | N/A | N/A | 15218 | 15233 | CCCATGAACACCATGC | 68 | 2003 |
| 882572 | N/A | N/A | 15635 | 15650 | GCCAAGACCAGCTCTT | 70 | 2004 |
| 882595 | N/A | N/A | 15872 | 15887 | CTACACCTACACAGGC | 84 | 2005 |
| 882618 | N/A | N/A | 16132 | 16147 | CGCTACAGCTTCTGCA | 80 | 2006 |
| 882642 | N/A | N/A | 16281 | 16296 | ATACAAAACGGACTGG | 85 | 2007 |
| 882665 | N/A | N/A | 16553 | 16568 | CACATAATCCAGTATC | 57 | 2008 |
| 882689 | N/A | N/A | 16773 | 16788 | AGGAACTAGTCGACAG | 60 | 2009 |
| 882713 | N/A | N/A | 17133 | 17148 | TGTAACTGAGGACTCA | 102 | 2010 |
| 882737 | N/A | N/A | 17405 | 17420 | AAATACGACAACTTTC | 79 | 2011 |
| 882761 | N/A | N/A | 17676 | 17691 | TGCTTGAATTCCTTGA | 33 | 2012 |
| 882785 | N/A | N/A | 17923 | 17938 | GCTCAGCATGCAAGCC | 100 | 2013 |
| 882809 | N/A | N/A | 18225 | 18240 | GCTTATCAATGCCAAG | 60 | 2014 |
| 882832 | N/A | N/A | 18716 | 18731 | AACTCATAGGTGTACA | 39 | 2015 |
| 882856 | N/A | N/A | 19154 | 19169 | TCAAGTAAAGTGATCA | 52 | 2016 |
| 882879 | N/A | N/A | 19387 | 19402 | CTATTAAACAGCACTC | 82 | 2017 |
| 882890 | N/A | N/A | 3949 | 3964 | GTGGGAGTCGGAGCTC | 83 | 2018 |
| 882906 | N/A | N/A | 13375 | 13390 | GCCAAGGACACCACCT | 102 | 2019 |
| 882908 | N/A | N/A | 14061 | 14076 | GTATTTGTCGAGATCA | 41 | 2020 |

TABLE 29

Percent control of human IRF4 mRNA with 3-10-3 cEt gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 33 | 195 |
| 690522 | 4228 | 4243 | 22345 | 22360 | AGTTGTAAATGAGTCG | 15 | 2021 |
| 881091 | 186 | 201 | 5213 | 5228 | GCGGAGCTTCCCGTTG | 67 | 2022 |
| 881114 | 495 | 510 | 6974 | 6989 | AACAATCCTGTACACT | 78 | 2023 |

TABLE 29-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881161 | 1088 | 1103 | 13641 | 13656 | GCATAGAGCCCGTCGG | 50 | 2024 |
| 881185 | 1272 | 1287 | 17065 | 17080 | AAAGCATAGAGTCACC | 66 | 2025 |
| 881209 | 1532 | 1547 | 19649 | 19664 | CCGTATCCCCGTATCA | 65 | 2026 |
| 881233 | 1891 | 1906 | 20008 | 20023 | TGGCAGTCTACAGAAC | 122 | 2027 |
| 881257 | 2001 | 2016 | 20118 | 20133 | GGCAAGTTTTCTCTGT | 64 | 2028 |
| 881281 | 2154 | 2169 | 20271 | 20286 | CAGCAAGTGTCTTCCA | 36 | 2029 |
| 881305 | 2313 | 2328 | 20430 | 20445 | GAAGTTTACTAACTGG | 43 | 2030 |
| 881329 | 2463 | 2478 | 20580 | 20595 | GCGAAGAATTTTAGCA | 88 | 2031 |
| 881353 | 2547 | 2562 | 20664 | 20679 | AAGGGAACAGATAGTT | 80 | 2032 |
| 881377 | 2775 | 2790 | 20892 | 20907 | GTAATTTTAAGGCCCT | 45 | 2033 |
| 881401 | 2846 | 2861 | 20963 | 20978 | AAGTGATAGGTATACT | 50 | 2034 |
| 881425 | 2965 | 2980 | 21082 | 21097 | GAGAGCTACGCAATCT | 43 | 2035 |
| 881449 | 3251 | 3266 | 21368 | 21383 | CACTTTTAGAGAGGAG | 38 | 2036 |
| 881473 | 3395 | 3410 | 21512 | 21527 | AACGAGGTAAATCTTC | 49 | 2037 |
| 881497 | 3484 | 3499 | 21601 | 21616 | CCAATACATATCCATG | 40 | 2038 |
| 881520 | 3566 | 3581 | 21683 | 21698 | TCCCTTAGGATAATAT | 52 | 2039 |
| 881544 | 3788 | 3803 | 21905 | 21920 | TCCACTGTTAAAGCAG | 45 | 2040 |
| 881568 | 3984 | 3999 | 22101 | 22116 | GAATGAGGAAGCCGTT | 61 | 2041 |
| 881611 | 4385 | 4400 | 22502 | 22517 | CAATACTGTAAGGGCT | 44 | 2042 |
| 881635 | 4507 | 4522 | 22624 | 22639 | GCCAAGAGGTGCGAGT | 65 | 2043 |
| 881659 | 4592 | 4607 | 22709 | 22724 | GGAAGTTTACACTGGA | 15 | 2044 |
| 881683 | 4808 | 4823 | 22925 | 22940 | ATCGAGATCAGTCTCA | 24 | 2045 |
| 881707 | 4991 | 5006 | 23108 | 23123 | CAACACGGGAATTTCC | 45 | 2046 |
| 881731 | 5191 | 5206 | 23308 | 23323 | CTACCTCAGTTTGTGA | 59 | 2047 |
| 881755 | N/A | N/A | 18767 | 18782 | CTAAACTCCTAAGTAC | 86 | 2048 |
| 881779 | N/A | N/A | 18827 | 18842 | GCTGAATGCTCTCCAT | 48 | 2049 |
| 881802 | N/A | N/A | 3965 | 3980 | GCTCAGCGCAGATGGG | 102 | 2050 |
| 881824 | N/A | N/A | 4310 | 4325 | CGCAAGGCTCGGAGCG | 90 | 2051 |
| 881847 | N/A | N/A | 4544 | 4559 | CCCGAATAGGACCCCT | 60 | 2052 |
| 881871 | N/A | N/A | 4932 | 4947 | AGGCACCTTCGCGGCC | 82 | 2053 |
| 881918 | N/A | N/A | 5754 | 5769 | CGCGGACGCACGGAGA | 81 | 2054 |
| 881939 | N/A | N/A | 5995 | 6010 | CGCGCAAAGGGCAAGG | 66 | 2055 |
| 881963 | N/A | N/A | 6292 | 6307 | GGGTATTTATAACCGG | 41 | 2056 |
| 881985 | N/A | N/A | 7032 | 7047 | TGCCTCTGTTAGGTGA | 66 | 2057 |
| 882009 | N/A | N/A | 7268 | 7283 | TTGAAAGACTAACTGG | 80 | 2058 |
| 882033 | N/A | N/A | 7580 | 7595 | TGTGACATAAAGGACC | 73 | 2059 |

TABLE 29-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882057 | N/A | N/A | 8040 | 8055 | GTTGGAGCAGCCATAG | 69 | 2060 |
| 882081 | N/A | N/A | 8329 | 8344 | CAAAAGTACCACAGGG | 60 | 2061 |
| 882104 | N/A | N/A | 8484 | 8499 | TTATTAGACTGACAGC | 63 | 2062 |
| 882128 | N/A | N/A | 9279 | 9294 | GCAATTAGCTCTTCTA | 79 | 2063 |
| 882151 | N/A | N/A | 9525 | 9540 | CTATATAAAAAGTGGG | 84 | 2064 |
| 882174 | N/A | N/A | 9837 | 9852 | TGCTAGATTCTCCCTG | 67 | 2065 |
| 882197 | N/A | N/A | 10114 | 10129 | TGGAAACCAGCCCTTG | 52 | 2066 |
| 882221 | N/A | N/A | 10250 | 10265 | ACCTACTCCATCACTT | 103 | 2067 |
| 882245 | N/A | N/A | 10559 | 10574 | CTGTAACTGACTAACA | 77 | 2068 |
| 882269 | N/A | N/A | 11022 | 11037 | AAGCAAGTGTCTAAAG | 71 | 2069 |
| 882293 | N/A | N/A | 11278 | 11293 | CTACACTTCCAAGCAA | 105 | 2070 |
| 882317 | N/A | N/A | 11535 | 11550 | TATAGTAGGTAAGATC | 87 | 2071 |
| 882341 | N/A | N/A | 11801 | 11816 | CTAGAAAGAGCTGGTA | 85 | 2072 |
| 882365 | N/A | N/A | 12087 | 12102 | TCAGACAGTGCGCCCC | 74 | 2073 |
| 882389 | N/A | N/A | 12379 | 12394 | AAATATCGCCCATGAG | 61 | 2074 |
| 882412 | N/A | N/A | 12763 | 12778 | TATATAGAATTAGGTG | 116 | 2075 |
| 882435 | N/A | N/A | 13115 | 13130 | TAAGGAACAAGTGTAT | 82 | 2076 |
| 882458 | N/A | N/A | 13393 | 13408 | CCGGAGTCAGTGCTGG | 107 | 2077 |
| 882480 | N/A | N/A | 14062 | 14077 | CGTATTTGTCGAGATC | 50 | 2078 |
| 882503 | N/A | N/A | 14256 | 14271 | TCACAGAGCCAACTTA | 112 | 2079 |
| 882526 | N/A | N/A | 14656 | 14671 | TTACACCCAGAAGTAC | 95 | 2080 |
| 882549 | N/A | N/A | 15312 | 15327 | GCCCATGTGAGCTCTT | 50 | 2081 |
| 882573 | N/A | N/A | 15704 | 15719 | GAACACTTTGAGGTGA | 86 | 2082 |
| 882596 | N/A | N/A | 15874 | 15889 | GACTACACCTACACAG | 68 | 2083 |
| 882619 | N/A | N/A | 16135 | 16150 | AGCCGCTACAGCTTCT | 108 | 2084 |
| 882643 | N/A | N/A | 16282 | 16297 | GATACAAAACGGACTG | 56 | 2085 |
| 882666 | N/A | N/A | 16556 | 16571 | GCCCACATAATCCAGT | 78 | 2086 |
| 882690 | N/A | N/A | 16774 | 16789 | GAGGAACTAGTCGACA | 61 | 2087 |
| 882714 | N/A | N/A | 17139 | 17154 | TAGGAGTGTAACTGAG | 63 | 2088 |
| 882738 | N/A | N/A | 17406 | 17421 | GAAATACGACAACTTT | 78 | 2089 |
| 882762 | N/A | N/A | 17693 | 17708 | TACGAGAGGGTCTGAT | 100 | 2090 |
| 882786 | N/A | N/A | 17936 | 17951 | TTTACCTGGTATTGCT | 62 | 2091 |
| 882810 | N/A | N/A | 18226 | 18241 | TGCTTATCAATGCCAA | 30 | 2092 |
| 882833 | N/A | N/A | 18717 | 18732 | GAACTCATAGGTGTAC | 33 | 2093 |
| 882880 | N/A | N/A | 19389 | 19404 | CACTATTAAACAGCAC | 81 | 2094 |
| 882916 | N/A | N/A | 19155 | 19170 | ATCAAGTAAAGTGATC | 71 | 2095 |

TABLE 30

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 29 | 195 |
| 690523 | 4230 | 4245 | 22347 | 22362 | TCAGTTGTAAATGAGT | 28 | 2096 |
| 881092 | 187 | 202 | 5214 | 5229 | GGCGGAGCTTCCCGTT | 74 | 2097 |
| 881115 | 498 | 513 | 6977 | 6992 | AGGAACAATCCTGTAC | 84 | 2098 |
| 881162 | 1089 | 1104 | 13642 | 13657 | CGCATAGAGCCCGTCG | 47 | 2099 |
| 881186 | 1273 | 1288 | 17066 | 17081 | CAAAGCATAGAGTCAC | 64 | 2100 |
| 881210 | 1534 | 1549 | 19651 | 19666 | CCCCGTATCCCCGTAT | 55 | 2101 |
| 881234 | 1896 | 1911 | 20013 | 20028 | AATGATGGCAGTCTAC | 67 | 2102 |
| 881258 | 2014 | 2029 | 20131 | 20146 | GTCAATACTGAAAGGC | 34 | 2103 |
| 881282 | 2155 | 2170 | 20272 | 20287 | TCAGCAAGTGTCTTCC | 34 | 2104 |
| 881306 | 2316 | 2331 | 20433 | 20448 | TAGGAAGTTTACTAAC | 64 | 2105 |
| 881330 | 2464 | 2479 | 20581 | 20596 | TGCGAAGAATTTTAGC | 59 | 2106 |
| 881354 | 2548 | 2563 | 20665 | 20680 | GAAGGGAACAGATAGT | 83 | 2107 |
| 881378 | 2776 | 2791 | 20893 | 20908 | AGTAATTTTAAGGCCC | 40 | 2108 |
| 881402 | 2847 | 2862 | 20964 | 20979 | TAAGTGATAGGTATAC | 40 | 2109 |
| 881426 | 2972 | 2987 | 21089 | 21104 | CACATTTGAGAGCTAC | 26 | 2110 |
| 881450 | 3252 | 3267 | 21369 | 21384 | ACACTTTTAGAGAGGA | 37 | 2111 |
| 881474 | 3396 | 3411 | 21513 | 21528 | GAACGAGGTAAATCTT | 44 | 2112 |
| 881498 | 3485 | 3500 | 21602 | 21617 | CCCAATACATATCCAT | 26 | 2113 |
| 881521 | 3600 | 3615 | 21717 | 21732 | CGTGAAACAGCAGTTC | 60 | 2114 |
| 881545 | 3789 | 3804 | 21906 | 21921 | CTCCACTGTTAAAGCA | 48 | 2115 |
| 881569 | 3986 | 4001 | 22103 | 22118 | AGGAATGAGGAAGCCG | 44 | 2116 |
| 881612 | 4387 | 4402 | 22504 | 22519 | AACAATACTGTAAGGG | 49 | 2117 |
| 881636 | 4508 | 4523 | 22625 | 22640 | AGCCAAGAGGTGCGAG | 62 | 2118 |
| 881660 | 4593 | 4608 | 22710 | 22725 | CGGAAGTTTACACTGG | 15 | 2119 |
| 881684 | 4809 | 4824 | 22926 | 22941 | CATCGAGATCAGTCTC | 35 | 2120 |
| 881708 | 4993 | 5008 | 23110 | 23125 | AGCAACACGGGAATTT | 43 | 2121 |
| 881732 | 5197 | 5212 | 23314 | 23329 | CATTATCTACCTCAGT | 65 | 2122 |
| 881756 | N/A | N/A | 18768 | 18783 | GCTAAACTCCTAAGTA | 70 | 2123 |
| 881780 | N/A | N/A | 18828 | 18843 | AGCTGAATGCTCTCCA | 22 | 2124 |
| 881803 | N/A | N/A | 3993 | 4008 | GGCCTTGGAGCCCAAA | 80 | 2125 |
| 881825 | N/A | N/A | 4311 | 4326 | ACGCAAGGCTCGGAGC | 79 | 2126 |
| 881848 | N/A | N/A | 4545 | 4560 | CCCCGAATAGGACCCC | 44 | 2127 |
| 881872 | N/A | N/A | 4937 | 4952 | GAAGAAGGCACCTTCG | 75 | 2128 |
| 881896 | N/A | N/A | 5646 | 5661 | GCAAACCCCTCAAGC | 80 | 2129 |
| 881919 | N/A | N/A | 5755 | 5770 | GCGCGGACGCACGGAG | 98 | 2130 |
| 881940 | N/A | N/A | 6001 | 6016 | TGCACTCGCGCAAAGG | 72 | 2131 |

TABLE 30-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881964 | N/A | N/A | 6315 | 6330 | GCCAAGTTGAAGACAC | 43 | 2132 |
| 881986 | N/A | N/A | 7057 | 7072 | AGTTAAGGTGCCTCAA | 101 | 2133 |
| 882010 | N/A | N/A | 7304 | 7319 | TAACAAGTTATCCAGT | 88 | 2134 |
| 882034 | N/A | N/A | 7593 | 7608 | TGCGAATGTGCCTTGT | 57 | 2135 |
| 882058 | N/A | N/A | 8095 | 8110 | CAGCACCGTGTGGAAA | 49 | 2136 |
| 882082 | N/A | N/A | 8335 | 8350 | TGGCACCAAAAGTACC | 66 | 2137 |
| 882105 | N/A | N/A | 8485 | 8500 | CTTATTAGACTGACAG | 59 | 2138 |
| 882129 | N/A | N/A | 9287 | 9302 | CCACATTAGCAATTAG | 81 | 2139 |
| 882152 | N/A | N/A | 9550 | 9565 | TTTATGAGCTTCCACA | 46 | 2140 |
| 882175 | N/A | N/A | 9843 | 9858 | CCGCATTGCTAGATTC | 28 | 2141 |
| 882198 | N/A | N/A | 10115 | 10130 | TTGGAAACCAGCCCTT | 61 | 2142 |
| 882222 | N/A | N/A | 10253 | 10268 | TCTACCTACTCCATCA | 53 | 2143 |
| 882246 | N/A | N/A | 10580 | 10595 | AGGAAACTTGGAGCGC | 23 | 2144 |
| 882270 | N/A | N/A | 11025 | 11040 | GCAAAGCAAGTGTCTA | 57 | 2145 |
| 882294 | N/A | N/A | 11313 | 11328 | GAAGGATGATCAGCTT | 74 | 2146 |
| 882318 | N/A | N/A | 11536 | 11551 | TTATAGTAGGTAAGAT | 98 | 2147 |
| 882342 | N/A | N/A | 11819 | 11834 | TGCAAGCCTCATTCAC | 58 | 2148 |
| 882366 | N/A | N/A | 12089 | 12104 | AGTCAGACAGTGCGCC | 90 | 2149 |
| 882390 | N/A | N/A | 12380 | 12395 | AAAATATCGCCCATGA | 59 | 2150 |
| 882413 | N/A | N/A | 12827 | 12842 | TGACATCATTTAGGTA | 46 | 2151 |
| 882436 | N/A | N/A | 13133 | 13148 | GGCCACCGACTCTTTT | 87 | 2152 |
| 882459 | N/A | N/A | 13780 | 13795 | ATAACGAGGTGCCTTA | 87 | 2153 |
| 882481 | N/A | N/A | 14077 | 14092 | CGCCACATCAGCAGAC | 88 | 2154 |
| 882527 | N/A | N/A | 14658 | 14673 | ACTTACACCCAGAAGT | 110 | 2155 |
| 882550 | N/A | N/A | 15328 | 15343 | GGCCTTAGCCTTCCTG | 83 | 2156 |
| 882574 | N/A | N/A | 15765 | 15780 | GCAGAAGCTGGTTGGC | 42 | 2157 |
| 882597 | N/A | N/A | 15877 | 15892 | TGAGACTACACCTACA | 81 | 2158 |
| 882620 | N/A | N/A | 16140 | 16155 | ACAGGAGCCGCTACAG | 69 | 2159 |
| 882644 | N/A | N/A | 16284 | 16299 | AAGATACAAAACGGAC | 61 | 2160 |
| 882667 | N/A | N/A | 16568 | 16583 | CCTCACTACAGAGCCC | 76 | 2161 |
| 882691 | N/A | N/A | 16778 | 16793 | TCAAGAGGAACTAGTC | 76 | 2162 |
| 882715 | N/A | N/A | 17140 | 17155 | GTAGGAGTGTAACTGA | 59 | 2163 |
| 882739 | N/A | N/A | 17407 | 17422 | GGAAATACGACAACTT | 37 | 2164 |
| 882763 | N/A | N/A | 17694 | 17709 | TTACGAGAGGGTCTGA | 49 | 2165 |
| 882787 | N/A | N/A | 17937 | 17952 | TTTTACCTGGTATTGC | 102 | 2166 |
| 882811 | N/A | N/A | 18247 | 18262 | GATCATCAACTTCTTA | 53 | 2167 |

TABLE 30-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882834 | N/A | N/A | 18719 | 18734 | TGGAACTCATAGGTGT | 38 | 2168 |
| 882857 | N/A | N/A | 19164 | 19179 | CTGCATCAAATCAAGT | 53 | 2169 |
| 882881 | N/A | N/A | 19390 | 19405 | TCACTATTAAACAGCA | 84 | 2170 |
| 882910 | N/A | N/A | 14263 | 14278 | GTTCATATCACAGAGC | 55 | 2171 |

TABLE 31

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 690526 | 4234 | 4249 | 22351 | 22366 | GGTTTCAGTTGTAAAT | 42 | 2172 |
| 881093 | 193 | 208 | 5220 | 5235 | GCCACTGGCGGAGCTT | 77 | 2173 |
| 881116 | 554 | 569 | 7872 | 7887 | ATGGACATCTGCGGGT | 50 | 2174 |
| 881163 | 1090 | 1105 | 13643 | 13658 | TCGCATAGAGCCCGTC | 43 | 2175 |
| 881187 | 1274 | 1289 | 17067 | 17082 | CCAAAGCATAGAGTCA | 42 | 2176 |
| 881211 | 1539 | 1554 | 19656 | 19671 | CAAGACCCCGTATCCC | 56 | 2177 |
| 881235 | 1897 | 1912 | 20014 | 20029 | CAATGATGGCAGTCTA | 60 | 2178 |
| 881259 | 2015 | 2030 | 20132 | 20147 | TGTCAATACTGAAAGG | 64 | 2179 |
| 881283 | 2156 | 2171 | 20273 | 20288 | CTCAGCAAGTGTCTTC | 55 | 2180 |
| 881307 | 2317 | 2332 | 20434 | 20449 | ATAGGAAGTTTACTAA | 87 | 2181 |
| 881331 | 2465 | 2480 | 20582 | 20597 | ATGCGAAGAATTTTAG | 79 | 2182 |
| 881355 | 2583 | 2598 | 20700 | 20715 | GGACAGCCAAACAAAC | 93 | 2183 |
| 881379 | 2778 | 2793 | 20895 | 20910 | CAAGTAATTTTAAGGC | 59 | 2184 |
| 881403 | 2849 | 2864 | 20966 | 20981 | TGTAAGTGATAGGTAT | 47 | 2185 |
| 881427 | 2973 | 2988 | 21090 | 21105 | ACACATTTGAGAGCTA | 31 | 2186 |
| 881451 | 3254 | 3269 | 21371 | 21386 | GGACACTTTTAGAGAG | 38 | 2187 |
| 881475 | 3397 | 3412 | 21514 | 21529 | AGAACGAGGTAAATCT | 60 | 2188 |
| 881499 | 3486 | 3501 | 21603 | 21618 | GCCCAATACATATCCA | 42 | 2189 |
| 881522 | 3601 | 3616 | 21718 | 21733 | CCGTGAAACAGCAGTT | 44 | 2190 |
| 881546 | 3791 | 3806 | 21908 | 21923 | AGCTCCACTGTTAAAG | 56 | 2191 |
| 881570 | 3999 | 4014 | 22116 | 22131 | CTTTATCAAGACAAGG | 44 | 2192 |
| 881613 | 4388 | 4403 | 22505 | 22520 | TAACAATACTGTAAGG | 55 | 2193 |
| 881637 | 4523 | 4538 | 22640 | 22655 | GCGGAGCATCAACAAA | 70 | 2194 |
| 881661 | 4594 | 4609 | 22711 | 22726 | ACGGAAGTTTACACTG | 23 | 2195 |
| 881685 | 4810 | 4825 | 22927 | 22942 | GCATCGAGATCAGTCT | 43 | 2196 |
| 881709 | 4994 | 5009 | 23111 | 23126 | AAGCAACACGGGAATT | 78 | 2197 |

TABLE 31-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881733 | 5198 | 5213 | 23315 | 23330 | GCATTATCTACCTCAG | 31 | 2198 |
| 881757 | N/A | N/A | 18769 | 18784 | AGCTAAACTCCTAAGT | 85 | 2199 |
| 881781 | N/A | N/A | 18832 | 18847 | GGCAAGCTGAATGCTC | 71 | 2200 |
| 881804 | N/A | N/A | 4002 | 4017 | AAGGAGGCGGGCCTTG | 98 | 2201 |
| 881826 | N/A | N/A | 4315 | 4330 | CCGCACGCAAGGCTCG | 84 | 2202 |
| 881849 | N/A | N/A | 4563 | 4578 | TCGCATCCAGACCCTT | 72 | 2203 |
| 881873 | N/A | N/A | 4939 | 4954 | CGGAAGAAGGCACCTT | 112 | 2204 |
| 881897 | N/A | N/A | 5647 | 5662 | CGCAAAACCCCTCAAG | 81 | 2205 |
| 881920 | N/A | N/A | 5760 | 5775 | CACAGGCGCGGACGCA | 86 | 2206 |
| 881941 | N/A | N/A | 6021 | 6036 | GTAACAACGACACACG | 41 | 2207 |
| 881965 | N/A | N/A | 6325 | 6340 | CCCTATCACTGCCAAG | 62 | 2208 |
| 881987 | N/A | N/A | 7065 | 7080 | CAGAATGAAGTTAAGG | 50 | 2209 |
| 882011 | N/A | N/A | 7325 | 7340 | GACTATTAGATAAGTA | 71 | 2210 |
| 882035 | N/A | N/A | 7602 | 7617 | CAGATGGCATGCGAAT | 65 | 2211 |
| 882059 | N/A | N/A | 8097 | 8112 | GGCAGCACCGTGTGGA | 47 | 2212 |
| 882083 | N/A | N/A | 8344 | 8359 | GGCTAAACCTGGCACC | 60 | 2213 |
| 882106 | N/A | N/A | 8486 | 8501 | CCTTATTAGACTGACA | 52 | 2214 |
| 882130 | N/A | N/A | 9288 | 9303 | GCCACATTAGCAATTA | 92 | 2215 |
| 882153 | N/A | N/A | 9557 | 9572 | CTTATTATTTATGAGC | 63 | 2216 |
| 882176 | N/A | N/A | 9845 | 9860 | TACCGCATTGCTAGAT | 77 | 2217 |
| 882199 | N/A | N/A | 10119 | 10134 | CATATTGGAAACCAGC | 27 | 2218 |
| 882223 | N/A | N/A | 10264 | 10279 | CAAGACAGGTCTCTAC | 66 | 2219 |
| 882247 | N/A | N/A | 10581 | 10596 | AAGGAAACTTGGAGCG | 41 | 2220 |
| 882271 | N/A | N/A | 11026 | 11041 | AGCAAAGCAAGTGTCT | 42 | 2221 |
| 882295 | N/A | N/A | 11321 | 11336 | TCAACCTGGAAGGATG | 70 | 2222 |
| 882319 | N/A | N/A | 11537 | 11552 | TTTATAGTAGGTAAGA | 94 | 2223 |
| 882343 | N/A | N/A | 11827 | 11842 | AAAAAAGGTGCAAGCC | 93 | 2224 |
| 882367 | N/A | N/A | 12093 | 12108 | AGCGAGTCAGACAGTG | 84 | 2225 |
| 882391 | N/A | N/A | 12382 | 12397 | TTAAAATATCGCCCAT | 68 | 2226 |
| 882414 | N/A | N/A | 12871 | 12886 | AGCAAGTCGGTCCACA | 46 | 2227 |
| 882437 | N/A | N/A | 13154 | 13169 | CAGCATATTACAAACG | 42 | 2228 |
| 882460 | N/A | N/A | 13781 | 13796 | GATAACGAGGTGCCTT | 82 | 2229 |
| 882504 | N/A | N/A | 14295 | 14310 | ACTCACTGGTTCTGAA | 86 | 2230 |
| 882528 | N/A | N/A | 14661 | 14676 | GTCACTTACACCCAGA | 48 | 2231 |
| 882551 | N/A | N/A | 15359 | 15374 | GTCCAGAGTCTTCAGA | 94 | 2232 |
| 882575 | N/A | N/A | 15772 | 15787 | TAATTATGCAGAAGCT | 103 | 2233 |

TABLE 31-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882598 | N/A | N/A | 15879 | 15894 | TCTGAGACTACACCTA | 73 | 2234 |
| 882621 | N/A | N/A | 16146 | 16161 | GTTGACACAGGAGCCG | 47 | 2235 |
| 882645 | N/A | N/A | 16285 | 16300 | AAAGATACAAAACGGA | 62 | 2236 |
| 882668 | N/A | N/A | 16581 | 16596 | TAAAACCTCATCCCCT | 126 | 2237 |
| 882692 | N/A | N/A | 16779 | 16794 | TTCAAGAGGAACTAGT | 94 | 2238 |
| 882716 | N/A | N/A | 17146 | 17161 | ACTATGGTAGGAGTGT | 75 | 2239 |
| 882740 | N/A | N/A | 17409 | 17424 | ATGGAAATACGACAAC | 65 | 2240 |
| 882764 | N/A | N/A | 17696 | 17711 | CATTACGAGAGGGTCT | 56 | 2241 |
| 882788 | N/A | N/A | 17940 | 17955 | AACTTTTACCTGGTAT | 72 | 2242 |
| 882812 | N/A | N/A | 18251 | 18266 | GGCCGATCATCAACTT | 93 | 2243 |
| 882835 | N/A | N/A | 18720 | 18735 | GTGGAACTCATAGGTG | 47 | 2244 |
| 882858 | N/A | N/A | 19173 | 19188 | TAACTAAAACTGCATC | 90 | 2245 |
| 882882 | N/A | N/A | 19391 | 19406 | CTCACTATTAAACAGC | 76 | 2246 |
| 882909 | N/A | N/A | 14080 | 14095 | AGCCGCCACATCAGCA | 79 | 2247 |

TABLE 32

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 26 | 195 |
| 881094 | 194 | 209 | 5221 | 5236 | AGCCACTGGCGGAGCT | 62 | 2248 |
| 881117 | 558 | 573 | 7876 | 7891 | GCTCATGGACATCTGC | 61 | 2249 |
| 881164 | 1097 | 1112 | 13650 | 13665 | AGTCTTTTCGCATAGA | 55 | 2250 |
| 881188 | 1276 | 1291 | 17069 | 17084 | CTCCAAAGCATAGAGT | 77 | 2251 |
| 881212 | 1685 | 1700 | 19802 | 19817 | AATCACTTGTCTTGGG | 40 | 2252 |
| 881236 | 1898 | 1913 | 20015 | 20030 | TCAATGATGGCAGTCT | 46 | 2253 |
| 881260 | 2021 | 2036 | 20138 | 20153 | AGTCAGTGTCAATACT | 53 | 2254 |
| 881284 | 2157 | 2172 | 20274 | 20289 | ACTCAGCAAGTGTCTT | 53 | 2255 |
| 881308 | 2341 | 2356 | 20458 | 20473 | GCTCATGTTTTTGAC | 44 | 2256 |
| 881332 | 2469 | 2484 | 20586 | 20601 | CTTTATGCGAAGAATT | 70 | 2257 |
| 881356 | 2587 | 2602 | 20704 | 20719 | CGCTGGACAGCCAAAC | 59 | 2258 |
| 881380 | 2780 | 2795 | 20897 | 20912 | GCCAAGTAATTTTAAG | 65 | 2259 |
| 881404 | 2850 | 2865 | 20967 | 20982 | ATGTAAGTGATAGGTA | 30 | 2260 |
| 881428 | 2995 | 3010 | 21112 | 21127 | TATCCATTAGAAAAGC | 37 | 2261 |
| 881452 | 3255 | 3270 | 21372 | 21387 | TGGACACTTTTAGAGA | 28 | 2262 |
| 881476 | 3398 | 3413 | 21515 | 21530 | CAGAACGAGGTAAATC | 41 | 2263 |

TABLE 32-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881500 | 3487 | 3502 | 21604 | 21619 | TGCCCAATACATATCC | 41 | 2264 |
| 881523 | 3611 | 3626 | 21728 | 21743 | GGTAAGGGCCCCGTGA | 67 | 2265 |
| 881547 | 3835 | 3850 | 21952 | 21967 | AAGGAGGTAGTGGCCC | 53 | 2266 |
| 881571 | 4009 | 4024 | 22126 | 22141 | GCCAATTCCACTTTAT | 36 | 2267 |
| 881590 | 4239 | 4254 | 22356 | 22371 | TCCTAGGTTTCAGTTG | 52 | 2268 |
| 881614 | 4389 | 4404 | 22506 | 22521 | GTAACAATACTGTAAG | 45 | 2269 |
| 881638 | 4524 | 4539 | 22641 | 22656 | GGCGGAGCATCAACAA | 40 | 2270 |
| 881662 | 4595 | 4610 | 22712 | 22727 | AACGGAAGTTTACACT | 41 | 2271 |
| 881686 | 4812 | 4827 | 22929 | 22944 | CTGCATCGAGATCAGT | 48 | 2272 |
| 881710 | 4996 | 5011 | 23113 | 23128 | TGAAGCAACACGGGAA | 40 | 2273 |
| 881734 | 5199 | 5214 | 23316 | 23331 | AGCATTATCTACCTCA | 22 | 2274 |
| 881758 | N/A | N/A | 18770 | 18785 | AAGCTAAACTCCTAAG | 85 | 2275 |
| 881782 | N/A | N/A | 18837 | 18852 | TCTAAGGCAAGCTGAA | 79 | 2276 |
| 881805 | N/A | N/A | 4003 | 4018 | CAAGGAGGCGGGCCTT | 102 | 2277 |
| 881827 | N/A | N/A | 4325 | 4340 | GGCTAGGCCACCGCAC | 72 | 2278 |
| 881850 | N/A | N/A | 4633 | 4648 | GAGGACCTCGCCTGCG | 102 | 2279 |
| 881874 | N/A | N/A | 4940 | 4955 | CCGGAAGAAGGCACCT | 83 | 2280 |
| 881898 | N/A | N/A | 5648 | 5663 | GCGCAAACCCCTCAA | 78 | 2281 |
| 881921 | N/A | N/A | 5763 | 5778 | CGGCACAGGCGCGGAC | 96 | 2282 |
| 881942 | N/A | N/A | 6047 | 6062 | GTAAACTGCCTTAGGG | 56 | 2283 |
| 881966 | N/A | N/A | 6369 | 6384 | AAAGACCCCAGCTATG | 77 | 2284 |
| 881988 | N/A | N/A | 7068 | 7083 | GCTCAGAATGAAGTTA | 52 | 2285 |
| 882012 | N/A | N/A | 7327 | 7342 | AAGACTATTAGATAAG | 78 | 2286 |
| 882036 | N/A | N/A | 7629 | 7644 | GTACAGGACAGGTAAA | 75 | 2287 |
| 882060 | N/A | N/A | 8103 | 8118 | ACCAATGGCAGCACCG | 39 | 2288 |
| 882084 | N/A | N/A | 8347 | 8362 | TATGGCTAAACCTGGC | 57 | 2289 |
| 882107 | N/A | N/A | 8487 | 8502 | CCCTTATTAGACTGAC | 33 | 2290 |
| 882131 | N/A | N/A | 9312 | 9327 | GACCAGGATTCGCCAT | 77 | 2291 |
| 882177 | N/A | N/A | 9850 | 9865 | TGAGTTACCGCATTGC | 20 | 2292 |
| 882200 | N/A | N/A | 10121 | 10136 | ACCATATTGGAAACCA | 26 | 2293 |
| 882224 | N/A | N/A | 10278 | 10293 | TGTTACCGATGCTTCA | 51 | 2294 |
| 882248 | N/A | N/A | 10606 | 10621 | GAAACGAGCCAGTGCA | 48 | 2295 |
| 882272 | N/A | N/A | 11027 | 11042 | GAGCAAAGCAAGTGTC | 58 | 2296 |
| 882296 | N/A | N/A | 11323 | 11338 | GCTCAACCTGGAAGGA | 75 | 2297 |
| 882320 | N/A | N/A | 11541 | 11556 | CTTCTTTATAGTAGGT | 80 | 2298 |
| 882344 | N/A | N/A | 11843 | 11858 | TCACGAGCACCTCAGA | 64 | 2299 |

TABLE 32-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882368 | N/A | N/A | 12111 | 12126 | TTCAACACACTGTCTG | 131 | 2300 |
| 882392 | N/A | N/A | 12386 | 12401 | CTCTTTAAAATATCGC | 44 | 2301 |
| 882415 | N/A | N/A | 12872 | 12887 | AAGCAAGTCGGTCCAC | 68 | 2302 |
| 882438 | N/A | N/A | 13161 | 13176 | TCTAAACCAGCATATT | 67 | 2303 |
| 882482 | N/A | N/A | 14085 | 14100 | AAAAGAGCCGCCACAT | 84 | 2304 |
| 882505 | N/A | N/A | 14321 | 14336 | CATGAAATCCAAGGTA | 51 | 2305 |
| 882529 | N/A | N/A | 14671 | 14686 | AAAAACTTGGGTCACT | 119 | 2306 |
| 882552 | N/A | N/A | 15366 | 15381 | CACCAAGGTCCAGAGT | 80 | 2307 |
| 882599 | N/A | N/A | 15893 | 15908 | TCACACTGCCGTGATC | 78 | 2308 |
| 882622 | N/A | N/A | 16151 | 16166 | AACGAGTTGACACAGG | 45 | 2309 |
| 882646 | N/A | N/A | 16314 | 16329 | GTACATCCTGAAGCCA | 74 | 2310 |
| 882669 | N/A | N/A | 16612 | 16627 | ATCAGAATGTTTCGAC | 54 | 2311 |
| 882693 | N/A | N/A | 16807 | 16822 | CCCCAGGGCCCTCGGT | 82 | 2312 |
| 882717 | N/A | N/A | 17147 | 17162 | CACTATGGTAGGAGTG | 112 | 2313 |
| 882741 | N/A | N/A | 17448 | 17463 | GGGCAACTTTAACCAT | 92 | 2314 |
| 882765 | N/A | N/A | 17699 | 17714 | GAACATTACGAGAGGG | 30 | 2315 |
| 882789 | N/A | N/A | 17945 | 17960 | GGTGTAACTTTTACCT | 89 | 2316 |
| 882813 | N/A | N/A | 18558 | 18573 | GATCATCAACTTCTTT | 57 | 2317 |
| 882836 | N/A | N/A | 18760 | 18775 | CCTAAGTACCTGAAAT | 89 | 2318 |
| 882859 | N/A | N/A | 19203 | 19218 | TCAAATCGACTGCCAC | 46 | 2319 |
| 882883 | N/A | N/A | 19392 | 19407 | GCTCACTATTAAACAG | 112 | 2320 |
| 882902 | N/A | N/A | 9579 | 9594 | CAATAATCTCCCAGCA | 63 | 2321 |
| 882907 | N/A | N/A | 13782 | 13797 | AGATAACGAGGTGCCT | 77 | 2322 |
| 882912 | N/A | N/A | 15773 | 15788 | TTAATTATGCAGAAGC | 87 | 2323 |

TABLE 33

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 26 | 195 |
| 881095 | 217 | 232 | 5244 | 5259 | TGCCGCTGTCGATCTG | 68 | 2324 |
| 881118 | 559 | 574 | 7877 | 7892 | GGCTCATGGACATCTG | 64 | 2325 |
| 881165 | 1103 | 1118 | 13656 | 13671 | TGGCACAGTCTTTTCG | 72 | 2326 |
| 881189 | 1341 | 1356 | 19458 | 19473 | GGCTAGCAGAGGTTCT | 49 | 2327 |
| 881213 | 1717 | 1732 | 19834 | 19849 | CGCTTTCACTAAAGTC | 29 | 2328 |
| 881237 | 1900 | 1915 | 20017 | 20032 | CATCAATGATGGCAGT | 50 | 2329 |

TABLE 33-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881261 | 2025 | 2040 | 20142 | 20157 | CTCTAGTCAGTGTCAA | 41 | 2330 |
| 881285 | 2158 | 2173 | 20275 | 20290 | CACTCAGCAAGTGTCT | 50 | 2331 |
| 881309 | 2358 | 2373 | 20475 | 20490 | TCCCATCCAAGAGTAG | 67 | 2332 |
| 881333 | 2470 | 2485 | 20587 | 20602 | TCTTTATGCGAAGAAT | 58 | 2333 |
| 881357 | 2600 | 2615 | 20717 | 20732 | CGCCATGGCTGATCGC | 47 | 2334 |
| 881381 | 2817 | 2832 | 20934 | 20949 | GTCTTTGGGATTCTAT | 35 | 2335 |
| 881405 | 2851 | 2866 | 20968 | 20983 | AATGTAAGTGATAGGT | 20 | 2336 |
| 881429 | 3024 | 3039 | 21141 | 21156 | TACTAGGTGCTTGTTG | 51 | 2337 |
| 881453 | 3256 | 3271 | 21373 | 21388 | GTGGACACTTTTAGAG | 48 | 2338 |
| 881477 | 3400 | 3415 | 21517 | 21532 | AGCAGAACGAGGTAAA | 30 | 2339 |
| 881501 | 3500 | 3515 | 21617 | 21632 | AAACACAGTCTGCTGC | 65 | 2340 |
| 881524 | 3612 | 3627 | 21729 | 21744 | AGGTAAGGGCCCCGTG | 53 | 2341 |
| 881548 | 3836 | 3851 | 21953 | 21968 | AAAGGAGGTAGTGGCC | 79 | 2342 |
| 881572 | 4022 | 4037 | 22139 | 22154 | TAAATTCTAGTTTGCC | 32 | 2343 |
| 881591 | 4258 | 4273 | 22375 | 22390 | CGCTCAGGACTCAGGG | 45 | 2344 |
| 881615 | 4390 | 4405 | 22507 | 22522 | GGTAACAATACTGTAA | 41 | 2345 |
| 881639 | 4525 | 4540 | 22642 | 22657 | TGGCGGAGCATCAACA | 63 | 2346 |
| 881663 | 4596 | 4611 | 22713 | 22728 | GAACGGAAGTTTACAC | 33 | 2347 |
| 881687 | 4817 | 4832 | 22934 | 22949 | TCCACCTGCATCGAGA | 53 | 2348 |
| 881711 | 4997 | 5012 | 23114 | 23129 | TTGAAGCAACACGGGA | 39 | 2349 |
| 881735 | 5202 | 5217 | 23319 | 23334 | CATAGCATTATCTACC | 57 | 2350 |
| 881759 | N/A | N/A | 18772 | 18787 | TTAAGCTAAACTCCTA | 90 | 2351 |
| 881783 | N/A | N/A | 18840 | 18855 | GCATCTAAGGCAAGCT | 66 | 2352 |
| 881806 | N/A | N/A | 4006 | 4021 | AGCCAAGGAGGCGGGC | 101 | 2353 |
| 881828 | N/A | N/A | 4334 | 4349 | CGCCAGGCCGGCTAGG | 90 | 2354 |
| 881851 | N/A | N/A | 4636 | 4651 | GCGGAGGACCTCGCCT | 92 | 2355 |
| 881875 | N/A | N/A | 4942 | 4957 | CCCCGGAAGAAGGCAC | 64 | 2356 |
| 881899 | N/A | N/A | 5654 | 5669 | ACGAACGCGCAAAACC | 94 | 2357 |
| 881922 | N/A | N/A | 5769 | 5784 | AGCCGCCGGCACAGGC | 99 | 2358 |
| 881943 | N/A | N/A | 6048 | 6063 | GGTAAACTGCCTTAGG | 75 | 2359 |
| 881967 | N/A | N/A | 6371 | 6386 | TGAAAGACCCCAGCTA | 96 | 2360 |
| 881989 | N/A | N/A | 7080 | 7095 | CTAGAAAGTGATGCTC | 61 | 2361 |
| 882013 | N/A | N/A | 7332 | 7347 | CACTAAAGACTATTAG | 95 | 2362 |
| 882037 | N/A | N/A | 7631 | 7646 | TTGTACAGGACAGGTA | 72 | 2363 |
| 882061 | N/A | N/A | 8109 | 8124 | ATCCACACCAATGGCA | 66 | 2364 |
| 882108 | N/A | N/A | 8494 | 8509 | AGGGAATCCCTTATTA | 94 | 2365 |

TABLE 33-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882132 | N/A | N/A | 9317 | 9332 | GGACAGACCAGGATTC | 75 | 2366 |
| 882154 | N/A | N/A | 9580 | 9595 | TCAATAATCTCCCAGC | 45 | 2367 |
| 882178 | N/A | N/A | 9853 | 9868 | GCCTGAGTTACCGCAT | 30 | 2368 |
| 882201 | N/A | N/A | 10122 | 10137 | TACCATATTGGAAACC | 52 | 2369 |
| 882225 | N/A | N/A | 10283 | 10298 | TTTACTGTTACCGATG | 52 | 2370 |
| 882249 | N/A | N/A | 10608 | 10623 | GAGAAACGAGCCAGTG | 61 | 2371 |
| 882273 | N/A | N/A | 11048 | 11063 | ATCTACTCCAGACCCC | 73 | 2372 |
| 882297 | N/A | N/A | 11324 | 11339 | GGCTCAACCTGGAAGG | 71 | 2373 |
| 882321 | N/A | N/A | 11552 | 11567 | CCTAGAGGTGCCTTCT | 59 | 2374 |
| 882345 | N/A | N/A | 11846 | 11861 | TACTCACGAGCACCTC | 59 | 2375 |
| 882369 | N/A | N/A | 12114 | 12129 | TGCTTCAACACACTGT | 97 | 2376 |
| 882393 | N/A | N/A | 12432 | 12447 | TAAACAAGATGAATCC | 56 | 2377 |
| 882416 | N/A | N/A | 12875 | 12890 | AAGAAGCAAGTCGGTC | 45 | 2378 |
| 882439 | N/A | N/A | 13162 | 13177 | GTCTAAACCAGCATAT | 81 | 2379 |
| 882461 | N/A | N/A | 13783 | 13798 | CAGATAACGAGGTGCC | 70 | 2380 |
| 882483 | N/A | N/A | 14086 | 14101 | GAAAAGAGCCGCCACA | 93 | 2381 |
| 882506 | N/A | N/A | 14331 | 14346 | GCTGAATTGTCATGAA | 64 | 2382 |
| 882553 | N/A | N/A | 15369 | 15384 | TGGCACCAAGGTCCAG | 99 | 2383 |
| 882576 | N/A | N/A | 15776 | 15791 | TCCTTAATTATGCAGA | 56 | 2384 |
| 882600 | N/A | N/A | 15895 | 15910 | ATTCACACTGCCGTGA | 66 | 2385 |
| 882623 | N/A | N/A | 16152 | 16167 | AAACGAGTTGACACAG | 80 | 2386 |
| 882670 | N/A | N/A | 16646 | 16661 | CAATTTATGCCATGGA | 38 | 2387 |
| 882694 | N/A | N/A | 16838 | 16853 | TAGCATGTATGCATTC | 48 | 2388 |
| 882718 | N/A | N/A | 17150 | 17165 | AGCCACTATGGTAGGA | 57 | 2389 |
| 882742 | N/A | N/A | 17471 | 17486 | ATCTTAACCTGGAGAA | 72 | 2390 |
| 882766 | N/A | N/A | 17703 | 17718 | TAGAGAACATTACGAG | 40 | 2391 |
| 882790 | N/A | N/A | 17976 | 17991 | CTAGAACATGATGAGA | 71 | 2392 |
| 882837 | N/A | N/A | 18921 | 18936 | TTATACTGTCTGGTTA | 56 | 2393 |
| 882860 | N/A | N/A | 19205 | 19220 | TTTCAAATCGACTGCC | 69 | 2394 |
| 882884 | N/A | N/A | 19400 | 19415 | TGCAACTGGCTCACTA | 83 | 2395 |
| 882900 | N/A | N/A | 8350 | 8365 | TCATATGGCTAAACCT | 51 | 2396 |
| 882911 | N/A | N/A | 14672 | 14687 | CAAAAACTTGGGTCAC | 80 | 2397 |
| 882914 | N/A | N/A | 16378 | 16393 | GTAACTTGACTTGAGA | 51 | 2398 |
| 882915 | N/A | N/A | 18567 | 18582 | AGCTGAGCTGATCATC | 44 | 2399 |

TABLE 34

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 24 | 195 |
| 881096 | 328 | 343 | 5355 | 5370 | CCTTGAAGAGCGCGGC | 76 | 2400 |
| 881119 | 594 | 609 | 7912 | 7927 | GAGCGAAGGGTAAGGC | 62 | 2401 |
| 881166 | 1121 | 1136 | 13674 | 13689 | TCCCAGTAGATCCTGC | 60 | 2402 |
| 881190 | 1354 | 1369 | 19471 | 19486 | AATATAGTTGTCTGGC | 50 | 2403 |
| 881214 | 1732 | 1747 | 19849 | 19864 | GGGCAGTCAATTGGAC | 75 | 2404 |
| 881238 | 1903 | 1918 | 20020 | 20035 | GATCATCAATGATGGC | 37 | 2405 |
| 881262 | 2033 | 2048 | 20150 | 20165 | AGTCATCACTCTAGTC | 47 | 2406 |
| 881286 | 2189 | 2204 | 20306 | 20321 | GGCACGGCTTCAGTCA | 25 | 2407 |
| 881310 | 2366 | 2381 | 20483 | 20498 | CAAAAATGTCCCATCC | 81 | 2408 |
| 881334 | 2471 | 2486 | 20588 | 20603 | TTCTTTATGCGAAGAA | 91 | 2409 |
| 881358 | 2609 | 2624 | 20726 | 20741 | CTTTAGTGTCGCCATG | 71 | 2410 |
| 881382 | 2822 | 2837 | 20939 | 20954 | TGGAGGTCTTTGGGAT | 42 | 2411 |
| 881406 | 2882 | 2897 | 20999 | 21014 | GTCTACTGCTGTACTT | 48 | 2412 |
| 881430 | 3025 | 3040 | 21142 | 21157 | TTACTAGGTGCTTGTT | 50 | 2413 |
| 881454 | 3258 | 3273 | 21375 | 21390 | TTGTGGACACTTTTAG | 51 | 2414 |
| 881478 | 3401 | 3416 | 21518 | 21533 | GAGCAGAACGAGGTAA | 45 | 2415 |
| 881502 | 3502 | 3517 | 21619 | 21634 | CGAAACACAGTCTGCT | 47 | 2416 |
| 881525 | 3616 | 3631 | 21733 | 21748 | TCACAGGTAAGGGCCC | 53 | 2417 |
| 881549 | 3837 | 3852 | 21954 | 21969 | GAAAGGAGGTAGTGGC | 77 | 2418 |
| 881573 | 4023 | 4038 | 22140 | 22155 | CTAAATTCTAGTTTGC | 79 | 2419 |
| 881592 | 4276 | 4291 | 22393 | 22408 | GACTAACTCTCCTGTT | 83 | 2420 |
| 881616 | 4391 | 4406 | 22508 | 22523 | TGGTAACAATACTGTA | 35 | 2421 |
| 881640 | 4533 | 4548 | 22650 | 22665 | GGCCTTCCTGGCGGAG | 78 | 2422 |
| 881664 | 4598 | 4613 | 22715 | 22730 | ATGAACGGAAGTTTAC | 46 | 2423 |
| 881688 | 4828 | 4843 | 22945 | 22960 | TCTCAAGGAGATCCAC | 99 | 2424 |
| 881712 | 4998 | 5013 | 23115 | 23130 | TTTGAAGCAACACGGG | 53 | 2425 |
| 881736 | 5203 | 5218 | 23320 | 23335 | GCATAGCATTATCTAC | 49 | 2426 |
| 881760 | N/A | N/A | 18774 | 18789 | ACTTAAGCTAAACTCC | 79 | 2427 |
| 881784 | N/A | N/A | 18841 | 18856 | AGCATCTAAGGCAAGC | 43 | 2428 |
| 881807 | N/A | N/A | 4042 | 4057 | CAGGAGCGCGGAGGGC | 89 | 2429 |
| 881829 | N/A | N/A | 4367 | 4382 | ACGACAGCTGCGGAGC | 73 | 2430 |
| 881852 | N/A | N/A | 4638 | 4653 | GCGCGGAGGACCTCGC | 90 | 2431 |
| 881876 | N/A | N/A | 5008 | 5023 | GACCACGAGGCCCCGG | 69 | 2432 |
| 881900 | N/A | N/A | 5656 | 5671 | GGACGAACGCGCAAAA | 65 | 2433 |
| 881923 | N/A | N/A | 5773 | 5788 | AAACAGCCGCCGGCAC | 89 | 2434 |
| 881944 | N/A | N/A | 6117 | 6132 | TCCCGGAGGAAGTCCC | 70 | 2435 |

TABLE 34-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881968 | N/A | N/A | 6377 | 6392 | GTAAACTGAAAGACCC | 65 | 2436 |
| 881990 | N/A | N/A | 7152 | 7167 | CATAACTCAGGCAAGG | 64 | 2437 |
| 882014 | N/A | N/A | 7335 | 7350 | ACTCACTAAAGACTAT | 82 | 2438 |
| 882038 | N/A | N/A | 7645 | 7660 | CTACAAGGTCTGAGTT | 83 | 2439 |
| 882062 | N/A | N/A | 8116 | 8131 | ACTTAAAATCCACACC | 93 | 2440 |
| 882085 | N/A | N/A | 8366 | 8381 | TTTATGTAAAGCTTCG | 25 | 2441 |
| 882109 | N/A | N/A | 8498 | 8513 | CCTCAGGGAATCCCTT | 70 | 2442 |
| 882133 | N/A | N/A | 9340 | 9355 | GGAAAGAGCTTTGGTG | 88 | 2443 |
| 882155 | N/A | N/A | 9581 | 9596 | CTCAATAATCTCCCAG | 47 | 2444 |
| 882179 | N/A | N/A | 9877 | 9892 | GTAACTAACTCAAAAG | 101 | 2445 |
| 882202 | N/A | N/A | 10125 | 10140 | CACTACCATATTGGAA | 78 | 2446 |
| 882226 | N/A | N/A | 10284 | 10299 | ATTTACTGTTACCGAT | 71 | 2447 |
| 882250 | N/A | N/A | 10609 | 10624 | GGAGAAACGAGCCAGT | 53 | 2448 |
| 882274 | N/A | N/A | 11052 | 11067 | CTACATCTACTCCAGA | 78 | 2449 |
| 882298 | N/A | N/A | 11332 | 11347 | TTATTTGTGGCTCAAC | 82 | 2450 |
| 882322 | N/A | N/A | 11554 | 11569 | AGCCTAGAGGTGCCTT | 59 | 2451 |
| 882346 | N/A | N/A | 11859 | 11874 | GGGCATCCTCAGTTAC | 67 | 2452 |
| 882370 | N/A | N/A | 12138 | 12153 | ACCCACATCACTGTCT | 85 | 2453 |
| 882394 | N/A | N/A | 12456 | 12471 | CTAAAACTGCGCTCTC | 76 | 2454 |
| 882417 | N/A | N/A | 12878 | 12893 | AGAAAGAAGCAAGTCG | 63 | 2455 |
| 882440 | N/A | N/A | 13169 | 13184 | TTAATCTGTCTAAACC | 84 | 2456 |
| 882462 | N/A | N/A | 13784 | 13799 | ACAGATAACGAGGTGC | 70 | 2457 |
| 882484 | N/A | N/A | 14116 | 14131 | TTCCAACCTTTATGAT | 93 | 2458 |
| 882507 | N/A | N/A | 14335 | 14350 | GTTCGCTGAATTGTCA | 63 | 2459 |
| 882530 | N/A | N/A | 14674 | 14689 | TACAAAAACTTGGGTC | 91 | 2460 |
| 882554 | N/A | N/A | 15406 | 15421 | TAGAAAGCCCTCACCT | 95 | 2461 |
| 882577 | N/A | N/A | 15781 | 15796 | GGGAATCCTTAATTAT | 88 | 2462 |
| 882601 | N/A | N/A | 15898 | 15913 | TACATTCACACTGCCG | 42 | 2463 |
| 882624 | N/A | N/A | 16154 | 16169 | AGAAACGAGTTGACAC | 85 | 2464 |
| 882647 | N/A | N/A | 16380 | 16395 | CAGTAACTTGACTTGA | 61 | 2465 |
| 882671 | N/A | N/A | 16647 | 16662 | CCAATTTATGCCATGG | 88 | 2466 |
| 882695 | N/A | N/A | 16857 | 16872 | GAACATCTCAGATACA | 58 | 2467 |
| 882719 | N/A | N/A | 17158 | 17173 | GAACAGGAAGCCACTA | 77 | 2468 |
| 882743 | N/A | N/A | 17481 | 17496 | TCTTACAGCAATCTTA | 68 | 2469 |
| 882767 | N/A | N/A | 17709 | 17724 | CTATGCTAGAGAACAT | 77 | 2470 |
| 882791 | N/A | N/A | 17977 | 17992 | GCTAGAACATGATGAG | 86 | 2471 |

TABLE 34-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882814 | N/A | N/A | 18570 | 18585 | GATAGCTGAGCTGATC | 68 | 2472 |
| 882838 | N/A | N/A | 18923 | 18938 | ATTTATACTGTCTGGT | 51 | 2473 |
| 882861 | N/A | N/A | 19211 | 19226 | TGTTACTTTCAAATCG | 52 | 2474 |
| 882885 | N/A | N/A | 19401 | 19416 | CTGCAACTGGCTCACT | 90 | 2475 |

TABLE 35

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 12 | 195 |
| 881097 | 329 | 344 | N/A | N/A | GCCTTGAAGAGCGCGG | 91 | 2476 |
| 881120 | 613 | 628 | N/A | N/A | TGTGAACCTGCTGGGC | 98 | 2477 |
| 881167 | 1189 | 1204 | 13742 | 13757 | CAAAGAGCTTGCAGGT | 96 | 2478 |
| 881191 | 1355 | 1370 | 19472 | 19487 | TAATATAGTTGTCTGG | 60 | 2479 |
| 881215 | 1738 | 1753 | 19855 | 19870 | GTAAGAGGGCAGTCAA | 56 | 2480 |
| 881239 | 1910 | 1925 | 20027 | 20042 | TCACAGTGATCATCAA | 57 | 2481 |
| 881263 | 2040 | 2055 | 20157 | 20172 | TACAAGCAGTCATCAC | 71 | 2482 |
| 881287 | 2190 | 2205 | 20307 | 20322 | AGGCACGGCTTCAGTC | 51 | 2483 |
| 881311 | 2382 | 2397 | 20499 | 20514 | TAGATTGTAGGACAGA | 72 | 2484 |
| 881335 | 2472 | 2487 | 20589 | 20604 | CTTCTTTATGCGAAGA | 105 | 2485 |
| 881359 | 2610 | 2625 | 20727 | 20742 | CCTTTAGTGTCGCCAT | 42 | 2486 |
| 881383 | 2824 | 2839 | 20941 | 20956 | AGTGGAGGTCTTTGGG | 45 | 2487 |
| 881407 | 2887 | 2902 | 21004 | 21019 | CCCCAGTCTACTGCTG | 53 | 2488 |
| 881431 | 3026 | 3041 | 21143 | 21158 | CTTACTAGGTGCTTGT | 62 | 2489 |
| 881455 | 3270 | 3285 | 21387 | 21402 | AAACACCCCTTCTTGT | 113 | 2490 |
| 881479 | 3404 | 3419 | 21521 | 21536 | TCTGAGCAGAACGAGG | 53 | 2491 |
| 881503 | 3503 | 3518 | 21620 | 21635 | ACGAAACACAGTCTGC | 48 | 2492 |
| 881526 | 3618 | 3633 | 21735 | 21750 | GGTCACAGGTAAGGGC | 75 | 2493 |
| 881550 | 3896 | 3911 | 22013 | 22028 | TCATACCCTGGATCAC | 57 | 2494 |
| 881574 | 4039 | 4054 | 22156 | 22171 | GTCCACTGAGTACAAA | 87 | 2495 |
| 881593 | 4278 | 4293 | 22395 | 22410 | GCGACTAACTCTCCTG | 30 | 2496 |
| 881617 | 4410 | 4425 | 22527 | 22542 | AATACCTACCTGCCCT | 85 | 2497 |
| 881641 | 4540 | 4555 | 22657 | 22672 | CACAAGTGGCCTTCCT | 55 | 2498 |
| 881665 | 4600 | 4615 | 22717 | 22732 | CAATGAACGGAAGTTT | 67 | 2499 |
| 881689 | 4837 | 4852 | 22954 | 22969 | CTATCAGGATCTCAAG | 91 | 2500 |
| 881713 | 5020 | 5035 | 23137 | 23152 | TGTTAAGTCCCATCTG | 75 | 2501 |

TABLE 35-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881737 | 5204 | 5219 | 23321 | 23336 | AGCATAGCATTATCTA | 66 | 2502 |
| 881761 | N/A | N/A | 18775 | 18790 | GACTTAAGCTAAACTC | 42 | 2503 |
| 881785 | N/A | N/A | 18842 | 18857 | CAGCATCTAAGGCAAG | 46 | 2504 |
| 881830 | N/A | N/A | 4368 | 4383 | GACGACAGCTGCGGAG | 55 | 2505 |
| 881853 | N/A | N/A | 4640 | 4655 | ACGCGCGGAGGACCTC | 87 | 2506 |
| 881877 | N/A | N/A | 5011 | 5026 | AGTGACCACGAGGCCC | 85 | 2507 |
| 881901 | N/A | N/A | 5657 | 5672 | CGGACGAACGCGCAAA | 61 | 2508 |
| 881924 | N/A | N/A | 5775 | 5790 | GAAAACAGCCGCCGGC | 74 | 2509 |
| 881945 | N/A | N/A | 6122 | 6137 | CAAATTCCCGGAGGAA | 95 | 2510 |
| 881969 | N/A | N/A | 6378 | 6393 | CGTAAACTGAAAGACC | 52 | 2511 |
| 881991 | N/A | N/A | 7153 | 7168 | ACATAACTCAGGCAAG | 99 | 2512 |
| 882015 | N/A | N/A | 7345 | 7360 | CAAAATAGTCACTCAC | 103 | 2513 |
| 882039 | N/A | N/A | 7646 | 7661 | TCTACAAGGTCTGAGT | 43 | 2514 |
| 882063 | N/A | N/A | 8119 | 8134 | CCAACTTAAAATCCAC | 91 | 2515 |
| 882086 | N/A | N/A | 8380 | 8395 | GATACTTGTACTGTTT | 22 | 2516 |
| 882110 | N/A | N/A | 8546 9066 | 8561 9081 | AAGAAGCACTGGCATT | 78 | 2517 |
| 882134 | N/A | N/A | 9341 | 9356 | GGGAAAGAGCTTTGGT | 95 | 2518 |
| 882156 | N/A | N/A | 9592 | 9607 | AAATATACCAGCTCAA | 75 | 2519 |
| 882180 | N/A | N/A | 9921 | 9936 | CCAAAGGGTTCAGTGT | 74 | 2520 |
| 882203 | N/A | N/A | 10128 | 10143 | CTCCACTACCATATTG | 99 | 2521 |
| 882227 | N/A | N/A | 10285 | 10300 | CATTTACTGTTACCGA | 21 | 2522 |
| 882251 | N/A | N/A | 10610 | 10625 | TGGAGAAACGAGCCAG | 62 | 2523 |
| 882275 | N/A | N/A | 11054 | 11069 | GTCTACATCTACTCCA | 62 | 2524 |
| 882299 | N/A | N/A | 11333 | 11348 | CTTATTTGTGGCTCAA | 45 | 2525 |
| 882323 | N/A | N/A | 11655 | 11670 | ACCTTAAGCTATTTGG | 39 | 2526 |
| 882347 | N/A | N/A | 11865 | 11880 | CCCAAAGGGCATCCTC | 59 | 2527 |
| 882371 | N/A | N/A | 12143 | 12158 | ACTTAACCCACATCAC | 122 | 2528 |
| 882395 | N/A | N/A | 12484 | 12499 | GGCTTTGTGTTTAAGT | 77 | 2529 |
| 882418 | N/A | N/A | 12890 | 12905 | TAACGGTGTTTCAGAA | 74 | 2530 |
| 882441 | N/A | N/A | 13173 | 13188 | CCATTTAATCTGTCTA | 72 | 2531 |
| 882463 | N/A | N/A | 13785 | 13800 | AACAGATAACGAGGTG | 104 | 2532 |
| 882485 | N/A | N/A | 14124 | 14139 | CAATATGCTTCCAACC | 115 | 2533 |
| 882508 | N/A | N/A | 14343 | 14358 | AGCCAGAGGTTCGCTG | 75 | 2534 |
| 882531 | N/A | N/A | 14677 | 14692 | GCTTACAAAAACTTGG | 74 | 2535 |
| 882555 | N/A | N/A | 15407 | 15422 | TTAGAAAGCCCTCACC | 116 | 2536 |
| 882578 | N/A | N/A | 15782 | 15797 | TGGGAATCCTTAATTA | 88 | 2537 |

TABLE 35-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882625 | N/A | N/A | 16155 | 16170 | AAGAAACGAGTTGACA | 78 | 2538 |
| 882648 | N/A | N/A | 16385 | 16400 | TGGAACAGTAACTTGA | 88 | 2539 |
| 882672 | N/A | N/A | 16648 | 16663 | ACCAATTTATGCCATG | 83 | 2540 |
| 882696 | N/A | N/A | 16860 | 16875 | TGTGAACATCTCAGAT | 88 | 2541 |
| 882720 | N/A | N/A | 17170 | 17185 | GGCCTTTACAAAGAAC | 119 | 2542 |
| 882744 | N/A | N/A | 17487 | 17502 | TAGCATTCTTACAGCA | 43 | 2543 |
| 882768 | N/A | N/A | 17726 | 17741 | GTTGAACCCATCTTGA | 84 | 2544 |
| 882792 | N/A | N/A | 17978 | 17993 | AGCTAGAACATGATGA | 95 | 2545 |
| 882815 | N/A | N/A | 18571 | 18586 | TGATAGCTGAGCTGAT | 63 | 2546 |
| 882839 | N/A | N/A | 18939 | 18954 | AGCTAACTGGCCTCAA | 77 | 2547 |
| 882862 | N/A | N/A | 19221 | 19236 | GGGTTAAAGATGTTAC | 50 | 2548 |
| 882886 | N/A | N/A | 19408 | 19423 | AGATATCCTGCAACTG | 109 | 2549 |
| 882891 | N/A | N/A | 4045 | 4060 | TCGCAGGAGCGCGGAG | 137 | 2550 |
| 882913 | N/A | N/A | 15899 | 15914 | ATACATTCACACTGCC | 55 | 2551 |

TABLE 36

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 26 | 195 |
| 881098 | 335 | 350 | N/A | N/A | GCCCAAGCCTTGAAGA | 85 | 2552 |
| 881121 | 620 | 635 | 9110 | 9125 | ATGTAGTTGTGAACCT | 61 | 2553 |
| 881168 | 1191 | 1206 | 13744 | 13759 | GTCAAAGAGCTTGCAG | 56 | 2554 |
| 881192 | 1356 | 1371 | 19473 | 19488 | ATAATATAGTTGTCTG | 65 | 2555 |
| 881216 | 1739 | 1754 | 19856 | 19871 | AGTAAGAGGGCAGTCA | 50 | 2556 |
| 881240 | 1919 | 1934 | 20036 | 20051 | GGTCAATTTTCACAGT | 36 | 2557 |
| 881264 | 2041 | 2056 | 20158 | 20173 | CTACAAGCAGTCATCA | 56 | 2558 |
| 881288 | 2192 | 2207 | 20309 | 20324 | ACAGGCACGGCTTCAG | 36 | 2559 |
| 881312 | 2384 | 2399 | 20501 | 20516 | ACTAGATTGTAGGACA | 109 | 2560 |
| 881336 | 2507 | 2522 | 20624 | 20639 | GTTCAAGTATTAAGAT | 71 | 2561 |
| 881360 | 2611 | 2626 | 20728 | 20743 | TCCTTTAGTGTCGCCA | 24 | 2562 |
| 881384 | 2825 | 2840 | 20942 | 20957 | AAGTGGAGGTCTTTGG | 34 | 2563 |
| 881432 | 3043 | 3058 | 21160 | 21175 | TAGGGATACAGCAGGC | 27 | 2564 |
| 881456 | 3272 | 3287 | 21389 | 21404 | ATAAACACCCCTTCTT | 70 | 2565 |
| 881480 | 3408 | 3423 | 21525 | 21540 | GGCCTCTGAGCAGAAC | 73 | 2566 |

TABLE 36-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 881504 | 3504 | 3519 | 21621 | 21636 | CACGAAACACAGTCTG | 48 | 2567 |
| 881527 | 3624 | 3639 | 21741 | 21756 | AAAGAGGGTCACAGGT | 66 | 2568 |
| 881551 | 3898 | 3913 | 22015 | 22030 | GGTCATACCCTGGATC | 51 | 2569 |
| 881575 | 4051 | 4066 | 22168 | 22183 | TTCAACAGCACTGTCC | 35 | 2570 |
| 881594 | 4284 | 4299 | 22401 | 22416 | TGTAGGGCGACTAACT | 79 | 2571 |
| 881618 | 4411 | 4426 | 22528 | 22543 | TAATACCTACCTGCCC | 96 | 2572 |
| 881642 | 4543 | 4558 | 22660 | 22675 | ACACACAAGTGGCCTT | 56 | 2573 |
| 881666 | 4601 | 4616 | 22718 | 22733 | GCAATGAACGGAAGTT | 55 | 2574 |
| 881690 | 4838 | 4853 | 22955 | 22970 | GCTATCAGGATCTCAA | 62 | 2575 |
| 881714 | 5021 | 5036 | 23138 | 23153 | CTGTTAAGTCCCATCT | 46 | 2576 |
| 881738 | 5205 | 5220 | 23322 | 23337 | CAGCATAGCATTATCT | 151 | 2577 |
| 881762 | N/A | N/A | 18777 | 18792 | ACGACTTAAGCTAAAC | 42 | 2578 |
| 881786 | N/A | N/A | 18846 | 18861 | TTTACAGCATCTAAGG | 66 | 2579 |
| 881808 | N/A | N/A | 4055 | 4070 | GGCGACCCCGTCGCAG | 70 | 2580 |
| 881831 | N/A | N/A | 4372 | 4387 | GGGCGACGACAGCTGC | 68 | 2581 |
| 881854 | N/A | N/A | 4642 | 4657 | CCACGCGCGGAGGACC | 81 | 2582 |
| 881878 | N/A | N/A | 5015 | 5030 | CGCCAGTGACCACGAG | 58 | 2583 |
| 881902 | N/A | N/A | 5659 | 5674 | CACGGACGAACGCGCA | 102 | 2584 |
| 881946 | N/A | N/A | 6124 | 6139 | ACCAAATTCCCGGAGG | 93 | 2585 |
| 881970 | N/A | N/A | 6413 | 6428 | GCATAGGTCCTTCAGA | 69 | 2586 |
| 881992 | N/A | N/A | 7154 | 7169 | CACATAACTCAGGCAA | 63 | 2587 |
| 882016 | N/A | N/A | 7347 | 7362 | TGCAAAATAGTCACTC | 52 | 2588 |
| 882040 | N/A | N/A | 7647 | 7662 | TTCTACAAGGTCTGAG | 53 | 2589 |
| 882064 | N/A | N/A | 8139 | 8154 | GCGGACACGCCCGACC | 85 | 2590 |
| 882087 | N/A | N/A | 8383 | 8398 | GGAGATACTTGTACTG | 34 | 2591 |
| 882111 | N/A | N/A | 8550 | 8565 | AGATAAGAAGCACTGG | 75 | 2592 |
|  |  |  | 8706 | 8721 |  |  |  |
|  |  |  | 8810 | 8825 |  |  |  |
|  |  |  | 8966 | 8981 |  |  |  |
|  |  |  | 9070 | 9085 |  |  |  |
| 882157 | N/A | N/A | 9593 | 9608 | GAAATATACCAGCTCA | 39 | 2593 |
| 882181 | N/A | N/A | 9957 | 9972 | GGCCAAATTGCAAAGG | 52 | 2594 |
| 882204 | N/A | N/A | 10149 | 10164 | TAGTTTTATGTTAGCC | 25 | 2595 |
| 882228 | N/A | N/A | 10287 | 10302 | TTCATTTACTGTTACC | 29 | 2596 |
| 882252 | N/A | N/A | 10615 | 10630 | GCTGATGGAGAAACGA | 93 | 2597 |
| 882276 | N/A | N/A | 11087 | 11102 | TAAATCACCCTGGTCA | 78 | 2598 |
| 882300 | N/A | N/A | 11347 | 11362 | GTAGAGGAGGAGGACT | 84 | 2599 |
| 882324 | N/A | N/A | 11660 | 11675 | TCCAAACCTTAAGCTA | 63 | 2600 |
| 882348 | N/A | N/A | 11891 | 11906 | AGCCTTCCTGCTCAGA | 45 | 2601 |

TABLE 36-continued

Percent control of human IRF4 mRNA with 3-10-3 cEt gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 882372 | N/A | N/A | 12144 | 12159 | GACTTAACCCACATCA | 266 | 2602 |
| 882396 | N/A | N/A | 12492 | 12507 | TCCCACTGGGCTTTGT | 68 | 2603 |
| 882419 | N/A | N/A | 12891 | 12906 | ATAACGGTGTTTCAGA | 53 | 2604 |
| 882442 | N/A | N/A | 13174 | 13189 | CCCATTTAATCTGTCT | 67 | 2605 |
| 882464 | N/A | N/A | 13787 | 13802 | CTAACAGATAACGAGG | 77 | 2606 |
| 882486 | N/A | N/A | 14129 | 14144 | GTTAACAATATGCTTC | 75 | 2607 |
| 882509 | N/A | N/A | 14347 | 14362 | AGCCAGCCAGAGGTTC | 70 | 2608 |
| 882532 | N/A | N/A | 14691 | 14706 | GAAAATCTGGATGAGC | 36 | 2609 |
| 882556 | N/A | N/A | 15437 | 15452 | AGCCAGTGCCAGTTCC | 61 | 2610 |
| 882579 | N/A | N/A | 15803 | 15818 | AGATAACATGAGAGTG | 59 | 2611 |
| 882602 | N/A | N/A | 15923 | 15938 | AATGACTTAGTCAGAA | 73 | 2612 |
| 882626 | N/A | N/A | 16159 | 16174 | GCAAAAGAAACGAGTT | 92 | 2613 |
| 882649 | N/A | N/A | 16387 | 16402 | GATGGAACAGTAACTT | 49 | 2614 |
| 882673 | N/A | N/A | 16663 | 16678 | ACGCAATGGCAAAAGA | 89 | 2615 |
| 882697 | N/A | N/A | 16887 | 16902 | TCTTACTCCGCTGAGT | 65 | 2616 |
| 882721 | N/A | N/A | 17224 | 17239 | TTCCAGGTCATTTGAC | 34 | 2617 |
| 882745 | N/A | N/A | 17492 | 17507 | CTAGATAGCATTCTTA | 61 | 2618 |
| 882769 | N/A | N/A | 17731 | 17746 | CCACAGTTGAACCCAT | 64 | 2619 |
| 882793 | N/A | N/A | 17982 | 17997 | TCAGAGCTAGAACATG | 62 | 2620 |
| 882816 | N/A | N/A | 18579 | 18594 | GATTGATGTGATAGCT | 44 | 2621 |
| 882840 | N/A | N/A | 18960 | 18975 | CTACTATTGTGGAAAA | 97 | 2622 |
| 882863 | N/A | N/A | 19230 | 19245 | CTTAATTCTGGGTTAA | 47 | 2623 |
| 882887 | N/A | N/A | 19417 | 19432 | ACATTACTGAGATATC | 84 | 2624 |
| 882895 | N/A | N/A | 5776 | 5791 | CGAAAACAGCCGCCGG | 85 | 2625 |
| 882901 | N/A | N/A | 9358 | 9373 | ACGCAGCCTCTAAGAA | 75 | 2626 |

Example 7: Effect of Mixed MOE and cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured MM.1R cells at a density of 5,000 cells per well were transfected by free uptake with 1,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set hIRF4_LTS34726 (forward sequence GGCAAAGAAAGCTCATCACAG, designated herein as SEQ ID NO: 3389; reverse sequence GGATTGCT-GATGTGTTCTGGTA designated herein as SEQ ID NO: 3390; probe sequence TAGCCCCTCAGGAAATGTC-CACTG, designated herein as SEQ ID: 3391) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Table 37 are cEt and/or MOE containing gapmers. The modified oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a MOE and/or cEt sugar modification. The "Motif" column describes the sugar modifications of each oligonucleotide.

"k" indicates a cEt sugar modification; "d" indicates deoxyribose; and "e" indicates a MOE modification. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 37 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 37

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 881450 | 3252 | 3267 | 21369 | 21384 | ACACTTTTAGAGAGGA | kkk-d10-kkk | 47 | 2111 |
| 881659 | 4592 | 4607 | 22709 | 22724 | GGAAGTTTACACTGGA | kkk-d10-kkk | 15 | 2044 |
| 935895 | 4200 | 4215 | 22317 | 22332 | TCTATAGTGTTCCAGG | kk-d9-ecckk | 50 | 1734 |
| 935896 | 3070 | 3085 | 21187 | 21202 | GCTTGATAAAGGCTGA | kk-d9-eeekk | 72 | 1505 |
| 935897 | 3251 | 3266 | 21368 | 21383 | CACTTTTAGAGAGGAG | kk-d9-eeekk | 67 | 2036 |
| 935898 | 4227 | 4242 | 22344 | 22359 | GTTGTAAATGAGTCGG | kk-d9-eeekk | 18 | 559 |
| 935899 | 4591 | 4606 | 22708 | 22723 | GAAGTTTACACTGGAT | kk-d9-eeekk | 72 | 1968 |
| 935900 | N/A | N/A | 8464 | 8479 | GCATTTTATCATCCGA | kk-d9-eeekk | 62 | 1605 |
| 935901 | N/A | N/A | 11115 | 11130 | GTGATGTCAGGTTTTC | kk-d9-eeekk | 62 | 2627 |
| 935902 | 5186 | 5201 | 23303 | 23318 | TCAGTTTGTGAAGCAT | kk-d9-eeekk | 61 | 649 |
| 935903 | 4171 | 4186 | 22288 | 22303 | TGCTTGAGGTTTTCCT | kk-d9-eeekk | 68 | 548 |
| 935904 | 2914 | 2929 | 21031 | 21046 | AGTATGAGAAACGGCC | kk-d9-eeekk | 84 | 1045 |
| 935905 | 4199 | 4214 | 22316 | 22331 | CTATAGTGTTCCAGGA | kk-d9-eeekk | 66 | 552 |
| 935906 | 3069 | 3084 | 21186 | 21201 | CTTGATAAAGGCTGAA | kk-d9-eeekk | 90 | 1427 |
| 935907 | 3250 | 3265 | 21367 | 21382 | ACTTTTAGAGAGGAGA | kk-d9-eeekk | 64 | 1960 |
| 935908 | 4226 | 4241 | 22343 | 22358 | TTGTAAATGAGTCGGT | kk-d9-eeekk | 52 | 195 |
| 935909 | 4593 | 4608 | 22710 | 22725 | CGGAAGTTTACACTGG | kk-d9-eeekk | 66 | 2119 |
| 935910 | N/A | N/A | 8466 | 8481 | AAGCATTTTATCATCC | kk-d9-eeekk | 79 | 2628 |
| 935911 | N/A | N/A | 11117 | 11132 | CAGTGATGTCAGGTTT | kk-d9-eeekk | 44 | 2629 |
| 935912 | 5188 | 5203 | 23305 | 23320 | CCTCAGTTTGTGAAGC | kk-d9-eeekk | 67 | 1894 |
| 935913 | 4173 | 4188 | 22290 | 22305 | ACTGCTTGAGGTTTTC | kk-d9-eeekk | 55 | 1356 |
| 935914 | 2916 | 2931 | 21033 | 21048 | GTAGTATGAGAAACGG | kk-d9-eeekk | 49 | 426 |
| 935915 | 4201 | 4216 | 22318 | 22333 | CTCTATAGTGTTCCAG | kk-d9-eeekk | 52 | 1811 |
| 935916 | 3071 | 3086 | 21188 | 21203 | AGCTTGATAAAGGCTG | kk-d9-eeekk | 97 | 1579 |
| 935917 | 3252 | 3267 | 21369 | 21384 | ACACTTTTAGAGAGGA | kk-d9-eeekk | 79 | 2111 |
| 935918 | 4228 | 4243 | 22345 | 22360 | AGTTGTAAATGAGTCG | kk-d9-eeekk | 34 | 2021 |
| 935919 | 4594 | 4609 | 22711 | 22726 | ACGGAAGTTTACACTG | kk-d9-eeekk | 85 | 2195 |
| 935920 | N/A | N/A | 8467 | 8482 | GAAGCATTTTATCATC | kk-d9-eeekk | 91 | 2630 |
| 935921 | N/A | N/A | 11118 | 11133 | GCAGTGATGTCAGGTT | kk-d9-eeekk | 19 | 2631 |
| 935922 | 5189 | 5204 | 23306 | 23321 | ACCTCAGTTTGTGAAG | kk-d9-eeekk | 96 | 1971 |

TABLE 37-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935923 | 4174 | 4189 | 22291 | 22306 | TACTGCTTGAGGTTTT | kk-d9-eeekk | 90 | 1433 |
| 935924 | 2917 | 2932 | 21034 | 21049 | TGTAGTATGAGAAACG | kk-d9-eeekk | 93 | 1197 |
| 935925 | 4202 | 4217 | 22319 | 22334 | TCTCTATAGTGTTCCA | kk-d9-eeekk | 43 | 2632 |
| 935926 | 3072 | 3087 | 21189 | 21204 | AAGCTTGATAAAGGCT | kk-d9-eeekk | 47 | 2633 |
| 935927 | 3253 | 3268 | 21370 | 21385 | GACACTTTTAGAGAGG | kk-d9-eeekk | 75 | 451 |
| 935928 | 4229 | 4244 | 22346 | 22361 | CAGTTGTAAATGAGTC | kk-d9-eeekk | 38 | 560 |
| 935929 | 4592 | 4607 | 22709 | 22724 | GGAAGTTTACACTGGA | kk-d9-ekeke | 36 | 2044 |
| 935930 | N/A | N/A | 8465 | 8480 | AGCATTTTATCATCCG | kk-d9-ekeke | 54 | 1679 |
| 935931 | N/A | N/A | 11116 | 11131 | AGTGATGTCAGGTTTT | kk-d9-ekeke | 67 | 1232 |
| 935932 | 5187 | 5202 | 23304 | 23319 | CTCAGTTTGTGAAGCA | kk-d9-ekeke | 72 | 1817 |
| 935933 | 4172 | 4187 | 22289 | 22304 | CTGCTTGAGGTTTTCC | kk-d9-ekeke | 51 | 1279 |
| 935934 | 2915 | 2930 | 21032 | 21047 | TAGTATGAGAAACGGC | kk-d9-ekeke | 50 | 1121 |
| 935935 | 4200 | 4215 | 22317 | 22332 | TCTATAGTGTTCCAGG | kk-d9-ekeke | 44 | 1734 |
| 935936 | 3070 | 3085 | 21187 | 21202 | GCTTGATAAAGGCTGA | kk-d9-ekeke | 61 | 1505 |
| 935937 | 3251 | 3266 | 21368 | 21383 | CACTTTTAGAGAGGAG | kk-d9-ekeke | 74 | 2036 |
| 935938 | 4227 | 4242 | 22344 | 22359 | GTTGTAAATGAGTCGG | kk-d9-ekeke | 52 | 559 |
| 935939 | 4591 | 4606 | 22708 | 22723 | GAAGTTTACACTGGAT | kk-d9-ekeke | 42 | 1968 |
| 935940 | N/A | N/A | 8464 | 8479 | GCATTTTATCATCCGA | kk-d9-ekeke | 56 | 1605 |
| 935941 | N/A | N/A | 11115 | 11130 | GTGATGTCAGGTTTTC | kk-d9-ekeke | 42 | 2627 |
| 935942 | 5186 | 5201 | 23303 | 23318 | TCAGTTTGTGAAGCAT | kk-d9-ekeke | 55 | 649 |
| 935943 | 4171 | 4186 | 22288 | 22303 | TGCTTGAGGTTTTCCT | kk-d9-ekeke | 55 | 548 |
| 935944 | 2914 | 2929 | 21031 | 21046 | AGTATGAGAAACGGCC | kk-d9-ekeke | 89 | 1045 |
| 935945 | 4199 | 4214 | 22316 | 22331 | CTATAGTGTTCCAGGA | kk-d9-ekeke | 52 | 552 |
| 935946 | 3069 | 3084 | 21186 | 21201 | CTTGATAAAGGCTGAA | kk-d9-ekeke | 81 | 1427 |
| 935947 | 3250 | 3265 | 21367 | 21382 | ACTTTTAGAGAGGAGA | kk-d9-ekeke | 48 | 1960 |
| 935948 | 4226 | 4241 | 22343 | 22358 | TTGTAAATGAGTCGGT | kk-d9-ekeke | 43 | 195 |
| 935949 | 4593 | 4608 | 22710 | 22725 | CGGAAGTTTACACTGG | kk-d9-ekeke | 67 | 2119 |
| 935950 | N/A | N/A | 8466 | 8481 | AAGCATTTTATCATCC | kk-d9-ekeke | 75 | 2628 |
| 935951 | N/A | N/A | 11117 | 11132 | CAGTGATGTCAGGTTT | kk-d9-ekeke | 53 | 2629 |
| 935952 | 5188 | 5203 | 23305 | 23320 | CCTCAGTTTGTGAAGC | kk-d9-ekeke | 79 | 1894 |
| 935953 | 4173 | 4188 | 22290 | 22305 | ACTGCTTGAGGTTTTC | kk-d9-ekeke | 60 | 1356 |
| 935954 | 2916 | 2931 | 21033 | 21048 | GTAGTATGAGAAACGG | kk-d9-ekeke | 65 | 426 |
| 935955 | 4201 | 4216 | 22318 | 22333 | CTCTATAGTGTTCCAG | kk-d9-ekeke | 57 | 1811 |
| 935956 | 3071 | 3086 | 21188 | 21203 | AGCTTGATAAAGGCTG | kk-d9-ekeke | 82 | 1579 |
| 935957 | 3252 | 3267 | 21369 | 21384 | ACACTTTTAGAGAGGA | kk-d9-ekeke | 59 | 2111 |
| 935958 | 4228 | 4243 | 22345 | 22360 | AGTTGTAAATGAGTCG | kk-d9-ekeke | 27 | 2021 |

TABLE 37-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935959 | 4594 | 4609 | 22711 | 22726 | ACGGAAGTTTACACTG | kk-d9-ekeke | 92 | 2195 |
| 935960 | N/A | N/A | 8467 | 8482 | GAAGCATTTTATCATC | kk-d9-ekeke | 94 | 2630 |
| 935961 | N/A | N/A | 11118 | 11133 | GCAGTGATGTCAGGTT | kk-d9-ekeke | 20 | 2631 |
| 935962 | 5189 | 5204 | 23306 | 23321 | ACCTCAGTTTGTGAAG | kk-d9-ekeke | 87 | 1971 |
| 935963 | 4174 | 4189 | 22291 | 22306 | TACTGCTTGAGGTTTT | kk-d9-ekeke | 82 | 1433 |
| 935964 | 2917 | 2932 | 21034 | 21049 | TGTAGTATGAGAAACG | kk-d9-ekeke | 87 | 1197 |
| 935965 | 4202 | 4217 | 22319 | 22334 | TCTCTATAGTGTTCCA | kk-d9-ekeke | 61 | 2632 |
| 935966 | 3072 | 3087 | 21189 | 21204 | AAGCTTGATAAAGGCT | kk-d9-ekeke | 62 | 2633 |
| 935967 | 3253 | 3268 | 21370 | 21385 | GACACTTTTAGAGAGG | kk-d9-ekeke | 78 | 451 |
| 935968 | 4229 | 4244 | 22346 | 22361 | CAGTTGTAAATGAGTC | kk-d9-ekeke | 28 | 560 |
| 935969 | 4592 | 4607 | 22709 | 22724 | GGAAGTTTACACTGGA | k-d9-kekeke | 68 | 2044 |
| 935970 | N/A | N/A | 8465 | 8480 | AGCATTTTATCATCCG | k-d9-kekeke | 76 | 1679 |

Example 8: Effect of Mixed MOE and cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured MM.1R cells at a density of 5,000 cells per well were transfected by free uptake with 1,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set hIRF4_LTS34726 (described hereinabove in Example 7) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 38 through 42 are cEt and/or MOE containing gapmers. The modified oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a MOE and/or cEt sugar modification. The "Motif" column describes the sugar modifications of each oligonucleotide. "k" indicates a cEt sugar modification; "d" indicates deoxyribose; and "e" indicates a MOE modification. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 38 through 42 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 38

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 37 | 195 |
| 881450 | 3252 | 3267 | 21369 | 21384 | ACACTTTTAGAGAGGA | kkk-d10-kkk | 53 | 2111 |
| 881659 | 4592 | 4607 | 22709 | 22724 | GGAAGTTTACACTGGA | kkk-d10-kkk | 14 | 2044 |
| 935570 | N/A | N/A | 8455 | 8470 | CATCCGAAAAGACTGG | kkk-d10-kkk | 86 | 2634 |

TABLE 38-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935571 | N/A | N/A | 8456 | 8471 | TCATCCGAAAAGACTG | kkk-d10-kkk | 84 | 2635 |
| 935572 | N/A | N/A | 8457 | 8472 | ATCATCCGAAAAGACT | kkk-d10-kkk | 96 | 2636 |
| 935573 | N/A | N/A | 8458 | 8473 | TATCATCCGAAAAGAC | kkk-d10-kkk | 97 | 2637 |
| 935574 | N/A | N/A | 8459 | 8474 | TTATCATCCGAAAAGA | kkk-d10-kkk | 96 | 2638 |
| 935575 | N/A | N/A | 8460 | 8475 | TTTATCATCCGAAAAG | kkk-d10-kkk | 93 | 2639 |
| 935576 | N/A | N/A | 8472 | 8487 | CAGCCGAAGCATTTTA | kkk-d10-kkk | 100 | 2640 |
| 935577 | N/A | N/A | 8473 | 8488 | ACAGCCGAAGCATTTT | kkk-d10-kkk | 92 | 2641 |
| 935578 | N/A | N/A | 8474 | 8489 | GACAGCCGAAGCATTT | kkk-d10-kkk | 94 | 2642 |
| 935580 | N/A | N/A | 11115 | 11130 | GTGATGTCAGGTTTTC | kkk-d10-kkk | 34 | 2627 |
| 935581 | N/A | N/A | 11117 | 11132 | CAGTGATGTCAGGTTT | kkk-d10-kkk | 38 | 2629 |
| 935582 | N/A | N/A | 11118 | 11133 | GCAGTGATGTCAGGTT | kkk-d10-kkk | 61 | 2631 |
| 935584 | N/A | N/A | 11124 | 11139 | CCACAAGCAGTGATGT | kkk-d10-kkk | 84 | 2643 |
| 935585 | N/A | N/A | 11125 | 11140 | ACCACAAGCAGTGATG | kkk-d10-kkk | 99 | 2644 |
| 935586 | 2905 | 2920 | 21022 | 21037 | AACGGCCTGGAGGTGA | kkk-d10-kkk | 99 | 2645 |
| 935587 | 2906 | 2921 | 21023 | 21038 | AAACGGCCTGGAGGTG | kkk-d10-kkk | 89 | 2646 |
| 935588 | 2907 | 2922 | 21024 | 21039 | GAAACGGCCTGGAGGT | kkk-d10-kkk | 83 | 2647 |
| 935590 | 2920 | 2935 | 21037 | 21052 | TCCTGTAGTATGAGAA | kkk-d10-kkk | 78 | 2648 |
| 935591 | 2922 | 2937 | 21039 | 21054 | TATCCTGTAGTATGAG | kkk-d10-kkk | 58 | 2649 |
| 935593 | 3072 | 3087 | 21189 | 21204 | AAGCTTGATAAAGGCT | kkk-d10-kkk | 97 | 2633 |
| 935597 | 3080 | 3095 | 21197 | 21212 | TGCTCACTAAGCTTGA | kkk-d10-kkk | 88 | 2650 |
| 935603 | 4178 | 4193 | 22295 | 22310 | TAATTACTGCTTGAGG | kkk-d10-kkk | 38 | 2651 |
| 935606 | 4194 | 4209 | 22311 | 22326 | GTGTTCCAGGAGATAT | kkk-d10-kkk | 70 | 2652 |
| 935608 | 4196 | 4211 | 22313 | 22328 | TAGTGTTCCAGGAGAT | kkk-d10-kkk | 47 | 2653 |
| 935611 | 4208 | 4223 | 22325 | 22340 | CTTGGTTCTCTATAGT | kkk-d10-kkk | 73 | 2654 |
| 935614 | 4597 | 4612 | 22714 | 22729 | TGAACGGAAGTTTACA | kkk-d10-kkk | 86 | 2655 |
| 935616 | 5190 | 5205 | 23307 | 23322 | TACCTCAGTTTGTGAA | kkk-d10-kkk | 89 | 2656 |
| 935618 | N/A | N/A | 8466 | 8481 | AAGCATTTTATCATCC | kkk-d10-kkk | 75 | 2628 |
| 935619 | N/A | N/A | 8467 | 8482 | GAAGCATTTTATCATC | kkk-d10-kkk | 96 | 2630 |
| 935620 | 4202 | 4217 | 22319 | 22334 | TCTCTATAGTGTTCCA | kkk-d10-kkk | 30 | 2632 |
| 935621 | 4592 | 4607 | 22709 | 22724 | GGAAGTTTACACTGGA | k-d10-kekek | 67 | 2044 |
| 935622 | N/A | N/A | 8465 | 8480 | AGCATTTTATCATCCG | k-d10-kekek | 64 | 1679 |
| 935623 | N/A | N/A | 11116 | 11131 | AGTGATGTCAGGTTTT | k-d10-kekek | 75 | 1232 |
| 935624 | 5187 | 5202 | 23304 | 23319 | CTCAGTTTGTGAAGCA | k-d10-kekek | 76 | 1817 |
| 935625 | 4172 | 4187 | 22289 | 22304 | CTGCTTGAGGTTTTCC | k-d10-kekek | 92 | 1279 |
| 935626 | 2915 | 2930 | 21032 | 21047 | TAGTATGAGAAACGGC | k-d10-kekek | 76 | 1121 |
| 935627 | 4200 | 4215 | 22317 | 22332 | TCTATAGTGTTCCAGG | k-d10-kekek | 84 | 1734 |

TABLE 38-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935628 | 3070 | 3085 | 21187 | 21202 | GCTTGATAAAGGCTGA | k-d10-kekek | 83 | 1505 |
| 935629 | 3251 | 3266 | 21368 | 21383 | CACTTTTAGAGAGGAG | k-d10-kekek | 81 | 2036 |
| 935630 | 4591 | 4606 | 22708 | 22723 | GAAGTTTACACTGGAT | k-d10-kekek | 73 | 1968 |
| 935631 | N/A | N/A | 8464 | 8479 | GCATTTTATCATCCGA | k-d10-kekek | 79 | 1605 |
| 935632 | N/A | N/A | 11115 | 11130 | GTGATGTCAGGTTTTC | k-d10-kekek | 78 | 2627 |
| 935633 | 5186 | 5201 | 23303 | 23318 | TCAGTTTGTGAAGCAT | k-d10-kekek | 79 | 649 |
| 935634 | 4171 | 4186 | 22288 | 22303 | TGCTTGAGGTTTTCCT | k-d10-kekek | 64 | 548 |
| 935635 | 2914 | 2929 | 21031 | 21046 | AGTATGAGAAACGGCC | k-d10-kekek | 90 | 1045 |
| 935636 | 4199 | 4214 | 22316 | 22331 | CTATAGTGTTCCAGGA | k-d10-kekek | 66 | 552 |
| 935637 | 3069 | 3084 | 21186 | 21201 | CTTGATAAAGGCTGAA | k-d10-kekek | 83 | 1427 |
| 935638 | 3250 | 3265 | 21367 | 21382 | ACTTTTAGAGAGGAGA | k-d10-kekek | 68 | 1960 |
| 935639 | 4593 | 4608 | 22710 | 22725 | CGGAAGTTTACACTGG | k-d10-kekek | 90 | 2119 |
| 935640 | N/A | N/A | 8466 | 8481 | AAGCATTTTATCATCC | k-d10-kekek | 86 | 2628 |
| 935641 | N/A | N/A | 11117 | 11132 | CAGTGATGTCAGGTTT | k-d10-kekek | 54 | 2629 |
| 935642 | 5188 | 5203 | 23305 | 23320 | CCTCAGTTTGTGAAGC | k-d10-kekek | 74 | 1894 |
| 935643 | 4173 | 4188 | 22290 | 22305 | ACTGCTTGAGGTTTTC | k-d10-kekek | 78 | 1356 |
| 935644 | 2916 | 2931 | 21033 | 21048 | GTAGTATGAGAAACGG | k-d10-kekek | 54 | 426 |
| 935645 | 4201 | 4216 | 22318 | 22333 | CTCTATAGTGTTCCAG | k-d10-kekek | 76 | 1811 |
| 935646 | 3071 | 3086 | 21188 | 21203 | AGCTTGATAAAGGCTG | k-d10-kekek | 99 | 1579 |
| 935647 | 3252 | 3267 | 21369 | 21384 | ACACTTTTAGAGAGGA | k-d10-kekek | 106 | 2111 |
| 935648 | 4228 | 4243 | 22345 | 22360 | AGTTGTAAATGAGTCG | k-d10-kekek | 56 | 2021 |
| 935649 | 4594 | 4609 | 22711 | 22726 | ACGGAAGTTTACACTG | k-d10-kekek | 93 | 2195 |
| 935650 | N/A | N/A | 8467 | 8482 | GAAGCATTTTATCATC | k-d10-kekek | 112 | 2630 |
| 935651 | N/A | N/A | 11118 | 11133 | GCAGTGATGTCAGGTT | k-d10-kekek | 64 | 2631 |
| 935652 | 5189 | 5204 | 23306 | 23321 | ACCTCAGTTTGTGAAG | k-d10-kekek | 82 | 1971 |
| 935653 | 4174 | 4189 | 22291 | 22306 | TACTGCTTGAGGTTTT | k-d10-kekek | 76 | 1433 |
| 935654 | 2917 | 2932 | 21034 | 21049 | TGTAGTATGAGAAACG | k-d10-kekek | 93 | 1197 |
| 935655 | 4202 | 4217 | 22319 | 22334 | TCTCTATAGTGTTCCA | k-d10-kekek | 39 | 2632 |
| 935656 | 3072 | 3087 | 21189 | 21204 | AAGCTTGATAAAGGCT | k-d10-kekek | 97 | 2633 |
| 935657 | 3253 | 3268 | 21370 | 21385 | GACACTTTTAGAGAGG | k-d10-kekek | 77 | 451 |
| 935658 | 4229 | 4244 | 22346 | 22361 | CAGTTGTAAATGAGTC | k-d10-kekek | 35 | 560 |
| 935659 | 4592 | 4607 | 22709 | 22724 | GGAAGTTTACACTGGA | kk-d9-kekek | 53 | 2044 |
| 935660 | N/A | N/A | 8465 | 8480 | AGCATTTTATCATCCG | kk-d9-kekek | 61 | 1679 |
| 935661 | N/A | N/A | 11116 | 11131 | AGTGATGTCAGGTTTT | kk-d9-kekek | 61 | 1232 |
| 935662 | 5187 | 5202 | 23304 | 23319 | CTCAGTTTGTGAAGCA | kk-d9-kekek | 78 | 1817 |
| 935663 | 4172 | 4187 | 22289 | 22304 | CTGCTTGAGGTTTTCC | kk-d9-kekek | 70 | 1279 |
| 935664 | 2915 | 2930 | 21032 | 21047 | TAGTATGAGAAACGGC | kk-d9-kekek | 73 | 1121 |

TABLE 38-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935665 | 4200 | 4215 | 22317 | 22332 | TCTATAGTGTTCCAGG | kk-d9-kekek | 72 | 1734 |
| 935666 | 3070 | 3085 | 21187 | 21202 | GCTTGATAAAGGCTGA | kk-d9-kekek | 93 | 1505 |

TABLE 39

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 37 | 195 |
| 881450 | 3252 | 3267 | 21369 | 21384 | ACACTTTTAGAGAGGA | kkk-d10-kkk | 49 | 2111 |
| 881659 | 4592 | 4607 | 22709 | 22724 | GGAAGTTTACACTGGA | kkk-d10-kkk | 15 | 2044 |
| 935667 | 3251 | 3266 | 21368 | 21383 | CACTTTTAGAGAGGA | kk-d9-kekek | 83 | 2036 |
| 935668 | 4591 | 4606 | 22708 | 22723 | GAAGTTTACACTGGAT | kk-d9-kekek | 45 | 1968 |
| 935669 | N/A | N/A | 8464 | 8479 | GCATTTTATCATCCGA | kk-d9-kekek | 52 | 1605 |
| 935670 | N/A | N/A | 11115 | 11130 | GTGATGTCAGGTTTTC | kk-d9-kekek | 60 | 2627 |
| 935671 | 5186 | 5201 | 23303 | 23318 | TCAGTTTGTGAAGCAT | kk-d9-kekek | 42 | 649 |
| 935672 | 4171 | 4186 | 22288 | 22303 | TGCTTGAGGTTTTCCT | kk-d9-kekek | 64 | 548 |
| 935673 | 2914 | 2929 | 21031 | 21046 | AGTATGAGAAACGGCC | kk-d9-kekek | 97 | 1045 |
| 935674 | 4199 | 4214 | 22316 | 22331 | CTATAGTGTTCCAGGA | kk-d9-kekek | 57 | 552 |
| 935675 | 3069 | 3084 | 21186 | 21201 | CTTGATAAAGGCTGAA | kk-d9-kekek | 88 | 1427 |
| 935676 | 3250 | 3265 | 21367 | 21382 | ACTTTTAGAGAGGAGA | kk-d9-kekek | 60 | 1960 |
| 935677 | 4593 | 4608 | 22710 | 22725 | CGGAAGTTTACACTGG | kk-d9-kekek | 80 | 2119 |
| 935678 | N/A | N/A | 8466 | 8481 | AAGCATTTTATCATCC | kk-d9-kekek | 82 | 2628 |
| 935679 | N/A | N/A | 11117 | 11132 | CAGTGATGTCAGGTTT | kk-d9-kekek | 36 | 2629 |
| 935680 | 5188 | 5203 | 23305 | 23320 | CCTCAGTTTGTGAAGC | kk-d9-kekek | 85 | 1894 |
| 935681 | 4173 | 4188 | 22290 | 22305 | ACTGCTTGAGGTTTTC | kk-d9-kekek | 76 | 1356 |
| 935682 | 2916 | 2931 | 21033 | 21048 | GTAGTATGAGAAACGG | kk-d9-kekek | 50 | 426 |
| 935683 | 4201 | 4216 | 22318 | 22333 | CTCTATAGTGTTCCAG | kk-d9-kekek | 78 | 1811 |
| 935684 | 3071 | 3086 | 21188 | 21203 | AGCTTGATAAAGGCTG | kk-d9-kekek | 84 | 1579 |
| 935685 | 3252 | 3267 | 21369 | 21384 | ACACTTTTAGAGAGGA | kk-d9-kekek | 73 | 2111 |
| 935686 | 4228 | 4243 | 22345 | 22360 | AGTTGTAAATGAGTCG | kk-d9-kekek | 44 | 2021 |
| 935687 | 4594 | 4609 | 22711 | 22726 | ACGGAAGTTTACACTG | kk-d9-kekek | 79 | 2195 |
| 935688 | N/A | N/A | 8467 | 8482 | GAAGCATTTTATCATC | kk-d9-kekek | 120 | 2630 |
| 935689 | N/A | N/A | 11118 | 11133 | GCAGTGATGTCAGGTT | kk-d9-kekek | 31 | 2631 |
| 935690 | 5189 | 5204 | 23306 | 23321 | ACCTCAGTTTGTGAAG | kk-d9-kekek | 87 | 1971 |
| 935691 | 4174 | 4189 | 22291 | 22306 | TACTGCTTGAGGTTTT | kk-d9-kekek | 78 | 1433 |

TABLE 39-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935692 | 2917 | 2932 | 21034 | 21049 | TGTAGTATGAGAAACG | kk-d9-kekek | 88 | 1197 |
| 935693 | 4202 | 4217 | 22319 | 22334 | TCTCTATAGTGTTCCA | kk-d9-kekek | 72 | 2632 |
| 935694 | 3072 | 3087 | 21189 | 21204 | AAGCTTGATAAAGGCT | kk-d9-kekek | 119 | 2633 |
| 935695 | 3253 | 3268 | 21370 | 21385 | GACACTTTTAGAGAGG | kk-d9-kekek | 83 | 451 |
| 935696 | 4229 | 4244 | 22346 | 22361 | CAGTTGTAAATGAGTC | kk-d9-kekek | 19 | 560 |
| 935697 | 4592 | 4607 | 22709 | 22724 | GGAAGTTTACACTGGA | kkk-d9-kkke | 22 | 2044 |
| 935698 | N/A | N/A | 8465 | 8480 | AGCATTTTATCATCCG | kkk-d9-kkke | 34 | 1679 |
| 935699 | N/A | N/A | 11116 | 11131 | AGTGATGTCAGGTTTT | kkk-d9-kkke | 35 | 1232 |
| 935700 | 5187 | 5202 | 23304 | 23319 | CTCAGTTTGTGAAGCA | kkk-d9-kkke | 31 | 1817 |
| 935701 | 4172 | 4187 | 22289 | 22304 | CTGCTTGAGGTTTTCC | kkk-d9-kkke | 35 | 1279 |
| 935702 | 2915 | 2930 | 21032 | 21047 | TAGTATGAGAAACGGC | kkk-d9-kkke | 52 | 1121 |
| 935703 | 4200 | 4215 | 22317 | 22332 | TCTATAGTGTTCCAGG | kkk-d9-kkke | 48 | 1734 |
| 935704 | 3070 | 3085 | 21187 | 21202 | GCTTGATAAAGGCTGA | kkk-d9-kkke | 77 | 1505 |
| 935705 | 3251 | 3266 | 21368 | 21383 | CACTTTTAGAGAGGAG | kkk-d9-kkke | 60 | 2036 |
| 935706 | 4591 | 4606 | 22708 | 22723 | GAAGTTTACACTGGAT | kkk-d9-kkke | 55 | 1968 |
| 935707 | N/A | N/A | 8464 | 8479 | GCATTTTATCATCCGA | kkk-d9-kkke | 38 | 1605 |
| 935708 | N/A | N/A | 11115 | 11130 | GTGATGTCAGGTTTTC | kkk-d9-kkke | 29 | 2627 |
| 935709 | 5186 | 5201 | 23303 | 23318 | TCAGTTTGTGAAGCAT | kkk-d9-kkke | 42 | 649 |
| 935710 | 4171 | 4186 | 22288 | 22303 | TGCTTGAGGTTTTCCT | kkk-d9-kkke | 54 | 548 |
| 935711 | 2914 | 2929 | 21031 | 21046 | AGTATGAGAAACGGCC | kkk-d9-kkke | 93 | 1045 |
| 935712 | 4199 | 4214 | 22316 | 22331 | CTATAGTGTTCCAGGA | kkk-d9-kkke | 69 | 552 |
| 935713 | 3069 | 3084 | 21186 | 21201 | CTTGATAAAGGCTGAA | kkk-d9-kkke | 64 | 1427 |
| 935714 | 3250 | 3265 | 21367 | 21382 | ACTTTTAGAGAGGAGA | kkk-d9-kkke | 64 | 1960 |
| 935715 | 4593 | 4608 | 22710 | 22725 | CGGAAGTTTACACTGG | kkk-d9-kkke | 75 | 2119 |
| 935716 | N/A | N/A | 8466 | 8481 | AAGCATTTTATCATCC | kkk-d9-kkke | 67 | 2628 |
| 935717 | N/A | N/A | 11117 | 11132 | CAGTGATGTCAGGTTT | kkk-d9-kkke | 51 | 2629 |
| 935718 | 5188 | 5203 | 23305 | 23320 | CCTCAGTTTGTGAAGC | kkk-d9-kkke | 98 | 1894 |
| 935719 | 4173 | 4188 | 22290 | 22305 | ACTGCTTGAGGTTTTC | kkk-d9-kkke | 48 | 1356 |
| 935720 | 2916 | 2931 | 21033 | 21048 | GTAGTATGAGAAACGG | kkk-d9-kkke | 60 | 426 |
| 935721 | 4201 | 4216 | 22318 | 22333 | CTCTATAGTGTTCCAG | kkk-d9-kkke | 35 | 1811 |
| 935722 | 3071 | 3086 | 21188 | 21203 | AGCTTGATAAAGGCTG | kkk-d9-kkke | 98 | 1579 |
| 935723 | 3252 | 3267 | 21369 | 21384 | ACACTTTTAGAGAGGA | kkk-d9-kkke | 71 | 2111 |
| 935724 | 4228 | 4243 | 22345 | 22360 | AGTTGTAAATGAGTCG | kkk-d9-kkke | 13 | 2021 |
| 935725 | 4594 | 4609 | 22711 | 22726 | ACGGAAGTTTACACTG | kkk-d9-kkke | 71 | 2195 |
| 935726 | N/A | N/A | 8467 | 8482 | GAAGCATTTTATCATC | kkk-d9-kkke | 99 | 2630 |
| 935727 | N/A | N/A | 11118 | 11133 | GCAGTGATGTCAGGTT | kkk-d9-kkke | 38 | 2631 |

TABLE 39-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935728 | 5189 | 5204 | 23306 | 23321 | ACCTCAGTTTGTGAAG | kkk-d9-kkke | 90 | 1971 |
| 935729 | 4174 | 4189 | 22291 | 22306 | TACTGCTTGAGGTTTT | kkk-d9-kkke | 87 | 1433 |
| 935730 | 2917 | 2932 | 21034 | 21049 | TGTAGTATGAGAAACG | kkk-d9-kkke | 67 | 1197 |
| 935731 | 4202 | 4217 | 22319 | 22334 | TCTCTATAGTGTTCCA | kkk-d9-kkke | 44 | 2632 |
| 935732 | 3072 | 3087 | 21189 | 21204 | AAGCTTGATAAAGGCT | kkk-d9-kkke | 95 | 2633 |
| 935733 | 3253 | 3268 | 21370 | 21385 | GACACTTTTAGAGAGG | kkk-d9-kkke | 76 | 451 |
| 935734 | 4229 | 4244 | 22346 | 22361 | CAGTTGTAAATGAGTC | kkk-d9-kkke | 32 | 560 |
| 935735 | 4592 | 4607 | 22709 | 22724 | GGAAGTTTACACTGGA | kk-d10-keke | 54 | 2044 |
| 935736 | N/A | N/A | 8465 | 8480 | AGCATTTTATCATCCG | kk-d10-keke | 67 | 1679 |
| 935737 | N/A | N/A | 11116 | 11131 | AGTGATGTCAGGTTTT | kk-d10-keke | 68 | 1232 |
| 935738 | 5187 | 5202 | 23304 | 23319 | CTCAGTTTGTGAAGCA | kk-d10-keke | 70 | 1817 |
| 935739 | 4172 | 4187 | 22289 | 22304 | CTGCTTGAGGTTTTCC | kk-d10-keke | 56 | 1279 |
| 935740 | 2915 | 2930 | 21032 | 21047 | TAGTATGAGAAACGGC | kk-d10-keke | 54 | 1121 |
| 935741 | 4200 | 4215 | 22317 | 22332 | TCTATAGTGTTCCAGG | kk-d10-keke | 34 | 1734 |
| 935742 | 3070 | 3085 | 21187 | 21202 | GCTTGATAAAGGCTGA | kk-d10-keke | 69 | 1505 |

TABLE 40

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 37 | 195 |
| 881450 | 3252 | 3267 | 21369 | 21384 | ACACTTTTAGAGAGGA | kkk-d10-kkk | 53 | 2111 |
| 881659 | 4592 | 4607 | 22709 | 22724 | GGAAGTTTACACTGGA | kkk-d10-kkk | 20 | 2044 |
| 935743 | 3251 | 3266 | 21368 | 21383 | CACTTTTAGAGAGGAG | kk-d10-keke | 73 | 2036 |
| 935744 | 4591 | 4606 | 22708 | 22723 | GAAGTTTACACTGGAT | kk-d10-keke | 54 | 1968 |
| 935745 | N/A | N/A | 8464 | 8479 | GCATTTTATCATCCGA | kk-d10-keke | 61 | 1605 |
| 935746 | N/A | N/A | 11115 | 11130 | GTGATGTCAGGTTTTC | kk-d10-keke | 82 | 2627 |
| 935747 | 5186 | 5201 | 23303 | 23318 | TCAGTTTGTGAAGCAT | kk-d10-keke | 67 | 649 |
| 935748 | 4171 | 4186 | 22288 | 22303 | TGCTTGAGGTTTTCCT | kk-d10-keke | 67 | 548 |
| 935749 | 2914 | 2929 | 21031 | 21046 | AGTATGAGAAACGGCC | kk-d10-keke | 91 | 1045 |
| 935750 | 4199 | 4214 | 22316 | 22331 | CTATAGTGTTCCAGGA | kk-d10-keke | 64 | 552 |
| 935751 | 3069 | 3084 | 21186 | 21201 | CTTGATAAAGGCTGAA | kk-d10-keke | 96 | 1427 |
| 935752 | 3250 | 3265 | 21367 | 21382 | ACTTTTAGAGAGGAGA | kk-d10-keke | 77 | 1960 |
| 935753 | 4593 | 4608 | 22710 | 22725 | CGGAAGTTTACACTGG | kk-d10-keke | 67 | 2119 |
| 935754 | N/A | N/A | 8466 | 8481 | AAGCATTTTATCATCC | kk-d10-keke | 80 | 2628 |

TABLE 40-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935755 | N/A | N/A | 11117 | 11132 | CAGTGATGTCAGGTTT | kk-d10-keke | 59 | 2629 |
| 935756 | 5188 | 5203 | 23305 | 23320 | CCTCAGTTTGTGAAGC | kk-d10-keke | 84 | 1894 |
| 935757 | 4173 | 4188 | 22290 | 22305 | ACTGCTTGAGGTTTTC | kk-d10-keke | 79 | 1356 |
| 935758 | 2916 | 2931 | 21033 | 21048 | GTAGTATGAGAAACGG | kk-d10-keke | 72 | 426 |
| 935759 | 4201 | 4216 | 22318 | 22333 | CTCTATAGTGTTCCAG | kk-d10-keke | 73 | 1811 |
| 935760 | 3071 | 3086 | 21188 | 21203 | AGCTTGATAAAGGCTG | kk-d10-keke | 99 | 1579 |
| 935761 | 3252 | 3267 | 21369 | 21384 | ACACTTTTAGAGAGGA | kk-d10-keke | 86 | 2111 |
| 935762 | 4228 | 4243 | 22345 | 22360 | AGTTGTAAATGAGTCG | kk-d10-keke | 41 | 2021 |
| 935763 | 4594 | 4609 | 22711 | 22726 | ACGGAAGTTTACACTG | kk-d10-keke | 87 | 2195 |
| 935764 | N/A | N/A | 8467 | 8482 | GAAGCATTTTATCATC | kk-d10-keke | 107 | 2630 |
| 935765 | N/A | N/A | 11118 | 11133 | GCAGTGATGTCAGGTT | kk-d10-keke | 33 | 2631 |
| 935766 | 5189 | 5204 | 23306 | 23321 | ACCTCAGTTTGTGAAG | kk-d10-keke | 112 | 1971 |
| 935767 | 4174 | 4189 | 22291 | 22306 | TACTGCTTGAGGTTTT | kk-d10-keke | 89 | 1433 |
| 935768 | 2917 | 2932 | 21034 | 21049 | TGTAGTATGAGAAACG | kk-d10-keke | 90 | 1197 |
| 935769 | 4202 | 4217 | 22319 | 22334 | TCTCTATAGTGTTCCA | kk-d10-keke | 73 | 2632 |
| 935770 | 3072 | 3087 | 21189 | 21204 | AAGCTTGATAAAGGCT | kk-d10-keke | 118 | 2633 |
| 935771 | 3253 | 3268 | 21370 | 21385 | GACACTTTTAGAGAGG | kk-d10-keke | 91 | 451 |
| 935772 | 4229 | 4244 | 22346 | 22361 | CAGTTGTAAATGAGTC | kk-d10-keke | 41 | 560 |
| 935773 | 4592 | 4607 | 22709 | 22724 | GGAAGTTTACACTGGA | kk-d9-kdkdk | 76 | 2044 |
| 935774 | N/A | N/A | 8465 | 8480 | AGCATTTTATCATCCG | kk-d9-kdkdk | 89 | 1679 |
| 935775 | N/A | N/A | 11116 | 11131 | ATGATGTCAGGTTTT | kk-d9-kdkdk | 69 | 1232 |
| 935776 | 5187 | 5202 | 23304 | 23319 | CTCAGTTTGTGAAGCA | kk-d9-kdkdk | 101 | 1817 |
| 935777 | 4172 | 4187 | 22289 | 22304 | CTGCTTGAGGTTTTCC | kk-d9-kdkdk | 64 | 1279 |
| 935778 | 2915 | 2930 | 21032 | 21047 | TAGTATGAGAAACGGC | kk-d9-kdkdk | 61 | 1121 |
| 935779 | 4200 | 4215 | 22317 | 22332 | TCTATAGTGTTCCAGG | kk-d9-kdkdk | 50 | 1734 |
| 935780 | 3070 | 3085 | 21187 | 21202 | GCTTGATAAAGGCTGA | kk-d9-kdkdk | 96 | 1505 |
| 935781 | 3251 | 3266 | 21368 | 21383 | CACTTTTAGAGAGGAG | kk-d9-kdkdk | 84 | 2036 |
| 935782 | 4227 | 4242 | 22344 | 22359 | GTTGTAAATGAGTCGG | kk-d9-kdkdk | 42 | 559 |
| 935783 | 4591 | 4606 | 22708 | 22723 | GAAGTTTACACTGGAT | kk-d9-kdkdk | 77 | 1968 |
| 935784 | N/A | N/A | 8464 | 8479 | GCATTTTATCATCCGA | kk-d9-kdkdk | 84 | 1605 |
| 935785 | N/A | N/A | 11115 | 11130 | GTGATGTCAGGTTTTC | kk-d9-kdkdk | 73 | 2627 |
| 935786 | 5186 | 5201 | 23303 | 23318 | TCAGTTTGTGAAGCAT | kk-d9-kdkdk | 75 | 649 |
| 935787 | 4171 | 4186 | 22288 | 22303 | TGCTTGAGGTTTTCCT | kk-d9-kdkdk | 55 | 548 |
| 935788 | 2914 | 2929 | 21031 | 21046 | AGTATGAGAAACGGCC | kk-d9-kdkdk | 94 | 1045 |
| 935789 | 4199 | 4214 | 22316 | 22331 | CTATAGTGTTCCAGGA | kk-d9-kdkdk | 51 | 552 |
| 935790 | 3069 | 3084 | 21186 | 21201 | CTTGATAAAGGCTGAA | kk-d9-kdkdk | 99 | 1427 |

TABLE 40-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935791 | 3250 | 3265 | 21367 | 21382 | ACTTTTAGAGAGGAGA | kk-d9-kdkdk | 66 | 1960 |
| 935792 | 4226 | 4241 | 22343 | 22358 | TTGTAAATGAGTCGGT | kk-d9-kdkdk | 57 | 195 |
| 935793 | 4593 | 4608 | 22710 | 22725 | CGGAAGTTTACACTGG | kk-d9-kdkdk | 87 | 2119 |
| 935794 | N/A | N/A | 8466 | 8481 | AAGCATTTTATCATCC | kk-d9-kdkdk | 97 | 2628 |
| 935795 | N/A | N/A | 11117 | 11132 | CAGTGATGTCAGGTTT | kk-d9-kdkdk | 53 | 2629 |
| 935796 | 5188 | 5203 | 23305 | 23320 | CCTCAGTTTGTGAAGC | kk-d9-kdkdk | 92 | 1894 |
| 935797 | 4173 | 4188 | 22290 | 22305 | ACTGCTTGAGGTTTTC | kk-d9-kdkdk | 81 | 1356 |
| 935798 | 2916 | 2931 | 21033 | 21048 | GTAGTATGAGAAACGG | kk-d9-kdkdk | 68 | 426 |
| 935799 | 4201 | 4216 | 22318 | 22333 | CTCTATAGTGTTCCAG | kk-d9-kdkdk | 69 | 1811 |
| 935800 | 3071 | 3086 | 21188 | 21203 | AGCTTGATAAAGGCTG | kk-d9-kdkdk | 103 | 1579 |
| 935801 | 3252 | 3267 | 21369 | 21384 | ACACTTTTAGAGAGGA | kk-d9-kdkdk | 97 | 2111 |
| 935802 | 4228 | 4243 | 22345 | 22360 | AGTTGTAAATGAGTCG | kk-d9-kdkdk | 61 | 2021 |
| 935803 | 4594 | 4609 | 22711 | 22726 | ACGGAAGTTTACACTG | kk-d9-kdkdk | 102 | 2195 |
| 935804 | N/A | N/A | 8467 | 8482 | GAAGCATTTTATCATC | kk-d9-kdkdk | 99 | 2630 |
| 935805 | N/A | N/A | 11118 | 11133 | GCAGTGATGTCAGGTT | kk-d9-kdkdk | 47 | 2631 |
| 935806 | 5189 | 5204 | 23306 | 23321 | ACCTCAGTTTGTGAAG | kk-d9-kdkdk | 103 | 1971 |
| 935807 | 4174 | 4189 | 22291 | 22306 | TACTGCTTGAGGTTTT | kk-d9-kdkdk | 85 | 1433 |
| 935808 | 2917 | 2932 | 21034 | 21049 | TGTAGTATGAGAAACG | kk-d9-kdkdk | 106 | 1197 |
| 935809 | 4202 | 4217 | 22319 | 22334 | TCTCTATAGTGTTCCA | kk-d9-kdkdk | 62 | 2632 |
| 935810 | 3072 | 3087 | 21189 | 21204 | AAGCTTGATAAAGGCT | kk-d9-kdkdk | 102 | 2633 |
| 935811 | 3253 | 3268 | 21370 | 21385 | GACACTTTTAGAGAGG | kk-d9-kdkdk | 86 | 451 |
| 935812 | 4229 | 4244 | 22346 | 22361 | CAGTTGTAAATGAGTC | kk-d9-kdkdk | 54 | 560 |
| 935813 | 4592 | 4607 | 22709 | 22724 | GGAAGTTTACACTGGA | kkk-d8-kekek | 57 | 2044 |
| 935814 | N/A | N/A | 8465 | 8480 | AGCATTTTATCATCCG | kkk-d8-kekek | 78 | 1679 |
| 935815 | N/A | N/A | 11116 | 11131 | AGTGATGTCAGGTTTT | kkk-d8-kekek | 63 | 1232 |
| 935816 | 5187 | 5202 | 23304 | 23319 | CTCAGTTTGTGAAGCA | kkk-d8-kekek | 63 | 1817 |
| 935817 | 4172 | 4187 | 22289 | 22304 | CTGCTTGAGGTTTTCC | kkk-d8-kekek | 74 | 1279 |
| 935818 | 2915 | 2930 | 21032 | 21047 | TAGTATGAGAAACGGC | kkk-d8-kekek | 70 | 1121 |

TABLE 41

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 34 | 195 |
| 881450 | 3252 | 3267 | 21369 | 21384 | ACACTTTTAGAGAGGA | kkk-d10-kkk | 63 | 2111 |
| 881659 | 4592 | 4607 | 22709 | 22724 | GGAAGTTTACACTGGA | kkk-d10-kkk | 17 | 2044 |
| 935819 | 4200 | 4215 | 22317 | 22332 | TCTATAGTGTTCCAGG | kkk-d8-kekek | 87 | 1734 |
| 935820 | 3070 | 3085 | 21187 | 21202 | GCTTGATAAAGGCTGA | kkk-d8-kekek | 99 | 1505 |
| 935821 | 3251 | 3266 | 21368 | 21383 | CACTTTTAGAGAGGAG | kkk-d8-kekek | 93 | 2036 |
| 935822 | 4591 | 4606 | 22708 | 22723 | GAAGTTTACACTGGAT | kkk-d8-kekek | 48 | 1968 |
| 935823 | N/A | N/A | 8464 | 8479 | GCATTTTATCATCCGA | kkk-d8-kekek | 55 | 1605 |
| 935824 | N/A | N/A | 11115 | 11130 | GTGATGTCAGGTTTTC | kkk-d8-kekek | 43 | 2627 |
| 935825 | 5186 | 5201 | 23303 | 23318 | TCAGTTTGTGAAGCAT | kkk-d8-kekek | 59 | 649 |
| 935826 | 4171 | 4186 | 22288 | 22303 | TGCTTGAGGTTTTCCT | kkk-d8-kekek | 73 | 548 |
| 935827 | 2914 | 2929 | 21031 | 21046 | AGTATGAGAAACGGCC | kkk-d8-kekek | 90 | 1045 |
| 935828 | 4199 | 4214 | 22316 | 22331 | CTATAGTGTTCCAGGA | kkk-d8-kekek | 77 | 552 |
| 935829 | 3069 | 3084 | 21186 | 21201 | CTTGATAAAGGCTGAA | kkk-d8-kekek | 88 | 1427 |
| 935830 | 3250 | 3265 | 21367 | 21382 | ACTTTTAGAGAGGAGA | kkk-d8-kekek | 79 | 1960 |
| 935831 | 4593 | 4608 | 22710 | 22725 | CGGAAGTTTACACTGG | kkk-d8-kekek | 82 | 2119 |
| 935832 | N/A | N/A | 8466 | 8481 | AAGCATTTTATCATCC | kkk-d8-kekek | 90 | 2628 |
| 935833 | N/A | N/A | 11117 | 11132 | CAGTGATGTCAGGTTT | kkk-d8-kekek | 44 | 2629 |
| 935834 | 5188 | 5203 | 23305 | 23320 | CCTCAGTTTGTGAAGC | kkk-d8-kekek | 97 | 1894 |
| 935835 | 4173 | 4188 | 22290 | 22305 | ACTGCTTGAGGTTTTC | kkk-d8-kekek | 68 | 1356 |
| 935836 | 2916 | 2931 | 21033 | 21048 | GTAGTATGAGAAACGG | kkk-d8-kekek | 57 | 426 |
| 935837 | 4201 | 4216 | 22318 | 22333 | CTCTATAGTGTTCCAG | kkk-d8-kekek | 85 | 1811 |
| 935838 | 3071 | 3086 | 21188 | 21203 | AGCTTGATAAAGGCTG | kkk-d8-kekek | 108 | 1579 |
| 935839 | 3252 | 3267 | 21369 | 21384 | ACACTTTTAGAGAGGA | kkk-d8-kekek | 85 | 2111 |
| 935840 | 4228 | 4243 | 22345 | 22360 | AGTTGTAAATGAGTCG | kkk-d8-kekek | 39 | 2021 |

TABLE 41-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935841 | 4594 | 4609 | 22711 | 22726 | ACGGAAGTTTACACTG | kkk-d8-kekek | 86 | 2195 |
| 935842 | N/A | N/A | 8467 | 8482 | GAAGCATTTTATCATC | kkk-d8-kekek | 105 | 2630 |
| 935843 | N/A | N/A | 11118 | 11133 | GCAGTGATGTCAGGTT | kkk-d8-kekek | 64 | 2631 |
| 935844 | 5189 | 5204 | 23306 | 23321 | ACCTCAGTTTGTGAAG | kkk-d8-kekek | 103 | 1971 |
| 935845 | 4174 | 4189 | 22291 | 22306 | TACTGCTTGAGGTTTT | kkk-d8-kekek | 108 | 1433 |
| 935846 | 2917 | 2932 | 21034 | 21049 | TGTAGTATGAGAAACG | kkk-d8-kekek | 77 | 1197 |
| 935847 | 4202 | 4217 | 22319 | 22334 | TCTCTATAGTGTTCCA | kkk-d8-kekek | 92 | 2632 |
| 935848 | 3072 | 3087 | 21189 | 21204 | AAGCTTGATAAAGGCT | kkk-d8-kekek | 104 | 2633 |
| 935849 | 3253 | 3268 | 21370 | 21385 | GACACTTTTAGAGAGG | kkk-d8-kekek | 108 | 451 |
| 935850 | 4229 | 4244 | 22346 | 22361 | CAGTTGTAAATGAGTC | kkk-d8-kekek | 24 | 560 |
| 935851 | 4592 | 4607 | 22709 | 22724 | GGAAGTTTACACTGGA | kkk-d9-keke | 22 | 2044 |
| 935852 | N/A | N/A | 8465 | 8480 | AGCATTTTATCATCCG | kkk-d9-keke | 58 | 1679 |
| 935853 | N/A | N/A | 11116 | 11131 | AGTGATGTCAGGTTTT | kkk-d9-keke | 41 | 1232 |
| 935854 | 5187 | 5202 | 23304 | 23319 | CTCAGTTTGTGAAGCA | kkk-d9-keke | 36 | 1817 |
| 935855 | 4172 | 4187 | 22289 | 22304 | CTGCTTGAGGTTTTCC | kkk-d9-keke | 50 | 1279 |
| 935856 | 2915 | 2930 | 21032 | 21047 | TAGTATGAGAAACGGC | kkk-d9-keke | 38 | 1121 |
| 935857 | 4200 | 4215 | 22317 | 22332 | TCTATAGTGTTCCAGG | kkk-d9-keke | 32 | 1734 |
| 935858 | 3070 | 3085 | 21187 | 21202 | GCTTGATAAAGGCTGA | kkk-d9-keke | 76 | 1505 |
| 935859 | 3251 | 3266 | 21368 | 21383 | CACTTTTAGAGAGGAG | kkk-d9-keke | 43 | 2036 |
| 935860 | 4591 | 4606 | 22708 | 22723 | GAAGTTTACACTGGAT | kkk-d9-keke | 51 | 1968 |
| 935861 | N/A | N/A | 8464 | 8479 | GCATTTTATCATCCGA | kkk-d9-keke | 68 | 1605 |
| 935862 | N/A | N/A | 11115 | 11130 | GTGATGTCAGGTTTTC | kkk-d9-keke | 66 | 2627 |
| 935863 | 5186 | 5201 | 23303 | 23318 | TCAGTTTGTGAAGCAT | kkk-d9-keke | 47 | 649 |
| 935864 | 4171 | 4186 | 22288 | 22303 | TGCTTGAGGTTTTCCT | kkk-d9-keke | 65 | 548 |
| 935865 | 2914 | 2929 | 21031 | 21046 | AGTATGAGAAACGGCC | kkk-d9-keke | 84 | 1045 |
| 935866 | 4199 | 4214 | 22316 | 22331 | CTATAGTGTTCCAGGA | kkk-d9-keke | 78 | 552 |
| 935867 | 3069 | 3084 | 21186 | 21201 | CTTGATAAAGGCTGAA | kkk-d9-keke | 76 | 1427 |
| 935868 | 3250 | 3265 | 21367 | 21382 | ACTTTTAGAGAGGAGA | kkk-d9-keke | 59 | 1960 |
| 935869 | 4593 | 4608 | 22710 | 22725 | CGGAAGTTTACACTGG | kkk-d9-keke | 58 | 2119 |
| 935870 | N/A | N/A | 8466 | 8481 | AAGCATTTTATCATCC | kkk-d9-keke | 79 | 2628 |
| 935871 | N/A | N/A | 11117 | 11132 | CAGTGATGTCAGGTTT | kkk-d9-keke | 66 | 2629 |

TABLE 41-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935872 | 5188 | 5203 | 23305 | 23320 | CCTCAGTTTGTGAAGC | kkk-d9-keke | 92 | 1894 |
| 935873 | 4173 | 4188 | 22290 | 22305 | ACTGCTTGAGGTTTTC | kkk-d9-keke | 62 | 1356 |
| 935874 | 2916 | 2931 | 21033 | 21048 | GTAGTATGAGAAACGG | kkk-d9-keke | 85 | 426 |
| 935875 | 4201 | 4216 | 22318 | 22333 | CTCTATAGTGTTCCAG | kkk-d9-keke | 51 | 1811 |
| 935876 | 3071 | 3086 | 21188 | 21203 | AGCTTGATAAAGGCTG | kkk-d9-keke | 108 | 1579 |
| 935877 | 3252 | 3267 | 21369 | 21384 | ACACTTTTAGAGAGGA | kkk-d9-keke | 63 | 2111 |
| 935878 | 4228 | 4243 | 22345 | 22360 | AGTTGTAAATGAGTCG | kkk-d9-keke | 23 | 2021 |
| 935879 | 4594 | 4609 | 22711 | 22726 | ACGGAAGTTTACACTG | kkk-d9-keke | 87 | 2195 |
| 935880 | N/A | N/A | 8467 | 8482 | GAAGCATTTATCATC | kkk-d9-keke | 92 | 2630 |
| 935881 | N/A | N/A | 11118 | 11133 | GCAGTGATGTCAGGTT | kkk-d9-keke | 44 | 2631 |
| 935882 | 5189 | 5204 | 23306 | 23321 | ACCTCAGTTTGTGAAG | kkk-d9-keke | 92 | 1971 |
| 935883 | 4174 | 4189 | 22291 | 22306 | TACTGCTTGAGGTTTT | kkk-d9-keke | 93 | 1433 |
| 935884 | 2917 | 2932 | 21034 | 21049 | TGTAGTATGAGAAACG | kkk-d9-keke | 71 | 1197 |
| 935885 | 4202 | 4217 | 22319 | 22334 | TCTCTATAGTGTTCCA | kkk-d9-keke | 67 | 2632 |
| 935886 | 3072 | 3087 | 21189 | 21204 | AAGCTTGATAAAGGCT | kkk-d9-keke | 118 | 2633 |
| 935887 | 3253 | 3268 | 21370 | 21385 | GACACTTTTAGAGAGG | kkk-d9-keke | 76 | 451 |
| 935888 | 4229 | 4244 | 22346 | 22361 | CAGTTGTAAATGAGTC | kkk-d9-keke | 42 | 560 |
| 935889 | 4592 | 4607 | 22709 | 22724 | GGAAGTTTACACTGGA | kk-d9-eeekk | 53 | 2044 |
| 935890 | N/A | N/A | 8465 | 8480 | AGCATTTATCATCCG | kk-d9-eeekk | 72 | 1679 |
| 935891 | N/A | N/A | 11116 | 11131 | AGTGATGTCAGGTTTT | kk-d9-eeekk | 75 | 1232 |
| 935892 | 5187 | 5202 | 23304 | 23319 | CTCAGTTTGTGAAGCA | kk-d9-eeekk | 82 | 1817 |
| 935893 | 4172 | 4187 | 22289 | 22304 | CTGCTTGAGGTTTTCC | kk-d9-eeekk | 69 | 1279 |
| 935894 | 2915 | 2930 | 21032 | 21047 | TAGTATGAGAAACGGC | kk-d9-eeekk | 63 | 1121 |

TABLE 42

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 31 | 195 |
| 881450 | 3252 | 3267 | 21369 | 21384 | ACACTTTTAGAGAGGA | kkk-d10-kkk | 54 | 2111 |
| 881659 | 4592 | 4607 | 22709 | 22724 | GGAAGTTTACACTGGA | kkk-d10-kkk | 15 | 2044 |
| 935971 | N/A | N/A | 11116 | 11131 | AGTGATGTCAGGTTTT | k-d9-kekeke | 60 | 1232 |
| 935972 | 5187 | 5202 | 23304 | 23319 | CTCAGTTTGTGAAGCA | k-d9-kekeke | 81 | 1817 |
| 935973 | 4172 | 4187 | 22289 | 22304 | CTGCTTGAGGTTTTCC | k-d9-kekeke | 80 | 1279 |
| 935974 | 2915 | 2930 | 21032 | 21047 | TAGTATGAGAAACGGC | k-d9-kekeke | 68 | 1121 |
| 935975 | 4200 | 4215 | 22317 | 22332 | TCTATAGTGTTCCAGG | k-d9-kekeke | 88 | 1734 |

TABLE 42-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 935976 | 3070 | 3085 | 21187 | 21202 | GCTTGATAAAGGCTGA | k-d9-kekeke | 101 | 1505 |
| 935977 | 3251 | 3266 | 21368 | 21383 | CACTTTTAGAGAGGAG | k-d9-kekeke | 91 | 2036 |
| 935978 | 4591 | 4606 | 22708 | 22723 | GAAGTTTACACTGGAT | k-d9-kekeke | 89 | 1968 |
| 935979 | N/A | N/A | 8464 | 8479 | GCATTTTATCATCCGA | k-d9-kekeke | 77 | 1605 |
| 935980 | N/A | N/A | 11115 | 11130 | GTGATGTCAGGTTTTC | k-d9-kekeke | 70 | 2627 |
| 935981 | 5186 | 5201 | 23303 | 23318 | TCAGTTTGTGAAGCAT | k-d9-kekeke | 91 | 649 |
| 935982 | 4171 | 4186 | 22288 | 22303 | TGCTTGAGGTTTTCCT | k-d9-kekeke | 91 | 548 |
| 935983 | 2914 | 2929 | 21031 | 21046 | AGTATGAGAAACGGCC | k-d9-kekeke | 96 | 1045 |
| 935984 | 4199 | 4214 | 22316 | 22331 | CTATAGTGTTCCAGGA | k-d9-kekeke | 88 | 552 |
| 935985 | 3069 | 3084 | 21186 | 21201 | CTTGATAAAGGCTGAA | k-d9-kekeke | 95 | 1427 |
| 935986 | 3250 | 3265 | 21367 | 21382 | ACTTTTAGAGAGGAGA | k-d9-kekeke | 83 | 1960 |
| 935987 | 4593 | 4608 | 22710 | 22725 | CGGAAGTTTACACTGG | k-d9-kekeke | 83 | 2119 |
| 935988 | N/A | N/A | 8466 | 8481 | AAGCATTTTATCATCC | k-d9-kekeke | 94 | 2628 |
| 935989 | N/A | N/A | 11117 | 11132 | CAGTGATGTCAGGTTT | k-d9-kekeke | 52 | 2629 |
| 935990 | 5188 | 5203 | 23305 | 23320 | CCTCAGTTTGTGAAGC | k-d9-kekeke | 89 | 1894 |
| 935991 | 4173 | 4188 | 22290 | 22305 | ACTGCTTGAGGTTTTC | k-d9-kekeke | 79 | 1356 |
| 935992 | 2916 | 2931 | 21033 | 21048 | GTAGTATGAGAAACGG | k-d9-kekeke | 72 | 426 |
| 935993 | 4201 | 4216 | 22318 | 22333 | CTCTATAGTGTTCCAG | k-d9-kekeke | 89 | 1811 |
| 935994 | 3071 | 3086 | 21188 | 21203 | AGCTTGATAAAGGCTG | k-d9-kekeke | 98 | 1579 |
| 935995 | 3252 | 3267 | 21369 | 21384 | ACACTTTTAGAGAGGA | k-d9-kekeke | 94 | 2111 |
| 935996 | 4228 | 4243 | 22345 | 22360 | AGTTGTAAATGAGTCG | k-d9-kekeke | 53 | 2021 |
| 935997 | 4594 | 4609 | 22711 | 22726 | ACGGAAGTTTACACTG | k-d9-kekeke | 98 | 2195 |
| 935998 | N/A | N/A | 8467 | 8482 | GAAGCATTTTATCATC | k-d9-kekeke | 96 | 2630 |
| 935999 | N/A | N/A | 11118 | 11133 | GCAGTGATGTCAGGTT | k-d9-kekeke | 67 | 2631 |
| 936000 | 5189 | 5204 | 23306 | 23321 | ACCTCAGTTTGTGAAG | k-d9-kekeke | 84 | 1971 |
| 936001 | 4174 | 4189 | 22291 | 22306 | TACTGCTTGAGGTTTT | k-d9-kekeke | 86 | 1433 |
| 936002 | 2917 | 2932 | 21034 | 21049 | TGTAGTATGAGAAACG | k-d9-kekeke | 86 | 1197 |
| 936003 | 4202 | 4217 | 22319 | 22334 | TCTCTATAGTGTTCCA | k-d9-kekeke | 82 | 2632 |
| 936004 | 3072 | 3087 | 21189 | 21204 | AAGCTTGATAAAGGCT | k-d9-kekeke | 98 | 2633 |
| 936005 | 3253 | 3268 | 21370 | 21385 | GACACTTTTAGAGAGG | k-d9-kekeke | 91 | 451 |
| 936006 | 4229 | 4244 | 22346 | 22361 | CAGTTGTAAATGAGTC | k-d9-kekeke | 38 | 560 |
| 936007 | 4592 | 4607 | 22709 | 22724 | GGAAGTTTACACTGGA | ekk-d9-kkce | 45 | 2044 |
| 936008 | N/A | N/A | 8465 | 8480 | AGCATTTTATCATCCG | ekk-d9-kkce | 57 | 1679 |
| 936009 | N/A | N/A | 11116 | 11131 | AGTGATGTCAGGTTTT | ekk-d9-kkee | 61 | 1232 |
| 936010 | 5187 | 5202 | 23304 | 23319 | CTCAGTTTGTGAAGCA | ekk-d9-kkee | 55 | 1817 |
| 936011 | 4172 | 4187 | 22289 | 22304 | CTGCTTGAGGTTTTCC | ekk-d9-kkee | 48 | 1279 |

TABLE 42-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 936012 | 2915 | 2930 | 21032 | 21047 | TAGTATGAGAAACGGC | ekk-d9-kkee | 62 | 1121 |
| 936013 | 4200 | 4215 | 22317 | 22332 | TCTATAGTGTTCCAGG | ekk-d9-kkee | 42 | 1734 |
| 936014 | 3070 | 3085 | 21187 | 21202 | GCTTGATAAAGGCTGA | ekk-d9-kkee | 65 | 1505 |
| 936015 | 3251 | 3266 | 21368 | 21383 | CACTTTTAGAGAGGAG | ekk-d9-kkee | 59 | 2036 |
| 936016 | 4227 | 4242 | 22344 | 22359 | GTTGTAAATGAGTCGG | ekk-d9-kkee | 31 | 559 |
| 936017 | 4591 | 4606 | 22708 | 22723 | GAAGTTTACACTGGAT | ekk-d9-kkee | 52 | 1968 |
| 936018 | N/A | N/A | 8464 | 8479 | GCATTTTATCATCCGA | ekk-d9-kkee | 39 | 1605 |
| 936019 | N/A | N/A | 11115 | 11130 | GTGATGTCAGGTTTTC | ekk-d9-kkee | 52 | 2627 |
| 936020 | 5186 | 5201 | 23303 | 23318 | TCAGTTTGTGAAGCAT | ekk-d9-kkee | 53 | 649 |
| 936021 | 4171 | 4186 | 22288 | 22303 | TGCTTGAGGTTTTCCT | ekk-d9-kkee | 65 | 548 |
| 936022 | 2914 | 2929 | 21031 | 21046 | AGTATGAGAAACGGCC | ekk-d9-kkee | 88 | 1045 |
| 936023 | 4199 | 4214 | 22316 | 22331 | CTATAGTGTTCCAGGA | ekk-d9-kkee | 92 | 552 |
| 936024 | 3069 | 3084 | 21186 | 21201 | CTTGATAAAGGCTGAA | ekk-d9-kkee | 83 | 1427 |
| 936025 | 3250 | 3265 | 21367 | 21382 | ACTTTTAGAGAGGAGA | ekk-d9-kkee | 72 | 1960 |
| 936026 | 4226 | 4241 | 22343 | 22358 | TTGTAAATGAGTCGGT | ekk-d9-kkee | 49 | 195 |
| 936027 | 4593 | 4608 | 22710 | 22725 | CGGAAGTTTACACTGG | ekk-d9-kkee | 76 | 2119 |
| 936028 | N/A | N/A | 8466 | 8481 | AAGCATTTTATCATCC | ekk-d9-kkee | 86 | 2628 |
| 936029 | N/A | N/A | 11117 | 11132 | CAGTGATGTCAGGTTT | ekk-d9-kkee | 80 | 2629 |
| 936030 | 5188 | 5203 | 23305 | 23320 | CCTCAGTTTGTGAAGC | ekk-d9-kkee | 89 | 1894 |
| 936031 | 4173 | 4188 | 22290 | 22305 | ACTGCTTGAGGTTTTC | ekk-d9-kkee | 54 | 1356 |
| 936032 | 2916 | 2931 | 21033 | 21048 | GTAGTATGAGAAACGG | ekk-d9-kkee | 71 | 426 |
| 936033 | 4201 | 4216 | 22318 | 22333 | CTCTATAGTGTTCCAG | ekk-d9-kkee | 41 | 1811 |
| 936034 | 3071 | 3086 | 21188 | 21203 | AGCTTGATAAAGGCTG | ekk-d9-kkee | 99 | 1579 |
| 936035 | 3252 | 3267 | 21369 | 21384 | ACACTTTTAGAGAGGA | ekk-d9-kkee | 71 | 2111 |
| 936036 | 4228 | 4243 | 22345 | 22360 | AGTTGTAAATGAGTCG | ekk-d9-kkee | 51 | 2021 |
| 936037 | 4594 | 4609 | 22711 | 22726 | ACGGAAGTTTACACTG | ekk-d9-kkee | 83 | 2195 |
| 936038 | N/A | N/A | 8467 | 8482 | GAAGCATTTTATCATC | ekk-d9-kkee | 99 | 2630 |
| 936039 | N/A | N/A | 11118 | 11133 | GCAGTGATGTCAGGTT | ekk-d9-kkee | 44 | 2631 |
| 936040 | 5189 | 5204 | 23306 | 23321 | ACCTCAGTTTGTGAAG | ekk-d9-kkee | 98 | 1971 |
| 936041 | 4174 | 4189 | 22291 | 22306 | TACTGCTTGAGGTTTT | ekk-d9-kkee | 94 | 1433 |
| 936042 | 2917 | 2932 | 21034 | 21049 | TGTAGTATGAGAAACG | ekk-d9-kkee | 94 | 1197 |
| 936043 | 4202 | 4217 | 22319 | 22334 | TCTCTATAGTGTTCCA | ekk-d9-kkee | 61 | 2632 |
| 936044 | 3072 | 3087 | 21189 | 21204 | AAGCTTGATAAAGGCT | ekk-d9-kkee | 101 | 2633 |
| 936045 | 3253 | 3268 | 21370 | 21385 | GACACTTTTAGAGAGG | ekk-d9-kkee | 76 | 451 |
| 936046 | 4229 | 4244 | 22346 | 22361 | CAGTTGTAAATGAGTC | ekk-d9-kkee | 45 | 560 |

Example 9: Effect of 3-10-3 cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured MM.1R cells at a density of 5,000 cells per well were transfected by free uptake with 1,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set hIRF4_LTS34726 (described hereinabove in Example 7) was used to measure mRNA levels. IRF4 mRNA levels were adjusted according to total RNA content, as measured by RIBOGREEN®. Results are presented in the table below as percent control of the amount of IRF4 mRNA, relative to untreated control (UTC) cells.

The modified oligonucleotides in Tables 43 through 52 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 43 through 52 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 43

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 37 | 195 |
| 969844 | N/A | N/A | 3801 | 3816 | CCTTACCTCGCCCTGG | 131 | 2657 |
| 969854 | N/A | N/A | 4265 | 4280 | CGCCAGCGGGTGAGCA | 81 | 2658 |
| 969864 | N/A | N/A | 4371 | 4386 | GGCGACGACAGCTGCG | 115 | 2659 |
| 969874 | N/A | N/A | 4518 | 4533 | AGCTAGCGCGCACTAA | 108 | 2660 |
| 969884 | N/A | N/A | 4836 | 4851 | TCCTGTAACGCACCCG | 113 | 2661 |
| 969894 | N/A | N/A | 5487 | 5502 | CCTGATGCCTCCGCCG | 94 | 2662 |
| 969904 | N/A | N/A | 5667 | 5682 | CGAGAACGCACGGACG | 111 | 2663 |
| 969914 | N/A | N/A | 5761 | 5776 | GCACAGGCGCGGACGC | 106 | 2664 |
| 969924 | N/A | N/A | 6002 | 6017 | GTGCACTCGCGCAAAG | 105 | 2665 |
| 969934 | N/A | N/A | 6266 | 6281 | TGCGGAGGTTCCTTGA | 88 | 2666 |
| 969944 | N/A | N/A | 6317 | 6332 | CTGCCAAGTTGAAGAC | 67 | 2667 |
| 969954 | N/A | N/A | 6407 | 6422 | GTCCTTCAGATTTACA | 117 | 2668 |
| 969964 | N/A | N/A | 6771 | 6786 | ATACATGTCTGGTTTA | 96 | 2669 |
| 969974 | 511 | 526 | 6990 | 7005 | TTTTGGCTCCCTCAGG | 103 | 2670 |
| 969984 | N/A | N/A | 7169 | 7184 | TTTCAACTTGTGACCC | 99 | 2671 |
| 969994 | N/A | N/A | 7222 | 7237 | ATACATTGAGGCATAC | 98 | 2672 |
| 970004 | N/A | N/A | 7577 | 7592 | GACATAAAGGACCCCG | 92 | 2673 |
| 970014 | N/A | N/A | 7639 | 7654 | GGTCTGAGTTGTACAG | 80 | 2674 |
| 970024 | N/A | N/A | 8104 | 8119 | CACCAATGGCAGCACC | 84 | 2675 |
| 970034 | N/A | N/A | 8221 | 8236 | CATGATAAGGCACTAC | 106 | 2676 |
| 970044 | N/A | N/A | 8384 | 8399 | TGGAGATACTTGTACT | 58 | 2677 |
| 970054 | N/A | N/A | 8489 | 8504 | ATCCCTTATTAGACTG | 107 | 2678 |

TABLE 43-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970064 | 645 | 660 | 9135 | 9150 | CCAGCTTCGGTCGAGG | 105 | 2679 |
| 970074 | 701 | 716 | 9191 | 9206 | GTCATGGGACATTGGT | 74 | 2680 |
| 970084 | N/A | N/A | 9431 | 9446 | CTGAGAGTAAACTTGG | 101 | 2681 |
| 970094 | N/A | N/A | 9582 | 9597 | GCTCAATAATCTCCCA | 100 | 2682 |
| 970104 | N/A | N/A | 9679 | 9694 | GTGTTTGCCATGGTAT | 43 | 2683 |
| 970114 | N/A | N/A | 9842 | 9857 | CGCATTGCTAGATTCT | 63 | 2684 |
| 970124 | N/A | N/A | 9987 | 10002 | GGATAACCTGAACATG | 91 | 2685 |
| 970134 | N/A | N/A | 10120 | 10135 | CCATATTGGAAACCAG | 90 | 2686 |
| 970144 | N/A | N/A | 10178 | 10193 | CAGTAAACGCAAGTCT | 114 | 2687 |
| 970154 | N/A | N/A | 10262 | 10277 | AGACAGGTCTCTACCT | 112 | 2688 |
| 970164 | N/A | N/A | 10449 | 10464 | TGCCAAAGAGCCCAAT | 119 | 2689 |
| 970174 | N/A | N/A | 10675 | 10690 | AACTAGCAGGGCACGC | 98 | 2690 |
| 970184 | 811 | 826 | 10876 | 10891 | GGACTCCGGGAGCCTG | 108 | 2691 |
| 970194 | N/A | N/A | 11103 | 11118 | TTTCTAATGGTGCTCC | 96 | 2692 |
| 970203 | N/A | N/A | 11365 | 11380 | AACTAATGTCCCCAGG | 112 | 2693 |
| 970213 | N/A | N/A | 11452 | 11467 | TTGTTTGCAAGCTATA | 64 | 2694 |
| 970223 | N/A | N/A | 11540 | 11555 | TTCTTTATAGTAGGTA | 85 | 2695 |
| 970233 | N/A | N/A | 11664 | 11679 | GAATTCCAAACCTTAA | 96 | 2696 |
| 970243 | N/A | N/A | 11946 | 11961 | ACACAAGTCTTAGGTG | 253 | 2697 |
| 970253 | N/A | N/A | 12007 | 12022 | TCAGAAATCACGAGGT | 57 | 2698 |
| 970263 | N/A | N/A | 12213 | 12228 | TAATCTGTATCATGCA | 78 | 2699 |
| 970273 | N/A | N/A | 12293 | 12308 | AGCTGCCACTGGTAAC | 100 | 2700 |
| 970283 | N/A | N/A | 12676 | 12691 | GGCCTTAATGGTGATT | 116 | 2701 |
| 970293 | N/A | N/A | 12929 | 12944 | GAAATGAACCCTAAGT | 105 | 2702 |
| 970303 | N/A | N/A | 13129 | 13144 | ACCGACTCTTTTTTTA | 102 | 2703 |
| 970313 | N/A | N/A | 13400 | 13415 | CAGAGCTCCGGAGTCA | 106 | 2704 |
| 970323 | N/A | N/A | 14015 | 14030 | GCGACTGCTGAAAACC | 104 | 2705 |
| 970333 | N/A | N/A | 14206 | 14221 | AGTACAGTCCACTCCA | 93 | 2706 |
| 970343 | N/A | N/A | 14248 | 14263 | CCAACTTATAGCACTC | 86 | 2707 |
| 970353 | N/A | N/A | 14673 | 14688 | ACAAAAACTTGGGTCA | 113 | 2708 |
| 970363 | N/A | N/A | 15188 | 15203 | GATGGGACCGCCCTGG | 113 | 2709 |
| 970373 | N/A | N/A | 15597 | 15612 | CTAGTCGCGCAAGTCT | 104 | 2710 |
| 970383 | N/A | N/A | 15852 | 15867 | CAGAATGGCGAGTTGG | 69 | 2711 |
| 970393 | N/A | N/A | 15918 | 15933 | CTTAGTCAGAATCTGT | 99 | 2712 |
| 970403 | N/A | N/A | 16174 | 16189 | TAAAATGTCACGCCCG | 100 | 2713 |
| 970413 | N/A | N/A | 16468 | 16483 | CACCAGCCATCGGCAG | 119 | 2714 |
| 970423 | N/A | N/A | 16699 | 16714 | AGTGAAGTCGGGAGAT | 92 | 2715 |

TABLE 43-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970433 | N/A | N/A | 16869 | 16884 | GGCTCTTGATGTGAAC | 112 | 2716 |
| 970443 | N/A | N/A | 16961 | 16976 | ATCACCGAACACACCA | 112 | 2717 |

TABLE 44

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 26 | 195 |
| 935583 | N/A | N/A | 11119 | 11134 | AGCAGTGATGTCAGGT | 16 | 2718 |
| 969845 | N/A | N/A | 4005 | 4020 | GCCAAGGAGGCGGGCC | 102 | 2719 |
| 969855 | N/A | N/A | 4294 | 4309 | ACCCAAATGTGGAGCT | 97 | 2720 |
| 969865 | N/A | N/A | 4377 | 4392 | GGAGAGGGCGACGACA | 101 | 2721 |
| 969875 | N/A | N/A | 4541 | 4556 | GAATAGGACCCCTATC | 103 | 2722 |
| 969885 | N/A | N/A | 4876 | 4891 | TCCGAGCTCGGCCCCC | 110 | 2723 |
| 969895 | N/A | N/A | 5506 | 5521 | TGCGGCTCCGGCGACG | 120 | 2724 |
| 969905 | N/A | N/A | 5670 | 5685 | AAACGAGAACGCACGG | 91 | 2725 |
| 969915 | N/A | N/A | 5766 | 5781 | CGCCGGCACAGGCGCG | 86 | 2726 |
| 969925 | N/A | N/A | 6006 | 6021 | GTGTGTGCACTCGCGC | 81 | 2727 |
| 969935 | N/A | N/A | 6269 | 6284 | AGATGCGGAGGTTCCT | 68 | 2728 |
| 969945 | N/A | N/A | 6324 | 6339 | CCTATCACTGCCAAGT | 103 | 2729 |
| 969955 | N/A | N/A | 6412 | 6427 | CATAGGTCCTTCAGAT | 105 | 2730 |
| 969965 | 414 | 429 | 6893 | 6908 | CAAAGCGCACCGCAGG | 104 | 2731 |
| 969975 | N/A | N/A | 6999 | 7014 | CCCTACCTTTTTTGGC | 107 | 2732 |
| 969985 | N/A | N/A | 7186 | 7201 | GCTGAACCCCACAGGA | 100 | 2733 |
| 969995 | N/A | N/A | 7223 | 7238 | TATACATTGAGGCATA | 93 | 2734 |
| 970005 | N/A | N/A | 7579 | 7594 | GTGACATAAAGGACCC | 90 | 2735 |
| 970015 | N/A | N/A | 7641 | 7656 | AAGGTCTGAGTTGTAC | 80 | 2736 |
| 970025 | N/A | N/A | 8130 | 8145 | CCCGACCCTCCCCAAC | 135 | 2737 |
| 970035 | N/A | N/A | 8223 | 8238 | CACATGATAAGGCACT | 79 | 2738 |
| 970045 | N/A | N/A | 8387 | 8402 | CAATGGAGATACTTGT | 116 | 2739 |
| 970055 | N/A | N/A | 8493 | 8508 | GGGAATCCCTTATTAG | 100 | 2740 |
| 970065 | 647 | 662 | 9137 | 9152 | CTCCAGCTTCGGTCGA | 91 | 2741 |
| 970075 | N/A | N/A | 9280 | 9295 | AGCAATTAGCTCTTCT | 89 | 2742 |
| 970085 | N/A | N/A | 9435 | 9450 | GATCCTGAGAGTAAAC | 94 | 2743 |
| 970095 | N/A | N/A | 9583 | 9598 | AGCTCAATAATCTCCC | 94 | 2744 |

TABLE 44-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970105 | N/A | N/A | 9740 | 9755 | CCACAATCAGCAAGTC | 100 | 2745 |
| 970115 | N/A | N/A | 9844 | 9859 | ACCGCATTGCTAGATT | 73 | 2746 |
| 970125 | N/A | N/A | 9995 | 10010 | GCAGCCAAGGATAACC | 94 | 2747 |
| 970135 | N/A | N/A | 10127 | 10142 | TCCACTACCATATTGG | 129 | 2748 |
| 970145 | N/A | N/A | 10180 | 10195 | AGCAGTAAACGCAAGT | 73 | 2749 |
| 970155 | N/A | N/A | 10268 | 10283 | GCTTCAAGACAGGTCT | 71 | 2750 |
| 970165 | N/A | N/A | 10477 | 10492 | GCTGAGAGTTCAGGTC | 93 | 2751 |
| 970175 | N/A | N/A | 10678 | 10693 | AGCAACTAGCAGGGCA | 102 | 2752 |
| 970185 | N/A | N/A | 11001 | 11016 | TCGAATCTGCCCAAAG | 77 | 2753 |
| 970204 | N/A | N/A | 11369 | 11384 | CCAGAACTAATGTCCC | 94 | 2754 |
| 970214 | N/A | N/A | 11455 | 11470 | TATTTGTTTGCAAGCT | 70 | 2755 |
| 970224 | N/A | N/A | 11549 | 11564 | AGAGGTGCCTTCTTTA | 82 | 2756 |
| 970234 | N/A | N/A | 11749 | 11764 | CCACAACTCTCGCCTC | 109 | 2757 |
| 970244 | N/A | N/A | 11948 | 11963 | CCACACAAGTCTTAGG | 85 | 2758 |
| 970254 | N/A | N/A | 12048 | 12063 | CGAGGTGATTCTCGGG | 85 | 2759 |
| 970264 | N/A | N/A | 12222 | 12237 | GCTGATAATTAATCTG | 109 | 2760 |
| 970274 | N/A | N/A | 12373 | 12388 | CGCCCATGAGTTGAAA | 87 | 2761 |
| 970284 | N/A | N/A | 12692 | 12707 | AAAGGGTAAGCACTGA | 81 | 2762 |
| 970294 | N/A | N/A | 12991 | 13006 | ATTTAAGTCATGTGTC | 83 | 2763 |
| 970304 | N/A | N/A | 13132 | 13147 | GCCACCGACTCTTTTT | 105 | 2764 |
| 970314 | N/A | N/A | 13416 | 13431 | CGGCAGTCTGCAAACA | 76 | 2765 |
| 970324 | N/A | N/A | 14016 | 14031 | GGCGACTGCTGAAAAC | 110 | 2766 |
| 970334 | N/A | N/A | 14207 | 14222 | CAGTACAGTCCACTCC | 95 | 2767 |
| 970344 | N/A | N/A | 14249 | 14264 | GCCAACTTATAGCACT | 62 | 2768 |
| 970354 | N/A | N/A | 14686 | 14701 | TCTGGATGAGCTTACA | 86 | 2769 |
| 970364 | N/A | N/A | 15375 | 15390 | ATCCACTGGCACCAAG | 95 | 2770 |
| 970374 | N/A | N/A | 15599 | 15614 | TTCTAGTCGCGCAAGT | 107 | 2771 |
| 970384 | N/A | N/A | 15866 | 15881 | CTACACAGGCTAATCA | 96 | 2772 |
| 970394 | N/A | N/A | 15920 | 15935 | GACTTAGTCAGAATCT | 90 | 2773 |
| 970404 | N/A | N/A | 16176 | 16191 | AATAAAATGTCACGCC | 80 | 2774 |
| 970414 | N/A | N/A | 16610 | 16625 | CAGAATGTTTCGACAT | 86 | 2775 |
| 970424 | N/A | N/A | 16703 | 16718 | CCACAGTGAAGTCGGG | 94 | 2776 |
| 970434 | N/A | N/A | 16885 | 16900 | TTACTCCGCTGAGTGG | 104 | 2777 |
| 970444 | N/A | N/A | 16964 | 16979 | CTCATCACCGAACACA | 92 | 2778 |

TABLE 45

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 33 | 195 |
| 969846 | N/A | N/A | 4037 | 4052 | GCGCGGAGGGCAGGCG | 132 | 2779 |
| 969856 | N/A | N/A | 4298 | 4313 | AGCGACCCAAATGTGG | 102 | 2780 |
| 969866 | N/A | N/A | 4407 | 4422 | GCCCGGGAGAGCGGAG | 132 | 2781 |
| 969876 | N/A | N/A | 4637 | 4652 | CGCGGAGGACCTCGCC | 107 | 2782 |
| 969886 | N/A | N/A | 4896 | 4911 | GCGGGCACAGCCGTCC | 121 | 2783 |
| 969896 | N/A | N/A | 5530 | 5545 | AGCCGAGGCCTCCTTT | 128 | 2784 |
| 969906 | N/A | N/A | 5673 | 5688 | TGGAAACGAGAACGCA | 107 | 2785 |
| 969916 | N/A | N/A | 5774 | 5789 | AAAACAGCCGCCGGCA | 109 | 2786 |
| 969926 | N/A | N/A | 6022 | 6037 | CGTAACAACGACACAC | 135 | 2787 |
| 969936 | N/A | N/A | 6272 | 6287 | GTGAGATGCGGAGGTT | 61 | 2788 |
| 969946 | N/A | N/A | 6360 | 6375 | AGCTATGCTCTAGGAA | 89 | 2789 |
| 969956 | N/A | N/A | 6414 | 6429 | CGCATAGGTCCTTCAG | 94 | 2790 |
| 969966 | 429 | 444 | 6908 | 6923 | GTCATTGCTCTTGTTC | 82 | 2791 |
| 969976 | N/A | N/A | 7004 | 7019 | AGAGCCCCTACCTTTT | 107 | 2792 |
| 969986 | N/A | N/A | 7188 | 7203 | ATGCTGAACCCCACAG | 84 | 2793 |
| 969996 | N/A | N/A | 7224 | 7239 | ATATACATTGAGGCAT | 131 | 2794 |
| 970006 | N/A | N/A | 7592 | 7607 | GCGAATGTGCCTTGTG | 88 | 2795 |
| 970016 | N/A | N/A | 7644 | 7659 | TACAAGGTCTGAGTTG | 106 | 2796 |
| 970026 | N/A | N/A | 8132 | 8147 | CGCCCGACCCTCCCCA | 124 | 2797 |
| 970036 | N/A | N/A | 8224 | 8239 | TCACATGATAAGGCAC | 81 | 2798 |
| 970046 | N/A | N/A | 8390 | 8405 | GGACAATGGAGATACT | 97 | 2799 |
| 970056 | N/A | N/A | 8496 | 8511 | TCAGGGAATCCCTTAT | 96 | 2800 |
| 970066 | 650 | 665 | 9140 | 9155 | TCCCTCCAGCTTCGGT | 121 | 2801 |
| 970076 | N/A | N/A | 9284 | 9299 | CATTAGCAATTAGCTC | 137 | 2802 |
| 970086 | N/A | N/A | 9437 | 9452 | TGGATCCTGAGAGTAA | 100 | 2803 |
| 970096 | N/A | N/A | 9587 | 9602 | TACCAGCTCAATAATC | 127 | 2804 |
| 970106 | N/A | N/A | 9744 | 9759 | TAATCCACAATCAGCA | 127 | 2805 |
| 970116 | N/A | N/A | 9847 | 9862 | GTTACCGCATTGCTAG | 84 | 2806 |
| 970126 | N/A | N/A | 10002 | 10017 | ACTACCTGCAGCCAAG | 96 | 2807 |
| 970136 | N/A | N/A | 10130 | 10145 | TCCTCCACTACCATAT | 113 | 2808 |
| 970146 | N/A | N/A | 10184 | 10199 | CCAGAGCAGTAAACGC | 89 | 2809 |
| 970156 | N/A | N/A | 10273 | 10288 | CCGATGCTTCAAGACA | 87 | 2810 |
| 970166 | N/A | N/A | 10489 | 10504 | GTTCACAACAGAGCTG | 116 | 2811 |
| 970176 | N/A | N/A | 10711 | 10726 | CGCCCAATCACCTTCC | 119 | 2812 |
| 970186 | N/A | N/A | 11005 | 11020 | CCCATCGAATCTGCCC | 124 | 2813 |
| 970195 | N/A | N/A | 11127 | 11142 | GAACCACAAGCAGTGA | 132 | 2814 |

TABLE 45-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970205 | N/A | N/A | 11371 | 11386 | GACCAGAACTAATGTC | 127 | 2815 |
| 970215 | N/A | N/A | 11468 | 11483 | CAGATTGAATCCATAT | 80 | 2816 |
| 970225 | N/A | N/A | 11553 | 11568 | GCCTAGAGGTGCCTTC | 87 | 2817 |
| 970235 | N/A | N/A | 11797 | 11812 | AAAGAGCTGGTAGGTC | 135 | 2818 |
| 970245 | N/A | N/A | 11960 | 11975 | CTCTTCAGGCACCCAC | 87 | 2819 |
| 970255 | N/A | N/A | 12052 | 12067 | CATTCGAGGTGATTCT | 89 | 2820 |
| 970265 | N/A | N/A | 12224 | 12239 | TGGCTGATAATTAATC | 105 | 2821 |
| 970275 | N/A | N/A | 12383 | 12398 | TTTAAAATATCGCCCA | 101 | 2822 |
| 970285 | N/A | N/A | 12694 | 12709 | TTAAAGGGTAAGCACT | 118 | 2823 |
| 970295 | N/A | N/A | 13039 | 13054 | ACTTGCTAAGTCTTAT | 87 | 2824 |
| 970305 | N/A | N/A | 13197 | 13212 | TGGAGAAGTCCCGTGG | 109 | 2825 |
| 970315 | N/A | N/A | 13769 | 13784 | CCTTACCTGACAAGAA | 111 | 2826 |
| 970325 | N/A | N/A | 14019 | 14034 | AGAGGCGACTGCTGAA | 119 | 2827 |
| 970335 | N/A | N/A | 14208 | 14223 | CCAGTACAGTCCACTC | 106 | 2828 |
| 970345 | N/A | N/A | 14332 | 14347 | CGCTGAATTGTCATGA | 101 | 2829 |
| 970355 | N/A | N/A | 14688 | 14703 | AATCTGGATGAGCTTA | 96 | 2830 |
| 970365 | N/A | N/A | 15410 | 15425 | TCATTAGAAAGCCCTC | 119 | 2831 |
| 970375 | N/A | N/A | 15602 | 15617 | AAGTTCTAGTCGCGCA | 89 | 2832 |
| 970385 | N/A | N/A | 15868 | 15883 | ACCTACACAGGCTAAT | 104 | 2833 |
| 970395 | N/A | N/A | 15986 | 16001 | GCTAACTTACAGGACT | 108 | 2834 |
| 970405 | N/A | N/A | 16252 | 16267 | AGACAAGTGCCCATCC | 99 | 2835 |
| 970415 | N/A | N/A | 16611 | 16626 | TCAGAATGTTTCGACA | 94 | 2836 |
| 970425 | N/A | N/A | 16712 | 16727 | GGTAGTAGACCACAGT | 77 | 2837 |
| 970435 | N/A | N/A | 16890 | 16905 | CACTCTTACTCCGCTG | 112 | 2838 |
| 970445 | N/A | N/A | 16966 | 16981 | CCCTCATCACCGAACA | 125 | 2839 |

TABLE 46

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 33 | 195 |
| 969847 | N/A | N/A | 4044 | 4059 | CGCAGGAGCGCGGAGG | 128 | 2840 |
| 969857 | N/A | N/A | 4302 | 4317 | TCGGAGCGACCCAAAT | 88 | 2841 |
| 969867 | N/A | N/A | 4444 | 4459 | ATTCCGCGCGCAGAGC | 121 | 2842 |
| 969877 | N/A | N/A | 4643 | 4658 | TCCACGCGCGGAGGAC | 143 | 2843 |

TABLE 46-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 969887 | N/A | N/A | 4928 | 4943 | ACCTTCGCGGCCGGCC | 142 | 2844 |
| 969897 | N/A | N/A | 5570 | 5585 | CGCCCAGGACCCGGCT | 101 | 2845 |
| 969907 | N/A | N/A | 5705 | 5720 | CGGGAGCCCGGAGGAA | 103 | 2846 |
| 969917 | N/A | N/A | 5782 | 5797 | GAGAGACGAAAACAGC | 95 | 2847 |
| 969927 | N/A | N/A | 6112 | 6127 | GAGGAAGTCCCCTTCC | 96 | 2848 |
| 969937 | N/A | N/A | 6274 | 6289 | GAGTGAGATGCGGAGG | 45 | 2849 |
| 969947 | N/A | N/A | 6364 | 6379 | CCCCAGCTATGCTCTA | 130 | 2850 |
| 969957 | N/A | N/A | 6416 | 6431 | GGCGCATAGGTCCTTC | 107 | 2851 |
| 969967 | 446 | 461 | 6925 | 6940 | TCAACCAGTTCCTCAA | 123 | 2852 |
| 969977 | N/A | N/A | 7008 | 7023 | CAGGAGAGCCCCTACC | 108 | 2853 |
| 969987 | N/A | N/A | 7191 | 7206 | CCTATGCTGAACCCCA | 112 | 2854 |
| 969997 | N/A | N/A | 7225 | 7240 | CATATACATTGAGGCA | 80 | 2855 |
| 970007 | N/A | N/A | 7598 | 7613 | TGGCATGCGAATGTGC | 121 | 2856 |
| 970017 | N/A | N/A | 7648 | 7663 | TTTCTACAAGGTCTGA | 97 | 2857 |
| 970027 | N/A | N/A | 8135 | 8150 | ACACGCCCGACCCTCC | 96 | 2858 |
| 970037 | N/A | N/A | 8231 | 8246 | TGTGGTTTCACATGAT | 79 | 2859 |
| 970047 | N/A | N/A | 8403 | 8418 | GGAGGATCATAAAGGA | 68 | 2860 |
| 970057 | N/A | N/A | 8520 | 8535 | GTGCTCTTACAGCCTC | 115 | 2861 |
| 970067 | 655 | 670 | 9145 | 9160 | CGTAGTCCCTCCAGCT | 73 | 2862 |
| 970077 | N/A | N/A | 9289 | 9304 | GGCCACATTAGCAATT | 100 | 2863 |
| 970087 | N/A | N/A | 9440 | 9455 | GCATGGATCCTGAGAG | 89 | 2864 |
| 970097 | N/A | N/A | 9600 | 9615 | TTCGAGAGAAATATAC | 78 | 2865 |
| 970107 | N/A | N/A | 9748 | 9763 | CATCTAATCCACAATC | 119 | 2866 |
| 970117 | N/A | N/A | 9849 | 9864 | GAGTTACCGCATTGCT | 53 | 2867 |
| 970127 | N/A | N/A | 10004 | 10019 | TCACTACCTGCAGCCA | 94 | 2868 |
| 970137 | N/A | N/A | 10133 | 10148 | AATTCCTCCACTACCA | 141 | 2869 |
| 970147 | N/A | N/A | 10187 | 10202 | GAGCCAGAGCAGTAAA | 102 | 2870 |
| 970157 | N/A | N/A | 10275 | 10290 | TACCGATGCTTCAAGA | 103 | 2871 |
| 970167 | N/A | N/A | 10499 | 10514 | CACAAAGCGGGTTCAC | 112 | 2872 |
| 970177 | N/A | N/A | 10777 | 10792 | AGAGAGTCCGACGCAC | 118 | 2873 |
| 970187 | N/A | N/A | 11006 | 11021 | TCCCATCGAATCTGCC | 105 | 2874 |
| 970196 | N/A | N/A | 11136 | 11151 | CGGTCAGCAGAACCAC | 108 | 2875 |
| 970206 | N/A | N/A | 11377 | 11392 | ATGAGGGACCAGAACT | 94 | 2876 |
| 970216 | N/A | N/A | 11470 | 11485 | ATCAGATTGAATCCAT | 77 | 2877 |
| 970226 | N/A | N/A | 11555 | 11570 | AAGCCTAGAGGTGCCT | 71 | 2878 |
| 970236 | N/A | N/A | 11813 | 11828 | CCTCATTCACAACTAG | 95 | 2879 |
| 970246 | N/A | N/A | 11963 | 11978 | CTACTCTTCAGGCACC | 82 | 2880 |

TABLE 46-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970256 | N/A | N/A | 12055 | 12070 | GGCCATTCGAGGTGAT | 99 | 2881 |
| 970266 | N/A | N/A | 12229 | 12244 | GCTCATGGCTGATAAT | 117 | 2882 |
| 970276 | N/A | N/A | 12385 | 12400 | TCTTTAAAATATCGCC | 145 | 2883 |
| 970286 | N/A | N/A | 12697 | 12712 | ACATTAAAGGGTAAGC | 123 | 2884 |
| 970296 | N/A | N/A | 13042 | 13057 | AGAACTTGCTAAGTCT | 134 | 2885 |
| 970306 | N/A | N/A | 13207 | 13222 | GGTCAACACTTGGAGA | 123 | 2886 |
| 970316 | N/A | N/A | 13771 | 13786 | TGCCTTACCTGACAAG | 96 | 2887 |
| 970326 | N/A | N/A | 14023 | 14038 | TTTAAGAGGCGACTGC | 200 | 2888 |
| 970336 | N/A | N/A | 14211 | 14226 | AAACCAGTACAGTCCA | 123 | 2889 |
| 970346 | N/A | N/A | 14431 | 14446 | CCCACGCGGGAGGCTC | 123 | 2890 |
| 970356 | N/A | N/A | 14706 | 14721 | CTTTGGGCACCAAAAG | 133 | 2891 |
| 970366 | N/A | N/A | 15411 | 15426 | TTCATTAGAAAGCCCT | 122 | 2892 |
| 970376 | N/A | N/A | 15606 | 15621 | TAGTAAGTTCTAGTCG | 113 | 2893 |
| 970386 | N/A | N/A | 15878 | 15893 | CTGAGACTACACCTAC | 140 | 2894 |
| 970396 | N/A | N/A | 15991 | 16006 | TTCTAGCTAACTTACA | 118 | 2895 |
| 970406 | N/A | N/A | 16271 | 16286 | GACTGGAACATTGTTG | 141 | 2896 |
| 970416 | N/A | N/A | 16639 | 16654 | TGCCATGGACAAGTTT | 118 | 2897 |
| 970426 | N/A | N/A | 16717 | 16732 | CAAAAGGTAGTAGACC | 89 | 2898 |
| 970436 | N/A | N/A | 16891 | 16906 | GCACTCTTACTCCGCT | 98 | 2899 |
| 970446 | N/A | N/A | 16970 | 16985 | GAAACCCTCATCACCG | 138 | 2900 |

TABLE 47

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 23 | 195 |
| 969848 | N/A | N/A | 4047 | 4062 | CGTCGCAGGAGCGCGG | 99 | 2901 |
| 969858 | N/A | N/A | 4313 | 4328 | GCACGCAAGGCTCGGA | 93 | 2902 |
| 969868 | N/A | N/A | 4446 | 4461 | GGATTCCGCGCGCAGA | 79 | 2903 |
| 969878 | N/A | N/A | 4677 | 4692 | CGCGACTCTGTCAGTT | 92 | 2904 |
| 969888 | N/A | N/A | 4981 | 4996 | CTGCGAAGCGCGCGCG | 106 | 2905 |
| 969898 | N/A | N/A | 5600 | 5615 | GCCTTCAGCGGTTTCC | 96 | 2906 |
| 969908 | N/A | N/A | 5719 | 5734 | ACGGAGGCGGCAGACG | 109 | 2907 |
| 969918 | N/A | N/A | 5785 | 5800 | GGTGAGAGACGAAAAC | 116 | 2908 |
| 969928 | N/A | N/A | 6115 | 6130 | CCGGAGGAAGTCCCCT | 100 | 2909 |

TABLE 47-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 969938 | N/A | N/A | 6277 | 6292 | GTAGAGTGAGATGCGG | 49 | 2910 |
| 969948 | N/A | N/A | 6397 | 6412 | TTTACACCGTTGCTCA | 97 | 2911 |
| 969958 | N/A | N/A | 6418 | 6433 | ATGGCGCATAGGTCCT | 105 | 2912 |
| 969968 | 450 | 465 | 6929 | 6944 | CCGCTCAACCAGTTCC | 112 | 2913 |
| 969978 | N/A | N/A | 7011 | 7026 | ATTCAGGAGAGCCCCT | 115 | 2914 |
| 969988 | N/A | N/A | 7193 | 7208 | CTCCTATGCTGAACCC | 91 | 2915 |
| 969998 | N/A | N/A | 7227 | 7242 | CCCATATACATTGAGG | 84 | 2916 |
| 970008 | N/A | N/A | 7603 | 7618 | ACAGATGGCATGCGAA | 81 | 2917 |
| 970018 | N/A | N/A | 7666 | 7681 | TGCTATTAAACTGATT | 103 | 2918 |
| 970028 | N/A | N/A | 8138 | 8153 | CGGACACGCCCGACCC | 93 | 2919 |
| 970038 | N/A | N/A | 8331 | 8346 | ACCAAAAGTACCACAG | 108 | 2920 |
| 970048 | N/A | N/A | 8445 | 8460 | GACTGGAGTGAACCCT | 62 | 2921 |
| 970058 | N/A | N/A | 8522 | 8537 | GGGTGCTCTTACAGCC | 102 | 2922 |
| 970068 | 677 | 692 | 9167 | 9182 | TCCGGGTGTGGCTGAT | 74 | 2923 |
| 970078 | N/A | N/A | 9310 | 9325 | CCAGGATTCGCCATGG | 87 | 2924 |
| 970088 | N/A | N/A | 9445 | 9460 | GCCTAGCATGGATCCT | 104 | 2925 |
| 970098 | N/A | N/A | 9605 | 9620 | CACTATTCGAGAGAAA | 70 | 2926 |
| 970108 | N/A | N/A | 9754 | 9769 | GGACCACATCTAATCC | 112 | 2927 |
| 970118 | N/A | N/A | 9852 | 9867 | CCTGAGTTACCGCATT | 76 | 2928 |
| 970128 | N/A | N/A | 10011 | 10026 | CACCTCTTCACTACCT | 100 | 2929 |
| 970138 | N/A | N/A | 10138 | 10153 | TAGCCAATTCCTCCAC | 99 | 2930 |
| 970148 | N/A | N/A | 10193 | 10208 | TCCATAGAGCCAGAGC | 80 | 2931 |
| 970158 | N/A | N/A | 10277 | 10292 | GTTACCGATGCTTCAA | 54 | 2932 |
| 970168 | N/A | N/A | 10550 | 10565 | ACTAACAGGGAGACTG | 119 | 2933 |
| 970178 | N/A | N/A | 10779 | 10794 | ACAGAGAGTCCGACGC | 108 | 2934 |
| 970188 | N/A | N/A | 11012 | 11027 | CTAAAGTCCCATCGAA | 102 | 2935 |
| 970197 | N/A | N/A | 11142 | 11157 | CTGAAACGGTCAGCAG | 97 | 2936 |
| 970207 | N/A | N/A | 11399 | 11414 | TAGGCACATCAATGTT | 88 | 2937 |
| 970217 | N/A | N/A | 11525 | 11540 | AAGATCTCCATGGTGC | 61 | 2938 |
| 970227 | N/A | N/A | 11557 | 11572 | CCAAGCCTAGAGGTGC | 79 | 2939 |
| 970237 | N/A | N/A | 11820 | 11835 | GTGCAAGCCTCATTCA | 81 | 2940 |
| 970247 | N/A | N/A | 11993 | 12008 | GTTGCCGAGATATAAA | 87 | 2941 |
| 970257 | N/A | N/A | 12085 | 12100 | AGACAGTGCGCCCAA | 117 | 2942 |
| 970267 | N/A | N/A | 12231 | 12246 | GTGCTCATGGCTGATA | 76 | 2943 |
| 970277 | N/A | N/A | 12455 | 12470 | TAAAACTGCGCTCTCT | 114 | 2944 |
| 970287 | N/A | N/A | 12860 | 12875 | CCACATACCTGAAACG | 109 | 2945 |
| 970297 | N/A | N/A | 13056 | 13071 | GAGCATCACTATTAAG | 86 | 2946 |

TABLE 47-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970307 | N/A | N/A | 13216 | 13231 | CATGAGCTCGGTCAAC | 101 | 2947 |
| 970317 | N/A | N/A | 13779 | 13794 | TAACGAGGTGCCTTAC | 87 | 2948 |
| 970327 | N/A | N/A | 14026 | 14041 | TGTTTTAAGAGGCGAC | 97 | 2949 |
| 970337 | N/A | N/A | 14217 | 14232 | TGTGCAAAACCAGTAC | 120 | 2950 |
| 970347 | N/A | N/A | 14448 | 14463 | GGGTAGAGCAGCTCCC | 116 | 2951 |
| 970357 | N/A | N/A | 14710 | 14725 | TTTGCTTTGGGCACCA | 76 | 2952 |
| 970367 | N/A | N/A | 15431 | 15446 | TGCCAGTTCCTTGTGA | 102 | 2953 |
| 970377 | N/A | N/A | 15607 | 15622 | ATAGTAAGTTCTAGTC | 89 | 2954 |
| 970387 | N/A | N/A | 15880 | 15895 | ATCTGAGACTACACCT | 108 | 2955 |
| 970397 | N/A | N/A | 16095 | 16110 | ATACACACCCTCGGGC | 110 | 2956 |
| 970407 | N/A | N/A | 16274 | 16289 | ACGGACTGGAACATTG | 62 | 2957 |
| 970417 | N/A | N/A | 16640 | 16655 | ATGCCATGGACAAGTT | 82 | 2958 |
| 970427 | N/A | N/A | 16728 | 16743 | CCACGAAGATTCAAAA | 107 | 2959 |
| 970437 | N/A | N/A | 16894 | 16909 | TGAGCACTCTTACTCC | 106 | 2960 |
| 970447 | N/A | N/A | 16976 | 16991 | TGTTCAGAAACCCTCA | 115 | 2961 |

TABLE 48

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 27 | 195 |
| 969849 | N/A | N/A | 4081 | 4096 | CGGTTAGCTCATCCCG | 95 | 2962 |
| 969859 | N/A | N/A | 4320 | 4335 | GGCCACCGCACGCAAG | 124 | 2963 |
| 969869 | N/A | N/A | 4488 | 4503 | CGACAAGTGGCGCAGA | 98 | 2964 |
| 969879 | N/A | N/A | 4805 | 4820 | CGACACGCGCCGCTCG | 62 | 2965 |
| 969889 | N/A | N/A | 4989 | 5004 | CTTTGAGGCTGCGAAG | 98 | 2966 |
| 969899 | N/A | N/A | 5610 | 5625 | GCCCGGCCGGGCCTTC | 104 | 2967 |
| 969909 | N/A | N/A | 5725 | 5740 | CCACGGACGGAGGCGG | 106 | 2968 |
| 969919 | N/A | N/A | 5793 | 5808 | AGAGACGCGGTGAGAG | 120 | 2969 |
| 969929 | N/A | N/A | 6123 | 6138 | CCAAATTCCCGGAGGA | 125 | 2970 |
| 969939 | N/A | N/A | 6280 | 6295 | CCGGTAGAGTGAGATG | 103 | 2971 |
| 969949 | N/A | N/A | 6398 | 6413 | ATTTACACCGTTGCTC | 87 | 2972 |
| 969959 | N/A | N/A | 6420 | 6435 | GAATGGCGCATAGGTC | 74 | 2973 |
| 969969 | 454 | 469 | 6933 | 6948 | GGCTCCGCTCAACCAG | 91 | 2974 |
| 969979 | N/A | N/A | 7026 | 7041 | TGTTAGGTGACCCAAA | 98 | 2975 |

TABLE 48-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 969989 | N/A | N/A | 7198 | 7213 | TAATTCTCCTATGCTG | 97 | 2976 |
| 969999 | N/A | N/A | 7243 | 7258 | ATTCAATGCACCCCCC | 98 | 2977 |
| 970009 | N/A | N/A | 7604 | 7619 | GACAGATGGCATGCGA | 84 | 2978 |
| 970019 | N/A | N/A | 7727 | 7742 | ATAACACGGTGTTGAC | 79 | 2979 |
| 970029 | N/A | N/A | 8140 | 8155 | GGCGGACACGCCCGAC | 93 | 2980 |
| 970039 | N/A | N/A | 8343 | 8358 | GCTAAACCTGGCACCA | 93 | 2981 |
| 970049 | N/A | N/A | 8451 | 8466 | CGAAAAGACTGGAGTG | 74 | 2982 |
| 970059 | N/A | N/A | 8784 | 8799 | GGGTTAAAGGAGTGCA | 100 | 2983 |
| 970069 | 681 | 696 | 9171 | 9186 | GATTTCCGGGTGTGGC | 25 | 2984 |
| 970079 | N/A | N/A | 9371 | 9386 | CCCCGAGCTGCACACG | 105 | 2985 |
| 970089 | N/A | N/A | 9457 | 9472 | ACGAAGGGCAGTGCCT | 105 | 2986 |
| 970099 | N/A | N/A | 9613 | 9628 | GAACACACCACTATTC | 120 | 2987 |
| 970109 | N/A | N/A | 9772 | 9787 | GGAACTCCCGAGGGCA | 87 | 2988 |
| 970119 | N/A | N/A | 9854 | 9869 | GGCCTGAGTTACCGCA | 92 | 2989 |
| 970129 | N/A | N/A | 10013 | 10028 | TACACCTCTTCACTAC | 118 | 2990 |
| 970139 | N/A | N/A | 10143 | 10158 | TATGTTAGCCAATTCC | 59 | 2991 |
| 970149 | N/A | N/A | 10196 | 10211 | AATTCCATAGAGCCAG | 82 | 2992 |
| 970159 | N/A | N/A | 10279 | 10294 | CTGTTACCGATGCTTC | 44 | 2993 |
| 970169 | N/A | N/A | 10558 | 10573 | TGTAACTGACTAACAG | 131 | 2994 |
| 970179 | N/A | N/A | 10783 | 10798 | CTAGACAGAGAGTCCG | 95 | 2995 |
| 970189 | N/A | N/A | 11017 | 11032 | AGTGTCTAAAGTCCCA | 58 | 2996 |
| 970198 | N/A | N/A | 11143 | 11158 | GCTGAAACGGTCAGCA | 92 | 2997 |
| 970208 | N/A | N/A | 11401 | 11416 | CTTAGGCACATCAATG | 92 | 2998 |
| 970218 | N/A | N/A | 11527 | 11542 | GTAAGATCTCCATGGT | 83 | 2999 |
| 970228 | N/A | N/A | 11566 | 11581 | GTGTGCTTGCCAAGCC | 34 | 3000 |
| 970238 | N/A | N/A | 11826 | 11841 | AAAAAGGTGCAAGCCT | 94 | 3001 |
| 970248 | N/A | N/A | 11996 | 12011 | GAGGTTGCCGAGATAT | 71 | 3002 |
| 970258 | N/A | N/A | 12094 | 12109 | AAGCGAGTCAGACAGT | 122 | 3003 |
| 970268 | N/A | N/A | 12278 | 12293 | CTGTATGGAACCCCAA | 97 | 3004 |
| 970278 | N/A | N/A | 12511 | 12526 | ATGTAAAGTCTGCTGA | 80 | 3005 |
| 970288 | N/A | N/A | 12862 | 12877 | GTCCACATACCTGAAA | 92 | 3006 |
| 970298 | N/A | N/A | 13059 | 13074 | ATAGAGCATCACTATT | 100 | 3007 |
| 970308 | N/A | N/A | 13219 | 13234 | CAGCATGAGCTCGGTC | 78 | 3008 |
| 970318 | N/A | N/A | 13786 | 13801 | TAACAGATAACGAGGT | 88 | 3009 |
| 970328 | N/A | N/A | 14054 | 14069 | TCGAGATCATAGTGCA | 71 | 3010 |
| 970338 | N/A | N/A | 14219 | 14234 | CCTGTGCAAAACCAGT | 110 | 3011 |
| 970348 | N/A | N/A | 14459 | 14474 | TGGCGAGTGGCGGGTA | 118 | 3012 |

TABLE 48-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970358 | N/A | N/A | 14733 | 14748 | AAGCTTAGTTATCTGG | 65 | 3013 |
| 970368 | N/A | N/A | 15573 | 15588 | AGGACACTCACAGGCG | 92 | 3014 |
| 970378 | N/A | N/A | 15614 | 15629 | CAGATTAATAGTAAGT | 112 | 3015 |
| 970388 | N/A | N/A | 15885 | 15900 | CCGTGATCTGAGACTA | 55 | 3016 |
| 970398 | N/A | N/A | 16144 | 16159 | TGACACAGGAGCCGCT | 85 | 3017 |
| 970408 | N/A | N/A | 16283 | 16298 | AGATACAAAACGGACT | 115 | 3018 |
| 970418 | N/A | N/A | 16642 | 16657 | TTATGCCATGGACAAG | 81 | 3019 |
| 970428 | N/A | N/A | 16730 | 16745 | ACCCACGAAGATTCAA | 117 | 3020 |
| 970438 | N/A | N/A | 16899 | 16914 | AGGAATGAGCACTCTT | 93 | 3021 |
| 970448 | N/A | N/A | 16984 | 16999 | AGAGACCATGTTCAGA | 88 | 3022 |
| 970608 | 1440 | 1455 | 19557 | 19572 | AGATCTGTGGTAATCT | 103 | 3023 |

TABLE 49

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 19 | 195 |
| 969850 | N/A | N/A | 4151 | 4166 | GGCAGTTGTGCCGTCT | 117 | 3024 |
| 969860 | N/A | N/A | 4342 | 4357 | AGGGACCGCGCCAGGC | 100 | 3025 |
| 969870 | N/A | N/A | 4490 | 4505 | AACGACAAGTGGCGCA | 88 | 3026 |
| 969880 | N/A | N/A | 4808 | 4823 | TCCCGACACGCGCCGC | 112 | 3027 |
| 969890 | N/A | N/A | 5006 | 5021 | CCACGAGGCCCCGGAG | 96 | 3028 |
| 969900 | N/A | N/A | 5655 | 5670 | GACGAACGCGCAAAAC | 85 | 3029 |
| 969910 | N/A | N/A | 5747 | 5762 | GCACGGAGAGGGCGAG | 96 | 3030 |
| 969920 | N/A | N/A | 5795 | 5810 | ACAGAGACGCGGTGAG | 86 | 3031 |
| 969930 | N/A | N/A | 6211 | 6226 | GGACTAAGGACAGCTG | 87 | 3032 |
| 969940 | N/A | N/A | 6283 | 6298 | TAACCGGTAGAGTGAG | 73 | 3033 |
| 969950 | N/A | N/A | 6400 | 6415 | AGATTTACACCGTTGC | 70 | 3034 |
| 969960 | N/A | N/A | 6423 | 6438 | AAAGAATGGCGCATAG | 90 | 3035 |
| 969970 | 471 | 486 | 6950 | 6965 | GTCTGAGATGTCCAGC | 93 | 3036 |
| 969980 | N/A | N/A | 7156 | 7171 | CCCACATAACTCAGGC | 116 | 3037 |
| 969990 | N/A | N/A | 7201 | 7216 | GATTAATTCTCCTATG | 119 | 3038 |
| 970000 | N/A | N/A | 7375 | 7390 | TGAGATATTCCTCTCA | 82 | 3039 |
| 970010 | N/A | N/A | 7628 | 7643 | TACAGGACAGGTAAAG | 129 | 3040 |
| 970020 | N/A | N/A | 7735 | 7750 | TAGAATGCATAACACG | 92 | 3041 |

TABLE 49-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970030 | N/A | N/A | 8142 | 8157 | CAGGCGGACACGCCCG | 105 | 3042 |
| 970040 | N/A | N/A | 8346 | 8361 | ATGGCTAAACCTGGCA | 78 | 3043 |
| 970050 | N/A | N/A | 8453 | 8468 | TCCGAAAAGACTGGAG | 107 | 3044 |
| 970060 | N/A | N/A | 9095 | 9110 | TGCTAAAGGAGTGCAG | 117 | 3045 |
| 970070 | 688 | 703 | 9178 | 9193 | GGTACGGGATTTCCGG | 88 | 3046 |
| 970080 | N/A | N/A | 9390 | 9405 | AGTGAGAAAACCCCCC | 92 | 3047 |
| 970090 | N/A | N/A | 9459 | 9474 | CCACGAAGGGCAGTGC | 100 | 3048 |
| 970100 | N/A | N/A | 9649 | 9664 | TTTAGTATCACCTCTA | 70 | 3049 |
| 970110 | N/A | N/A | 9795 | 9810 | AGGGAGCTCATTTTGA | 108 | 3050 |
| 970120 | N/A | N/A | 9857 | 9872 | GAAGGCCTGAGTTACC | 71 | 3051 |
| 970130 | N/A | N/A | 10022 | 10037 | AAAGAGTGGTACACCT | 90 | 3052 |
| 970140 | N/A | N/A | 10154 | 10169 | GGAGCTAGTTTTATGT | 128 | 3053 |
| 970150 | N/A | N/A | 10201 | 10216 | TTACTAATTCCATAGA | 97 | 3054 |
| 970160 | N/A | N/A | 10280 | 10295 | ACTGTTACCGATGCTT | 57 | 3055 |
| 970170 | N/A | N/A | 10561 | 10576 | CTCTGTAACTGACTAA | 84 | 3056 |
| 970180 | N/A | N/A | 10827 | 10842 | TGTCACCTGGCAACCT | 104 | 3057 |
| 970190 | N/A | N/A | 11019 | 11034 | CAAGTGTCTAAAGTCC | 97 | 3058 |
| 970199 | N/A | N/A | 11144 | 11159 | GGCTGAAACGGTCAGC | 127 | 3059 |
| 970209 | N/A | N/A | 11404 | 11419 | ACTCTTAGGCACATCA | 73 | 3060 |
| 970219 | N/A | N/A | 11529 | 11544 | AGGTAAGATCTCCATG | 68 | 3061 |
| 970229 | N/A | N/A | 11654 | 11669 | CCTTAAGCTATTTGGT | 886 | 3062 |
| 970239 | N/A | N/A | 11848 | 11863 | GTTACTCACGAGCACC | 117 | 3063 |
| 970249 | N/A | N/A | 11998 | 12013 | ACGAGGTTGCCGAGAT | 38 | 3064 |
| 970259 | N/A | N/A | 12098 | 12113 | CTGAAAGCGAGTCAGA | 94 | 3065 |
| 970269 | N/A | N/A | 12279 | 12294 | ACTGTATGGAACCCCA | 70 | 3066 |
| 970279 | N/A | N/A | 12513 | 12528 | TCATGTAAAGTCTGCT | 79 | 3067 |
| 970289 | N/A | N/A | 12876 | 12891 | AAAGAAGCAAGTCGGT | 102 | 3068 |
| 970299 | N/A | N/A | 13062 | 13077 | ATTATAGAGCATCACT | 106 | 3069 |
| 970309 | N/A | N/A | 13308 | 13323 | CCACATGTCCCGTGGG | 128 | 3070 |
| 970319 | N/A | N/A | 13788 | 13803 | TCTAACAGATAACGAG | 103 | 3071 |
| 970329 | N/A | N/A | 14089 | 14104 | CCTGAAAAGAGCCGCC | 103 | 3072 |
| 970339 | N/A | N/A | 14227 | 14242 | TAACTTCTCCTGTGCA | 85 | 3073 |
| 970349 | N/A | N/A | 14644 | 14659 | GTACGAGCACATGTCA | 100 | 3074 |
| 970359 | N/A | N/A | 14741 | 14756 | CTGGCCTGAAGCTTAG | 75 | 3075 |
| 970369 | N/A | N/A | 15587 | 15602 | AAGTCTACAGCCCCAG | 105 | 3076 |
| 970379 | N/A | N/A | 15668 | 15683 | GCACAGCCCTTGGTTA | 97 | 3077 |
| 970389 | N/A | N/A | 15890 | 15905 | CACTGCCGTGATCTGA | 91 | 3078 |

TABLE 49-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970399 | N/A | N/A | 16153 | 16168 | GAAACGAGTTGACACA | 100 | 3079 |
| 970409 | N/A | N/A | 16333 | 16348 | CGCTTGTGGATATACA | 100 | 3080 |
| 970419 | N/A | N/A | 16650 | 16665 | AGACCAATTTATGCCA | 93 | 3081 |
| 970429 | N/A | N/A | 16739 | 16754 | CAGCATTGGACCCACG | 96 | 3082 |
| 970439 | N/A | N/A | 16901 | 16916 | AGAGGAATGAGCACTC | 95 | 3083 |
| 970449 | N/A | N/A | 17002 | 17017 | TGTAGAAGCCCACAAG | 107 | 3084 |
| 970609 | 1443 | 1458 | 19560 | 19575 | GATAGATCTGTGGTAA | 78 | 3085 |

TABLE 50

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 21 | 195 |
| 969851 | N/A | N/A | 4214 | 4229 | GGAACGAAGAGCAGGG | 88 | 3086 |
| 969861 | N/A | N/A | 4344 | 4359 | GCAGGGACCGCGCCAG | 90 | 3087 |
| 969871 | N/A | N/A | 4493 | 4508 | GCAAACGACAAGTGGC | 115 | 3088 |
| 969881 | N/A | N/A | 4823 | 4838 | CCGCAGCCCAAAGGCT | 96 | 3089 |
| 969891 | N/A | N/A | 5046 | 5061 | CGCACTCCGGGCACCC | 89 | 3090 |
| 969901 | N/A | N/A | 5658 | 5673 | ACGGACGAACGCGCAA | 107 | 3091 |
| 969911 | N/A | N/A | 5751 | 5766 | GGACGCACGGAGAGGG | 85 | 3092 |
| 969921 | N/A | N/A | 5799 | 5814 | AGAAACAGAGACGCGG | 89 | 3093 |
| 969931 | N/A | N/A | 6213 | 6228 | TAGGACTAAGGACAGC | 105 | 3094 |
| 969941 | N/A | N/A | 6288 | 6303 | ATTTATAACCGGTAGA | 72 | 3095 |
| 969951 | N/A | N/A | 6401 | 6416 | CAGATTTACACCGTTG | 85 | 3096 |
| 969961 | N/A | N/A | 6540 | 6555 | GCATAGGCATCCTTCC | 92 | 3097 |
| 969971 | 474 | 489 | 6953 | 6968 | CGGGTCTGAGATGTCC | 102 | 3098 |
| 969981 | N/A | N/A | 7160 | 7175 | GTGACCCACATAACTC | 93 | 3099 |
| 969991 | N/A | N/A | 7205 | 7220 | GTGTGATTAATTCTCC | 36 | 3100 |
| 970001 | N/A | N/A | 7377 | 7392 | GATGAGATATTCCTCT | 124 | 3101 |
| 970011 | N/A | N/A | 7630 | 7645 | TGTACAGGACAGGTAA | 92 | 3102 |
| 970021 | N/A | N/A | 7783 | 7798 | ACCTAACTAAATGTCA | 124 | 3103 |
| 970031 | N/A | N/A | 8149 | 8164 | ATTCCAACAGGCGGAC | 98 | 3104 |
| 970041 | N/A | N/A | 8348 | 8363 | ATATGGCTAAACCTGG | 82 | 3105 |
| 970051 | N/A | N/A | 8454 | 8469 | ATCCGAAAGACTGGA | 120 | 3106 |
| 970061 | N/A | N/A | 9103 | 9118 | TGTGAACCTGCTAAAG | 110 | 3107 |

TABLE 50-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970071 | 690 | 705 | 9180 | 9195 | TTGGTACGGGATTTCC | 66 | 3108 |
| 970081 | N/A | N/A | 9412 | 9427 | TGGGATGCCACCATCC | 102 | 3109 |
| 970091 | N/A | N/A | 9466 | 9481 | TAAGATCCCACGAAGG | 91 | 3110 |
| 970101 | N/A | N/A | 9659 | 9674 | CCGTTCCTTTTTTAGT | 103 | 3111 |
| 970111 | N/A | N/A | 9834 | 9849 | TAGATTCTCCCTGCAC | 82 | 3112 |
| 970121 | N/A | N/A | 9914 | 9929 | GTTCAGTGTGTTGACC | 70 | 3113 |
| 970131 | N/A | N/A | 10100 | 10115 | TGCTGCAAATCCCTCT | 79 | 3114 |
| 970141 | N/A | N/A | 10159 | 10174 | TTTCAGGAGCTAGTTT | 92 | 3115 |
| 970151 | N/A | N/A | 10206 | 10221 | CATGGTTACTAATTCC | 75 | 3116 |
| 970161 | N/A | N/A | 10281 | 10296 | TACTGTTACCGATGCT | 63 | 3117 |
| 970171 | N/A | N/A | 10568 | 10583 | GCGCTCTCTCTGTAAC | 107 | 3118 |
| 970181 | 763 | 778 | 10828 | 10843 | CTGTCACCTGGCAACC | 89 | 3119 |
| 970191 | N/A | N/A | 11085 | 11100 | AATCACCCTGGTCACC | 99 | 3120 |
| 970200 | N/A | N/A | 11334 | 11349 | ACTTATTTGTGGCTCA | 64 | 3121 |
| 970210 | N/A | N/A | 11407 | 11422 | ATTACTCTTAGGCACA | 70 | 3122 |
| 970220 | N/A | N/A | 11531 | 11546 | GTAGGTAAGATCTCCA | 78 | 3123 |
| 970230 | N/A | N/A | 11656 | 11671 | AACCTTAAGCTATTTG | 49 | 3124 |
| 970240 | N/A | N/A | 11851 | 11866 | TCAGTTACTCACGAGC | 103 | 3125 |
| 970250 | N/A | N/A | 12002 | 12017 | AATCACGAGGTTGCCG | 106 | 3126 |
| 970260 | N/A | N/A | 12149 | 12164 | TTTGAGACTTAACCCA | 69 | 3127 |
| 970270 | N/A | N/A | 12281 | 12296 | TAACTGTATGGAACCC | 72 | 3128 |
| 970280 | N/A | N/A | 12590 | 12605 | CTGGATATGTGGTGTT | 70 | 3129 |
| 970290 | N/A | N/A | 12892 | 12907 | TATAACGGTGTTTCAG | 64 | 3130 |
| 970300 | N/A | N/A | 13066 | 13081 | TCCTATTATAGAGCAT | 97 | 3131 |
| 970310 | N/A | N/A | 13352 | 13367 | AACGACTCCACAGAGC | 96 | 3132 |
| 970320 | N/A | N/A | 13880 | 13895 | GCCGAAGTCAACAGGA | 117 | 3133 |
| 970330 | N/A | N/A | 14115 | 14130 | TCCAACCTTTATGATT | 103 | 3134 |
| 970340 | N/A | N/A | 14229 | 14244 | TATAACTTCTCCTGTG | 93 | 3135 |
| 970350 | N/A | N/A | 14647 | 14662 | GAAGTACGAGCACATG | 82 | 3136 |
| 970360 | N/A | N/A | 14988 | 15003 | CAGCACCGTGGTGCGA | 127 | 3137 |
| 970370 | N/A | N/A | 15589 | 15604 | GCAAGTCTACAGCCCC | 51 | 3138 |
| 970380 | N/A | N/A | 15801 | 15816 | ATAACATGAGAGTGTT | 117 | 3139 |
| 970390 | N/A | N/A | 15892 | 15907 | CACACTGCCGTGATCT | 80 | 3140 |
| 970400 | N/A | N/A | 16156 | 16171 | AAAGAAACGAGTTGAC | 86 | 3141 |
| 970410 | N/A | N/A | 16379 | 16394 | AGTAACTTGACTTGAG | 103 | 3142 |
| 970420 | N/A | N/A | 16658 | 16673 | ATGGCAAAGACCAAT | 105 | 3143 |
| 970430 | N/A | N/A | 16746 | 16761 | TGCTTTGCAGCATTGG | 70 | 3144 |

TABLE 50-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970440 | N/A | N/A | 16927 | 16942 | AGCTTACTGTGATTCT | 87 | 3145 |
| 970450 | 1250 | 1265 | 17043 | 17058 | CTTGGCAGGGAGCGGC | 75 | 3146 |
| 970610 | 1445 | 1460 | 19562 | 19577 | CGGATAGATCTGTGGT | 54 | 3147 |

TABLE 51

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 28 | 195 |
| 969852 | N/A | N/A | 4219 | 4234 | CCTTAGGAACGAAGAG | 106 | 3148 |
| 969862 | N/A | N/A | 4346 | 4361 | AGGCAGGGACCGCGCC | 111 | 3149 |
| 969872 | N/A | N/A | 4495 | 4510 | CTGCAAACGACAAGTG | 118 | 3150 |
| 969882 | N/A | N/A | 4829 | 4844 | ACGCACCCGCAGCCCA | 110 | 3151 |
| 969892 | N/A | N/A | 5052 | 5067 | AGGCACCGCACTCCGG | 113 | 3152 |
| 969902 | N/A | N/A | 5661 | 5676 | CGCACGGACGAACGCG | 117 | 3153 |
| 969912 | N/A | N/A | 5753 | 5768 | GCGGACGCACGGAGAG | 109 | 3154 |
| 969922 | N/A | N/A | 5878 | 5893 | GCTAGCAGGAGCGAGA | 105 | 3155 |
| 969932 | N/A | N/A | 6215 | 6230 | CCTAGGACTAAGGACA | 103 | 3156 |
| 969942 | N/A | N/A | 6291 | 6306 | GGTATTTATAACCGGT | 90 | 3157 |
| 969952 | N/A | N/A | 6402 | 6417 | TCAGATTTACACCGTT | 86 | 3158 |
| 969962 | N/A | N/A | 6543 | 6558 | GTTGCATAGGCATCCT | 73 | 3159 |
| 969972 | 483 | 498 | 6962 | 6977 | CACTTTGTACGGGTCT | 89 | 3160 |
| 969982 | N/A | N/A | 7164 | 7179 | ACTTGTGACCCACATA | 104 | 3161 |
| 969992 | N/A | N/A | 7207 | 7222 | CAGTGTGATTAATTCT | 83 | 3162 |
| 970002 | N/A | N/A | 7563 | 7578 | CGCCAGCCAGATGTTT | 115 | 3163 |
| 970012 | N/A | N/A | 7632 | 7647 | GTTGTACAGGACAGGT | 67 | 3164 |
| 970022 | N/A | N/A | 7792 | 7807 | CAGGAACTGACCTAAC | 107 | 3165 |
| 970032 | N/A | N/A | 8152 | 8167 | CATATTCCAACAGGCG | 101 | 3166 |
| 970042 | N/A | N/A | 8351 | 8366 | GTCATATGGCTAAACC | 77 | 3167 |
| 970052 | N/A | N/A | 8478 | 8493 | GACTGACAGCCGAAGC | 73 | 3168 |
| 970062 | 626 | 641 | 9116 | 9131 | GGCATCATGTAGTTGT | 101 | 3169 |
| 970072 | 693 | 708 | 9183 | 9198 | ACATTGGTACGGGATT | 98 | 3170 |
| 970082 | N/A | N/A | 9420 | 9435 | CTTGGCTGTGGGATGC | 79 | 3171 |
| 970092 | N/A | N/A | 9469 | 9484 | AAATAAGATCCCACGA | 107 | 3172 |
| 970102 | N/A | N/A | 9668 | 9683 | GGTATTTTTCCGTTCC | 70 | 3173 |

TABLE 51-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970112 | N/A | N/A | 9836 | 9851 | GCTAGATTCTCCCTGC | 113 | 3174 |
| 970122 | N/A | N/A | 9922 | 9937 | TCCAAAGGGTTCAGTG | 93 | 3175 |
| 970132 | N/A | N/A | 10104 | 10119 | CCCTTGCTGCAAATCC | 104 | 3176 |
| 970142 | N/A | N/A | 10173 | 10188 | AACGCAAGTCTGAATT | 97 | 3177 |
| 970152 | N/A | N/A | 10209 | 10224 | TCCCATGGTTACTAAT | 110 | 3178 |
| 970162 | N/A | N/A | 10286 | 10301 | TCATTTACTGTTACCG | 44 | 3179 |
| 970172 | 769 | 784 | 10604 | 10619 | AACGAGCCAGTGCACA | 101 | 3180 |
| 970182 | N/A | N/A | 10834 | 10849 | AGGTTCCTGTCACCTG | 107 | 3181 |
| 970192 | N/A | N/A | 11095 | 11110 | GGTGCTCCTAAATCAC | 101 | 3182 |
| 970201 | N/A | N/A | 11335 | 11350 | GACTTATTTGTGGCTC | 80 | 3183 |
| 970211 | N/A | N/A | 11410 | 11425 | TGTATTACTCTTAGGC | 35 | 3184 |
| 970221 | N/A | N/A | 11538 | 11553 | CTTTATAGTAGGTAAG | 101 | 3185 |
| 970231 | N/A | N/A | 11658 | 11673 | CAAACCTTAAGCTATT | 66 | 3186 |
| 970241 | N/A | N/A | 11928 | 11943 | CAAGACAAGGGTTTGA | 103 | 3187 |
| 970251 | N/A | N/A | 12003 | 12018 | AAATCACGAGGTTGCC | 79 | 3188 |
| 970261 | N/A | N/A | 12208 | 12223 | TGTATCATGCATACCA | 97 | 3189 |
| 970271 | N/A | N/A | 12285 | 12300 | CTGGTAACTGTATGGA | 83 | 3190 |
| 970281 | N/A | N/A | 12591 | 12606 | ACTGGATATGTGGTGT | 90 | 3191 |
| 970291 | N/A | N/A | 12894 | 12909 | AATATAACGGTGTTTC | 92 | 3192 |
| 970301 | N/A | N/A | 13111 | 13126 | GAACAAGTGTATCTTT | 95 | 3193 |
| 970311 | N/A | N/A | 13370 | 13385 | GGACACCACCTCGAGG | 99 | 3194 |
| 970321 | N/A | N/A | 13912 | 13927 | TCTACTGGAGTCAAGC | 70 | 3195 |
| 970331 | N/A | N/A | 14194 | 14209 | TCCACCCTCCGTCTCA | 109 | 3196 |
| 970341 | N/A | N/A | 14231 | 14246 | CCTATAACTTCTCCTG | 107 | 3197 |
| 970351 | N/A | N/A | 14650 | 14665 | CCAGAAGTACGAGCAC | 103 | 3198 |
| 970361 | N/A | N/A | 14990 | 15005 | TGCAGCACCGTGGTGC | 101 | 3199 |
| 970371 | N/A | N/A | 15592 | 15607 | CGCGCAAGTCTACAGC | 87 | 3200 |
| 970381 | N/A | N/A | 15812 | 15827 | TCCAACCCTAGATAAC | 105 | 3201 |
| 970391 | N/A | N/A | 15894 | 15909 | TTCACACTGCCGTGAT | 112 | 3202 |
| 970401 | N/A | N/A | 16161 | 16176 | CCGCAAAAGAAACGAG | 107 | 3203 |
| 970411 | N/A | N/A | 16386 | 16401 | ATGGAACAGTAACTTG | 97 | 3204 |
| 970421 | N/A | N/A | 16666 | 16681 | GTCACGCAATGGCAAA | 102 | 3205 |
| 970431 | N/A | N/A | 16770 | 16785 | AACTAGTCGACAGCTA | 107 | 3206 |
| 970441 | N/A | N/A | 16933 | 16948 | AGCAAGAGCTTACTGT | 106 | 3207 |
| 970451 | 1254 | 1269 | 17047 | 17062 | GAATCTTGGCAGGGAG | 100 | 3208 |
| 970611 | 1451 | 1466 | 19568 | 19583 | GAATGGCGGATAGATC | 103 | 3209 |

TABLE 52

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 609408 | 4226 | 4241 | 22343 | 22358 | TTGTAAATGAGTCGGT | 27 | 195 |
| 969853 | N/A | N/A | 4221 | 4236 | CCCCTTAGGAACGAAG | 106 | 3210 |
| 969863 | N/A | N/A | 4362 | 4377 | AGCTGCGGAGCCTGGG | 69 | 3211 |
| 969873 | N/A | N/A | 4499 | 4514 | GGCTCTGCAAACGACA | 100 | 3212 |
| 969883 | N/A | N/A | 4833 | 4848 | TGTAACGCACCCGCAG | 104 | 3213 |
| 969893 | N/A | N/A | 5464 | 5479 | GTCCGCCCCGCGCGGT | 97 | 3214 |
| 969903 | N/A | N/A | 5665 | 5680 | AGAACGCACGGACGAA | 99 | 3215 |
| 969913 | N/A | N/A | 5756 | 5771 | GGCGCGGACGCACGGA | 90 | 3216 |
| 969923 | N/A | N/A | 5996 | 6011 | TCGCGCAAAGGGCAAG | 104 | 3217 |
| 969933 | N/A | N/A | 6264 | 6279 | CGGAGGTTCCTTGAGG | 58 | 3218 |
| 969943 | N/A | N/A | 6293 | 6308 | TGGGTATTTATAACCG | 96 | 3219 |
| 969953 | N/A | N/A | 6405 | 6420 | CCTTCAGATTTACACC | 109 | 3220 |
| 969963 | N/A | N/A | 6545 | 6560 | ATGTTGCATAGGCATC | 90 | 3221 |
| 969973 | 489 | 504 | 6968 | 6983 | CCTGTACACTTTGTAC | 102 | 3222 |
| 969983 | N/A | N/A | 7167 | 7182 | TCAACTTGTGACCCAC | 86 | 3223 |
| 969993 | N/A | N/A | 7216 | 7231 | TGAGGCATACAGTGTG | 82 | 3224 |
| 970003 | N/A | N/A | 7575 | 7590 | CATAAAGGACCCCGCC | 105 | 3225 |
| 970013 | N/A | N/A | 7636 | 7651 | CTGAGTTGTACAGGAC | 45 | 3226 |
| 970023 | N/A | N/A | 8100 | 8115 | AATGGCAGCACCGTGT | 100 | 3227 |
| 970033 | N/A | N/A | 8216 | 8231 | TAAGGCACTACTTCCA | 90 | 3228 |
| 970043 | N/A | N/A | 8382 | 8397 | GAGATACTTGTACTGT | 51 | 3229 |
| 970053 | N/A | N/A | 8480 | 8495 | TAGACTGACAGCCGAA | 97 | 3230 |
| 970063 | 630 | 645 | 9120 | 9135 | GGGTGGCATCATGTAG | 73 | 3231 |
| 970073 | 699 | 714 | 9189 | 9204 | CATGGGACATTGGTAC | 82 | 3232 |
| 970083 | N/A | N/A | 9429 | 9444 | GAGAGTAAACTTGGCT | 88 | 3233 |
| 970093 | N/A | N/A | 9552 | 9567 | TATTTATGAGCTTCCA | 79 | 3234 |
| 970103 | N/A | N/A | 9671 | 9686 | CATGGTATTTTCCGT | 62 | 3235 |
| 970113 | N/A | N/A | 9838 | 9853 | TTGCTAGATTCTCCCT | 84 | 3236 |
| 970123 | N/A | N/A | 9927 | 9942 | AAACATCCAAAGGGTT | 101 | 3237 |
| 970133 | N/A | N/A | 10106 | 10121 | AGCCCTTGCTGCAAAT | 111 | 3238 |
| 970143 | N/A | N/A | 10176 | 10191 | GTAAACGCAAGTCTGA | 86 | 3239 |
| 970153 | N/A | N/A | 10212 | 10227 | CTTTCCCATGGTTACT | 92 | 3240 |
| 970163 | N/A | N/A | 10306 | 10321 | CACCTGATCTTGCTGC | 88 | 3241 |
| 970173 | N/A | N/A | 10613 | 10628 | TGATGGAGAAACGAGC | 102 | 3242 |
| 970183 | 772 | 787 | 10837 | 10852 | AAAAGGTTCCTGTCAC | 105 | 3243 |
| 970193 | N/A | N/A | 11100 | 11115 | CTAATGGTGCTCCTAA | 96 | 3244 |
| 970202 | N/A | N/A | 11338 | 11353 | GAGGACTTATTTGTGG | 78 | 3245 |

TABLE 52-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | IRF4 (% UTC) | SEQ ID NO |
|---|---|---|---|---|---|---|---|
| 970212 | N/A | N/A | 11412 | 11427 | TGTGTATTACTCTTAG | 25 | 3246 |
| 970222 | N/A | N/A | 11539 | 11554 | TCTTTATAGTAGGTAA | 86 | 3247 |
| 970232 | N/A | N/A | 11662 | 11677 | ATTCCAAACCTTAAGC | 101 | 3248 |
| 970242 | N/A | N/A | 11931 | 11946 | GTTCAAGACAAGGGTT | 85 | 3249 |
| 970252 | N/A | N/A | 12006 | 12021 | CAGAAATCACGAGGTT | 75 | 3250 |
| 970262 | N/A | N/A | 12211 | 12226 | ATCTGTATCATGCATA | 76 | 3251 |
| 970272 | N/A | N/A | 12291 | 12306 | CTGCCACTGGTAACTG | 79 | 3252 |
| 970282 | N/A | N/A | 12657 | 12672 | GGGTGGTAGAATGTGA | 67 | 3253 |
| 970292 | N/A | N/A | 12926 | 12941 | ATGAACCCTAAGTTTA | 104 | 3254 |
| 970302 | N/A | N/A | 13114 | 13129 | AAGGAACAAGTGTATC | 87 | 3255 |
| 970312 | N/A | N/A | 13395 | 13410 | CTCCGGAGTCAGTGCT | 99 | 3256 |
| 970322 | N/A | N/A | 13961 | 13976 | GACCATCTGATCCGGA | 98 | 3257 |
| 970332 | N/A | N/A | 14203 | 14218 | ACAGTCCACTCCACCC | 86 | 3258 |
| 970342 | N/A | N/A | 14245 | 14260 | ACTTATAGCACTCTCC | 99 | 3259 |
| 970352 | N/A | N/A | 14669 | 14684 | AAACTTGGGTCACTTA | 95 | 3260 |
| 970362 | N/A | N/A | 15148 | 15163 | CTTAGAATGAGAGGTG | 99 | 3261 |
| 970372 | N/A | N/A | 15595 | 15610 | AGTCGCGCAAGTCTAC | 100 | 3262 |
| 970382 | N/A | N/A | 15846 | 15861 | GGCGAGTTGGCACAAT | 51 | 3263 |
| 970392 | N/A | N/A | 15896 | 15911 | CATTCACACTGCCGTG | 94 | 3264 |
| 970402 | N/A | N/A | 16163 | 16178 | GCCCGCAAAAGAAACG | 98 | 3265 |
| 970412 | N/A | N/A | 16416 | 16431 | TCTGAGTAGACTTCTT | 86 | 3266 |
| 970422 | N/A | N/A | 16670 | 16685 | CGTAGTCACGCAATGG | 85 | 3267 |
| 970432 | N/A | N/A | 16772 | 16787 | GGAACTAGTCGACAGC | 82 | 3268 |
| 970442 | N/A | N/A | 16958 | 16973 | ACCGAACACACCAGGT | 114 | 3269 |
| 970452 | 1277 | 1292 | 17070 | 17085 | TCTCCAAAGCATAGAG | 108 | 3270 |
| 970612 | 1465 | 1480 | 19582 | 19597 | ATTCTTGAATAGAGGA | 84 | 3271 |

Example 10: Effect of Mixed MOE and cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured MM.1R cells at a density of 5,000 cells per well were transfected by free uptake with 1,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set hIRF4_LTS34726 (described hereinabove in Example 7) was used to measure mRNA levels. IRF4 mRNA levels were adjusted according to total RNA content, as measured by RIBOGREEN®. Results are presented in the tables below as percent control of the amount of IRF4 mRNA, relative to untreated control (UTC) cells.

The modified oligonucleotides in Tables 53 through 58 are cEt and/or MOE containing gapmers. The modified oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a MOE and/or cEt sugar modification. The "Motif" column describes the sugar modifications of each oligonucleotide. "k" indicates a cEt sugar modification; "d" indicates deoxyribose; and "c" indicates a MOE modification. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Tables 53 through 58 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 53

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 13 | 195 |
| 881450 | 3252 | 3267 | 21369 | 21384 | ACACTTTTAGAGAGGA | kkk-d10-kkk | 27 | 2111 |
| 881659 | 4592 | 4607 | 22709 | 22724 | GGAAGTTTACACTGGA | kkk-d10-kkk | 4 | 2044 |
| 1013023 | N/A | N/A | 10142 | 10157 | ATGTTAGCCAATTCCT | k-d10-kekek | 100 | 3272 |
| 1013024 | N/A | N/A | 10143 | 10158 | TATGTTAGCCAATTCC | k-d10-kekek | 99 | 2991 |
| 1013025 | N/A | N/A | 10144 | 10159 | TTATGTTAGCCAATTC | k-d10-kekek | 98 | 3273 |
| 1013026 | N/A | N/A | 10145 | 10160 | TTTATGTTAGCCAATT | k-d10-kekek | 100 | 3274 |
| 1013032 | N/A | N/A | 10278 | 10293 | TGTTACCGATGCTTCA | k-d10-kekek | 74 | 2294 |
| 1013033 | N/A | N/A | 10279 | 10294 | CTGTTACCGATGCTTC | k-d10-kekek | 64 | 2993 |
| 1013034 | N/A | N/A | 10280 | 10295 | ACTGTTACCGATGCTT | k-d10-kekek | 80 | 3055 |
| 1013035 | N/A | N/A | 10281 | 10296 | TACTGTTACCGATGCT | k-d10-kekek | 90 | 3117 |
| 1013046 | N/A | N/A | 11016 | 11031 | GTGTCTAAAGTCCCAT | k-d10-kekek | 66 | 3275 |
| 1013047 | N/A | N/A | 11017 | 11032 | AGTGTCTAAAGTCCCA | k-d10-kekek | 101 | 2996 |
| 1013048 | N/A | N/A | 11018 | 11033 | AAGTGTCTAAAGTCCC | k-d10-kekek | 101 | 3276 |
| 1013049 | N/A | N/A | 11019 | 11034 | CAAGTGTCTAAAGTCC | k-d10-kekek | 93 | 3058 |
| 1013053 | N/A | N/A | 11119 | 11134 | AGCAGTGATGTCAGGT | k-d10-kekek | 23 | 2718 |
| 1013054 | N/A | N/A | 11120 | 11135 | AAGCAGTGATGTCAGG | k-d10-kekek | 72 | 3277 |
| 1013055 | N/A | N/A | 11121 | 11136 | CAAGCAGTGATGTCAG | k-d10-kekek | 65 | 3278 |
| 1013060 | N/A | N/A | 11395 | 11410 | CACATCAATGTTTTAG | k-d10-kekek | 55 | 3279 |
| 1013061 | N/A | N/A | 11396 | 11411 | GCACATCAATGTTTTA | k-d10-kekek | 87 | 1159 |
| 1013062 | N/A | N/A | 11397 | 11412 | GGCACATCAATGTTTT | k-d10-kekek | 72 | 3280 |
| 1013063 | N/A | N/A | 11398 | 11413 | AGGCACATCAATGTTT | k-d10-kekek | 95 | 1233 |
| 1013074 | N/A | N/A | 11411 | 11426 | GTGTATTACTCTTAGG | k-d10-kekek | 16 | 1540 |
| 1013075 | N/A | N/A | 11412 | 11427 | TGTGTATTACTCTTAG | k-d10-kekek | 42 | 3246 |
| 1013076 | N/A | N/A | 11413 | 11428 | ATGTGTATTACTCTTA | k-d10-kekek | 83 | 3281 |
| 1013077 | N/A | N/A | 11414 | 11429 | AATGTGTATTACTCTT | k-d10-kekek | 76 | 3282 |
| 1013090 | N/A | N/A | 11565 | 11580 | TGTGCTTGCCAAGCCT | k-d10-kekek | 101 | 3283 |
| 1013091 | N/A | N/A | 11566 | 11581 | GTGTGCTTGCCAAGCC | k-d10-kekek | 60 | 3000 |
| 1013092 | N/A | N/A | 11567 | 11582 | CGTGTGCTTGCCAAGC | k-d10-kekek | 70 | 3284 |
| 1013093 | N/A | N/A | 11568 | 11583 | ACGTGTGCTTGCCAAG | k-d10-kekek | 53 | 3285 |
| 1013125 | N/A | N/A | 12514 | 12529 | TTCATGTAAAGTCTGC | k-d10-kekek | 98 | 3286 |

TABLE 53-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1013126 | N/A | N/A | 12515 | 12530 | GTTCATGTAAAGTCTG | k-d10-kekek | 55 | 934 |
| 1013127 | N/A | N/A | 12516 | 12531 | AGTTCATGTAAAGTCT | k-d10-kekek | 75 | 755 |
| 1013128 | N/A | N/A | 12517 | 12532 | AAGTTCATGTAAAGTC | k-d10-kekek | 86 | 3287 |
| 1013462 | N/A | N/A | 10142 | 10157 | ATGTTAGCCAATTCCT | kk-d9-kekek | 72 | 3272 |
| 1013463 | N/A | N/A | 10143 | 10158 | TATGTTAGCCAATTCC | kk-d9-kekek | 92 | 2991 |
| 1013464 | N/A | N/A | 10144 | 10159 | TTATGTTAGCCAATTC | kk-d9-kekek | 89 | 3273 |
| 1013465 | N/A | N/A | 10145 | 10160 | TTTATGTTAGCCAATT | kk-d9-kekek | 91 | 3274 |
| 1013471 | N/A | N/A | 10278 | 10293 | TGTTACCGATGCTTCA | kk-d9-kekek | 72 | 2294 |
| 1013472 | N/A | N/A | 10279 | 10294 | CTGTTACCGATGCTTC | kk-d9-kekek | 48 | 2993 |
| 1013473 | N/A | N/A | 10280 | 10295 | ACTGTTACCGATGCTT | kk-d9-kekek | 70 | 3055 |
| 1013474 | N/A | N/A | 10281 | 10296 | TACTGTTACCGATGCT | kk-d9-kekek | 91 | 3117 |
| 1013485 | N/A | N/A | 11016 | 11031 | GTGTCTAAAGTCCCAT | kk-d9-kekek | 87 | 3275 |
| 1013486 | N/A | N/A | 11017 | 11032 | AGTGTCTAAAGTCCCA | kk-d9-kekek | 74 | 2996 |
| 1013487 | N/A | N/A | 11018 | 11033 | AAGTGTCTAAAGTCCC | kk-d9-kekek | 88 | 3276 |
| 1013488 | N/A | N/A | 11019 | 11034 | CAAGTGTCTAAAGTCC | kk-d9-kekek | 85 | 3058 |
| 1013492 | N/A | N/A | 11119 | 11134 | AGCAGTGATGTCAGGT | kk-d9-kekek | 34 | 2718 |
| 1013493 | N/A | N/A | 11120 | 11135 | AAGCAGTGATGTCAGG | kk-d9-kekek | 57 | 3277 |
| 1013494 | N/A | N/A | 11121 | 11136 | CAAGCAGTGATGTCAG | kk-d9-kekek | 49 | 3278 |
| 1013499 | N/A | N/A | 11395 | 11410 | CACATCAATGTTTTAG | kk-d9-kekek | 81 | 3279 |
| 1013500 | N/A | N/A | 11396 | 11411 | GCACATCAATGTTTTA | kk-d9-kekek | 82 | 1159 |
| 1013501 | N/A | N/A | 11397 | 11412 | GGCACATCAATGTTTT | kk-d9-kekek | 77 | 3280 |
| 1013502 | N/A | N/A | 11398 | 11413 | AGGCACATCAATGTTT | kk-d9-kekek | 84 | 1233 |
| 1013513 | N/A | N/A | 11411 | 11426 | GTGTATTACTCTTAGG | kk-d9-kekek | 14 | 1540 |
| 1013514 | N/A | N/A | 11412 | 11427 | TGTGTATTACTCTTAG | kk-d9-kekek | 13 | 3246 |
| 1013515 | N/A | N/A | 11413 | 11428 | ATGTGTATTACTCTTA | kk-d9-kekek | 46 | 3281 |
| 1013516 | N/A | N/A | 11414 | 11429 | AATGTGTATTACTCTT | kk-d9-kekek | 48 | 3282 |
| 1013529 | N/A | N/A | 11565 | 11580 | TGTGCTTGCCAAGCCT | kk-d9-kekek | 98 | 3283 |

TABLE 54

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 11 | 195 |
| 881450 | 3252 | 3267 | 21369 | 21384 | ACACTTTTAGAGAGGA | kkk-d10-kkk | 27 | 2111 |
| 881659 | 4592 | 4607 | 22709 | 22724 | GGAAGTTTACACTGGA | kkk-d10-kkk | 3 | 2044 |
| 1013530 | N/A | N/A | 11566 | 11581 | GTGTGCTTGCCAAGCC | kk-d9-kekek | 59 | 3000 |

TABLE 54-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1013531 | N/A | N/A | 11567 | 11582 | CGTGTGCTTGCCAAGC | kk-d9-kekek | 51 | 3284 |
| 1013532 | N/A | N/A | 11568 | 11583 | ACGTGTGCTTGCCAAG | kk-d9-kekek | 51 | 3285 |
| 1013564 | N/A | N/A | 12514 | 12529 | TTCATGTAAAGTCTGC | kk-d9-kekek | 90 | 3286 |
| 1013565 | N/A | N/A | 12515 | 12530 | GTTCATGTAAAGTCTG | kk-d9-kekek | 58 | 934 |
| 1013566 | N/A | N/A | 12516 | 12531 | AGTTCATGTAAAGTCT | kk-d9-kekek | 58 | 755 |
| 1013567 | N/A | N/A | 12517 | 12532 | AAGTTCATGTAAAGTC | kk-d9-kekek | 66 | 3287 |
| 1013902 | N/A | N/A | 10142 | 10157 | ATGTTAGCCAATTCCT | kk-d10-keke | 80 | 3272 |
| 1013903 | N/A | N/A | 10143 | 10158 | TATGTTAGCCAATTCC | kk-d10-keke | 92 | 2991 |
| 1013904 | N/A | N/A | 10144 | 10159 | TTATGTTAGCCAATTC | kk-d10-keke | 89 | 3273 |
| 1013905 | N/A | N/A | 10145 | 10160 | TTTATGTTAGCCAATT | kk-d10-keke | 89 | 3274 |
| 1013911 | N/A | N/A | 10278 | 10293 | TGTTACCGATGCTTCA | kk-d10-keke | 75 | 2294 |
| 1013912 | N/A | N/A | 10279 | 10294 | CTGTTACCGATGCTTC | kk-d10-keke | 57 | 2993 |
| 1013913 | N/A | N/A | 10280 | 10295 | ACTGTTACCGATGCTT | kk-d10-keke | 70 | 3055 |
| 1013914 | N/A | N/A | 10281 | 10296 | TACTGTTACCGATGCT | kk-d10-keke | 76 | 3117 |
| 1013925 | N/A | N/A | 11016 | 11031 | GTGTCTAAAGTCCCAT | kk-d10-keke | 91 | 3275 |
| 1013926 | N/A | N/A | 11017 | 11032 | AGTGTCTAAAGTCCCA | kk-d10-keke | 68 | 2996 |
| 1013927 | N/A | N/A | 11018 | 11033 | AAGTGTCTAAAGTCCC | kk-d10-keke | 90 | 3276 |
| 1013928 | N/A | N/A | 11019 | 11034 | CAAGTGTCTAAAGTCC | kk-d10-keke | 84 | 3058 |
| 1013932 | N/A | N/A | 11119 | 11134 | AGCAGTGATGTCAGGT | kk-d10-keke | 33 | 2718 |
| 1013933 | N/A | N/A | 11120 | 11135 | AAGCAGTGATGTCAGG | kk-d10-keke | 26 | 3277 |
| 1013934 | N/A | N/A | 11121 | 11136 | CAAGCAGTGATGTCAG | kk-d10-keke | 80 | 3278 |
| 1013939 | N/A | N/A | 11395 | 11410 | CACATCAATGTTTTAG | kk-d10-keke | 75 | 3279 |
| 1013940 | N/A | N/A | 11396 | 11411 | GCACATCAATGTTTTA | kk-d10-keke | 51 | 1159 |
| 1013941 | N/A | N/A | 11397 | 11412 | GGCACATCAATGTTTT | kk-d10-keke | 91 | 3280 |
| 1013942 | N/A | N/A | 11398 | 11413 | AGGCACATCAATGTTT | kk-d10-keke | 84 | 1233 |
| 1013953 | N/A | N/A | 11411 | 11426 | GTGTATTACTCTTAGG | kk-d10-keke | 22 | 1540 |
| 1013954 | N/A | N/A | 11412 | 11427 | TGTGTATTACTCTTAG | kk-d10-keke | 49 | 3246 |
| 1013955 | N/A | N/A | 11413 | 11428 | ATGTGTATTACTCTTA | kk-d10-keke | 53 | 3281 |
| 1013956 | N/A | N/A | 11414 | 11429 | AATGTGTATTACTCTT | kk-d10-keke | 92 | 3282 |
| 1013969 | N/A | N/A | 11565 | 11580 | TGTGCTTGCCAAGCCT | kk-d10-keke | 74 | 3283 |
| 1013970 | N/A | N/A | 11566 | 11581 | GTGTGCTTGCCAAGCC | kk-d10-keke | 63 | 3000 |
| 1013971 | N/A | N/A | 11567 | 11582 | CGTGTGCTTGCCAAGC | kk-d10-keke | 45 | 3284 |
| 1013972 | N/A | N/A | 11568 | 11583 | ACGTGTGCTTGCCAAG | kk-d10-keke | 94 | 3285 |
| 1014004 | N/A | N/A | 12514 | 12529 | TTCATGTAAAGTCTGC | kk-d10-keke | 51 | 3286 |
| 1014005 | N/A | N/A | 12515 | 12530 | GTTCATGTAAAGTCTG | kk-d10-keke | 69 | 934 |

TABLE 54-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014006 | N/A | N/A | 12516 | 12531 | AGTTCATGTAAAGTCT | kk-d10-keke | 55 | 755 |
| 1014007 | N/A | N/A | 12517 | 12532 | AAGTTCATGTAAAGTC | kk-d10-keke | 72 | 3287 |

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 9 | 195 |
| 881450 | 3252 | 3267 | 21369 | 21384 | ACACTTTTAGAGAGGA | kkk-d10-kkk | 17 | 2111 |
| 881659 | 4592 | 4607 | 22709 | 22724 | GGAAGTTTACACTGGA | kkk-d10-kkk | 2 | 2044 |
| 1014342 | N/A | N/A | 10142 | 10157 | ATGTTAGCCAATTCCT | kk-d9-kdkdk | 70 | 3272 |
| 1014343 | N/A | N/A | 10143 | 10158 | TATGTTAGCCAATTCC | kk-d9-kdkdk | 98 | 2991 |
| 1014344 | N/A | N/A | 10144 | 10159 | TTATGTTAGCCAATTC | kk-d9-kdkdk | 83 | 3273 |
| 1014345 | N/A | N/A | 10145 | 10160 | TTTATGTTAGCCAATT | kk-d9-kdkdk | 89 | 3274 |
| 1014351 | N/A | N/A | 10278 | 10293 | TGTTACCGATGCTTCA | kk-d9-kdkdk | 65 | 2294 |
| 1014352 | N/A | N/A | 10279 | 10294 | CTGTTACCGATGCTTC | kk-d9-kdkdk | 42 | 2993 |
| 1014353 | N/A | N/A | 10280 | 10295 | ACTGTTACCGATGCTT | kk-d9-kdkdk | 78 | 3055 |
| 1014354 | N/A | N/A | 10281 | 10296 | TACTGTTACCGATGCT | kk-d9-kdkdk | 93 | 3117 |
| 1014365 | N/A | N/A | 11016 | 11031 | GTGTCTAAAGTCCCAT | kk-d9-kdkdk | 80 | 3275 |
| 1014366 | N/A | N/A | 11017 | 11032 | AGTGTCTAAAGTCCCA | kk-d9-kdkdk | 86 | 2996 |
| 1014367 | N/A | N/A | 11018 | 11033 | AAGTGTCTAAAGTCCC | kk-d9-kdkdk | 87 | 3276 |
| 1014368 | N/A | N/A | 11019 | 11034 | CAAGTGTCTAAAGTCC | kk-d9-kdkdk | 97 | 3058 |
| 1014372 | N/A | N/A | 11119 | 11134 | AGCAGTGATGTCAGGT | kk-d9-kdkdk | 45 | 2718 |
| 1014373 | N/A | N/A | 11120 | 11135 | AAGCAGTGATGTCAGG | kk-d9-kdkdk | 40 | 3277 |
| 1014374 | N/A | N/A | 11121 | 11136 | CAAGCAGTGATGTCAG | kk-d9-kdkdk | 54 | 3278 |
| 1014379 | N/A | N/A | 11395 | 11410 | CACATCAATGTTTTAG | kk-d9-kdkdk | 72 | 3279 |
| 1014380 | N/A | N/A | 11396 | 11411 | GCACATCAATGTTTTA | kk-d9-kdkdk | 89 | 1159 |
| 1014381 | N/A | N/A | 11397 | 11412 | GGCACATCAATGTTTT | kk-d9-kdkdk | 74 | 3280 |
| 1014382 | N/A | N/A | 11398 | 11413 | AGGCACATCAATGTTT | kk-d9-kdkdk | 96 | 1233 |
| 1014393 | N/A | N/A | 11411 | 11426 | GTGTATTACTCTTAGG | kk-d9-kdkdk | 11 | 1540 |
| 1014394 | N/A | N/A | 11412 | 11427 | TGTGTATTACTCTTAG | kk-d9-kdkdk | 19 | 3246 |
| 1014395 | N/A | N/A | 11413 | 11428 | ATGTGTATTACTCTTA | kk-d9-kdkdk | 56 | 3281 |
| 1014396 | N/A | N/A | 11414 | 11429 | AATGTGTATTACTCTT | kk-d9-kdkdk | 90 | 3282 |
| 1014409 | N/A | N/A | 11565 | 11580 | TGTGCTTGCCAAGCCT | kk-d9-kdkdk | 77 | 3283 |
| 1014410 | N/A | N/A | 11566 | 11581 | GTGTGCTTGCCAAGCC | kk-d9-kdkdk | 41 | 3000 |
| 1014411 | N/A | N/A | 11567 | 11582 | CGTGTGCTTGCCAAGC | kk-d9-kdkdk | 33 | 3284 |

-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014412 | N/A | N/A | 11568 | 11583 | ACGTGTGCTTGCCAAG | kk-d9-kdkdk | 25 | 3285 |
| 1014444 | N/A | N/A | 12514 | 12529 | TTCATGTAAAGTCTGC | kk-d9-kdkdk | 86 | 3286 |
| 1014445 | N/A | N/A | 12515 | 12530 | GTTCATGTAAAGTCTG | kk-d9-kdkdk | 66 | 934 |
| 1014446 | N/A | N/A | 12516 | 12531 | AGTTCATGTAAAGTCT | kk-d9-kdkdk | 68 | 755 |
| 1014447 | N/A | N/A | 12517 | 12532 | AAGTTCATGTAAAGTC | kk-d9-kdkdk | 68 | 3287 |
| 1014783 | N/A | N/A | 10142 | 10157 | ATGTTAGCCAATTCCT | kk-d9-eeekk | 83 | 3272 |
| 1014784 | N/A | N/A | 10143 | 10158 | TATGTTAGCCAATTCC | kk-d9-eeekk | 92 | 2991 |
| 1014785 | N/A | N/A | 10144 | 10159 | TTATGTTAGCCAATTC | kk-d9-eeekk | 86 | 3273 |
| 1014786 | N/A | N/A | 10145 | 10160 | TTTATGTTAGCCAATT | kk-d9-eeekk | 97 | 3274 |
| 1014792 | N/A | N/A | 10278 | 10293 | TGTTACCGATGCTTCA | kk-d9-eeekk | 69 | 2294 |
| 1014793 | N/A | N/A | 10279 | 10294 | CTGTTACCGATGCTTC | kk-d9-eeekk | 36 | 2993 |
| 1014794 | N/A | N/A | 10280 | 10295 | ACTGTTACCGATGCTT | kk-d9-eeekk | 73 | 3055 |
| 1014795 | N/A | N/A | 10281 | 10296 | TACTGTTACCGATGCT | kk-d9-eeekk | 71 | 3117 |
| 1014806 | N/A | N/A | 11016 | 11031 | GTGTCTAAAGTCCCAT | kk-d9-eeekk | 77 | 3275 |
| 1014807 | N/A | N/A | 11017 | 11032 | AGTGTCTAAAGTCCCA | kk-d9-eeekk | 74 | 2996 |
| 1014808 | N/A | N/A | 11018 | 11033 | AAGTGTCTAAAGTCCC | kk-d9-eeekk | 79 | 3276 |
| 1014809 | N/A | N/A | 11019 | 11034 | CAAGTGTCTAAAGTCC | kk-d9-eeekk | 78 | 3058 |
| 1014813 | N/A | N/A | 11119 | 11134 | AGCAGTGATGTCAGGT | kk-d9-eeekk | 31 | 2718 |
| 1014814 | N/A | N/A | 11120 | 11135 | AAGCAGTGATGTCAGG | kk-d9-eeekk | 38 | 3277 |
| 1014815 | N/A | N/A | 11121 | 11136 | CAAGCAGTGATGTCAG | kk-d9-eeekk | 85 | 3278 |
| 1014820 | N/A | N/A | 11395 | 11410 | CACATCAATGTTTTAG | kk-d9-ceekk | 88 | 3279 |
| 1014821 | N/A | N/A | 11396 | 11411 | GCACATCAATGTTTTA | kk-d9-ceekk | 80 | 1159 |
| 1014822 | N/A | N/A | 11397 | 11412 | GGCACATCAATGTTTT | kk-d9-ceekk | 78 | 3280 |
| 1014823 | N/A | N/A | 11398 | 11413 | AGGCACATCAATGTTT | kk-d9-ceekk | 64 | 1233 |
| 1014834 | N/A | N/A | 11411 | 11426 | GTGTATTACTCTTAGG | kk-d9-eeekk | 12 | 1540 |

TABLE 56

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 14 | 195 |
| 881450 | 3252 | 3267 | 21369 | 21384 | ACACTTTTAGAGAGGA | kkk-d10-kkk | 24 | 2111 |
| 881659 | 4592 | 4607 | 22709 | 22724 | GGAAGTTTACACTGGA | kkk-d10-kkk | 2 | 2044 |
| 1014835 | N/A | N/A | 11412 | 11427 | TGTGTATTACTCTTAG | kk-d9-eeekk | 59 | 3246 |
| 1014836 | N/A | N/A | 11413 | 11428 | ATGTGTATTACTCTTA | kk-d9-eeekk | 60 | 3281 |

TABLE 56-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014837 | N/A | N/A | 11414 | 11429 | AATGTGTATTACTCTT | kk-d9-eeekk | 85 | 3282 |
| 1014850 | N/A | N/A | 11565 | 11580 | TGTGCTTGCCAAGCCT | kk-d9-eeekk | 55 | 3283 |
| 1014851 | N/A | N/A | 11566 | 11581 | GTGTGCTTGCCAAGCC | kk-d9-eeekk | 25 | 3000 |
| 1014852 | N/A | N/A | 11567 | 11582 | CGTGTGCTTGCCAAGC | kk-d9-eeekk | 40 | 3284 |
| 1014853 | N/A | N/A | 11568 | 11583 | ACGTGTGCTTGCCAAG | kk-d9-eeekk | 56 | 3285 |
| 1014885 | N/A | N/A | 12514 | 12529 | TTCATGTAAAGTCTGC | kk-d9-eeekk | 73 | 3286 |
| 1014886 | N/A | N/A | 12515 | 12530 | GTTCATGTAAAGTCTG | kk-d9-eeekk | 71 | 934 |
| 1014887 | N/A | N/A | 12516 | 12531 | AGTTCATGTAAAGTCT | kk-d9-eeekk | 59 | 755 |
| 1014888 | N/A | N/A | 12517 | 12532 | AAGTTCATGTAAAGTC | kk-d9-eeekk | 79 | 3287 |
| 1015224 | N/A | N/A | 10142 | 10157 | ATGTTAGCCAATTCCT | kk-d9-ekeke | 73 | 3272 |
| 1015225 | N/A | N/A | 10143 | 10158 | TATGTTAGCCAATTCC | kk-d9-ekeke | 98 | 2991 |
| 1015226 | N/A | N/A | 10144 | 10159 | TTATGTTAGCCAATTC | kk-d9-ekeke | 91 | 3273 |
| 1015227 | N/A | N/A | 10145 | 10160 | TTTATGTTAGCCAATT | kk-d9-ekeke | 88 | 3274 |
| 1015233 | N/A | N/A | 10278 | 10293 | TGTTACCGATGCTTCA | kk-d9-ekeke | 65 | 2294 |
| 1015234 | N/A | N/A | 10279 | 10294 | CTGTTACCGATGCTTC | kk-d9-ekeke | 50 | 2993 |
| 1015235 | N/A | N/A | 10280 | 10295 | ACTGTTACCGATGCTT | kk-d9-ekeke | 77 | 3055 |
| 1015236 | N/A | N/A | 10281 | 10296 | TACTGTTACCGATGCT | kk-d9-ekeke | 78 | 3117 |
| 1015247 | N/A | N/A | 11016 | 11031 | GTGTCTAAAGTCCCAT | kk-d9-ekeke | 68 | 3275 |
| 1015248 | N/A | N/A | 11017 | 11032 | AGTGTCTAAAGTCCCA | kk-d9-ekeke | 82 | 2996 |
| 1015249 | N/A | N/A | 11018 | 11033 | AAGTGTCTAAAGTCCC | kk-d9-ekeke | 87 | 3276 |
| 1015250 | N/A | N/A | 11019 | 11034 | CAAGTGTCTAAAGTCC | kk-d9-ekeke | 77 | 3058 |
| 1015254 | N/A | N/A | 11119 | 11134 | AGCAGTGATGTCAGGT | kk-d9-ekeke | 28 | 2718 |
| 1015255 | N/A | N/A | 11120 | 11135 | AAGCAGTGATGTCAGG | kk-d9-ekeke | 35 | 3277 |
| 1015256 | N/A | N/A | 11121 | 11136 | CAAGCAGTGATGTCAG | kk-d9-ekeke | 74 | 3278 |
| 1015261 | N/A | N/A | 11395 | 11410 | CACATCAATGTTTTAG | kk-d9-ekeke | 72 | 3279 |
| 1015262 | N/A | N/A | 11396 | 11411 | GCACATCAATGTTTTA | kk-d9-ekeke | 90 | 1159 |
| 1015263 | N/A | N/A | 11397 | 11412 | GGCACATCAATGTTTT | kk-d9-ekeke | 78 | 3280 |
| 1015264 | N/A | N/A | 11398 | 11413 | AGGCACATCAATGTTT | kk-d9-ekeke | 58 | 1233 |
| 1015275 | N/A | N/A | 11411 | 11426 | GTGTATTACTCTTAGG | kk-d9-ekeke | 11 | 1540 |
| 1015276 | N/A | N/A | 11412 | 11427 | TGTGTATTACTCTTAG | kk-d9-ekeke | 46 | 3246 |
| 1015277 | N/A | N/A | 11413 | 11428 | ATGTGTATTACTCTTA | kk-d9-ekeke | 40 | 3281 |
| 1015278 | N/A | N/A | 11414 | 11429 | AATGTGTATTACTCTT | kk-d9-ekeke | 76 | 3282 |
| 1015291 | N/A | N/A | 11565 | 11580 | TGTGCTTGCCAAGCCT | kk-d9-ekeke | 79 | 3283 |
| 1015292 | N/A | N/A | 11566 | 11581 | GTGTGCTTGCCAAGCC | kk-d9-ekeke | 83 | 3000 |
| 1015293 | N/A | N/A | 11567 | 11582 | CGTGTGCTTGCCAAGC | kk-d9-ekeke | 53 | 3284 |
| 1015294 | N/A | N/A | 11568 | 11583 | ACGTGTGCTTGCCAAG | kk-d9-ekeke | 41 | 3285 |
| 1015326 | N/A | N/A | 12514 | 12529 | TTCATGTAAAGTCTGC | kk-d9-ekeke | 68 | 3286 |

TABLE 56-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1015327 | N/A | N/A | 12515 | 12530 | GTTCATGTAAAGTCTG | kk-d9-ekeke | 64 | 934 |
| 1015328 | N/A | N/A | 12516 | 12531 | AGTTCATGTAAAGTCT | kk-d9-ekeke | 49 | 755 |
| 1015329 | N/A | N/A | 12517 | 12532 | AAGTTCATGTAAAGTC | kk-d9-ekeke | 66 | 3287 |

TABLE 57

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 18 | 195 |
| 881450 | 3252 | 3267 | 21369 | 21384 | ACACTTTTAGAGAGGA | kkk-d10-kkk | 28 | 2111 |
| 881659 | 4592 | 4607 | 22709 | 22724 | GGAAGTTTACACTGGA | kkk-d10-kkk | 4 | 2044 |
| 1012810 | N/A | N/A | 10142 | 10157 | ATGTTAGCCAATTCCT | kkk-d10-kkk | 70 | 3272 |
| 1012811 | N/A | N/A | 10144 | 10159 | TTATGTTAGCCAATTC | kkk-d10-kkk | 91 | 3273 |
| 1012812 | N/A | N/A | 10145 | 10160 | TTTATGTTAGCCAATT | kkk-d10-kkk | 75 | 3274 |
| 1012816 | N/A | N/A | 11016 | 11031 | GTGTCTAAAGTCCCAT | kkk-d10-kkk | 82 | 3275 |
| 1012817 | N/A | N/A | 11018 | 11033 | AAGTGTCTAAAGTCCC | kkk-d10-kkk | 50 | 3276 |
| 1012819 | N/A | N/A | 11120 | 11135 | AAGCAGTGATGTCAGG | kkk-d10-kkk | 34 | 3277 |
| 1012820 | N/A | N/A | 11121 | 11136 | CAAGCAGTGATGTCAG | kkk-d10-kkk | 40 | 3278 |
| 1012821 | N/A | N/A | 11395 | 11410 | CACATCAATGTTTTAG | kkk-d10-kkk | 34 | 3279 |
| 1012822 | N/A | N/A | 11397 | 11412 | GGCACATCAATGTTTT | kkk-d10-kkk | 82 | 3280 |
| 1012826 | N/A | N/A | 11413 | 11428 | ATGTGTATTACTCTTA | kkk-d10-kkk | 48 | 3281 |
| 1012827 | N/A | N/A | 11414 | 11429 | AATGTGTATTACTCTT | kkk-d10-kkk | 47 | 3282 |
| 1012835 | N/A | N/A | 11565 | 11580 | TGTGCTTGCCAAGCCT | kkk-d10-kkk | 62 | 3283 |
| 1012836 | N/A | N/A | 11567 | 11582 | CGTGTGCTTGCCAAGC | kkk-d10-kkk | 33 | 3284 |
| 1012837 | N/A | N/A | 11568 | 11583 | ACGTGTGCTTGCCAAG | kkk-d10-kkk | 46 | 3285 |
| 1012845 | N/A | N/A | 12514 | 12529 | TTCATGTAAAGTCTGC | kkk-d10-kkk | 43 | 3286 |
| 1012846 | N/A | N/A | 12517 | 12532 | AAGTTCATGTAAAGTC | kkk-d10-kkk | 57 | 3287 |
| 1015665 | N/A | N/A | 10142 | 10157 | ATGTTAGCCAATTCCT | k-d9-kekeke | 100 | 3272 |
| 1015666 | N/A | N/A | 10143 | 10158 | TATGTTAGCCAATTCC | k-d9-kekeke | 90 | 2991 |
| 1015667 | N/A | N/A | 10144 | 10159 | TTATGTTAGCCAATTC | k-d9-kekeke | 91 | 3273 |
| 1015668 | N/A | N/A | 10145 | 10160 | TTTATGTTAGCCAATT | k-d9-kekeke | 95 | 3274 |
| 1015674 | N/A | N/A | 10278 | 10293 | TGTTACCGATGCTTCA | k-d9-kekeke | 90 | 2294 |
| 1015675 | N/A | N/A | 10279 | 10294 | CTGTTACCGATGCTTC | k-d9-kekeke | 98 | 2993 |
| 1015676 | N/A | N/A | 10280 | 10295 | ACTGTTACCGATGCTT | k-d9-kekeke | 102 | 3055 |
| 1015677 | N/A | N/A | 10281 | 10296 | TACTGTTACCGATGCT | k-d9-kekeke | 82 | 3117 |

TABLE 57-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1015688 | N/A | N/A | 11016 | 11031 | GTGTCTAAAGTCCCAT | k-d9-kekeke | 95 | 3275 |
| 1015689 | N/A | N/A | 11017 | 11032 | AGTGTCTAAAGTCCCA | k-d9-kekeke | 112 | 2996 |
| 1015690 | N/A | N/A | 11018 | 11033 | AAGTGTCTAAAGTCCC | k-d9-kekeke | 96 | 3276 |
| 1015691 | N/A | N/A | 11019 | 11034 | CAAGTGTCTAAAGTCC | k-d9-kekeke | 89 | 3058 |
| 1015695 | N/A | N/A | 11119 | 11134 | AGCAGTGATGTCAGGT | k-d9-kekeke | 74 | 2718 |
| 1015696 | N/A | N/A | 11120 | 11135 | AAGCAGTGATGTCAGG | k-d9-kekeke | 66 | 3277 |
| 1015697 | N/A | N/A | 11121 | 11136 | CAAGCAGTGATGTCAG | k-d9-kekeke | 90 | 3278 |
| 1015702 | N/A | N/A | 11395 | 11410 | CACATCAATGTTTTAG | k-d9-kekeke | 102 | 3279 |
| 1015703 | N/A | N/A | 11396 | 11411 | GCACATCAATGTTTTA | k-d9-kekeke | 83 | 1159 |
| 1015704 | N/A | N/A | 11397 | 11412 | GGCACATCAATGTTTT | k-d9-kekeke | 91 | 3280 |
| 1015705 | N/A | N/A | 11398 | 11413 | AGGCACATCAATGTTT | k-d9-kekeke | 109 | 1233 |
| 1015716 | N/A | N/A | 11411 | 11426 | GTGTATTACTCTTAGG | k-d9-kekeke | 16 | 1540 |
| 1015717 | N/A | N/A | 11412 | 11427 | TGTGTATTACTCTTAG | k-d9-kekeke | 68 | 3246 |
| 1015718 | N/A | N/A | 11413 | 11428 | ATGTGTATTACTCTTA | k-d9-kekeke | 64 | 3281 |
| 1015719 | N/A | N/A | 11414 | 11429 | AATGTGTATTACTCTT | k-d9-kekeke | 88 | 3282 |
| 1015732 | N/A | N/A | 11565 | 11580 | TGTGCTTGCCAAGCCT | k-d9-kekeke | 103 | 3283 |
| 1015733 | N/A | N/A | 11566 | 11581 | GTGTGCTTGCCAAGCC | k-d9-kekeke | 94 | 3000 |
| 1015734 | N/A | N/A | 11567 | 11582 | CGTGTGCTTGCCAAGC | k-d9-kekeke | 76 | 3284 |
| 1015735 | N/A | N/A | 11568 | 11583 | ACGTGTGCTTGCCAAG | k-d9-kekeke | 60 | 3285 |
| 1015767 | N/A | N/A | 12514 | 12529 | TTCATGTAAAGTCTGC | k-d9-kekeke | 91 | 3286 |
| 1015768 | N/A | N/A | 12515 | 12530 | GTTCATGTAAAGTCTG | k-d9-kekeke | 76 | 934 |
| 1015769 | N/A | N/A | 12516 | 12531 | AGTTCATGTAAAGTCT | k-d9-kekeke | 71 | 755 |
| 1015770 | N/A | N/A | 12517 | 12532 | AAGTTCATGTAAAGTC | k-d9-kekeke | 86 | 3287 |

TABLE 58

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 11 | 195 |
| 881450 | 3252 | 3267 | 21369 | 21384 | ACACTTTTAGAGAGGA | kkk-d10-kkk | 29 | 2111 |
| 881659 | 4592 | 4607 | 22709 | 22724 | GGAAGTTTACACTGGA | kkk-d10-kkk | 4 | 2044 |
| 935595 | 3075 | 3090 | 21192 | 21207 | ACTAAGCTTGATAAAG | kkk-d10-kkk | 86 | 3288 |
| 935607 | 4195 | 4210 | 22312 | 22327 | AGTGTTCCAGGAGATA | kkk-d10-kkk | 20 | 3289 |
| 1012769 | N/A | N/A | 4810 | 4825 | GCTCCCGACACGCGCC | kkk-d10-kkk | 97 | 3290 |
| 1012772 | N/A | N/A | 6267 | 6282 | ATGCGGAGGTTCCTTG | kkk-d10-kkk | 53 | 3291 |
| 1012774 | N/A | N/A | 6271 | 6286 | TGAGATGCGGAGGTTC | kkk-d10-kkk | 67 | 3292 |

TABLE 58-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1012775 | N/A | N/A | 6273 | 6288 | AGTGAGATGCGGAGGT | kkk-d10-kkk | 35 | 3293 |
| 1012776 | N/A | N/A | 6275 | 6290 | AGAGTGAGATGCGGAG | kkk-d10-kkk | 35 | 3294 |
| 1012778 | N/A | N/A | 6281 | 6296 | ACCGGTAGAGTGAGAT | kkk-d10-kkk | 84 | 3295 |
| 1012782 | N/A | N/A | 7634 | 7649 | GAGTTGTACAGGACAG | kkk-d10-kkk | 49 | 3296 |
| 1012785 | N/A | N/A | 7638 | 7653 | GTCTGAGTTGTACAGG | kkk-d10-kkk | 48 | 3297 |
| 1012786 | N/A | N/A | 7640 | 7655 | AGGTCTGAGTTGTACA | kkk-d10-kkk | 45 | 3298 |
| 1012788 | N/A | N/A | 8386 | 8401 | AATGGAGATACTTGTA | kkk-d10-kkk | 74 | 3299 |
| 1012790 | N/A | N/A | 8389 | 8404 | GACAATGGAGATACTT | kkk-d10-kkk | 67 | 3300 |
| 1012791 | 678 | 693 | 9168 | 9183 | TTCCGGGTGTGGCTGA | kkk-d10-kkk | 75 | 3301 |
| 1012793 | 680 | 695 | 9170 | 9185 | ATTTCCGGGTGTGGCT | kkk-d10-kkk | 93 | 3302 |
| 1012795 | N/A | N/A | 9667 | 9682 | GTATTTTTCCGTTCCT | kkk-d10-kkk | 16 | 3303 |
| 1012796 | N/A | N/A | 9670 | 9685 | ATGGTATTTTTCCGTT | kkk-d10-kkk | 68 | 3304 |
| 1012799 | N/A | N/A | 9677 | 9692 | GTTTGCCATGGTATTT | kkk-d10-kkk | 59 | 3305 |
| 1012804 | N/A | N/A | 9840 | 9855 | CATTGCTAGATTCTCC | kkk-d10-kkk | 82 | 3306 |
| 1012806 | N/A | N/A | 9846 | 9861 | TTACCGCATTGCTAGA | kkk-d10-kkk | 87 | 3307 |
| 1012808 | N/A | N/A | 9851 | 9866 | CTGAGTTACCGCATTG | kkk-d10-kkk | 51 | 3308 |
| 1012809 | N/A | N/A | 10139 | 10154 | TTAGCCAATTCCTCCA | kkk-d10-kkk | 64 | 3309 |
| 1012813 | N/A | N/A | 10274 | 10289 | ACCGATGCTTCAAGAC | kkk-d10-kkk | 69 | 3310 |
| 1012814 | N/A | N/A | 10276 | 10291 | TTACCGATGCTTCAAG | kkk-d10-kkk | 84 | 3311 |
| 1012815 | N/A | N/A | 10282 | 10297 | TTACTGTTACCGATGC | kkk-d10-kkk | 74 | 3312 |
| 1012818 | N/A | N/A | 11020 | 11035 | GCAAGTGTCTAAAGTC | kkk-d10-kkk | 51 | 3313 |
| 1012823 | N/A | N/A | 11400 | 11415 | TTAGGCACATCAATGT | kkk-d10-kkk | 88 | 3314 |
| 1012825 | N/A | N/A | 11406 | 11421 | TTACTCTTAGGCACAT | kkk-d10-kkk | 56 | 3315 |
| 1012828 | N/A | N/A | 11523 | 11538 | GATCTCCATGGTGCAG | kkk-d10-kkk | 78 | 3316 |
| 1012831 | N/A | N/A | 11530 | 11545 | TAGGTAAGATCTCCAT | kkk-d10-kkk | 65 | 3317 |
| 1012834 | N/A | N/A | 11564 | 11579 | GTGCTTGCCAAGCCTA | kkk-d10-kkk | 73 | 3318 |
| 1012840 | N/A | N/A | 11659 | 11674 | CCAAACCTTAAGCTAT | kkk-d10-kkk | 82 | 3319 |
| 1012841 | N/A | N/A | 11663 | 11678 | AATTCCAAACCTTAAG | kkk-d10-kkk | 102 | 3320 |
| 1012843 | N/A | N/A | 11995 | 12010 | AGGTTGCCGAGATATA | kkk-d10-kkk | 46 | 3321 |
| 1012844 | N/A | N/A | 11997 | 12012 | CGAGGTTGCCGAGATA | kkk-d10-kkk | 34 | 3322 |
| 1012848 | N/A | N/A | 14251 | 14266 | GAGCCAACTTATAGCA | kkk-d10-kkk | 89 | 3323 |
| 1012850 | N/A | N/A | 14253 | 14268 | CAGAGCCAACTTATAG | kkk-d10-kkk | 70 | 3324 |
| 1012852 | N/A | N/A | 14734 | 14749 | GAAGCTTAGTTATCTG | kkk-d10-kkk | 55 | 3325 |
| 1012855 | N/A | N/A | 14739 | 14754 | GGCCTGAAGCTTAGTT | kkk-d10-kkk | 105 | 3326 |
| 1012859 | N/A | N/A | 15594 | 15609 | GTCGCGCAAGTCTACA | kkk-d10-kkk | 96 | 3327 |
| 1012860 | N/A | N/A | 15841 | 15856 | GTTGGCACAATTCTCT | kkk-d10-kkk | 78 | 3328 |

TABLE 58-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1012864 | N/A | N/A | 15845 | 15860 | GCGAGTTGGCACAATT | kkk-d10-kkk | 73 | 3329 |
| 1012866 | N/A | N/A | 15848 | 15863 | ATGGCGAGTTGGCACA | kkk-d10-kkk | 51 | 3330 |
| 1012867 | N/A | N/A | 15850 | 15865 | GAATGGCGAGTTGGCA | kkk-d10-kkk | 61 | 3331 |
| 1012869 | N/A | N/A | 15884 | 15899 | CGTGATCTGAGACTAC | kkk-d10-kkk | 75 | 3332 |
| 1012872 | N/A | N/A | 15889 | 15904 | ACTGCCGTGATCTGAG | kkk-d10-kkk | 66 | 3333 |
| 1012920 | 1441 | 1456 | 19558 | 19573 | TAGATCTGTGGTAATC | kkk-d10-kkk | 80 | 3334 |
| 1012921 | 1450 | 1465 | 19567 | 19582 | AATGGCGGATAGATCT | kkk-d10-kkk | 90 | 3335 |

Example 11: Effect of Mixed MOE and cEt Gapmers with Phosphorothioate Internucleoside Linkages on Human IRF4 In Vitro, Single Dose Modified oligonucleotides complementary to a human IRF4 nucleic acid were designed and tested for their effect on IRF4 mRNA in vitro.

Cultured MM.1R cells at a density of 5,000 cells per well were transfected by free uptake with 1,000 nM concentration of modified oligonucleotide or no modified oligonucleotide for untreated controls. After approximately 24 hours, RNA was isolated from the cells and IRF4 mRNA levels were measured by quantitative real-time PCR. Human primer probe set RTS4522 (forward sequence CGGAAATCCCGTACCAATGT, designated herein as SEQ ID NO: 3392; reverse sequence TGGCAACCATTTTCACAAGCT designated herein as SEQ ID NO: 3393; probe sequence TTTGGACCCCGCGGCCAC, designated herein as SEQ ID: 3394) was used to measure mRNA levels. IRF4 mRNA levels were adjusted according to total RNA content, as measured by RIBOGREEN®. Results are presented in the tables below as percent control of the amount of IRF4 mRNA, relative to untreated control (UTC) cells.

The modified oligonucleotides in Tables 59 through 64 are cEt and/or MOE containing gapmers. The modified oligonucleotides have a central gap segment comprising 2'-deoxynucleosides which is flanked by wing segments on the 5' direction and the 3' direction. At least one nucleoside in the 5' wing segment and/or one nucleoside in the 3' wing segment has a MOE and/or cEt sugar modification. The "Motif" column describes the sugar modifications of each oligonucleotide. "k" indicates a cEt sugar modification; "d" indicates deoxyribose; and "e" indicates a MOE modification. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 59 through 64 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity. As shown below, modified oligonucleotides complementary to human IRF4 reduced the amount of human IRF4 mRNA.

TABLE 59

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 24 | 195 |
| 881450 | 3252 | 3267 | 21369 | 21384 | ACACTTTTAGAGAGGA | kkk-d10-kkk | 29 | 2111 |
| 881659 | 4592 | 4607 | 22709 | 22724 | GGAAGTTTACACTGGA | kkk-d10-kkk | 14 | 2044 |
| 1013023 | N/A | N/A | 10142 | 10157 | ATGTTAGCCAATTCCT | k-d10-kekek | 93 | 3272 |
| 1013024 | N/A | N/A | 10143 | 10158 | TATGTTAGCCAATTCC | k-d10-kekek | 99 | 2991 |
| 1013025 | N/A | N/A | 10144 | 10159 | TTATGTTAGCCAATTC | k-d10-kekek | 94 | 3273 |
| 1013026 | N/A | N/A | 10145 | 10160 | TTTATGTTAGCCAATT | k-d10-kekek | 112 | 3274 |
| 1013032 | N/A | N/A | 10278 | 10293 | TGTTACCGATGCTTCA | k-d10-kekek | 82 | 2294 |
| 1013033 | N/A | N/A | 10279 | 10294 | CTGTTACCGATGCTTC | k-d10-kekek | 74 | 2993 |

TABLE 59-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1013034 | N/A | N/A | 10280 | 10295 | ACTGTTACCGATGCTT | k-d10-kekek | 80 | 3055 |
| 1013035 | N/A | N/A | 10281 | 10296 | TACTGTTACCGATGCT | k-d10-kekek | 98 | 3117 |
| 1013046 | N/A | N/A | 11016 | 11031 | GTGTCTAAAGTCCCAT | k-d10-kekek | 77 | 3275 |
| 1013047 | N/A | N/A | 11017 | 11032 | AGTGTCTAAAGTCCCA | k-d10-kekek | 97 | 2996 |
| 1013048 | N/A | N/A | 11018 | 11033 | AAGTGTCTAAAGTCCC | k-d10-kekek | 101 | 3276 |
| 1013049 | N/A | N/A | 11019 | 11034 | CAAGTGTCTAAAGTCC | k-d10-kekek | 88 | 3058 |
| 1013053 | N/A | N/A | 11119 | 11134 | AGCAGTGATGTCAGGT | k-d10-kekek | 33 | 2718 |
| 1013054 | N/A | N/A | 11120 | 11135 | AAGCAGTGATGTCAGG | k-d10-kekek | 61 | 3277 |
| 1013055 | N/A | N/A | 11121 | 11136 | CAAGCAGTGATGTCAG | k-d10-kekek | 57 | 3278 |
| 1013060 | N/A | N/A | 11395 | 11410 | CACATCAATGTTTTAG | k-d10-kekek | 81 | 3279 |
| 1013061 | N/A | N/A | 11396 | 11411 | GCACATCAATGTTTTA | k-d10-kekek | 100 | 1159 |
| 1013062 | N/A | N/A | 11397 | 11412 | GGCACATCAATGTTTT | k-d10-kekek | 75 | 3280 |
| 1013063 | N/A | N/A | 11398 | 11413 | AGGCACATCAATGTTT | k-d10-kekek | 95 | 1233 |
| 1013074 | N/A | N/A | 11411 | 11426 | GTGTATTACTCTTAGG | k-d10-kekek | 20 | 1540 |
| 1013075 | N/A | N/A | 11412 | 11427 | TGTGTATTACTCTTAG | k-d10-kekek | 44 | 3246 |
| 1013076 | N/A | N/A | 11413 | 11428 | ATGTGTATTACTCTTA | k-d10-kekek | 96 | 3281 |
| 1013077 | N/A | N/A | 11414 | 11429 | AATGTGTATTACTCTT | k-d10-kekek | 71 | 3282 |
| 1013090 | N/A | N/A | 11565 | 11580 | TGTGCTTGCCAAGCCT | k-d10-kekek | 97 | 3283 |
| 1013091 | N/A | N/A | 11566 | 11581 | GTGTGCTTGCCAAGCC | k-d10-kekek | 77 | 3000 |
| 1013092 | N/A | N/A | 11567 | 11582 | CGTGTGCTTGCCAAGC | k-d10-kekek | 68 | 3284 |
| 1013093 | N/A | N/A | 11568 | 11583 | ACGTGTGCTTGCCAAG | k-d10-kekek | 63 | 3285 |
| 1013125 | N/A | N/A | 12514 | 12529 | TTCATGTAAAGTCTGC | k-d10-kekek | 118 | 3286 |
| 1013126 | N/A | N/A | 12515 | 12530 | GTTCATGTAAAGTCTG | k-d10-kekek | 78 | 934 |
| 1013127 | N/A | N/A | 12516 | 12531 | AGTTCATGTAAAGTCT | k-d10-kekek | 78 | 755 |
| 1013128 | N/A | N/A | 12517 | 12532 | AAGTTCATGTAAAGTC | k-d10-kekek | 94 | 3287 |
| 1013207 | N/A | N/A | 18073 | 18088 | GTTGGCTGGTCTTTGT | k-d10-kekek | 77 | 3336 |
| 1013208 | N/A | N/A | 18074 | 18089 | GGTTGGCTGGTCTTTG | k-d10-kekek | 53 | 3337 |
| 1013209 | N/A | N/A | 18075 | 18090 | TGGTTGGCTGGTCTTT | k-d10-kekek | 91 | 3338 |
| 1013210 | N/A | N/A | 18076 | 18091 | TTGGTTGGCTGGTCTT | k-d10-kekek | 66 | 3339 |
| 1013213 | N/A | N/A | 18087 | 18102 | TTATATACTGGTTGGT | k-d10-kekek | 78 | 1179 |
| 1013214 | N/A | N/A | 18088 | 18103 | ATTATATACTGGTTGG | k-d10-kekek | 78 | 3340 |
| 1013215 | N/A | N/A | 18089 | 18104 | GATTATATACTGGTTG | k-d10-kekek | 52 | 1254 |
| 1013216 | N/A | N/A | 18090 | 18105 | GGATTATATACTGGTT | k-d10-kekek | 65 | 1330 |
| 1013217 | N/A | N/A | 18091 | 18106 | GGGATTATATACTGGT | k-d10-kekek | 66 | 3341 |
| 1013218 | N/A | N/A | 18092 | 18107 | TGGGATTATATACTGG | k-d10-kekek | 57 | 3342 |
| 1013232 | N/A | N/A | 18571 | 18586 | TGATAGCTGAGCTGAT | k-d10-kekek | 78 | 2546 |

TABLE 59-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1013233 | N/A | N/A | 18572 | 18587 | GTGATAGCTGAGCTGA | k-d10-kekek | 71 | 3343 |
| 1013234 | N/A | N/A | 18573 | 18588 | TGTGATAGCTGAGCTG | k-d10-kekek | 102 | 3344 |
| 1013235 | N/A | N/A | 18574 | 18589 | ATGTGATAGCTGAGCT | k-d10-kekek | 103 | 3345 |
| 1013236 | N/A | N/A | 18575 | 18590 | GATGTGATAGCTGAGC | k-d10-kekek | 50 | 3346 |
| 1013237 | N/A | N/A | 18576 | 18591 | TGATGTGATAGCTGAG | k-d10-kekek | 82 | 3347 |
| 1013238 | N/A | N/A | 18577 | 18592 | TTGATGTGATAGCTGA | k-d10-kekek | 88 | 3348 |
| 1013252 | N/A | N/A | 18611 | 18626 | AGTGACTTGCATCCAT | k-d10-kekek | 98 | 3349 |
| 1013253 | N/A | N/A | 18612 | 18627 | CAGTGACTTGCATCCA | k-d10-kekek | 71 | 3350 |
| 1013254 | N/A | N/A | 18613 | 18628 | ACAGTGACTTGCATCC | k-d10-kekek | 105 | 3351 |
| 1013255 | N/A | N/A | 18614 | 18629 | GACAGTGACTTGCATC | k-d10-kekek | 92 | 3352 |
| 1013462 | N/A | N/A | 10142 | 10157 | ATGTTAGCCAATTCCT | kk-d9-kekek | 56 | 3272 |
| 1013463 | N/A | N/A | 10143 | 10158 | TATGTTAGCCAATTCC | kk-d9-kekek | 97 | 2991 |
| 1013464 | N/A | N/A | 10144 | 10159 | TTATGTTAGCCAATTC | kk-d9-kekek | 81 | 3273 |
| 1013465 | N/A | N/A | 10145 | 10160 | TTTATGTTAGCCAATT | kk-d9-kekek | 85 | 3274 |
| 1013471 | N/A | N/A | 10278 | 10293 | TGTTACCGATGCTTCA | kk-d9-kekek | 79 | 2294 |
| 1013472 | N/A | N/A | 10279 | 10294 | CTGTTACCGATGCTTC | kk-d9-kekek | 56 | 2993 |
| 1013473 | N/A | N/A | 10280 | 10295 | ACTGTTACCGATGCTT | kk-d9-kekek | 82 | 3055 |
| 1013474 | N/A | N/A | 10281 | 10296 | TACTGTTACCGATGCT | kk-d9-kekek | 73 | 3117 |
| 1013485 | N/A | N/A | 11016 | 11031 | GTGTCTAAAGTCCCAT | kk-d9-kekek | 61 | 3275 |
| 1013486 | N/A | N/A | 11017 | 11032 | AGTGTCTAAAGTCCCA | kk-d9-kekek | 91 | 2996 |
| 1013487 | N/A | N/A | 11018 | 11033 | AAGTGTCTAAAGTCCC | kk-d9-kekek | 78 | 3276 |
| 1013488 | N/A | N/A | 11019 | 11034 | CAAGTGTCTAAAGTCC | kk-d9-kekek | 94 | 3058 |
| 1013492 | N/A | N/A | 11119 | 11134 | AGCAGTGATGTCAGGT | kk-d9-kekek | 33 | 2718 |
| 1013493 | N/A | N/A | 11120 | 11135 | AAGCAGTGATGTCAGG | kk-d9-kekek | 56 | 3277 |
| 1013494 | N/A | N/A | 11121 | 11136 | CAAGCAGTGATGTCAG | kk-d9-kekek | 48 | 3278 |
| 1013499 | N/A | N/A | 11395 | 11410 | CACATCAATGTTTTAG | kk-d9-kekek | 66 | 3279 |
| 1013500 | N/A | N/A | 11396 | 11411 | GCACATCAATGTTTTA | kk-d9-kekek | 85 | 1159 |
| 1013501 | N/A | N/A | 11397 | 11412 | GGCACATCAATGTTTT | kk-d9-kekek | 81 | 3280 |
| 1013502 | N/A | N/A | 11398 | 11413 | AGGCACATCAATGTTT | kk-d9-kekek | 81 | 1233 |
| 1013513 | N/A | N/A | 11411 | 11426 | GTGTATTACTCTTAGG | kk-d9-kekek | 22 | 1540 |
| 1013514 | N/A | N/A | 11412 | 11427 | TGTGTATTACTCTTAG | kk-d9-kekek | 21 | 3246 |
| 1013515 | N/A | N/A | 11413 | 11428 | ATGTGTATTACTCTTA | kk-d9-kekek | 51 | 3281 |
| 1013516 | N/A | N/A | 11414 | 11429 | AATGTGTATTACTCTT | kk-d9-kekek | 59 | 3282 |
| 1013529 | N/A | N/A | 11565 | 11580 | TGTGCTTGCCAAGCCT | kk-d9-kekek | 82 | 3283 |

TABLE 60

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 18 | 195 |
| 881450 | 3252 | 3267 | 21369 | 21384 | ACACTTTTAGAGAGGA | kkk-d10-kkk | 36 | 2111 |
| 881659 | 4592 | 4607 | 22709 | 22724 | GGAAGTTTACACTGGA | kkk-d10-kkk | 10 | 2044 |
| 1013530 | N/A | N/A | 11566 | 11581 | GTGTGCTTGCCAAGCC | kk-d9-kekek | 61 | 3000 |
| 1013531 | N/A | N/A | 11567 | 11582 | CGTGTGCTTGCCAAGC | kk-d9-kekek | 57 | 3284 |
| 1013532 | N/A | N/A | 11568 | 11583 | ACGTGTGCTTGCCAAG | kk-d9-kekek | 56 | 3285 |
| 1013564 | N/A | N/A | 12514 | 12529 | TTCATGTAAAGTCTGC | kk-d9-kekek | 88 | 3286 |
| 1013565 | N/A | N/A | 12515 | 12530 | GTTCATGTAAAGTCTG | kk-d9-kekek | 66 | 934 |
| 1013566 | N/A | N/A | 12516 | 12531 | AGTTCATGTAAAGTCT | kk-d9-kekek | 69 | 755 |
| 1013567 | N/A | N/A | 12517 | 12532 | AAGTTCATGTAAAGTC | kk-d9-kekek | 73 | 3287 |
| 1013646 | N/A | N/A | 18073 | 18088 | GTTGGCTGGTCTTTGT | kk-d9-kekek | 38 | 3336 |
| 1013647 | N/A | N/A | 18074 | 18089 | GGTTGGCTGGTCTTTG | kk-d9-kekek | 33 | 3337 |
| 1013648 | N/A | N/A | 18075 | 18090 | TGGTTGGCTGGTCTTT | kk-d9-kekek | 56 | 3338 |
| 1013649 | N/A | N/A | 18076 | 18091 | TTGGTTGGCTGGTCTT | kk-d9-kekek | 35 | 3339 |
| 1013652 | N/A | N/A | 18087 | 18102 | TTATATACTGGTTGGT | kk-d9-kekek | 50 | 1179 |
| 1013653 | N/A | N/A | 18088 | 18103 | ATTATATACTGGTTGG | kk-d9-kekek | 48 | 3340 |
| 1013654 | N/A | N/A | 18089 | 18104 | GATTATATACTGGTTG | kk-d9-kekek | 55 | 1254 |
| 1013655 | N/A | N/A | 18090 | 18105 | GGATTATATACTGGTT | kk-d9-kekek | 35 | 1330 |
| 1013656 | N/A | N/A | 18091 | 18106 | GGGATTATATACTGGT | kk-d9-kekek | 60 | 3341 |
| 1013657 | N/A | N/A | 18092 | 18107 | TGGGATTATATACTGG | kk-d9-kekek | 58 | 3342 |
| 1013672 | N/A | N/A | 18572 | 18587 | GTGATAGCTGAGCTGA | kk-d9-kekek | 61 | 3343 |
| 1013673 | N/A | N/A | 18573 | 18588 | TGTGATAGCTGAGCTG | kk-d9-kekek | 83 | 3344 |
| 1013674 | N/A | N/A | 18574 | 18589 | ATGTGATAGCTGAGCT | kk-d9-kekek | 76 | 3345 |
| 1013675 | N/A | N/A | 18575 | 18590 | GATGTGATAGCTGAGC | kk-d9-kekek | 69 | 3346 |
| 1013676 | N/A | N/A | 18576 | 18591 | TGATGTGATAGCTGAG | kk-d9-kekek | 102 | 3347 |
| 1013677 | N/A | N/A | 18577 | 18592 | TTGATGTGATAGCTGA | kk-d9-kekek | 76 | 3348 |
| 1013691 | N/A | N/A | 18611 | 18626 | AGTGACTTGCATCCAT | kk-d9-kekek | 73 | 3349 |
| 1013692 | N/A | N/A | 18612 | 18627 | CAGTGACTTGCATCCA | kk-d9-kekek | 74 | 3350 |
| 1013693 | N/A | N/A | 18613 | 18628 | ACAGTGACTTGCATCC | kk-d9-kekek | 68 | 3351 |
| 1013694 | N/A | N/A | 18614 | 18629 | GACAGTGACTTGCATC | kk-d9-kekek | 95 | 3352 |
| 1013902 | N/A | N/A | 10142 | 10157 | ATGTTAGCCAATTCCT | kk-d10-keke | 85 | 3272 |
| 1013903 | N/A | N/A | 10143 | 10158 | TATGTTAGCCAATTCC | kk-d10-keke | 75 | 2991 |
| 1013904 | N/A | N/A | 10144 | 10159 | TTATGTTAGCCAATTC | kk-d10-keke | 84 | 3273 |
| 1013905 | N/A | N/A | 10145 | 10160 | TTTATGTTAGCCAATT | kk-d10-keke | 105 | 3274 |
| 1013911 | N/A | N/A | 10278 | 10293 | TGTTACCGATGCTTCA | kk-d10-keke | 58 | 2294 |
| 1013912 | N/A | N/A | 10279 | 10294 | CTGTTACCGATGCTTC | kk-d10-keke | 63 | 2993 |
| 1013913 | N/A | N/A | 10280 | 10295 | ACTGTTACCGATGCTT | kk-d10-keke | 52 | 3055 |

TABLE 60-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1013914 | N/A | N/A | 10281 | 10296 | TACTGTTACCGATGCT | kk-d10-keke | 83 | 3117 |
| 1013925 | N/A | N/A | 11016 | 11031 | GTGTCTAAAGTCCCAT | kk-d10-keke | 94 | 3275 |
| 1013926 | N/A | N/A | 11017 | 11032 | AGTGTCTAAAGTCCCA | kk-d10-keke | 61 | 2996 |
| 1013927 | N/A | N/A | 11018 | 11033 | AAGTGTCTAAAGTCCC | kk-d10-keke | 88 | 3276 |
| 1013928 | N/A | N/A | 11019 | 11034 | CAAGTGTCTAAAGTCC | kk-d10-keke | 83 | 3058 |
| 1013932 | N/A | N/A | 11119 | 11134 | AGCAGTGATGTCAGGT | kk-d10-keke | 36 | 2718 |
| 1013933 | N/A | N/A | 11120 | 11135 | AAGCAGTGATGTCAGG | kk-d10-keke | 24 | 3277 |
| 1013934 | N/A | N/A | 11121 | 11136 | CAAGCAGTGATGTCAG | kk-d10-keke | 74 | 3278 |
| 1013939 | N/A | N/A | 11395 | 11410 | CACATCAATGTTTTAG | kk-d10-keke | 61 | 3279 |
| 1013940 | N/A | N/A | 11396 | 11411 | GCACATCAATGTTTTA | kk-d10-keke | 50 | 1159 |
| 1013941 | N/A | N/A | 11397 | 11412 | GGCACATCAATGTTTT | kk-d10-keke | 91 | 3280 |
| 1013942 | N/A | N/A | 11398 | 11413 | AGGCACATCAATGTTT | kk-d10-keke | 86 | 1233 |
| 1013953 | N/A | N/A | 11411 | 11426 | GTGTATTACTCTTAGG | kk-d10-keke | 28 | 1540 |
| 1013954 | N/A | N/A | 11412 | 11427 | TGTGTATTACTCTTAG | kk-d10-keke | 61 | 3246 |
| 1013955 | N/A | N/A | 11413 | 11428 | ATGTGTATTACTCTTA | kk-d10-keke | 52 | 3281 |
| 1013956 | N/A | N/A | 11414 | 11429 | AATGTGTATTACTCTT | kk-d10-keke | 78 | 3282 |
| 1013969 | N/A | N/A | 11565 | 11580 | TGTGCTTGCCAAGCCT | kk-d10-keke | 70 | 3283 |
| 1013970 | N/A | N/A | 11566 | 11581 | GTGTGCTTGCCAAGCC | kk-d10-keke | 53 | 3000 |
| 1013971 | N/A | N/A | 11567 | 11582 | CGTGTGCTTGCCAAGC | kk-d10-keke | 55 | 3284 |
| 1013972 | N/A | N/A | 11568 | 11583 | ACGTGTGCTTGCCAAG | kk-d10-keke | 74 | 3285 |
| 1014004 | N/A | N/A | 12514 | 12529 | TTCATGTAAAGTCTGC | kk-d10-keke | 72 | 3286 |
| 1014005 | N/A | N/A | 12515 | 12530 | GTTCATGTAAAGTCTG | kk-d10-keke | 58 | 934 |
| 1014006 | N/A | N/A | 12516 | 12531 | AGTTCATGTAAAGTCT | kk-d10-keke | 51 | 755 |
| 1014007 | N/A | N/A | 12517 | 12532 | AAGTTCATGTAAAGTC | kk-d10-keke | 80 | 3287 |
| 1014086 | N/A | N/A | 18073 | 18088 | GTTGGCTGGTCTTTGT | kk-d10-keke | 75 | 3336 |
| 1014087 | N/A | N/A | 18074 | 18089 | GGTTGGCTGGTCTTTG | kk-d10-keke | 24 | 3337 |
| 1014088 | N/A | N/A | 18075 | 18090 | TGGTTGGCTGGTCTTT | kk-d10-keke | 20 | 3338 |
| 1014089 | N/A | N/A | 18076 | 18091 | TTGGTTGGCTGGTCTT | kk-d10-keke | 73 | 3339 |
| 1014092 | N/A | N/A | 18087 | 18102 | TTATATACTGGTTGGT | kk-d10-keke | 53 | 1179 |
| 1014093 | N/A | N/A | 18088 | 18103 | ATTATATACTGGTTGG | kk-d10-keke | 68 | 3340 |
| 1014094 | N/A | N/A | 18089 | 18104 | GATTATATACTGGTTG | kk-d10-keke | 55 | 1254 |
| 1014095 | N/A | N/A | 18090 | 18105 | GGATTATATACTGGTT | kk-d10-keke | 22 | 1330 |
| 1014096 | N/A | N/A | 18091 | 18106 | GGGATTATATACTGGT | kk-d10-keke | 54 | 3341 |
| 1014097 | N/A | N/A | 18092 | 18107 | TGGGATTATATACTGG | kk-d10-keke | 32 | 3342 |
| 1014111 | N/A | N/A | 18571 | 18586 | TGATAGCTGAGCTGAT | kk-d10-keke | 117 | 2546 |
| 1014112 | N/A | N/A | 18572 | 18587 | GTGATAGCTGAGCTGA | kk-d10-keke | 65 | 3343 |

TABLE 60-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014113 | N/A | N/A | 18573 | 18588 | TGTGATAGCTGAGCTG | kk-d10-keke | 84 | 3344 |
| 1014114 | N/A | N/A | 18574 | 18589 | ATGTGATAGCTGAGCT | kk-d10-keke | 96 | 3345 |
| 1014115 | N/A | N/A | 18575 | 18590 | GATGTGATAGCTGAGC | kk-d10-keke | 36 | 3346 |
| 1014116 | N/A | N/A | 18576 | 18591 | TGATGTGATAGCTGAG | kk-d10-keke | 46 | 3347 |
| 1014117 | N/A | N/A | 18577 | 18592 | TTGATGTGATAGCTGA | kk-d10-keke | 89 | 3348 |

TABLE 61

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 24 | 195 |
| 881450 | 3252 | 3267 | 21369 | 21384 | ACACTTTTAGAGAGGA | kkk-d10-kkk | 32 | 2111 |
| 881659 | 4592 | 4607 | 22709 | 22724 | GGAAGTTTACACTGGA | kkk-d10-kkk | 11 | 2044 |
| 1014131 | N/A | N/A | 18611 | 18626 | AGTGACTTGCATCCAT | kk-d10-keke | 50 | 3349 |
| 1014132 | N/A | N/A | 18612 | 18627 | CAGTGACTTGCATCCA | kk-d10-keke | 67 | 3350 |
| 1014133 | N/A | N/A | 18613 | 18628 | ACAGTGACTTGCATCC | kk-d10-keke | 70 | 3351 |
| 1014134 | N/A | N/A | 18614 | 18629 | GACAGTGACTTGCATC | kk-d10-keke | 75 | 3352 |
| 1014342 | N/A | N/A | 10142 | 10157 | ATGTTAGCCAATTCCT | kk-d9-kdkdk | 97 | 3272 |
| 1014343 | N/A | N/A | 10143 | 10158 | TATGTTAGCCAATTCC | kk-d9-kdkdk | 66 | 2991 |
| 1014344 | N/A | N/A | 10144 | 10159 | TTATGTTAGCCAATTC | kk-d9-kdkdk | 74 | 3273 |
| 1014345 | N/A | N/A | 10145 | 10160 | TTTATGTTAGCCAATT | kk-d9-kdkdk | 66 | 3274 |
| 1014351 | N/A | N/A | 10278 | 10293 | TGTTACCGATGCTTCA | kk-d9-kdkdk | 74 | 2294 |
| 1014352 | N/A | N/A | 10279 | 10294 | CTGTTACCGATGCTTC | kk-d9-kdkdk | 48 | 2993 |
| 1014353 | N/A | N/A | 10280 | 10295 | ACTGTTACCGATGCTT | kk-d9-kdkdk | 69 | 3055 |
| 1014354 | N/A | N/A | 10281 | 10296 | TACTGTTACCGATGCT | kk-d9-kdkdk | 82 | 3117 |
| 1014365 | N/A | N/A | 11016 | 11031 | GTGTCTAAAGTCCCAT | kk-d9-kdkdk | 95 | 3275 |
| 1014366 | N/A | N/A | 11017 | 11032 | AGTGTCTAAAGTCCCA | kk-d9-kdkdk | 105 | 2996 |
| 1014367 | N/A | N/A | 11018 | 11033 | AAGTGTCTAAAGTCCC | kk-d9-kdkdk | 79 | 3276 |
| 1014368 | N/A | N/A | 11019 | 11034 | CAAGTGTCTAAAGTCC | kk-d9-kdkdk | 71 | 3058 |
| 1014372 | N/A | N/A | 11119 | 11134 | AGCAGTGATGTCAGGT | kk-d9-kdkdk | 52 | 2718 |
| 1014373 | N/A | N/A | 11120 | 11135 | AAGCAGTGATGTCAGG | kk-d9-kdkdk | 39 | 3277 |
| 1014374 | N/A | N/A | 11121 | 11136 | CAAGCAGTGATGTCAG | kk-d9-kdkdk | 51 | 3278 |
| 1014379 | N/A | N/A | 11395 | 11410 | CACATCAATGTTTTAG | kk-d9-kdkdk | 63 | 3279 |
| 1014380 | N/A | N/A | 11396 | 11411 | GCACATCAATGTTTTA | kk-d9-kdkdk | 93 | 1159 |
| 1014381 | N/A | N/A | 11397 | 11412 | GGCACATCAATGTTTT | kk-d9-kdkdk | 84 | 3280 |
| 1014382 | N/A | N/A | 11398 | 11413 | AGGCACATCAATGTTT | kk-d9-kdkdk | 81 | 1233 |

TABLE 61-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014393 | N/A | N/A | 11411 | 11426 | GTGTATTACTCTTAGG | kk-d9-kdkdk | 17 | 1540 |
| 1014394 | N/A | N/A | 11412 | 11427 | TGTGTATTACTCTTAG | kk-d9-kdkdk | 29 | 3246 |
| 1014395 | N/A | N/A | 11413 | 11428 | ATGTGTATTACTCTTA | kk-d9-kdkdk | 68 | 3281 |
| 1014396 | N/A | N/A | 11414 | 11429 | AATGTGTATTACTCTT | kk-d9-kdkdk | 85 | 3282 |
| 1014409 | N/A | N/A | 11565 | 11580 | TGTGCTTGCCAAGCCT | kk-d9-kdkdk | 79 | 3283 |
| 1014410 | N/A | N/A | 11566 | 11581 | GTGTGCTTGCCAAGCC | kk-d9-kdkdk | 41 | 3000 |
| 1014411 | N/A | N/A | 11567 | 11582 | CGTGTGCTTGCCAAGC | kk-d9-kdkdk | 47 | 3284 |
| 1014412 | N/A | N/A | 11568 | 11583 | ACGTGTGCTTGCCAAG | kk-d9-kdkdk | 34 | 3285 |
| 1014444 | N/A | N/A | 12514 | 12529 | TTCATGTAAAGTCTGC | kk-d9-kdkdk | 65 | 3286 |
| 1014445 | N/A | N/A | 12515 | 12530 | GTTCATGTAAAGTCTG | kk-d9-kdkdk | 64 | 934 |
| 1014446 | N/A | N/A | 12516 | 12531 | AGTTCATGTAAAGTCT | kk-d9-kdkdk | 53 | 755 |
| 1014447 | N/A | N/A | 12517 | 12532 | AAGTTCATGTAAAGTC | kk-d9-kdkdk | 66 | 3287 |
| 1014526 | N/A | N/A | 18073 | 18088 | GTTGGCTGGTCTTTGT | kk-d9-kdkdk | 44 | 3336 |
| 1014527 | N/A | N/A | 18074 | 18089 | GGTTGGCTGGTCTTTG | kk-d9-kdkdk | 36 | 3337 |
| 1014528 | N/A | N/A | 18075 | 18090 | TGGTTGGCTGGTCTTT | kk-d9-kdkdk | 49 | 3338 |
| 1014529 | N/A | N/A | 18076 | 18091 | TTGGTTGGCTGGTCTT | kk-d9-kdkdk | 45 | 3339 |
| 1014532 | N/A | N/A | 18087 | 18102 | TTATATACTGGTTGGT | kk-d9-kdkdk | 82 | 1179 |
| 1014533 | N/A | N/A | 18088 | 18103 | ATTATATACTGGTTGG | kk-d9-kdkdk | 72 | 3340 |
| 1014534 | N/A | N/A | 18089 | 18104 | GATTATATACTGGTTG | kk-d9-kdkdk | 65 | 1254 |
| 1014535 | N/A | N/A | 18090 | 18105 | GGATTATATACTGGTT | kk-d9-kdkdk | 41 | 1330 |
| 1014536 | N/A | N/A | 18091 | 18106 | GGGATTATATACTGGT | kk-d9-kdkdk | 59 | 3341 |
| 1014537 | N/A | N/A | 18092 | 18107 | TGGGATTATATACTGG | kk-d9-kdkdk | 75 | 3342 |
| 1014551 | N/A | N/A | 18571 | 18586 | TGATAGCTGAGCTGAT | kk-d9-kdkdk | 122 | 2546 |
| 1014552 | N/A | N/A | 18572 | 18587 | GTGATAGCTGAGCTGA | kk-d9-kdkdk | 66 | 3343 |
| 1014553 | N/A | N/A | 18573 | 18588 | TGTGATAGCTGAGCTG | kk-d9-kdkdk | 53 | 3344 |
| 1014554 | N/A | N/A | 18574 | 18589 | ATGTGATAGCTGAGCT | kk-d9-kdkdk | 73 | 3345 |
| 1014555 | N/A | N/A | 18575 | 18590 | GATGTGATAGCTGAGC | kk-d9-kdkdk | 66 | 3346 |
| 1014556 | N/A | N/A | 18576 | 18591 | TGATGTGATAGCTGAG | kk-d9-kdkdk | 86 | 3347 |
| 1014557 | N/A | N/A | 18577 | 18592 | TTGATGTGATAGCTGA | kk-d9-kdkdk | 64 | 3348 |
| 1014571 | N/A | N/A | 18611 | 18626 | AGTGACTTGCATCCAT | kk-d9-kdkdk | 78 | 3349 |
| 1014572 | N/A | N/A | 18612 | 18627 | CAGTGACTTGCATCCA | kk-d9-kdkdk | 64 | 3350 |
| 1014573 | N/A | N/A | 18613 | 18628 | ACAGTGACTTGCATCC | kk-d9-kdkdk | 82 | 3351 |
| 1014574 | N/A | N/A | 18614 | 18629 | GACAGTGACTTGCATC | kk-d9-kdkdk | 107 | 3352 |
| 1014783 | N/A | N/A | 10142 | 10157 | ATGTTAGCCAATTCCT | kk-d9-ecekk | 94 | 3272 |
| 1014784 | N/A | N/A | 10143 | 10158 | TATGTTAGCCAATTCC | kk-d9-ecekk | 73 | 2991 |
| 1014785 | N/A | N/A | 10144 | 10159 | TTATGTTAGCCAATTC | kk-d9-ecekk | 91 | 3273 |

TABLE 61-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014786 | N/A | N/A | 10145 | 10160 | TTTATGTTAGCCAATT | kk-d9-eeekk | 79 | 3274 |
| 1014792 | N/A | N/A | 10278 | 10293 | TGTTACCGATGCTTCA | kk-d9-eeekk | 61 | 2294 |
| 1014793 | N/A | N/A | 10279 | 10294 | CTGTTACCGATGCTTC | kk-d9-eeekk | 44 | 2993 |
| 1014794 | N/A | N/A | 10280 | 10295 | ACTGTTACCGATGCTT | kk-d9-eeekk | 66 | 3055 |
| 1014795 | N/A | N/A | 10281 | 10296 | TACTGTTACCGATGCT | kk-d9-eeekk | 92 | 3117 |
| 1014806 | N/A | N/A | 11016 | 11031 | GTGTCTAAAGTCCCAT | kk-d9-eeekk | 123 | 3275 |
| 1014807 | N/A | N/A | 11017 | 11032 | AGTGTCTAAAGTCCCA | kk-d9-eeekk | 88 | 2996 |
| 1014808 | N/A | N/A | 11018 | 11033 | AAGTGTCTAAAGTCCC | kk-d9-eeekk | 54 | 3276 |
| 1014809 | N/A | N/A | 11019 | 11034 | CAAGTGTCTAAAGTCC | kk-d9-eeekk | 69 | 3058 |
| 1014813 | N/A | N/A | 11119 | 11134 | AGCAGTGATGTCAGGT | kk-d9-eeekk | 44 | 2718 |
| 1014814 | N/A | N/A | 11120 | 11135 | AAGCAGTGATGTCAGG | kk-d9-eeekk | 49 | 3277 |
| 1014815 | N/A | N/A | 11121 | 11136 | CAAGCAGTGATGTCAG | kk-d9-eeekk | 92 | 3278 |
| 1014820 | N/A | N/A | 11395 | 11410 | CACATCAATGTTTTAG | kk-d9-eeekk | 89 | 3279 |
| 1014821 | N/A | N/A | 11396 | 11411 | GCACATCAATGTTTTA | kk-d9-eeekk | 80 | 1159 |
| 1014822 | N/A | N/A | 11397 | 11412 | GGCACATCAATGTTTT | kk-d9-eeekk | 64 | 3280 |
| 1014823 | N/A | N/A | 11398 | 11413 | AGGCACATCAATGTTT | kk-d9-eeekk | 57 | 1233 |
| 1014834 | N/A | N/A | 11411 | 11426 | GTGTATTACTCTTAGG | kk-d9-eeekk | 25 | 1540 |

TABLE 62

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 26 | 195 |
| 881450 | 3252 | 3267 | 21369 | 21384 | ACACTTTTAGAGAGGA | kkk-d10-kkk | 39 | 2111 |
| 881659 | 4592 | 4607 | 22709 | 22724 | GGAAGTTTACACTGGA | kkk-d10-kkk | 9 | 2044 |
| 1014835 | N/A | N/A | 11412 | 11427 | TGTGTATTACTCTTAG | kk-d9-eeekk | 76 | 3246 |
| 1014836 | N/A | N/A | 11413 | 11428 | ATGTGTATTACTCTTA | kk-d9-eeekk | 56 | 3281 |
| 1014837 | N/A | N/A | 11414 | 11429 | AATGTGTATTACTCTT | kk-d9-eeekk | 83 | 3282 |
| 1014850 | N/A | N/A | 11565 | 11580 | TGTGCTTGCCAAGCCT | kk-d9-eeekk | 60 | 3283 |
| 1014851 | N/A | N/A | 11566 | 11581 | GTGTGCTTGCCAAGCC | kk-d9-eeekk | 38 | 3000 |
| 1014852 | N/A | N/A | 11567 | 11582 | CGTGTGCTTGCCAAGC | kk-d9-eeekk | 34 | 3284 |
| 1014853 | N/A | N/A | 11568 | 11583 | ACGTGTGCTTGCCAAG | kk-d9-eeekk | 57 | 3285 |
| 1014885 | N/A | N/A | 12514 | 12529 | TTCATGTAAAGTCTGC | kk-d9-eeekk | 65 | 3286 |
| 1014886 | N/A | N/A | 12515 | 12530 | GTTCATGTAAAGTCTG | kk-d9-eeekk | 76 | 934 |
| 1014887 | N/A | N/A | 12516 | 12531 | AGTTCATGTAAAGTCT | kk-d9-eeekk | 70 | 755 |
| 1014888 | N/A | N/A | 12517 | 12532 | AAGTTCATGTAAAGTC | kk-d9-eeekk | 97 | 3287 |

TABLE 62-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1014967 | N/A | N/A | 18073 | 18088 | GTTGGCTGGTCTTTGT | kk-d9-eeekk | 76 | 3336 |
| 1014968 | N/A | N/A | 18074 | 18089 | GGTTGGCTGGTCTTTG | kk-d9-eeekk | 31 | 3337 |
| 1014969 | N/A | N/A | 18075 | 18090 | TGGTTGGCTGGTCTTT | kk-d9-eeekk | 60 | 3338 |
| 1014970 | N/A | N/A | 18076 | 18091 | TTGGTTGGCTGGTCTT | kk-d9-eeekk | 50 | 3339 |
| 1014973 | N/A | N/A | 18087 | 18102 | TTATATACTGGTTGGT | kk-d9-eeekk | 60 | 1179 |
| 1014974 | N/A | N/A | 18088 | 18103 | ATTATATACTGGTTGG | kk-d9-eeekk | 63 | 3340 |
| 1014975 | N/A | N/A | 18089 | 18104 | GATTATATACTGGTTG | kk-d9-eeekk | 58 | 1254 |
| 1014976 | N/A | N/A | 18090 | 18105 | GGATTATATACTGGTT | kk-d9-eeekk | 22 | 1330 |
| 1014977 | N/A | N/A | 18091 | 18106 | GGGATTATATACTGGT | kk-d9-eeekk | 65 | 3341 |
| 1014978 | N/A | N/A | 18092 | 18107 | TGGGATTATATACTGG | kk-d9-eeekk | 46 | 3342 |
| 1014992 | N/A | N/A | 18571 | 18586 | TGATAGCTGAGCTGAT | kk-d9-eeekk | 102 | 2546 |
| 1014993 | N/A | N/A | 18572 | 18587 | GTGATAGCTGAGCTGA | kk-d9-eeekk | 87 | 3343 |
| 1014994 | N/A | N/A | 18573 | 18588 | TGTGATAGCTGAGCTG | kk-d9-eeekk | 88 | 3344 |
| 1014995 | N/A | N/A | 18574 | 18589 | ATGTGATAGCTGAGCT | kk-d9-eeekk | 100 | 3345 |
| 1014996 | N/A | N/A | 18575 | 18590 | GATGTGATAGCTGAGC | kk-d9-eeekk | 48 | 3346 |
| 1014997 | N/A | N/A | 18576 | 18591 | TGATGTGATAGCTGAG | kk-d9-eeekk | 53 | 3347 |
| 1014998 | N/A | N/A | 18577 | 18592 | TTGATGTGATAGCTGA | kk-d9-eeekk | 83 | 3348 |
| 1015012 | N/A | N/A | 18611 | 18626 | AGTGACTTGCATCCAT | kk-d9-eeekk | 48 | 3349 |
| 1015013 | N/A | N/A | 18612 | 18627 | CAGTGACTTGCATCCA | kk-d9-eeekk | 72 | 3350 |
| 1015014 | N/A | N/A | 18613 | 18628 | ACAGTGACTTGCATCC | kk-d9-eeekk | 73 | 3351 |
| 1015015 | N/A | N/A | 18614 | 18629 | GACAGTGACTTGCATC | kk-d9-eeekk | 76 | 3352 |
| 1015224 | N/A | N/A | 10142 | 10157 | ATGTTAGCCAATTCCT | kk-d9-ekeke | 70 | 3272 |
| 1015225 | N/A | N/A | 10143 | 10158 | TATGTTAGCCAATTCC | kk-d9-ekeke | 110 | 2991 |
| 1015226 | N/A | N/A | 10144 | 10159 | TTATGTTAGCCAATTC | kk-d9-ekeke | 92 | 3273 |
| 1015227 | N/A | N/A | 10145 | 10160 | TTTATGTTAGCCAATT | kk-d9-ekeke | 113 | 3274 |
| 1015233 | N/A | N/A | 10278 | 10293 | TGTTACCGATGCTTCA | kk-d9-ekeke | 51 | 2294 |
| 1015234 | N/A | N/A | 10279 | 10294 | CTGTTACCGATGCTTC | kk-d9-ekeke | 40 | 2993 |
| 1015235 | N/A | N/A | 10280 | 10295 | ACTGTTACCGATGCTT | kk-d9-ekeke | 63 | 3055 |
| 1015236 | N/A | N/A | 10281 | 10296 | TACTGTTACCGATGCT | kk-d9-ekeke | 86 | 3117 |
| 1015247 | N/A | N/A | 11016 | 11031 | GTGTCTAAAGTCCCAT | kk-d9-ekeke | 77 | 3275 |
| 1015248 | N/A | N/A | 11017 | 11032 | AGTGTCTAAAGTCCCA | kk-d9-ekeke | 81 | 2996 |
| 1015249 | N/A | N/A | 11018 | 11033 | AAGTGTCTAAAGTCCC | kk-d9-ekeke | 101 | 3276 |
| 1015250 | N/A | N/A | 11019 | 11034 | CAAGTGTCTAAAGTCC | kk-d9-ekeke | 75 | 3058 |
| 1015254 | N/A | N/A | 11119 | 11134 | AGCAGTGATGTCAGGT | kk-d9-ekeke | 30 | 2718 |
| 1015255 | N/A | N/A | 11120 | 11135 | AAGCAGTGATGTCAGG | kk-d9-ekeke | 35 | 3277 |
| 1015256 | N/A | N/A | 11121 | 11136 | CAAGCAGTGATGTCAG | kk-d9-ekeke | 66 | 3278 |

TABLE 62-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1015261 | N/A | N/A | 11395 | 11410 | CACATCAATGTTTTAG | kk-d9-ekeke | 73 | 3279 |
| 1015262 | N/A | N/A | 11396 | 11411 | GCACATCAATGTTTTA | kk-d9-ekeke | 88 | 1159 |
| 1015263 | N/A | N/A | 11397 | 11412 | GGCACATCAATGTTTT | kk-d9-ekeke | 74 | 3280 |
| 1015264 | N/A | N/A | 11398 | 11413 | AGGCACATCAATGTTT | kk-d9-ekeke | 65 | 1233 |
| 1015275 | N/A | N/A | 11411 | 11426 | GTGTATTACTCTTAGG | kk-d9-ekeke | 16 | 1540 |
| 1015276 | N/A | N/A | 11412 | 11427 | TGTGTATTACTCTTAG | kk-d9-ekeke | 34 | 3246 |
| 1015277 | N/A | N/A | 11413 | 11428 | ATGTGTATTACTCTTA | kk-d9-ekeke | 39 | 3281 |
| 1015278 | N/A | N/A | 11414 | 11429 | AATGTGTATTACTCTT | kk-d9-ekeke | 70 | 3282 |
| 1015291 | N/A | N/A | 11565 | 11580 | TGTGCTTGCCAAGCCT | kk-d9-ekeke | 99 | 3283 |
| 1015292 | N/A | N/A | 11566 | 11581 | GTGTGCTTGCCAAGCC | kk-d9-ekeke | 81 | 3000 |
| 1015293 | N/A | N/A | 11567 | 11582 | CGTGTGCTTGCCAAGC | kk-d9-ekeke | 64 | 3284 |
| 1015294 | N/A | N/A | 11568 | 11583 | ACGTGTGCTTGCCAAG | kk-d9-ekeke | 39 | 3285 |
| 1015326 | N/A | N/A | 12514 | 12529 | TTCATGTAAAGTCTGC | kk-d9-ekeke | 61 | 3286 |
| 1015327 | N/A | N/A | 12515 | 12530 | GTTCATGTAAAGTCTG | kk-d9-ekeke | 68 | 934 |
| 1015328 | N/A | N/A | 12516 | 12531 | AGTTCATGTAAAGTCT | kk-d9-ekeke | 51 | 755 |
| 1015329 | N/A | N/A | 12517 | 12532 | AAGTTCATGTAAAGTC | kk-d9-ekeke | 71 | 3287 |
| 1015408 | N/A | N/A | 18073 | 18088 | GTTGGCTGGTCTTTGT | kk-d9-ekeke | 77 | 3336 |
| 1015409 | N/A | N/A | 18074 | 18089 | GGTTGGCTGGTCTTTG | kk-d9-ekeke | 27 | 3337 |
| 1015410 | N/A | N/A | 18075 | 18090 | TGGTTGGCTGGTCTTT | kk-d9-ekeke | 40 | 3338 |
| 1015411 | N/A | N/A | 18076 | 18091 | TTGGTTGGCTGGTCTT | kk-d9-ekeke | 66 | 3339 |
| 1015414 | N/A | N/A | 18087 | 18102 | TTATATACTGGTTGGT | kk-d9-ekeke | 36 | 1179 |
| 1015415 | N/A | N/A | 18088 | 18103 | ATTATATACTGGTTGG | kk-d9-ekeke | 57 | 3340 |
| 1015416 | N/A | N/A | 18089 | 18104 | GATTATATACTGGTTG | kk-d9-ekeke | 54 | 1254 |
| 1015417 | N/A | N/A | 18090 | 18105 | GGATTATATACTGGTT | kk-d9-ekeke | 21 | 1330 |
| 1015418 | N/A | N/A | 18091 | 18106 | GGGATTATATACTGGT | kk-d9-ekeke | 66 | 3341 |
| 1015419 | N/A | N/A | 18092 | 18107 | TGGGATTATATACTGG | kk-d9-ekeke | 37 | 3342 |
| 1015433 | N/A | N/A | 18571 | 18586 | TGATAGCTGAGCTGAT | kk-d9-ekeke | 85 | 2546 |
| 1015434 | N/A | N/A | 18572 | 18587 | GTGATAGCTGAGCTGA | kk-d9-ekeke | 76 | 3343 |
| 1015435 | N/A | N/A | 18573 | 18588 | TGTGATAGCTGAGCTG | kk-d9-ekeke | 59 | 3344 |

TABLE 63

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 33 | 195 |
| 881450 | 3252 | 3267 | 21369 | 21384 | ACACTTTTAGAGAGGA | kkk-d10-kkk | 30 | 2111 |

TABLE 63-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 881659 | 4592 | 4607 | 22709 | 22724 | GGAAGTTTACACTGGA | kkk-d10-kkk | 13 | 2044 |
| 1012810 | N/A | N/A | 10142 | 10157 | ATGTTAGCCAATTCCT | kkk-d10-kkk | 67 | 3272 |
| 1012811 | N/A | N/A | 10144 | 10159 | TTATGTTAGCCAATTC | kkk-d10-kkk | 78 | 3273 |
| 1012812 | N/A | N/A | 10145 | 10160 | TTTATGTTAGCCAATT | kkk-d10-kkk | 87 | 3274 |
| 1012816 | N/A | N/A | 11016 | 11031 | GTGTCTAAAGTCCCAT | kkk-d10-kkk | 72 | 3275 |
| 1012817 | N/A | N/A | 11018 | 11033 | AAGTGTCTAAAGTCCC | kkk-d10-kkk | 59 | 3276 |
| 1012819 | N/A | N/A | 11120 | 11135 | AAGCAGTGATGTCAGG | kkk-d10-kkk | 34 | 3277 |
| 1012820 | N/A | N/A | 11121 | 11136 | CAAGCAGTGATGTCAG | kkk-d10-kkk | 49 | 3278 |
| 1012821 | N/A | N/A | 11395 | 11410 | CACATCAATGTTTTAG | kkk-d10-kkk | 25 | 3279 |
| 1012822 | N/A | N/A | 11397 | 11412 | GGCACATCAATGTTTT | kkk-d10-kkk | 86 | 3280 |
| 1012826 | N/A | N/A | 11413 | 11428 | ATGTGTATTACTCTTA | kkk-d10-kkk | 51 | 3281 |
| 1012827 | N/A | N/A | 11414 | 11429 | AATGTGTATTACTCTT | kkk-d10-kkk | 59 | 3282 |
| 1012835 | N/A | N/A | 11565 | 11580 | TGTGCTTGCCAAGCCT | kkk-d10-kkk | 51 | 3283 |
| 1012836 | N/A | N/A | 11567 | 11582 | CGTGTGCTTGCCAAGC | kkk-d10-kkk | 34 | 3284 |
| 1012837 | N/A | N/A | 11568 | 11583 | ACGTGTGCTTGCCAAG | kkk-d10-kkk | 45 | 3285 |
| 1012845 | N/A | N/A | 12514 | 12529 | TTCATGTAAAGTCTGC | kkk-d10-kkk | 45 | 3286 |
| 1012846 | N/A | N/A | 12517 | 12532 | AAGTTCATGTAAAGTC | kkk-d10-kkk | 59 | 3287 |
| 1015436 | N/A | N/A | 18574 | 18589 | ATGTGATAGCTGAGCT | kk-d9-ekeke | 98 | 3345 |
| 1015437 | N/A | N/A | 18575 | 18590 | GATGTGATAGCTGAGC | kk-d9-ekeke | 47 | 3346 |
| 1015438 | N/A | N/A | 18576 | 18591 | TGATGTGATAGCTGAG | kk-d9-ekeke | 40 | 3347 |
| 1015439 | N/A | N/A | 18577 | 18592 | TTGATGTGATAGCTGA | kk-d9-ekeke | 72 | 3348 |
| 1015453 | N/A | N/A | 18611 | 18626 | AGTGACTTGCATCCAT | kk-d9-ekeke | 66 | 3349 |
| 1015454 | N/A | N/A | 18612 | 18627 | CAGTGACTTGCATCCA | kk-d9-ekeke | 66 | 3350 |
| 1015455 | N/A | N/A | 18613 | 18628 | ACAGTGACTTGCATCC | kk-d9-ekeke | 91 | 3351 |
| 1015456 | N/A | N/A | 18614 | 18629 | GACAGTGACTTGCATC | kk-d9-ekeke | 70 | 3352 |
| 1015665 | N/A | N/A | 10142 | 10157 | ATGTTAGCCAATTCCT | k-d9-kekeke | 95 | 3272 |
| 1015666 | N/A | N/A | 10143 | 10158 | TATGTTAGCCAATTCC | k-d9-kekeke | 86 | 2991 |
| 1015667 | N/A | N/A | 10144 | 10159 | TTATGTTAGCCAATTC | k-d9-kekeke | 98 | 3273 |
| 1015668 | N/A | N/A | 10145 | 10160 | TTTATGTTAGCCAATT | k-d9-kekeke | 86 | 3274 |
| 1015674 | N/A | N/A | 10278 | 10293 | TGTTACCGATGCTTCA | k-d9-kekeke | 87 | 2294 |
| 1015675 | N/A | N/A | 10279 | 10294 | CTGTTACCGATGCTTC | k-d9-kekeke | 76 | 2993 |
| 1015676 | N/A | N/A | 10280 | 10295 | ACTGTTACCGATGCTT | k-d9-kekeke | 83 | 3055 |
| 1015677 | N/A | N/A | 10281 | 10296 | TACTGTTACCGATGCT | k-d9-kekeke | 82 | 3117 |
| 1015688 | N/A | N/A | 11016 | 11031 | GTGTCTAAAGTCCCAT | k-d9-kekeke | 95 | 3275 |
| 1015689 | N/A | N/A | 11017 | 11032 | AGTGTCTAAAGTCCCA | k-d9-kekeke | 88 | 2996 |
| 1015690 | N/A | N/A | 11018 | 11033 | AAGTGTCTAAAGTCCC | k-d9-kekeke | 95 | 3276 |

TABLE 63-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1015691 | N/A | N/A | 11019 | 11034 | CAAGTGTCTAAAGTCC | k-d9-kekeke | 90 | 3058 |
| 1015695 | N/A | N/A | 11119 | 11134 | AGCAGTGATGTCAGGT | k-d9-kekeke | 64 | 2718 |
| 1015696 | N/A | N/A | 11120 | 11135 | AAGCAGTGATGTCAGG | k-d9-kekeke | 65 | 3277 |
| 1015697 | N/A | N/A | 11121 | 11136 | CAAGCAGTGATGTCAG | k-d9-kekeke | 88 | 3278 |
| 1015702 | N/A | N/A | 11395 | 11410 | CACATCAATGTTTTAG | k-d9-kekeke | 82 | 3279 |
| 1015703 | N/A | N/A | 11396 | 11411 | GCACATCAATGTTTTA | k-d9-kekeke | 85 | 1159 |
| 1015704 | N/A | N/A | 11397 | 11412 | GGCACATCAATGTTTT | k-d9-kekeke | 94 | 3280 |
| 1015705 | N/A | N/A | 11398 | 11413 | AGGCACATCAATGTTT | k-d9-kekeke | 97 | 1233 |
| 1015716 | N/A | N/A | 11411 | 11426 | GTGTATTACTCTTAGG | k-d9-kekeke | 23 | 1540 |
| 1015717 | N/A | N/A | 11412 | 11427 | TGTGTATTACTCTTAG | k-d9-kekeke | 48 | 3246 |
| 1015718 | N/A | N/A | 11413 | 11428 | ATGTGTATTACTCTTA | k-d9-kekeke | 51 | 3281 |
| 1015719 | N/A | N/A | 11414 | 11429 | AATGTGTATTACTCTT | k-d9-kekeke | 85 | 3282 |
| 1015732 | N/A | N/A | 11565 | 11580 | TGTGCTTGCCAAGCCT | k-d9-kekeke | 84 | 3283 |
| 1015733 | N/A | N/A | 11566 | 11581 | GTGTGCTTGCCAAGCC | k-d9-kekeke | 78 | 3000 |
| 1015734 | N/A | N/A | 11567 | 11582 | CGTGTGCTTGCCAAGC | k-d9-kekeke | 89 | 3284 |
| 1015735 | N/A | N/A | 11568 | 11583 | ACGTGTGCTTGCCAAG | k-d9-kekeke | 65 | 3285 |
| 1015767 | N/A | N/A | 12514 | 12529 | TTCATGTAAAGTCTGC | k-d9-kekeke | 97 | 3286 |
| 1015768 | N/A | N/A | 12515 | 12530 | GTTCATGTAAAGTCTG | k-d9-kekeke | 90 | 934 |
| 1015769 | N/A | N/A | 12516 | 12531 | AGTTCATGTAAAGTCT | k-d9-kekeke | 90 | 755 |
| 1015770 | N/A | N/A | 12517 | 12532 | AAGTTCATGTAAAGTC | k-d9-kekeke | 79 | 3287 |
| 1015849 | N/A | N/A | 18073 | 18088 | GTTGGCTGGTCTTTGT | k-d9-kekeke | 82 | 3336 |
| 1015850 | N/A | N/A | 18074 | 18089 | GGTTGGCTGGTCTTTG | k-d9-kekeke | 74 | 3337 |
| 1015851 | N/A | N/A | 18075 | 18090 | TGGTTGGCTGGTCTTT | k-d9-kekeke | 69 | 3338 |
| 1015852 | N/A | N/A | 18076 | 18091 | TTGGTTGGCTGGTCTT | k-d9-kekeke | 107 | 3339 |
| 1015855 | N/A | N/A | 18087 | 18102 | TTATATACTGGTTGGT | k-d9-kekeke | 80 | 1179 |
| 1015856 | N/A | N/A | 18088 | 18103 | ATTATATACTGGTTGG | k-d9-kekeke | 73 | 3340 |
| 1015857 | N/A | N/A | 18089 | 18104 | GATTATATACTGGTTG | k-d9-kekeke | 88 | 1254 |
| 1015858 | N/A | N/A | 18090 | 18105 | GGATTATATACTGGTT | k-d9-kekeke | 90 | 1330 |
| 1015859 | N/A | N/A | 18091 | 18106 | GGGATTATATACTGGT | k-d9-kekeke | 71 | 3341 |
| 1015860 | N/A | N/A | 18092 | 18107 | TGGGATTATATACTGG | k-d9-kekeke | 60 | 3342 |
| 1015874 | N/A | N/A | 18571 | 18586 | TGATAGCTGAGCTGAT | k-d9-kekeke | 83 | 2546 |
| 1015875 | N/A | N/A | 18572 | 18587 | GTGATAGCTGAGCTGA | k-d9-kekeke | 84 | 3343 |
| 1015876 | N/A | N/A | 18573 | 18588 | TGTGATAGCTGAGCTG | k-d9-kekeke | 82 | 3344 |
| 1015877 | N/A | N/A | 18574 | 18589 | ATGTGATAGCTGAGCT | k-d9-kekeke | 85 | 3345 |
| 1015878 | N/A | N/A | 18575 | 18590 | GATGTGATAGCTGAGC | k-d9-kekeke | 82 | 3346 |
| 1015879 | N/A | N/A | 18576 | 18591 | TGATGTGATAGCTGAG | k-d9-kekeke | 53 | 3347 |
| 1015880 | N/A | N/A | 18577 | 18592 | TTGATGTGATAGCTGA | k-d9-kekeke | 66 | 3348 |

TABLE 63-continued

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1015894 | N/A | N/A | 18611 | 18626 | AGTGACTTGCATCCAT | k-d9-kekeke | 92 | 3349 |
| 1015895 | N/A | N/A | 18612 | 18627 | CAGTGACTTGCATCCA | k-d9-kekeke | 81 | 3350 |
| 1015896 | N/A | N/A | 18613 | 18628 | ACAGTGACTTGCATCC | k-d9-kekeke | 94 | 3351 |
| 1015897 | N/A | N/A | 18614 | 18629 | GACAGTGACTTGCATC | k-d9-kekeke | 100 | 3352 |

TABLE 64

Percent control of human IRF4 mRNA with gapmers with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 609408 | 4226 | 4241 | 22343 | 22358 | TTGTAAATGAGTCGGT | kkk-d10-kkk | 23 | 195 |
| 881450 | 3252 | 3267 | 21369 | 21384 | ACACTTTTAGAGAGGA | kkk-d10-kkk | 35 | 2111 |
| 881659 | 4592 | 4607 | 22709 | 22724 | GGAAGTTTACACTGGA | kkk-d10-kkk | 9 | 2044 |
| 935595 | 3075 | 3090 | 21192 | 21207 | ACTAAGCTTGATAAAG | kkk-d10-kkk | 95 | 3288 |
| 935607 | 4195 | 4210 | 22312 | 22327 | AGTGTTCCAGGAGATA | kkk-d10-kkk | 28 | 3289 |
| 1012769 | N/A | N/A | 4810 | 4825 | GCTCCCGACACGCGCC | kkk-d10-kkk | 81 | 3290 |
| 1012772 | N/A | N/A | 6267 | 6282 | ATGCGGAGGTTCCTTG | kkk-d10-kkk | 48 | 3291 |
| 1012774 | N/A | N/A | 6271 | 6286 | TGAGATGCGGAGGTTC | kkk-d10-kkk | 73 | 3292 |
| 1012775 | N/A | N/A | 6273 | 6288 | AGTGAGATGCGGAGGT | kkk-d10-kkk | 35 | 3293 |
| 1012776 | N/A | N/A | 6275 | 6290 | AGAGTGAGATGCGGAG | kkk-d10-kkk | 37 | 3294 |
| 1012778 | N/A | N/A | 6281 | 6296 | ACCGGTAGAGTGAGAT | kkk-d10-kkk | 98 | 3295 |
| 1012782 | N/A | N/A | 7634 | 7649 | GAGTTGTACAGGACAG | kkk-d10-kkk | 48 | 3296 |
| 1012785 | N/A | N/A | 7638 | 7653 | GTCTGAGTTGTACAGG | kkk-d10-kkk | 43 | 3297 |
| 1012786 | N/A | N/A | 7640 | 7655 | AGGTCTGAGTTGTACA | kkk-d10-kkk | 55 | 3298 |
| 1012788 | N/A | N/A | 8386 | 8401 | AATGGAGATACTTGTA | kkk-d10-kkk | 74 | 3299 |
| 1012790 | N/A | N/A | 8389 | 8404 | GACAATGGAGATACTT | kkk-d10-kkk | 63 | 3300 |
| 1012795 | N/A | N/A | 9667 | 9682 | GTATTTTCCGTTCCT | kkk-d10-kkk | 16 | 3303 |
| 1012796 | N/A | N/A | 9670 | 9685 | ATGGTATTTTTCCGTT | kkk-d10-kkk | 57 | 3304 |
| 1012799 | N/A | N/A | 9677 | 9692 | GTTTGCCATGGTATTT | kkk-d10-kkk | 50 | 3305 |
| 1012804 | N/A | N/A | 9840 | 9855 | CATTGCTAGATTCTCC | kkk-d10-kkk | 70 | 3306 |
| 1012806 | N/A | N/A | 9846 | 9861 | TTACCGCATTGCTAGA | kkk-d10-kkk | 74 | 3307 |
| 1012808 | N/A | N/A | 9851 | 9866 | CTGAGTTACCGCATTG | kkk-d10-kkk | 46 | 3308 |
| 1012809 | N/A | N/A | 10139 | 10154 | TTAGCCAATTCCTCCA | kkk-d10-kkk | 53 | 3309 |
| 1012813 | N/A | N/A | 10274 | 10289 | ACCGATGCTTCAAGAC | kkk-d10-kkk | 44 | 3310 |
| 1012814 | N/A | N/A | 10276 | 10291 | TTACCGATGCTTCAAG | kkk-d10-kkk | 81 | 3311 |
| 1012815 | N/A | N/A | 10282 | 10297 | TTACTGTTACCGATGC | kkk-d10-kkk | 65 | 3312 |

TABLE 64-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1012818 | N/A | N/A | 11020 | 11035 | GCAAGTGTCTAAAGTC | kkk-d10-kkk | 47 | 3313 |
| 1012823 | N/A | N/A | 11400 | 11415 | TTAGGCACATCAATGT | kkk-d10-kkk | 83 | 3314 |
| 1012825 | N/A | N/A | 11406 | 11421 | TTACTCTTAGGCACAT | kkk-d10-kkk | 55 | 3315 |
| 1012828 | N/A | N/A | 11523 | 11538 | GATCTCCATGGTGCAG | kkk-d10-kkk | 88 | 3316 |
| 1012831 | N/A | N/A | 11530 | 11545 | TAGGTAAGATCTCCAT | kkk-d10-kkk | 67 | 3317 |
| 1012834 | N/A | N/A | 11564 | 11579 | GTGCTTGCCAAGCCTA | kkk-d10-kkk | 64 | 3318 |
| 1012840 | N/A | N/A | 11659 | 11674 | CCAAACCTTAAGCTAT | kkk-d10-kkk | 66 | 3319 |
| 1012841 | N/A | N/A | 11663 | 11678 | AATTCCAAACCTTAAG | kkk-d10-kkk | 74 | 3320 |
| 1012843 | N/A | N/A | 11995 | 12010 | AGGTTGCCGAGATATA | kkk-d10-kkk | 33 | 3321 |
| 1012844 | N/A | N/A | 11997 | 12012 | CGAGGTTGCCGAGATA | kkk-d10-kkk | 40 | 3322 |
| 1012848 | N/A | N/A | 14251 | 14266 | GAGCCAACTTATAGCA | kkk-d10-kkk | 92 | 3323 |
| 1012850 | N/A | N/A | 14253 | 14268 | CAGAGCCAACTTATAG | kkk-d10-kkk | 57 | 3324 |
| 1012852 | N/A | N/A | 14734 | 14749 | GAAGCTTAGTTATCTG | kkk-d10-kkk | 61 | 3325 |
| 1012855 | N/A | N/A | 14739 | 14754 | GGCCTGAAGCTTAGTT | kkk-d10-kkk | 94 | 3326 |
| 1012859 | N/A | N/A | 15594 | 15609 | GTCGCGCAAGTCTACA | kkk-d10-kkk | 84 | 3327 |
| 1012860 | N/A | N/A | 15841 | 15856 | GTTGGCACAATTCTCT | kkk-d10-kkk | 84 | 3328 |
| 1012864 | N/A | N/A | 15845 | 15860 | GCGAGTTGGCACAATT | kkk-d10-kkk | 63 | 3329 |
| 1012866 | N/A | N/A | 15848 | 15863 | ATGGCGAGTTGGCACA | kkk-d10-kkk | 52 | 3330 |
| 1012867 | N/A | N/A | 15850 | 15865 | GAATGGCGAGTTGGCA | kkk-d10-kkk | 60 | 3331 |
| 1012869 | N/A | N/A | 15884 | 15899 | CGTGATCTGAGACTAC | kkk-d10-kkk | 64 | 3332 |
| 1012872 | N/A | N/A | 15889 | 15904 | ACTGCCGTGATCTGAG | kkk-d10-kkk | 71 | 3333 |
| 1012875 | N/A | N/A | 17236 | 17251 | TTACGCTTATTTTTCC | kkk-d10-kkk | 61 | 3353 |
| 1012879 | N/A | N/A | 17473 | 17488 | CAATCTTAACCTGGAG | kkk-d10-kkk | 60 | 3354 |
| 1012881 | N/A | N/A | 18073 | 18088 | GTTGGCTGGTCTTTGT | kkk-d10-kkk | 37 | 3336 |
| 1012882 | N/A | N/A | 18075 | 18090 | TGGTTGGCTGGTCTTT | kkk-d10-kkk | 12 | 3338 |
| 1012883 | N/A | N/A | 18076 | 18091 | TTGGTTGGCTGGTCTT | kkk-d10-kkk | 24 | 3339 |
| 1012884 | N/A | N/A | 18083 | 18098 | ATACTGGTTGGTTGGC | kkk-d10-kkk | 31 | 3355 |
| 1012885 | N/A | N/A | 18250 | 18265 | GCCGATCATCAACTTC | kkk-d10-kkk | 74 | 3356 |
| 1012888 | N/A | N/A | 18254 | 18269 | CCCGGCCGATCATCAA | kkk-d10-kkk | 77 | 3357 |
| 1012889 | N/A | N/A | 18569 | 18584 | ATAGCTGAGCTGATCA | kkk-d10-kkk | 70 | 3358 |
| 1012890 | N/A | N/A | 18573 | 18588 | TGTGATAGCTGAGCTG | kkk-d10-kkk | 53 | 3344 |
| 1012891 | N/A | N/A | 18574 | 18589 | ATGTGATAGCTGAGCT | kkk-d10-kkk | 74 | 3345 |
| 1012892 | N/A | N/A | 18576 | 18591 | TGATGTGATAGCTGAG | kkk-d10-kkk | 41 | 3347 |
| 1012893 | N/A | N/A | 18577 | 18592 | TTGATGTGATAGCTGA | kkk-d10-kkk | 45 | 3348 |
| 1012895 | N/A | N/A | 18581 | 18596 | TGGATTGATGTGATAG | kkk-d10-kkk | 52 | 3359 |
| 1012897 | N/A | N/A | 18607 | 18622 | ACTTGCATCCATGTCA | kkk-d10-kkk | 65 | 3360 |
| 1012899 | N/A | N/A | 18610 | 18625 | GTGACTTGCATCCATG | kkk-d10-kkk | 38 | 3361 |

TABLE 64-continued

Percent control of human IRF4 mRNA with gapmers
with phosphorothioate internucleoside linkages

| Compound Number | SEQ ID: 1 Start Site | SEQ ID: 1 Stop Site | SEQ ID: 2 Start Site | SEQ ID: 2 Stop Site | Sequence | Motif | IRF4 (% UTC) | SEQ ID NO |
|---|---|---|---|---|---|---|---|---|
| 1012900 | N/A | N/A | 18611 | 18626 | AGTGACTTGCATCCAT | kkk-d10-kkk | 33 | 3349 |
| 1012901 | N/A | N/A | 18613 | 18628 | ACAGTGACTTGCATCC | kkk-d10-kkk | 66 | 3351 |
| 1012902 | N/A | N/A | 18614 | 18629 | GACAGTGACTTGCATC | kkk-d10-kkk | 76 | 3352 |
| 1012903 | N/A | N/A | 18722 | 18737 | AAGTGGAACTCATAGG | kkk-d10-kkk | 75 | 3362 |
| 1012904 | N/A | N/A | 19021 | 19036 | ATCTGTATAGTTCTCA | kkk-d10-kkk | 45 | 3363 |
| 1012906 | N/A | N/A | 19023 | 19038 | TAATCTGTATAGTTCT | kkk-d10-kkk | 58 | 3364 |
| 1012907 | 1344 | 1359 | 19461 | 19476 | TCTGGCTAGCAGAGGT | kkk-d10-kkk | 74 | 3365 |
| 1012911 | 1412 | 1427 | 19529 | 19544 | ATGTGTTCTGGTAAAT | kkk-d10-kkk | 66 | 3366 |
| 1012914 | 1422 | 1437 | 19539 | 19554 | TGGATTGCTGATGTGT | kkk-d10-kkk | 29 | 3367 |
| 1012915 | 1424 | 1439 | 19541 | 19556 | TCTGGATTGCTGATGT | kkk-d10-kkk | 64 | 3368 |
| 1012918 | 1427 | 1442 | 19544 | 19559 | TCTTCTGGATTGCTGA | kkk-d10-kkk | 80 | 3369 |
| 1012919 | 1429 | 1444 | 19546 | 19561 | AATCTTCTGGATTGCT | kkk-d10-kkk | 86 | 3370 |
| 1012920 | 1441 | 1456 | 19558 | 19573 | TAGATCTGTGGTAATC | kkk-d10-kkk | 94 | 3334 |
| 1012921 | 1450 | 1465 | 19567 | 19582 | AATGGCGGATAGATCT | kkk-d10-kkk | 75 | 3335 |

Example 12: Effect of Modified Oligonucleotides on Human IRF4 In Vitro, Multiple Doses Modified oligonucleotides selected from the examples above were tested at various doses in SK-MEL-28 cells. Cells were plated at a density of 20,000 cells per well and transfected using electroporation with 185 nM, 555 nM, 1,666 nM, 5,000 nM, and 15,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set RTS3114 (described hereinabove in Example 1) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 65

Dose-dependent reduction of human IRF4 mRNA by modified oligonucleotides

| Compound Number | IRF4 expression (% LTC) | | | | |
|---|---|---|---|---|---|
| | 185 nM | 555 nM | 1,666 nM | 5,000 nM | 15,000 nM |
| 609311 | 91 | 79 | 68 | 36 | 9 |
| 609312 | 93 | 91 | 78 | 42 | 13 |
| 609328 | 99 | 73 | 57 | 37 | 14 |
| 609332 | 99 | 92 | 62 | 38 | 15 |
| 609333 | 90 | 82 | 59 | 32 | 11 |
| 609334 | 80 | 71 | 50 | 30 | 11 |
| 609337 | 84 | 81 | 57 | 40 | 15 |
| 609343 | 87 | 80 | 56 | 26 | 11 |
| 609354 | 87 | 79 | 46 | 25 | 10 |
| 609357 | 85 | 80 | 50 | 29 | 9 |
| 609391 | 94 | 82 | 53 | 28 | 10 |
| 609398 | 81 | 77 | 39 | 24 | 8 |
| 609407 | 80 | 71 | 40 | 25 | 11 |
| 609408 | 102 | 73 | 49 | 19 | 12 |

TABLE 66

Dose-dependent reduction of human IRF4 mRNA by modified oligonucleotides

| Compound Number | IRF4 expression (% UTC) | | | | |
|---|---|---|---|---|---|
| | 185 nM | 555 nM | 1,666 nM | 5,000 nM | 15,000 nM |
| 609394 | 94 | 82 | 59 | 52 | 22 |
| 609397 | 86 | 77 | 57 | 42 | 24 |
| 609405 | 84 | 86 | 75 | 40 | 36 |
| 609408 | 100 | 92 | 62 | 33 | 27 |
| 609416 | 89 | 80 | 54 | 43 | 17 |
| 609419 | 84 | 75 | 66 | 44 | 19 |
| 609422 | 104 | 87 | 69 | 50 | 14 |
| 609530 | 96 | 99 | 78 | 71 | 49 |
| 609533 | 96 | 91 | 80 | 55 | 37 |
| 609546 | 96 | 107 | 84 | 66 | 25 |
| 609571 | 94 | 86 | 78 | 58 | 38 |
| 609591 | 102 | 95 | 94 | 50 | 19 |

TABLE 66-continued

Dose-dependent reduction of human IRF4 mRNA by modified oligonucleotides

| Compound Number | IRF4 expression (% UTC) | | | | |
|---|---|---|---|---|---|
| | 185 nM | 555 nM | 1,666 nM | 5,000 nM | 15,000 nM |
| 609592 | 98 | 89 | 67 | 43 | 31 |
| 609594 | 86 | 73 | 68 | 43 | 26 |

TABLE 67

Dose-dependent reduction of human IRF4 mRNA by modified oligonucleotides

| Compound Number | IRF4 expression (% UTC) | | | | |
|---|---|---|---|---|---|
| | 185 nM | 555 nM | 1,666 nM | 5,000 nM | 15,000 nM |
| 609394 | 95 | 76 | 60 | 52 | 20 |
| 609397 | 90 | 74 | 59 | 45 | 22 |
| 609405 | 96 | 82 | 77 | 46 | 37 |
| 609408 | 99 | 84 | 62 | 39 | 27 |
| 609416 | 95 | 76 | 51 | 39 | 21 |
| 609419 | 96 | 73 | 71 | 41 | 18 |
| 609422 | 90 | 83 | 82 | 48 | 17 |
| 609530 | 104 | 99 | 81 | 74 | 45 |
| 609533 | 91 | 97 | 79 | 58 | 32 |
| 609546 | 91 | 88 | 85 | 63 | 28 |
| 609571 | 96 | 95 | 78 | 56 | 35 |
| 609591 | 110 | 83 | 76 | 49 | 21 |
| 609592 | 94 | 88 | 73 | 43 | 38 |
| 609594 | 87 | 84 | 68 | 45 | 28 |

TABLE 68

Dose-dependent reduction of human IRF4 mRNA by modified oligonucleotides

| Compound Number | IRF4 expression (% UTC) | | | | |
|---|---|---|---|---|---|
| | 185 nM | 555 nM | 1,666 nM | 5,000 nM | 15,000 nM |
| 609394 | 101 | 94 | 61 | 25 | 6 |
| 609397 | 99 | 75 | 46 | 23 | 13 |
| 609405 | 97 | 80 | 53 | 17 | 4 |
| 609408 | 87 | 88 | 39 | 15 | 5 |
| 609416 | 99 | 83 | 47 | 18 | 6 |
| 609419 | 88 | 84 | 54 | 23 | 9 |
| 609422 | 111 | 92 | 66 | 17 | 2 |
| 609530 | 100 | 92 | 63 | 37 | 17 |
| 609533 | 92 | 84 | 65 | 38 | 19 |
| 609546 | 83 | 97 | 72 | 50 | 11 |
| 609571 | 94 | 90 | 72 | 47 | 17 |
| 609591 | 103 | 88 | 53 | 24 | 9 |
| 609592 | 90 | 90 | 55 | 24 | 8 |
| 609594 | 82 | 75 | 52 | 33 | 28 |

Example 13: Effect of Modified Oligonucleotides on Human IRF4 In Vitro, Multiple Doses Modified oligonucleotides selected from the examples above were tested at various doses in SK-MEL-28 cells. Cells were plated at a density of 20,000 cells per well and transfected using electroporation with 500 nM, 1,000 nM, 2,000 nM, 4,000 nM, and 8,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set RTS3114 (described hereinabove in Example 1) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 69

Dose-dependent reduction of human IRF4 mRNA by modified oligonucleotides

| Compound Number | IRF4 expression (% UTC) | | | | |
|---|---|---|---|---|---|
| | 500 nM | 1,000 nM | 2,000 nM | 4,000 nM | 8,000 nM |
| 609408 | 70 | 52 | 46 | 26 | 29 |
| 666273 | 85 | 97 | 76 | 53 | 27 |
| 666333 | 77 | 78 | 64 | 42 | 24 |
| 666347 | 80 | 74 | 56 | 37 | 19 |
| 666351 | 79 | 68 | 59 | 53 | 24 |
| 666378 | 71 | 57 | 43 | 28 | 20 |
| 666392 | 77 | 64 | 42 | 37 | 34 |
| 666431 | 85 | 69 | 47 | 41 | 24 |
| 666440 | 69 | 55 | 38 | 21 | 27 |
| 666441 | 79 | 60 | 47 | 29 | 26 |
| 666442 | 62 | 50 | 35 | 21 | 19 |
| 666443 | 71 | 62 | 46 | 32 | 13 |
| 666449 | 53 | 47 | 31 | 20 | 19 |
| 666458 | 69 | 52 | 41 | 22 | 25 |
| 666471 | 57 | 50 | 23 | 23 | 11 |

TABLE 70

Dose-dependent reduction of human IRF4 mRNA by modified oligonucleotides

| Compound Number | IRF4 expression (% UTC) | | | | |
|---|---|---|---|---|---|
| | 500 nM | 1,000 nM | 2,000 nM | 4,000 nM | 8,000 nM |
| 609408 | 71 | 58 | 47 | 37 | 19 |
| 666475 | 54 | 42 | 26 | 22 | 32 |
| 666496 | 54 | 45 | 30 | 18 | 13 |
| 666512 | 76 | 70 | 49 | 29 | 36 |
| 666534 | 64 | 55 | 33 | 19 | 9 |
| 666575 | 71 | 53 | 31 | 24 | 34 |
| 666582 | 80 | 58 | 45 | 28 | 30 |
| 666584 | 88 | 63 | 58 | 35 | 21 |
| 666586 | 49 | 28 | 29 | 19 | 21 |
| 666587 | 61 | 44 | 26 | 14 | 19 |
| 666605 | 68 | 55 | 38 | 32 | 18 |
| 666625 | 71 | 63 | 45 | 30 | 17 |
| 666640 | 73 | 59 | 39 | 42 | 18 |
| 666645 | 83 | 64 | 55 | 37 | 34 |
| 666649 | 80 | 55 | 48 | 35 | 21 |

TABLE 71

Dose-dependent reduction of human IRF4 mRNA by modified oligonucleotides

| Compound Number | IRF4 expression (% UTC) | | | | |
|---|---|---|---|---|---|
| | 500 nM | 1,000 nM | 2,000 nM | 4,000 nM | 8,000 nM |
| 609408 | 74 | 57 | 65 | 47 | 23 |
| 666663 | 78 | 78 | 43 | 34 | 67 |
| 666664 | 77 | 64 | 43 | 31 | 62 |
| 666678 | 57 | 42 | 23 | 25 | 59 |
| 666681 | 74 | 59 | 47 | 28 | 60 |
| 666683 | 64 | 47 | 35 | 38 | 55 |
| 666714 | 81 | 77 | 54 | 47 | 75 |
| 666726 | 75 | 60 | 33 | 28 | 56 |
| 666727 | 83 | 65 | 42 | 31 | 72 |

TABLE 71-continued

Dose-dependent reduction of human IRF4 mRNA by modified oligonucleotides

| Compound | IRF4 expression (% UTC) | | | | |
|---|---|---|---|---|---|
| Number | 500 nM | 1,000 nM | 2,000 nM | 4,000 nM | 8,000 nM |
| 666769 | 98 | 94 | 94 | 87 | 71 |
| 666773 | 83 | 81 | 71 | 47 | 36 |
| 666782 | 78 | 79 | 49 | 44 | 23 |
| 666787 | 75 | 66 | 44 | 32 | 26 |
| 666792 | 84 | 75 | 61 | 46 | 32 |
| 666815 | 81 | 80 | 47 | 50 | 32 |

Example 14: Effect of Modified Oligonucleotides on Human IRF4 In Vitro, Multiple Doses Modified oligonucleotides selected from the examples above were tested at various doses in SK-MEL-28 cells. Cells were plated at a density of 20,000 cells per well and transfected using electroporation with 296 nM, 888 nM, 2,666 nM, and 8,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set RTS3114 (described hereinabove in Example 1) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 72

Dose-dependent reduction of human IRF4 mRNA by modified oligonucleotides

| Compound | IRF4 expression (% UTC) | | | | $IC_{50}$ |
|---|---|---|---|---|---|
| Number | 296 nM | 888 nM | 2,666 nM | 8,000 nM | (µM) |
| 609408 | 96 | 53 | 25 | 9 | 1.3 |
| 881193 | 90 | 72 | 54 | 23 | 2.5 |
| 881218 | 86 | 70 | 44 | 38 | 2.9 |
| 881242 | 106 | 65 | 38 | 27 | 2.2 |
| 881290 | 77 | 56 | 44 | 27 | 1.6 |
| 881385 | 99 | 106 | 84 | 54 | >8.0 |
| 881409 | 91 | 82 | 51 | 28 | 2.9 |
| 881434 | 78 | 59 | 29 | 14 | 1.2 |
| 881506 | 61 | 37 | 15 | 11 | 0.5 |
| 881667 | 80 | 63 | 41 | 16 | 1.5 |
| 881993 | 94 | 101 | 73 | 43 | >8.0 |
| 882066 | 99 | 72 | 53 | 25 | 2.7 |
| 882325 | 76 | 55 | 36 | 31 | 1.5 |
| 882326 | 79 | 73 | 42 | 31 | 2.3 |
| 882398 | 83 | 56 | 32 | 16 | 1.3 |
| 882699 | 88 | 81 | 65 | 50 | >8.0 |
| 882722 | 97 | 102 | 84 | 58 | >8.0 |
| 882818 | 134 | 94 | 75 | 31 | 4.8 |
| 882898 | 80 | 66 | 48 | 26 | 2.1 |

TABLE 73

Dose-dependent reduction of human IRF4 mRNA by modified oligonucleotides

| Compound | IRF4 expression (% UTC) | | | | $IC_{50}$ |
|---|---|---|---|---|---|
| Number | 296 nM | 888 nM | 2,666 nM | 8,000 nM | (µM) |
| 609408 | 85 | 50 | 22 | 11 | 1.1 |
| 881411 | 101 | 70 | 45 | 22 | 2.3 |
| 881412 | 105 | 74 | 33 | 21 | 2.1 |
| 881460 | 71 | 50 | 26 | 17 | 0.9 |
| 881530 | 83 | 57 | 34 | 20 | 1.4 |
| 881577 | 89 | 71 | 39 | 20 | 1.9 |
| 881578 | 67 | 48 | 32 | 18 | 0.8 |
| 881597 | 83 | 69 | 49 | 30 | 2.4 |
| 881717 | 70 | 46 | 20 | 15 | 0.8 |
| 881718 | 91 | 62 | 31 | 20 | 1.6 |
| 881741 | 73 | 49 | 24 | 16 | 0.9 |
| 881742 | 64 | 42 | 22 | 14 | 0.6 |
| 881973 | 79 | 58 | 43 | 35 | 2.0 |
| 882352 | 112 | 59 | 36 | 16 | 1.9 |
| 882725 | 90 | 68 | 43 | 20 | 2.0 |
| 882749 | 94 | 83 | 49 | 23 | 2.7 |
| 882797 | 69 | 52 | 27 | 16 | 0.9 |
| 882819 | 97 | 82 | 61 | 28 | 3.5 |
| 882866 | 136 | 119 | 65 | 28 | 4.5 |

TABLE 74

Dose-dependent reduction of human IRF4 mRNA by modified oligonucleotides

| Compound | IRF4 expression (% UTC) | | | | $IC_{50}$ |
|---|---|---|---|---|---|
| Number | 296 nM | 888 nM | 2,666 nM | 8,000 nM | (µM) |
| 609408 | 96 | 45 | 25 | 15 | 1.3 |
| 881127 | 100 | 72 | 44 | 21 | 2.3 |
| 881317 | 74 | 48 | 33 | 18 | 1.0 |
| 881389 | 79 | 67 | 42 | 23 | 1.8 |
| 881413 | 59 | 43 | 35 | 20 | 0.6 |
| 881414 | 97 | 79 | 37 | 20 | 2.2 |
| 881437 | 91 | 67 | 36 | 21 | 1.8 |
| 881581 | 62 | 43 | 27 | 21 | 0.6 |
| 881671 | 80 | 66 | 47 | 41 | 3.1 |
| 881743 | 68 | 55 | 30 | 24 | 1.0 |
| 881791 | 81 | 61 | 34 | 13 | 1.3 |
| 882069 | 74 | 60 | 39 | 30 | 1.6 |
| 882070 | 81 | 60 | 42 | 33 | 2.0 |
| 882162 | 79 | 67 | 42 | 17 | 1.6 |
| 882185 | 73 | 50 | 24 | 22 | 1.0 |
| 882282 | 65 | 38 | 22 | 14 | 0.6 |
| 882305 | 62 | 43 | 15 | 19 | 0.5 |
| 882376 | 97 | 88 | 61 | 33 | 4.1 |
| 882377 | 82 | 46 | 22 | 13 | 1.0 |

TABLE 75

Dose-dependent reduction of human IRF4 mRNA by modified oligonucleotides

| Compound | IRF4 expression (% UTC) | | | | $IC_{50}$ |
|---|---|---|---|---|---|
| Number | 296 nM | 888 nM | 2,666 nM | 8,000 nM | (µM) |
| 609408 | 69 | 41 | 21 | 11 | 0.7 |
| 881391 | 100 | 67 | 36 | 21 | 2.0 |
| 881439 | 76 | 48 | 32 | 19 | 1.1 |
| 881511 | 82 | 73 | 36 | 26 | 2.0 |
| 881558 | 70 | 49 | 29 | 14 | 0.9 |
| 881582 | 61 | 42 | 21 | 15 | 0.5 |
| 881601 | 92 | 76 | 47 | 18 | 2.2 |
| 881648 | 78 | 68 | 36 | 21 | 1.6 |
| 881672 | 66 | 51 | 30 | 18 | 0.8 |
| 881744 | 95 | 78 | 43 | 19 | 2.2 |

TABLE 75-continued

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 881746 | 69 | 41 | 26 | 15 | 0.7 |
| 881975 | 101 | 91 | 63 | 51 | >8.0 |
| 881999 | 71 | 53 | 31 | 26 | 1.1 |
| 882210 | 91 | 78 | 50 | 22 | 2.5 |
| 882283 | 79 | 55 | 29 | 17 | 1.2 |
| 882354 | 81 | 57 | 34 | 20 | 1.4 |
| 882379 | 108 | 86 | 60 | 25 | 3.4 |
| 882800 | 77 | 55 | 28 | 15 | 1.1 |
| 882870 | 69 | 42 | 23 | 12 | 0.7 |

TABLE 76

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 81 | 47 | 29 | 18 | 1.1 |
| 881296 | 84 | 60 | 57 | 38 | 3.2 |
| 881440 | 75 | 74 | 46 | 26 | 2.2 |
| 881441 | 93 | 68 | 34 | 26 | 2.0 |
| 881465 | 85 | 63 | 38 | 29 | 1.9 |
| 881512 | 82 | 60 | 38 | 27 | 1.7 |
| 881559 | 84 | 62 | 47 | 31 | 2.2 |
| 881747 | 80 | 57 | 37 | 26 | 1.5 |
| 881955 | 73 | 66 | 35 | 30 | 1.6 |
| 882072 | 82 | 73 | 51 | 32 | 2.8 |
| 882142 | 85 | 68 | 48 | 31 | 2.5 |
| 882214 | 77 | 46 | 30 | 13 | 1.0 |
| 882309 | 74 | 54 | 51 | 24 | 1.6 |
| 882310 | 81 | 35 | 31 | 14 | 0.9 |
| 882357 | 74 | 58 | 35 | 31 | 1.5 |
| 882495 | 93 | 76 | 52 | 33 | 3.2 |
| 882565 | 90 | 77 | 55 | 33 | 3.3 |
| 882777 | 96 | 75 | 35 | 33 | 2.5 |
| 882871 | 67 | 49 | 44 | 21 | 1.1 |

TABLE 77

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 83 | 48 | 25 | 15 | 1.1 |
| 881322 | 98 | 71 | 42 | 17 | 2.0 |
| 881371 | 91 | 70 | 37 | 22 | 1.9 |
| 881394 | 77 | 47 | 27 | 14 | 1.0 |
| 881395 | 77 | 49 | 26 | 15 | 1.0 |
| 881442 | 51 | 36 | 22 | 9 | 0.3 |
| 881514 | 88 | 75 | 46 | 21 | 2.2 |
| 881561 | 92 | 62 | 38 | 18 | 1.7 |
| 881585 | 76 | 52 | 34 | 23 | 1.2 |
| 881724 | 100 | 72 | 39 | 22 | 2.2 |
| 881748 | 81 | 61 | 34 | 20 | 1.5 |
| 881749 | 70 | 46 | 27 | 12 | 0.8 |
| 881773 | 88 | 59 | 33 | 20 | 1.5 |
| 882215 | 83 | 60 | 50 | 26 | 2.0 |
| 882311 | 82 | 63 | 36 | 21 | 1.6 |
| 882358 | 80 | 52 | 32 | 17 | 1.2 |
| 882359 | 91 | 57 | 34 | 11 | 1.4 |
| 882383 | 92 | 86 | 64 | 37 | 4.8 |
| 882429 | 74 | 52 | 32 | 11 | 1.0 |

TABLE 78

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 85 | 53 | 36 | 14 | 1.3 |
| 881133 | 101 | 88 | 76 | 63 | >8.0 |
| 881204 | 92 | 79 | 50 | 26 | 2.7 |
| 881396 | 71 | 46 | 29 | 16 | 0.9 |
| 881515 | 90 | 67 | 44 | 21 | 2.0 |
| 881516 | 81 | 49 | 35 | 17 | 1.2 |
| 881588 | 69 | 52 | 26 | 18 | 0.9 |
| 881726 | 73 | 42 | 44 | 8 | 1.0 |
| 881727 | 66 | 50 | 35 | 19 | 0.9 |
| 881750 | 73 | 49 | 19 | 17 | 0.9 |
| 882077 | 93 | 78 | 54 | 37 | 3.7 |
| 882099 | 61 | 46 | 18 | 23 | 0.6 |
| 882169 | 101 | 84 | 51 | 18 | 2.6 |
| 882170 | 92 | 76 | 39 | 25 | 2.2 |
| 882313 | 87 | 60 | 32 | 18 | 1.5 |
| 882384 | 93 | 68 | 40 | 18 | 1.9 |
| 882408 | 84 | 61 | 41 | 19 | 1.6 |
| 882709 | 104 | 106 | 108 | 98 | >8.0 |
| 882758 | 82 | 53 | 36 | 17 | 1.3 |

TABLE 79

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 83 | 49 | 25 | 10 | 1.1 |
| 881279 | 87 | 73 | 43 | 22 | 2.1 |
| 881399 | 79 | 49 | 23 | 24 | 1.1 |
| 881422 | 85 | 63 | 44 | 29 | 2.1 |
| 881470 | 109 | 92 | 54 | 19 | 3.0 |
| 881494 | 68 | 50 | 33 | 20 | 0.9 |
| 881495 | 68 | 46 | 24 | 17 | 0.8 |
| 881517 | 75 | 41 | 14 | 12 | 0.7 |
| 881542 | 76 | 55 | 31 | 13 | 1.1 |
| 881589 | 80 | 48 | 26 | 10 | 1.0 |
| 881607 | 90 | 64 | 32 | 19 | 1.6 |
| 881608 | 73 | 45 | 22 | 21 | 0.8 |
| 881728 | 58 | 32 | 17 | 11 | 0.4 |
| 881729 | 94 | 75 | 40 | 29 | 2.4 |
| 881752 | 75 | 47 | 28 | 14 | 0.9 |
| 882409 | 86 | 66 | 42 | 20 | 1.8 |
| 882432 | 101 | 67 | 34 | 12 | 1.7 |
| 882433 | 72 | 38 | 25 | 16 | 0.7 |
| 882806 | 92 | 35 | 45 | 34 | 1.7 |

TABLE 80

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 99 | 55 | 43 | 12 | 1.7 |
| 690521 | 88 | 58 | 36 | 21 | 1.6 |
| 881112 | 133 | 107 | 73 | 56 | >8.0 |
| 881183 | 109 | 93 | 58 | 31 | 3.9 |
| 881280 | 94 | 61 | 40 | 23 | 1.9 |
| 881303 | 90 | 79 | 55 | 28 | 3.0 |
| 881304 | 94 | 86 | 86 | 37 | 7.9 |
| 881327 | 125 | 115 | 71 | 44 | 6.9 |
| 881448 | 82 | 58 | 36 | 21 | 1.5 |
| 881496 | 72 | 55 | 34 | 21 | 1.2 |

TABLE 80-continued

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 881543 | 86 | 67 | 37 | 24 | 1.8 |
| 881610 | 71 | 49 | 22 | 13 | 0.8 |
| 881657 | 83 | 61 | 46 | 29 | 2.0 |
| 881658 | 77 | 53 | 29 | 13 | 1.1 |
| 881753 | 81 | 70 | 48 | 20 | 2.0 |
| 881962 | 87 | 67 | 49 | 29 | 2.5 |
| 882268 | 110 | 72 | 50 | 31 | 3.0 |
| 882479 | 96 | 81 | 45 | 42 | 3.7 |
| 882761 | 76 | 67 | 37 | 25 | 1.6 |

TABLE 81

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 87 | 48 | 28 | 15 | 1.2 |
| 690522 | 63 | 32 | 13 | 11 | 0.4 |
| 690523 | 90 | 61 | 37 | 19 | 1.7 |
| 881281 | 95 | 69 | 49 | 32 | 2.8 |
| 881305 | 76 | 60 | 42 | 23 | 1.6 |
| 881425 | 71 | 53 | 34 | 21 | 1.1 |
| 881426 | 73 | 45 | 29 | 19 | 0.9 |
| 881449 | 65 | 50 | 28 | 16 | 0.8 |
| 881497 | 129 | 95 | 57 | 19 | 3.3 |
| 881498 | 98 | 71 | 34 | 16 | 1.9 |
| 881659 | 53 | 25 | 13 | 9 | <0.3 |
| 881660 | 65 | 32 | 17 | 10 | 0.5 |
| 881683 | 74 | 60 | 37 | 22 | 1.4 |
| 881780 | 82 | 54 | 34 | 17 | 1.3 |
| 881963 | 91 | 66 | 39 | 33 | 2.3 |
| 882175 | 79 | 43 | 24 | 12 | 0.9 |
| 882246 | 69 | 44 | 29 | 11 | 0.8 |
| 882810 | 100 | 66 | 45 | 25 | 2.3 |
| 882833 | 101 | 86 | 57 | 23 | 3.1 |

TABLE 82

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 87 | 51 | 28 | 14 | 1.2 |
| 881258 | 115 | 91 | 60 | 31 | 3.9 |
| 881282 | 104 | 89 | 42 | 32 | 3.1 |
| 881404 | 89 | 81 | 43 | 27 | 2.5 |
| 881427 | 87 | 65 | 48 | 19 | 1.9 |
| 881450 | 63 | 42 | 26 | 12 | 0.6 |
| 881451 | 100 | 77 | 49 | 30 | 2.9 |
| 881452 | 77 | 67 | 49 | 27 | 2.2 |
| 881499 | 84 | 74 | 44 | 35 | 2.7 |
| 881661 | 122 | 92 | 51 | 23 | 3.2 |
| 881684 | 106 | 89 | 55 | 33 | 3.8 |
| 881733 | 82 | 63 | 32 | 29 | 1.7 |
| 881734 | 72 | 49 | 34 | 23 | 1.0 |
| 881941 | 94 | 86 | 60 | 41 | 5.2 |
| 882177 | 94 | 62 | 35 | 30 | 2.0 |
| 882199 | 90 | 81 | 38 | 16 | 2.0 |
| 882200 | 89 | 60 | 36 | 22 | 1.7 |
| 882247 | 79 | 60 | 47 | 33 | 2.2 |
| 882765 | 101 | 82 | 57 | 30 | 3.5 |

TABLE 83

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 87 | 49 | 30 | 11 | 1.2 |
| 881213 | 85 | 67 | 50 | 20 | 2.1 |
| 881238 | 83 | 58 | 33 | 19 | 1.4 |
| 881286 | 64 | 51 | 35 | 22 | 0.9 |
| 881381 | 77 | 55 | 34 | 26 | 1.3 |
| 881382 | 83 | 71 | 49 | 37 | 3.0 |
| 881405 | 86 | 58 | 42 | 16 | 1.6 |
| 881477 | 80 | 62 | 56 | 28 | 2.4 |
| 881478 | 102 | 69 | 47 | 30 | 2.7 |
| 881571 | 109 | 90 | 47 | 27 | 3.1 |
| 881572 | 87 | 67 | 39 | 25 | 1.9 |
| 881616 | 104 | 76 | 47 | 36 | 3.3 |
| 881663 | 130 | 108 | 63 | 32 | 4.6 |
| 881784 | 117 | 87 | 50 | 35 | 3.7 |
| 882085 | 82 | 66 | 46 | 27 | 2.1 |
| 882107 | 109 | 83 | 74 | 37 | 5.5 |
| 882178 | 114 | 69 | 36 | 16 | 2.1 |
| 882601 | 123 | 99 | 64 | 26 | 4.0 |
| 882670 | 91 | 85 | 66 | 34 | 4.7 |

TABLE 84

Dose-dependent reduction of human IRF4 mRNA by modified oligonucleotides

| Compound Number | IRF4 expression (% UTC) | | | | IC$_{50}$ (µM) |
|---|---|---|---|---|---|
| | 296 nM | 888 nM | 2,666 nM | 8,000 nM | |
| 609408 | 101 | 60 | 32 | 14 | 1.6 |
| 881240 | 103 | 79 | 47 | 23 | 2.6 |
| 881359 | 124 | 89 | 57 | 35 | 4.1 |
| 881360 | 83 | 58 | 40 | 22 | 1.6 |
| 881384 | 85 | 72 | 42 | 39 | 2.8 |
| 881432 | 73 | 62 | 49 | 29 | 2.0 |
| 881575 | 92 | 67 | 52 | 40 | 3.4 |
| 881593 | 84 | 71 | 57 | 31 | 3.1 |
| 881761 | 94 | 93 | 72 | 56 | >8.0 |
| 882039 | 95 | 79 | 68 | 50 | >8.0 |
| 882086 | 96 | 79 | 50 | 25 | 2.7 |
| 882087 | 72 | 55 | 36 | 32 | 1.4 |
| 882204 | 67 | 77 | 38 | 30 | 1.9 |
| 882227 | 111 | 90 | 54 | 47 | 5.2 |
| 882228 | 96 | 75 | 52 | 40 | 3.8 |
| 882323 | 106 | 87 | 62 | 34 | 4.3 |
| 882532 | 114 | 85 | 54 | 33 | 3.7 |
| 882721 | 98 | 78 | 69 | 45 | 6.6 |
| 882744 | 84 | 79 | 50 | 31 | 2.9 |

Example 15: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 74 nM, 222 nM, 666 nM, and 2,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set hIRF4_LTS34726 (described hereinabove in Example 7) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 85

Dose-dependent reduction of human IRF4 mRNA by modified oligonucleotides

| Compound Number | IRF4 expression (% UTC) | | | | IC$_{50}$ (µM) |
|---|---|---|---|---|---|
| | 74 nM | 222 nM | 666 nM | 2,000 nM | |
| 609408 | 86 | 66 | 43 | 17 | 0.4 |
| 935580 | 89 | 62 | 34 | 10 | 0.4 |
| 935603 | 91 | 69 | 46 | 23 | 0.5 |
| 935620 | 84 | 64 | 37 | 15 | 0.4 |
| 935658 | 82 | 56 | 37 | 15 | 0.3 |
| 935898 | 74 | 47 | 24 | 7 | 0.2 |
| 935911 | 100 | 88 | 66 | 43 | 1.5 |
| 935918 | 90 | 75 | 45 | 23 | 0.6 |
| 935921 | 80 | 52 | 27 | 9 | 0.3 |
| 935925 | 98 | 67 | 62 | 36 | 0.9 |
| 935928 | 90 | 72 | 48 | 23 | 0.6 |
| 935929 | 96 | 85 | 60 | 36 | 1.1 |
| 935935 | 95 | 83 | 63 | 32 | 1.0 |
| 935939 | 86 | 74 | 50 | 41 | 0.9 |
| 935941 | 86 | 84 | 70 | 41 | 1.7 |
| 935948 | 86 | 62 | 45 | 24 | 0.5 |
| 935958 | 83 | 56 | 33 | 14 | 0.3 |
| 935961 | 78 | 51 | 27 | 8 | 0.3 |
| 935968 | 88 | 61 | 35 | 12 | 0.4 |

TABLE 86

Dose-dependent reduction of human IRF4 mRNA by modified oligonucleotides

| Compound Number | IRF4 expression (% UTC) | | | | IC$_{50}$ (µM) |
|---|---|---|---|---|---|
| | 74 nM | 222 nM | 666 nM | 2,000 nM | |
| 609408 | 79 | 59 | 37 | 14 | 0.3 |
| 935581 | 78 | 61 | 38 | 15 | 0.4 |
| 935608 | 85 | 71 | 48 | 20 | 0.5 |
| 935655 | 93 | 88 | 70 | 46 | >2.0 |
| 935679 | 92 | 72 | 47 | 23 | 0.6 |
| 935689 | 86 | 63 | 40 | 19 | 0.4 |
| 935696 | 72 | 45 | 22 | 9 | 0.2 |
| 935697 | 80 | 55 | 23 | 9 | 0.3 |
| 935698 | 83 | 68 | 39 | 17 | 0.4 |
| 935699 | 87 | 60 | 36 | 14 | 0.4 |
| 935700 | 72 | 59 | 26 | 7 | 0.3 |
| 935701 | 82 | 64 | 40 | 18 | 0.4 |
| 935707 | 84 | 68 | 49 | 23 | 0.5 |
| 935708 | 84 | 59 | 34 | 15 | 0.4 |
| 935721 | 86 | 70 | 46 | 24 | 0.5 |
| 935724 | 73 | 39 | 20 | 5 | 0.2 |
| 935727 | 85 | 67 | 49 | 27 | 0.6 |
| 935734 | 74 | 58 | 35 | 16 | 0.3 |
| 935741 | 85 | 68 | 42 | 17 | 0.4 |

TABLE 87

Dose-dependent reduction of human IRF4 mRNA by modified oligonucleotides

| Compound Number | IRF4 expression (% UTC) | | | | IC$_{50}$ (µM) |
|---|---|---|---|---|---|
| | 74 nM | 222 nM | 666 nM | 2,000 nM | |
| 609408 | 77 | 60 | 41 | 16 | 0.4 |
| 935668 | 94 | 78 | 51 | 25 | 0.7 |
| 935671 | 91 | 73 | 54 | 27 | 0.7 |
| 935686 | 90 | 69 | 53 | 34 | 0.8 |
| 935709 | 72 | 78 | 57 | 36 | 0.9 |

TABLE 87-continued

Dose-dependent reduction of human IRF4 mRNA by modified oligonucleotides

| Compound Number | IRF4 expression (% UTC) | | | | IC$_{50}$ (µM) |
|---|---|---|---|---|---|
| | 74 nM | 222 nM | 666 nM | 2,000 nM | |
| 935731 | 80 | 66 | 52 | 36 | 0.7 |
| 935762 | 72 | 56 | 35 | 19 | 0.3 |
| 935765 | 75 | 55 | 37 | 15 | 0.3 |
| 935772 | 81 | 65 | 51 | 27 | 0.6 |
| 935779 | 78 | 72 | 55 | 28 | 0.7 |
| 935782 | 66 | 55 | 36 | 15 | 0.2 |
| 935789 | 81 | 77 | 58 | 32 | 0.9 |
| 935795 | 95 | 77 | 60 | 33 | 0.9 |
| 935805 | 85 | 68 | 42 | 21 | 0.5 |
| 935850 | 74 | 48 | 25 | 12 | 0.2 |
| 935851 | 78 | 54 | 26 | 9 | 0.3 |
| 935854 | 79 | 64 | 35 | 14 | 0.3 |
| 935857 | 78 | 66 | 44 | 19 | 0.4 |
| 935878 | 71 | 42 | 24 | 10 | 0.2 |

TABLE 88

Dose-dependent reduction of human IRF4 mRNA by modified oligonucleotides

| Compound Number | IRF4 expression (% UTC) | | | | IC$_{50}$ (µM) |
|---|---|---|---|---|---|
| | 74 nM | 222 nM | 666 nM | 2,000 nM | |
| 609408 | 79 | 62 | 39 | 15 | 0.4 |
| 881450 | 100 | 75 | 56 | 28 | 0.8 |
| 881659 | 76 | 45 | 21 | 5 | 0.2 |
| 935824 | 86 | 65 | 46 | 23 | 0.5 |
| 935833 | 81 | 60 | 44 | 26 | 0.5 |
| 935840 | 82 | 54 | 51 | 27 | 0.5 |
| 935853 | 85 | 64 | 45 | 21 | 0.5 |
| 935856 | 92 | 71 | 50 | 29 | 0.7 |
| 935859 | 90 | 81 | 63 | 36 | 1.1 |
| 935888 | 79 | 72 | 43 | 20 | 0.5 |
| 936006 | 80 | 64 | 41 | 21 | 0.4 |
| 936007 | 87 | 65 | 34 | 13 | 0.4 |
| 936011 | 94 | 79 | 62 | 40 | 1.2 |
| 936013 | 78 | 67 | 48 | 26 | 0.5 |
| 936016 | 83 | 62 | 43 | 21 | 0.4 |
| 936018 | 82 | 66 | 43 | 17 | 0.4 |
| 936033 | 80 | 63 | 47 | 25 | 0.5 |
| 936039 | 85 | 67 | 48 | 25 | 0.5 |
| 936046 | 88 | 66 | 49 | 30 | 0.6 |

Example 16: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 74 nM, 222 nM, 666 nM, and 2,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set hIRF4_LTS34726 (described hereinabove in Example 7) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 89

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 609311 | 94 | 106 | 100 | 87 |
| 609312 | 97 | 96 | 103 | 93 |
| 609328 | 87 | 86 | 88 | 83 |
| 609337 | 94 | 98 | 99 | 96 |
| 609354 | 93 | 88 | 76 | 50 |
| 609357 | 101 | 87 | 90 | 61 |
| 609408 | 83 | 57 | 35 | 11 |
| 609422 | 96 | 100 | 90 | 76 |
| 609530 | 103 | 94 | 94 | 87 |
| 609533 | 103 | 103 | 91 | 75 |
| 609546 | 100 | 103 | 107 | 97 |
| 609591 | 93 | 94 | 89 | 68 |
| 609592 | 95 | 94 | 88 | 76 |

TABLE 90

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 609408 | 93 | 61 | 37 | 12 |
| 609592 | 97 | 85 | 88 | 81 |
| 609594 | 98 | 97 | 81 | 85 |
| 881127 | 96 | 98 | 87 | 66 |
| 881183 | 93 | 89 | 75 | 55 |
| 881193 | 25 | 21 | 17 | 13 |
| 881204 | 97 | 82 | 49 | 26 |
| 881955 | 97 | 73 | 44 | 16 |
| 881962 | 119 | 96 | 93 | 67 |
| 881963 | 104 | 119 | 104 | 91 |
| 881973 | 99 | 95 | 89 | 74 |
| 881999 | 98 | 91 | 80 | 46 |
| 882066 | 108 | 103 | 104 | 94 |
| 882069 | 109 | 99 | 91 | 65 |
| 882070 | 108 | 106 | 81 | 68 |
| 882072 | 112 | 104 | 94 | 72 |
| 882077 | 107 | 122 | 101 | 102 |
| 882085 | 96 | 85 | 71 | 37 |
| 882086 | 90 | 77 | 50 | 17 |

TABLE 91

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 609408 | 84 | 68 | 36 | 12 |
| 882087 | 84 | 75 | 52 | 23 |
| 882142 | 95 | 99 | 82 | 68 |
| 882162 | 87 | 94 | 76 | 49 |
| 882169 | 97 | 79 | 59 | 41 |
| 882170 | 86 | 77 | 60 | 28 |
| 882175 | 98 | 101 | 72 | 46 |
| 882177 | 94 | 96 | 80 | 60 |
| 882178 | 103 | 105 | 109 | 95 |
| 882185 | 100 | 95 | 87 | 63 |
| 882199 | 98 | 105 | 98 | 85 |
| 882200 | 111 | 118 | 101 | 87 |
| 882204 | 101 | 96 | 78 | 61 |
| 882214 | 113 | 106 | 96 | 80 |
| 882215 | 112 | 113 | 110 | 104 |
| 882227 | 114 | 100 | 109 | 90 |

TABLE 91-continued

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 882228 | 101 | 92 | 85 | 63 |
| 882247 | 114 | 105 | 104 | 102 |
| 882268 | 108 | 94 | 89 | 67 |

TABLE 92

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 609408 | 81 | 69 | 39 | 9 |
| 882283 | 98 | 94 | 86 | 54 |
| 882309 | 85 | 93 | 79 | 49 |
| 882310 | 91 | 94 | 85 | 92 |
| 882311 | 83 | 74 | 59 | 18 |
| 882313 | 87 | 73 | 57 | 25 |
| 882323 | 92 | 95 | 81 | 50 |
| 882325 | 99 | 87 | 62 | 31 |
| 882326 | 100 | 98 | 100 | 68 |
| 882352 | 93 | 91 | 78 | 62 |
| 882354 | 96 | 93 | 78 | 66 |
| 882357 | 103 | 84 | 78 | 48 |
| 882358 | 90 | 74 | 42 | 13 |
| 882359 | 109 | 112 | 104 | 91 |
| 882376 | 104 | 107 | 97 | 86 |
| 882377 | 98 | 94 | 89 | 64 |
| 882379 | 101 | 101 | 108 | 101 |
| 882383 | 106 | 112 | 104 | 104 |
| 882384 | 101 | 98 | 80 | 62 |

TABLE 93

Dose-dependent reduction of human IRF4 mRNA by modified oligonucleotides

| Compound Number | IRF4 expression (% UTC) | | | |
|---|---|---|---|---|
| | 74 nM | 222 nM | 666 nM | 2,000 nM |
| 609408 | 74 | 64 | 38 | 13 |
| 882398 | 81 | 74 | 63 | 28 |
| 882408 | 88 | 77 | 64 | 37 |
| 882409 | 101 | 67 | 89 | 92 |
| 882429 | 98 | 90 | 90 | 89 |
| 882432 | 88 | 93 | 91 | 83 |
| 882479 | 86 | 91 | 89 | 56 |
| 882495 | 83 | 100 | 96 | 87 |
| 882532 | 89 | 101 | 126 | N/A |
| 882565 | 107 | 109 | 109 | 92 |
| 882601 | 103 | 98 | 85 | 91 |
| 882670 | 104 | 95 | 91 | 60 |
| 882721 | 98 | 97 | 91 | 73 |
| 882725 | 93 | 92 | 80 | 72 |
| 882744 | 100 | 66 | 73 | 48 |
| 882749 | 89 | 92 | 77 | 55 |
| 882758 | 88 | 79 | 72 | 56 |
| 882761 | 87 | 88 | 77 | 61 |
| 882765 | 89 | 103 | 94 | 98 |

TABLE 94

Dose-dependent reduction of human IRF4 mRNA by modified oligonucleotides

| Compound | IRF4 expression (% UTC) | | | |
|---|---|---|---|---|
| Number | 74 nM | 222 nM | 666 nM | 2,000 nM |
| 609408 | 54 | 34 | 41 | N/A |
| 881450 | 65 | 59 | 29 | 11 |
| 881659 | 45 | 19 | 6 | 2 |
| 882777 | 109 | 133 | 93 | 105 |
| 882797 | 113 | 106 | 93 | 63 |
| 882800 | 112 | 83 | 56 | 22 |
| 882806 | 100 | 115 | 107 | 91 |
| 882810 | 88 | 88 | 84 | 50 |

Example 17: Design of 3-10-3 cEt Gapmers with Phosphorothioate Internucleoside Linkages Modified oligonucleotides complementary to a human IRF4 nucleic acid were designed. The modified oligonucleotides in Table 95 are 3-10-3 cEt gapmers. The gapmers are 16 nucleobases in length, wherein the central gap segment comprises ten 2'-deoxynucleosides and is flanked by wing segments on both the 5' end and on the 3' end comprising three cEt nucleosides. The sugar motif for the gapmers is (from 5' to 3'): kkkddddddddddkkk; wherein represents a 2'-deoxyribose sugar and 'k' represents a cEt modified sugar. Each internucleoside linkage is a phosphorothioate internucleoside linkage and each cytosine residue is a 5-methylcytosine. "Start Site" indicates the 5'-most nucleoside to which the gapmer is complementary in the human nucleic acid sequence. "Stop Site" indicates the 3'-most nucleoside to which the gapmer is complementary in the human nucleic acid sequence.

Each modified oligonucleotide listed in Table 95 below is complementary to human IRF4 nucleic acid sequences SEQ ID NO: 1 or SEQ ID NO: 2, as indicated. 'N/A' indicates that the modified oligonucleotide is not complementary to that particular nucleic acid sequence with 100% complementarity.

TABLE 95

Dose-dependent reduction of human IRF4 mRNA by modified oligonucleotides

| Compound Number | SEQ ID NO: 1 Start Site | SEQ ID NO: 1 Stop Site | SEQ ID NO: 2 Start Site | SEQ ID NO: 2 Stop Site | Sequence | SEQ ID NO |
|---|---|---|---|---|---|---|
| 970454 | N/A | N/A | 17700 | 17715 | AGAACATTACGAGAGG | 3371 |
| 970466 | N/A | N/A | 18074 | 18089 | GGTTGGCTGGTCTTTG | 3337 |
| 970500 | N/A | N/A | 18088 | 18103 | ATTATATACTGGTTGG | 3340 |
| 970524 | N/A | N/A | 18248 | 18263 | CGATCATCAACTTCTT | 3372 |
| 970527 | N/A | N/A | 18572 | 18587 | GTGATAGCTGAGCTGA | 3343 |
| 970539 | N/A | N/A | 18583 | 18598 | ACTGGATTGATGTGAT | 3373 |
| 970545 | N/A | N/A | 18718 | 18733 | GGAACTCATAGGTGTA | 3374 |
| 970546 | 1415 | 1430 | 19532 | 19547 | CTGATGTGTTCTGGTA | 3375 |
| 970547 | N/A | N/A | 17235 | 17250 | TACGCTTATTTTCCA | 3376 |
| 970548 | N/A | N/A | 17474 | 17489 | GCAATCTTAACCTGGA | 3377 |
| 970552 | N/A | N/A | 18580 | 18595 | GGATTGATGTGATAGC | 3378 |
| 970554 | N/A | N/A | 19020 | 19035 | TCTGTATAGTTCTCAA | 3379 |
| 970574 | 1350 | 1365 | 19467 | 19482 | TAGTTGTCTGGCTAGC | 3380 |
| 970597 | N/A | N/A | 18575 | 18590 | GATGTGATAGCTGAGC | 3346 |
| 970598 | N/A | N/A | 18612 | 18627 | CAGTGACTTGCATCCA | 3350 |
| 970600 | 1346 | 1361 | 19463 | 19478 | TGTCTGGCTAGCAGAG | 3381 |
| 970602 | 1396 | 1411 | 19513 | 19528 | CGTAGCCCCTCAGGAA | 3382 |
| 970603 | 1423 | 1438 | 19540 | 19555 | CTGGATTGCTGATGTG | 3383 |

Example 18: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 62.5 nM, 250 nM, 1,000 nM, and 4,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set hIRF4_LTS34726 (described hereinabove in Example 7) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 96

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 84 | 55 | 28 | 7 |
| 935583 | 99 | 77 | 32 | 8 |
| 969936 | 86 | 88 | 61 | 34 |
| 969937 | 94 | 100 | 75 | 33 |
| 969938 | 104 | 84 | 60 | 30 |
| 970044 | 115 | 107 | 79 | 42 |
| 970069 | 86 | 111 | 97 | 67 |
| 970104 | 101 | 87 | 60 | 30 |
| 970114 | 109 | 96 | 73 | 45 |
| 970117 | 109 | 84 | 48 | 19 |
| 970139 | 78 | 60 | 44 | 24 |
| 970158 | 101 | 102 | 81 | 46 |
| 970159 | 82 | 64 | 45 | 18 |
| 970189 | 85 | 66 | 42 | 25 |
| 970217 | 96 | 90 | 71 | 44 |
| 970228 | 65 | 77 | 37 | 13 |
| 970253 | 111 | 105 | 100 | 63 |
| 970344 | 83 | 117 | 124 | 92 |
| 970388 | 100 | 87 | 70 | 29 |

TABLE 97

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 92 | 55 | 28 | 8 |
| 969879 | 106 | 110 | 107 | 113 |
| 969933 | 94 | 71 | 48 | 36 |
| 969991 | 115 | 92 | 56 | 13 |
| 970013 | 96 | 78 | 48 | 19 |
| 970043 | 102 | 82 | 43 | 16 |
| 970103 | 96 | 64 | 52 | 34 |
| 970160 | 111 | 96 | 75 | 35 |
| 970161 | 106 | 104 | 82 | 62 |
| 970162 | 94 | 82 | 60 | 18 |
| 970211 | 93 | 79 | 59 | 32 |
| 970212 | 97 | 80 | 38 | 7 |
| 970230 | 110 | 105 | 84 | 52 |
| 970231 | 113 | 105 | 114 | 94 |
| 970249 | 116 | 93 | 59 | 22 |
| 970358 | 113 | 110 | 87 | 55 |
| 970370 | 107 | 93 | 77 | 32 |
| 970382 | 113 | 97 | 70 | 40 |
| 970610 | 125 | 103 | 88 | 50 |

TABLE 98

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 84 | 56 | 30 | 7 |
| 970454 | 98 | 84 | 59 | 35 |
| 970466 | 102 | 84 | 51 | 34 |
| 970500 | 97 | 85 | 61 | 23 |
| 970524 | 76 | 50 | 28 | 8 |
| 970527 | 87 | 62 | 30 | 11 |
| 970539 | 98 | 94 | 75 | 35 |
| 970545 | 89 | 74 | 47 | 25 |
| 970546 | 86 | 73 | 55 | 31 |
| 970547 | 99 | 71 | 49 | 35 |
| 970548 | 103 | 92 | 63 | 30 |
| 970552 | 93 | 76 | 41 | 12 |
| 970554 | 102 | 84 | 58 | 31 |
| 970574 | 96 | 84 | 68 | 32 |
| 970597 | 38 | 21 | 15 | 8 |
| 970598 | 60 | 57 | 47 | 25 |
| 970600 | 49 | 35 | 29 | 21 |
| 970602 | 41 | 39 | 32 | 19 |
| 970603 | 55 | 47 | 44 | 17 |

Example 19: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 62.5 nM, 250 nM, 1,000 nM, and 4,000 nM concentrations of modified oligonucleotide, as specified in the tables below. After a treatment period of approximately 24 hours, RNA was isolated from the cells and IRF4 mRNA levels were measured by RT-qPCR. Human IRF4 primwr probe set RTS4523 (forward sequence AAGCCTTGGCGTTCTCAGACT, designated herein as SEQ ID NO: 3386; reverse sequence TCAGCTCCTTCACGAGGATTTC, designated herein as SEQ ID NO: 3387; probe sequence CCGGCTGCACATCTGCCTGTACTACC, designated herein as SEQ ID: 3388), was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the table below, IRF4 mRNA levels were reduced in a dose-dependent manner in cells treated with modified oligonucleotides.

TABLE 99

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 75 | 51 | 31 | 10 |
| 970454 | 88 | 80 | 49 | 34 |
| 970466 | 85 | 80 | 65 | 30 |
| 970500 | 91 | 75 | 43 | 26 |
| 970524 | 77 | 50 | 25 | 7 |
| 970527 | 83 | 53 | 25 | 12 |
| 970539 | 91 | 80 | 61 | 31 |
| 970545 | 68 | 58 | 35 | 20 |
| 970546 | 64 | 59 | 47 | 30 |
| 970547 | 88 | 56 | 44 | 23 |
| 970548 | 97 | 92 | 62 | 29 |
| 970552 | 76 | 80 | 40 | 12 |
| 970554 | 100 | 74 | 60 | 29 |
| 970574 | 93 | 76 | 67 | 32 |
| 970597 | 93 | 99 | 78 | 51 |
| 970598 | 80 | 76 | 62 | 39 |
| 970600 | 82 | 87 | 80 | 63 |
| 970602 | 85 | 80 | 66 | 41 |
| 970603 | 83 | 77 | 64 | 29 |

Example 20: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 62.5 nM, 250 nM, 1,000 nM, and 4,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set hIRF4_LTS34726 (described hereinabove in Example 7) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 100

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 72 | 43 | 19 | 4 |
| 881955 | 89 | 69 | 40 | 10 |
| 881962 | 107 | 92 | 66 | 23 |
| 881963 | 116 | 116 | 99 | 88 |
| 881973 | 109 | 101 | 86 | 59 |
| 881999 | 117 | 98 | 72 | 32 |
| 882066 | 110 | 114 | 107 | 105 |
| 882069 | 100 | 95 | 75 | 43 |
| 882070 | 101 | 94 | 82 | 42 |
| 882072 | 95 | 98 | 83 | 59 |
| 882077 | 101 | 96 | 90 | 68 |
| 882085 | 96 | 71 | 49 | 13 |
| 882086 | 92 | 68 | 37 | 8 |
| 882087 | 98 | 74 | 45 | 13 |
| 882142 | 103 | 89 | 80 | 56 |
| 882162 | 94 | 80 | 61 | 27 |
| 882169 | 102 | 93 | 93 | 77 |
| 882170 | 99 | 84 | 71 | 35 |
| 882175 | 89 | 75 | 45 | 21 |

TABLE 101

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 73 | 43 | 19 | 4 |
| 882177 | 83 | 66 | 38 | 11 |
| 882178 | 101 | 100 | 87 | 59 |
| 882185 | 99 | 90 | 73 | 41 |
| 882199 | 108 | 111 | 96 | 82 |
| 882200 | 112 | 106 | 97 | 66 |
| 882204 | 96 | 82 | 55 | 22 |
| 882214 | 98 | 92 | 53 | 12 |
| 882215 | 118 | 112 | 117 | 106 |
| 882228 | 89 | 75 | 46 | 15 |
| 882246 | 101 | 98 | 85 | 58 |
| 882247 | 97 | 101 | 92 | 74 |
| 882268 | 101 | 88 | 78 | 49 |
| 882283 | 104 | 95 | 86 | 48 |
| 882309 | 87 | 76 | 59 | 31 |
| 882310 | 96 | 103 | 105 | 107 |
| 882311 | 99 | 99 | 119 | 99 |
| 882313 | 98 | 82 | 61 | 31 |
| 882323 | 89 | 89 | 81 | 68 |

TABLE 102

Dose-dependent reduction of human IRF4 mRNA by modified oligonucleotides

| Compound Number | IRF4 expression (% UTC) | | | |
|---|---|---|---|---|
| | 62.5 nM | 250 nM | 1,000 nM | 4,000 nM |
| 609408 | 74 | 49 | 23 | 5 |
| 882325 | 94 | 95 | 85 | 45 |
| 882326 | 101 | 98 | 86 | 64 |
| 882352 | 97 | 88 | 75 | 48 |
| 882354 | 103 | 91 | 52 | 38 |
| 882357 | 106 | 91 | 68 | 36 |
| 882358 | 96 | 92 | 74 | 37 |
| 882359 | 98 | 99 | 94 | 64 |
| 882377 | 104 | 99 | 82 | 43 |
| 882384 | 96 | 82 | 67 | 39 |
| 882398 | 85 | 63 | 36 | 10 |
| 882408 | 91 | 68 | 41 | 11 |
| 882409 | 105 | 94 | 75 | 44 |
| 882429 | 105 | 99 | 90 | 74 |
| 882432 | 101 | 102 | 102 | 103 |
| 882479 | 98 | 99 | 94 | 83 |
| 882495 | 97 | 94 | 89 | 74 |
| 882532 | 93 | 92 | 78 | 41 |
| 882565 | 100 | 99 | 94 | 88 |

TABLE 103

Dose-dependent reduction of human IRF4
mRNA by modified oligonucleotides

| Compound | IRF4 expression (% UTC) | | | |
|---|---|---|---|---|
| Number | 62.5 nM | 250 nM | 1,000 nM | 4,000 nM |
| 609408 | 77 | 50 | 23 | 6 |
| 881955 | 92 | 75 | 43 | 11 |
| 881962 | 96 | 91 | 64 | 26 |
| 881963 | 95 | 100 | 93 | 76 |
| 882725 | 102 | 102 | 96 | 78 |
| 882744 | 104 | 107 | 93 | 74 |
| 882749 | 102 | 94 | 79 | 55 |
| 882758 | 108 | 94 | 76 | 44 |
| 882761 | 106 | 99 | 77 | 47 |
| 882765 | 99 | 89 | 61 | 34 |
| 882777 | 105 | 111 | 108 | 90 |
| 882797 | 107 | 96 | 78 | 44 |
| 882800 | 89 | 68 | 36 | 9 |
| 882806 | 99 | 96 | 84 | 60 |
| 882810 | 94 | 93 | 65 | 31 |
| 882833 | 101 | 102 | 83 | 67 |
| 882870 | 98 | 88 | 69 | 34 |
| 882871 | 103 | 90 | 75 | 55 |
| 882898 | 101 | 88 | 72 | 45 |

Example 21: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 62.5 nM, 250 nM, 1,000 nM, and 4,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set RTS4523 (described hereinabove in Example 19) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the table below, IRF4 mRNA levels were reduced in a dose-dependent manner in cells treated with modified oligonucleotides.

TABLE 104

Dose-dependent reduction of human IRF4
mRNA by modified oligonucleotides

| Compound | IRF4 expression (% UTC) | | | |
|---|---|---|---|---|
| Number | 62.5 nM | 250 nM | 1,000 nM | 4,000 nM |
| 609408 | 84 | 47 | 22 | 5 |
| 881955 | 82 | 64 | 33 | 8 |
| 881962 | 109 | 79 | 63 | 25 |
| 881963 | 99 | 78 | 74 | 66 |
| 882725 | 85 | 72 | 76 | 60 |
| 882744 | 85 | 104 | 80 | 60 |
| 882749 | 114 | 95 | 64 | 50 |
| 882758 | 111 | 98 | 67 | 37 |
| 882761 | 114 | 108 | 75 | 32 |
| 882765 | 85 | 75 | 52 | 27 |
| 882777 | 83 | 95 | 79 | 63 |
| 882797 | 80 | 72 | 59 | 40 |
| 882800 | 53 | 60 | 28 | 7 |
| 882806 | 108 | 95 | 78 | 55 |
| 882810 | 128 | 119 | 69 | 34 |
| 882833 | 94 | 91 | 75 | 69 |
| 882870 | 114 | 97 | 71 | 31 |
| 882871 | 79 | 82 | 55 | 40 |
| 882898 | 81 | 73 | 58 | 34 |

Example 22: Effect of Modified Oligonucleotides on Human IRF4 In Vitro, Multiple Doses Modified oligonucleotides selected from the examples above were tested at various doses in MM.1R cells. Cells were plated at a density of 5,000 cells per well and transfected by free uptake with 62.5 nM, 250 nM, 1,000 nM, and 4,000 nM concentrations of modified oligonucleotide, as specified in the tables below. After a treatment period of approximately 24 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 105

Dose-dependent reduction of human IRF4
mRNA by modified oligonucleotides

| Compound | IRF4 expression (% UTC) | | | | $IC_{50}$ |
|---|---|---|---|---|---|
| Number | 62.5 nM | 250 nM | 1,000 nM | 4,000 nM | (µM) |
| 609408 | 61 | 41 | 26 | 12 | 0.1 |
| 881450 | 68 | 59 | 41 | 26 | 0.4 |
| 881659 | 59 | 34 | 16 | 9 | 0.1 |
| 1013053 | 63 | 50 | 32 | 16 | 0.2 |
| 1013074 | 89 | 71 | 49 | 14 | 0.7 |
| 1013492 | 66 | 46 | 36 | 21 | 0.2 |
| 1013513 | 72 | 64 | 37 | 21 | 0.4 |
| 1013514 | 81 | 68 | 41 | 15 | 0.5 |
| 1013647 | 66 | 56 | 37 | 18 | 0.3 |
| 1013933 | 92 | 78 | 44 | 13 | 0.7 |
| 1013953 | 97 | 62 | 40 | 13 | 0.6 |
| 1014087 | 82 | 67 | 40 | 28 | 0.7 |
| 1014088 | 59 | 44 | 32 | 15 | 0.2 |
| 1014095 | 42 | 35 | 24 | 12 | <0.1 |
| 1014097 | 79 | 57 | 40 | 17 | 0.4 |
| 1014393 | 60 | 49 | 26 | 9 | 0.2 |
| 1014394 | 46 | 38 | 28 | 9 | <0.1 |
| 1014412 | 85 | 57 | 44 | 23 | 0.6 |
| 1014834 | 50 | 40 | 22 | 9 | <0.1 |

TABLE 106

Dose-dependent reduction of human IRF4
mRNA by modified oligonucleotides

| Compound | IRF4 expression (% UTC) | | | | $IC_{50}$ |
|---|---|---|---|---|---|
| Number | 62.5 nM | 250 nM | 1,000 nM | 4,000 nM | (µM) |
| 609408 | 63 | 46 | 28 | 15 | 0.2 |
| 881659 | 58 | 32 | 16 | 9 | 0.1 |

TABLE 106-continued

Dose-dependent reduction of human IRF4 mRNA by modified oligonucleotides

| Compound Number | IRF4 expression (% UTC) | | | | IC$_{50}$ ($\mu$M) |
|---|---|---|---|---|---|
| | 62.5 nM | 250 nM | 1,000 nM | 4,000 nM | |
| 935607 | 57 | 41 | 28 | 16 | 0.1 |
| 1012795 | 66 | 43 | 26 | 7 | 0.2 |
| 1012819 | 92 | 75 | 35 | 25 | 0.7 |
| 1012821 | 52 | 38 | 28 | 11 | 0.1 |
| 1012836 | 103 | 69 | 44 | 19 | 0.8 |
| 1012882 | 94 | 60 | 31 | 11 | 0.5 |
| 1012883 | 60 | 42 | 28 | 11 | 0.1 |
| 1012884 | 49 | 39 | 25 | 14 | <0.1 |
| 1012900 | 90 | 72 | 42 | 22 | 0.7 |
| 1012914 | 55 | 42 | 25 | 10 | 0.1 |
| 1014968 | 56 | 48 | 35 | 16 | 0.2 |
| 1014976 | 76 | 43 | 37 | 14 | 0.3 |
| 1015254 | 68 | 46 | 31 | 14 | 0.2 |
| 1015275 | 86 | 61 | 24 | 12 | 0.4 |
| 1015409 | 66 | 53 | 34 | 16 | 0.3 |
| 1015417 | 76 | 56 | 37 | 16 | 0.4 |
| 1015716 | 59 | 46 | 24 | 10 | 0.1 |

Example 23: Effect of Modified Oligonucleotides on Human IRF4 In Vitro, Multiple Doses Modified oligonucleotides selected from the examples above were tested at various doses in KMS11 cells for their effects on target knockdown and on cell line proliferation.

Target Knockdown

KMS11 cells were plated at a density of 10,000 cells per well and transfected by free uptake with 8 nM, 40 nM, 200 nM, and 1,000 nM concentrations of modified oligonucleotide, as specified in the tables below. After a treatment period of approximately 48 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 107

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 79 | 67 | 38 | 14 |
| 935762 | 79 | 41 | 17 | 10 |
| 935918 | 71 | 35 | 14 | 10 |
| 936007 | 81 | 67 | 25 | 14 |
| 970527 | 90 | 53 | 23 | 15 |
| 882085 | 86 | 56 | 24 | 11 |
| 882408 | 74 | 70 | 37 | 17 |

TABLE 108

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 92 | 69 | 30 | 13 |
| 882800 | 78 | 52 | 24 | 10 |
| 969933 | 96 | 88 | 72 | 61 |
| 1012795 | 70 | 41 | 18 | 9 |
| 1012821 | 84 | 53 | 39 | 20 |
| 1012884 | 85 | 51 | 26 | 17 |
| 1014095 | 82 | 41 | 19 | 10 |

TABLE 109

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 89 | 67 | 30 | 14 |
| 1014393 | 80 | 50 | 22 | 12 |
| 1014394 | 86 | 74 | 38 | 19 |
| 1014834 | 86 | 51 | 17 | 9 |
| 1015716 | 95 | 78 | 43 | 17 |
| 881413 | 92 | 64 | 35 | 13 |
| 881449 | 94 | 85 | 48 | 22 |

TABLE 110

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 98 | 78 | 33 | 15 |
| 935658 | 87 | 61 | 23 | 13 |
| 935696 | 90 | 48 | 17 | 11 |
| 935898 | 103 | 81 | 50 | 31 |
| 935928 | 92 | 48 | 17 | 11 |
| 935968 | 95 | 52 | 17 | 11 |
| 936006 | 99 | 81 | 38 | 19 |

Proliferation

KMS11 cells were plated at a density of 2,000 cells per well and transfected by free uptake with 8 nM, 40 nM, 200 nM, and 1,000 nM concentrations of modified oligonucleotide, as specified in the tables below. After seven days, CellTiterGlo-2.0 (Promega) was added and luminescence was measured on Glomax (Promega).

TABLE 111

Dose-dependent reduction of KMS11 proliferation by modified oligonucleotides

| Compound Number | IRF4 proliferation (% UTC) | | | |
|---|---|---|---|---|
| | 8 nM | 40 nM | 200 nM | 1,000 nM |
| 690890 | 93 | 79 | 22 | 7 |
| 935762 | 89 | 34 | 9 | 6 |
| 935918 | 85 | 28 | 8 | 7 |
| 936007 | 93 | 66 | 20 | 8 |
| 970527 | 92 | 50 | 11 | 5 |

TABLE 111-continued

Dose-dependent reduction of KMS11 proliferation by modified oligonucleotides

| Compound Number | IRF4 proliferation (% UTC) | | | |
|---|---|---|---|---|
| | 8 nM | 40 nM | 200 nM | 1,000 nM |
| 882085 | 97 | 55 | 11 | 6 |
| 882408 | 95 | 68 | 25 | 10 |

TABLE 112

Dose-dependent reduction of KMS11 proliferation by modified oligonucleotides

| Compound Number | IRF4 proliferation (% UTC) | | | |
|---|---|---|---|---|
| | 8 nM | 40 nM | 200 nM | 1,000 nM |
| 690890 | 98 | 82 | 26 | 9 |
| 882800 | 87 | 48 | 16 | 9 |
| 969933 | 93 | 86 | 79 | 78 |
| 1012795 | 89 | 25 | 4 | 1 |
| 1012821 | 98 | 47 | 22 | 5 |
| 1012884 | 104 | 61 | 24 | 12 |
| 1014095 | 95 | 35 | 15 | 13 |

TABLE 113

Dose-dependent reduction of KMS11 proliferation by modified oligonucleotides

| Compound Number | IRF4 proliferation (% UTC) | | | |
|---|---|---|---|---|
| | 8 nM | 40 nM | 200 nM | 1,000 nM |
| 690890 | 91 | 67 | 21 | 7 |
| 1014393 | 89 | 45 | 15 | 9 |
| 1014394 | 91 | 70 | 26 | 11 |
| 1014834 | 86 | 43 | 12 | 6 |
| 1015716 | 92 | 78 | 32 | 12 |
| 881413 | 98 | 67 | 15 | 11 |
| 881449 | 97 | 81 | 39 | 21 |

TABLE 114

Dose-dependent reduction of KMS11 proliferation by modified oligonucleotides

| Compound Number | IRF4 proliferation (% UTC) | | | |
|---|---|---|---|---|
| | 8 nM | 40 nM | 200 nM | 1,000 nM |
| 690890 | 90 | 77 | 22 | 8 |
| 935658 | 91 | 51 | 11 | 7 |
| 935696 | 86 | 29 | 7 | 6 |
| 935898 | 96 | 82 | 56 | 38 |
| 935928 | 94 | 45 | 9 | 7 |
| 935968 | 94 | 49 | 10 | 5 |
| 936006 | 97 | 80 | 26 | 12 |

Example 24: Effect of Modified Oligonucleotides on Human IRF4 In Vitro, Multiple Doses Modified oligonucleotides selected from the examples above were tested at various doses in H929 cells for their effects on target knockdown and on cell line proliferation.

Target Knockdown

H929 cells were plated at a density of 10,000 cells per well and transfected by free uptake with 8 nM, 40 nM, 200 nM, and 1,000 nM concentrations of modified oligonucleotide or 0.67 nM, 2 nM, 6.67 nM or 20 nM concentrations of modified oligonucleotide, as specified in the tables below. After a treatment period of approximately 48 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to that of untreated control (UTC) cells. As illustrated in the tables below, IRF4 mRNA levels were reduced in a dose-dependent manner in cells treated with modified oligonucleotides.

TABLE 115

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 88 | 66 | 39 | 34 |
| 935762 | 76 | 47 | 29 | 31 |
| 935918 | 70 | 43 | 34 | 24 |
| 936007 | 85 | 62 | 39 | 32 |
| 970527 | 83 | 49 | 41 | 24 |
| 882085 | 107 | 70 | 48 | 16 |
| 882408 | 99 | 88 | 59 | 42 |

TABLE 116

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 69 | 53 | 35 | 30 |
| 882800 | 63 | 62 | 38 | 28 |
| 969933 | 112 | 95 | 87 | 83 |
| 1012795 | 72 | 67 | 45 | 31 |
| 1012821 | 69 | 86 | 47 | 35 |
| 1012884 | 82 | 88 | 51 | 32 |
| 1014095 | 71 | 68 | 31 | 21 |

TABLE 117

Dose-dependent reduction of human IRF4 mRNA by modified oligonucleotides

| Compound Number | IRF4 expression (% UTC) | | | |
|---|---|---|---|---|
| | 8 nM | 40 nM | 200 nM | 1,000 nM |
| 609408 | 88 | 57 | 31 | 37 |
| 1014393 | 70 | 43 | 38 | 24 |
| 1014394 | 83 | 60 | 43 | 32 |
| 1014834 | 84 | 45 | 33 | 23 |
| 1015716 | 88 | 75 | 46 | 17 |
| 881413 | 86 | 67 | 46 | 24 |
| 881449 | 109 | 90 | 63 | 51 |

TABLE 118

Dose-dependent reduction of human IRF4
mRNA by modified oligonucleotides

| Compound | IRF4 expression (% UTC) | | | |
|---|---|---|---|---|
| Number | 0.67 nM | 2 nM | 6.67 nM | 20 nM |
| 609408 | 74 | 53 | 26 | 37 |
| 935658 | 84 | 75 | 48 | 32 |
| 935696 | 78 | 59 | 33 | 26 |
| 935898 | 94 | 79 | 55 | 43 |
| 935928 | 74 | 54 | 36 | 28 |
| 935968 | 99 | 73 | 55 | 40 |
| 936006 | 91 | 74 | 61 | 52 |

Proliferation

H929 cells were plated at a density of 2,000 cells per well and transfected by free uptake with 8 nM, 40 nM, 200 nM, and 1,000 nM concentrations of modified oligonucleotide, as specified in the tables below. After seven days, CellTiterGlo-2.0 (Promega) was added and luminescence was measured on Glomax (Promega).

TABLE 119

Dose-dependent reduction of H929 proliferation
by modified oligonucleotides

| Compound | IRF4 proliferation (% UTC) | | | |
|---|---|---|---|---|
| Number | 8 nM | 40 nM | 200 nM | 1,000 nM |
| 690890 | 94 | 69 | 32 | 12 |
| 935762 | 71 | 27 | 16 | 3 |
| 935918 | 87 | 58 | 26 | 2 |
| 936007 | 89 | 64 | 26 | 3 |
| 970527 | 95 | 58 | 15 | 1 |
| 882085 | 96 | 65 | 24 | 1 |
| 882408 | 88 | 65 | 45 | 9 |

TABLE 120

Dose-dependent reduction of H929 proliferation
by modified oligonucleotides

| Compound | IRF4 proliferation (% UTC) | | | |
|---|---|---|---|---|
| Number | 8 nM | 40 nM | 200 nM | 1,000 nM |
| 690890 | 73 | 75 | 21 | 6 |
| 882800 | 89 | 87 | 30 | 4 |
| 969933 | 92 | 90 | 77 | 77 |
| 1012795 | 89 | 86 | 36 | 4 |
| 1012821 | 95 | 86 | 41 | 13 |
| 1012884 | 68 | 62 | 9 | 2 |
| 1014095 | 78 | 63 | 22 | 5 |

TABLE 121

Dose-dependent reduction of H929 proliferation
by modified oligonucleotides

| Compound | IRF4 proliferation (% UTC) | | | |
|---|---|---|---|---|
| Number | 8 nM | 40 nM | 200 nM | 1,000 nM |
| 690890 | 86 | 74 | 48 | 30 |
| 1014393 | 95 | 65 | 30 | 2 |
| 1014394 | 77 | 53 | 35 | 6 |
| 1014834 | 89 | 61 | 34 | 2 |
| 1015716 | 99 | 74 | 31 | 2 |

TABLE 121-continued

Dose-dependent reduction of H929 proliferation
by modified oligonucleotides

| Compound | IRF4 proliferation (% UTC) | | | |
|---|---|---|---|---|
| Number | 8 nM | 40 nM | 200 nM | 1,000 nM |
| 881413 | 85 | 53 | 33 | 4 |
| 881449 | 94 | 76 | 54 | 25 |

TABLE 122

Dose-dependent reduction of H929 proliferation
by modified oligonucleotides

| Compound | IRF4 proliferation (% UTC) | | | |
|---|---|---|---|---|
| Number | 8 nM | 40 nM | 200 nM | 1,000 nM |
| 690890 | 92 | 79 | 52 | 30 |
| 935658 | 95 | 62 | 23 | 7 |
| 935696 | 84 | 60 | 32 | 3 |
| 935898 | 101 | 87 | 62 | 26 |
| 935928 | 75 | 50 | 25 | 6 |
| 935968 | 96 | 66 | 40 | 10 |
| 936006 | 98 | 73 | 38 | 9 |

Example 25: Effect of Modified Oligonucleotides on Human IRF4 In Vitro, Multiple Doses Modified oligonucleotides selected from the examples above were tested at various doses in ABC-DLBCL lines U2932 and TMD8 for their effects on target knockdown and on cell line proliferation.

Target Knockdown

Cells were plated at a density of 10,000 cells per well and transfected by free uptake with 50 nM, 200 nM, 1,000 nM, or 5,000 nM concentrations of modified oligonucleotide, as specified in the tables below. Control oligonucleotide ION 792169, a 3-10-3 cEt gapmer with the sequence CGCCGA-TAAGGTACAC (SEQ ID NO: 3384), was also included. After a treatment period of approximately 48 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to untreated control (UTC) cells. As illustrated in the tables below, IRF4 mRNA levels were reduced in a dose-dependent manner in cells treated with modified oligonucleotides.

TABLE 123

Dose-dependent reduction of IRF4 expression
by modified oligonucleotides in U2932 cells

| Compound | IRF4 expression (% UTC) | | | |
|---|---|---|---|---|
| Number | 50 nM | 200 nM | 1,000 nM | 5,000 nM |
| 792169 | 98 | 102 | 102 | 99 |
| 690890 | 84 | 64 | 55 | 38 |
| 882800 | 85 | 63 | 51 | 38 |
| 695696 | 71 | 62 | 54 | 49 |
| 695968 | 84 | 70 | 55 | 43 |
| 695918 | 83 | 64 | 47 | 33 |

TABLE 124

Dose-dependent reduction of IRF4 expression
by modified oligonucleotides in TMD8 cells

| Compound | IRF4 expression (% UTC) | | | |
|---|---|---|---|---|
| Number | 50 nM | 200 nM | 1,000 nM | 5,000 nM |
| 792169 | 115 | 99 | 99 | 91 |
| 690890 | 97 | 75 | 53 | 26 |
| 882800 | 97 | 64 | 38 | 19 |
| 695696 | 94 | 68 | 45 | 29 |
| 695968 | 95 | 63 | 46 | 25 |
| 695918 | 105 | 65 | 44 | 24 |

Proliferation

Cells were plated at a density of 2,000 cells per well and transfected by free uptake with 50 nM, 200 nM, 1,000 nM, or 5,000 nM concentrations of modified oligonucleotide, as specified in the tables below. After seven days, CellTiterGlo-2.0 (Promega) was added and luminescence was measured on Glomax (Promega).

TABLE 125

Dose-dependent reduction of proliferation
of U2932 cells by modified oligonucleotides

| Compound | IRF4 proliferation (% UTC) | | | |
|---|---|---|---|---|
| Number | 50 nM | 200 nM | 1,000 nM | 5,000 nM |
| 792169 | 99 | 115 | 111 | 75 |
| 690890 | 111 | 109 | 63 | 2 |
| 882800 | 113 | 103 | 40 | 2 |
| 695696 | 107 | 111 | 77 | 17 |
| 695968 | 102 | 101 | 74 | 24 |
| 695918 | 89 | 100 | 70 | 7 |

TABLE 126

Dose-dependent reduction of proliferation
of TMD8 cells by modified oligonucleotides

| Compound | IRF4 proliferation (% UTC) | | | |
|---|---|---|---|---|
| Number | 50 nM | 200 nM | 1,000 nM | 5,000 nM |
| 792169 | 93 | 108 | 102 | 98 |
| 690890 | 110 | 120 | 118 | 17 |
| 882800 | 132 | 149 | 108 | 27 |
| 695696 | 125 | 143 | 94 | 5 |
| 695968 | 85 | 131 | 131 | 10 |
| 695918 | 139 | 130 | 122 | 4 |

Example 26: Effect of Modified Oligonucleotides on Human IRF4 In Vitro, Multiple Doses Modified oligonucleotides selected from the examples above were tested at various doses in ALCL cell lines for their effects on target knockdown and on cell line proliferation.

Target Knockdown

Cells were plated at a density of 10,000 cells per well and transfected by free uptake with 16 nM, 80 nM, or 400 nM concentrations of modified oligonucleotide, or 40 nM, 200 nM, 1,000 nM, or 5,000 nM concentrations of modified oligonucleotide, as specified in the tables below. After a treatment period of approximately 48 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to untreated control (UTC) cells. Control oligonucleotide 549148, a 3-10-3 cEt gapmer with the sequence GGCTACTACGCCGTCA (SEQ ID NO: 3385), was also included. As illustrated in the tables below, IRF4 mRNA levels were reduced in a dose-dependent manner in cells treated with modified oligonucleotides.

TABLE 127

Dose-dependent reduction of IRF4 expression by
modified oligonucleotides in Karpas299 cells

| Compound | IRF4 expression (% UTC) | | | |
|---|---|---|---|---|
| Number | 16 nM | 80 nM | 400 nM | 2,000 nM |
| 549148 | 92 | 85 | 86 | 83 |
| 609408 | 85 | 65 | 39 | 23 |
| 609416 | 82 | 75 | 66 | 53 |

TABLE 128

Dose-dependent reduction of IRF4 expression
by modified oligonucleotides in SupM2 cells

| Compound | IRF4 expression (% UTC) | | | |
|---|---|---|---|---|
| Number | 40 nM | 200 nM | 1,000 nM | 5,000 nM |
| 549148 | 109 | 100 | 118 | 117 |
| 609408 | 83 | 91 | 32 | 10 |
| 609416 | 93 | 85 | 48 | 21 |

Proliferation

Cells were plated at a density of 2,000 cells per well and transfected by free uptake with 50 nM, 200 nM, 1,000 nM, or 5,000 nM concentrations of modified oligonucleotide, as specified in the tables below. After seven days, CellTiterGlo-2.0 (Promega) was added and luminescence was measured on Glomax (Promega).

TABLE 129

Dose-dependent reduction of proliferation of
Karpas299 cells by modified oligonucleotides

| Compound | IRF4 proliferation (% UTC) | | | |
|---|---|---|---|---|
| Number | 50 nM | 200 nM | 1,000 nM | 5,000 nM |
| 549148 | 99 | 106 | 106 | 89 |
| 609408 | 105 | 91 | 31 | 22 |
| 609416 | 104 | 119 | 72 | 59 |

TABLE 130

Dose-dependent reduction of proliferation
of SupM2 cells by modified oligonucleotides

| Compound | IRF4 proliferation (% UTC) | | | |
|---|---|---|---|---|
| Number | 16 nM | 80 nM | 400 nM | 2,000 nM |
| 549148 | 93 | 97 | 94 | 85 |
| 609408 | 93 | 96 | 55 | 3 |
| 609416 | 93 | 98 | 49 | 15 |

Example 27: Effect of Modified Oligonucleotides on Human IRF4 In Vitro, Multiple Doses Modified oligonucleotides selected from the examples above were tested at various doses in mantle cell lymphoma (MCL) lines MAVER1, JVM2, Granta519, Mino, and Z138 for their effects on target knockdown and on cell line proliferation.

Target Knockdown

Cells were plated at a density of 10,000 cells per well and transfected by free uptake with 40 nM, 200 nM, 1,000 nM, or 5,000 nM concentrations of modified oligonucleotide, as specified in the tables below. Control oligonucleotide 549148, a 3-10-3 cEt gapmer with the sequence GGCTAC-TACGCCGTCA (SEQ ID NO: 3385), was also included. After a treatment period of approximately 48 hours, RNA was isolated from the cells and IRF4 mRNA levels were measured by RT-qPCR. Human IRF4 primer probe set RTS4522 (described hereinabove in Example 11) was used to measure mRNA levels. IRF4 mRNA levels were adjusted according to total RNA content, as measured by RiboGreen. Results are presented as the percent level of IRF4 mRNA transcript, relative to untreated control (UTC) cells. As illustrated in the tables below, IRF4 mRNA levels were reduced in a dose-dependent manner in cells treated with modified oligonucleotides.

TABLE 131

Dose-dependent reduction of IRF4 expression by modified oligonucleotides in MAVER1 cells

| Compound Number | IRF4 expression (% UTC) | | | |
|---|---|---|---|---|
| | 40 nM | 200 nM | 1,000 nM | 5,000 nM |
| 549148 | 115 | 103 | 96 | 99 |
| 609408 | 121 | 102 | 80 | 35 |
| 609416 | 108 | 109 | 87 | 65 |

TABLE 132

Dose-dependent reduction of IRF4 expression by modified oligonucleotides in JVM2 cells

| Compound Number | IRF4 expression (% UTC) | | | |
|---|---|---|---|---|
| | 40 nM | 200 nM | 1,000 nM | 5,000 nM |
| 549148 | 108 | 114 | 108 | 100 |
| 609408 | 90 | 72 | 66 | 39 |
| 609416 | 101 | 82 | 74 | 93 |

TABLE 133

Dose-dependent reduction of IRF4 expression by modified oligonucleotides in Granta519 cells

| Compound Number | IRF4 expression (% UTC) | | | |
|---|---|---|---|---|
| | 40 nM | 200 nM | 1,000 nM | 5,000 nM |
| 549148 | 106 | 95 | 95 | 65 |
| 609408 | 176 | 165 | 134 | 122 |
| 609416 | 119 | 168 | 130 | 97 |
| 690890 | 161 | 160 | 143 | 102 |

TABLE 134

Dose-dependent reduction of IRF4 expression by modified oligonucleotides in Mino cells

| Compound Number | IRF4 expression (% UTC) | | | |
|---|---|---|---|---|
| | 40 nM | 200 nM | 1,000 nM | 5,000 nM |
| 549148 | 123 | 116 | 112 | 78 |
| 609408 | 124 | 109 | 67 | 31 |
| 609416 | 123 | 119 | 113 | 92 |
| 690890 | 122 | 116 | 103 | 42 |

TABLE 135

Dose-dependent reduction of IRF4 expression by modified oligonucleotides in Z138 cells

| Compound Number | IRF4 expression (% UTC) | | | |
|---|---|---|---|---|
| | 40 nM | 200 nM | 1,000 nM | 5,000 nM |
| 549148 | 68 | 72 | 78 | 19 |
| 609408 | 67 | 69 | 78 | 59 |
| 609416 | 76 | 69 | 89 | 72 |
| 690890 | 69 | 67 | 78 | 28 |

Proliferation

Cells were plated at a density of 2,000 cells per well and transfected by free uptake with 50 nM, 200 nM, 1,000 nM, or 5,000 nM concentrations of modified oligonucleotide, as specified in the tables below. After seven days, CellTiterGlo-2.0 (Promega) was added and luminescence was measured on Glomax (Promega).

TABLE 136

Dose-dependent reduction of proliferation of MAVER1 cells by modified oligonucleotides

| Compound Number | IRF4 proliferation (% UTC) | | | |
|---|---|---|---|---|
| | 80 nM | 400 nM | 2,000 nM | 10,000 nM |
| 549148 | 108 | 103 | 104 | 102 |
| 609408 | 104 | 102 | 83 | 40 |
| 609416 | 106 | 100 | 94 | 60 |

TABLE 137

Dose-dependent reduction of proliferation of JVM2 cells by modified oligonucleotides

| Compound Number | IRF4 proliferation (% UTC) | | | |
|---|---|---|---|---|
| | 80 nM | 400 nM | 2,000 nM | 10,000 nM |
| 549148 | 108 | 114 | 108 | 100 |
| 609408 | 117 | 95 | 66 | 37 |
| 609416 | 114 | 101 | 97 | 86 |

TABLE 138

Dose-dependent reduction of proliferation of
Granta519 cells by modified oligonucleotides

| Compound | IRF4 proliferation (% UTC) | | | |
|---|---|---|---|---|
| Number | 80 nM | 400 nM | 2,000 nM | 10,000 nM |
| 549148 | 110 | 99 | 95 | 106 |
| 609408 | 34 | 10 | 4 | 2 |
| 609416 | 85 | 44 | 19 | 9 |
| 690890 | 58 | 24 | 12 | 7 |

TABLE 139

Dose-dependent reduction of proliferation
of Mino cells by modified oligonucleotides

| Compound | IRF4 proliferation (% UTC) | | | |
|---|---|---|---|---|
| Number | 80 nM | 400 nM | 2,000 nM | 10,000 nM |
| 549148 | 90 | 103 | 106 | 101 |
| 609408 | 93 | 82 | 54 | 22 |
| 609416 | 94 | 84 | 68 | 56 |
| 690890 | 88 | 77 | 68 | 49 |

TABLE 140

Dose-dependent reduction of proliferation
of Z138 cells by modified oligonucleotides

| Compound | IRF4 proliferation (% UTC) | | | |
|---|---|---|---|---|
| Number | 80 nM | 400 nM | 2,000 nM | 10,000 nM |
| 549148 | 91 | 88 | 89 | 82 |
| 609408 | 98 | 83 | 70 | 46 |
| 609416 | 91 | 82 | 74 | 56 |
| 690890 | 95 | 84 | 74 | 50 |

Example 28: In Vivo Activity in MM1.R Xenograft Model

A xenograft MM1.R model was used to evaluate activity of modified oligonucleotides targeted to human IRF4. Female NOD/SCID mice (JAX) at 4-6 weeks of age were given a subcuntaneous injection of 6 million MM1.R cells to form a xenograft tumor. Two weeks later, groups of 3 mice were administered 25, 50, or 100 mg/kg/dose modified oligonucleotide once a day for three days by subcutaneous injection. One group of mice received subcutaneous injections of PBS once a day for three days. The saline-injected group served as the control group to which oligonucleotide-treated groups were compared. Mice were sacrificed 48 hours after the final dose and tumors were collected for further analysis.

RNA Analysis

RNA was extracted from tumor tissue for RT-PCR analysis, which was performed as described above. Data were analyzed with primer probe set 34726, described above in Example 7 or primer probe set 35624 (forward sequence TCCCGTGTTGCTTCAAACT, designated herein as SEQ ID NO: 3395; reverse sequence TACCTGCTGGCAGTTCTTTC, designated herein as SEQ ID NO: 3396; probe sequence ACAGATGGGACTTAACAGGCAATGGG, designated herein as SEQ ID: 3397), which specifically detect human IRF4, as indicated in the tables below. Results are presented as percent change of mRNA, relative to PBS control, normalized with human B-Actin levels from the human tumor cells and mouse stromal cells using human specific primer probe set 5002 (forward sequence CGGACTATGACTTAGTTGCGTTAC; designated herein as SEQ ID NO: 3398; reverse sequence GCCATGCCAATCTCATCTTGT, designated herein as SEQ ID NO: 3399; probe sequence CCTTTCTTGACAAAACCTAACTTGCGCAGA, designated herein as SEQ ID NO: 3400).

TABLE 141

Activity of modified oligonucleotides in MM1.R xenograft model

| Compound ID | Dose | PPset | IRF4 mRNA (% PBS) |
|---|---|---|---|
| PBS | n/a | 34726 | 100 |
| 690890 | 25 | 34726 | 59 |
|  | 50 | 34726 | 53 |
|  | 100 | 34726 | 24 |
| 882800 | 50 | 34726 | 43 |
|  | 100 | 34726 | 18 |
| 935658 | 50 | 34726 | 52 |
|  | 100 | 34726 | 22 |
| 935918 | 50 | 34726 | 39 |
|  | 100 | 34726 | 18 |
| 935968 | 50 | 34726 | 52 |
|  | 100 | 34726 | 22 |
| 1012795 | 50 | 34726 | 45 |
|  | 100 | 34726 | 26 |
| 1014095 | 50 | 34726 | 71 |
|  | 100 | 34726 | 34 |
| 1014834 | 50 | 34726 | 56 |
|  | 100 | 34726 | 32 |
| 935762 | 50 | 34726 | 31 |
|  | 100 | 34726 | 27 |

TABLE 142

Activity of modified oligonucleotides in MM1.R xenograft model

| PBS | n/a | 34726 | 100 |
|---|---|---|---|
| 935696 | 50 | 34726 | 28 |
|  | 100 | 34726 | 13 |

TABLE 143

Activity of modified oligonucleotides in MM1.R xenograft model

| Compound ID | Dose | Ppset | IRF4 mRNA (% PBS) |
|---|---|---|---|
| PBS | n/a | 35624 | 100 |
| 690890 | 50 | 35624 | 55 |
|  | 100 | 35624 | 33 |
| 882800 | 50 | 35624 | 51 |
|  | 100 | 35624 | 31 |
| 935658 | 50 | 35624 | 56 |
|  | 100 | 35624 | 27 |
| 935918 | 50 | 35624 | 39 |
|  | 100 | 35624 | 9.9 |
| 935968 | 50 | 35624 | 26 |
|  | 100 | 35624 | 9.1 |
| 1012795 | 50 | 35624 | 18 |
|  | 100 | 35624 | 21 |
| 1014095 | 50 | 35624 | 28 |
|  | 100 | 35624 | 27 |
| 1014834 | 50 | 35624 | 33 |
|  | 100 | 35624 | 15 |
| 935762 | 50 | 35624 | 37 |
|  | 100 | 35624 | 22 |
| 935696 | 50 | 35624 | 19 |
|  | 100 | 35624 | 15 |

Protein Analysis

Levels of hIRF4 protein were measured in the xenograft tumors by a human-specific IRF4 antibody (abeam EP5699) on the WES system (ProteinSimple).

Levels of Igλ, a clinically-relevant biomarker for MM, were also measured on the WES system. Reductions of hIRF4 and Igλ were observed.

TABLE 144

Protein Levels in MM1.R Xenografts

| Compound ID | Dose (mg/kg/day) | IRF4 Protein (% PBS) | Igλ Protein (% PBS) |
|---|---|---|---|
| PBS | n/a | 100 | 100 |
| 690890 | 50 | 53 | 83 |
|  | 100 | 28 | 64 |
| 882800 | 50 | 67 | 88 |
|  | 100 | 27 | 68 |
| 935918 | 50 | 41 | 103 |
|  | 100 | 17 | 57 |
| 935968 | 50 | 36 | 91 |
|  | 100 | 15 | 52 |
| 1012795 | 50 | 32 | 105 |
|  | 100 | 14 | 60 |
| 1014095 | 50 | 35 | 78 |
|  | 100 | 15 | 56 |
| 1014834 | 50 | 57 | 83 |
|  | 100 | 31 | 69 |
| 935762 | 50 | 46 | 69 |
|  | 100 | 22 | 54 |
| 935696 | 50 | 26 | 40 |
|  | 100 | 15 | 37 |
| 935658 | 50 | 45 | 102 |
|  | 100 | 24 | 80 |

Example 29: Anti-Tumor Activity of Modified Oligonucleotides in a MM1.R Xenograft Model A xenograft MM1.R model was used to evaluate activity of modified oligonucleotides targeted to human IRF4. Female NOD-SCID mice at 5-6 weeks of age were given a subcuntaneous injection of 3 million MM1.R cells to form a xenograft tumor. 23 days later, groups of 8 mice were administered 50 mg/kg/dose modified oligonucleotide five times a week by subcutaneous injection for 3.5 weeks. One group of mice received subcutaneous injections of PBS five times a week. The saline-injected group served as the control group to which oligonucleotide-treated groups were compared. Tumor volume was estimated by caliper measurement. Mice were sacrificed 24 hours after the last dose and tissue was collected for RNA and protein analysis.

Tumor Volume

TABLE 145

Tumor volume (mm³)

| Compound ID | Days after MM1.R Cell Injection | | | | | | |
|---|---|---|---|---|---|---|---|
|  | 23 | 27 | 30 | 34 | 37 | 41 | 44 |
| PBS | 215 | 374 | 590 | 936 | 1597 | 1877* | 2530* |
| 792169 | 228 | 400 | 615 | 1194 | 1451 | 1669* | 2394* |
| 1014834 | 225 | 319 | 451 | 606 | 931 | 1202 | 1733 |
| 1014095 | 222 | 291 | 504 | 554 | 886 | 795* | 932* |
| 1012795 | 221 | 355 | 459 | 472 | 610* | n.d. | n.d. |
| 935968 | 210 | 313 | 463 | 587 | 771 | 447* | 585* |
| 935918 | 219 | 346 | 569 | 705 | 899 | 746* | 1024* |
| 935696 | 219 | 357 | 422 | 422 | 379 | 364 | 426 |
| 935658 | 269 | 340 | 557 | 619 | 856 | 983 | 1299 |
| 935762 | 220 | 290 | 397 | 488* | 593* | 770* | 949* |

TABLE 145-continued

Tumor volume (mm³)

| Compound ID | Days after MM1.R Cell Injection | | | | | | |
|---|---|---|---|---|---|---|---|
|  | 23 | 27 | 30 | 34 | 37 | 41 | 44 |
| 882800 | 218 | 394 | 520 | 735 | 1075 | 907* | 1279* |
| 690890 | 216 | 307 | 419 | 498 | 643 | 830 | 1191 |

*Values represent the average of 3-7 mice

Body Weight

Body weights were measured throughout the study as a measure of tolerability.

TABLE 146

Body Weight (% of Day 23)

| Compound ID | Days after MM1.R Cell Injection | | | | | | |
|---|---|---|---|---|---|---|---|
|  | 23 | 27 | 30 | 34 | 37 | 41 | 44 |
| PBS | 100 | 101 | 101 | 106 | 104* | 111* | 115* |
| 792169 | 100 | 106 | 106 | 116 | 121* | 121* | 126* |
| 1014834 | 100 | 102 | 101 | 103 | 107 | 107 | 108 |
| 1014095 | 100 | 100 | 98 | 98 | 98* | 98* | 95* |
| 1012795 | 100 | 101 | 97 | 82 | n.d. | n.d. | n.d. |
| 935968 | 100 | 102 | 101 | 103 | 102* | 102* | 101* |
| 935918 | 100 | 101 | 101 | 102 | 100* | 100* | 98* |
| 935762 | 100 | 102 | 99 | 103 | 104 | 104 | 100 |
| 935696 | 100 | 104 | 103 | 105 | 101 | 101 | 97 |
| 935658 | 100 | 100 | 100 | 100 | 98 | 98 | 95 |
| 882800 | 100 | 102 | 101 | 106 | 103* | 103* | 98* |
| 690890 | 100 | 100 | 97 | 96 | 93 | 93 | 94 |

*Values represent the average of 3-7 animals

Liver Function

To evaluate the effect of modified oligonucleotides on hepatic function, plasma levels of transaminases were measured using an automated clinical chemistry analyzer (Hitachi Olympus AU400e, Melville, NY). Plasma levels of ALT (alanine transaminase) were measured and the results are presented in the table below expressed in IU/L.

TABLE 147

Liver Transaminases

| Compound ID | ALT (IU/L) |
|---|---|
| PBS | 24 |
| 792169 | 45 |
| 1014834 | 894 |
| 1014095 | 1601 |
| 1012795 | 1915 |
| 935968 | 289 |
| 935918 | 192 |
| 935762 | 1016 |
| 935696 | 1334 |
| 935658 | 91 |
| 882800 | 5219 |
| 690890 | 496 |

RNA and Protein Analysis

IRF4 mRNA in tumor samples was measured by RT-PCR using PPset RTS34726, described above. IRF4 protein in tumor samples was determined by western blot as described in Example 28 above.

TABLE 148

IRF4 Protein and mRNA Levels

|  | hIRF4 mRNA Level | hIRF4 Protein Level |
|---|---|---|
| PBS | 98 | 100 |
| 792169 | 159 | 110 |
| 1014834 | 53 | 39 |
| 1014095 | 58 | 43 |
| 1012795 | 37 | n.d. |
| 935968 | 41 | 35 |
| 935918 | 28 | 31 |
| 935762 | 47 | 34 |
| 935696 | 39 | 27 |
| 935658 | 51 | 43 |
| 882800 | 57 | 32 |
| 690890 | 49 | 46 |

Example 30: Efficacy of Modified Oligonucleotides Targeted to hIRF4 in a Systemically Disseminated MM1.R Model with Bone Marrow Involvement A systemically disseminated MM1.R model was used to evaluate activity of modified oligonucleotides targeted to human IRF4. Female nod-scid IL2Rγ$^{null}$ mice at 4-6 weeks of age were first administered 50 mg/kg cyclophosphamide on day 0, and on day 1 were administrated 10 million MM1.R cells via an intravenous injection. On day 14, plasma human Igλ was tested by ELISA and mice were randomized to groups based on these results. Starting on day 21, groups of 4 mice were administered 50 mg/kg/day modified oligonucleotide once a day for three days, and sacrificed 48 hours after the last dose. Levels of hIRF4 mRNA were measured in bone marrow. The tumor burden was measured by measuring levels of hActin mRNA. Results are presented as percent change of mRNA, relative to PBS control treated mice.

TABLE 149

Bone marrow IRF4 mRNA and Tumor Burden.

| Compound ID | IRF4 mRNA in bone marrow (% PBS) | Tumor Burden |
|---|---|---|
| PBS | 100 | 4276 |
| 792169 | 70 | 830 |
| 882800 | 24 | 33 |
| 935918 | 36* | 118 |
| 935696 | 38* | 559 |
| 935968 | 34* | 18 |

*Values represent the average of 1-3 mice, excluding mice with undetectable hIRF mRNA levels in bone marrow.

Example 31: Efficacy of Modified Oligonucleotides Targeted to hIRF4 in a Systemically Disseminated MM1.R Model with Bone Marrow Involvement A systemically disseminated MM1.R model was used to evaluate activity of modified oligonucleotides targeted to human IRF4. Female NOD-SCID IL2Rγ$^{null}$ mice at 4-6 weeks of age were first administered 50 mg/kg cyclophosphamide on day 0, and on day 1 were administrated 10 million MM1.R cells via an intravenous injection. On day 14, serum human Igλ was tested by ELISA and mice were randomized to groups based on these results. Starting on day 15, groups of ten mice were administered modified oligonucleotide with a loading dose of 50 mg/kg/day for 1 week, and then 3 doses a week at 50 mg/kg/day continuing until animal death, bodyweight drop of <20% or paralysis. One group often mice was administered PBS as a control, and another group was administered the control oligonucleotide 792169.

TABLE 150

Survival Percentage

| Treatment | Compound ID | | | | | |
|---|---|---|---|---|---|---|
| Day | PBS | 792169 | 882800 | 935918 | 935696 | 935968 |
| 0 | 100 | 100 | 100 | 100 | 100 | 100 |
| 40 | 90 | 60 | 100 | 100 | 100 | 100 |
| 42 | 90 | 60 | 90 | 100 | 90 | 100 |
| 43 | 60 | 60 | 90 | 100 | 90 | 100 |
| 44 | 40 | 20 | 90 | 100 | 90 | 100 |
| 45 | 20 | 0 | 90 | 100 | 80 | 100 |
| 46 | 0 | 0 | 90 | 100 | 80 | 100 |
| 49 | 0 | 0 | 70 | 90 | 80 | 100 |
| 51 | 0 | 0 | 70 | 90 | 80 | 100 |

Example 32: Activity of Modified Oligonucleotides Targeting hIRF4 in a TMD8 Human ABC-DLBCL Tumor Model A xenograft tumor model was used to evaluate activity of modified oligonucleotides targeted to human IRF4. 4 million ABC-DLBCL TMD8 cells were implanted into the flanks of 5 week old female NOD/SCID mice. When tumors reached an average volume of 100 mm$^3$, approximately two weeks post-implantation, groups of eight mice mice were administered 50 mg/kg/day modified oligonucleotide for two weeks. Mice were sacrificed after the last dose and tumors were collected for mRNA analysis.

Tumor volume was estimated with caliper measurement. Levels of hIRF4 mRNA were measured in tumor tissue and normalized to control animals.

TABLE 151

Tumor volume (mm$^3$)

| | Days post-implantation | | | | | | |
|---|---|---|---|---|---|---|---|
| Compound ID | 15 | 19 | 22 | 25 | 27 | 29 | 32 |
| | Tumor Volume (mm$^3$) | | | | | | |
| PBS | 112 | 276 | 602 | 872 | 1162 | 1365 | 2012 |
| 792169 | 112 | 232 | 488 | 797 | 1044 | 1359 | 1850 |
| 690890 | 114 | 206 | 392 | 481 | 589 | 675 | 777 |
| 882800 | 113 | 227 | 417 | 603 | 712 | 729 | 860 |
| 935696 | 113 | 225 | 448 | 570 | 676 | 761 | 729 |

TABLE 152 hIRF4 mRNA levels

| | hIRF4 mRNA Level |
|---|---|
| PBS | 100 |
| 792169 | 127 |
| 690890 | 84 |
| 882800 | 72 |
| 935696 | 58 |

Example 33: Tolerability of Modified Oligonucleotides Targeting hIRF4 in Balb/c Mice Balb/c mice are frequently utilized for safety and efficacy testing. The mice were treated with antisense oligonucleotides selected from studies described above and evaluated for changes in the levels of various plasma chemistry markers.

Treatment

Groups of 4-6 week old male Balb/c mice were injected subcutaneously twice a week for four weeks with 50 mg/kg of modified oligonucleotides (100 mg/kg/week dose). One group of male Balb/c mice was injected subcutaneously twice a week for 4 weeks with PBS. Mice were euthanized 48 hours after the last dose, and organs and plasma were harvested for further analysis.

Plasma Chemistry Markers

To evaluate the effect of modified oligonucleotides on liver and kidney function, plasma levels of transaminases, bilirubin, and BUN were measured using an automated clinical chemistry analyzer (Hitachi Olympus AU400e, Melville, NY). The results are presented in the table below. Modified oligonucleotides that caused changes in the levels of any of the liver or kidney function markers outside the expected range for modified oligonucleotides were excluded in further studies.

TABLE 153

Plasma chemistry markers in Balb/c mouse plasma at week 4

| Compound ID | ALT (U/L) | AST (U/L) | BUN (mg/dL) | T. Bil (mg/dL) |
|---|---|---|---|---|
| PBS | 37 | 84 | 22.9 | 0.25 |
| 609296 | n.d. | n.d. | n.d. | n.d. |
| 609343 | n.d. | n.d. | n.d. | n.d. |
| 609354 | n.d. | n.d. | n.d. | n.d. |
| 609357 | n.d. | n.d. | n.d. | n.d. |
| 609391 | 1799 | 1362 | 16.7 | 0.31 |
| 609408 | 859 | 507 | 18.4 | 0.28 |
| 609416 | 93 | 114 | 21.1 | 0.23 |
| 609296 | n.d. | n.d. | n.d. | n.d. |
| 609547 | 982 | 802 | 27.3 | 0.34 |
| 609592 | 53 | 170 | 21.2 | 0.25 |

TABLE 154

Plasma chemistry markers in Balb/c mouse plasma at week 4

| Compound ID | ALT (U/L) | AST (U/L) | BUN (mg/dL) | T. Bil (mg/dL) |
|---|---|---|---|---|
| PBS | 35.8 | 53 | 21.1 | 0.25 |
| 666431 | 85.5 | 120 | 21.1 | 0.29 |
| 666440 | 8173 | 3432 | 26.2 | 3.84 |
| 666449 | 150 | 124 | 24.9 | 0.18 |
| 666471 | n.d. | n.d. | n.d. | n.d. |
| 666475 | 1989 | 1607 | 25.0 | 0.23 |
| 666496 | 2926 | 2423 | 22.4 | 0.30 |
| 666569 | 3427 | 3288 | 23.8 | 0.23 |
| 666575 | 525 | 385 | 24.5 | 0.21 |
| 666582 | 3543 | 2893 | 20.0 | 0.44 |
| 666584 | 43.3 | 57 | 25.4 | 0.21 |
| 666586 | 2970 | 2051 | 23.8 | 0.26 |
| 666587 | 1057 | 964 | 28.1 | 0.16 |
| 666649 | 4662 | 3970 | 23.8 | 10.99 |
| 666683 | 1363 | 1657 | 21.3 | 0.19 |

TABLE 155

Plasma chemistry markers in Balb/c mouse plasma at week 4

| Compound ID | ALT (U/L) | AST (U/L) | BUN (mg/dL) | T. Bil (mg/dL) |
|---|---|---|---|---|
| PBS | 32 | 89 | 24.1 | 0.29 |
| 609555 | 737 | 238 | 25.9 | 0.15 |
| 666772 | n.d. | n.d. | n.d. | n.d |
| 666775 | n.d. | n.d. | n.d. | n.d |
| 668818 | n.d. | n.d. | n.d. | n.d |
| 668849 | 105 | 131 | 24.7 | 0.12 |
| 668850 | 547 | 394 | 27.8 | 0.11 |
| 668902 | 53 | 103 | 21.5 | 0.18 |
| 668934 | n.d. | n.d. | n.d. | n.d |
| 668936 | 2260 | 3211 | 24.8 | 0.13 |
| 668937 | 39 | 89 | 23.2 | 0.14 |
| 668947 | n.d. | n.d. | n.d. | n.d |
| 668998 | 102 | 101 | 21.7 | 0.14 |
| 668999 | 625 | 404 | 28.9 | 0.21 |
| 669018 | 198 | 157 | 28.1 | 0.17 |
| 669022 | 33 | 60 | 19.9 | 0.19 |
| 669040 | 176 | 170 | 23.2 | 0.11 |
| 669066 | 589 | 300 | 23.8 | 0.27 |
| 669067 | n.d. | n.d. | n.d. | n.d |
| 669068 | 95 | 137 | 20.0 | 0.16 |
| 669075 | 647 | 400 | 19.4 | 0.15 |

TABLE 156

Plasma chemistry markers in Balb/c mouse plasma at week 4

| Compound ID | ALT (U/L) | AST (U/L) | BUN (mg/dL) | T. Bil (mg/dL) |
|---|---|---|---|---|
| PBS | 21 | 77 | 22.8 | 0.16 |
| 690508 | n.d. | n.d. | n.d. | n.d. |
| 690509 | n.d. | n.d. | n.d. | n.d. |
| 690510 | n.d. | n.d. | n.d. | n.d. |
| 690511 | n.d. | n.d. | n.d. | n.d. |
| 690512 | n.d. | n.d. | n.d. | n.d. |
| 690514 | 595 | 440 | 19.3 | 0.15 |
| 690515 | n.d. | n.d. | n.d. | n.d. |
| 690522 | 2440 | 1878 | 26.6 | 0.23 |
| 690527 | n.d. | n.d. | n.d. | n.d. |
| 690861 | 933 | 752 | 12.2 | 0.19 |
| 690863 | 889 | 798 | 17.0 | 0.56 |
| 690865 | n.d. | n.d. | n.d. | n.d. |
| 690873 | 1844 | 1160 | 16.6 | 0.28 |
| 690875 | 887 | 770 | 16.3 | 0.16 |
| 690877 | n.d. | n.d. | n.d. | n.d. |
| 690879 | 887 | 652 | 22.2 | 0.21 |
| 690881 | 442 | 320 | 23.0 | 0.12 |
| 690883 | 1505 | 901 | 38.9 | 0.34 |
| 690890 | 76 | 64 | 25.6 | 0.14 |
| 690892 | 56 | 126 | 23.9 | 0.17 |
| 690898 | 47 | 120 | 27.4 | 0.11 |
| 691028 | n.d. | n.d. | n.d. | n.d. |
| 691032 | 588 | 216 | 216 | 0.16 |
| 691033 | 709 | 451 | 31.4 | 0.13 |

Organ Weights

Liver, kidney, and spleen weights were measured at the end of the study, and are presented as the percent change compared to PBS-treated animals in the table below. Modified oligonucleotides that caused any changes in organ weights outside the expected range for modified oligonucleotides were excluded from further studies.

TABLE 157

Organ Weights (g)

| Compound ID | Liver | Kidney | Spleen |
|---|---|---|---|
| PBS | 1.25 | 0.39 | 0.11 |
| 609296 | n.d. | n.d. | n.d. |
| 609343 | n.d. | n.d. | n.d. |
| 609354 | n.d. | n.d. | n.d. |
| 609357 | n.d. | n.d. | n.d. |
| 609391 | 1.29 | 0.32 | 0.23 |
| 609408 | 1.48 | 0.37 | 0.14 |
| 609416 | 1.57 | 0.38 | 0.14 |
| 609296 | n.d. | n.d. | n.d. |
| 609547 | 2.56 | 0.35 | 0.55 |
| 609592 | 1.41 | 0.37 | 0.13 |

TABLE 158

Organ Weights (g)

| Compound ID | Liver | Kidney | Spleen |
|---|---|---|---|
| PBS | 1.30 | 0.40 | 0.10 |
| 666431 | 1.21 | 0.38 | 0.15 |
| 666440 | 2.38 | 0.37 | 0.10 |
| 666449 | 1.39 | 0.40 | 0.11 |
| 666471 | n.d. | n.d. | n.d. |
| 666475 | 1.49 | 0.40 | 0.10 |
| 666496 | 1.66 | 0.44 | 0.12 |
| 666569 | 1.09 | 0.34 | 0.13 |
| 666575 | 1.33 | 0.37 | 0.10 |
| 666582 | 2.03 | 0.42 | 0.13 |
| 666584 | 1.34 | 0.40 | 0.11 |
| 666586 | 1.36 | 0.29 | 0.12 |
| 666587 | 1.77 | 0.38 | 0.11 |
| 666649 | 0.81 | 0.30 | 0.07 |
| 666683 | 2.05 | 0.38 | 0.12 |

TABLE 159

Organ weights (g)

| Compound ID | Liver (g) | Kidney (g) | Spleen (g) |
|---|---|---|---|
| PBS | 1.49 | 0.43 | 0.12 |
| 609555 | 1.50 | 0.36 | 0.17 |
| 666772 | n.d. | n.d. | n.d. |
| 666775 | n.d. | n.d. | n.d. |
| 668818 | n.d. | n.d. | n.d. |
| 668849 | 1.75 | 0.41 | 0.22 |
| 668850 | 1.96 | 0.41 | 0.16 |
| 668902 | 1.50 | 0.39 | 0.12 |
| 668934 | n.d. | n.d. | n.d. |
| 668936 | 1.97 | 0.33 | 0.13 |
| 668937 | 1.58 | 0.41 | 0.14 |
| 668947 | n.d. | n.d. | n.d. |
| 668998 | 1.53 | 0.38 | 0.16 |
| 668999 | 1.64 | 0.38 | 0.13 |
| 669018 | 1.92 | 0.41 | 0.14 |
| 669022 | 1.47 | 0.41 | 0.12 |
| 669040 | 1.66 | 0.44 | 0.11 |
| 669066 | 1.64 | 0.39 | 0.15 |
| 669067 | 1.52 | 0.38 | 0.13 |
| 669068 | n.d. | n.d. | n.d. |
| 669075 | 1.43 | 0.36 | 0.17 |

TABLE 160

Organ weights (g)

| Compound ID | Liver (g) | Kidney (g) | Spleen (g) |
|---|---|---|---|
| PBS | 0.86 | 0.29 | 0.10 |
| 690508 | n.d. | n.d. | n.d. |
| 690509 | n.d. | n.d. | n.d. |
| 690510 | n.d. | n.d. | n.d. |
| 690511 | n.d. | n.d. | n.d. |
| 690512 | n.d. | n.d. | n.d. |
| 690514 | 1.68 | 0.28 | 0.19 |
| 690515 | n.d. | n.d. | n.d. |
| 690522 | 1.40 | 0.26 | 0.11 |
| 690527 | n.d. | n.d. | n.d. |
| 690861 | 1.29 | 0.27 | 0.12 |
| 690863 | 1.27 | 0.27 | 0.15 |
| 690865 | n.d. | n.d. | n.d. |
| 690873 | 1.17 | 0.28 | 0.14 |
| 690875 | 1.36 | 0.28 | 0.17 |
| 690877 | n.d. | n.d. | n.d. |
| 690879 | 1.04 | 0.26 | 0.14 |
| 690881 | 1.19 | 0.28 | 0.13 |
| 690883 | 1.59 | 0.30 | 0.10 |
| 690890 | 0.97 | 0.27 | 0.13 |
| 690892 | 1.08 | 0.30 | 0.17 |
| 690898 | 1.08 | 0.30 | 0.15 |
| 691028 | n.d. | n.d. | n.d. |
| 691032 | 1.33 | 0.29 | 0.1525 |
| 691033 | 1.625 | 0.3175 | 0.125 |

Example 34: Tolerability of Modified Oligonucleotides Targeting hIRF4 in CD1 Mice CD1® mice (Charles River, MA) are frequently utilized for safety and efficacy testing. The mice were treated with antisense oligonucleotides selected from studies described above and evaluated for changes in the levels of various plasma chemistry markers.

Treatment

Groups of 4-6 week old male CD1 mice were injected subcutaneously twice a week for four weeks with 50 mg/kg of modified oligonucleotides (100 mg/kg/week dose). One group of male CD1 mice was injected subcutaneously twice a week for 4 weeks with PBS. Mice were euthanized 48 hours after the last dose, and organs and plasma were harvested for further analysis.

Plasma Chemistry Markers

To evaluate the effect of modified oligonucleotides on liver and kidney function, plasma levels of transaminases, bilirubin, and BUN were measured using an automated clinical chemistry analyzer (Hitachi Olympus AU400e, Melville, NY). The results are presented in the table below. Modified oligonucleotides that caused changes in the levels of any of the liver or kidney function markers outside the expected range for modified oligonucleotides were excluded in further studies.

TABLE 161

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 27 | 65 | 19.7 | 0.19 |
| 881413 | 43 | 78 | 19.3 | 0.18 |
| 881442 | 594 | 484 | 23.1 | 0.24 |
| 881449 | 36 | 52 | 19.9 | 0.24 |
| 881450 | 100 | 146 | 20.8 | 0.18 |
| 881506 | 683 | 417 | 8.7 | 0.18 |
| 881517 | 121 | 103 | 22.1 | 0.16 |
| 881581 | 501 | 413 | 23.7 | 0.27 |

TABLE 161-continued

Plasma chemistry markers in CD1 mouse plasma at week 4

| Compound ID | ALT (U/L) | AST (U/L) | BUN (mg/dL) | T. Bil (mg/dL) |
|---|---|---|---|---|
| 881610 | 44 | 79 | 18.5 | 0.19 |
| 881658 | 39 | 66 | 16.0 | 0.17 |
| 881659 | 4924 | 3485 | 15.3 | 5.48 |
| 881660 | 267 | 176 | 19.7 | 0.16 |
| 881728 | 644 | 389 | 21.1 | 0.23 |
| 881742 | 780 | 443 | 17.6 | 0.23 |
| 882099 | 3607 | 1971 | 23.1 | 0.28 |
| 882282 | n.d. | n.d. | n.d. | n.d. |
| 882305 | 2688 | 1379 | 24.9 | 0.31 |
| 882433 | 2683 | 1944 | 19.5 | 0.42 |

TABLE 162

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 23 | 69 | 17.0 | 0.19 |
| 881449 | 34 | 65 | 19.2 | 0.23 |
| 881582 | 206 | 211 | 18.6 | 0.15 |
| 881588 | 902 | 829 | 15.2 | 0.32 |
| 881658 | 334 | 226 | 14.0 | 0.18 |
| 881727 | 1120 | 748 | 16.8 | 0.40 |
| 792169 | 23 | 43 | 18.0 | 0.21 |

TABLE 163

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 25 | 41 | 22.2 | 0.17 |
| 935765 | n.d. | n.d. | n.d. | n.d. |
| 935580 | n.d. | n.d. | n.d. | n.d. |
| 935805 | n.d. | n.d. | n.d. | n.d. |
| 935853 | n.d. | n.d. | n.d. | n.d. |
| 935824 | n.d. | n.d. | n.d. | n.d. |
| 935581 | n.d. | n.d. | n.d. | n.d. |
| 935689 | n.d. | n.d. | n.d. | n.d. |
| 935698 | 1462 | 1523 | 17.5 | 0.19 |
| 935699 | n.d. | n.d. | n.d. | n.d. |
| 935707 | 1334 | 703 | 17.3 | 0.21 |
| 935679 | n.d. | n.d. | n.d. | n.d. |
| 935727 | n.d. | n.d. | n.d. | n.d. |
| 935795 | n.d. | n.d. | n.d. | n.d. |
| 935898 | 101 | 129 | 20.3 | 0.18 |
| 935782 | 680 | 278 | 19.0 | 0.20 |
| 935878 | 1805 | 1128 | 19.1 | 0.21 |
| 935850 | 661 | 492 | 21.2 | 0.08 |
| 935724 | 1630 | 1341 | 19.9 | 0.25 |
| 935658 | 53 | 65 | 19.5 | 0.24 |
| 935762 | 106 | 132 | 18.0 | 0.18 |
| 935851 | 513 | 300 | 18.0 | 0.13 |

TABLE 164

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 19 | 34 | 18.6 | 0.17 |
| 935921 | 708 | 372 | 15.5 | 0.19 |
| 935961 | 1068 | 754 | 14.8 | 0.28 |
| 936018 | 609 | 358 | 17.9 | 0.14 |
| 936039 | n.d. | n.d. | n.d. | n.d. |
| 935708 | n.d. | n.d. | n.d. | n.d. |
| 935958 | 97 | 117 | 17.5 | 0.10 |
| 935854 | 304 | 205 | 18.6 | 0.14 |
| 935968 | 53 | 70 | 18.9 | 0.12 |
| 935620 | 1883 | 2950 | 17.2 | 1.17 |
| 935697 | 1504 | 763 | 16.9 | 0.22 |
| 935700 | 722 | 480 | 18.8 | 0.18 |
| 935734 | 1253 | 500 | 17.9 | 0.17 |
| 935857 | 1270 | 1233 | 17.7 | 0.29 |
| 936016 | 731 | 571 | 22.7 | 0.15 |
| 936006 | 38 | 47 | 16.9 | 0.13 |
| 936007 | 131 | 152 | 18.1 | 0.10 |
| 935948 | 192 | 183 | 19.5 | 0.15 |
| 935603 | 193 | 260 | 17.0 | 0.19 |
| 935701 | 426 | 277 | 18.0 | 0.06 |
| 935928 | 69 | 84 | 17.4 | 0.10 |

TABLE 165

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 23 | 44 | 22.5 | 0.20 |
| 969991 | n.d. | n.d. | n.d. | n.d. |
| 970013 | n.d. | n.d. | n.d. | n.d. |
| 970043 | 636 | 610 | 19.6 | 0.33 |
| 970103 | 786 | 512 | 20.1 | 0.17 |
| 970117 | 1786 | 877 | 22.5 | 0.29 |
| 970139 | 1011 | 1244 | 21.0 | 1.69 |
| 970159 | 1772 | 3821 | 15.7 | 2.68 |
| 970162 | 470 | 422 | 18.0 | 0.15 |
| 970189 | 353 | 377 | 21.0 | 0.19 |
| 970212 | 1714 | 1062 | 22.7 | 1.00 |
| 970524 | n.d. | n.d. | n.d. | n.d. |
| 970527 | 182 | 181 | 18.1 | 0.12 |

TABLE 166

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 24 | 99 | 20.1 | 0.21 |
| 881955 | 4127 | 3743 | 45.7 | 2.61 |
| 882085 | 53 | 73 | 22.3 | 0.18 |
| 882086 | 2522 | 2002 | 25.5 | 0.43 |
| 882087 | 377 | 276 | 23.1 | 0.15 |
| 882175 | 575 | 554 | 9.4 | 0.68 |
| 882177 | 2666 | 3030 | 26.6 | 4.87 |
| 882228 | 893 | 1659 | 19.3 | 0.22 |
| 882398 | 980 | 1070 | 22.1 | 7.91 |
| 882408 | 46 | 69 | 17.9 | 0.17 |
| 882800 | 70 | 84 | 23.4 | 0.20 |
| 969933 | 383 | 272 | 21.7 | 0.15 |
| 969936 | n.d. | n.d. | n.d. | n.d. |
| 969938 | 1142 | 1009 | 18.1 | 0.76 |
| 970211 | 301 | 224 | 20.1 | 0.15 |
| 970249 | 1724 | 2104 | 20.0 | 6.21 |
| 970545 | 836 | 1049 | 24.8 | 0.34 |
| 970546 | 1248 | 1334 | 23.8 | 0.31 |
| 970547 | 878 | 665 | 18.4 | 0.53 |
| 970548 | 1607 | 3352 | 17.7 | 4.86 |
| 970552 | n.d. | n.d. | n.d. | n.d. |

TABLE 167

Plasma chemistry markers in CD1 mouse plasma at week 4

| Compound ID | ALT (U/L) | AST (U/L) | BUN (mg/dL) | T. Bil (mg/dL) |
|---|---|---|---|---|
| PBS | 23 | 44 | 19.7 | 0.22 |
| 1012795 | 143 | 235 | 20.9 | 0.16 |
| 1012821 | 1189 | 1434 | 24.6 | 0.22 |
| 1012884 | 1523 | 1939 | 27.0 | 0.69 |
| 1014095 | 63 | 71 | 19.4 | 0.18 |
| 1014393 | 666 | 627 | 19.3 | 0.25 |
| 1014394 | 117 | 129 | 17.8 | 0.16 |
| 1014834 | 301 | 190 | 19.7 | 0.21 |
| 1015716 | 230 | 205 | 18.4 | 0.17 |

TABLE 168

Plasma chemistry markers in CD1 mice plasma at week 4

| Compound ID | ALT (U/L) | AST (U/L) | T. Bil (mg/dL) | BUN (mg/dL) | Albumin |
|---|---|---|---|---|---|
| PBS | 21 | 45 | 0.190 | 21.8 | 2.54 |
| 935918 | 87 | 91 | 0.118 | 18.8 | 2.07 |
| 935696 | 71 | 108 | 0.143 | 21.7 | 2.22 |

Organ Weights

Liver, kidney, and spleen weights were measured at the end of the study, and are presented as the percent change compared to PBS-treated animals in the table below. Modified oligonucleotides that caused any changes in organ weights outside the expected range for modified oligonucleotides were excluded from further studies.

TABLE 169

Organ Weights (g)

| Compound ID | Liver | Kidney | Spleen |
|---|---|---|---|
| PBS | 2.1 | 0.56 | 0.141 |
| 881413 | 2.2 | 0.57 | 0.217 |
| 881442 | 2.7 | 0.52 | 0.186 |
| 881449 | 2.1 | 0.47 | 0.169 |
| 881450 | 2.2 | 0.50 | 0.151 |
| 881506 | 2.9 | 0.62 | 0.191 |
| 881517 | 2.4 | 0.48 | 0.180 |
| 881581 | 2.2 | 0.51 | 0.192 |
| 881610 | 1.9 | 0.53 | 0.165 |
| 881658 | 2.0 | 0.54 | 0.158 |
| 881659 | 1.7 | 0.43 | 0.153 |
| 881660 | 1.9 | 0.52 | 0.175 |
| 881728 | 2.3 | 0.48 | 0.161 |
| 881742 | 1.9 | 0.48 | 0.127 |
| 882099 | 2.2 | 0.47 | 0.193 |
| 882282 | n.d. | n.d. | n.d. |
| 882305 | 2.1 | 0.52 | 0.181 |
| 882433 | 2.0 | 0.54 | 0.155 |

TABLE 170

Organ weights (g)

| Compound ID | Liver | Kidney | Spleen |
|---|---|---|---|
| PBS | 1.8 | 0.54 | 0.111 |
| 881449 | 2.1 | 0.54 | 0.146 |
| 881582 | 2.0 | 0.48 | 0.177 |
| 881588 | 1.9 | 0.39 | 0.171 |
| 881658 | 2.2 | 0.58 | 0.188 |
| 881727 | 2.1 | 0.51 | 0.201 |
| 792169 | 1.9 | 0.55 | 0.128 |
| UTC | 2.0 | 0.69 | 0.144 |

TABLE 171

Organ weights (g)

| Compound ID | Liver | Kidney | Spleen |
|---|---|---|---|
| PBS | 2.0 | 0.50 | 0.109 |
| 935765 | n.d. | n.d. | n.d. |
| 935580 | n.d. | n.d. | n.d. |
| 935805 | n.d. | n.d. | n.d. |
| 935853 | n.d. | n.d. | n.d. |
| 935824 | n.d. | n.d. | n.d. |
| 935581 | n.d. | n.d. | n.d. |
| 935689 | n.d. | n.d. | n.d. |
| 935698 | 2.4 | 0.55 | 0.213 |
| 935699 | n.d. | n.d. | n.d. |
| 935707 | 2.3 | 0.54 | 0.199 |
| 935679 | n.d. | n.d. | n.d. |
| 935727 | n.d. | n.d. | n.d. |
| 935795 | n.d. | n.d. | n.d. |
| 935898 | 2.2 | 0.58 | 0.245 |
| 935782 | 2.9 | 0.56 | 0.279 |
| 935878 | 2.7 | 0.56 | 0.192 |
| 935850 | 2.8 | 0.70 | 0.203 |
| 935724 | 2.6 | 0.45 | 0.110 |
| 935658 | 2.0 | 0.71 | 0.205 |
| 935762 | 2.3 | 0.57 | 0.197 |
| 935851 | 2.4 | 0.60 | 0.176 |

TABLE 172

Organ weights (g)

| Compound ID | Liver | Kidney | Spleen |
|---|---|---|---|
| PBS | 1.9 | 0.52 | 0.117 |
| 935921 | 2.3 | 0.51 | 0.219 |
| 935961 | 2.1 | 0.53 | 0.190 |
| 936018 | 2.2 | 0.41 | 0.200 |
| 936039 | n.d. | n.d. | n.d. |
| 935708 | n.d. | n.d. | n.d. |
| 935958 | 2.2 | 0.47 | 0.219 |
| 935854 | 2.0 | 0.44 | 0.102 |
| 935968 | 2.4 | 0.58 | 0.157 |
| 935620 | 3.2 | 0.57 | 0.243 |
| 935697 | 2.9 | 0.56 | 0.208 |
| 935700 | 2.0 | 0.49 | 0.121 |
| 935734 | 2.7 | 0.55 | 0.162 |
| 935857 | 1.5 | 0.34 | 0.110 |
| 936016 | 2.8 | 0.57 | 0.416 |
| 936006 | 2.3 | 0.48 | 0.136 |
| 936007 | 2.3 | 0.55 | 0.149 |
| 935948 | 1.9 | 0.54 | 0.166 |
| 935603 | 1.6 | 0.49 | 0.125 |
| 935701 | 1.9 | 0.43 | 0.144 |
| 935928 | 2.3 | 0.53 | 0.155 |

TABLE 173

Organ weights (g)

| Compound ID | Liver | Kidney | Spleen |
|---|---|---|---|
| PBS | 1.8 | 0.51 | 0.133 |
| 969991 | n.d. | n.d. | n.d. |
| 970013 | n.d. | n.d. | n.d. |

TABLE 173-continued

Organ weights (g)

| Compound ID | Liver | Kidney | Spleen |
|---|---|---|---|
| 970043 | 2.3 | 0.48 | 0.238 |
| 970103 | 2.2 | 0.54 | 0.175 |
| 970117 | 3.2 | 0.48 | 0.255 |
| 970139 | 2.7 | 0.56 | 0.210 |
| 970159 | 2.7 | 0.62 | 0.183 |
| 970162 | 2.2 | 0.54 | 0.215 |
| 970189 | 3.1 | 0.45 | 0.135 |
| 970212 | 2.3 | 0.45 | 0.218 |
| 970524 | n.d. | n.d. | n.d. |
| 970527 | 2.4 | 0.60 | 0.178 |

TABLE 174

Organ weights (g)

| Compound ID | Liver | Kidney | Spleen |
|---|---|---|---|
| PBS | 1.7 | 0.42 | 0.095 |
| 881955 | 1.8 | 0.32 | 0.110 |
| 882085 | 2.0 | 0.45 | 0.110 |
| 882086 | 4.9 | 0.41 | 0.258 |
| 882087 | 2.4 | 0.47 | 0.130 |
| 882175 | 1.4 | 0.46 | 0.098 |
| 882177 | 3.6 | 0.43 | 0.185 |
| 882228 | 2.8 | 0.49 | 0.193 |
| 882398 | 1.7 | 0.44 | 0.113 |
| 882408 | 2.0 | 0.51 | 0.135 |
| 882800 | 1.9 | 0.41 | 0.128 |
| 969933 | 2.2 | 0.50 | 0.145 |
| 969936 | n.d. | n.d. | n.d. |
| 969938 | 1.8 | 0.45 | 0.150 |
| 970211 | 2.1 | 0.40 | 0.143 |
| 970249 | 3.3 | 0.65 | 0.190 |
| 970545 | 2.5 | 0.44 | 0.133 |
| 970546 | 0.9 | 0.28 | 0.060 |
| 970547 | 2.1 | 0.50 | 0.243 |
| 970548 | 2.8 | 0.52 | 0.260 |
| 970552 | n.d. | n.d. | n.d. |

TABLE 175

Organ weights (g)

| Compound | Liver | Kidney | Spleen |
|---|---|---|---|
| PBS | 1.78 | 0.56 | 0.115 |
| 935918 | 2.44 | 0.62 | 0.167 |
| 935696 | 2.20 | 0.61 | 0.352 |

Example 35: Tolerability of Modified Oligonucleotides Targeting hIRF4 in Sprague-Dawley Rats Sprague-Dawley rats are a multipurpose model used for safety and efficacy evaluations. The rats were treated with modified antisense oligonucleotides from the studies described in the Examples above and evaluated for changes in the levels of various plasma chemistry markers.

Treatment

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with 50 mg/kg of ISIS oligonucleotide (50 mg/kg weekly dose). Forty eight hours after the last dose, rats were euthanized and organs and plasma were harvested for further analysis.

Liver and Kidney Function

To evaluate the effect of modified oligonucleotides on hepatic function, plasma levels of transaminases were measured using an automated clinical chemistry analyzer (Hitachi Olympus AU400e, Melville, NY). Plasma levels of ALT (alanine transaminase), AST (aspartate transaminase), blood urea nitrogen (BUN), and *T. bilirubin* were measured and the results are presented in the table below. Plasma levels of bilirubin were also measured using the same clinical chemistry analyzer and the results are also presented in the table below. Values represent the % change normalized to PBS-treated animals. Modified oligonucleotides that caused changes in the levels of any markers of liver function outside the expected range for antisense oligonucleotides were excluded in further studies.

TABLE 176

Liver function markers in Sprague-Dawley rats

| Compound ID | ALT (IU/L) | AST (IU/L) | T. Bil (mg/dL) | BUN (mg/dL) | Albumin (g/dL) |
|---|---|---|---|---|---|
| PBS | 47 | 67 | 0.14 | 16.4 | 3.92 |
| 690898 | 41 | 73 | 0.17 | 20.7 | 3.19 |
| 881413 | 42 | 61 | 0.18 | 18.1 | 3.66 |
| 881449 | 47 | 67 | 0.26 | 19.7 | 3.77 |
| 935658 | 47 | 55 | 0.16 | 17.4 | 3.80 |
| 935696 | 41 | 70 | 0.18 | 16.9 | 3.55 |
| 935898 | 72 | 81 | 0.19 | 18.0 | 4.23 |
| 935928 | 189 | 188 | 0.19 | 19.7 | 3.59 |
| 935968 | 39 | 85 | 0.21 | 17.2 | 3.61 |
| 936006 | 40 | 55 | 0.14 | 14.3 | 3.97 |

TABLE 177

Liver function markers in Sprague-Dawley rats

| Compound ID | ALT (IU/L) | AST (IU/L) | T. Bil (mg/dL) | BUN (mg/dL) | Albumin (g/dL) |
|---|---|---|---|---|---|
| PBS | 34 | 58 | 0.09 | 15.7 | 2.20 |
| 690890 | 32 | 70 | 0.16 | 20.1 | 2.39 |
| 690892 | 42 | 77 | 0.15 | 18.5 | 1.82 |
| 882085 | 68 | 73 | 0.09 | 47.1 | 1.36 |
| 882800 | 40 | 100 | 0.16 | 20.2 | 2.30 |
| 970527 | 45 | 80 | 0.12 | 19.8 | 2.09 |

TABLE 178

Liver function markers in Sprague-Dawley rats

| Compound ID | ALT (IU/L) | AST (IU/L) | T. Bil (mg/dL) | BUN (mg/dL) | Albumin (g/dL) |
|---|---|---|---|---|---|
| PBS | 41 | 70 | 0.14 | 14.4 | 3.60 |
| 882408 | 38 | 68 | 0.15 | 17.0 | 2.80 |
| 1012795 | 25 | 70 | 0.09 | 22.3 | 2.47 |
| 1014095 | 37 | 101 | 0.12 | 20.3 | 2.41 |
| 1014393 | 41 | 70 | 0.09 | 20.3 | 2.28 |
| 1014394 | 32 | 74 | 0.08 | 21.1 | 2.53 |
| 1014834 | 34 | 68 | 0.10 | 14.2 | 3.04 |

TABLE 179

Liver function markers in Sprague-Dawley rats

| Compound ID | ALT (IU/L) | AST (IU/L) | T. Bil (mg/dL) | BUN (mg/dL) | Albumin (g/dL) |
|---|---|---|---|---|---|
| PBS | 55 | 51 | 0.15 | 17.1 | 3.04 |
| 935762 | 35 | 53 | 0.14 | 18.7 | 2.63 |
| 935918 | 31 | 55 | 0.15 | 19.7 | 2.60 |

Hematology Assays

Blood obtained from all rat groups were sent to Antech Diagnostics for hematocrit (HCT) measurements and analysis, as well as measurements of the various blood cells, such as WBC, RBC, and total hemoglobin content. The results are presented in the table below. Modified oligonucleotides that caused changes in the levels of any of the hematology markers outside the expected range for antisense oligonucleotides were excluded in further studies.

TABLE 180

Hematology markers in Sprague-Dawley rats

| Compound ID | WBC (K/µL) | RBC (M/µL) | HGB (g/dL) | HCT (%) | LYM (/µL) | MON (/µL) | EOS (/µL) | BAS (/µL) | PLT (K/µL) | Retic (K/µL) |
|---|---|---|---|---|---|---|---|---|---|---|
| PBS | 10.38 | 8.15 | 14.80 | 43.9 | 8711 | 357 | 68.3 | 12.3 | 868 | 252 |
| 690898 | 17.83 | 6.46 | 12.27 | 37.1 | 15745 | 1109 | 75.0 | 145.0 | 214 | 201 |
| 881413 | 7.08 | 6.71 | 12.55 | 36.6 | 6342 | 286 | 44.3 | 15.3 | 523 | 152 |
| 881449 | 6.68 | 7.53 | 13.60 | 39.8 | 5414 | 396 | 153.0 | 27.5 | 583 | 133 |
| 935658 | 9.73 | 7.97 | 14.53 | 42.4 | 8250 | 777 | 19.7 | 70.0 | 685 | 138 |
| 935696 | 7.80 | 7.33 | 13.10 | 38.6 | 6354 | 645 | 48.8 | 23.0 | 480 | 97 |
| 935898 | 7.75 | 8.64 | 15.20 | 43.3 | 6248 | 529 | 29.3 | 26.8 | 712 | 114 |
| 935928 | 13.15 | 7.36 | 13.23 | 40.1 | 7231 | 1177 | 8.5 | 90.3 | 476 | 160 |
| 935968 | 6.15 | 6.17 | 11.28 | 33.7 | 5292 | 436 | 8.0 | 68.8 | 462 | 178 |
| 936006 | 7.28 | 8.07 | 14.45 | 42.7 | 5875 | 729 | 20.3 | 57.3 | 621 | 220 |

TABLE 181

Hematology markers in Sprague-Dawley rats

| Compound ID | WBC (K/µL) | RBC (M/µL) | HGB (g/dL) | HCT (%) | LYM (/µL) | MON (/µL) | EOS (/µL) | BAS (/µL) | PLT (K/µL) | Retic (K/µL) |
|---|---|---|---|---|---|---|---|---|---|---|
| PBS | 4.35 | 5.18 | 9.68 | 29.4 | 3546 | 116 | 102.8 | 10.5 | 292 | 136 |
| 690890 | 4.75 | 4.84 | 8.98 | 27.4 | 3844 | 325 | 25.3 | 55.0 | 190 | 113 |
| 690892 | 4.70 | 5.46 | 10.65 | 31.4 | 3917 | 276 | 42.3 | 34.5 | 184 | 120 |
| 882085 | 7.18 | 5.18 | 9.43 | 29.2 | 5159 | 758 | 73.0 | 24.5 | 352 | 122 |
| 882800 | 5.10 | 5.08 | 9.13 | 27.9 | 4190 | 479 | 46.0 | 40.3 | 165 | 157 |
| 970527 | 9.60 | 6.10 | 10.88 | 32.4 | 7990 | 846 | 28.3 | 50.8 | 249 | 123 |

TABLE 182

Hematology markers in Sprague-Dawley rats

| Compound ID | WBC (K/µL) | RBC (M/µL) | HGB (g/dL) | HCT (%) | LYM (/µL) | MON (/µL) | EOS (/µL) | BAS (/µL) | PLT (K/µL) | Retic (K/µL) |
|---|---|---|---|---|---|---|---|---|---|---|
| PBS | 9.35 | 7.81 | 14.28 | 46.6 | 7820 | 330 | 208.3 | 11.3 | 344 | 214 |
| 882408 | 13.25 | 9.46 | 16.73 | 52.0 | 8387 | 1020 | 35.3 | 29.3 | 407 | 163 |
| 1012795 | 15.20 | 4.86 | 10.03 | 33.6 | 11767 | 1996 | 28.5 | 12.8 | 149 | 304 |
| 1014095 | 18.55 | 6.93 | 12.35 | 41.4 | 11958 | 1500 | 95.0 | 22.3 | 727 | 281 |
| 1014393 | 21.90 | 7.25 | 13.08 | 41.8 | 17709 | 2038 | 50.5 | 156.3 | 491 | 123 |
| 1014394 | 23.55 | 7.21 | 13.58 | 43.3 | 19656 | 2121 | 31.8 | 67.5 | 270 | 207 |
| 1014834 | 14.43 | 7.97 | 14.65 | 45.9 | 12543 | 1009 | 42.3 | 180.0 | 395 | 182 |

TABLE 183

| Hematology markers in Sprague-Dawley rats | | | | | | | | | | |
|---|---|---|---|---|---|---|---|---|---|---|
| Compound ID | WBC (K/µL) | RBC (M/µL) | HGB (g/dL) | HCT (%) | LYM (/µL) | MON (/µL) | EOS (/µL) | BAS (/µL) | PLT (K/µL) | Retic (K/µL) |
| PBS | 11.13 | 9.45 | 16.70 | 52.8 | 9156 | 686 | 103 | 8.0 | 82 | 238 |
| 935762 | 14.53 | 7.72 | 13.43 | 42.4 | 13586 | 510 | 0 | 29.3 | 92 | 232 |
| 935918 | 9.25 | 7.08 | 12.50 | 40.5 | 8509 | 456 | 51 | 5.0 | 92 | 286 |

Organ Weights

Liver, heart, spleen and kidney weights were measured at the end of the study, and are presented in the table below. Modified oligonucleotides that caused any changes in organ weights outside the expected range for antisense oligonucleotides were excluded from further studies.

TABLE 184

| Organ weights (g) | | | |
|---|---|---|---|
| Compound ID | Liver (g) | Kidney (g) | Spleen (g) |
| PBS | 15.8 | 2.91 | 0.90 |
| 690898 | 16.9 | 3.18 | 3.65 |
| 881413 | 15.0 | 2.83 | 1.32 |
| 881449 | 15.4 | 3.07 | 1.19 |
| 935658 | 13.8 | 2.40 | 1.33 |
| 935696 | 12.6 | 2.60 | 1.22 |
| 935898 | 12.0 | 2.44 | 1.07 |
| 935928 | 16.8 | 3.23 | 1.94 |
| 935968 | 14.9 | 2.85 | 1.56 |
| 936006 | 14.2 | 2.75 | 1.59 |

TABLE 185

| Organ weights (g) | | | |
|---|---|---|---|
| Compound ID | Liver (g) | Kidney (g) | Spleen (g) |
| PBS | 15.2 | 3.38 | 0.72 |
| 690890 | 15.8 | 3.17 | 1.62 |
| 690892 | 15.2 | 3.27 | 1.72 |
| 882085 | 12.5 | 3.78 | 1.41 |
| 882800 | 17.0 | 3.46 | 3.24 |
| 970527 | 14.0 | 3.72 | 1.94 |

TABLE 186

| Organ weights (g) | | | |
|---|---|---|---|
| Compound ID | Liver (g) | Kidney (g) | Spleen (g) |
| PBS | 18.6 | 3.70 | 0.92 |
| 882408 | 15.1 | 3.60 | 1.51 |
| 1012795 | 18.9 | 3.70 | 4.06 |
| 1014095 | 18.2 | 3.63 | 3.05 |
| 1014393 | 15.9 | 3.98 | 2.30 |
| 1014394 | 18.3 | 4.41 | 2.79 |
| 1014834 | 14.4 | 3.35 | 5.01 |

TABLE 187

| Organ weights (g) | | | |
|---|---|---|---|
| Compound ID | Liver (g) | Kidney (g) | Spleen (g) |
| PBS | 14.6 | 3.20 | 0.88 |
| 935762 | 16.1 | 3.43 | 1.73 |
| 935918 | 18.7 | 3.89 | 2.01 |

Example 36: Tolerability of Modified Oligonucleotides in Non-Human Primates

Modified oligonucleotides described above were further evaluated for potency in non-human primates.

Treatment

Male cynomolgus monkeys were divided into groups of 4 non-human primates (NHP) each. Groups received a dose of 40 mg/kg of modified oligonucleotide by subcutaneous injection on day 1, 3, 5, and 7, and then once/week for six weeks. One group of NHP received doses of PBS. The PBS-injected group served as the control group to which oligonucleotide-treated groups were compared. After six weeks, NHP were sacrificed and tissues were collected for analysis.

Tolerability

To evaluate the effect of these antisense oligonucleotides on liver and kidney function, samples of blood, plasma, serum and urine were collected from all study groups on day 44. The blood samples were collected via femoral venipuncture, 48 hrs post-dosing. The monkeys were fasted overnight prior to blood collection. Approximately 1.5 mL of blood was collected from each animal into tubes without anticoagulant for serum separation. Levels of the various markers were measured using an automated clinical chemistry analyzer (Hitachi Olympus AU400e, Melville, NY). Total urine protein and urine creatinine levels were measured, and the ratio of total urine protein to creatinine (P/C Ratio) was determined.

To evaluate the effect of the antisense oligonucleotides on hepatic function, plasma concentrations of transaminases (ALT, AST), Albumin (Alb) and total bilirubin ("T. Bil") were measured. To evaluate the effect of the antisense oligonucleotides on kidney function, plasma concentrations of blood urea nitrogen (BUN) and creatinine (Cre) were measured. Urine levels of albumin (Alb), creatinine (Cre) and total urine protein (Micro Total Protein (MTP)) were measured, and the ratio of total urine protein to creatinine (P/C ratio) was determined.

To evaluate any inflammatory effect of the ISIS oligonucleotides in cynomolgus monkeys, C-reactive protein (CRP), which is synthesized in the liver and which serves as a marker of inflammation, was measured on day 44. For this, blood samples were taken from fasted monkeys, the tubes were kept at room temperature for a minimum of 90 min., and centrifuged at 3,000 rpm for 10 min at room temperature to obtain serum. The results are presented in the Tables below and indicate that most of the antisense oligonucleotides targeting human IRF4 were well tolerated in cynomolgus monkeys. ION 935918 and 935968 were well tolerated.

TABLE 188

Serum and urine clinical chemistry

| ISIS No. | Serum (day 44) | | | | | | | | Urine (day 42) | | |
| --- | --- | --- | --- | --- | --- | --- | --- | --- | --- | --- | --- |
| | C3 mg/dL | ALT U/L | AST U/L | Alb g/dL | BUN mg/dL | CRP mg/L | Cre mg/dL | T. bil mg/dL | Alb g/dL | Cre mg/dL | P/C ratio |
| PBS | 120.73 | 48.00 | 69.10 | 4.35 | 25.60 | 1.66 | 0.858 | 0.29 | 0.35 | 55.0 | 0.00 |
| 690890 | 71.20 | 50.18 | 75.20 | 3.66 | 26.10 | 9.52 | 0.988 | 0.23 | 0.53 | 56.2 | 0.04 |
| 935658 | 95.90 | 42.33 | 81.85 | 3.99 | 21.70 | 4.53 | 0.808 | 0.29 | 0.68 | 39.0 | 0.12 |
| 935696 | 88.58 | 48.32 | 62.78 | 4.03 | 26.06 | 6.55 | 0.780 | 0.26 | 0.18 | 36.6 | 0.04 |
| 935762 | 100.10 | 47.58 | 52.63 | 3.91 | 24.98 | 6.88 | 0.76 | 0.25 | 0.03 | 37.9 | 0.01 |
| 935918 | 94.45 | 49.45 | 79.20 | 4.05 | 29.85 | 4.65 | 0.90 | 0.24 | 0.12 | 60.2 | 0.01 |
| 935968 | 108.83 | 54.45 | 83.33 | 4.10 | 28.68 | 6.65 | 0.813 | 0.23 | 0.10 | 38.8 | 0.07 |
| 882800 | 100.83 | 46.55 | 61.80 | 4.00 | 24.10 | 2.53 | 0.818 | 0.22 | 0.36 | 34.9 | 0.14 |
| 1012795 | 82.05 | 37.08 | 51.40 | 3.05 | 27.45 | 21.28 | 0.763 | 0.20 | 0.50 | 55.0 | 0.10 |
| 1014095 | 85.83 | 38.15 | 46.85 | 2.81 | 15.10 | 11.16 | 0.593 | 0.15 | 0.03 | 43.9 | 0.07 |
| 1014834 | 89.13 | 54.73 | 75.28 | 3.88 | 23.65 | 7.03 | 0.978 | 0.25 | 0.14 | 75.9 | 0.05 |

TABLE 189

Body Weight

| Compound ID | Body Weight (g) day 1 | Body weight (g) day 42 |
| --- | --- | --- |
| PBS | 2521 | 2594 |
| 690890 | 2508 | 2514 |
| 935658 | 2499 | 2557 |
| 935696 | 2412 | 2511 |
| 935762 | 2473 | 2653 |
| 935918 | 2483 | 2657 |
| 935968 | 2605 | 2798 |
| 882800 | 2577 | 2676 |
| 1012795 | 2623 | 2577 |
| 1014095 | 2567 | 2719 |
| 1014834 | 2556 | 2685 |

RNA Analysis

RNA was extracted from various tissues for real-time PCR analysis of mRNA expression of IRF4 as in previous examples. Results are presented as percent change of mRNA, relative to PBS control, normalized with NHP Cyclophylin A. As shown in the table below, treatment with modified oligonucleotides resulted in reduction of IRF4 mRNA in comparison to the PBS control with some of the treatment groups.

TABLE 190

% Inhibition of cynomolgus IRF4

| Compound ID | Bone marrow | PBMC | Spleen |
| --- | --- | --- | --- |
| PBS | 100 | 100 | 100 |
| 690890* | 98 | 119 | 205 |
| 935658* | 174 | 170 | 200 |
| 935696* | 71 | 80 | 125 |
| 935762* | 112 | 90 | 129 |
| 935918* | 98 | 41 | 192 |
| 935968* | 129 | 49 | 131 |
| 882800*** | 107 | 75 | 133 |
| 1012795* | 97 | 95 | 151 |
| 1014095*** | 80 | 80 | 188 |
| 1014834* | 139 | 180 | 192 |

*Compounds have one mismatch to cynomolgus monkey IRF4;
***compounds have three mismatches to cynomolgus monkey IRF4.

Example 37: Viscosity

Viscosity of modified oligonucleotide solutions was measured. The viscocity of 935918 is compatible with weekly subcutaneous injection, and the viscosities of both 935918 and 935968 are compatible with IV dosing.

TABLE 191

Viscosity

| Compound ID | Dose (mg/mL) by weight | Viscocity (cP) |
| --- | --- | --- |
| 690890 | 300 | 16.14 |
| 935658 | 300 | 48.79 |
| 935696 | 300 | 120.2 |
| 935762 | 300 | 11.39 |
| 935918 | 100 | 2.12 |
| 935968 | 300 | 53.76 |
| 882800 | 100 | 3.4 |

SEQUENCE LISTING

The patent contains a lengthy sequence listing. A copy of the sequence listing is available in electronic form from the USPTO web site (https://seqdata.uspto.gov/?pageRequest=docDetail&DocID=US12042510B2). An electronic copy of the sequence listing will also be available from the USPTO upon request and payment of the fee set forth in 37 CFR 1.19(b)(3).

What is claimed:

1. A compound comprising a modified oligonucleotide 15 to 30 linked nucleosides in length having a nucleobase sequence comprising at least 15 contiguous nucleobases of the nucleobase sequence of SEQ ID NO: 2021, or a pharmaceutically acceptable salt thereof.

2. The compound of claim 1, wherein the modified oligonucleotide comprises a nucleobase sequence of SEQ ID NO: 2021.

3. The compound of claim 1, wherein the modified oligonucleotide consists of a nucleobase sequence of SEQ ID NO: 2021.

4. The compound of claim 1, wherein the modified oligonucleotide comprises at least one modified internucleoside linkage, at least one modified sugar, or at least one modified nucleobase.

5. The compound of claim 4, wherein the modified internucleoside linkage is a phosphorothioate internucleoside linkage.

6. The compound of claim 4, wherein the modified sugar is a bicyclic sugar.

7. The compound of claim 6, wherein the bicyclic sugar is selected from the group consisting of: 4'-(CH$_2$)-O-2' (LNA); 4'-(CH$_2$)2-O-2' (ENA); and 4'-CH(CH$_3$)-O-2'(cEt).

8. The compound of claim 4, wherein the modified sugar is 2'-O-methoxyethyl.

9. The compound of claim 4, wherein the modified nucleobase is 5-methylcytosine.

10. The compound of claim 1, wherein the modified oligonucleotide comprises:
a gap segment consisting of linked deoxyribonucleotides;
a 5' wing segment consisting of linked nucleosides; and
a 3' wing segment consisting of linked nucleosides;
wherein the gap segment is positioned between the 5' wing segment and the 3' wing segment and wherein each nucleoside of each wing segment comprises a modified sugar.

11. The compound of claim 10, wherein:
the gap segment consists of ten linked deoxynucleosides;
the 5' wing segment consists of two linked nucleosides; and
the 3' wing segment consists of four linked nucleosides;
wherein the gap segment is positioned between the 5' wing segment and the 3' wing segment; wherein each nucleoside of the 5' wing segment comprises a cEt nucleoside; wherein the 3' wing segment comprises a cEt nucleoside, a 2'-O-methoxymethyl nucleoside, a cEt nucleoside, and a 2'-O-methoxymethyl nucleoside in the 5' to 3' direction; wherein each internucleoside linkage is a phosphorothioate linkage; and wherein each cytosine is a 5-methylcytosine.

12. The compound of claim 1, wherein the compound is a sodium salt.

13. A composition comprising the compound of claim 1 and a pharmaceutically acceptable carrier.

14. A method for treating or ameliorating a cancer in an individual comprising administering a composition of claim 13.

15. The method of claim 14, wherein the cancer is a blood cancer, myeloma, multiple myeloma, B cell malignancy, lymphoma, B cell lymphoma, T cell lymphoma, or leukemia.

16. The method of claim 14, wherein the cancer is multiple myeloma.

17. The method of claim 14, wherein the composition is administered parenterally.

* * * * *